US012492412B2

(12) United States Patent
Do et al.

(10) Patent No.: US 12,492,412 B2
(45) Date of Patent: Dec. 9, 2025

(54) VECTOR COMPOSITIONS AND METHODS OF USING SAME FOR TREATMENT OF LYSOSOMAL STORAGE DISORDERS

(71) Applicant: M6P THERAPEUTICS (SWITZERLAND) LLC, Schaffhausen (CH)

(72) Inventors: Cuong Do, Mendham, NJ (US); Lin Liu, St. Louis, MO (US)

(73) Assignee: M6P TERAPEUTICS (SWITZERLAND) LLC, Schaffhausen (CH)

( * ) Notice: Subject to any disclaimer, the term of this patent is extended or adjusted under 35 U.S.C. 154(b) by 861 days.

(21) Appl. No.: 17/624,196

(22) PCT Filed: Jul. 2, 2020

(86) PCT No.: PCT/US2020/040770

§ 371 (c)(1),
(2) Date: Dec. 30, 2021

(87) PCT Pub. No.: WO2021/003442

PCT Pub. Date: Jan. 7, 2021

(65) Prior Publication Data

US 2022/0380800 A1 Dec. 1, 2022

Related U.S. Application Data

(60) Provisional application No. 62/869,781, filed on Jul. 2, 2019, provisional application No. 62/869,808, filed on Jul. 2, 2019.

(51) Int. Cl.

| | |
|---|---|
| ***C12N 15/86*** | (2006.01) |
| ***A61P 3/00*** | (2006.01) |
| ***C12N 9/12*** | (2006.01) |
| ***C12N 15/52*** | (2006.01) |

(52) U.S. Cl.

CPC ................ *C12N 15/86* (2013.01); *A61P 3/00* (2018.01); *C12N 9/1288* (2013.01); *C12N 15/52* (2013.01)

(58) Field of Classification Search

None

See application file for complete search history.

(56) References Cited

U.S. PATENT DOCUMENTS

| | | | |
|---|---|---|---|
| 5,350,674 | A | 9/1994 | Boenisch et al. |
| 5,399,346 | A | 3/1995 | Anderson et al. |
| 5,478,745 | A | 12/1995 | Samulski et al. |
| 5,580,859 | A | 12/1996 | Felgner et al. |
| 5,585,362 | A | 12/1996 | Wilson et al. |
| 5,589,466 | A | 12/1996 | Felgner et al. |
| 6,156,303 | A | 12/2000 | Russell et al. |
| 6,326,193 | B1 | 12/2001 | Liu et al. |
| 7,282,199 | B2 | 10/2007 | Gao et al. |
| 2015/0030582 | A1 | 1/2015 | Harvey et al. |

FOREIGN PATENT DOCUMENTS

| | | | | |
|---|---|---|---|---|
| WO | 200129058 | A1 | 4/2001 | |
| WO | 200196584 | A2 | 12/2001 | |
| WO | 2003042397 | A2 | 5/2003 | |
| WO | 2005033321 | A2 | 4/2005 | |
| WO | WO-2018064667 | A1 * | 4/2018 | ........... C12N 9/1288 |

OTHER PUBLICATIONS

English translation of First Office Action issued in related CN Application No. 202080061537.2; dated May 5, 2023; China National Intellectual Property Administration; 14 pages.
English translation of Second Office Action issued in related CN Application No. 202080061537.2; dated Feb. 23, 2024; China National Intellectual Property Administration; 16 pages.
English translation of Decision on Rejection issued in related CN Application No. 202080061537.2; dated May 10, 2024; China National Intellectual Property Administration; 12 pages.
English translation of Office Action issued in related JP Application No. 2022-500533; dated Jun. 10, 2024; 4 pages.
English translation of Search Report issued in related TW Application No. 109122470; dated Jun. 26, 2024; 1 page.
International Search Report and Written Opinion in related International Application No. PCT/US2020/040770; mailed Oct. 7, 2020; 10 pages.
Molecular Therapy: Methods & Clinical Development, 2017, vol. 5, pp. 59-65, http://dx.doi.org/10.1016/j. omtm.2017.03.006; 8 pages.
Human Gene Therapy, 2014, vol. 25, pp. 506-516, DOI: 10.1089/hum.2013.238; 12 pages.
Molecular Genetics and Metabolism, 2013, vol. 108, Issue 2, S19; 4 pages.
Evan Woodley et al: "Efficacy of a Bicistronic Vector for Correction of Sandhoff Disease in a Mouse Model", Molecular Therapy Methods & Clinical Develop, vol. 12, Mar. 1, 2019 (Mar. 1, 2019), pp. 47-57.
Arfi et al: "Bicistronic lentiviral vector corrects beta-hexosaminidase deficiency in transduced and cross-corrected human Sandhoff fibroblasts", Neurobiology of Disease, Elsevier, Amsterdam, NL, vol. 20, No. 2, Nov. 1, 2005 (Nov. 1, 2005), pp. 583-593.
Ryan et al., 1991, J Gen Virol 72:2727-2732.

(Continued)

*Primary Examiner* — Anna Skibinsky
*Assistant Examiner* — Catherine L McCormick
(74) *Attorney, Agent, or Firm* — Reed Smith LLP; Hallie H. Wimberly

(57) ABSTRACT

Provided herein are compositions and methods of using a bicistronic vector for treating or preventing a lysosomal storage disorder (LSD) in a subject. The disclosed compositions comprise a bicistronic vector comprising a promoter, an Internal Ribosome Entry Site (IRES), a polynucleotide encoding a lysosomal enzyme and a polynucleotide encoding a modified GlcNAc-1 phosphotransferase (GlcNAc-1 PTase). The present methods comprise administering to the subject a pharmaceutical composition comprising the bicistronic vector as disclosed herein.

15 Claims, 31 Drawing Sheets

Specification includes a Sequence Listing.

(56) References Cited

OTHER PUBLICATIONS

De Felipe et al., 2006, Trends Biotechnol 24:68-75.
Ui-Tei et al., 2000 FEBS Letters 479: 79-82.
K. Fisher et al., 1996 J. Virol., 70:520-532.

* cited by examiner

Fig A&B. Binding of expressed GBA enzymes to M6P receptor

Fig C. 4 hour cell uptake of GBA enzymes in patient fibroblast cells

Fig D. Enzyme thermostability study at 37C, neutral pH

Fig E. Binding of expressed GBA enzymes to M6P receptor

Fig A&B. Binding of expressed GAA enzymes to M6P receptor

Fig C. 4 hour cell uptake of GAA enzymes in patient fibroblast cells

Fig A&B. Binding of expressed GALC enzymes to MSP receptor

Fig C. 4 hour cell uptake of GALC enzymes in enzyme deficient mouse fibroblast cells Fig A&B. Binding of expressed NAGLU enzymes to M6P receptor Fig C. 4 hour cell uptake of NAGLU enzymes in patient fibroblast cells Fig A&B. Binding of expressed GLA enzymes to M6P receptor Fig C. 4 hour cell uptake of GLA enzymes in patient fibroblast cells Fig A&B. Binding of expressed LAMAN enzymes to M6P receptor Fig C. 4 hour cell uptake of LAMAN enzymes in patient fibroblast cells

A

B

A B C

A

SDS-PAGE Gel:
1: MWM;
2: M0611;
3: LAMAN;
4: LAMAN.

B

| | Protein Conc. (mg/mL) | Absolute Activity (nmol/hr/mg) | Yield (mg) | SDS-PAGE Gel (Lane) | Batch No |
|---|---|---|---|---|---|
| M0611 | 16.0 | 343,000 | 15.2 | 2 | P-0030 |
| LAMAN | 18.4 | 404,000 | 17.4 | 3 | P-0031 |
| LAMAN | 20.4 | 568,000 | 19 | 4 | P-0032 |

C

A

B

A

S1-S3 is suitable for the gene therapy of ML II disease

1. Full activity comparing to full length GNPTAB gene.
2. Small gene size (~1.7Kb) for AAV package.

B

B

A 2 weeks post AAV9 injection in Gaucher mice, the Gcase activity and GC content were checked in the liver and lung.

SEQUENCE LISTING

```
<160> NUMBER OF SEQ ID NOS: 164

<210> SEQ ID NO 1
<211> LENGTH: 7709
<212> TYPE: DNA
<213> ORGANISM: artificial sequence
<220> FEATURE:
```

<223> OTHER INFORMATION: expression vector

<400> SEQUENCE: 1
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
gtttaaactt aagcttggta ccgagctcgg atccactagt ccagtgtggt ggaattctgc 960
agatatccag cacagtggcg gccgctgatt aacctcagga ctagtggtta ttttccacca 1020
tattgccgtc ttttggcaat gtgagggccc ggaaacctgg ccctgtcttc ttgacgagca 1080
ttcctagggg tctttcccct ctcgccaaag gaatgcaagg tctgttgaat gtcgtgaagg 1140
aagcagttcc tctggaagct tcttgaagac aaacaacgtc tgtagcgacc ctttgcaggc 1200
agcggaaccc cccacctggc gacaggtgcc tctgcggcca aaagccacgt gtataagata 1260
cacctgcaaa ggcggcacaa ccccagtgcc acgttgtgag ttggatagtt gtggaaagag 1320
tcaaatggct cacctcaagc gtattcaaca aggggctgaa ggatgcccag aaggtacccc 1380
attgtatggg atctgatctg gggcctcggt gcacatgctt tacatgtgtt tagtcgaggt 1440
taaaaaacgt ctaggccccc cgaaccacgg ggacgtggtt ttcctttgaa agtttgttaa 1500
catgctgttc aagctcctgc agagacagac ctatacctgc ctgtcccaca ggtatgggct 1560
ctacgtgtgc ttcttgggcg tcgttgtcac catcgtctcc gccttccagt tcggagaggt 1620
ggttctggaa tggagccgag atcaatacca tgttttgttt gattcctata gagacaatat 1680
tgctggaaag tcctttcaga atcggctttg tctgcccatg ccgattgacg ttgtttacac 1740
ctgggtgaat ggcacagatc ttgaactact gaaggaacta acagaattaa aaagatcaaa 1800
acgtgatcca ttaataccag aatgtcaagg taaacaaaca ccagaaaaag ataaatgtta 1860
tagagatgac atctctgcca gtcgttttga agataacgaa gaactgaggt actcattgcg 1920
atctatcgag aggcatgcac catgggttcg gaatattttc attgtcacca acgggcagat 1980
tccatcctgg ctgaaccttg acaatcctcg agtgacaata gtaacacacc aggatgtttt 2040
tcgaaatttg agccacttgc ctacctttag ttcacctgct attgaaagtc acattcatcg 2100
catcgaaggg ctgtcccaga agtttattta cctaaatgat gatgtcatgt ttgggaagga 2160
tgtctggcca gatgattttt acagtcactc caaaggccag aaggtttatt tgacatggcc 2220
tgtgccaaac ggaggtagcg gaggtgatac atttgcagat tccctcagat atgtaaataa 2280

```
aattctaaat agcaagtttg gattcacatc gcggaaagtc cctgctcaca tgcctcacat   2340
gattgaccgg attgttatgc aagaactgca agatatgttc cctgaagaat ttgacaagac   2400
gtcatttcac aaagtgcgcc attctgagga tatgcagttt gccttctctt atttttatta   2460
tctcatgagt gcagtgcagc cactgaatat atctcaagtc tttgatgaag ttgatacaga   2520
tcaatctggt gtcttgtctg acagagaaat ccgaacactg gctaccagaa ttcacgaact   2580
gccgttaagt ttgcaggatt tgacaggtct ggaacacatg ctaataaatt gctcaaaaat   2640
gcttcctgct gatatcacgc agctaaataa tattccacca actcaggaat cctactatga   2700
tcccaacctg ccaccggtca ctaaaagtct agtaacaaac tgtaaaccag taactgacaa   2760
aatccacaaa gcatataagg acaaaaacaa atataggttt gaaatcatgg gagaagaaga   2820
aatcgctttt aaaatgattc gtaccaacgt ttctcatgtg gttggccagt tggatgacat   2880
aagaaaaaac cctaggaagt ttgtttgcct gaatgacaac attgaccaca atcataaaga   2940
tgctcagaca gtgaaggctg ttctcaggga cttctatgaa tccatgttcc ccataccttc   3000
ccaatttgaa ctgccaagag agtatcgaaa ccgtttcctt catatgcatg agctgcagga   3060
atggagggct tatcgagaca aattgaagtt ttggacccat tgtgtactag caacattgat   3120
tatgtttact atattctcat tttttgctga gcagttaatt gcacttaagc ggaagatatt   3180
tcccagaagg aggatacaca aagaagctag tcccaatcga atcagagtat ctagaggagg   3240
taagcctatc cctaaccctc tcctcggtct cgattctacg tgagtttaaa cccgctgatc   3300
agcctcgact gtgccttcta gttgccagcc atctgttgtt tgcccctccc ccgtgccttc   3360
cttgaccctg gaaggtgcca ctcccactgt cctttcctaa taaaatgagg aaattgcatc   3420
gcattgtctg agtaggtgtc attctattct ggggggtggg gtggggcagg acagcaaggg   3480
ggaggattgg gaagacaata gcaggcatgc tggggatgcg gtgggctcta tggcttctga   3540
ggcggaaaga accagctggg gctctagggg gtatccccac gcgccctgta gcggcgcatt   3600
aagcgcggcg ggtgtggtgg ttacgcgcag cgtgaccgct acacttgcca gcgccctagc   3660
gcccgctcct ttcgctttct tcccttcctt tctcgccacg ttcgccggct ttccccgtca   3720
agctctaaat cgggggctcc ctttagggtt ccgatttagt gctttacggc acctcgaccc   3780
caaaaaactt gattagggtg atggttcacg tagtgggcca tcgccctgat agacggtttt   3840
tcgccctttg acgttggagt ccacgttctt taatagtgga ctcttgttcc aaactggaac   3900
aacactcaac cctatctcgg tctattcttt tgatttataa gggattttgc cgatttcggc   3960
ctattggtta aaaaatgagc tgatttaaca aaaatttaac gcgaattaat tctgtggaat   4020
gtgtgtcagt tagggtgtgg aaagtcccca ggctccccag caggcagaag tatgcaaagc   4080
atgcatctca attagtcagc aaccaggtgt ggaaagtccc caggctcccc agcaggcaga   4140
agtatgcaaa gcatgcatct caattagtca gcaaccatag tcccgcccct aactccgccc   4200
atcccgcccc taactccgcc cagttccgcc cattctccgc cccatggctg actaattttt   4260
tttatttatg cagaggccga ggccgcctct gcctctgagc tattccagaa gtagtgagga   4320
ggcttttttg gaggcctagg cttttgcaaa aagctcccgg gagcttgtat atccattttc   4380
ggatctgatc aagagacagg atgaggatcg tttcgcatga ttgaacaaga tggattgcac   4440
gcaggttctc cggccgcttg ggtggagagg ctattcggct atgactgggc acaacagaca   4500
atcggctgct ctgatgccgc cgtgttccgg ctgtcagcgc aggggcgccc ggttcttttt   4560
gtcaagaccg acctgtccgg tgccctgaat gaactgcagg acgaggcagc gcggctatcg   4620
```

-continued

```
tggctggcca cgacgggcgt tccttgcgca gctgtgctcg acgttgtcac tgaagcggga   4680
agggactggc tgctattggg cgaagtgccg gggcaggatc tcctgtcatc tcaccttgct   4740
cctgccgaga aagtatccat catggctgat gcaatgcggc ggctgcatac gcttgatccg   4800
gctacctgcc cattcgacca ccaagcgaaa catcgcatcg agcgagcacg tactcggatg   4860
gaagccggtc ttgtcgatca ggatgatctg gacgaagagc atcaggggct cgcgccagcc   4920
gaactgttcg ccaggctcaa ggcgcgcatg cccgacggcg aggatctcgt cgtgacccat   4980
ggcgatgcct gcttgccgaa tatcatggtg gaaaatggcc gcttttctgg attcatcgac   5040
tgtggccggc tgggtgtggc ggaccgctat caggacatag cgttggctac ccgtgatatt   5100
gctgaagagc ttggcggcga atgggctgac cgcttcctcg tgctttacgg tatcgccgct   5160
cccgattcgc agcgcatcgc cttctatcgc cttcttgacg agttcttctg agcgggactc   5220
tggggttcga aatgaccgac caagcgacgc ccaacctgcc atcacgagat ttcgattcca   5280
ccgccgcctt ctatgaaagg ttgggcttcg gaatcgtttt ccgggacgcc ggctggatga   5340
tcctccagcg cggggatctc atgctggagt tcttcgccca ccccaacttg tttattgcag   5400
cttataatgg ttacaaataa agcaatagca tcacaaattt cacaaataaa gcattttttt   5460
cactgcattc tagttgtggt ttgtccaaac tcatcaatgt atcttatcat gtctgtatac   5520
cgtcgacctc tagctagagc ttggcgtaat catggtcata gctgtttcct gtgtgaaatt   5580
gttatccgct cacaattcca cacaacatac gagccggaag cataaagtgt aaagcctggg   5640
gtgcctaatg agtgagctaa ctcacattaa ttgcgttgcg ctcactgccc gctttccagt   5700
cgggaaacct gtcgtgccag ctgcattaat gaatcggcca acgcgcgggg agaggcggtt   5760
tgcgtattgg gcgctcttcc gcttcctcgc tcactgactc gctgcgctcg gtcgttcggc   5820
tgcggcgagc ggtatcagct cactcaaagg cggtaatacg gttatccaca gaatcagggg   5880
ataacgcagg aaagaacatg tgagcaaaag gccagcaaaa ggccaggaac cgtaaaaagg   5940
ccgcgttgct ggcgtttttc cataggctcc gcccccctga cgagcatcac aaaaatcgac   6000
gctcaagtca gaggtggcga aacccgacag gactataaag ataccaggcg tttccccctg   6060
gaagctccct cgtgcgctct cctgttccga ccctgccgct taccggatac ctgtccgcct   6120
ttctcccttc gggaagcgtg gcgctttctc atagctcacg ctgtaggtat ctcagttcgg   6180
tgtaggtcgt tcgctccaag ctgggctgtg tgcacgaacc ccccgttcag cccgaccgct   6240
gcgccttatc cggtaactat cgtcttgagt ccaacccggt aagacacgac ttatcgccac   6300
tggcagcagc cactggtaac aggattagca gagcgaggta tgtaggcggt gctacagagt   6360
tcttgaagtg gtggcctaac tacggctaca ctagaagaac agtatttggt atctgcgctc   6420
tgctgaagcc agttaccttc ggaaaaagag ttggtagctc ttgatccggc aaacaaacca   6480
ccgctggtag cggttttttt gtttgcaagc agcagattac gcgcagaaaa aaaggatctc   6540
aagaagatcc tttgatcttt tctacggggt ctgacgctca gtggaacgaa aactcacgtt   6600
aagggatttt ggtcatgaga ttatcaaaaa ggatcttcac ctagatcctt ttaaattaaa   6660
aatgaagttt taaatcaatc taaagtatat atgagtaaac ttggtctgac agttaccaat   6720
gcttaatcag tgaggcacct atctcagcga tctgtctatt tcgttcatcc atagttgcct   6780
gactccccgt cgtgtagata actacgatac gggagggctt accatctggc cccagtgctg   6840
caatgatacc gcgagaccca cgctcaccgg ctccagattt atcagcaata aaccagccag   6900
ccggaagggc cgagcgcaga agtggtcctg caactttatc cgcctccatc cagtctatta   6960
attgttgccg ggaagctaga gtaagtagtt cgccagttaa tagtttgcgc aacgttgttg   7020
```

```
ccattgctac aggcatcgtg gtgtcacgct cgtcgtttgg tatggcttca ttcagctccg   7080

gttcccaacg atcaaggcga gttacatgat cccccatgtt gtgcaaaaaa gcggttagct   7140

ccttcggtcc tccgatcgtt gtcagaagta agttggccgc agtgttatca ctcatggtta   7200

tggcagcact gcataattct cttactgtca tgccatccgt aagatgcttt tctgtgactg   7260

gtgagtactc aaccaagtca ttctgagaat agtgtatgcg gcgaccgagt tgctcttgcc   7320

cggcgtcaat acgggataat accgcgccac atagcagaac tttaaaagtg ctcatcattg   7380

gaaaacgttc ttcggggcga aaactctcaa ggatcttacc gctgttgaga tccagttcga   7440

tgtaacccac tcgtgcaccc aactgatctt cagcatcttt tactttcacc agcgtttctg   7500

ggtgagcaaa aacaggaagg caaaatgccg caaaaaaggg aataagggcg acacggaaat   7560

gttgaatact catactcttc ctttttcaat attattgaag catttatcag ggttattgtc   7620

tcatgagcgg atacatattt gaatgtattt agaaaaataa acaaataggg gttccgcgca   7680

catttccccg aaaagtgcca cctgacgtc                                     7709


<210> SEQ ID NO 2
<211> LENGTH: 508
<212> TYPE: DNA
<213> ORGANISM: Cytomegalovirus

<400> SEQUENCE: 2

cgttacataa cttacggtaa atggcccgcc tggctgaccg cccaacgacc cccgcccatt     60

gacgtcaata atgacgtatg ttcccatagt aacgccaata gggactttcc attgacgtca    120

atgggtggag tatttacggt aaactgccca cttggcagta catcaagtgt atcatatgcc    180

aagtacgccc cctattgacg tcaatgacgg taaatggccc gcctggcatt atgcccagta    240

catgacctta tgggactttc ctacttggca gtacatctac gtattagtca tcgctattac    300

catggtgatg cggttttggc agtacatcaa tgggcgtgga tagcggtttg actcacgggg    360

atttccaagt ctccacccca ttgacgtcaa tgggagtttg ttttggcacc aaaatcaacg    420

ggactttcca aaatgtcgta acaactccgc cccattgacg caaatgggcg gtaggcgtgt    480

acggtgggag gtctatataa gcagagct                                       508


<210> SEQ ID NO 3
<211> LENGTH: 486
<212> TYPE: DNA
<213> ORGANISM: EMC virus

<400> SEQUENCE: 3

ggttattttc caccatattg ccgtcttttg gcaatgtgag ggcccggaaa cctggccctg     60

tcttcttgac gagcattcct aggggtcttt cccctctcgc caaaggaatg caaggtctgt    120

tgaatgtcgt gaaggaagca gttcctctgg aagcttcttg aagacaaaca acgtctgtag    180

cgaccctttg caggcagcgg aaccccccac ctggcgacag gtgcctctgc ggccaaaagc    240

cacgtgtata agatacacct gcaaaggcgg cacaacccca gtgccacgtt gtgagttgga    300

tagttgtgga aagagtcaaa tggctcacct caagcgtatt caacaagggg ctgaaggatg    360

cccagaaggt accccattgt atgggatctg atctggggcc tcggtgcaca tgctttacat    420

gtgtttagtc gaggttaaaa aacgtctagg ccccccgaac cacggggacg tggttttcct    480

ttgaaa                                                               486


<210> SEQ ID NO 4
```

<211> LENGTH: 1728
<212> TYPE: DNA
<213> ORGANISM: artificial sequence
<220> FEATURE:
<223> OTHER INFORMATION: modified GlcNAc-1 phosphotransferase

<400> SEQUENCE: 4

```
atgctgttca agctcctgca gagacagacc tatacctgcc tgtcccacag gtatgggctc     60
tacgtgtgct tcttgggcgt cgttgtcacc atcgtctccg ccttccagtt cggagaggtg    120
gttctggaat ggagccgaga tcaataccat gttttgtttg attcctatag agacaatatt    180
gctggaaagt cctttcagaa tcggctttgt ctgcccatgc cgattgacgt tgtttacacc    240
tgggtgaatg gcacagatct tgaactactg aaggaactaa cagaattaaa aagatcaaaa    300
cgtgatccat taataccaga atgtcaaggt aaacaaacac cagaaaaaga taaatgttat    360
agagatgaca tctctgccag tcgttttgaa gataacgaag aactgaggta ctcattgcga    420
tctatcgaga ggcatgcacc atgggttcgg aatattttca ttgtcaccaa cgggcagatt    480
ccatcctggc tgaaccttga caatcctcga gtgacaatag taacacacca ggatgttttt    540
cgaaatttga gccacttgcc tacctttagt tcacctgcta ttgaaagtca cattcatcgc    600
atcgaagggc tgtcccagaa gtttatttac ctaaatgatg atgtcatgtt tgggaaggat    660
gtctggccag atgattttta cagtcactcc aaaggccaga aggtttattt gacatggcct    720
gtgccaaacg gaggtagcgg aggtgataca tttgcagatt ccctcagata tgtaaataaa    780
attctaaata gcaagtttgg attcacatcg cggaaagtcc ctgctcacat gcctcacatg    840
attgaccgga ttgttatgca agaactgcaa gatatgttcc ctgaagaatt tgacaagacg    900
tcatttcaca aagtgcgcca ttctgaggat atgcagtttg ccttctctta tttttattat    960
ctcatgagtg cagtgcagcc actgaatata tctcaagtct ttgatgaagt tgatacagat   1020
caatctggtg tcttgtctga cagagaaatc cgaacactgg ctaccagaat tcacgaactg   1080
ccgttaagtt tgcaggattt gacaggtctg gaacacatgc taataaattg ctcaaaaatg   1140
cttcctgctg atatcacgca gctaaataat attccaccaa ctcaggaatc ctactatgat   1200
cccaacctgc caccggtcac taaaagtcta gtaacaaact gtaaaccagt aactgacaaa   1260
atccacaaag catataagga caaaaacaaa tataggtttg aaatcatggg agaagaagaa   1320
atcgctttta aaatgattcg taccaacgtt tctcatgtgg ttggccagtt ggatgacata   1380
agaaaaaacc ctaggaagtt tgtttgcctg aatgacaaca ttgaccacaa tcataaagat   1440
gctcagacag tgaaggctgt tctcagggac ttctatgaat ccatgttccc catacccttcc  1500
caatttgaac tgccaagaga gtatcgaaac cgtttccttc atatgcatga gctgcaggaa   1560
tggagggctt atcgagacaa attgaagttt tggacccatt gtgtactagc aacattgatt   1620
atgtttacta tattctcatt ttttgctgag cagttaattg cacttaagcg gaagatattt   1680
cccagaagga ggatacacaa agaagctagt cccaatcgaa tcagagta                1728
```

<210> SEQ ID NO 5
<211> LENGTH: 1611
<212> TYPE: DNA
<213> ORGANISM: Homo sapiens

<400> SEQUENCE: 5

```
atggagtttt caagtccttc cagagaggaa tgtcccaagc ctttgagtag ggtaagcatc     60
atggctggca gcctcacagg attgcttcta cttcaggcag tgtcgtgggc atcaggtgcc    120
cgcccctgca tccctaaaag cttcggctac agctcggtgg tgtgtgtctg caatgccaca    180
```

```
tactgtgact cctttgaccc cccgaccttt cctgcccttg gtaccttcag ccgctatgag    240
agtacacgca gtgggcgacg gatggagctg agtatggggc ccatccaggc taatcacacg    300
ggcacaggcc tgctactgac cctgcagcca gaacagaagt tccagaaagt gaagggattt    360
ggaggggcca tgacagatgc tgctgctctc aacatccttg ccctgtcacc ccctgcccaa    420
aatttgctac ttaaatcgta cttctctgaa gaaggaatcg gatataacat catccgggta    480
cccatggcca gctgtgactt ctccatccgc acctacacct atgcagacac ccctgatgat    540
ttccagttgc acaacttcag cctcccagag gaagatacca agctcaagat acccctgatt    600
caccgagccc tgcagttggc ccagcgtccc gtttcactcc ttgccagccc ctggacatca    660
cccacttggc tcaagaccaa tggagcggtg aatgggaagg ggtcactcaa gggacagccc    720
ggagacatct accaccagac ctgggccaga tactttgtga agttcctgga tgcctatgct    780
gagcacaagt tacagttctg ggcagtgaca gctgaaaatg agccttctgc tgggctgttg    840
agtggatacc ccttccagtg cctgggcttc acccctgaac atcagcgaga cttcattgcc    900
cgtgacctag gtcctaccct cgccaacagt actcaccaca atgtccgcct actcatgctg    960
gatgaccaac gcttgctgct gccccactgg gcaaaggtgg tactgacaga cccagaagca   1020
gctaaatatg ttcatggcat tgctgtacat tggtacctgg actttctggc tccagccaaa   1080
gccaccctag gggagacaca ccgcctgttc cccaacacca tgctctttgc ctcagaggcc   1140
tgtgtgggct ccaagttctg ggagcagagt gtgcggctag gctcctggga tcgagggatg   1200
cagtacagcc acagcatcat cacgaacctc ctgtaccatg tggtcggctg gaccgactgg   1260
aaccttgccc tgaaccccga aggaggaccc aattgggtgc gtaactttgt cgacagtccc   1320
atcattgtag acatcaccaa ggacacgttt tacaaacagc ccatgttcta ccaccttggc   1380
cacttcagca agttcattcc tgagggctcc cagagagtgg ggctggttgc cagtcagaag   1440
aacgacctgg acgcagtggc actgatgcat cccgatggct ctgctgttgt ggtcgtgcta   1500
aaccgctcct ctaaggatgt gcctcttacc atcaaggatc ctgctgtggg cttcctggag   1560
acaatctcac ctggctactc cattcacacc tacctgtggc gtcgccagtg a             1611
```

```
<210> SEQ ID NO 6
<211> LENGTH: 2052
<212> TYPE: DNA
<213> ORGANISM: Mus musculus
<220> FEATURE:
<221> NAME/KEY: misc_feature
<222> LOCATION: (922)..(922)
<223> OTHER INFORMATION: n is a, c, g, or t
<220> FEATURE:
<221> NAME/KEY: misc_feature
<222> LOCATION: (930)..(930)
<223> OTHER INFORMATION: n is a, c, g, or t

<400> SEQUENCE: 6

atggctaaca gccaacctaa ggcttcccag caacgccaag caaaagtcat gaccgccgcc     60
gcgggctcgg cgagccgtgt tgcggtgccc ttattgttgt gtgcgctgct agtgcccggt    120
ggcgcctacg tgctggacga ctctgacggc ctgggcagag agttcgacgg catcggcgct    180
gtgtctggcg gcggagccac aagcagactg ctggtcaact accccgagcc ctacagaagc    240
gagatcctgg actacctgtt caagcccaac ttcggcgcca gcctgcacat cctgaaggtg    300
gaaatcggcg gcgacggcca gaccaccgac ggcacagagc ccagccacat gcactacgag    360
ctggatgaga actacttcag aggctacgag tggtggctga tgaaggaagc caagaagaga    420
```

-continued aaccccgaca tcatcctgat gggcctgcct tggagcttcc ccggctggct gggcaagggc 480
ttcagctggc cctacgtgaa cctgcagctg accgcctact acgtcgtgcg gtggattctg 540
ggcgccaagc actaccacga cctggacatc gactacatcg gcatctggaa cgagaggccc 600
ttcgacgcca actacatcaa agaactgagg aagatgctgg attaccaggg cctgcagaga 660
gtgcggatca ttgccagcga caacctgtgg gagcccatca gcagctccct gctgctggac 720
caggacctgt ggaaggtcgt cgacgtgatc ggcgcccact accctggcac ctacaccgtg 780
tggaacgcca agatgagcgg caagaagctg tggtccagcg aggacttcag caccatcaac 840
agcaacgtgg gagccggctg ctggtccaga atcctgaacc agaattacat caacggcaac 900
atgaccagca caatcgcctg gnaacctggn ggccagctac tacgaggact gccctacggc 960
agatccggcc tgatgaccgc ccaggaacct tggagcggcc actacgtggt ggcttcccca 1020
atctgggtgt ccgcccacac cacccagttc acccagcctg gctggtacta cctgaaaacc 1080
gtgggccacc tggaaaaggg cggcagctac gtggccctga ccgatggcct gggcaacctg 1140
accatcatca tcgagacaat gagccaccag cacagcatgt gcatcagacc ctacctgccc 1200
tactacaacg tgtcccacca gctggccaca ttcaccctga agggcagcct gagagagatc 1260
caggaactgc aggtctggta caccaagctg ggcacccccc agcagagact gcacttcaag 1320
cagctggaca ccctgtggct gctggacggc agcggcagct tcaccctgga actggaagag 1380
gacgaaatct tcaccctgac cacactgacc accggcagaa agggcagcta ccccccacct 1440
cctagcagca agccattccc caccaactac aaggacgact tcaacgtgga atacccccctg 1500 ttcagcgagg cccccaactt cgccgaccag accggcgtgt tcgagtacta catgaacaac 1560
gaggacagag agcacaggtt caccctgaga caggtgctga accagaggcc catcacctgg 1620
gctgccgacg ccagcagcac catctccgtg atcggggacc accactggac caacatgacc 1680
gtgcagtgcg acgtgtacat cgagacacct agaagcggcg gagtgtttat cgccggcaga 1740
gtgaacaagg gcggcatcct gatcagatcc gctacaggcg tgttcttctg gatcttcgcc 1800
aacggcagct acagagtgac cgccgacctg ggcggctgga tcacatacgc ctctggccac 1860
gccgacgtga ccgccaagag atggtacacc ctgaccctgg gcatcaaggg ctacttcgcc 1920
ttcggcatgc tgaacggcac catcctgtgg aagaacgtgc gcgtgaagta ccccggccac 1980
ggctgggctg ccatcggcac ccacacattc gagttcgccc agttcgacaa ctttcgcgtg 2040
gaagctgctc gc 2052

<210> SEQ ID NO 7
<211> LENGTH: 1290
<212> TYPE: DNA
<213> ORGANISM: Homo sapien

<400> SEQUENCE: 7
atgcagctga ggaacccaga actacatctg ggctgcgcgc ttgcgcttcg cttcctggcc 60
ctcgtttcct gggacatccc tggggctaga gcactggaca atggattggc aaggacgcct 120
accatgggct ggctgcactg ggagcgcttc atgtgcaacc ttgactgcca ggaagagcca 180
gattcctgca tcagtgagaa gctcttcatg gagatggcag agctcatggt ctcagaaggc 240
tggaaggatg caggttatga gtacctctgc attgatgact gttggatggc tccccaaaga 300
gattcagaag gcagacttca ggcagaccct cagcgctttc ctcatgggat tcgccagcta 360
gctaattatg ttcacagcaa aggactgaag ctagggattt atgcagatgt tggaaataaa 420
acctgcgcag gcttccctgg gagttttgga tactacgaca ttgatgccca gacctttgct 480

```
gactggggag tagatctgct aaaatttgat ggttgttact gtgacagttt ggaaaatttg    540
gcagatggtt ataagcacat gtccttggcc ctgaatagga ctggcagaag cattgtgtac    600
tcctgtgagt ggcctcttta tatgtggccc tttcaaaagc ccaattatac agaaatccga    660
cagtactgca atcactggcg aaattttgct gacattgatg attcctggaa aagtataaag    720
agtatcttgg actggacatc ttttaaccag gagagaattg ttgatgttgc tggaccaggg    780
ggttggaatg acccagatat gttagtgatt ggcaactttg gcctcagctg gaatcagcaa    840
gtaactcaga tggccctctg ggctatcatg gctgctcctt tattcatgtc taatgacctc    900
cgacacatca gccctcaagc caaagctctc cttcaggata aggacgtaat tgccatcaat    960
caggacccct tgggcaagca agggtaccag cttagacagg gagacaactt tgaagtgtgg   1020
gaacgacctc tctcaggctt agcctgggct gtagctatga taaaccggca ggagattggt   1080
ggacctcgct cttataccat cgcagttgct tccctgggta aaggagtggc ctgtaatcct   1140
gcctgcttca tcacacagct cctccctgtg aaaaggaagc tagggttcta tgaatggact   1200
tcaaggttaa gaagtcacat aaatcccaca ggcactgttt tgcttcagct agaaaataca   1260
atgcagatgt cattaaaaga cttactttaa                                    1290
```

<210> SEQ ID NO 8
<211> LENGTH: 2232
<212> TYPE: DNA
<213> ORGANISM: Homo sapiens

<400> SEQUENCE: 8

```
atggaggcgg tggcggtggc cgcggcggtg ggggtccttc tcctggccgg ggccgggggc     60
gcggcaggcg acgaggcccg ggaggcggcg gccgtgcggg cgctcgtggc ccggctgctg    120
gggccaggcc ccgcggccga cttctccgtg tcggtggagc gcgctctggc tgccaagccg    180
ggcttggaca cctacagcct gggcggcggc ggcgcggcgc gcgtgcgggt gcgcggctcc    240
acgggcgtgg cggccgccgc ggggctgcac cgctacctgc gcgacttctg tggctgccac    300
gtggcctggt ccggctctca gctgcgcctg ccgcggccac tgccagccgt gccgggggag    360
ctgaccgagg ccacgcccaa caggtaccgc tattaccaga atgtgtgcac gcaaagctac    420
tctttcgtgt ggtgggactg ggcccgctgg gagcgagaga tagactggat ggcgctgaat    480
ggcatcaacc tggcactggc ctggagcggc caggaggcca tctggcagcg ggtgtacctg    540
gccttgggcc tgacccaggc agagatcaat gagttcttta ctggtcctgc cttcctggcc    600
tgggggcgaa tgggcaacct gcacacctgg gatggccccc tgccccctc ctggcacatc     660
aagcagcttt acctgcagca ccgggtcctg gaccagatgc gctccttcgg catgacccca    720
gtgctgcctg cattcgcggg gcatgttccc gaggctgtca ccagggtgtt ccctcaggtc    780
aatgtcacga agatgggcag ttggggccac tttaactgtt cctactcctg ctccttcctt    840
ctggctccgg aagaccccat attccccatc atcgggagcc tcttcctgcg agagctgatc    900
aaagagtttg gcacagacca catctatggg gccgacactt tcaatgagat gcagccacct    960
tcctcagagc cctcctacct tgccgcagcc accactgccg tctatgaggc catgactgca   1020
gtggatactg aggctgtgtg gctgctccaa ggctggctct tccagcacca gccgcagttc   1080
tgggggcccg cccagatcag ggctgtgctg ggagctgtgc cccgtggccg cctcctggtt   1140
ctggacctgt ttgctgagag ccagcctgtg tatacccgca ctgcctcctt ccagggccag   1200
cccttcatct ggtgcatgct gcacaacttt gggggaaacc atggtctttt tggagcccta   1260
```

```
gaggctgtga acggaggccc agaagctgcc cgcctcttcc ccaactccac catggtaggc   1320

acgggcatgg cccccgaggg catcagccag aacgaagtgg tctattccct catggctgag   1380

ctgggctggc gaaaggaccc agtgccagat ttggcagcct gggtgaccag ctttgccgcc   1440

cggcggtatg ggtctcccca cccggacgca ggggcagcgt ggaggctact gctccggagt   1500

gtgtacaact gctccgggga ggcctgcagg ggccacaatc gtagcccgct ggtcaggcgg   1560

ccgtccctac agatgaatac cagcatctgg tacaaccgat ctgatgtgtt tgaggcctgg   1620

cggctgctgc tcacatctgc tccctccctg gccaccagcc ccgccttccg ctacgacctg   1680

ctggacctca ctcggcaggc agtgcaggag ctggtcagct tgtactatga ggaggcaaga   1740

agcgcctacc tgagcaagga gctggcctcc ctgttgaggg ctggaggcgt cctggcctat   1800

gagctgctgc cggcactgga cgaggtgctg gctagtgaca gccgcttctt gctgggcagc   1860

tggctagagc aggcccgagc agcggcagtc agtgaggccg aggccgattt ctacgagcag   1920

aacagccgct accagctgac cttgtggggg ccagaaggca acatcctgga ctatgccaac   1980

aagcagctgg cggggttggt ggccaactac tacacccctc gctggcggct tttcctggag   2040

gcgctggttg acagtgtggc ccagggcatc cctttccaac agcaccagtt tgacaaaaat   2100

gtcttccaac tggagcaggc cttcgttctc agcaagcaga ggtaccccag ccagccgcga   2160

ggagacactg tggacctggc caagaagatc ttcctcaaat attacccccg ctgggtggcc   2220

ggctcttggt ga                                                       2232
```

<210> SEQ ID NO 9
<211> LENGTH: 2860
<212> TYPE: DNA
<213> ORGANISM: Homo sapiens

<400> SEQUENCE: 9

```
atgggagtga ggcacccgcc ctgctcccac cggctcctgg ccgtctgcgc cctcgtgtcc     60

ttggcaaccg ctgcactcct ggggcacatc ctactccatg atttcctgct ggttccccga    120

gagctgagtg gctcctcccc agtcctggag gagactcacc cagctcacca gcagggagcc    180

agcagaccag ggccccggga tgcccaggca caccccggcc gtcccagagc agtgcccaca    240

cagtgcgacg tcccccccaa cagccgcttc gattgcgccc ctgacaaggc catcacccag    300

gaacagtgcg aggcccgcgg ctgttgctac atccctgcaa agcaggggct gcagggagcc    360

cagatggggc agccctggtg cttcttccca cccagctacc ccagctacaa gctggagaac    420

ctgagctcct ctgaaatggg ctacacggcc accctgaccc gtaccacccc caccttcttc    480

cccaaggaca tcctgaccct gcggctggac gtgatgatgg agactgagaa ccgcctccac    540

ttcacgatca aagatccagc taacaggcgc tacgaggtgc ccttggagac cccgcatgtc    600

cacagccggg caccgtcccc actctacagc gtggagttct ccgaggagcc cttcggggtg    660

atcgtgcgcc ggcagctgga cggccgcgtg ctgctgaaca cgacggtggc gcccctgttc    720

tttgcggacc agttccttca gctgtccacc tcgctgccct cgcagtatat cacaggcctc    780

gccgagcacc tcagtcccct gatgctcagc accagctgga ccaggatcac cctgtggaac    840

cgggaccttg cgcccacgcc cggtgcgaac ctctacgggt ctcacccttt ctacctggcg    900

ctggaggacg gcgggtcggc acacggggtg ttcctgctaa acagcaatgc catggatgtg    960

gtcctgcagc cgagccctgc ccttagctgg aggtcgacag gtgggatcct ggatgtctac   1020

atcttcctgg gcccagagcc caagagcgtg gtgcagcagt acctggacgt tgtgggatac   1080

ccgttcatgc cgccatactg ggccctgggc ttccacctgt gccgctgggg ctactcctcc   1140
```

```
accgctatca cccgccaggt ggtggagaac atgaccaggg cccacttccc cctggacgtc   1200

cagtggaacg acctggacta catggactcc cggagggact tcacgttcaa caaggatggc   1260

ttccgggact tcccggccat ggtgcaggag ctgcaccagg gcggccggcg ctacatgatg   1320

atcgtggatc ctgccatcag cagctcgggc cctgccggga gctacaggcc ctacgacgag   1380

ggtctgcgga gggggtttt catcaccaac gagaccggcc agccgctgat tgggaaggta    1440

tggcccgggt ccactgcctt ccccgacttc accaacccca cagccctggc ctggtgggag   1500

gacatggtgg ctgagttcca tgaccaggtg cccttcgacg gcatgtggat tgacatgaac   1560

gagccttcca acttcatcag gggctctgag gacggctgcc ccaacaatga gctggagaac   1620

ccaccctacg tgcctggggt ggttgggggg accctccagg cggccaccat ctgtgcctcc   1680

agccaccagt ttctctccac acactacaac ctgcacaacc tctacggcct gaccgaagcc   1740

atcgcctccc acagggcgct ggtgaaggct cgggggacac gcccatttgt gatctcccgc   1800

tcgacctttg ctggccacgg ccgatacgcc ggccactgga cgggggacgt gtggagctcc   1860

tgggagcagc tcgcctcctc cgtgccagaa atcctgcagt ttaacctgct gggggtgcct   1920

ctggtcgggg ccgacgtctg cggcttcctg ggcaacacct cagaggagct gtgtgtgcgc   1980

tggacccagc tgggggcctt ctacccottc atgcggaacc acaacagcct gctcagtctg   2040

ccccaggagc cgtacagctt cagcgagccg gcccagcagg ccatgaggaa ggccctcacc   2100

ctgcgctacg cactcctccc ccacctctac acactgttcc accaggccca cgtcgcgggg   2160

gagaccgtgg cccggcccct cttcctggag ttccccaagg actctagcac ctggactgtg   2220

gaccaccagc tcctgtgggg ggaggccctg ctcatcaccc cagtgctcca ggccgggaag   2280

gccgaagtga ctggctactt ccccttgggc acatggtacg acctgcagac ggtgccagta   2340

gaggcccttg gcagcctccc acccccacct gcagctcccc gtgagccagc catccacagc   2400

gaggggcagt gggtgacgct gccggccccc ctggacacca tcaacgtcca cctccgggct   2460

gggtacatca tcccctgca gggccctggc ctcacaacca cagagtcccg ccagcagccc    2520

atggccctgg ctgtggccct gaccaagggt ggggaggccc gaggggagct gttctgggac   2580

gatggagaga gcctggaagt gctggagcga ggggcctaca cacaggtcat cttcctggcc   2640

aggaataaca cgatcgtgaa tgagctggta cgtgtgacca gtgagggagc tggcctgcag   2700

ctgcagaagg tgactgtcct gggcgtggcc acggcgcccc agcaggtcct ctccaacggt   2760

gtccctgtct ccaacttcac ctacagcccc gacaccaagg tcctggacat ctgtgtctcg   2820

ctgttgatgg gagagcagtt tctcgtcagc tggtgttags                          2860
```

<210> SEQ ID NO 10
<211> LENGTH: 3033
<212> TYPE: DNA
<213> ORGANISM: Homo sapiens

<400> SEQUENCE: 10

```
atgggcgcct acgcgcgggc ttcgggggtc tgcgctcgcg gctgcctgga ctcagcaggc     60

ccctggacca tgtcccgcgc cctgcggcca ccgctcccgc ctctctgctt tttccttttg    120

ttgctggcgg ctgccggtgc tcgggccggg ggatacgaga catgccccac agtgcagccg    180

aacatgctga acgtgcacct gctgcctcac acacatgatg acgtgggctg gctcaaaacc    240

gtggaccagt acttttatgg aatcaagaat gacatccagc acgccggtgt gcagtacatc    300

ctggactcgg tcatctctgc cttgctggca gatcccaccc gtcgcttcat ttacgtggag    360
```

```
attgccttct tctcccgttg gtggcaccag cagacaaatg ccacacagga agtcgtgcga    420
gaccttgtgc gccaggggcg cctggagttc gccaatggtg gctgggtgat gaacgatgag    480
gcagccaccc actacggtgc catcgtggac cagatgacac ttgggctgcg ctttctggag    540
gacacatttg gcaatgatgg gcgaccccgt gtggcctggc acattgaccc cttcggccac    600
tctcgggagc aggcctcgct gtttgcgcag atgggcttcg acggcttctt ctttgggcgc    660
cttgattatc aagataagtg ggtacggatg cagaagctgg agatggagca ggtgtggcgg    720
gccagcacca gcctgaagcc cccgaccgcg gacctcttca ctggtgtgct tcccaatggt    780
tacaacccgc caaggaatct gtgctgggat gtgctgtgtg tcgatcagcc gctggtggag    840
gaccctcgca gccccgagta caacgccaag gagctggtcg attacttcct aaatgtggcc    900
actgcccagg gccggtatta ccgcaccaac cacactgtga tgaccatggg ctcggacttc    960
caatatgaga atgccaacat gtggttcaag aaccttgaca agctcatccg gctggtaaat   1020
gcgcagcagg caaaaggaag cagtgtccat gttctctact ccaccccgc ttgttacctc   1080
tgggagctga acaaggccaa cctcacctgg tcagtgaaac atgacgactt cttcccttac   1140
gcggatggcc cccaccagtt ctggaccggt tacttttcca gtcggccggc cctcaaacgc   1200
tacgagcgcc tcagctacaa cttcctgcag gtgtgcaacc agctggaggc gctggtgggc   1260
ctggcggcca acgtgggacc ctatggctcc ggagacagtg cacccctcaa tgaggcgatg   1320
gctgtgctcc agcatcacga cgccgtcagc ggcacctccc gccagcacgt ggccaacgac   1380
tacgcgcgcc agcttgcggc aggctggggg ccttgcgagg ttcttctgag caacgcgctg   1440
gcgcggctca gaggcttcaa agatcacttc accttttgcc aacagctaaa catcagcatc   1500
tgcccgctca gccagacggc ggcgcgcttc caggtcatcg tttataatcc cctggggcgg   1560
aaggtgaatt ggatggtacg gctgccggtc agcgaaggcg ttttcgttgt gaaggacccc   1620
aatggcagga cagtgcccag cgatgtggta atatttccca gctcagacag ccaggcgcac   1680
cctccggagc tgctgttctc agcctcactg cccgccctgg gcttcagcac ctattcagta   1740
gcccaggtgc ctcgctggaa gccccaggcc cgcgcaccac agcccatccc cagaagatcc   1800
tggtcccctg ctttaaccat cgaaaatgag cacatccggg caacgtttga tcctgacaca   1860
gggctgttga tggagattat gaacatgaat cagcaactcc tgctgcctgt tcgccagacc   1920
ttcttctggt acaacgccag tataggtgac aacgaaagtg accaggcctc aggtgcctac   1980
atcttcagac ccaaccaaca gaaaccgctg cctgtgagcc gctgggctca gatccacctg   2040
gtgaagacac ccttggtgca ggaggtgcac cagaacttct cagcttggtg ttcccaggtg   2100
gttcgcctgt acccaggaca gcggcacctg gagctagagt ggtcggtggg gccgatacct   2160
gtgggcgaca cctgggggaa ggaggtcatc agccgttttg acacaccgct ggagacaaag   2220
ggacgcttct acacagacag caatggccgg gagatcctgg agaggaggcg ggattatcga   2280
cccacctgga aactgaacca gacggagccc gtggcaggaa actactatcc agtcaacacc   2340
cggatttaca tcacggatgg aaacatgcag ctgactgtgc tgactgaccg ctcccagggg   2400
ggcagcagcc tgagagatgg ctcgctggag ctcatggtgc accgaaggct gctgaaggac   2460
gatggacgcg gagtatcgga gccactaatg gagaacgggt cgggggcgtg ggtgcgaggg   2520
cgccacctgg tgctgctgga cacagcccag gctgcagccg ccggacaccg gctcctggcg   2580
gagcaggagg tcctggcccc tcaggtggtg ctggccccgg gtggcggcgc cgcctacaat   2640
ctcggggctc ctccgcgcac gcagttctca gggctgcgca gggacctgcc gccctcggtg   2700
cacctgctca cgctggccag ctggggcccc gaaatggtgc tgctgcgctt ggagcaccag   2760
```

tttgccgtag gagaggattc cggacgtaac ctgagcgccc ccgttacctt gaacttgagg 2820
gacctgttct ccaccttcac catcacccgc ctgcaggaga ccacgctggt ggccaaccag 2880
ctccgcgagg cagcctccag gctcaagtgg acaacaaaca caggccccac accccaccaa 2940
actccgtacc agctggaccc ggccaacatc acgctggaac ccatggaaat ccgcactttc 3000
ctggcctcag ttcaatggaa ggaggtggat ggt 3033

<210> SEQ ID NO 11
<211> LENGTH: 32
<212> TYPE: DNA
<213> ORGANISM: artificial sequence
<220> FEATURE:
<223> OTHER INFORMATION: GBA forward primer

<400> SEQUENCE: 11
ctgctagcca ccatggagtt ttcaagtcct tc 32

<210> SEQ ID NO 12
<211> LENGTH: 31
<212> TYPE: DNA
<213> ORGANISM: artificial sequence
<220> FEATURE:
<223> OTHER INFORMATION: GBA reverse primer

<400> SEQUENCE: 12
atagcggccg ctcactggcg acgccacagg t 31

<210> SEQ ID NO 13
<211> LENGTH: 35
<212> TYPE: DNA
<213> ORGANISM: artificial sequence
<220> FEATURE:
<223> OTHER INFORMATION: GAA forward primer

<400> SEQUENCE: 13
ctgctagcca ccatgggagt gaggcacccg ccctg 35

<210> SEQ ID NO 14
<211> LENGTH: 38
<212> TYPE: DNA
<213> ORGANISM: artificial sequence
<220> FEATURE:
<223> OTHER INFORMATION: GAA reverse primer

<400> SEQUENCE: 14
atagcggccg ctcaacacca gctgacgaga aactgctc 38

<210> SEQ ID NO 15
<211> LENGTH: 35
<212> TYPE: DNA
<213> ORGANISM: artificial sequence
<220> FEATURE:
<223> OTHER INFORMATION: GALC forward primer

<400> SEQUENCE: 15
ctgctagcca ccatggctaa cagccaacct aaggc 35

<210> SEQ ID NO 16
<211> LENGTH: 39
<212> TYPE: DNA
<213> ORGANISM: artificial sequence
<220> FEATURE:
<223> OTHER INFORMATION: GALC reverse primer

<400> SEQUENCE: 16
atagcggccg ctcagcgagc agcttccacg cgaaagttg 39

<210> SEQ ID NO 17
<211> LENGTH: 34
<212> TYPE: DNA
<213> ORGANISM: artificial sequence
<220> FEATURE:
<223> OTHER INFORMATION: NAGLU forward primer

<400> SEQUENCE: 17
ctgctagcca ccatggaagc cgtggctgtc gcag 34

<210> SEQ ID NO 18
<211> LENGTH: 37
<212> TYPE: DNA
<213> ORGANISM: artificial sequence
<220> FEATURE:
<223> OTHER INFORMATION: NAGLU reverse primer

<400> SEQUENCE: 18
atagcggccg ctcaccaact accagccacc catctag 37

<210> SEQ ID NO 19
<211> LENGTH: 33
<212> TYPE: DNA
<213> ORGANISM: artificial sequence
<220> FEATURE:
<223> OTHER INFORMATION: GLA forward primer

<400> SEQUENCE: 19
ctggatccac catgcagctg aggaacccag aac 33

<210> SEQ ID NO 20
<211> LENGTH: 38
<212> TYPE: DNA
<213> ORGANISM: artificial sequence
<220> FEATURE:
<223> OTHER INFORMATION: GLA reverse primer

<400> SEQUENCE: 20
atagcggccg ctcaaagtaa gtcttttaat gacatctg 38

<210> SEQ ID NO 21
<211> LENGTH: 35
<212> TYPE: DNA
<213> ORGANISM: artificial sequence
<220> FEATURE:
<223> OTHER INFORMATION: LAMAN reverse primer

<400> SEQUENCE: 21
ctgctagcca ccatgggcgc ctacgcgcgg gcttc 35

<210> SEQ ID NO 22
<211> LENGTH: 38
<212> TYPE: DNA
<213> ORGANISM: artificial sequence
<220> FEATURE:
<223> OTHER INFORMATION: LAMAN reverse primer

<400> SEQUENCE: 22
atagcggccg ctcaaccatc cacctccttc cattgaac 38

<210> SEQ ID NO 23
<211> LENGTH: 3749

<212> TYPE: DNA
<213> ORGANISM: Homo sapiens

<400> SEQUENCE: 23

```
aaaagctatg actgcggccg cgggttcggc gggccgcgcc gcggtgccct tgctgctgtg     60
tgcgctgctg gcgcccggcg gcgcgtacgt gctcgacgac tccgacgggc tgggccggga    120
gttcgacggc atcggcgcgg tcagcggcgg cggggcaacc tcccgacttc tagtaaatta    180
cccagagccc tatcgttctc agatattgga ttatctcttt aagccgaatt ttggtgcctc    240
tttgcatatt ttaaaagtgg aaataggtgg tgatgggcag acaacagatg gcactgagcc    300
ctcccacatg cattatgcac tagatgagaa ttatttccga ggatacgagt ggtggttgat    360
gaaagaagct aagaagagga atcccaatat tacactcatt gggttgccat ggtcattccc    420
tggatggctg ggaaaaggtt tcgactggcc ttatgtcaat cttcagctga ctgcctatta    480
tgtcgtgacc tggattgtgg gcgccaagcg ttaccatgat ttggacattg attatattgg    540
aatttggaat gagaggtcat ataatgccaa ttatattaag atattaagaa aaatgctgaa    600
ttatcaaggt ctccagcgag tgaaaatcat agcaagtgat aatctctggg agtccatctc    660
tgcatccatg ctccttgatg ccgaactctt caaggtggtt gatgttatag ggctcatta     720
tcctggaacc cattcagcaa aagatgcaaa gttgactggg aagaagcttt ggtcttctga    780
agactttagc actttaaata gtgacatggg tgcaggctgc tggggtcgca ttttaaatca    840
gaattatatc aatggctata tgacttccac aatcgcatgg aatttagtgg ctagttacta    900
tgaacagttg ccttatggga gatgcgggtt gatgacggcc caggagccat ggagtgggca    960
ctacgtggta gaatctcctg tctgggtatc agctcatacc actcagttta ctcaacctgg   1020
ctggtattac ctgaagacag ttggccattt agagaaagga ggaagctacg tagctctgac   1080
tgatggctta gggaacctca ccatcatcat tgaaaccatg agtcataaac attctaagtg   1140
catacggcca tttcttcctt atttcaatgt gtcacaacaa tttgccacct ttgttcttaa   1200
gggatctttt agtgaaatac cagagctaca ggtatggtat accaaacttg gaaaaacatc   1260
cgaaagattt ctttttaagc agctggattc tctatggctc cttgacagcg atggcagttt   1320
cacactgagc ctgcatgaag atgagctgtt cacactcacc actctcacca ctggtcgcaa   1380
aggcagctac ccgcttcctc caaaatccca gcccttccca agtacctata aggatgattt   1440
caatgttgat tacccatttt ttagtgaagc tccaaacttt gctgatcaaa ctggtgtatt   1500
tgaatatttt acaaatattg aagaccctgg cgagcatcac ttcacgctac gccaagttct   1560
caaccagaga cccattacgt gggctgccga tgcatccaac acaatcagta ttataggaga   1620
ctacaactgg accaatctga ctacaaagtg tgatgtttac atagagaccc ctgacacagg   1680
aggtgtgttc attgcaggaa gagtaaataa aggtggtatt ttgattagaa gtgccagagg   1740
aattttcttc tggatttttg caaatggatc ttacagggtt acaggtgatt tagctggatg   1800
gattatatat gctttaggac gtgttgaagt tacagcaaaa aaatggtata cactcacgtt   1860
aactattaag ggtcatttcg cctctggcat gctgaatgac aagtctctgt ggacagacat   1920
ccctgtgaat tttccaaaga atggctgggc tgcaattgga actcactcct ttgaatttgc   1980
acagtttgac aactttcttg tggaagccac acgctaatac ttaacagggc atcatagaat   2040
actctggatt ttcttccctt ctttttggtt ttggttcaga gccaattctt gtttcattgg   2100
aacagtatat gaggcttttg agactaaaaa taatgaagag taaaagggga gagaaattta   2160
tttttaattt accctgtgga agattttatt agaattaatt ccaaggggaa aactggtgaa   2220
```

```
tctttaacat tacctggtgt gttccctaac attcaaactg tgcattggcc atacccttag   2280
gagtggtttg agtagtacag acctcgaagc cttgctgcta acactgaggt agctctcttc   2340
atcttatttg caagcggtcc tgtagatggc agtaacttga tcatcactga gatgtattta   2400
tgcatgctga ccgtgtgtcc aagtgagcca gtgtcttcat cacaagatga tgctgccata   2460
atagaaagct gaagaacact agaagtagct ttttgaaaac cacttcaacc tgttatgctt   2520
tatgctctaa aaagtatttt ttttattttc ctttttaaga tgatactttt gaaatgcagg   2580
atatgatgag tgggatgatt ttaaaaatgc ctctttaata aactacctct aacactattt   2640
ctgtggtaat agatattagc agattaattg ggttatttgc attatttaat ttttttgatt   2700
ccaagttttg gtcttgtaac cactataact ctctgtgaac atttttccag gtggctggaa   2760
gaaggaagaa aacctgatat agccaatgct gttgtagtcg tttcctcagc ctcatctcac   2820
tgtgctgtgg tctgtcctca catgtgcact ggtaacagac tcacacagct gatgaatgct   2880
tttctctcct tatgtgtgga aggaggggag cacttagaca tttgctaact cccagaattg   2940
gatcatctcc taagatgtac ttacttttta aagtccaaat atgtttatat ttaaatatac   3000
gtgagcatgt tcatcatgtt gtatgattta tactaagcat taatgtggct ctatgtagca   3060
aatcagttat tcatgtaggt aaagtaaatc tagaattatt tataagaatt actcattgaa   3120
ctaattctac tatttaggaa tttgtaagag tctaacatag gcttagctac agtgaagttt   3180
tgcattgctt ttgaagacaa gaagataagt gctagaataa ataagattac agagaaaatt   3240
ttttgttaaa accaagtgat ttccagctga tgtatctaat attttttaaa acgaacatta   3300
tagaggtgta atttatttac aataaaatgt tcctacttta aatatacaat tcagtgagtt   3360
ttgataaatt gatataccca tgtaaccaac actccagtca agcttcagaa tatttccatc   3420
accccagaag gttctcttgt atacctgctc agtcagttcc tttcactccc gattgttggc   3480
agccattgat aggaattcta tcactatagg ttagttttct ttgttccaga acatcatgaa   3540
agcggcgtca tgtactgtgt attcttatga atggtttctt tccatcagca taatgatttg   3600
agatttgtcc atgttgtgtg attcagtggt ttgttccttc ttatttctga agagttttcc   3660
attgtatgaa tataccacaa tttgtttcct ccccaccagt ttctgatact acaattaaaa   3720
ctgtctacat ttacaaaaaa aaaaaaaaa                                   3749
```

<210> SEQ ID NO 24
<211> LENGTH: 1248
<212> TYPE: DNA
<213> ORGANISM: Homo sapiens

<400> SEQUENCE: 24

```
atgactgggg agcgacccag cacggcgctc ccggacagac gctgggggcc gcggattctg     60
ggcttctggg gaggctgtag ggtttgggtg tttgccgcga tcttcctgct gctgtctctg    120
gcagcctcct ggtccaaggc tgagaacgac ttcggtctgg tgcagccgct ggtgaccatg    180
gagcaactgc tgtgggtgag cgggagacag atcggctcag tggacacctt ccgcatcccg    240
ctcatcacag ccactccgcg gggcactctt ctcgcctttg ctgaggcgag gaaaatgtcc    300
tcatccgatg agggggccaa gttcatcgcc ctgcggaggt ccatggacca gggcagcaca    360
tggtctccta cagcgttcat tgtcaatgat ggggatgtcc ccgatgggct gaaccttggg    420
gcagtagtga gcgatgttga gacaggagta gtatttcttt tctactccct ttgtgctcac    480
aaggccggct gccaggtggc ctctaccatg ttggtatgga gcaaggatga tggtgtttcc    540
tggagcacac cccggaatct ctccctggat attggcactg aagtgtttgc ccctggaccg    600
```

```
ggctctggta ttcagaaaca gcgggagcca cggaagggcc gcctcatcgt gtgtggccat    660

gggacgctgg agcgggacgg agtcttctgt ctcctcagcg atgatcatgg tgcctcctgg    720

cgctacggaa gtggggtcag cggcatcccc tacggtcagc ccaagcagga aaatgatttc    780

aatcctgatg aatgccagcc ctatgagctc ccagatggct cagtcgtcat caatgcccga    840

aaccagaaca actaccactg ccactgccga attgtcctcc gcagctatga tgcctgtgat    900

acactaaggc cccgtgatgt gaccttcgac cctgagctcg tggaccctgt ggtagctgca    960

ggagctgtag tcaccagctc cggcattgtc ttcttctcca acccagcaca tccagagttc   1020

cgagtgaacc tgaccctgcg atggagcttc agcaatggta cctcatggcg gaaagagaca   1080

gtccagctat ggccaggccc cagtggctat tcatccctgg caaccctgga gggcagcatg   1140

gatggagagg agcaggcccc ccagctctac gtcctgtatg agaaaggccg gaaccactac   1200

acagagagca tctccgtggc caaaatcagt gtctatggga cactctga                1248
```

<210> SEQ ID NO 25
<211> LENGTH: 415
<212> TYPE: PRT
<213> ORGANISM: Homo sapiens

<400> SEQUENCE: 25

```
Met Thr Gly Glu Arg Pro Ser Thr Ala Leu Pro Asp Arg Arg Trp Gly
1               5                   10                  15

Pro Arg Ile Leu Gly Phe Trp Gly Gly Cys Arg Val Trp Val Phe Ala
            20                  25                  30

Ala Ile Phe Leu Leu Leu Ser Leu Ala Ala Ser Trp Ser Lys Ala Glu
        35                  40                  45

Asn Asp Phe Gly Leu Val Gln Pro Leu Val Thr Met Glu Gln Leu Leu
    50                  55                  60

Trp Val Ser Gly Arg Gln Ile Gly Ser Val Asp Thr Phe Arg Ile Pro
65                  70                  75                  80

Leu Ile Thr Ala Thr Pro Arg Gly Thr Leu Leu Ala Phe Ala Glu Ala
                85                  90                  95

Arg Lys Met Ser Ser Ser Asp Glu Gly Ala Lys Phe Ile Ala Leu Arg
            100                 105                 110

Arg Ser Met Asp Gln Gly Ser Thr Trp Ser Pro Thr Ala Phe Ile Val
        115                 120                 125

Asn Asp Gly Asp Val Pro Asp Gly Leu Asn Leu Gly Ala Val Val Ser
    130                 135                 140

Asp Val Glu Thr Gly Val Val Phe Leu Phe Tyr Ser Leu Cys Ala His
145                 150                 155                 160

Lys Ala Gly Cys Gln Val Ala Ser Thr Met Leu Val Trp Ser Lys Asp
                165                 170                 175

Asp Gly Val Ser Trp Ser Thr Pro Arg Asn Leu Ser Leu Asp Ile Gly
            180                 185                 190

Thr Glu Val Phe Ala Pro Gly Pro Gly Ser Gly Ile Gln Lys Gln Arg
        195                 200                 205

Glu Pro Arg Lys Gly Arg Leu Ile Val Cys Gly His Gly Thr Leu Glu
    210                 215                 220

Arg Asp Gly Val Phe Cys Leu Leu Ser Asp Asp His Gly Ala Ser Trp
225                 230                 235                 240

Arg Tyr Gly Ser Gly Val Ser Gly Ile Pro Tyr Gly Gln Pro Lys Gln
                245                 250                 255
```

```
Glu Asn Asp Phe Asn Pro Asp Glu Cys Gln Pro Tyr Glu Leu Pro Asp
            260                 265                 270

Gly Ser Val Val Ile Asn Ala Arg Asn Gln Asn Asn Tyr His Cys His
        275                 280                 285

Cys Arg Ile Val Leu Arg Ser Tyr Asp Ala Cys Asp Thr Leu Arg Pro
    290                 295                 300

Arg Asp Val Thr Phe Asp Pro Glu Leu Val Asp Pro Val Val Ala Ala
305                 310                 315                 320

Gly Ala Val Val Thr Ser Ser Gly Ile Val Phe Phe Ser Asn Pro Ala
                325                 330                 335

His Pro Glu Phe Arg Val Asn Leu Thr Leu Arg Trp Ser Phe Ser Asn
            340                 345                 350

Gly Thr Ser Trp Arg Lys Glu Thr Val Gln Leu Trp Pro Gly Pro Ser
        355                 360                 365

Gly Tyr Ser Ser Leu Ala Thr Leu Glu Gly Ser Met Asp Gly Glu Glu
    370                 375                 380

Gln Ala Pro Gln Leu Tyr Val Leu Tyr Glu Lys Gly Arg Asn His Tyr
385                 390                 395                 400

Thr Glu Ser Ile Ser Val Ala Lys Ile Ser Val Tyr Gly Thr Leu
                405                 410                 415


<210> SEQ ID NO 26
<211> LENGTH: 1497
<212> TYPE: DNA
<213> ORGANISM: Homo sapiens

<400> SEQUENCE: 26

atgacttcca gtccccgggc gcctcctgga gagcaaggac gcgggggagc agagatgatc      60

cgagccgcgc cgccgccgct gttcctgctg ctgctgctgc tgctgctgct agtgtcctgg     120

gcgtcccgag gcgaggcagc ccccgaccag gacgagatcc agcgcctccc cgggctggcc     180

aagcagccgt ctttccgcca gtactccggc tacctcaaag gctccggctc caagcacctc     240

cactactggt ttgtggagtc ccagaaggat cccgagaaca gccctgtggt gctttggctc     300

aatgggggtc ccggctgcag ctcactagat gggctcctca cagagcatgg ccccttcctg     360

gtccagccag atggtgtcac cctggagtac aacccctatt cttggaatct gattgccaat     420

gtgttatacc tggagtcccc agctggggtg ggcttctcct actccgatga caagttttat     480

gcaactaatg acactgaggt cgcccagagc aattttgagg cccttcaaga tttcttccgc     540

ctctttccgg agtacaagaa caacaaactt ttcctgaccg gggagagcta tgctggcatc     600

tacatcccca ccctggccgt gctggtcatg caggatccca gcatgaacct tcaggggctg     660

gctgtgggca atggactctc ctcctatgag cagaatgaca actccctggt ctactttgcc     720

tactaccatg gccttctggg gaacaggctt tggtcttctc tccagaccca ctgctgctct     780

caaaacaagt gtaacttcta tgacaacaaa gacctggaat gcgtgaccaa tcttcaggaa     840

gtggcccgca tcgtgggcaa ctctggcctc aacatctaca atctctatgc cccgtgtgct     900

ggaggggtgc ccagccattt taggtatgag aaggacactg ttgtggtcca ggatttgggc     960

aacatcttca ctcgcctgcc actcaagcgg atgtggcatc aggcactgct gcgctcaggg    1020

gataaagtgc gcatggaccc cccctgcacc aacacaacag ctgcttccac ctacctcaac    1080

aacccgtacg tgcggaaggc cctcaacatc ccggagcagc tgccacaatg ggacatgtgc    1140

aactttctgg taaacttaca gtaccgccgt ctctaccgaa gcatgaactc ccagtatctg    1200

aagctgctta gctcacagaa ataccagatc ctattatata atggagatgt agacatggcc    1260
```

tgcaatttca tgggggatga gtggtttgtg gattccctca accagaagat ggaggtgcag 1320
cgccggccct ggttagtgaa gtacggggac agcggggagc agattgccgg cttcgtgaag 1380
gagttctccc acatcgcctt tctcacgatc aagggcgccg gccacatggt tcccaccgac 1440
aagcccctcg ctgccttcac catgttctcc cgcttcctga acaagcagcc atactga 1497

<210> SEQ ID NO 27
<211> LENGTH: 480
<212> TYPE: PRT
<213> ORGANISM: Homo sapiens

<400> SEQUENCE: 27

Met Ile Arg Ala Ala Pro Pro Pro Leu Phe Leu Leu Leu Leu Leu Leu
1 5 10 15

Leu Leu Leu Val Ser Trp Ala Ser Arg Gly Glu Ala Ala Pro Asp Gln
20 25 30

Asp Glu Ile Gln Arg Leu Pro Gly Leu Ala Lys Gln Pro Ser Phe Arg
35 40 45

Gln Tyr Ser Gly Tyr Leu Lys Gly Ser Gly Ser Lys His Leu His Tyr
50 55 60

Trp Phe Val Glu Ser Gln Lys Asp Pro Glu Asn Ser Pro Val Val Leu
65 70 75 80

Trp Leu Asn Gly Gly Pro Gly Cys Ser Ser Leu Asp Gly Leu Leu Thr
85 90 95

Glu His Gly Pro Phe Leu Val Gln Pro Asp Gly Val Thr Leu Glu Tyr
100 105 110

Asn Pro Tyr Ser Trp Asn Leu Ile Ala Asn Val Leu Tyr Leu Glu Ser
115 120 125

Pro Ala Gly Val Gly Phe Ser Tyr Ser Asp Asp Lys Phe Tyr Ala Thr
130 135 140

Asn Asp Thr Glu Val Ala Gln Ser Asn Phe Glu Ala Leu Gln Asp Phe
145 150 155 160

Phe Arg Leu Phe Pro Glu Tyr Lys Asn Asn Lys Leu Phe Leu Thr Gly
165 170 175

Glu Ser Tyr Ala Gly Ile Tyr Ile Pro Thr Leu Ala Val Leu Val Met
180 185 190

Gln Asp Pro Ser Met Asn Leu Gln Gly Leu Ala Val Gly Asn Gly Leu
195 200 205

Ser Ser Tyr Glu Gln Asn Asp Asn Ser Leu Val Tyr Phe Ala Tyr Tyr
210 215 220

His Gly Leu Leu Gly Asn Arg Leu Trp Ser Ser Leu Gln Thr His Cys
225 230 235 240

Cys Ser Gln Asn Lys Cys Asn Phe Tyr Asp Asn Lys Asp Leu Glu Cys
245 250 255

Val Thr Asn Leu Gln Glu Val Ala Arg Ile Val Gly Asn Ser Gly Leu
260 265 270

Asn Ile Tyr Asn Leu Tyr Ala Pro Cys Ala Gly Gly Val Pro Ser His
275 280 285

Phe Arg Tyr Glu Lys Asp Thr Val Val Val Gln Asp Leu Gly Asn Ile
290 295 300

Phe Thr Arg Leu Pro Leu Lys Arg Met Trp His Gln Ala Leu Leu Arg
305 310 315 320

Ser Gly Asp Lys Val Arg Met Asp Pro Pro Cys Thr Asn Thr Thr Ala
325 330 335

```
Ala Ser Thr Tyr Leu Asn Asn Pro Tyr Val Arg Lys Ala Leu Asn Ile
            340                 345                 350

Pro Glu Gln Leu Pro Gln Trp Asp Met Cys Asn Phe Leu Val Asn Leu
        355                 360                 365

Gln Tyr Arg Arg Leu Tyr Arg Ser Met Asn Ser Gln Tyr Leu Lys Leu
    370                 375                 380

Leu Ser Ser Gln Lys Tyr Gln Ile Leu Leu Tyr Asn Gly Asp Val Asp
385                 390                 395                 400

Met Ala Cys Asn Phe Met Gly Asp Glu Trp Phe Val Asp Ser Leu Asn
                405                 410                 415

Gln Lys Met Glu Val Gln Arg Arg Pro Trp Leu Val Lys Tyr Gly Asp
            420                 425                 430

Ser Gly Glu Gln Ile Ala Gly Phe Val Lys Glu Phe Ser His Ile Ala
        435                 440                 445

Phe Leu Thr Ile Lys Gly Ala Gly His Met Val Pro Thr Asp Lys Pro
    450                 455                 460

Leu Ala Ala Phe Thr Met Phe Ser Arg Phe Leu Asn Lys Gln Pro Tyr
465                 470                 475                 480


<210> SEQ ID NO 28
<211> LENGTH: 3036
<212> TYPE: DNA
<213> ORGANISM: Homo sapiens

<400> SEQUENCE: 28

atgggcgcct acgcgcgggc ttcgggggtc tgcgctcgcg gctgcctgga ctcagcaggc     60

ccctggacca tgtcccgcgc cctgcggcca ccgctcccgc ctctctgctt tttccttttg    120

ttgctggcgg ctgccggtgc tcgggccggg ggatacgaga catgccccac agtgcagccg    180

aacatgctga acgtgcacct gctgcctcac acacatgatg acgtgggctg gctcaaaacc    240

gtggaccagt acttttatgg aatcaagaat gacatccagc acgccggtgt gcagtacatc    300

ctggactcgg tcatctctgc cttgctggca gatcccaccc gtcgcttcat ttacgtggag    360

attgccttct tctcccgttg gtggcaccag cagacaaatg ccacacagga agtcgtgcga    420

gaccttgtgc gccaggggcg cctggagttc gccaatggtg gctgggtgat gaacgatgag    480

gcagccaccc actacggtgc catcgtggac cagatgacac ttgggctgcg ctttctggag    540

gacacatttg gcaatgatgg gcgaccccgt gtggcctggc acattgaccc cttcggccac    600

tctcgggagc aggcctcgct gtttgcgcag atgggcttcg acggcttctt ctttgggcgc    660

cttgattatc aagataagtg ggtacggatg cagaagctgg agatggagca ggtgtggcgg    720

gccagcacca gcctgaagcc cccgaccgcg gacctcttca ctggtgtgct tcccaatggt    780

tacaacccgc caaggaatct gtgctgggat gtgctgtgtg tcgatcagcc gctggtggag    840

gaccctcgca gccccgagta caacgccaag gagctggtcg attacttcct aaatgtggcc    900

actgcccagg gccggtatta ccgcaccaac cacactgtga tgaccatggg ctcggacttc    960

caatatgaga atgccaacat gtggttcaag aaccttgaca agctcatccg gctggtaaat   1020

gcgcagcagg caaaaggaag cagtgtccat gttctctact ccacccccgc ttgttacctc   1080

tgggagctga acaaggccaa cctcacctgg tcagtgaaac atgacgactt cttcccttac   1140

gcggatggcc cccaccagtt ctggaccggt tacttttcca gtcggccggc cctcaaacgc   1200

tacgagcgcc tcagctacaa cttcctgcag gtgtgcaacc agctggaggc gctggtgggc   1260

ctggcggcca acgtgggacc ctatggctcc ggagacagtg cacccctcaa tgaggcgatg   1320
```

```
gctgtgctcc agcatcacga cgccgtcagc ggcacctccc gccagcacgt ggccaacgac   1380

tacgcgcgcc agcttgcggc aggctggggg ccttgcgagg ttcttctgag caacgcgctg   1440

gcgcggctca gaggcttcaa agatcacttc accttttgcc aacagctaaa catcagcatc   1500

tgcccgctca gccagacggc ggcgcgcttc caggtcatcg tttataatcc cctggggcgg   1560

aaggtgaatt ggatggtacg gctgccggtc agcgaaggcg ttttcgttgt gaaggacccc   1620

aatggcagga cagtgcccag cgatgtggta atatttccca gctcagacag ccaggcgcac   1680

cctccggagc tgctgttctc agcctcactg cccgccctgg gcttcagcac ctattcagta   1740

gcccaggtgc ctcgctggaa gccccaggcc cgcgcaccac agcccatccc cagaagatcc   1800

tggtcccctg ctttaaccat cgaaaatgag cacatccggg caacgtttga tcctgacaca   1860

gggctgttga tggagattat gaacatgaat cagcaactcc tgctgcctgt tcgccagacc   1920

ttcttctggt acaacgccag tataggtgac aacgaaagtg accaggcctc aggtgcctac   1980

atcttcagac ccaaccaaca gaaaccgctg cctgtgagcc gctgggctca gatccacctg   2040

gtgaagacac ccttggtgca ggaggtgcac cagaacttct cagcttggtg ttcccaggtg   2100

gttcgcctgt acccaggaca gcggcacctg gagctagagt ggtcggtggg gccgataccct   2160

gtgggcgaca cctgggggaa ggaggtcatc agccgttttg acacaccgct ggagacaaag   2220

ggacgcttct acacagacag caatggccgg gagatcctgg agaggaggcg ggattatcga   2280

cccacctgga aactgaacca gacggagccc gtggcaggaa actactatcc agtcaacacc   2340

cggatttaca tcacggatgg aaacatgcag ctgactgtgc tgactgaccg ctcccagggg   2400

ggcagcagcc tgagagatgg ctcgctggag ctcatggtgc accgaaggct gctgaaggac   2460

gatggacgcg gagtatcgga gccactaatg gagaacgggt cgggggcgtg ggtgcgaggg   2520

cgccacctgg tgctgctgga cacagcccag gctgcagccg ccggacaccg gctcctggcg   2580

gagcaggagg tcctggcccc tcaggtggtg ctggccccgg gtggcggcgc cgcctacaat   2640

ctcggggctc ctccgcgcac gcagttctca gggctgcgca gggacctgcc gccctcggtg   2700

cacctgctca cgctggccag ctggggcccc gaaatggtgc tgctgcgctt ggagcaccag   2760

tttgccgtag gagaggattc cggacgtaac ctgagcgccc ccgttacctt gaacttgagg   2820

gacctgttct ccaccttcac catcacccgc ctgcaggaga ccacgctggt ggccaaccag   2880

ctccgcgagg cagcctccag gctcaagtgg acaacaaaca caggccccac accccaccaa   2940

actccgtacc agctggaccc ggccaacatc acgctggaac ccatggaaat ccgcactttc   3000

ctggcctcag ttcaatggaa ggaggtggat ggttag                             3036
```

<210> SEQ ID NO 29
<211> LENGTH: 1011
<212> TYPE: PRT
<213> ORGANISM: Homo sapiens

<400> SEQUENCE: 29

```
Met Gly Ala Tyr Ala Arg Ala Ser Gly Val Cys Ala Arg Gly Cys Leu
1               5                   10                  15

Asp Ser Ala Gly Pro Trp Thr Met Ser Arg Ala Leu Arg Pro Pro Leu
            20                  25                  30

Pro Pro Leu Cys Phe Phe Leu Leu Leu Leu Ala Ala Ala Gly Ala Arg
        35                  40                  45

Ala Gly Gly Tyr Glu Thr Cys Pro Thr Val Gln Pro Asn Met Leu Asn
    50                  55                  60
```

-continued

```
Val His Leu Leu Pro His Thr His Asp Asp Val Gly Trp Leu Lys Thr
65                  70                  75                  80

Val Asp Gln Tyr Phe Tyr Gly Ile Lys Asn Asp Ile Gln His Ala Gly
                85                  90                  95

Val Gln Tyr Ile Leu Asp Ser Val Ile Ser Ala Leu Leu Ala Asp Pro
            100                 105                 110

Thr Arg Arg Phe Ile Tyr Val Glu Ile Ala Phe Phe Ser Arg Trp Trp
        115                 120                 125

His Gln Gln Thr Asn Ala Thr Gln Glu Val Val Arg Asp Leu Val Arg
    130                 135                 140

Gln Gly Arg Leu Glu Phe Ala Asn Gly Gly Trp Val Met Asn Asp Glu
145                 150                 155                 160

Ala Ala Thr His Tyr Gly Ala Ile Val Asp Gln Met Thr Leu Gly Leu
                165                 170                 175

Arg Phe Leu Glu Asp Thr Phe Gly Asn Asp Gly Arg Pro Arg Val Ala
            180                 185                 190

Trp His Ile Asp Pro Phe Gly His Ser Arg Glu Gln Ala Ser Leu Phe
        195                 200                 205

Ala Gln Met Gly Phe Asp Gly Phe Phe Phe Gly Arg Leu Asp Tyr Gln
    210                 215                 220

Asp Lys Trp Val Arg Met Gln Lys Leu Glu Met Glu Gln Val Trp Arg
225                 230                 235                 240

Ala Ser Thr Ser Leu Lys Pro Pro Thr Ala Asp Leu Phe Thr Gly Val
                245                 250                 255

Leu Pro Asn Gly Tyr Asn Pro Pro Arg Asn Leu Cys Trp Asp Val Leu
            260                 265                 270

Cys Val Asp Gln Pro Leu Val Glu Asp Pro Arg Ser Pro Glu Tyr Asn
        275                 280                 285

Ala Lys Glu Leu Val Asp Tyr Phe Leu Asn Val Ala Thr Ala Gln Gly
    290                 295                 300

Arg Tyr Tyr Arg Thr Asn His Thr Val Met Thr Met Gly Ser Asp Phe
305                 310                 315                 320

Gln Tyr Glu Asn Ala Asn Met Trp Phe Lys Asn Leu Asp Lys Leu Ile
                325                 330                 335

Arg Leu Val Asn Ala Gln Gln Ala Lys Gly Ser Ser Val His Val Leu
            340                 345                 350

Tyr Ser Thr Pro Ala Cys Tyr Leu Trp Glu Leu Asn Lys Ala Asn Leu
        355                 360                 365

Thr Trp Ser Val Lys His Asp Asp Phe Phe Pro Tyr Ala Asp Gly Pro
    370                 375                 380

His Gln Phe Trp Thr Gly Tyr Phe Ser Ser Arg Pro Ala Leu Lys Arg
385                 390                 395                 400

Tyr Glu Arg Leu Ser Tyr Asn Phe Leu Gln Val Cys Asn Gln Leu Glu
                405                 410                 415

Ala Leu Val Gly Leu Ala Ala Asn Val Gly Pro Tyr Gly Ser Gly Asp
            420                 425                 430

Ser Ala Pro Leu Asn Glu Ala Met Ala Val Leu Gln His His Asp Ala
        435                 440                 445

Val Ser Gly Thr Ser Arg Gln His Val Ala Asn Asp Tyr Ala Arg Gln
    450                 455                 460

Leu Ala Ala Gly Trp Gly Pro Cys Glu Val Leu Leu Ser Asn Ala Leu
465                 470                 475                 480

Ala Arg Leu Arg Gly Phe Lys Asp His Phe Thr Phe Cys Gln Gln Leu
```

```
                485                 490                 495

Asn Ile Ser Ile Cys Pro Leu Ser Gln Thr Ala Ala Arg Phe Gln Val
            500                 505                 510

Ile Val Tyr Asn Pro Leu Gly Arg Lys Val Asn Trp Met Val Arg Leu
        515                 520                 525

Pro Val Ser Glu Gly Val Phe Val Val Lys Asp Pro Asn Gly Arg Thr
    530                 535                 540

Val Pro Ser Asp Val Val Ile Phe Pro Ser Ser Asp Ser Gln Ala His
545                 550                 555                 560

Pro Pro Glu Leu Leu Phe Ser Ala Ser Leu Pro Ala Leu Gly Phe Ser
                565                 570                 575

Thr Tyr Ser Val Ala Gln Val Pro Arg Trp Lys Pro Gln Ala Arg Ala
            580                 585                 590

Pro Gln Pro Ile Pro Arg Arg Ser Trp Ser Pro Ala Leu Thr Ile Glu
        595                 600                 605

Asn Glu His Ile Arg Ala Thr Phe Asp Pro Asp Thr Gly Leu Leu Met
    610                 615                 620

Glu Ile Met Asn Met Asn Gln Gln Leu Leu Leu Pro Val Arg Gln Thr
625                 630                 635                 640

Phe Phe Trp Tyr Asn Ala Ser Ile Gly Asp Asn Glu Ser Asp Gln Ala
                645                 650                 655

Ser Gly Ala Tyr Ile Phe Arg Pro Asn Gln Gln Lys Pro Leu Pro Val
            660                 665                 670

Ser Arg Trp Ala Gln Ile His Leu Val Lys Thr Pro Leu Val Gln Glu
        675                 680                 685

Val His Gln Asn Phe Ser Ala Trp Cys Ser Gln Val Val Arg Leu Tyr
    690                 695                 700

Pro Gly Gln Arg His Leu Glu Leu Glu Trp Ser Val Gly Pro Ile Pro
705                 710                 715                 720

Val Gly Asp Thr Trp Gly Lys Glu Val Ile Ser Arg Phe Asp Thr Pro
                725                 730                 735

Leu Glu Thr Lys Gly Arg Phe Tyr Thr Asp Ser Asn Gly Arg Glu Ile
            740                 745                 750

Leu Glu Arg Arg Arg Asp Tyr Arg Pro Thr Trp Lys Leu Asn Gln Thr
        755                 760                 765

Glu Pro Val Ala Gly Asn Tyr Tyr Pro Val Asn Thr Arg Ile Tyr Ile
    770                 775                 780

Thr Asp Gly Asn Met Gln Leu Thr Val Leu Thr Asp Arg Ser Gln Gly
785                 790                 795                 800

Gly Ser Ser Leu Arg Asp Gly Ser Leu Glu Leu Met Val His Arg Arg
                805                 810                 815

Leu Leu Lys Asp Asp Gly Arg Gly Val Ser Glu Pro Leu Met Glu Asn
            820                 825                 830

Gly Ser Gly Ala Trp Val Arg Gly Arg His Leu Val Leu Leu Asp Thr
        835                 840                 845

Ala Gln Ala Ala Ala Ala Gly His Arg Leu Leu Ala Glu Gln Glu Val
    850                 855                 860

Leu Ala Pro Gln Val Val Leu Ala Pro Gly Gly Gly Ala Ala Tyr Asn
865                 870                 875                 880

Leu Gly Ala Pro Pro Arg Thr Gln Phe Ser Gly Leu Arg Arg Asp Leu
                885                 890                 895

Pro Pro Ser Val His Leu Leu Thr Leu Ala Ser Trp Gly Pro Glu Met
            900                 905                 910
```

```
Val Leu Leu Arg Leu Glu His Gln Phe Ala Val Gly Glu Asp Ser Gly
        915                 920                 925

Arg Asn Leu Ser Ala Pro Val Thr Leu Asn Leu Arg Asp Leu Phe Ser
    930                 935                 940

Thr Phe Thr Ile Thr Arg Leu Gln Glu Thr Thr Leu Val Ala Asn Gln
945                 950                 955                 960

Leu Arg Glu Ala Ala Ser Arg Leu Lys Trp Thr Thr Asn Thr Gly Pro
                965                 970                 975

Thr Pro His Gln Thr Pro Tyr Gln Leu Asp Pro Ala Asn Ile Thr Leu
            980                 985                 990

Glu Pro Met Glu Ile Arg Thr Phe  Leu Ala Ser Val Gln  Trp Lys Glu
        995                 1000                1005

Val Asp  Gly
    1010


<210> SEQ ID NO 30
<211> LENGTH: 2640
<212> TYPE: DNA
<213> ORGANISM: Homo sapiens

<400> SEQUENCE: 30

atgcgcctcc acctgctcct gctgctcgcg ctgtgcggtg caggcaccac cgccgcggag      60

ctcagttaca gcttgcgtgg caactggagc atctgcaatg ggaacggctc gctggagctg     120

cccggggcgg tccctggctg cgtgcacagc gccttgttcc agcagggcct gatccaggat     180

tcttactaca gatttaatga ccttaactac agatgggtct ctttggataa ctggacctat     240

agcaaagaat ttaaaatccc ctttgaaatt agcaaatggc aaaaagtaaa tttgattctt     300

gagggagtgg atacggtttc aaaaatcctg ttcaatgaag tcactattgg ggaaacagac     360

aatatgttca atagatatag ctttgatatt accaacgtgg tcagggacgt gaactccatt     420

gagctgcgtt tccagtcagc ggtgttgtat gcagcacagc agagcaaagc tcacactcgc     480

taccaggttc ccccagactg ccctccactt gtgcagaagg gtgaatgcca tgtcaacttt     540

gttcggaagg agcaatgttc ctttagttgg gactgggggc cttcctttcc tacccaggga     600

atctggaaag atgttagaat tgaagcctat aatatttgtc acctgaacta cttcacattt     660

tccccaatat atgataagag tgcccaggag tggaatctgg aaatagagtc tacatttgat     720

gttgtcagct caaagccagt tggtggtcaa gtgatcgtag ccatccctaa gttgcaaaca     780

caacagacat acagcattga acttcaacct gggaaaagga ttgttgagct atttgtgaac     840

attagcaaga atattactgt agaaacttgg tggcctcatg gacatggaaa ccagactggg     900

tacaacatga ctgttctttt tgaactggat ggaggcttaa atattgaaaa atcagctaag     960

gtttatttta ggacagtgga acttatagaa gagcctataa aagggtctcc tggtttgagt    1020

ttctatttca aaattaatgg atttcccata tttctaaaag gctcaaactg gatcccagca    1080

gattcattcc aggaccgagt aacctctgag ttgttacggc tcctttttaca gtctgttgtg   1140

gatgctaata tgaatactct tcgggtttgg ggaggaggaa tttatgagca ggatgaattc    1200

tatgaactct gtgatgaact aggaataatg gtatggcagg attttatgtt tgcctgtgcc    1260

ctttatccaa ctgatcaggg cttcctggat tcagtgacag cagaagttgc ctaccagatc    1320

aagagactga aatctcatcc ttctatcatc atatggagtg gcaataatga aaatgaggag    1380

gcgctgatga tgaattggta tcatatcagt ttcactgacc ggccaatcta catcaaggac    1440

tatgtgacac tctatgtgaa aaacatcaga gagctcgtac tggcaggaga caagagtcgt    1500
```

```
cctttatta cgtccagtcc tacaaatggg gctgaaactg ttgcagaagc ctgggtctct   1560

caaaacccta atagcaatta ttttggtgat gtacattttt atgactatat cagtgattgc   1620

tggaactgga aagttttccc aaaagctcga tttgcatctg aatatggata tcagtcctgg   1680

ccgtccttca gtacattaga aaaggtctcg tctacagagg actggtcttt caatagcaag   1740

ttttcacttc atcgacaaca tcacgaaggt ggtaacaaac aaatgcttta tcaggctgga   1800

cttcatttca aactccccca aagcacagat ccattacgca catttaaaga taccatctac   1860

cttactcagg tgatgcaggc ccagtgtgtc aaaacagaaa ctgaattcta ccgccgtagt   1920

cgcagcgaga tagtggatca gcaagggcac acgatggggg cactttattg gcagttgaat   1980

gacatctggc aagctccttc ctgggcttct cttgagtacg gaggaaagtg gaaaatgctt   2040

cattactttg ctcagaattt ctttgctcca ctgttgccag taggctttga gaatgaaaac   2100

acgttctata tctatggtgt gtcagatctt cactcggatt attcgatgac actcagtgtg   2160

agagtccata catggagctc cctggagccc gtgtgctctc gtgtgactga acgttttgtg   2220

atgaaaggag gagaggctgt ctgcctttat gaggagccag tgtctgaatt gctgaggaga   2280

tgtgggaatt gcacacggga aagctgtgtg gtttcctttt acctttcagc tgaccatgaa   2340

ctcctgagcc cgaccaacta ccacttcttg tcctcaccga aggaggccgt ggggctctgc   2400

aaggcgcaga tcactgccat catctctcag caaggtgaca tatttgtttt tgacctggag   2460

acctcagctg tcgctccctt tgtttggttg gatgtaggaa gcatcccagg gagatttagt   2520

gacaatggtt tcctcatgac tgagaagaca cgaactatat tattttaccc ttgggagccc   2580

accagcaaga atgagttgga gcaatctttt catgtgacct ccttaacaga tatttactga   2640
```

```
<210> SEQ ID NO 31
<211> LENGTH: 879
<212> TYPE: PRT
<213> ORGANISM: Homo sapiens

<400> SEQUENCE: 31

Met Arg Leu His Leu Leu Leu Leu Leu Ala Leu Cys Gly Ala Gly Thr
1               5                   10                  15

Thr Ala Ala Glu Leu Ser Tyr Ser Leu Arg Gly Asn Trp Ser Ile Cys
            20                  25                  30

Asn Gly Asn Gly Ser Leu Glu Leu Pro Gly Ala Val Pro Gly Cys Val
        35                  40                  45

His Ser Ala Leu Phe Gln Gln Gly Leu Ile Gln Asp Ser Tyr Tyr Arg
    50                  55                  60

Phe Asn Asp Leu Asn Tyr Arg Trp Val Ser Leu Asp Asn Trp Thr Tyr
65                  70                  75                  80

Ser Lys Glu Phe Lys Ile Pro Phe Glu Ile Ser Lys Trp Gln Lys Val
                85                  90                  95

Asn Leu Ile Leu Glu Gly Val Asp Thr Val Ser Lys Ile Leu Phe Asn
            100                 105                 110

Glu Val Thr Ile Gly Glu Thr Asp Asn Met Phe Asn Arg Tyr Ser Phe
        115                 120                 125

Asp Ile Thr Asn Val Val Arg Asp Val Asn Ser Ile Glu Leu Arg Phe
    130                 135                 140

Gln Ser Ala Val Leu Tyr Ala Ala Gln Gln Ser Lys Ala His Thr Arg
145                 150                 155                 160

Tyr Gln Val Pro Pro Asp Cys Pro Pro Leu Val Gln Lys Gly Glu Cys
                165                 170                 175
```

```
His Val Asn Phe Val Arg Lys Glu Gln Cys Ser Phe Ser Trp Asp Trp
            180                 185                 190

Gly Pro Ser Phe Pro Thr Gln Gly Ile Trp Lys Asp Val Arg Ile Glu
        195                 200                 205

Ala Tyr Asn Ile Cys His Leu Asn Tyr Phe Thr Phe Ser Pro Ile Tyr
    210                 215                 220

Asp Lys Ser Ala Gln Glu Trp Asn Leu Glu Ile Glu Ser Thr Phe Asp
225                 230                 235                 240

Val Val Ser Ser Lys Pro Val Gly Gly Gln Val Ile Val Ala Ile Pro
                245                 250                 255

Lys Leu Gln Thr Gln Gln Thr Tyr Ser Ile Glu Leu Gln Pro Gly Lys
            260                 265                 270

Arg Ile Val Glu Leu Phe Val Asn Ile Ser Lys Asn Ile Thr Val Glu
        275                 280                 285

Thr Trp Trp Pro His Gly His Gly Asn Gln Thr Gly Tyr Asn Met Thr
    290                 295                 300

Val Leu Phe Glu Leu Asp Gly Gly Leu Asn Ile Glu Lys Ser Ala Lys
305                 310                 315                 320

Val Tyr Phe Arg Thr Val Glu Leu Ile Glu Glu Pro Ile Lys Gly Ser
                325                 330                 335

Pro Gly Leu Ser Phe Tyr Phe Lys Ile Asn Gly Phe Pro Ile Phe Leu
            340                 345                 350

Lys Gly Ser Asn Trp Ile Pro Ala Asp Ser Phe Gln Asp Arg Val Thr
        355                 360                 365

Ser Glu Leu Leu Arg Leu Leu Leu Gln Ser Val Val Asp Ala Asn Met
    370                 375                 380

Asn Thr Leu Arg Val Trp Gly Gly Gly Ile Tyr Glu Gln Asp Glu Phe
385                 390                 395                 400

Tyr Glu Leu Cys Asp Glu Leu Gly Ile Met Val Trp Gln Asp Phe Met
                405                 410                 415

Phe Ala Cys Ala Leu Tyr Pro Thr Asp Gln Gly Phe Leu Asp Ser Val
            420                 425                 430

Thr Ala Glu Val Ala Tyr Gln Ile Lys Arg Leu Lys Ser His Pro Ser
        435                 440                 445

Ile Ile Ile Trp Ser Gly Asn Asn Glu Asn Glu Glu Ala Leu Met Met
    450                 455                 460

Asn Trp Tyr His Ile Ser Phe Thr Asp Arg Pro Ile Tyr Ile Lys Asp
465                 470                 475                 480

Tyr Val Thr Leu Tyr Val Lys Asn Ile Arg Glu Leu Val Leu Ala Gly
                485                 490                 495

Asp Lys Ser Arg Pro Phe Ile Thr Ser Ser Pro Thr Asn Gly Ala Glu
            500                 505                 510

Thr Val Ala Glu Ala Trp Val Ser Gln Asn Pro Asn Ser Asn Tyr Phe
        515                 520                 525

Gly Asp Val His Phe Tyr Asp Tyr Ile Ser Asp Cys Trp Asn Trp Lys
    530                 535                 540

Val Phe Pro Lys Ala Arg Phe Ala Ser Glu Tyr Gly Tyr Gln Ser Trp
545                 550                 555                 560

Pro Ser Phe Ser Thr Leu Glu Lys Val Ser Ser Thr Glu Asp Trp Ser
                565                 570                 575

Phe Asn Ser Lys Phe Ser Leu His Arg Gln His His Glu Gly Gly Asn
            580                 585                 590
```

```
Lys Gln Met Leu Tyr Gln Ala Gly Leu His Phe Lys Leu Pro Gln Ser
        595                 600                 605

Thr Asp Pro Leu Arg Thr Phe Lys Asp Thr Ile Tyr Leu Thr Gln Val
    610                 615                 620

Met Gln Ala Gln Cys Val Lys Thr Glu Thr Glu Phe Tyr Arg Arg Ser
625                 630                 635                 640

Arg Ser Glu Ile Val Asp Gln Gln Gly His Thr Met Gly Ala Leu Tyr
                645                 650                 655

Trp Gln Leu Asn Asp Ile Trp Gln Ala Pro Ser Trp Ala Ser Leu Glu
            660                 665                 670

Tyr Gly Gly Lys Trp Lys Met Leu His Tyr Phe Ala Gln Asn Phe Phe
        675                 680                 685

Ala Pro Leu Leu Pro Val Gly Phe Glu Asn Glu Asn Thr Phe Tyr Ile
    690                 695                 700

Tyr Gly Val Ser Asp Leu His Ser Asp Tyr Ser Met Thr Leu Ser Val
705                 710                 715                 720

Arg Val His Thr Trp Ser Ser Leu Glu Pro Val Cys Ser Arg Val Thr
                725                 730                 735

Glu Arg Phe Val Met Lys Gly Gly Glu Ala Val Cys Leu Tyr Glu Glu
            740                 745                 750

Pro Val Ser Glu Leu Leu Arg Arg Cys Gly Asn Cys Thr Arg Glu Ser
        755                 760                 765

Cys Val Val Ser Phe Tyr Leu Ser Ala Asp His Glu Leu Leu Ser Pro
    770                 775                 780

Thr Asn Tyr His Phe Leu Ser Ser Pro Lys Glu Ala Val Gly Leu Cys
785                 790                 795                 800

Lys Ala Gln Ile Thr Ala Ile Ile Ser Gln Gln Gly Asp Ile Phe Val
                805                 810                 815

Phe Asp Leu Glu Thr Ser Ala Val Ala Pro Phe Val Trp Leu Asp Val
            820                 825                 830

Gly Ser Ile Pro Gly Arg Phe Ser Asp Asn Gly Phe Leu Met Thr Glu
        835                 840                 845

Lys Thr Arg Thr Ile Leu Phe Tyr Pro Trp Glu Pro Thr Ser Lys Asn
    850                 855                 860

Glu Leu Glu Gln Ser Phe His Val Thr Ser Leu Thr Asp Ile Tyr
865                 870                 875
```

<210> SEQ ID NO 32
<211> LENGTH: 1041
<212> TYPE: DNA
<213> ORGANISM: Homo sapiens

<400> SEQUENCE: 32

```
atggcgcgga agtcgaactt gcctgtgctt ctcgtgccgt ttctgctctg ccaggcccta      60

gtgcgctgct ccagccctct gcccctggtc gtcaacactt ggccctttaa gaatgcaacc     120

gaagcagcgt ggagggcatt agcatctgga ggctctgccc tggatgcagt ggagagcggc     180

tgtgccatgt gtgagagaga gcagtgtgac ggctctgtag gctttggagg aagtcctgat     240

gaacttggag aaaccacact agatgccatg atcatggatg gcactactat ggatgtagga     300

gcagtaggag atctcagacg aattaaaaat gctattggtg tggcacggaa agtactggaa     360

catacaacac acacactttt agtaggagag tcagccacca catttgctca aagtatgggg     420

tttatcaatg aagacttatc taccactgct tctcaagctc ttcattcaga ttggcttgct     480

cggaattgcc agccaaatta ttggaggaat gttataccag atccctcaaa atactgcgga     540
```

ccctacaaac cacctggtat cttaaagcag gatattccta tccataaaga aacagaagat 600
gatcgtggtc atgacactat tggcatggtt gtaatccata agacaggaca tattgctgct 660
ggtacatcta caaatggtat aaaattcaaa atacatggcc gtgtaggaga ctcaccaata 720
cctggagctg gagcctatgc tgacgatact gcaggggcag ccgcagccac tgggaatggt 780
gatatattga tgcgcttcct gccaagctac caagctgtag aatacatgag aagaggagaa 840
gatccaacca tagcttgcca aaaagtgatt tcaagaatcc agaagcattt tccagaattc 900
tttggggctg ttatatgtgc caatgtgact ggaagttacg gtgctgcttg caataaactt 960
tcaacattta ctcagtttag tttcatggtt tataattccg aaaaaaatca gccaactgag 1020
gaaaaagtgg actgcatcta a 1041

<210> SEQ ID NO 33
<211> LENGTH: 346
<212> TYPE: PRT
<213> ORGANISM: Homo sapiens

<400> SEQUENCE: 33

Met Ala Arg Lys Ser Asn Leu Pro Val Leu Leu Val Pro Phe Leu Leu
1 5 10 15

Cys Gln Ala Leu Val Arg Cys Ser Ser Pro Leu Pro Leu Val Val Asn
20 25 30

Thr Trp Pro Phe Lys Asn Ala Thr Glu Ala Ala Trp Arg Ala Leu Ala
35 40 45

Ser Gly Gly Ser Ala Leu Asp Ala Val Glu Ser Gly Cys Ala Met Cys
50 55 60

Glu Arg Glu Gln Cys Asp Gly Ser Val Gly Phe Gly Gly Ser Pro Asp
65 70 75 80

Glu Leu Gly Glu Thr Thr Leu Asp Ala Met Ile Met Asp Gly Thr Thr
85 90 95

Met Asp Val Gly Ala Val Gly Asp Leu Arg Arg Ile Lys Asn Ala Ile
100 105 110

Gly Val Ala Arg Lys Val Leu Glu His Thr Thr His Thr Leu Leu Val
115 120 125

Gly Glu Ser Ala Thr Thr Phe Ala Gln Ser Met Gly Phe Ile Asn Glu
130 135 140

Asp Leu Ser Thr Thr Ala Ser Gln Ala Leu His Ser Asp Trp Leu Ala
145 150 155 160

Arg Asn Cys Gln Pro Asn Tyr Trp Arg Asn Val Ile Pro Asp Pro Ser
165 170 175

Lys Tyr Cys Gly Pro Tyr Lys Pro Pro Gly Ile Leu Lys Gln Asp Ile
180 185 190

Pro Ile His Lys Glu Thr Glu Asp Asp Arg Gly His Asp Thr Ile Gly
195 200 205

Met Val Val Ile His Lys Thr Gly His Ile Ala Ala Gly Thr Ser Thr
210 215 220

Asn Gly Ile Lys Phe Lys Ile His Gly Arg Val Gly Asp Ser Pro Ile
225 230 235 240

Pro Gly Ala Gly Ala Tyr Ala Asp Asp Thr Ala Gly Ala Ala Ala Ala
245 250 255

Thr Gly Asn Gly Asp Ile Leu Met Arg Phe Leu Pro Ser Tyr Gln Ala
260 265 270

Val Glu Tyr Met Arg Arg Gly Glu Asp Pro Thr Ile Ala Cys Gln Lys

```
        275                 280                 285

Val Ile Ser Arg Ile Gln Lys His Phe Pro Glu Phe Phe Gly Ala Val
    290                 295                 300

Ile Cys Ala Asn Val Thr Gly Ser Tyr Gly Ala Ala Cys Asn Lys Leu
305                 310                 315                 320

Ser Thr Phe Thr Gln Phe Ser Phe Met Val Tyr Asn Ser Glu Lys Asn
                325                 330                 335

Gln Pro Thr Glu Glu Lys Val Asp Cys Ile
            340                 345


<210> SEQ ID NO 34
<211> LENGTH: 1401
<212> TYPE: DNA
<213> ORGANISM: Homo sapiens

<400> SEQUENCE: 34

atgcgggctc cggggatgag gtcgcggccg gcgggtcccg cgctgttgct gctgctgctc      60

ttcctcggag cggccgagtc ggtgcgtcgg gcccagcctc cgcgccgcta caccccagac     120

tggccgagcc tggattctcg gccgctgccg gcctggttcg acgaagccaa gttcggggtg     180

ttcatccact ggggcgtgtt ctcggtgccc gcctggggca gcgagtggtt ctggtggcac     240

tggcagggcg aggggcggcc gcagtaccag cgcttcatgc gcgacaacta cccgcccggc     300

ttcagctacg ccgacttcgg accgcagttc actgcgcgct tcttccaccc ggaggagtgg     360

gccgacctct tccaggccgc gggcgccaag tatgtagttt tgacgacaaa gcatcacgaa     420

ggcttcacaa actggccgag tcctgtgtct tggaactgga actccaaaga cgtggggcct     480

catcgggatt tggttggtga attgggaaca gctctccgga agaggaacat ccgctatgga     540

ctataccact cactcttaga gtggttccat ccactctatc tacttgataa gaaaaatggc     600

ttcaaaacac agcattttgt cagtgcaaaa acaatgccag agctgtacga ccttgttaac     660

agctataaac ctgatctgat ctggtctgat ggggagtggg aatgtcctga tacttactgg     720

aactccacaa attttctttc atggctctac aatgacagcc ctgtcaagga tgaggtggta     780

gtaaatgacc gatggggtca gaactgttcc tgtcaccatg gaggatacta taactgtgaa     840

gataaattca agccacagag cttgccagat cacaagtggg agatgtgcac cagcattgac     900

aagttttcct ggggctatcg tcgtgacatg gcattgtctg atgttacaga agaatctgaa     960

atcatttcgg aactggttca gacagtaagt ttgggaggca actatcttct gaacattgga    1020

ccaactaaag atggactgat tgttcccatc ttccaagaaa ggcttcttgc tgttgggaaa    1080

tggctgagca tcaatgggga ggctatctat gcctccaaac catggcgggt gcaatgggaa    1140

aagaacacaa catctgtatg gtatacctca aagggatcgg ctgtttatgc catttttctg    1200

cactggccag aaaatggagt cttaaacctt gaatccccca taactacctc aactacaaag    1260

ataacaatgc tgggaattca aggagatctg aagtggtcca cagatccaga taaaggtctc    1320

ttcatctctc taccccagtt gccaccctct gctgtccccg cagagtttgc ttggactata    1380

aagctgacag gagtgaagta a                                              1401


<210> SEQ ID NO 35
<211> LENGTH: 466
<212> TYPE: PRT
<213> ORGANISM: Homo sapiens

<400> SEQUENCE: 35

Met Arg Ala Pro Gly Met Arg Ser Arg Pro Ala Gly Pro Ala Leu Leu
```

-continued

```
1               5                   10                  15

Leu Leu Leu Leu Phe Leu Gly Ala Ala Glu Ser Val Arg Arg Ala Gln
            20                  25                  30

Pro Pro Arg Arg Tyr Thr Pro Asp Trp Pro Ser Leu Asp Ser Arg Pro
        35                  40                  45

Leu Pro Ala Trp Phe Asp Glu Ala Lys Phe Gly Val Phe Ile His Trp
    50                  55                  60

Gly Val Phe Ser Val Pro Ala Trp Gly Ser Glu Trp Phe Trp Trp His
65                  70                  75                  80

Trp Gln Gly Glu Gly Arg Pro Gln Tyr Gln Arg Phe Met Arg Asp Asn
                85                  90                  95

Tyr Pro Pro Gly Phe Ser Tyr Ala Asp Phe Gly Pro Gln Phe Thr Ala
            100                 105                 110

Arg Phe Phe His Pro Glu Glu Trp Ala Asp Leu Phe Gln Ala Ala Gly
        115                 120                 125

Ala Lys Tyr Val Val Leu Thr Thr Lys His His Glu Gly Phe Thr Asn
    130                 135                 140

Trp Pro Ser Pro Val Ser Trp Asn Trp Asn Ser Lys Asp Val Gly Pro
145                 150                 155                 160

His Arg Asp Leu Val Gly Glu Leu Gly Thr Ala Leu Arg Lys Arg Asn
                165                 170                 175

Ile Arg Tyr Gly Leu Tyr His Ser Leu Leu Glu Trp Phe His Pro Leu
            180                 185                 190

Tyr Leu Leu Asp Lys Lys Asn Gly Phe Lys Thr Gln His Phe Val Ser
        195                 200                 205

Ala Lys Thr Met Pro Glu Leu Tyr Asp Leu Val Asn Ser Tyr Lys Pro
    210                 215                 220

Asp Leu Ile Trp Ser Asp Gly Glu Trp Glu Cys Pro Asp Thr Tyr Trp
225                 230                 235                 240

Asn Ser Thr Asn Phe Leu Ser Trp Leu Tyr Asn Asp Ser Pro Val Lys
                245                 250                 255

Asp Glu Val Val Val Asn Asp Arg Trp Gly Gln Asn Cys Ser Cys His
            260                 265                 270

His Gly Gly Tyr Tyr Asn Cys Glu Asp Lys Phe Lys Pro Gln Ser Leu
        275                 280                 285

Pro Asp His Lys Trp Glu Met Cys Thr Ser Ile Asp Lys Phe Ser Trp
    290                 295                 300

Gly Tyr Arg Arg Asp Met Ala Leu Ser Asp Val Thr Glu Glu Ser Glu
305                 310                 315                 320

Ile Ile Ser Glu Leu Val Gln Thr Val Ser Leu Gly Gly Asn Tyr Leu
                325                 330                 335

Leu Asn Ile Gly Pro Thr Lys Asp Gly Leu Ile Val Pro Ile Phe Gln
            340                 345                 350

Glu Arg Leu Leu Ala Val Gly Lys Trp Leu Ser Ile Asn Gly Glu Ala
        355                 360                 365

Ile Tyr Ala Ser Lys Pro Trp Arg Val Gln Trp Glu Lys Asn Thr Thr
    370                 375                 380

Ser Val Trp Tyr Thr Ser Lys Gly Ser Ala Val Tyr Ala Ile Phe Leu
385                 390                 395                 400

His Trp Pro Glu Asn Gly Val Leu Asn Leu Glu Ser Pro Ile Thr Thr
                405                 410                 415

Ser Thr Thr Lys Ile Thr Met Leu Gly Ile Gln Gly Asp Leu Lys Trp
            420                 425                 430
```

```
Ser Thr Asp Pro Asp Lys Gly Leu Phe Ile Ser Leu Pro Gln Leu Pro
        435                 440                 445

Pro Ser Ala Val Pro Ala Glu Phe Ala Trp Thr Ile Lys Leu Thr Gly
    450                 455                 460

Val Lys
465


<210> SEQ ID NO 36
<211> LENGTH: 2232
<212> TYPE: DNA
<213> ORGANISM: Homo sapiens

<400> SEQUENCE: 36

atggaggcgg tggcggtggc cgcggcggtg ggggtccttc tcctggccgg ggccgggggc      60

gcggcaggcg acgaggcccg ggaggcggcg gccgtgcggg cgctcgtggc ccggctgctg     120

gggccaggcc ccgcggccga cttctccgtg tcggtggagc gcgctctggc tgccaagccg     180

ggcttggaca cctacagcct gggcggcggc ggcgcggcgc gcgtgcgggt gcgcggctcc     240

acgggcgtgg cggccgccgc ggggctgcac cgctacctgc gcgacttctg tggctgccac     300

gtggcctggt ccggctctca gctgcgcctg ccgcggccac tgccagccgt gccgggggag     360

ctgaccgagg ccacgcccaa caggtaccgc tattaccaga atgtgtgcac gcaaagctac     420

tctttcgtgt ggtgggactg ggcccgctgg gagcgagaga tagactggat ggcgctgaat     480

ggcatcaacc tggcactggc ctggagcggc caggaggcca tctggcagcg ggtgtacctg     540

gccttgggcc tgacccaggc agagatcaat gagttcttta ctggtcctgc cttcctggcc     600

tgggggcgaa tgggcaacct gcacacctgg gatggccccc tgccccccc ctggcacatc     660

aagcagcttt acctgcagca ccgggtcctg gaccagatgc gctccttcgg catgacccca     720

gtgctgcctg cattcgcggg gcatgttccc gaggctgtca ccagggtgtt ccctcaggtc     780

aatgtcacga agatgggcag ttggggccac tttaactgtt cctactcctg ctccttcctt     840

ctggctccgg aagaccccat attccccatc atcgggagcc tcttcctgcg agagctgatc     900

aaagagtttg gcacagacca catctatggg gccgacactt tcaatgagat gcagccacct     960

tcctcagagc cctcctacct tgccgcagcc accactgccg tctatgaggc catgactgca    1020

gtggatactg aggctgtgtg gctgctccaa ggctggctct tccagcacca gccgcagttc    1080

tgggggcccg cccagatcag ggctgtgctg ggagctgtgc cccgtggccg cctcctggtt    1140

ctggacctgt ttgctgagag ccagcctgtg tatacccgca ctgcctcctt ccagggccag    1200

cccttcatct ggtgcatgct gcacaacttt gggggaaacc atggtctttt tggagcccta    1260

gaggctgtga acggaggccc agaagctgcc cgcctcttcc ccaactccac catggtaggc    1320

acgggcatgg cccccgaggg catcagccag aacgaagtgg tctattccct catggctgag    1380

ctgggctggc gaaaggaccc agtgccagat ttggcagcct gggtgaccag ctttgccgcc    1440

cggcggtatg ggtctcccca cccggacgca ggggcagcgt ggaggctact gctccggagt    1500

gtgtacaact gctccgggga ggcctgcagg ggccacaatc gtagcccgct ggtcaggcgg    1560

ccgtccctac agatgaatac cagcatctgg tacaaccgat ctgatgtgtt tgaggcctgg    1620

cggctgctgc tcacatctgc tccctccctg gccaccagcc ccgccttccg ctacgacctg    1680

ctggacctca ctcggcaggc agtgcaggag ctggtcagct tgtactatga ggaggcaaga    1740

agcgcctacc tgagcaagga gctggcctcc ctgttgaggg ctggaggcgt cctggcctat    1800

gagctgctgc cggcactgga cgaggtgctg gctagtgaca gccgcttctt gctgggcagc    1860
```

tggctagagc aggcccgagc agcggcagtc agtgaggccg aggccgattt ctacgagcag 1920
aacagccgct accagctgac cttgtggggg ccagaaggca acatcctgga ctatgccaac 1980
aagcagctgg cggggttggt ggccaactac tacacccctc gctggcggct tttcctggag 2040
gcgctggttg acagtgtggc ccagggcatc cctttccaac agcaccagtt tgacaaaaat 2100
gtcttccaac tggagcaggc cttcgttctc agcaagcaga ggtaccccag ccagccgcga 2160
ggagacactg tggacctggc caagaagatc ttcctcaaat attacccccg ctgggtggcc 2220
ggctcttggt ga 2232

<210> SEQ ID NO 37
<211> LENGTH: 743
<212> TYPE: PRT
<213> ORGANISM: Homo sapiens

<400> SEQUENCE: 37

Met Glu Ala Val Ala Val Ala Ala Ala Val Gly Val Leu Leu Leu Ala
1 5 10 15

Gly Ala Gly Gly Ala Ala Gly Asp Glu Ala Arg Glu Ala Ala Ala Val
20 25 30

Arg Ala Leu Val Ala Arg Leu Leu Gly Pro Gly Pro Ala Ala Asp Phe
35 40 45

Ser Val Ser Val Glu Arg Ala Leu Ala Ala Lys Pro Gly Leu Asp Thr
50 55 60

Tyr Ser Leu Gly Gly Gly Gly Ala Ala Arg Val Arg Val Arg Gly Ser
65 70 75 80

Thr Gly Val Ala Ala Ala Ala Gly Leu His Arg Tyr Leu Arg Asp Phe
85 90 95

Cys Gly Cys His Val Ala Trp Ser Gly Ser Gln Leu Arg Leu Pro Arg
100 105 110

Pro Leu Pro Ala Val Pro Gly Glu Leu Thr Glu Ala Thr Pro Asn Arg
115 120 125

Tyr Arg Tyr Tyr Gln Asn Val Cys Thr Gln Ser Tyr Ser Phe Val Trp
130 135 140

Trp Asp Trp Ala Arg Trp Glu Arg Glu Ile Asp Trp Met Ala Leu Asn
145 150 155 160

Gly Ile Asn Leu Ala Leu Ala Trp Ser Gly Gln Glu Ala Ile Trp Gln
165 170 175

Arg Val Tyr Leu Ala Leu Gly Leu Thr Gln Ala Glu Ile Asn Glu Phe
180 185 190

Phe Thr Gly Pro Ala Phe Leu Ala Trp Gly Arg Met Gly Asn Leu His
195 200 205

Thr Trp Asp Gly Pro Leu Pro Pro Ser Trp His Ile Lys Gln Leu Tyr
210 215 220

Leu Gln His Arg Val Leu Asp Gln Met Arg Ser Phe Gly Met Thr Pro
225 230 235 240

Val Leu Pro Ala Phe Ala Gly His Val Pro Glu Ala Val Thr Arg Val
245 250 255

Phe Pro Gln Val Asn Val Thr Lys Met Gly Ser Trp Gly His Phe Asn
260 265 270

Cys Ser Tyr Ser Cys Ser Phe Leu Leu Ala Pro Glu Asp Pro Ile Phe
275 280 285

Pro Ile Ile Gly Ser Leu Phe Leu Arg Glu Leu Ile Lys Glu Phe Gly
290 295 300

```
Thr Asp His Ile Tyr Gly Ala Asp Thr Phe Asn Glu Met Gln Pro Pro
305                 310                 315                 320

Ser Ser Glu Pro Ser Tyr Leu Ala Ala Ala Thr Thr Ala Val Tyr Glu
                325                 330                 335

Ala Met Thr Ala Val Asp Thr Glu Ala Val Trp Leu Leu Gln Gly Trp
            340                 345                 350

Leu Phe Gln His Gln Pro Gln Phe Trp Gly Pro Ala Gln Ile Arg Ala
        355                 360                 365

Val Leu Gly Ala Val Pro Arg Gly Arg Leu Leu Val Leu Asp Leu Phe
    370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
        435                 440                 445

Ser Gln Asn Glu Val Val Tyr Ser Leu Met Ala Glu Leu Gly Trp Arg
    450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
        515                 520                 525

Ile Trp Tyr Asn Arg Ser Asp Val Phe Glu Ala Trp Arg Leu Leu Leu
    530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
        595                 600                 605

Val Leu Ala Ser Asp Ser Arg Phe Leu Leu Gly Ser Trp Leu Glu Gln
    610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
        675                 680                 685

Gly Ile Pro Phe Gln Gln His Gln Phe Asp Lys Asn Val Phe Gln Leu
    690                 695                 700

Glu Gln Ala Phe Val Leu Ser Lys Gln Arg Tyr Pro Ser Gln Pro Arg
705                 710                 715                 720
```

```
Gly Asp Thr Val Asp Leu Ala Lys Lys Ile Phe Leu Lys Tyr Tyr Pro
                725                 730                 735

Arg Trp Val Ala Gly Ser Trp
            740


<210> SEQ ID NO 38
<211> LENGTH: 2034
<212> TYPE: DNA
<213> ORGANISM: Homo sapiens

<400> SEQUENCE: 38

atgccggggt tcctggttcg catcctccct ctgttgctgg ttctgctgct tctgggccct      60

acgcgcggct tgcgcaatgc cacccagagg atgtttgaaa ttgactatag ccgggactcc     120

ttcctcaagg atggccagcc atttcgctac atctcaggaa gcattcacta ctcccgtgtg     180

ccccgcttct actggaagga ccggctgctg aagatgaaga tggctgggct gaacgccatc     240

cagacgtatg tgccctggaa ctttcatgag ccctggccag gacagtacca gttttctgag     300

gaccatgatg tggaatattt tcttcggctg gctcatgagc tgggactgct ggttatcctg     360

aggcccgggc cctacatctg tgcagagtgg gaaatgggag gattacctgc ttggctgcta     420

gagaaagagt ctattcttct ccgctcctcc gacccagatt acctggcagc tgtggacaag     480

tggttgggag tccttctgcc caagatgaag cctctcctct atcagaatgg agggccagtt     540

ataacagtgc aggttgaaaa tgaatatggc agctactttg cctgtgattt tgactacctg     600

cgcttcctgc agaagcgctt tcgccaccat ctgggggatg atgtggttct gtttaccact     660

gatggagcac ataaaacatt cctgaaatgt ggggccctgc agggcctcta caccacggtg     720

gactttggaa caggcagcaa catcacagat gctttcctaa gccagaggaa gtgtgagccc     780

aaaggaccct tgatcaattc tgaattctat actggctggc tagatcactg gggccaacct     840

cactccacaa tcaagaccga agcagtggct tcctccctct atgatatact tgcccgtggg     900

gcgagtgtga acttgtacat gtttataggt gggaccaatt ttgcctattg gaatggggcc     960

aactcaccct atgcagcaca gcccaccagc tacgactatg atgccccact gagtgaggct    1020

ggggacctca ctgagaagta ttttgctctg cgaaacatca tccagaagtt tgaaaaagta    1080

ccagaaggtc ctatccctcc atctacacca aagtttgcat atggaaaggt cactttggaa    1140

aagttaaaga cagtgggagc agctctggac attctgtgtc cctctgggcc catcaaaagc    1200

ctttatccct tgacatttat ccaggtgaaa cagcattatg ggtttgtgct gtaccggaca    1260

acacttcctc aagattgcag caacccagca cctctctctt caccccctcaa tggagtccac    1320

gatcgagcat atgttgctgt ggatgggatc cccccaggggag tccttgagcg aaacaatgtg    1380

atcactctga acataacagg gaaagctgga gccactctgg accttctggt agagaacatg    1440

ggacgtgtga actatggtgc atatatcaac gattttaagg gtttggtttc taacctgact    1500

ctcagttcca atatcctcac ggactggacg atctttccac tggacactga ggatgcagtg    1560

tgcagccacc tgggggggctg gggacaccgt gacagtggcc accatgatga agcctgggcc    1620

cacaactcat ccaactacac gctcccggcc ttttatatgg ggaacttctc cattcccagt    1680

gggatcccag acttgcccca ggacaccttt atccagtttc ctggatggac caagggccag    1740

gtctggatta atggctttaa ccttggccgc tattggccag cccggggccc tcagttgacc    1800

ttgtttgtgc cccagcacat cctgatgacc tcggccccaa acaccatcac cgtgctggaa    1860

ctggagtggg caccctgcag cagtgatgat ccagaactat gtgctgtgac gttcgtggac    1920

aggccagtta ttggctcatc tgtgacctac gatcatccct ccaaacctgt tgaaaaaaga    1980
```

ctcatgcccc cacccccgca aaaaaacaaa gattcatggc tggaccatgt atga 2034

<210> SEQ ID NO 39
<211> LENGTH: 677
<212> TYPE: PRT
<213> ORGANISM: Homo sapiens

<400> SEQUENCE: 39

Met Pro Gly Phe Leu Val Arg Ile Leu Pro Leu Leu Leu Val Leu Leu
1 5 10 15

Leu Leu Gly Pro Thr Arg Gly Leu Arg Asn Ala Thr Gln Arg Met Phe
20 25 30

Glu Ile Asp Tyr Ser Arg Asp Ser Phe Leu Lys Asp Gly Gln Pro Phe
35 40 45

Arg Tyr Ile Ser Gly Ser Ile His Tyr Ser Arg Val Pro Arg Phe Tyr
50 55 60

Trp Lys Asp Arg Leu Leu Lys Met Lys Met Ala Gly Leu Asn Ala Ile
65 70 75 80

Gln Thr Tyr Val Pro Trp Asn Phe His Glu Pro Trp Pro Gly Gln Tyr
85 90 95

Gln Phe Ser Glu Asp His Asp Val Glu Tyr Phe Leu Arg Leu Ala His
100 105 110

Glu Leu Gly Leu Leu Val Ile Leu Arg Pro Gly Pro Tyr Ile Cys Ala
115 120 125

Glu Trp Glu Met Gly Gly Leu Pro Ala Trp Leu Leu Glu Lys Glu Ser
130 135 140

Ile Leu Leu Arg Ser Ser Asp Pro Asp Tyr Leu Ala Ala Val Asp Lys
145 150 155 160

Trp Leu Gly Val Leu Leu Pro Lys Met Lys Pro Leu Leu Tyr Gln Asn
165 170 175

Gly Gly Pro Val Ile Thr Val Gln Val Glu Asn Glu Tyr Gly Ser Tyr
180 185 190

Phe Ala Cys Asp Phe Asp Tyr Leu Arg Phe Leu Gln Lys Arg Phe Arg
195 200 205

His His Leu Gly Asp Asp Val Val Leu Phe Thr Thr Asp Gly Ala His
210 215 220

Lys Thr Phe Leu Lys Cys Gly Ala Leu Gln Gly Leu Tyr Thr Thr Val
225 230 235 240

Asp Phe Gly Thr Gly Ser Asn Ile Thr Asp Ala Phe Leu Ser Gln Arg
245 250 255

Lys Cys Glu Pro Lys Gly Pro Leu Ile Asn Ser Glu Phe Tyr Thr Gly
260 265 270

Trp Leu Asp His Trp Gly Gln Pro His Ser Thr Ile Lys Thr Glu Ala
275 280 285

Val Ala Ser Ser Leu Tyr Asp Ile Leu Ala Arg Gly Ala Ser Val Asn
290 295 300

Leu Tyr Met Phe Ile Gly Gly Thr Asn Phe Ala Tyr Trp Asn Gly Ala
305 310 315 320

Asn Ser Pro Tyr Ala Ala Gln Pro Thr Ser Tyr Asp Tyr Asp Ala Pro
325 330 335

Leu Ser Glu Ala Gly Asp Leu Thr Glu Lys Tyr Phe Ala Leu Arg Asn
340 345 350

Ile Ile Gln Lys Phe Glu Lys Val Pro Glu Gly Pro Ile Pro Pro Ser
355 360 365

```
Thr Pro Lys Phe Ala Tyr Gly Lys Val Thr Leu Glu Lys Leu Lys Thr
    370                 375                 380

Val Gly Ala Ala Leu Asp Ile Leu Cys Pro Ser Gly Pro Ile Lys Ser
385                 390                 395                 400

Leu Tyr Pro Leu Thr Phe Ile Gln Val Lys Gln His Tyr Gly Phe Val
                405                 410                 415

Leu Tyr Arg Thr Thr Leu Pro Gln Asp Cys Ser Asn Pro Ala Pro Leu
            420                 425                 430

Ser Ser Pro Leu Asn Gly Val His Asp Arg Ala Tyr Val Ala Val Asp
        435                 440                 445

Gly Ile Pro Gln Gly Val Leu Glu Arg Asn Asn Val Ile Thr Leu Asn
    450                 455                 460

Ile Thr Gly Lys Ala Gly Ala Thr Leu Asp Leu Leu Val Glu Asn Met
465                 470                 475                 480

Gly Arg Val Asn Tyr Gly Ala Tyr Ile Asn Asp Phe Lys Gly Leu Val
                485                 490                 495

Ser Asn Leu Thr Leu Ser Ser Asn Ile Leu Thr Asp Trp Thr Ile Phe
            500                 505                 510

Pro Leu Asp Thr Glu Asp Ala Val Arg Ser His Leu Gly Gly Trp Gly
        515                 520                 525

His Arg Asp Ser Gly His His Asp Glu Ala Trp Ala His Asn Ser Ser
    530                 535                 540

Asn Tyr Thr Leu Pro Ala Phe Tyr Met Gly Asn Phe Ser Ile Pro Ser
545                 550                 555                 560

Gly Ile Pro Asp Leu Pro Gln Asp Thr Phe Ile Gln Phe Pro Gly Trp
                565                 570                 575

Thr Lys Gly Gln Val Trp Ile Asn Gly Phe Asn Leu Gly Arg Tyr Trp
            580                 585                 590

Pro Ala Arg Gly Pro Gln Leu Thr Leu Phe Val Pro Gln His Ile Leu
        595                 600                 605

Met Thr Ser Ala Pro Asn Thr Ile Thr Val Leu Glu Leu Glu Trp Ala
    610                 615                 620

Pro Cys Ser Ser Asp Asp Pro Glu Leu Cys Ala Val Thr Phe Val Asp
625                 630                 635                 640

Arg Pro Val Ile Gly Ser Ser Val Thr Tyr Asp His Pro Ser Lys Pro
                645                 650                 655

Val Glu Lys Arg Leu Met Pro Pro Pro Pro Gln Lys Asn Lys Asp Ser
            660                 665                 670

Trp Leu Asp His Val
        675
```

<210> SEQ ID NO 40
<211> LENGTH: 1590
<212> TYPE: DNA
<213> ORGANISM: Homo sapiens

<400> SEQUENCE: 40

```
atgacaagct ccaggctttg gttttcgctg ctgctggcgg cagcgttcgc aggacgggcg     60

acggccctct ggccctggcc tcagaacttc caaacctccg accagcgcta cgtcctttac    120

ccgaacaact ttcaattcca gtacgatgtc agctcggccg cgcagcccgg ctgctcagtc    180

ctcgacgagg ccttccagcg ctatcgtgac ctgcttttcg gttccgggtc ttggccccgt    240

ccttacctca cagggaaacg gcatacactg gagaagaatg tgttggttgt ctctgtagtc    300
```

```
acacctggat gtaaccagct tcctactttg gagtcagtgg agaattatac cctgaccata    360

aatgatgacc agtgtttact cctctctgag actgtctggg gagctctccg aggtctggag    420

acttttagcc agcttgtttg gaaatctgct gagggcacat tctttatcaa caagactgag    480

attgaggact ttccccgctt tcctcaccgg ggcttgctgt tggatacatc tcgccattac    540

ctgccactct ctagcatcct ggacactctg gatgtcatgg cgtacaataa attgaacgtg    600

ttccactggc atctggtaga tgatccttcc ttcccatatg agagcttcac ttttccagag    660

ctcatgagaa aggggtccta caaccctgtc acccacatct acacagcaca ggatgtgaag    720

gaggtcattg aatacgcacg gctccggggt atccgtgtgc ttgcagagtt tgacactcct    780

ggccacactt tgtcctgggg accaggtatc cctggattac tgactccttg ctactctggg    840

tctgagccct ctggcacctt tggaccagtg aatcccagtc tcaataatac ctatgagttc    900

atgagcacat tcttcttaga agtcagctct gtcttcccag atttttatct tcatcttgga    960

ggagatgagg ttgatttcac ctgctggaag tccaacccag agatccagga ctttatgagg   1020

aagaaaggct tcggtgagga cttcaagcag ctggagtcct tctacatcca gacgctgctg   1080

gacatcgtct cttcttatgg caagggctat gtggtgtggc aggaggtgtt tgataataaa   1140

gtaaagattc agccagacac aatcatacag gtgtggcgag aggatattcc agtgaactat   1200

atgaaggagc tggaactggt caccaaggcc ggcttccggg cccttctctc tgcccccctgg  1260

tacctgaacc gtatatccta tggccctgac tggaaggatt tctacatagt ggaacccctg   1320

gcatttgaag gtacccctga gcagaaggct ctggtgattg gtggagaggc ttgtatgtgg   1380

ggagaatatg tggacaacac aaacctggtc cccaggctct ggcccagagc aggggctgtt   1440

gccgaaaggc tgtggagcaa caagttgaca tctgacctga catttgccta tgaacgtttg   1500

tcacacttcc gctgtgaatt gctgaggcga ggtgtccagg cccaacccct caatgtaggc   1560

ttctgtgagc aggagtttga acagacctga                                     1590
```

```
<210> SEQ ID NO 41
<211> LENGTH: 529
<212> TYPE: PRT
<213> ORGANISM: Homo sapiens

<400> SEQUENCE: 41

Met Thr Ser Ser Arg Leu Trp Phe Ser Leu Leu Leu Ala Ala Ala Phe
1               5                   10                  15

Ala Gly Arg Ala Thr Ala Leu Trp Pro Trp Pro Gln Asn Phe Gln Thr
            20                  25                  30

Ser Asp Gln Arg Tyr Val Leu Tyr Pro Asn Asn Phe Gln Phe Gln Tyr
        35                  40                  45

Asp Val Ser Ser Ala Ala Gln Pro Gly Cys Ser Val Leu Asp Glu Ala
    50                  55                  60

Phe Gln Arg Tyr Arg Asp Leu Leu Phe Gly Ser Gly Ser Trp Pro Arg
65                  70                  75                  80

Pro Tyr Leu Thr Gly Lys Arg His Thr Leu Glu Lys Asn Val Leu Val
                85                  90                  95

Val Ser Val Val Thr Pro Gly Cys Asn Gln Leu Pro Thr Leu Glu Ser
            100                 105                 110

Val Glu Asn Tyr Thr Leu Thr Ile Asn Asp Asp Gln Cys Leu Leu Leu
        115                 120                 125

Ser Glu Thr Val Trp Gly Ala Leu Arg Gly Leu Glu Thr Phe Ser Gln
    130                 135                 140
```

```
Leu Val Trp Lys Ser Ala Glu Gly Thr Phe Phe Ile Asn Lys Thr Glu
145                 150                 155                 160

Ile Glu Asp Phe Pro Arg Phe Pro His Arg Gly Leu Leu Leu Asp Thr
                165                 170                 175

Ser Arg His Tyr Leu Pro Leu Ser Ser Ile Leu Asp Thr Leu Asp Val
            180                 185                 190

Met Ala Tyr Asn Lys Leu Asn Val Phe His Trp His Leu Val Asp Asp
        195                 200                 205

Pro Ser Phe Pro Tyr Glu Ser Phe Thr Phe Pro Glu Leu Met Arg Lys
    210                 215                 220

Gly Ser Tyr Asn Pro Val Thr His Ile Tyr Thr Ala Gln Asp Val Lys
225                 230                 235                 240

Glu Val Ile Glu Tyr Ala Arg Leu Arg Gly Ile Arg Val Leu Ala Glu
                245                 250                 255

Phe Asp Thr Pro Gly His Thr Leu Ser Trp Gly Pro Gly Ile Pro Gly
            260                 265                 270

Leu Leu Thr Pro Cys Tyr Ser Gly Ser Glu Pro Ser Gly Thr Phe Gly
        275                 280                 285

Pro Val Asn Pro Ser Leu Asn Asn Thr Tyr Glu Phe Met Ser Thr Phe
    290                 295                 300

Phe Leu Glu Val Ser Ser Val Phe Pro Asp Phe Tyr Leu His Leu Gly
305                 310                 315                 320

Gly Asp Glu Val Asp Phe Thr Cys Trp Lys Ser Asn Pro Glu Ile Gln
                325                 330                 335

Asp Phe Met Arg Lys Lys Gly Phe Gly Glu Asp Phe Lys Gln Leu Glu
            340                 345                 350

Ser Phe Tyr Ile Gln Thr Leu Leu Asp Ile Val Ser Ser Tyr Gly Lys
        355                 360                 365

Gly Tyr Val Val Trp Gln Glu Val Phe Asp Asn Lys Val Lys Ile Gln
    370                 375                 380

Pro Asp Thr Ile Ile Gln Val Trp Arg Glu Asp Ile Pro Val Asn Tyr
385                 390                 395                 400

Met Lys Glu Leu Glu Leu Val Thr Lys Ala Gly Phe Arg Ala Leu Leu
                405                 410                 415

Ser Ala Pro Trp Tyr Leu Asn Arg Ile Ser Tyr Gly Pro Asp Trp Lys
            420                 425                 430

Asp Phe Tyr Ile Val Glu Pro Leu Ala Phe Glu Gly Thr Pro Glu Gln
        435                 440                 445

Lys Ala Leu Val Ile Gly Gly Glu Ala Cys Met Trp Gly Glu Tyr Val
    450                 455                 460

Asp Asn Thr Asn Leu Val Pro Arg Leu Trp Pro Arg Ala Gly Ala Val
465                 470                 475                 480

Ala Glu Arg Leu Trp Ser Asn Lys Leu Thr Ser Asp Leu Thr Phe Ala
                485                 490                 495

Tyr Glu Arg Leu Ser His Phe Arg Cys Glu Leu Leu Arg Arg Gly Val
            500                 505                 510

Gln Ala Gln Pro Leu Asn Val Gly Phe Cys Glu Gln Glu Phe Glu Gln
        515                 520                 525

Thr


<210> SEQ ID NO 42
<211> LENGTH: 1671
<212> TYPE: DNA
<213> ORGANISM: Homo sapiens
```

<400> SEQUENCE: 42
atggagctgt gcgggctggg gctgccccgg ccgcccatgc tgctggcgct gctgttggcg 60
acactgctgg cggcgatgtt ggcgctgctg actcaggtgg cgctggtggt gcaggtggcg 120
gaggcggctc gggccccgag cgtctcggcc aagccggggc cggcgctgtg gcccctgccg 180
ctcttggtga agatgacccc gaacctgctg catctcgccc cggagaactt ctacatcagc 240
cacagcccca attccacggc gggcccctcc tgcaccctgc tggaggaagc gtttcgacga 300
tatcatggct atatttttgg tttctacaag tggcatcatg aacctgctga attccaggct 360
aaaacccagg ttcagcaact tcttgtctca atcacccttc agtcagagtg tgatgctttc 420
cccaacatat cttcagatga gtcttatact ttacttgtga aagaaccagt ggctgtcctt 480
aaggccaaca gagtttgggg agcattacga ggtttagaga cctttagcca gttagtttat 540
caagattctt atggaacttt caccatcaat gaatccacca ttattgattc tccaaggttt 600
tctcacagag gaattttgat tgatacatcc agacattatc tgccagttaa gattattctt 660
aaaactctgg atgccatggc ttttaataag tttaatgttc ttcactggca catagttgat 720
gaccagtctt tcccatatca gagcatcact tttcctgagt taagcaataa aggaagctat 780
tctttgtctc atgtttatac accaaatgat gtccgtatgg tgattgaata tgccagatta 840
cgaggaattc gagtcctgcc agaatttgat acccctgggc atacactatc ttggggaaaa 900
ggtcagaaag acctcctgac tccatgttac agtagacaaa acaagttgga ctcttttgga 960
cctataaacc ctactctgaa tacaacatac agcttcctta ctacattttt caaagaaatt 1020
agtgaggtgt ttccagatca attcattcat ttgggaggag atgaagtgga atttaaatgt 1080
tgggaatcaa atccaaaaat tcaagatttc atgaggcaaa aaggctttgg cacagatttt 1140
aagaaactag aatctttcta cattcaaaag gttttggata ttattgcaac cataaacaag 1200
ggatccattg tctggcagga ggtttttgat gataaagcaa agcttgcgcc gggcacaata 1260
gttgaagtat ggaaagacag cgcatatcct gaggaactca gtagagtcac agcatctggc 1320
ttccctgtaa tcctttctgc tccttggtac ttagatttga ttagctatgg acaagattgg 1380
aggaaatact ataaagtgga acctcttgat tttggcggta ctcagaaaca gaaacaactt 1440
ttcattggtg gagaagcttg tctatgggga gaatatgtgg atgcaactaa cctcactcca 1500
agattatggc ctcgggcaag tgctgttggt gagagactct ggagttccaa agatgtcaga 1560
gatatggatg acgcctatga cagactgaca aggcaccgct gcaggatggt cgaacgtgga 1620
atagctgcac aacctcttta tgctggatat tgtaaccatg agaacatgta a 1671

<210> SEQ ID NO 43
<211> LENGTH: 556
<212> TYPE: PRT
<213> ORGANISM: Homo sapiens

<400> SEQUENCE: 43

Met Glu Leu Cys Gly Leu Gly Leu Pro Arg Pro Pro Met Leu Leu Ala
1               5                   10                  15

Leu Leu Leu Ala Thr Leu Leu Ala Ala Met Leu Ala Leu Leu Thr Gln
            20                  25                  30

Val Ala Leu Val Val Gln Val Ala Glu Ala Ala Arg Ala Pro Ser Val
        35                  40                  45

Ser Ala Lys Pro Gly Pro Ala Leu Trp Pro Leu Pro Leu Ser Val Lys
    50                  55                  60

-continued

Met Thr Pro Asn Leu Leu His Leu Ala Pro Glu Asn Phe Tyr Ile Ser
65 70 75 80

His Ser Pro Asn Ser Thr Ala Gly Pro Ser Cys Thr Leu Leu Glu Glu
85 90 95

Ala Phe Arg Arg Tyr His Gly Tyr Ile Phe Gly Phe Tyr Lys Trp His
100 105 110

His Glu Pro Ala Glu Phe Gln Ala Lys Thr Gln Val Gln Gln Leu Leu
115 120 125

Val Ser Ile Thr Leu Gln Ser Glu Cys Asp Ala Phe Pro Asn Ile Ser
130 135 140

Ser Asp Glu Ser Tyr Thr Leu Leu Val Lys Glu Pro Val Ala Val Leu
145 150 155 160

Lys Ala Asn Arg Val Trp Gly Ala Leu Arg Gly Leu Glu Thr Phe Ser
165 170 175

Gln Leu Val Tyr Gln Asp Ser Tyr Gly Thr Phe Thr Ile Asn Glu Ser
180 185 190

Thr Ile Ile Asp Ser Pro Arg Phe Ser His Arg Gly Ile Leu Ile Asp
195 200 205

Thr Ser Arg His Tyr Leu Pro Val Lys Ile Ile Leu Lys Thr Leu Asp
210 215 220

Ala Met Ala Phe Asn Lys Phe Asn Val Leu His Trp His Ile Val Asp
225 230 235 240

Asp Gln Ser Phe Pro Tyr Gln Ser Ile Thr Phe Pro Glu Leu Ser Asn
245 250 255

Lys Gly Ser Tyr Ser Leu Ser His Val Tyr Thr Pro Asn Asp Val Arg
260 265 270

Met Val Ile Glu Tyr Ala Arg Leu Arg Gly Ile Arg Val Leu Pro Glu
275 280 285

Phe Asp Thr Pro Gly His Thr Leu Ser Trp Gly Lys Gly Gln Lys Asp
290 295 300

Leu Leu Thr Pro Cys Tyr Ser Arg Gln Asn Lys Leu Asp Ser Phe Gly
305 310 315 320

Pro Ile Asn Pro Thr Leu Asn Thr Thr Tyr Ser Phe Leu Thr Thr Phe
325 330 335

Phe Lys Glu Ile Ser Glu Val Phe Pro Asp Gln Phe Ile His Leu Gly
340 345 350

Gly Asp Glu Val Glu Phe Lys Cys Trp Glu Ser Asn Pro Lys Ile Gln
355 360 365

Asp Phe Met Arg Gln Lys Gly Phe Gly Thr Asp Phe Lys Lys Leu Glu
370 375 380

Ser Phe Tyr Ile Gln Lys Val Leu Asp Ile Ile Ala Thr Ile Asn Lys
385 390 395 400

Gly Ser Ile Val Trp Gln Glu Val Phe Asp Asp Lys Ala Lys Leu Ala
405 410 415

Pro Gly Thr Ile Val Glu Val Trp Lys Asp Ser Ala Tyr Pro Glu Glu
420 425 430

Leu Ser Arg Val Thr Ala Ser Gly Phe Pro Val Ile Leu Ser Ala Pro
435 440 445

Trp Tyr Leu Asp Leu Ile Ser Tyr Gly Gln Asp Trp Arg Lys Tyr Tyr
450 455 460

Lys Val Glu Pro Leu Asp Phe Gly Gly Thr Gln Lys Gln Lys Gln Leu
465 470 475 480

Phe Ile Gly Gly Glu Ala Cys Leu Trp Gly Glu Tyr Val Asp Ala Thr

```
                485                 490                 495

Asn Leu Thr Pro Arg Leu Trp Pro Arg Ala Ser Ala Val Gly Glu Arg
            500                 505                 510

Leu Trp Ser Ser Lys Asp Val Arg Asp Met Asp Asp Ala Tyr Asp Arg
        515                 520                 525

Leu Thr Arg His Arg Cys Arg Met Val Glu Arg Gly Ile Ala Ala Gln
    530                 535                 540

Pro Leu Tyr Ala Gly Tyr Cys Asn His Glu Asn Met
545                 550                 555


<210> SEQ ID NO 44
<211> LENGTH: 582
<212> TYPE: DNA
<213> ORGANISM: Homo sapiens

<400> SEQUENCE: 44

atgcagtccc tgatgcaggc tcccctcctg atcgccctgg gcttgcttct cgcggcccct      60

gcgcaagccc acctgaaaaa gccatcccag ctcagtagct tttcctggga taactgtgat     120

gaagggaagg accctgcggt gatcagaagc ctgactctgg agcctgaccc catcatcgtt     180

cctggaaatg tgaccctcag tgtcatgggc agcaccagtg tcccccctgag ttctcctctg    240

aaggtggatt tagttttgga gaaggaggtg gctggcctct ggatcaagat cccatgcaca     300

gactacattg gcagctgtac ctttgaacac ttctgtgatg tgcttgacat gttaattcct     360

actggggagc cctgcccaga gcccctgcgt acctatgggc ttccttgcca ctgtcccttc     420

aaagaaggaa cctactcact gcccaagagc gaattcgttg tgcctgacct ggagctgccc     480

agttggctca ccaccgggaa ctaccgcata gagagcgtcc tgagcagcag tgggaagcgt     540

ctgggctgca tcaagatcgc tgcctctcta aagggcatat aa                        582


<210> SEQ ID NO 45
<211> LENGTH: 193
<212> TYPE: PRT
<213> ORGANISM: Homo sapiens

<400> SEQUENCE: 45

Met Gln Ser Leu Met Gln Ala Pro Leu Leu Ile Ala Leu Gly Leu Leu
1               5                   10                  15

Leu Ala Ala Pro Ala Gln Ala His Leu Lys Lys Pro Ser Gln Leu Ser
            20                  25                  30

Ser Phe Ser Trp Asp Asn Cys Asp Glu Gly Lys Asp Pro Ala Val Ile
        35                  40                  45

Arg Ser Leu Thr Leu Glu Pro Asp Pro Ile Ile Val Pro Gly Asn Val
    50                  55                  60

Thr Leu Ser Val Met Gly Ser Thr Ser Val Pro Leu Ser Ser Pro Leu
65                  70                  75                  80

Lys Val Asp Leu Val Leu Glu Lys Glu Val Ala Gly Leu Trp Ile Lys
                85                  90                  95

Ile Pro Cys Thr Asp Tyr Ile Gly Ser Cys Thr Phe Glu His Phe Cys
            100                 105                 110

Asp Val Leu Asp Met Leu Ile Pro Thr Gly Glu Pro Cys Pro Glu Pro
        115                 120                 125

Leu Arg Thr Tyr Gly Leu Pro Cys His Cys Pro Phe Lys Glu Gly Thr
    130                 135                 140

Tyr Ser Leu Pro Lys Ser Glu Phe Val Val Pro Asp Leu Glu Leu Pro
145                 150                 155                 160
```

```
Ser Trp Leu Thr Thr Gly Asn Tyr Arg Ile Glu Ser Val Leu Ser Ser
                165                 170                 175

Ser Gly Lys Arg Leu Gly Cys Ile Lys Ile Ala Ala Ser Leu Lys Gly
            180                 185                 190

Ile


<210> SEQ ID NO 46
<211> LENGTH: 1611
<212> TYPE: DNA
<213> ORGANISM: Homo sapiens

<400> SEQUENCE: 46

atggagtttt caagtccttc cagagaggaa tgtcccaagc ctttgagtag ggtaagcatc      60

atggctggca gcctcacagg attgcttcta cttcaggcag tgtcgtgggc atcaggtgcc     120

cgcccctgca tccctaaaag cttcggctac agctcggtgg tgtgtgtctg caatgccaca     180

tactgtgact cctttgaccc cccgaccttt cctgcccttg gtaccttcag ccgctatgag     240

agtacacgca gtgggcgacg gatggagctg agtatggggc ccatccaggc taatcacacg     300

ggcacaggcc tgctactgac cctgcagcca gaacagaagt tccagaaagt gaagggattt     360

ggaggggcca tgacagatgc tgctgctctc aacatccttg ccctgtcacc ccctgcccaa     420

aatttgctac ttaaatcgta cttctctgaa gaaggaatcg gatataacat catccgggta     480

cccatggcca gctgtgactt ctccatccgc acctacacct atgcagacac ccctgatgat     540

ttccagttgc acaacttcag cctcccagag gaagatacca agctcaagat acccctgatt     600

caccgagccc tgcagttggc ccagcgtccc gtttcactcc ttgccagccc ctggacatca     660

cccacttggc tcaagaccaa tggagcggtg aatgggaagg ggtcactcaa gggacagccc     720

ggagacatct accaccagac ctgggccaga tactttgtga agttcctgga tgcctatgct     780

gagcacaagt tacagttctg ggcagtgaca gctgaaaatg agccttctgc tgggctgttg     840

agtggatacc ccttccagtg cctgggcttc acccctgaac atcagcgaga cttcattgcc     900

cgtgacctag gtcctaccct cgccaacagt actcaccaca atgtccgcct actcatgctg     960

gatgaccaac gcttgctgct gccccactgg gcaaaggtgg tactgacaga cccagaagca    1020

gctaaatatg ttcatggcat tgctgtacat tggtacctgg actttctggc tccagccaaa    1080

gccaccctag gggagacaca ccgcctgttc cccaacacca tgctctttgc ctcagaggcc    1140

tgtgtgggct ccaagttctg ggagcagagt gtgcggctag gctcctggga tcgagggatg    1200

cagtacagcc acagcatcat cacgaacctc ctgtaccatg tggtcggctg gaccgactgg    1260

aaccttgccc tgaaccccga aggaggaccc aattgggtgc gtaactttgt cgacagtccc    1320

atcattgtag acatcaccaa ggacacgttt tacaaacagc ccatgttcta ccaccttggc    1380

cacttcagca agttcattcc tgagggctcc cagagagtgg ggctggttgc cagtcagaag    1440

aacgacctgg acgcagtggc actgatgcat cccgatggct ctgctgttgt ggtcgtgcta    1500

aaccgctcct ctaaggatgt gcctcttacc atcaaggatc ctgctgtggg cttcctggag    1560

acaatctcac ctggctactc cattcacacc tacctgtggc gtcgccagtg a             1611


<210> SEQ ID NO 47
<211> LENGTH: 536
<212> TYPE: PRT
<213> ORGANISM: Homo sapiens

<400> SEQUENCE: 47
```

```
Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
    290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
        355                 360                 365

Leu Phe Pro Asn Thr Met Leu Phe Ala Ser Glu Ala Cys Val Gly Ser
    370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
```

```
            420                 425                 430

Val Arg Asn Phe Val Asp Ser Pro Ile Ile Val Asp Ile Thr Lys Asp
        435                 440                 445

Thr Phe Tyr Lys Gln Pro Met Phe Tyr His Leu Gly His Phe Ser Lys
    450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
        515                 520                 525

His Thr Tyr Leu Trp Arg Arg Gln
    530                 535


<210> SEQ ID NO 48
<211> LENGTH: 1575
<212> TYPE: DNA
<213> ORGANISM: Homo sapiens

<400> SEQUENCE: 48

atgtacgccc tcttcctcct ggccagcctc ctgggcgcgg ctctagccgg cccggtcctt      60

ggactgaaag aatgcaccag ggctcggca gtgtggtgcc agaatgtgaa gacggcgtcc      120

gactgcgggg cagtgaagca ctgcctgcag accgtttgga acaagccaac agtgaaatcc     180

cttccctgcg acatatgcaa agacgttgtc accgcagctg gtgatatgct gaaggacaat     240

gccactgagg aggagatcct tgtttacttg gagaagacct gtgactggct tccgaaaccg     300

aacatgtctg cttcatgcaa ggagatagtg gactcctacc tccctgtcat cctggacatc     360

attaaaggag aaatgagccg tcctggggag gtgtgctctg ctctcaacct ctgcgagtct     420

ctccagaagc acctagcaga gctgaatcac cagaagcagc tggagtccaa taagatccca     480

gagctggaca tgactgaggt ggtggccccc ttcatggcca acatccctct cctcctctac     540

cctcaggacg gcccccgcag caagccccag ccaaaggata atggggacgt ttgccaggac     600

tgcattcaga tggtgactga catccagact gctgtacgga ccaactccac ctttgtccag     660

gccttggtgg aacatgtcaa ggaggagtgt gaccgcctgg gccctggcat ggccgacata     720

tgcaagaact atatcagcca gtattctgaa attgctatcc agatgatgat gcacatgcaa     780

cccaaggaga tctgtgcgct ggttgggttc tgtgatgagg tgaaagagat gcccatgcag     840

actctggtcc ccgccaaagt ggcctccaag aatgtcatcc ctgccctgga actggtggag     900

cccattaaga agcacgaggt cccagcaaag tctgatgttt actgtgaggt gtgtgaattc     960

ctggtgaagg aggtgaccaa gctgattgac aacaacaaga ctgagaaaga aatactcgac    1020

gcttttgaca aaatgtgctc gaagctgccg aagtccctgt cggaagagtg ccaggaggtg    1080

gtggacacgt acggcagctc catcctgtcc atcctgctgg aggaggtcag ccctgagctg    1140

gtgtgcagca tgctgcacct ctgctctggc acgcggctgc ctgcactgac cgttcacgtg    1200

actcagccaa aggacggtgg cttctgcgaa gtgtgcaaga agctggtggg ttatttggat    1260

cgcaacctgg agaaaaacag caccaagcag gagatcctgg ctgctcttga gaaaggctgc    1320

agcttcctgc cagaccctta ccagaagcag tgtgatcagt ttgtggcaga gtacgagccc    1380

gtgctgatcg agatcctggt ggaggtgatg gatccttcct tcgtgtgctt gaaaattgga    1440
```

```
gcctgcccct cggcccataa gcccttgttg ggaactgaga agtgtatatg gggcccaagc   1500

tactggtgcc agaacacaga gacagcagcc cagtgcaatg ctgtcgagca ttgcaaacgc   1560

catgtgtgga actag                                                    1575


<210> SEQ ID NO 49
<211> LENGTH: 524
<212> TYPE: PRT
<213> ORGANISM: Homo sapiens

<400> SEQUENCE: 49

Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Glu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
        115                 120                 125

Gly Glu Val Cys Ser Ala Leu Asn Leu Cys Glu Ser Leu Gln Lys His
    130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

Asp Asn Gly Asp Val Cys Gln Asp Cys Ile Gln Met Val Thr Asp Ile
        195                 200                 205

Gln Thr Ala Val Arg Thr Asn Ser Thr Phe Val Gln Ala Leu Val Glu
    210                 215                 220

His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
                245                 250                 255

Met His Met Gln Pro Lys Glu Ile Cys Ala Leu Val Gly Phe Cys Asp
            260                 265                 270

Glu Val Lys Glu Met Pro Met Gln Thr Leu Val Pro Ala Lys Val Ala
        275                 280                 285

Ser Lys Asn Val Ile Pro Ala Leu Glu Leu Val Glu Pro Ile Lys Lys
    290                 295                 300

His Glu Val Pro Ala Lys Ser Asp Val Tyr Cys Glu Val Cys Glu Phe
305                 310                 315                 320

Leu Val Lys Glu Val Thr Lys Leu Ile Asp Asn Asn Lys Thr Glu Lys
                325                 330                 335

Glu Ile Leu Asp Ala Phe Asp Lys Met Cys Ser Lys Leu Pro Lys Ser
            340                 345                 350
```

Leu Ser Glu Glu Cys Gln Glu Val Val Asp Thr Tyr Gly Ser Ser Ile
355 360 365

Leu Ser Ile Leu Leu Glu Glu Val Ser Pro Glu Leu Val Cys Ser Met
370 375 380

Leu His Leu Cys Ser Gly Thr Arg Leu Pro Ala Leu Thr Val His Val
385 390 395 400

Thr Gln Pro Lys Asp Gly Gly Phe Cys Glu Val Cys Lys Lys Leu Val
405 410 415

Gly Tyr Leu Asp Arg Asn Leu Glu Lys Asn Ser Thr Lys Gln Glu Ile
420 425 430

Leu Ala Ala Leu Glu Lys Gly Cys Ser Phe Leu Pro Asp Pro Tyr Gln
435 440 445

Lys Gln Cys Asp Gln Phe Val Ala Glu Tyr Glu Pro Val Leu Ile Glu
450 455 460

Ile Leu Val Glu Val Met Asp Pro Ser Phe Val Cys Leu Lys Ile Gly
465 470 475 480

Ala Cys Pro Ser Ala His Lys Pro Leu Leu Gly Thr Glu Lys Cys Ile
485 490 495

Trp Gly Pro Ser Tyr Trp Cys Gln Asn Thr Glu Thr Ala Ala Gln Cys
500 505 510

Asn Ala Val Glu His Cys Lys Arg His Val Trp Asn
515 520

<210> SEQ ID NO 50
<211> LENGTH: 80
<212> TYPE: PRT
<213> ORGANISM: Homo sapiens

<400> SEQUENCE: 50

Ser Asp Val Tyr Cys Glu Val Cys Glu Phe Leu Val Lys Glu Val Thr
1 5 10 15

Lys Leu Ile Asp Asn Asn Lys Thr Glu Lys Glu Ile Leu Asp Ala Phe
20 25 30

Asp Lys Met Cys Ser Lys Leu Pro Lys Ser Leu Ser Glu Glu Cys Gln
35 40 45

Glu Val Val Asp Thr Tyr Gly Ser Ser Ile Leu Ser Ile Leu Leu Glu
50 55 60

Glu Val Ser Pro Glu Leu Val Cys Ser Met Leu His Leu Cys Ser Gly
65 70 75 80

<210> SEQ ID NO 51
<211> LENGTH: 79
<212> TYPE: PRT
<213> ORGANISM: Homo sapiens

<400> SEQUENCE: 51

Gly Asp Val Cys Gln Asp Cys Ile Gln Met Val Thr Asp Ile Gln Thr
1 5 10 15

Ala Val Arg Thr Asn Ser Thr Phe Val Gln Ala Leu Val Glu His Val
20 25 30

Lys Glu Glu Cys Asp Arg Leu Gly Pro Gly Met Ala Asp Ile Cys Lys
35 40 45

Asn Tyr Ile Ser Gln Tyr Ser Glu Ile Ala Ile Gln Met Met Met His
50 55 60

Met Gln Pro Lys Glu Ile Cys Ala Leu Val Gly Phe Cys Asp Glu
65 70 75

<210> SEQ ID NO 52
<211> LENGTH: 1272
<212> TYPE: DNA
<213> ORGANISM: Homo sapiens

<400> SEQUENCE: 52
atgggcatgt accctggcgt cctggtgccc agctcccggg ggggcctgcc cctggaggag 60
gtgaccgtgg ccgaagtcct ggctgcccga ggctacctca caggaatggc cggcaagtgg 120
caccttgggg tggggcctga gggggccttc ctgccccccc atcagggctt ccatcgattt 180
ctaggcatcc cgtactccca cgaccagggc ccctgccaga acctgacctg cttcccgccg 240
gccactcctt gcgacggtgg ctgtgaccag ggcctggtcc ccatcccact gttggccaac 300
ctgtccgtgg aggcgcagcc cccctggctg cccggactag aggcccgcta catggctttc 360
gcccatgacc tcatggccga cgcccagcgc caggatcgcc ccttcttcct gtactatgcc 420
tctcaccaca cccactaccc tcagttcagt gggcagagct ttgcagagcg ttcaggccgc 480
gggccatttg gggactccct gatggagctg gatgcagctg tggggaccct gatgacagcc 540
ataggggacc tggggctgct tgaagagacg ctggtcatct tcactgcaga caatggacct 600
gagaccatgc gtatgtcccg aggcggctgc tccggtctct tgcggtgtgg aaagggaacg 660
acctacgagg gcggtgtccg agagcctgcc ttggccttct ggccaggtca tatcgctccc 720
ggcgtgaccc acgagctggc cagctccctg gacctgctgc ctaccctggc agccctggct 780
ggggccccac tgcccaatgt caccttggat ggctttgacc tcagcccctt gctgctgggc 840
acaggcaaga gccctcggca gtctctcttc ttctacccgt cctacccaga cgaggtccgt 900
ggggtttttg ctgtgcggac tggaaagtac aaggctcact tcttcaccca gggctctgcc 960
cacagtgata ccactgcaga ccctgcctgc cacgcctcca gctctctgac tgctcatgag 1020
cccccgctgc tctatgacct gtccaaggac cctggtgaga actacaacct gctggggggt 1080
gtggccgggg ccaccccaga ggtgctgcaa gccctgaaac agcttcagct gctcaaggcc 1140
cagttagacg cagctgtgac cttcggcccc agccaggtgg cccggggcga ggaccccgcc 1200
ctgcagatct gctgtcatcc tggctgcacc ccccgcccag cttgctgcca ttgcccagat 1260
ccccatgcct ga 1272

<210> SEQ ID NO 53
<211> LENGTH: 507
<212> TYPE: PRT
<213> ORGANISM: Homo sapiens

<400> SEQUENCE: 53

Met Gly Ala Pro Arg Ser Leu Leu Leu Ala Leu Ala Ala Gly Leu Ala
1               5                   10                  15

Val Ala Arg Pro Pro Asn Ile Val Leu Ile Phe Ala Asp Asp Leu Gly
            20                  25                  30

Tyr Gly Asp Leu Gly Cys Tyr Gly His Pro Ser Ser Thr Thr Pro Asn
        35                  40                  45

Leu Asp Gln Leu Ala Ala Gly Gly Leu Arg Phe Thr Asp Phe Tyr Val
    50                  55                  60

Pro Val Ser Leu Cys Thr Pro Ser Arg Ala Ala Leu Leu Thr Gly Arg
65                  70                  75                  80

Leu Pro Val Arg Met Gly Met Tyr Pro Gly Val Leu Val Pro Ser Ser
                85                  90                  95

-continued

```
Arg Gly Gly Leu Pro Leu Glu Glu Val Thr Val Ala Glu Val Leu Ala
            100                 105                 110

Ala Arg Gly Tyr Leu Thr Gly Met Ala Gly Lys Trp His Leu Gly Val
        115                 120                 125

Gly Pro Glu Gly Ala Phe Leu Pro Pro His Gln Gly Phe His Arg Phe
    130                 135                 140

Leu Gly Ile Pro Tyr Ser His Asp Gln Gly Pro Cys Gln Asn Leu Thr
145                 150                 155                 160

Cys Phe Pro Pro Ala Thr Pro Cys Asp Gly Gly Cys Asp Gln Gly Leu
                165                 170                 175

Val Pro Ile Pro Leu Leu Ala Asn Leu Ser Val Glu Ala Gln Pro Pro
            180                 185                 190

Trp Leu Pro Gly Leu Glu Ala Arg Tyr Met Ala Phe Ala His Asp Leu
        195                 200                 205

Met Ala Asp Ala Gln Arg Gln Asp Arg Pro Phe Phe Leu Tyr Tyr Ala
    210                 215                 220

Ser His His Thr His Tyr Pro Gln Phe Ser Gly Gln Ser Phe Ala Glu
225                 230                 235                 240

Arg Ser Gly Arg Gly Pro Phe Gly Asp Ser Leu Met Glu Leu Asp Ala
                245                 250                 255

Ala Val Gly Thr Leu Met Thr Ala Ile Gly Asp Leu Gly Leu Leu Glu
            260                 265                 270

Glu Thr Leu Val Ile Phe Thr Ala Asp Asn Gly Pro Glu Thr Met Arg
        275                 280                 285

Met Ser Arg Gly Gly Cys Ser Gly Leu Leu Arg Cys Gly Lys Gly Thr
    290                 295                 300

Thr Tyr Glu Gly Gly Val Arg Glu Pro Ala Leu Ala Phe Trp Pro Gly
305                 310                 315                 320

His Ile Ala Pro Gly Val Thr His Glu Leu Ala Ser Ser Leu Asp Leu
                325                 330                 335

Leu Pro Thr Leu Ala Ala Leu Ala Gly Ala Pro Leu Pro Asn Val Thr
            340                 345                 350

Leu Asp Gly Phe Asp Leu Ser Pro Leu Leu Leu Gly Thr Gly Lys Ser
        355                 360                 365

Pro Arg Gln Ser Leu Phe Phe Tyr Pro Ser Tyr Pro Asp Glu Val Arg
    370                 375                 380

Gly Val Phe Ala Val Arg Thr Gly Lys Tyr Lys Ala His Phe Phe Thr
385                 390                 395                 400

Gln Gly Ser Ala His Ser Asp Thr Thr Ala Asp Pro Ala Cys His Ala
                405                 410                 415

Ser Ser Ser Leu Thr Ala His Glu Pro Pro Leu Leu Tyr Asp Leu Ser
            420                 425                 430

Lys Asp Pro Gly Glu Asn Tyr Asn Leu Leu Gly Gly Val Ala Gly Ala
        435                 440                 445

Thr Pro Glu Val Leu Gln Ala Leu Lys Gln Leu Gln Leu Leu Lys Ala
    450                 455                 460

Gln Leu Asp Ala Ala Val Thr Phe Gly Pro Ser Gln Val Ala Arg Gly
465                 470                 475                 480

Glu Asp Pro Ala Leu Gln Ile Cys Cys His Pro Gly Cys Thr Pro Arg
                485                 490                 495

Pro Ala Cys Cys His Cys Pro Asp Pro His Ala
            500                 505
```

<210> SEQ ID NO 54
<211> LENGTH: 1125
<212> TYPE: DNA
<213> ORGANISM: Homo sapiens

<400> SEQUENCE: 54

```
atggctgcgc ccgcactagg gctggtgtgt ggacgttgcc ctgagctggg tctcgtcctc      60

ttgctgctgc tgctctcgct gctgtgtgga gcggcaggga gccaggaggc cgggaccggt     120

gcgggcgcgg ggtcccttgc gggttcttgc ggctgcggca cgccccagcg gcctggcgcc     180

catggcagtt cggcagccgc tcaccgatac tcgcgggagg ctaacgctcc gggccccgta     240

cccggagagc ggcaactcgc gcactcaaag atggtcccca tccctgctgg agtatttaca     300

atgggcacag atgatcctca gataaagcag gatggggaag cacctgcgag gagagttact     360

attgatgcct tttacatgga tgcctatgaa gtcagtaata ctgaatttga gaagtttgtg     420

aactcaactg gctatttgac agaggctgag aagtttggcg actcctttgt ctttgaaggc     480

atgttgagtg agcaagtgaa gaccaatatt caacaggcag ttgcagctgc tccctggtgg     540

ttacctgtga aaggcgctaa ctggagacac ccagaagggc ctgactctac tattctgcac     600

aggccggatc atccagttct ccatgtgtcc tggaatgatg cggttgccta ctgcacttgg     660

gcagggaagc ggctgcccac ggaagctgag tgggaataca gctgtcgagg aggcctgcat     720

aatagacttt tcccctgggg caacaaactg cagcccaaag gccagcatta tgccaacatt     780

tggcagggcg agtttccggt gaccaacact ggtgaggatg gcttccaagg aactgcgcct     840

gttgatgcct tccctcccaa tggttatggc ttatacaaca tagtggggaa cgcatgggaa     900

tggacttcag actggtggac tgttcatcat tctgttgaag aaacgcttaa cccaaaaggt     960

ccccccttctg ggaaagaccg agtgaagaaa ggtggatcct acatgtgcca taggtcttat    1020

tgttacaggt atcgctgtgc tgctcggagc cagaacacac ctgatagctc tgcttcgaat    1080

ctgggattcc gctgtgcagc cgaccgcctg cccactatgg actga                     1125
```

<210> SEQ ID NO 55
<211> LENGTH: 374
<212> TYPE: PRT
<213> ORGANISM: Homo sapiens

<400> SEQUENCE: 55

```
Met Ala Ala Pro Ala Leu Gly Leu Val Cys Gly Arg Cys Pro Glu Leu
1               5                   10                  15

Gly Leu Val Leu Leu Leu Leu Leu Leu Ser Leu Leu Cys Gly Ala Ala
            20                  25                  30

Gly Ser Gln Glu Ala Gly Thr Gly Ala Gly Ala Gly Ser Leu Ala Gly
        35                  40                  45

Ser Cys Gly Cys Gly Thr Pro Gln Arg Pro Gly Ala His Gly Ser Ser
    50                  55                  60

Ala Ala Ala His Arg Tyr Ser Arg Glu Ala Asn Ala Pro Gly Pro Val
65                  70                  75                  80

Pro Gly Glu Arg Gln Leu Ala His Ser Lys Met Val Pro Ile Pro Ala
                85                  90                  95

Gly Val Phe Thr Met Gly Thr Asp Asp Pro Gln Ile Lys Gln Asp Gly
            100                 105                 110

Glu Ala Pro Ala Arg Arg Val Thr Ile Asp Ala Phe Tyr Met Asp Ala
        115                 120                 125

Tyr Glu Val Ser Asn Thr Glu Phe Glu Lys Phe Val Asn Ser Thr Gly
    130                 135                 140
```

```
Tyr Leu Thr Glu Ala Glu Lys Phe Gly Asp Ser Phe Val Phe Glu Gly
145                 150                 155                 160

Met Leu Ser Glu Gln Val Lys Thr Asn Ile Gln Gln Ala Val Ala Ala
                165                 170                 175

Ala Pro Trp Trp Leu Pro Val Lys Gly Ala Asn Trp Arg His Pro Glu
            180                 185                 190

Gly Pro Asp Ser Thr Ile Leu His Arg Pro Asp His Pro Val Leu His
        195                 200                 205

Val Ser Trp Asn Asp Ala Val Ala Tyr Cys Thr Trp Ala Gly Lys Arg
    210                 215                 220

Leu Pro Thr Glu Ala Glu Trp Glu Tyr Ser Cys Arg Gly Gly Leu His
225                 230                 235                 240

Asn Arg Leu Phe Pro Trp Gly Asn Lys Leu Gln Pro Lys Gly Gln His
                245                 250                 255

Tyr Ala Asn Ile Trp Gln Gly Glu Phe Pro Val Thr Asn Thr Gly Glu
            260                 265                 270

Asp Gly Phe Gln Gly Thr Ala Pro Val Asp Ala Phe Pro Pro Asn Gly
        275                 280                 285

Tyr Gly Leu Tyr Asn Ile Val Gly Asn Ala Trp Glu Trp Thr Ser Asp
    290                 295                 300

Trp Trp Thr Val His His Ser Val Glu Glu Thr Leu Asn Pro Lys Gly
305                 310                 315                 320

Pro Pro Ser Gly Lys Asp Arg Val Lys Lys Gly Gly Ser Tyr Met Cys
                325                 330                 335

His Arg Ser Tyr Cys Tyr Arg Tyr Arg Cys Ala Ala Arg Ser Gln Asn
            340                 345                 350

Thr Pro Asp Ser Ser Ala Ser Asn Leu Gly Phe Arg Cys Ala Ala Asp
        355                 360                 365

Arg Leu Pro Thr Met Asp
    370
```

<210> SEQ ID NO 56
<211> LENGTH: 1989
<212> TYPE: DNA
<213> ORGANISM: Homo sapiens

<400> SEQUENCE: 56

```
atggctgagt ggctactctc ggcttcctgg caacgccgag cgaaagctat gactgcggcc     60

gcgggttcgg cgggccgcgc cgcggtgccc ttgctgctgt gtgcgctgct ggcgcccggc    120

ggcgcgtacg tgctcgacga ctccgacggg ctgggccggg agttcgacgg catcggcgcg    180

gtcagcggcg gcgggccgaa ttttggtgcc tctttgcata ttttaaaagt ggaaataggt    240

ggtgatgggc agacaacaga cggcactgag ccctcccaca tgcattatgc actagatgag    300

aattatttcc gaggatacga gtggtggttg atgaaagaag ctaagaagag gaatcccaat    360

attacactca ttgggttgcc atggtcattc cctggatggc tgggaaaagg tttcgactgg    420

ccttatgtca atcttcagct gactgcctat tatgtcgtga cctggattgt gggcgccaag    480

cgttaccatg atttggacat tgattatatt ggaatttgga atgagaggtc atataatgcc    540

aattatatta agatattaag aaaaatgctg aattatcaag gtctccagcg agtgaaaatc    600

atagcaagtg ataatctctg ggagtccatc tctgcatcca tgctccttga tgccgaactc    660

ttcaaggtgg ttgatgttat aggggctcat tatcctggaa cccattcagc aaaagatgca    720

aagttgactg ggaagaagct ttggtcttct gaagacttta gcactttaaa tagtgacatg    780
```

```
ggtgcaggct gctggggtcg cattttaaat cagaattata tcaatggcta tatgacttcc    840

acaatcgcat ggaatttagt ggctagttac tatgaacagt tgccttatgg gagatgcggg    900

ttgatgacgg cccaggagcc atggagtggg cactacgtgg tagaatctcc tgtctgggta    960

tcagctcata ccactcagtt tactcaacct ggctggtatt acctgaagac agttggccat   1020

ttagagaaag gaggaagcta cgtagctctg actgatggct tagggaacct caccatcatc   1080

attgaaacca tgagtcataa acattctaag tgcatacggc catttcttcc ttatttcaat   1140

gtgtcacaac aatttgccac ctttgttctt aagggatctt ttagtgaaat accagagcta   1200

caggtatggt ataccaaact tggaaaaaca tccgaaagat ttctttttaa gcagctggat   1260

tctctatggc tccttgacag cgatggcagt ttcacactga gcctgcatga agatgagctg   1320

ttcacactca ccactctcac cactggtcgc aaaggcagct acccgcttcc tccaaaatcc   1380

cagcccttcc caagtaccta taaggatgat ttcaatgttg attacccatt ttttagtgaa   1440

gctccaaact ttgctgatca aactggtgta tttgaatatt ttacaaatat tgaagaccct   1500

ggcgagcatc acttcacgct acgccaagtt ctcaaccaga gacccattac atgggctgcc   1560

gatgcatcca acacaatcag tattatagga gactacaact ggaccaatct gactataaag   1620

tgtgatgtat acatagagac ccctgacaca ggaggtgtgt tcattgcagg aagagtaaat   1680

aaaggtggta ttttgattag aagtgccaga ggaattttct tctggatttt tgcaaatgga   1740

tcttacaggg ttacaggtga tttagctgga tggattatat atgctttagg acgtgttgaa   1800

gttacagcaa aaaaatggta tacactcacg ttaactatta agggtcattt cacctctggc   1860

atgctgaatg acaagtctct gtggacagac atccctgtga attttccaaa gaatggctgg   1920

gctgcaattg gaactcactc ctttgaattt gcacagtttg acaactttct tgtggaagcc   1980

acacgctaa                                                           1989
```

<210> SEQ ID NO 57
<211> LENGTH: 685
<212> TYPE: PRT
<213> ORGANISM: Homo sapiens

<400> SEQUENCE: 57

```
Met Ala Glu Trp Leu Leu Ser Ala Ser Trp Gln Arg Arg Ala Lys Ala
1               5                   10                  15

Met Thr Ala Ala Ala Gly Ser Ala Gly Arg Ala Ala Val Pro Leu Leu
            20                  25                  30

Leu Cys Ala Leu Leu Ala Pro Gly Gly Ala Tyr Val Leu Asp Asp Ser
        35                  40                  45

Asp Gly Leu Gly Arg Glu Phe Asp Gly Ile Gly Ala Val Ser Gly Gly
    50                  55                  60

Gly Ala Thr Ser Arg Leu Leu Val Asn Tyr Pro Glu Pro Tyr Arg Ser
65                  70                  75                  80

Gln Ile Leu Asp Tyr Leu Phe Lys Pro Asn Phe Gly Ala Ser Leu His
                85                  90                  95

Ile Leu Lys Val Glu Ile Gly Gly Asp Gly Gln Thr Thr Asp Gly Thr
            100                 105                 110

Glu Pro Ser His Met His Tyr Ala Leu Asp Glu Asn Tyr Phe Arg Gly
        115                 120                 125

Tyr Glu Trp Trp Leu Met Lys Glu Ala Lys Lys Arg Asn Pro Asn Ile
    130                 135                 140

Thr Leu Ile Gly Leu Pro Trp Ser Phe Pro Gly Trp Leu Gly Lys Gly
```

-continued

```
145                 150                 155                 160

Phe Asp Trp Pro Tyr Val Asn Leu Gln Leu Thr Ala Tyr Tyr Val Val
                165                 170                 175

Thr Trp Ile Val Gly Ala Lys Arg Tyr His Asp Leu Asp Ile Asp Tyr
            180                 185                 190

Ile Gly Ile Trp Asn Glu Arg Ser Tyr Asn Ala Asn Tyr Ile Lys Ile
        195                 200                 205

Leu Arg Lys Met Leu Asn Tyr Gln Gly Leu Gln Arg Val Lys Ile Ile
    210                 215                 220

Ala Ser Asp Asn Leu Trp Glu Ser Ile Ser Ala Ser Met Leu Leu Asp
225                 230                 235                 240

Ala Glu Leu Phe Lys Val Val Asp Val Ile Gly Ala His Tyr Pro Gly
                245                 250                 255

Thr His Ser Ala Lys Asp Ala Lys Leu Thr Gly Lys Lys Leu Trp Ser
            260                 265                 270

Ser Glu Asp Phe Ser Thr Leu Asn Ser Asp Met Gly Ala Gly Cys Trp
        275                 280                 285

Gly Arg Ile Leu Asn Gln Asn Tyr Ile Asn Gly Tyr Met Thr Ser Thr
    290                 295                 300

Ile Ala Trp Asn Leu Val Ala Ser Tyr Tyr Glu Gln Leu Pro Tyr Gly
305                 310                 315                 320

Arg Cys Gly Leu Met Thr Ala Gln Glu Pro Trp Ser Gly His Tyr Val
                325                 330                 335

Val Glu Ser Pro Val Trp Val Ser Ala His Thr Thr Gln Phe Thr Gln
            340                 345                 350

Pro Gly Trp Tyr Tyr Leu Lys Thr Val Gly His Leu Glu Lys Gly Gly
        355                 360                 365

Ser Tyr Val Ala Leu Thr Asp Gly Leu Gly Asn Leu Thr Ile Ile Ile
    370                 375                 380

Glu Thr Met Ser His Lys His Ser Lys Cys Ile Arg Pro Phe Leu Pro
385                 390                 395                 400

Tyr Phe Asn Val Ser Gln Gln Phe Ala Thr Phe Val Leu Lys Gly Ser
                405                 410                 415

Phe Ser Glu Ile Pro Glu Leu Gln Val Trp Tyr Thr Lys Leu Gly Lys
            420                 425                 430

Thr Ser Glu Arg Phe Leu Phe Lys Gln Leu Asp Ser Leu Trp Leu Leu
        435                 440                 445

Asp Ser Asp Gly Ser Phe Thr Leu Ser Leu His Glu Asp Glu Leu Phe
    450                 455                 460

Thr Leu Thr Thr Leu Thr Thr Gly Arg Lys Gly Ser Tyr Pro Leu Pro
465                 470                 475                 480

Pro Lys Ser Gln Pro Phe Pro Ser Thr Tyr Lys Asp Asp Phe Asn Val
                485                 490                 495

Asp Tyr Pro Phe Phe Ser Glu Ala Pro Asn Phe Ala Asp Gln Thr Gly
            500                 505                 510

Val Phe Glu Tyr Phe Thr Asn Ile Glu Asp Pro Gly Glu His His Phe
        515                 520                 525

Thr Leu Arg Gln Val Leu Asn Gln Arg Pro Ile Thr Trp Ala Ala Asp
    530                 535                 540

Ala Ser Asn Thr Ile Ser Ile Ile Gly Asp Tyr Asn Trp Thr Asn Leu
545                 550                 555                 560

Thr Ile Lys Cys Asp Val Tyr Ile Glu Thr Pro Asp Thr Gly Gly Val
                565                 570                 575
```

```
Phe Ile Ala Gly Arg Val Asn Lys Gly Gly Ile Leu Ile Arg Ser Ala
            580                 585                 590

Arg Gly Ile Phe Phe Trp Ile Phe Ala Asn Gly Ser Tyr Arg Val Thr
        595                 600                 605

Gly Asp Leu Ala Gly Trp Ile Ile Tyr Ala Leu Gly Arg Val Glu Val
    610                 615                 620

Thr Ala Lys Lys Trp Tyr Thr Leu Thr Leu Thr Ile Lys Gly His Phe
625                 630                 635                 640

Thr Ser Gly Met Leu Asn Asp Lys Ser Leu Trp Thr Asp Ile Pro Val
                645                 650                 655

Asn Phe Pro Lys Asn Gly Trp Ala Ala Ile Gly Thr His Ser Phe Glu
            660                 665                 670

Phe Ala Gln Phe Asp Asn Phe Leu Val Glu Ala Thr Arg
        675                 680                 685


<210> SEQ ID NO 58
<211> LENGTH: 1290
<212> TYPE: DNA
<213> ORGANISM: Homo sapiens

<400> SEQUENCE: 58

atgcagctga ggaacccaga actacatctg ggctgcgcgc ttgcgcttcg cttcctggcc     60

ctcgtttcct gggacatccc tggggctaga gcactggaca atggattggc aaggacgcct    120

accatgggct ggctgcactg ggagcgcttc atgtgcaacc ttgactgcca ggaagagcca    180

gattcctgca tcagtgagaa gctcttcatg gagatggcag agctcatggt ctcagaaggc    240

tggaaggatg caggttatga gtacctctgc attgatgact gttggatggc tccccaaaga    300

gattcagaag gcagacttca ggcagaccct cagcgctttc ctcatgggat tcgccagcta    360

gctaattatg ttcacagcaa aggactgaag ctagggattt atgcagatgt tggaaataaa    420

acctgcgcag gcttccctgg gagttttgga tactacgaca ttgatgccca gacctttgct    480

gactggggag tagatctgct aaaatttgat ggttgttact gtgacagttt ggaaaatttg    540

gcagatggtt ataagcacat gtccttggcc ctgaatagga ctggcagaag cattgtgtac    600

tcctgtgagt ggcctcttta tatgtggccc tttcaaaagc ccaattatac agaaatccga    660

cagtactgca atcactggcg aaattttgct gacattgatg attcctggaa aagtataaag    720

agtatcttgg actggacatc ttttaaccag gagagaattg ttgatgttgc tggaccaggg    780

ggttggaatg acccagatat gttagtgatt ggcaactttg gcctcagctg gaatcagcaa    840

gtaactcaga tggccctctg ggctatcatg gctgctcctt tattcatgtc taatgacctc    900

cgacacatca gccctcaagc caaagctctc cttcaggata aggacgtaat tgccatcaat    960

caggacccct tgggcaagca agggtaccag cttagacagg gagacaactt tgaagtgtgg   1020

gaacgacctc tctcaggctt agcctgggct gtagctatga taaaccggca ggagattggt   1080

ggacctcgct cttataccat cgcagttgct tccctgggta aaggagtggc ctgtaatcct   1140

gcctgcttca tcacacagct cctccctgtg aaaaggaagc tagggttcta tgaatggact   1200

tcaaggttaa gaagtcacat aaatcccaca ggcactgttt tgcttcagct agaaaataca   1260

atgcagatgt cattaaaaga cttactttaa                                     1290


<210> SEQ ID NO 59
<211> LENGTH: 429
<212> TYPE: PRT
<213> ORGANISM: Homo sapiens
```

<400> SEQUENCE: 59

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln

```
            405                 410                 415

Leu Glu Asn Thr Met Gln Met Ser Leu Lys Asp Leu Leu
        420                 425


<210> SEQ ID NO 60
<211> LENGTH: 1653
<212> TYPE: DNA
<213> ORGANISM: Homo sapiens

<400> SEQUENCE: 60

atgccgccac cccggaccgg ccgaggcctt ctctggctgg gtctggttct gagctccgtc      60

tgcgtcgccc tcggatccga aacgcaggcc aactcgacca cagatgctct gaacgttctt     120

ctcatcatcg tggatgacct gcgcccctcc ctgggctgtt atggggataa gctggtgagg     180

tccccaaata ttgaccaact ggcatcccac agcctcctct tccagaatgc ctttgcgcag     240

caagcagtgt gcgccccgag ccgcgtttct ttcctcactg gcaggagacc tgacaccacc     300

cgcctgtacg acttcaactc ctactggagg gtgcacgctg gaaacttctc caccatcccc     360

cagtacttca aggagaatgg ctatgtgacc atgtcggtgg gaaaagtctt tcaccctggg     420

atatcttcta accataccga tgattctccg tatagctggt cttttccacc ttatcatcct     480

tcctctgaga agtatgaaaa cactaagaca tgtcgagggc cagatggaga actccatgcc     540

aacctgcttt gccctgtgga tgtgctggat gttcccgagg gcaccttgcc tgacaaacag     600

agcactgagc aagccataca gttgttggaa aagatgaaaa cgtcagccag tcctttcttc     660

ctggccgttg ggtatcataa gccacacatc cccttcagat accccaagga atttcagaag     720

ttgtatccct tggagaacat caccctggcc cccgatcccg aggtccctga tggcctaccc     780

cctgtggcct acaacccctg gatggacatc aggcaacggg aagacgtcca agccttaaac     840

atcagtgtgc cgtatggtcc aattcctgtg gactttcagc ggaaaatccg ccagagctac     900

tttgcctctg tgtcatattt ggatacacag gtcggccgcc tcttgagtgc tttggacgat     960

cttcagctgg ccaacagcac catcattgca tttacctcgg atcatgggtg ggctctaggt    1020

gaacatggag aatgggccaa atacagcaat tttgatgttg ctacccatgt tcccctgata    1080

ttctatgttc ctggaaggac ggcttcactt ccggaggcag gcgagaagct tttcccttac    1140

ctcgaccctt ttgattccgc ctcacagttg atggagccag gcaggcaatc catggacctt    1200

gtggaacttg tgtctctttt tcccacgctg gctggacttg caggactgca ggttccacct    1260

cgctgccccg ttccttcatt tcacgttgag ctgtgcagag aaggcaagaa ccttctgaag    1320

cattttcgat tccgtgactt ggaagaggat ccgtacctcc ctggtaatcc ccgtgaactg    1380

attgcctata gccagtatcc ccggccttca gacatccctc agtggaattc tgacaagccg    1440

agtttaaaag atataaagat catgggctat tccatacgca ccatagacta taggtatact    1500

gtgtgggttg gcttcaatcc tgatgaattt ctagctaact tttctgacat ccatgcaggg    1560

gaactgtatt ttgtggattc tgacccattg caggatcaca atatgtataa tgattcccaa    1620

ggtggagatc ttttccagtt gttgatgcct tga                                 1653


<210> SEQ ID NO 61
<211> LENGTH: 550
<212> TYPE: PRT
<213> ORGANISM: Homo sapiens

<400> SEQUENCE: 61

Met Pro Pro Pro Arg Thr Gly Arg Gly Leu Leu Trp Leu Gly Leu Val
1               5                   10                  15
```

```
Leu Ser Ser Val Cys Val Ala Leu Gly Ser Glu Thr Gln Ala Asn Ser
            20                  25                  30

Thr Thr Asp Ala Leu Asn Val Leu Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
    210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
    290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Ile Phe Tyr Val Pro Gly Arg Thr Ala
        355                 360                 365

Ser Leu Pro Glu Ala Gly Glu Lys Leu Phe Pro Tyr Leu Asp Pro Phe
    370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430
```

```
Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
    450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
        515                 520                 525

Pro Leu Gln Asp His Asn Met Tyr Asn Asp Ser Gln Gly Gly Asp Leu
    530                 535                 540

Phe Gln Leu Leu Met Pro
545                 550


<210> SEQ ID NO 62
<211> LENGTH: 1962
<212> TYPE: DNA
<213> ORGANISM: Homo sapiens

<400> SEQUENCE: 62

atgcgtcccc tgcgcccccg cgccgcgctg ctggcgctcc tggcctcgct cctggccgcg     60

cccccggtgg ccccggccga ggccccgcac ctggtgcatg tggacgcggc ccgcgcgctg    120

tggcccctgc ggcgcttctg gaggagcaca ggcttctgcc ccccgctgcc acacagccag    180

gctgaccagt acgtcctcag ctgggaccag cagctcaacc tcgcctatgt gggcgccgtc    240

cctcaccgcg gcatcaagca ggtccggacc cactggctgc tggagcttgt caccaccagg    300

gggtccactg gacggggcct gagctacaac ttcacccacc tggacgggta cctggacctt    360

ctcagggaga accagctcct cccagggttt gagctgatgg gcagcgcctc gggccacttc    420

actgactttg aggacaagca gcaggtgttt gagtggaagg acttggtctc cagcctggcc    480

aggagataca tcggtaggta cggactggcg catgtttcca agtggaactt cgagacgtgg    540

aatgagccag accaccacga ctttgacaac gtctccatga ccatgcaagg cttcctgaac    600

tactacgatg cctgctcgga gggtctgcgc gccgccagcc ccgccctgcg gctgggaggc    660

cccggcgact ccttccacac cccaccgcga tccccgctga gctggggcct cctgcgccac    720

tgccacgacg gtaccaactt cttcactggg gaggcgggcg tgcggctgga ctacatctcc    780

ctccacagga agggtgcgcg cagctccatc tccatcctgg agcaggagaa ggtcgtcgcg    840

cagcagatcc ggcagctctt ccccaagttc gcggacaccc ccatttacaa cgacgaggcg    900

gacccgctgg tgggctggtc cctgccacag ccgtggaggg cggacgtgac ctacgcggcc    960

atggtggtga aggtcatcgc gcagcatcag aacctgctac tggccaacac cacctccgcc   1020

ttcccctacg cgctcctgag caacgacaat gccttcctga gctaccaccc gcaccccttc   1080

gcgcagcgca cgctcaccgc gcgcttccag gtcaacaaca cccgcccgcc gcacgtgcag   1140

ctgttgcgca agccggtgct cacggccatg gggctgctgg cgctgctgga tgaggagcag   1200

ctctgggccg aagtgtcgca ggccgggacc gtcctggaca gcaaccacac ggtgggcgtc   1260

ctggccagcg cccaccgccc ccagggcccg gccgacgcct ggcgcgccgc ggtgctgatc   1320

tacgcgagcg acgacacccg cgcccacccc aaccgcagcg tcgcggtgac cctgcggctg   1380

cgcggggtgc cccccggccc gggcctggtc tacgtcacgc gctacctgga caacgggctc   1440
```

```
tgcagccccg acggcgagtg gcggcgcctg ggccggcccg tcttccccac ggcagagcag   1500

ttccggcgca tgcgcgcggc tgaggacccg gtggccgcgg cgccccgccc cttacccgcc   1560

ggcggccgcc tgaccctgcg ccccgcgctg cggctgccgt cgcttttgct ggtgcacgtg   1620

tgtgcgcgcc ccgagaagcc gcccgggcag gtcacgcggc tccgcgccct gcccctgacc   1680

caagggcagc tggttctggt ctggtcggat gaacacgtgg gctccaagtg cctgtggaca   1740

tacgagatcc agttctctca ggacggtaag gcgtacaccc cggtcagcag gaagccatcg   1800

accttcaacc tctttgtgtt cagcccagac acaggtgctg tctctggctc ctaccgagtt   1860

cgagccctgg actactgggc ccgaccaggc cccttctcgg accctgtgcc gtacctggag   1920

gtccctgtgc caagagggcc cccatccccg ggcaatccat ga                      1962
```

<210> SEQ ID NO 63
<211> LENGTH: 653
<212> TYPE: PRT
<213> ORGANISM: Homo sapiens

<400> SEQUENCE: 63

```
Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
            20                  25                  30

His Val Asp Ala Ala Arg Ala Leu Trp Pro Leu Arg Arg Phe Trp Arg
        35                  40                  45

Ser Thr Gly Phe Cys Pro Pro Leu Pro His Ser Gln Ala Asp Gln Tyr
    50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
            100                 105                 110

His Leu Asp Gly Tyr Leu Asp Leu Leu Arg Glu Asn Gln Leu Leu Pro
        115                 120                 125

Gly Phe Glu Leu Met Gly Ser Ala Ser Gly His Phe Thr Asp Phe Glu
    130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
        195                 200                 205

Leu Arg Ala Ala Ser Pro Ala Leu Arg Leu Gly Gly Pro Gly Asp Ser
    210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
            260                 265                 270

Leu Glu Gln Glu Lys Val Val Ala Gln Gln Ile Arg Gln Leu Phe Pro
```

```
        275                 280                 285

Lys Phe Ala Asp Thr Pro Ile Tyr Asn Asp Glu Ala Asp Pro Leu Val
    290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
        355                 360                 365

Phe Gln Val Asn Asn Thr Arg Pro Pro His Val Gln Leu Leu Arg Lys
    370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Asp Thr Arg Ala
        435                 440                 445

His Pro Asn Arg Ser Val Ala Val Thr Leu Arg Leu Arg Gly Val Pro
    450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
        515                 520                 525

Ala Leu Arg Leu Pro Ser Leu Leu Leu Val His Val Cys Ala Arg Pro
    530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
            580                 585                 590

Thr Pro Val Ser Arg Lys Pro Ser Thr Phe Asn Leu Phe Val Phe Ser
        595                 600                 605

Pro Asp Thr Gly Ala Val Ser Gly Ser Tyr Arg Val Arg Ala Leu Asp
    610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
                645                 650
```

<210> SEQ ID NO 64
<211> LENGTH: 1509
<212> TYPE: DNA
<213> ORGANISM: Homo sapiens

<400> SEQUENCE: 64

```
atgagctgcc ccgtgcccgc ctgctgcgcg ctgctgctag tcctggggct ctgccgggcg      60

cgtccccgga acgcactgct gctcctcgcg gatgacggag gctttgagag tggcgcgtac     120

aacaacagcg ccatcgccac cccgcacctg gacgccttgg cccgccgcag cctcctcttt     180

cgcaatgcct tcacctcggt cagcagctgc tctcccagcc gcgccagcct cctcactggc     240

ctgccccagc atcagaatgg gatgtacggg ctgcaccagg acgtgcacca cttcaactcc     300

ttcgacaagg tgcggagcct gccgctgctg ctcagccaag ctggtgtgcg cacaggcatc     360

atcgggaaga agcacgtggg gccggagacc gtgtacccgt ttgactttgc gtacacggag     420

gagaatggct ccgtcctcca ggtggggcgg aacatcacta gaattaagct gctcgtccgg     480

aaattcctgc agactcagga tgaccggcct ttcttcctct acgtcgcctt ccacgacccc     540

caccgctgtg ggcactccca gccccagtac ggaaccttct gtgagaagtt tggcaacgga     600

gagagcggca tgggtcgtat cccagactgg acccccccagg cctacgaccc actggacgtg     660

ctggtgcctt acttcgtccc caacaccccg gcagcccgag ccgacctggc cgctcagtac     720

accaccgtcg gccgcatgga ccaaggagtt ggactggtgc tccaggagct gcgtgacgcc     780

ggtgtcctga acgacacact ggtgatcttc acgtccgaca acgggatccc cttccccagc     840

ggcaggacca acctgtactg gccgggcact gctgaaccct tactggtgtc atccccggag     900

cacccaaaac gctggggcca agtcagcgag gcctacgtga gcctcctaga cctcacgccc     960

accatcttgg attggttctc gatcccgtac cccagctacg ccatctttgg ctcgaagacc    1020

atccacctca ctggccggtc cctcctgccg gcgctggagg ccgagcccct ctgggccacc    1080

gtctttggca gccagagcca ccacgaggtc accatgtcct accccatgcg ctccgtgcag    1140

caccggcact tccgcctcgt gcacaacctc aacttcaaga tgccctttcc catcgaccag    1200

gacttctacg tctcacccac cttccaggac ctcctgaacc gcaccacagc tggtcagccc    1260

acgggctggt acaaggacct ccgtcattac tactaccggg cgcgctggga gctctacgac    1320

cggagccggg acccccacga gacccagaac ctggccaccg acccgcgctt tgctcagctt    1380

ctggagatgc ttcgggacca gctggccaag tggcagtggg agacccacga cccctgggtg    1440

tgcgcccccg acggcgtcct ggaggagaag ctctctcccc agtgccagcc cctccacaat    1500

gagctgtga                                                            1509
```

```
<210> SEQ ID NO 65
<211> LENGTH: 502
<212> TYPE: PRT
<213> ORGANISM: Homo sapiens

<400> SEQUENCE: 65

Met Ser Cys Pro Val Pro Ala Cys Cys Ala Leu Leu Leu Val Leu Gly
1               5                   10                  15

Leu Cys Arg Ala Arg Pro Arg Asn Ala Leu Leu Leu Leu Ala Asp Asp
            20                  25                  30

Gly Gly Phe Glu Ser Gly Ala Tyr Asn Asn Ser Ala Ile Ala Thr Pro
        35                  40                  45

His Leu Asp Ala Leu Ala Arg Arg Ser Leu Leu Phe Arg Asn Ala Phe
    50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
```

```
            100                 105                 110

Gln Ala Gly Val Arg Thr Gly Ile Ile Gly Lys Lys His Val Gly Pro
        115                 120                 125

Glu Thr Val Tyr Pro Phe Asp Phe Ala Tyr Thr Glu Glu Asn Gly Ser
    130                 135                 140

Val Leu Gln Val Gly Arg Asn Ile Thr Arg Ile Lys Leu Leu Val Arg
145                 150                 155                 160

Lys Phe Leu Gln Thr Gln Asp Asp Arg Pro Phe Phe Leu Tyr Val Ala
                165                 170                 175

Phe His Asp Pro His Arg Cys Gly His Ser Gln Pro Gln Tyr Gly Thr
            180                 185                 190

Phe Cys Glu Lys Phe Gly Asn Gly Glu Ser Gly Met Gly Arg Ile Pro
        195                 200                 205

Asp Trp Thr Pro Gln Ala Tyr Asp Pro Leu Asp Val Leu Val Pro Tyr
    210                 215                 220

Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
                245                 250                 255

Leu Arg Asp Ala Gly Val Leu Asn Asp Thr Leu Val Ile Phe Thr Ser
            260                 265                 270

Asp Asn Gly Ile Pro Phe Pro Ser Gly Arg Thr Asn Leu Tyr Trp Pro
        275                 280                 285

Gly Thr Ala Glu Pro Leu Leu Val Ser Ser Pro Glu His Pro Lys Arg
    290                 295                 300

Trp Gly Gln Val Ser Glu Ala Tyr Val Ser Leu Leu Asp Leu Thr Pro
305                 310                 315                 320

Thr Ile Leu Asp Trp Phe Ser Ile Pro Tyr Pro Ser Tyr Ala Ile Phe
                325                 330                 335

Gly Ser Lys Thr Ile His Leu Thr Gly Arg Ser Leu Leu Pro Ala Leu
            340                 345                 350

Glu Ala Glu Pro Leu Trp Ala Thr Val Phe Gly Ser Gln Ser His His
        355                 360                 365

Glu Val Thr Met Ser Tyr Pro Met Arg Ser Val Gln His Arg His Phe
    370                 375                 380

Arg Leu Val His Asn Leu Asn Phe Lys Met Pro Phe Pro Ile Asp Gln
385                 390                 395                 400

Asp Phe Tyr Val Ser Pro Thr Phe Gln Asp Leu Leu Asn Arg Thr Thr
                405                 410                 415

Ala Gly Gln Pro Thr Gly Trp Tyr Lys Asp Leu Arg His Tyr Tyr Tyr
            420                 425                 430

Arg Ala Arg Trp Glu Leu Tyr Asp Arg Ser Arg Asp Pro His Glu Thr
        435                 440                 445

Gln Asn Leu Ala Thr Asp Pro Arg Phe Ala Gln Leu Leu Glu Met Leu
    450                 455                 460

Arg Asp Gln Leu Ala Lys Trp Gln Trp Glu Thr His Asp Pro Trp Val
465                 470                 475                 480

Cys Ala Pro Asp Gly Val Leu Glu Glu Lys Leu Ser Pro Gln Cys Gln
                485                 490                 495

Pro Leu His Asn Glu Leu
            500
```

<210> SEQ ID NO 66

<211> LENGTH: 1908
<212> TYPE: DNA
<213> ORGANISM: Homo sapiens

<400> SEQUENCE: 66
atgagcgggg cgggcagggc gctggccgcg ctgctgctgg ccgcgtccgt gctgagcgcc 60
gcgctgctgg cccccggcgg ctcttcgggg cgcgatgccc aggccgcgcc gccacgagac 120
ttagacaaaa aaagacatgc agagctgaag atggatcagg ctttgctact catccataat 180
gaacttctct ggaccaactt gaccgtctac tggaaatctg aatgctgtta tcactgcttg 240
tttcaggttc tggtaaacgt tcctcagagt ccaaaagcag ggaagcctag tgctgcagct 300
gcctctgtca gcacccagca cggatctatc ctgcagctga acgacacctt ggaagagaaa 360
gaagtttgta ggttggaata cagatttgga gaatttggaa actattctct cttggtaaag 420
aacatccata atggagttag tgaaattgcc tgtgacctgg ctgtgaacga ggatccagtt 480
gatagtaacc ttcctgtgag cattgcattc cttattggtc ttgctgtcat cattgtgata 540
tcctttctga ggctcttgtt gagtttggat gactttaaca attggatttc taaagccata 600
agttctcgag aaactgatcg cctcatcaat tctgagctgg gatctcccag caggacagac 660
cctctcgatg gtgatgttca gccagcaacg tggcgtctat ctgccctgcc gccccgcctc 720
cgcagcgtgg acaccttcag gggattgct cttatactca tggtctttgt caattatgga 780
ggaggaaaat attggtactt caaacatgca agttggaatg ggctgacagt ggctgacctc 840
gtgttcccgt ggtttgtatt tattatggga tcttccattt ttctatcgat gacttctata 900
ctgcaacggg ggtgttcaaa attcagattg ctggggaaga ttgcatggag gagtttcctg 960
ttaatctgca taggaattat cattgtgaat cccaattatt gccttggtcc attgtcttgg 1020
gacaaggtgc gcattcctgg tgtgctgcag cgattgggag tgacatactt tgtggttgct 1080
gtgttggagc tcctctttgc taaacctgtg cctgaacatt gtgcctcgga gaggagctgc 1140
ctttctcttc gagacatcac gtccagctgg ccccagtggc tgctcatcct ggtgctggaa 1200
ggcctgtggc tgggcttgac attcctcctg ccagtccctg ggtgccctac tggttatctt 1260
ggtcctgggg gcattggaga ttttggcaag tatccaaatt gcactggagg agctgcaggc 1320
tacatcgacc gcctgctgct gggagacgat cacctttacc agcacccatc ttctgctgta 1380
ctttaccaca ccgaggtggc ctatgacccc gagggcatcc tgggcaccat caactccatc 1440
gtgatggcct ttttaggagt tcaggcagga aaaatactat tgtattacaa ggctcggacc 1500
aaagacatcc tgattcgatt cactgcttgg tgttgtattc ttgggctcat ttctgttgct 1560
ctgacgaagg tttctgaaaa tgaaggcttt attccagtaa acaaaaatct ctggtccctt 1620
tcgtatgtca ctacgctcag ttcttttgcc ttcttcatcc tgctggtcct gtacccagtt 1680
gtggatgtga aggggctgtg gacaggaacc ccattctttt atccaggaat gaattccatt 1740
ctggtatatg tcggccacga ggtgtttgag aactacttcc cctttcagtg gaagctgaag 1800
gacaaccagt cccacaagga gcacctgact cagaacatcg tcgccactgc cctctgggtg 1860
ctcattgcct acatcctcta tagaaagaag attttttgga aaatctga 1908

<210> SEQ ID NO 67
<211> LENGTH: 663
<212> TYPE: PRT
<213> ORGANISM: Homo sapiens

<400> SEQUENCE: 67

Met Thr Gly Ala Arg Ala Ser Ala Ala Glu Gln Arg Arg Ala Gly Arg

-continued

```
1               5                   10                  15

Ser Gly Gln Ala Arg Ala Ala Glu Arg Ala Ala Gly Met Ser Gly Ala
            20                  25                  30

Gly Arg Ala Leu Ala Ala Leu Leu Leu Ala Ala Ser Val Leu Ser Ala
        35                  40                  45

Ala Leu Leu Ala Pro Gly Gly Ser Ser Gly Arg Asp Ala Gln Ala Ala
    50                  55                  60

Pro Pro Arg Asp Leu Asp Lys Lys Arg His Ala Glu Leu Lys Met Asp
65                  70                  75                  80

Gln Ala Leu Leu Leu Ile His Asn Glu Leu Leu Trp Thr Asn Leu Thr
                85                  90                  95

Val Tyr Trp Lys Ser Glu Cys Cys Tyr His Cys Leu Phe Gln Val Leu
            100                 105                 110

Val Asn Val Pro Gln Ser Pro Lys Ala Gly Lys Pro Ser Ala Ala Ala
        115                 120                 125

Ala Ser Val Ser Thr Gln His Gly Ser Ile Leu Gln Leu Asn Asp Thr
    130                 135                 140

Leu Glu Glu Lys Glu Val Cys Arg Leu Glu Tyr Arg Phe Gly Glu Phe
145                 150                 155                 160

Gly Asn Tyr Ser Leu Leu Val Lys Asn Ile His Asn Gly Val Ser Glu
                165                 170                 175

Ile Ala Cys Asp Leu Ala Val Asn Glu Asp Pro Val Asp Ser Asn Leu
            180                 185                 190

Pro Val Ser Ile Ala Phe Leu Ile Gly Leu Ala Val Ile Ile Val Ile
        195                 200                 205

Ser Phe Leu Arg Leu Leu Leu Ser Leu Asp Asp Phe Asn Asn Trp Ile
    210                 215                 220

Ser Lys Ala Ile Ser Ser Arg Glu Thr Asp Arg Leu Ile Asn Ser Glu
225                 230                 235                 240

Leu Gly Ser Pro Ser Arg Thr Asp Pro Leu Asp Gly Asp Val Gln Pro
                245                 250                 255

Ala Thr Trp Arg Leu Ser Ala Leu Pro Pro Arg Leu Arg Ser Val Asp
            260                 265                 270

Thr Phe Arg Gly Ile Ala Leu Ile Leu Met Val Phe Val Asn Tyr Gly
        275                 280                 285

Gly Gly Lys Tyr Trp Tyr Phe Lys His Ala Ser Trp Asn Gly Leu Thr
    290                 295                 300

Val Ala Asp Leu Val Phe Pro Trp Phe Val Phe Ile Met Gly Ser Ser
305                 310                 315                 320

Ile Phe Leu Ser Met Thr Ser Ile Leu Gln Arg Gly Cys Ser Lys Phe
                325                 330                 335

Arg Leu Leu Gly Lys Ile Ala Trp Arg Ser Phe Leu Leu Ile Cys Ile
            340                 345                 350

Gly Ile Ile Ile Val Asn Pro Asn Tyr Cys Leu Gly Pro Leu Ser Trp
        355                 360                 365

Asp Lys Val Arg Ile Pro Gly Val Leu Gln Arg Leu Gly Val Thr Tyr
    370                 375                 380

Phe Val Val Ala Val Leu Glu Leu Leu Phe Ala Lys Pro Val Pro Glu
385                 390                 395                 400

His Cys Ala Ser Glu Arg Ser Cys Leu Ser Leu Arg Asp Ile Thr Ser
                405                 410                 415

Ser Trp Pro Gln Trp Leu Leu Ile Leu Val Leu Glu Gly Leu Trp Leu
            420                 425                 430
```

```
Gly Leu Thr Phe Leu Leu Pro Val Pro Gly Cys Pro Thr Gly Tyr Leu
        435                 440                 445

Gly Pro Gly Gly Ile Gly Asp Phe Gly Lys Tyr Pro Asn Cys Thr Gly
    450                 455                 460

Gly Ala Ala Gly Tyr Ile Asp Arg Leu Leu Leu Gly Asp Asp His Leu
465                 470                 475                 480

Tyr Gln His Pro Ser Ser Ala Val Leu Tyr His Thr Glu Val Ala Tyr
                485                 490                 495

Asp Pro Glu Gly Ile Leu Gly Thr Ile Asn Ser Ile Val Met Ala Phe
            500                 505                 510

Leu Gly Val Gln Ala Gly Lys Ile Leu Leu Tyr Tyr Lys Ala Arg Thr
        515                 520                 525

Lys Asp Ile Leu Ile Arg Phe Thr Ala Trp Cys Cys Ile Leu Gly Leu
    530                 535                 540

Ile Ser Val Ala Leu Thr Lys Val Ser Glu Asn Glu Gly Phe Ile Pro
545                 550                 555                 560

Val Asn Lys Asn Leu Trp Ser Leu Ser Tyr Val Thr Thr Leu Ser Ser
                565                 570                 575

Phe Ala Phe Phe Ile Leu Leu Val Leu Tyr Pro Val Val Asp Val Lys
            580                 585                 590

Gly Leu Trp Thr Gly Thr Pro Phe Phe Tyr Pro Gly Met Asn Ser Ile
        595                 600                 605

Leu Val Tyr Val Gly His Glu Val Phe Glu Asn Tyr Phe Pro Phe Gln
    610                 615                 620

Trp Lys Leu Lys Asp Asn Gln Ser His Lys Glu His Leu Thr Gln Asn
625                 630                 635                 640

Ile Val Ala Thr Ala Leu Trp Val Leu Ile Ala Tyr Ile Leu Tyr Arg
                645                 650                 655

Lys Lys Ile Phe Trp Lys Ile
            660
```

<210> SEQ ID NO 68
<211> LENGTH: 1956
<212> TYPE: DNA
<213> ORGANISM: Homo sapiens

<400> SEQUENCE: 68

```
atggcccggg ggtcggcggt tgcctgggcg gcgctcgggc cgttgttgtg ggctgcgcg     60

ctggggctgc agggcgggat gctgtacccc caggagagcc cgtcgcggga gtgcaaggag    120

ctggacggcc tctggagctt ccgcgccgac ttctctgaca accgacgccg ggcttcgag     180

gagcagtggt accggcggcc gctgtgggag tcaggcccca ccgtggacat gccagttccc    240

tccagcttca atgacatcag ccaggactgg cgtctgcggc attttgtcgg ctgggtgtgg    300

tacgaacggg aggtgatcct gccggagcga tggacccagg acctgcgcac aagagtggtg    360

ctgaggattg gcagtgccca ttcctatgcc atcgtgtggg tgaatggggt cgacacgcta    420

gagcatgagg ggggctacct ccccttcgag gccgacatca gcaacctggt ccaggtgggg    480

cccctgccct cccggctccg aatcactatc gccatcaaca acacactcac ccccaccacc    540

ctgccaccag ggaccatcca atacctgact gacacctcca agtatcccaa gggttacttt    600

gtccagaaca catattttga ctttttcaac tacgctggac tgcagcggtc tgtacttctg    660

tacacgacac ccaccaccta catcgatgac atcaccgtca ccaccagcgt ggagcaagac    720

agtgggctgg tgaattacca gatctctgtc aagggcagta acctgttcaa gttggaagtg    780
```

cgtcttttgg atgcagaaaa caaagtcgtg gcgaatggga ctgggaccca gggccaactt 840
aaggtgccag gtgtcagcct ctggtggccg tacctgatgc acgaacgccc tgcctatctg 900
tattcattgg aggtgcagct gactgcacag acgtcactgg ggcctgtgtc tgacttctac 960
acactccctg tggggatccg cactgtggct gtcaccaaga gccagttcct catcaatggg 1020
aaacctttct atttccacgg tgtcaacaag catgaggatg cggacatccg agggaagggc 1080
ttcgactggc cgctgctggt gaaggacttc aacctgcttc gctggcttgg tgccaacgct 1140
ttccgtacca gccactaccc ctatgcagag gaagtgatgc agatgtgtga ccgctatggg 1200
attgtggtca tcgatgagtg tcccggcgtg ggcctggcgc tgccgcagtt cttcaacaac 1260
gtttctctgc atcaccacat gcaggtgatg gaagaagtgg tgcgtaggga caagaaccac 1320
cccgcggtcg tgatgtggtc tgtggccaac gagcctgcgt cccacctaga atctgctggc 1380
tactacttga agatggtgat cgctcacacc aaatccttgg acccctcccg gcctgtgacc 1440
tttgtgagca actctaacta tgcagcagac aagggggctc cgtatgtgga tgtgatctgt 1500
ttgaacagct actactcttg gtatcacgac tacgggcacc tggagttgat tcagctgcag 1560
ctggccaccc agtttgagaa ctggtataag aagtatcaga agcccattat tcagagcgag 1620
tatggagcag aaacgattgc agggtttcac caggatccac ctctgatgtt cactgaagag 1680
taccagaaaa gtctgctaga gcagtaccat ctgggtctgg atcaaaaacg cagaaaatac 1740
gtggttggag agctcatttg gaattttgcc gatttcatga ctgaacagtc accgacgaga 1800
gtgctgggga ataaaaaggg gatcttcact cggcagagac aaccaaaaag tgcagcgttc 1860
cttttgcgag agagatactg gaagattgcc aatgaaacca ggtatcccca ctcagtagcc 1920
aagtcacaat gtttggaaaa cagcctgttt acttga 1956

<210> SEQ ID NO 69
<211> LENGTH: 651
<212> TYPE: PRT
<213> ORGANISM: Homo sapiens

<400> SEQUENCE: 69

Met Ala Arg Gly Ser Ala Val Ala Trp Ala Ala Leu Gly Pro Leu Leu
1               5                   10                  15

Trp Gly Cys Ala Leu Gly Leu Gln Gly Gly Met Leu Tyr Pro Gln Glu
            20                  25                  30

Ser Pro Ser Arg Glu Cys Lys Glu Leu Asp Gly Leu Trp Ser Phe Arg
        35                  40                  45

Ala Asp Phe Ser Asp Asn Arg Arg Arg Gly Phe Glu Glu Gln Trp Tyr
    50                  55                  60

Arg Arg Pro Leu Trp Glu Ser Gly Pro Thr Val Asp Met Pro Val Pro
65                  70                  75                  80

Ser Ser Phe Asn Asp Ile Ser Gln Asp Trp Arg Leu Arg His Phe Val
                85                  90                  95

Gly Trp Val Trp Tyr Glu Arg Glu Val Ile Leu Pro Glu Arg Trp Thr
            100                 105                 110

Gln Asp Leu Arg Thr Arg Val Val Leu Arg Ile Gly Ser Ala His Ser
        115                 120                 125

Tyr Ala Ile Val Trp Val Asn Gly Val Asp Thr Leu Glu His Glu Gly
    130                 135                 140

Gly Tyr Leu Pro Phe Glu Ala Asp Ile Ser Asn Leu Val Gln Val Gly
145                 150                 155                 160

-continued

```
Pro Leu Pro Ser Arg Leu Arg Ile Thr Ile Ala Ile Asn Asn Thr Leu
                165                 170                 175

Thr Pro Thr Thr Leu Pro Pro Gly Thr Ile Gln Tyr Leu Thr Asp Thr
            180                 185                 190

Ser Lys Tyr Pro Lys Gly Tyr Phe Val Gln Asn Thr Tyr Phe Asp Phe
        195                 200                 205

Phe Asn Tyr Ala Gly Leu Gln Arg Ser Val Leu Leu Tyr Thr Thr Pro
    210                 215                 220

Thr Thr Tyr Ile Asp Asp Ile Thr Val Thr Thr Ser Val Glu Gln Asp
225                 230                 235                 240

Ser Gly Leu Val Asn Tyr Gln Ile Ser Val Lys Gly Ser Asn Leu Phe
                245                 250                 255

Lys Leu Glu Val Arg Leu Leu Asp Ala Glu Asn Lys Val Val Ala Asn
            260                 265                 270

Gly Thr Gly Thr Gln Gly Gln Leu Lys Val Pro Gly Val Ser Leu Trp
        275                 280                 285

Trp Pro Tyr Leu Met His Glu Arg Pro Ala Tyr Leu Tyr Ser Leu Glu
    290                 295                 300

Val Gln Leu Thr Ala Gln Thr Ser Leu Gly Pro Val Ser Asp Phe Tyr
305                 310                 315                 320

Thr Leu Pro Val Gly Ile Arg Thr Val Ala Val Thr Lys Ser Gln Phe
                325                 330                 335

Leu Ile Asn Gly Lys Pro Phe Tyr Phe His Gly Val Asn Lys His Glu
            340                 345                 350

Asp Ala Asp Ile Arg Gly Lys Gly Phe Asp Trp Pro Leu Leu Val Lys
        355                 360                 365

Asp Phe Asn Leu Leu Arg Trp Leu Gly Ala Asn Ala Phe Arg Thr Ser
    370                 375                 380

His Tyr Pro Tyr Ala Glu Glu Val Met Gln Met Cys Asp Arg Tyr Gly
385                 390                 395                 400

Ile Val Val Ile Asp Glu Cys Pro Gly Val Gly Leu Ala Leu Pro Gln
                405                 410                 415

Phe Phe Asn Asn Val Ser Leu His His His Met Gln Val Met Glu Glu
            420                 425                 430

Val Val Arg Arg Asp Lys Asn His Pro Ala Val Val Met Trp Ser Val
        435                 440                 445

Ala Asn Glu Pro Ala Ser His Leu Glu Ser Ala Gly Tyr Tyr Leu Lys
    450                 455                 460

Met Val Ile Ala His Thr Lys Ser Leu Asp Pro Ser Arg Pro Val Thr
465                 470                 475                 480

Phe Val Ser Asn Ser Asn Tyr Ala Ala Asp Lys Gly Ala Pro Tyr Val
                485                 490                 495

Asp Val Ile Cys Leu Asn Ser Tyr Tyr Ser Trp Tyr His Asp Tyr Gly
            500                 505                 510

His Leu Glu Leu Ile Gln Leu Gln Leu Ala Thr Gln Phe Glu Asn Trp
        515                 520                 525

Tyr Lys Lys Tyr Gln Lys Pro Ile Ile Gln Ser Glu Tyr Gly Ala Glu
    530                 535                 540

Thr Ile Ala Gly Phe His Gln Asp Pro Pro Leu Met Phe Thr Glu Glu
545                 550                 555                 560

Tyr Gln Lys Ser Leu Leu Glu Gln Tyr His Leu Gly Leu Asp Gln Lys
                565                 570                 575

Arg Arg Lys Tyr Val Val Gly Glu Leu Ile Trp Asn Phe Ala Asp Phe
```

```
        580                 585                 590

Met Thr Glu Gln Ser Pro Thr Arg Val Leu Gly Asn Lys Lys Gly Ile
        595                 600                 605

Phe Thr Arg Gln Arg Gln Pro Lys Ser Ala Ala Phe Leu Leu Arg Glu
    610                 615                 620

Arg Tyr Trp Lys Ile Ala Asn Glu Thr Arg Tyr Pro His Ser Val Ala
625                 630                 635                 640

Lys Ser Gln Cys Leu Glu Asn Ser Leu Phe Thr
                645                 650


<210> SEQ ID NO 70
<211> LENGTH: 1659
<212> TYPE: DNA
<213> ORGANISM: Homo sapiens

<400> SEQUENCE: 70

atgcggctcc tgcctctagc cccaggtcgg ctccggcggg gcagccccg ccacctgccc      60

tcctgcagcc cagcgctgct actgctggtg ctgggcggct gcctgggggt cttcggggtg     120

gctgcgggaa cccggaggcc caacgtggtg ctgctcctca cggacgacca ggacgaagtg     180

ctcggcggca tgacaccgct aaagaaaacc aaagctctca tcggagagat ggggatgact     240

ttttccagtg cttatgtgcc aagtgctctc tgctgcccca gcagagccag tatcctgaca     300

ggaaagtacc cacataatca tcacgttgtg aacaacactc tggaggggaa ctgcagtagt     360

aagtcctggc agaagatcca agaaccaaat actttcccag caattctcag atcaatgtgt     420

ggttatcaga cctttttgc agggaaatat ttaaatgagt acggagcccc agatgcaggt     480

ggactagaac acgttcctct gggttggagt tactggtatg ccttggaaaa gaattctaag     540

tattataatt acaccctgtc tatcaatggg aaggcacgga agcatggtga aaactatagt     600

gtggactacc tgacagatgt tttggctaat gtctccttgg actttctgga ctacaagtcc     660

aactttgagc ccttcttcat gatgatcgcc actccagcgc ctcattcgcc ttggacagct     720

gcacctcagt accagaaggc tttccagaat gtctttgcac caagaaacaa gaacttcaac     780

atccatggaa cgaacaagca ctggttaatt aggcaagcca agactccaat gactaattct     840

tcaatacagt tttagataa tgcatttagg aaaaggtggc aaactctcct ctcagttgat     900

gaccttgtgg agaaactggt caagaggctg gagttcactg gggagctcaa caacacttac     960

atcttctata cctcagacaa tggctatcac acaggacagt ttccttgcc aatagacaag    1020

agacagctgt atgagtttga tatcaaagtt ccactgttgg ttcgaggacc tgggatcaaa    1080

ccaaatcaga caagcaagat gctggttgcc aacattgact tgggtcctac tattttggac    1140

attgctggct acgacctaaa taagacacag atggatggga tgtccttatt gcccattttg    1200

agaggtgcca gtaacttgac ctggcgatca gatgtcctgg tggaatacca aggagaaggc    1260

cgtaacgtca ctgacccaac atgcccttcc ctgagtcctg gcgtatctca atgcttccca    1320

gactgtgtat gtgaagatgc ttataacaat acctatgcct gtgtgaggac aatgtcagca    1380

ttgtggaatt tgcagtattg cgagtttgat gaccaggagg tgtttgtaga agtctataat    1440

ctgactgcag acccagacca gatcactaac attgctaaaa ccatagaccc agagctttta    1500

ggaaagatga actatcggtt aatgatgtta cagtcctgtt ctgggccaac ctgtcgcact    1560

ccaggggttt ttgaccccgg atacaggttt gaccccgtc tcatgttcag caatcgcggc    1620

agtgtcagga ctcgaagatt ttccaaacat cttctgtag                           1659
```

<210> SEQ ID NO 71
<211> LENGTH: 552
<212> TYPE: PRT
<213> ORGANISM: Homo sapiens

<400> SEQUENCE: 71

```
Met Arg Leu Leu Pro Leu Ala Pro Gly Arg Leu Arg Arg Gly Ser Pro
1               5                   10                  15

Arg His Leu Pro Ser Cys Ser Pro Ala Leu Leu Leu Leu Val Leu Gly
            20                  25                  30

Gly Cys Leu Gly Val Phe Gly Val Ala Ala Gly Thr Arg Arg Pro Asn
        35                  40                  45

Val Val Leu Leu Leu Thr Asp Asp Gln Asp Glu Val Leu Gly Gly Met
    50                  55                  60

Thr Pro Leu Lys Lys Thr Lys Ala Leu Ile Gly Glu Met Gly Met Thr
65                  70                  75                  80

Phe Ser Ser Ala Tyr Val Pro Ser Ala Leu Cys Cys Pro Ser Arg Ala
                85                  90                  95

Ser Ile Leu Thr Gly Lys Tyr Pro His Asn His His Val Val Asn Asn
            100                 105                 110

Thr Leu Glu Gly Asn Cys Ser Ser Lys Ser Trp Gln Lys Ile Gln Glu
        115                 120                 125

Pro Asn Thr Phe Pro Ala Ile Leu Arg Ser Met Cys Gly Tyr Gln Thr
    130                 135                 140

Phe Phe Ala Gly Lys Tyr Leu Asn Glu Tyr Gly Ala Pro Asp Ala Gly
145                 150                 155                 160

Gly Leu Glu His Val Pro Leu Gly Trp Ser Tyr Trp Tyr Ala Leu Glu
                165                 170                 175

Lys Asn Ser Lys Tyr Tyr Asn Tyr Thr Leu Ser Ile Asn Gly Lys Ala
            180                 185                 190

Arg Lys His Gly Glu Asn Tyr Ser Val Asp Tyr Leu Thr Asp Val Leu
        195                 200                 205

Ala Asn Val Ser Leu Asp Phe Leu Asp Tyr Lys Ser Asn Phe Glu Pro
    210                 215                 220

Phe Phe Met Met Ile Ala Thr Pro Ala Pro His Ser Pro Trp Thr Ala
225                 230                 235                 240

Ala Pro Gln Tyr Gln Lys Ala Phe Gln Asn Val Phe Ala Pro Arg Asn
                245                 250                 255

Lys Asn Phe Asn Ile His Gly Thr Asn Lys His Trp Leu Ile Arg Gln
            260                 265                 270

Ala Lys Thr Pro Met Thr Asn Ser Ser Ile Gln Phe Leu Asp Asn Ala
        275                 280                 285

Phe Arg Lys Arg Trp Gln Thr Leu Leu Ser Val Asp Asp Leu Val Glu
    290                 295                 300

Lys Leu Val Lys Arg Leu Glu Phe Thr Gly Glu Leu Asn Asn Thr Tyr
305                 310                 315                 320

Ile Phe Tyr Thr Ser Asp Asn Gly Tyr His Thr Gly Gln Phe Ser Leu
                325                 330                 335

Pro Ile Asp Lys Arg Gln Leu Tyr Glu Phe Asp Ile Lys Val Pro Leu
            340                 345                 350

Leu Val Arg Gly Pro Gly Ile Lys Pro Asn Gln Thr Ser Lys Met Leu
        355                 360                 365

Val Ala Asn Ile Asp Leu Gly Pro Thr Ile Leu Asp Ile Ala Gly Tyr
    370                 375                 380
```

```
Asp Leu Asn Lys Thr Gln Met Asp Gly Met Ser Leu Leu Pro Ile Leu
385                 390                 395                 400

Arg Gly Ala Ser Asn Leu Thr Trp Arg Ser Asp Val Leu Val Glu Tyr
                405                 410                 415

Gln Gly Glu Gly Arg Asn Val Thr Asp Pro Thr Cys Pro Ser Leu Ser
            420                 425                 430

Pro Gly Val Ser Gln Cys Phe Pro Asp Cys Val Cys Glu Asp Ala Tyr
        435                 440                 445

Asn Asn Thr Tyr Ala Cys Val Arg Thr Met Ser Ala Leu Trp Asn Leu
    450                 455                 460

Gln Tyr Cys Glu Phe Asp Asp Gln Glu Val Phe Val Glu Val Tyr Asn
465                 470                 475                 480

Leu Thr Ala Asp Pro Asp Gln Ile Thr Asn Ile Ala Lys Thr Ile Asp
                485                 490                 495

Pro Glu Leu Leu Gly Lys Met Asn Tyr Arg Leu Met Met Leu Gln Ser
            500                 505                 510

Cys Ser Gly Pro Thr Cys Arg Thr Pro Gly Val Phe Asp Pro Gly Tyr
        515                 520                 525

Arg Phe Asp Pro Arg Leu Met Phe Ser Asn Arg Gly Ser Val Arg Thr
    530                 535                 540

Arg Arg Phe Ser Lys His Leu Leu
545                 550


<210> SEQ ID NO 72
<211> LENGTH: 1602
<212> TYPE: DNA
<213> ORGANISM: Homo sapiens

<400> SEQUENCE: 72

atgggtccgc gcggcgcggc gagcttgccc cgaggccccg gacctcggcg gctgctcctc     60

cccgtcgtcc tcccgctgct gctgctgctg ttgttggcgc cgccgggctc gggcgccggg    120

gccagccggc cgccccacct ggtcttcttg ctggcagacg acctaggctg gaacgacgtc    180

ggcttccacg gctcccgcat ccgcacgccg cacctggacg cgctggcggc cggcggggtg    240

ctcctggaca actactacac gcagccgctg tgcacgccgt cgcggagcca gctgctcact    300

ggccgctacc agatccgtac aggtttacag caccaaataa tctggccctg tcagcccagc    360

tgtgttcctc tggatgaaaa actcctgccc cagctcctaa aagaagcagg ttatactacc    420

catatggtcg gaaaatggca cctgggaatg taccggaaag aatgccttcc aacccgccga    480

ggatttgata cctactttgg atatctcctg ggtagtgaag attattattc ccatgaacgc    540

tgtacattaa ttgacgctct gaatgtcaca cgatgtgctc ttgattttcg agatggcgaa    600

gaagttgcaa caggatataa aaatatgtat tcaacaaaca tattcaccaa aagggctata    660

gccctcataa ctaaccatcc accagagaag cctctgtttc tctaccttgc tctccagtct    720

gtgcatgagc cccttcaggt ccctgaggaa tacttgaagc catatgactt tatccaagac    780

aagaacaggc atcactatgc aggaatggtg tcccttatgg atgaagcagt aggaaatgtc    840

actgcagctt taaaaagcag tgggctctgg aacaacacgg tgttcatctt ttctacagat    900

aacggagggc agactttggc aggggggtaat aactggcccc ttcgaggaag aaaatggagc    960

ctgtgggaag gaggcgtccg aggggtgggc tttgtggcaa gcccccttgct gaagcagaag   1020

ggcgtgaaga accgggagct catccacatc tctgactggc tgccaacact cgtgaagctg   1080

gccaggggac acaccaatgg cacaaagcct ctggatggct tcgacgtgtg gaaaaccatc   1140
```

```
agtgaaggaa gcccatcccc cagaattgag ctgctgcata atattgaccc gaacttcgtg   1200

gactcttcac cgtgtcccag gaacagcatg gctccagcaa aggatgactc ttctcttcca   1260

gaatattcag cctttaacac atctgtccat gctgcaatta gacatggaaa ttggaaactc   1320

ctcacgggct acccaggctg tggttactgg ttccctccac cgtctcaata caatgtttct   1380

gagataccct catcagaccc accaaccaag accctctggc tctttgatat tgatcgggac   1440

cctgaagaaa gacatgacct gtccagagaa tatcctcaca tcgtcacaaa gctcctgtcc   1500

cgcctacagt tctaccataa acactcagtc cccgtgtact tccctgcaca ggacccccgc   1560

tgtgatccca aggccactgg ggtgtggggc ccttggatgt ag                      1602
```

<210> SEQ ID NO 73
<211> LENGTH: 533
<212> TYPE: PRT
<213> ORGANISM: Homo sapiens

<400> SEQUENCE: 73

```
Met Gly Pro Arg Gly Ala Ala Ser Leu Pro Arg Gly Pro Gly Pro Arg
1               5                   10                  15

Arg Leu Leu Leu Pro Val Val Leu Pro Leu Leu Leu Leu Leu Leu Leu
            20                  25                  30

Ala Pro Pro Gly Ser Gly Ala Gly Ala Ser Arg Pro Pro His Leu Val
        35                  40                  45

Phe Leu Leu Ala Asp Asp Leu Gly Trp Asn Asp Val Gly Phe His Gly
    50                  55                  60

Ser Arg Ile Arg Thr Pro His Leu Asp Ala Leu Ala Ala Gly Gly Val
65                  70                  75                  80

Leu Leu Asp Asn Tyr Tyr Thr Gln Pro Leu Cys Thr Pro Ser Arg Ser
                85                  90                  95

Gln Leu Leu Thr Gly Arg Tyr Gln Ile Arg Thr Gly Leu Gln His Gln
            100                 105                 110

Ile Ile Trp Pro Cys Gln Pro Ser Cys Val Pro Leu Asp Glu Lys Leu
        115                 120                 125

Leu Pro Gln Leu Leu Lys Glu Ala Gly Tyr Thr Thr His Met Val Gly
    130                 135                 140

Lys Trp His Leu Gly Met Tyr Arg Lys Glu Cys Leu Pro Thr Arg Arg
145                 150                 155                 160

Gly Phe Asp Thr Tyr Phe Gly Tyr Leu Leu Gly Ser Glu Asp Tyr Tyr
                165                 170                 175

Ser His Glu Arg Cys Thr Leu Ile Asp Ala Leu Asn Val Thr Arg Cys
            180                 185                 190

Ala Leu Asp Phe Arg Asp Gly Glu Glu Val Ala Thr Gly Tyr Lys Asn
        195                 200                 205

Met Tyr Ser Thr Asn Ile Phe Thr Lys Arg Ala Ile Ala Leu Ile Thr
    210                 215                 220

Asn His Pro Pro Glu Lys Pro Leu Phe Leu Tyr Leu Ala Leu Gln Ser
225                 230                 235                 240

Val His Glu Pro Leu Gln Val Pro Glu Glu Tyr Leu Lys Pro Tyr Asp
                245                 250                 255

Phe Ile Gln Asp Lys Asn Arg His His Tyr Ala Gly Met Val Ser Leu
            260                 265                 270

Met Asp Glu Ala Val Gly Asn Val Thr Ala Ala Leu Lys Ser Ser Gly
        275                 280                 285

Leu Trp Asn Asn Thr Val Phe Ile Phe Ser Thr Asp Asn Gly Gly Gln
```

290 295 300

Thr Leu Ala Gly Gly Asn Asn Trp Pro Leu Arg Gly Arg Lys Trp Ser
305 310 315 320

Leu Trp Glu Gly Gly Val Arg Gly Val Gly Phe Val Ala Ser Pro Leu
325 330 335

Leu Lys Gln Lys Gly Val Lys Asn Arg Glu Leu Ile His Ile Ser Asp
340 345 350

Trp Leu Pro Thr Leu Val Lys Leu Ala Arg Gly His Thr Asn Gly Thr
355 360 365

Lys Pro Leu Asp Gly Phe Asp Val Trp Lys Thr Ile Ser Glu Gly Ser
370 375 380

Pro Ser Pro Arg Ile Glu Leu Leu His Asn Ile Asp Pro Asn Phe Val
385 390 395 400

Asp Ser Ser Pro Cys Pro Arg Asn Ser Met Ala Pro Ala Lys Asp Asp
405 410 415

Ser Ser Leu Pro Glu Tyr Ser Ala Phe Asn Thr Ser Val His Ala Ala
420 425 430

Ile Arg His Gly Asn Trp Lys Leu Leu Thr Gly Tyr Pro Gly Cys Gly
435 440 445

Tyr Trp Phe Pro Pro Pro Ser Gln Tyr Asn Val Ser Glu Ile Pro Ser
450 455 460

Ser Asp Pro Pro Thr Lys Thr Leu Trp Leu Phe Asp Ile Asp Arg Asp
465 470 475 480

Pro Glu Glu Arg His Asp Leu Ser Arg Glu Tyr Pro His Ile Val Thr
485 490 495

Lys Leu Leu Ser Arg Leu Gln Phe Tyr His Lys His Ser Val Pro Val
500 505 510

Tyr Phe Pro Ala Gln Asp Pro Arg Cys Asp Pro Lys Ala Thr Gly Val
515 520 525

Trp Gly Pro Trp Met
530

<210> SEQ ID NO 74
<211> LENGTH: 1308
<212> TYPE: DNA
<213> ORGANISM: Homo sapiens

<400> SEQUENCE: 74
atggcagccc acctgcttcc catctgcgcc ctcttcctga ccttactcga tatggcccaa 60
ggctttaggg gcccccttgct acccaaccgg cccttcacca ccgtctggaa tgcaaacacc 120
cagtggtgcc tggagaggca cggtgtggac gtggatgtca gtgtcttcga tgtggtagcc 180
aacccagggc agaccttccg cggccctgac atgacaattt tctatagctc ccagctgggc 240
acctacccct actacacgcc cactggggag cctgtgtttg gtggtctgcc ccagaatgcc 300
agcctgattg cccacctggc ccgcacattc caggacatcc tggctgccat acctgctcct 360
gacttctcag ggctggcagt catcgactgg gaggcatggc gcccacgctg ggccttcaac 420
tgggacacca aggacattta ccggcagcgc tcacgggcac tggtacaggc acagcaccct 480
gattggccag ctcctcaggt ggaggcagta gcccaggacc agttccaggg agctgcacgg 540
gcctggatgg caggcaccct ccagctgggg cgggcactgc gtcctcgcgg cctctggggc 600
ttctatggct tccctgactg ctacaactat gactttctaa gccccaacta caccggccag 660
tgcccatcag gcatccgtgc ccaaaatgac cagctagggt ggctgtgggg ccagagccgt 720

```
gccctctatc ccagcatcta catgcccgca gtgctggagg gcacagggaa gtcacagatg    780

tatgtgcaac accgtgtggc cgaggcattc cgtgtggctg tggctgctgg tgaccccaat    840

ctgccggtgc tgccctatgt ccagatcttc tatgacacga caaaccactt tctgcccctg    900

gatgagctgg agcacagcct gggggagagt gcggcccagg gggcagctgg agtggtgctc    960

tgggtgagct gggaaaatac aagaaccaag gaatcatgtc aggccatcaa ggagtatatg   1020

gacactacac tggggccctt catcctgaac gtgaccagtg ggcccttctt ctgcagtcaa   1080

gccctgtgct ccggccatgg ccgctgtgtc cgccgcacca gccaccccaa agccctcctc   1140

ctccttaacc ctgccagttt ctccatccag ctcacgcctg gtggtgggcc cctgagcctg   1200

cggggtgccc tctcacttga agatcaggca cagatggctg tggagttcaa atgtcgatgc   1260

taccctggct ggcaggcacc gtggtgtgag cggaagagca tgtggtga                1308
```

<210> SEQ ID NO 75
<211> LENGTH: 435
<212> TYPE: PRT
<213> ORGANISM: Homo sapiens

<400> SEQUENCE: 75

```
Met Ala Ala His Leu Leu Pro Ile Cys Ala Leu Phe Leu Thr Leu Leu
1               5                   10                  15

Asp Met Ala Gln Gly Phe Arg Gly Pro Leu Leu Pro Asn Arg Pro Phe
            20                  25                  30

Thr Thr Val Trp Asn Ala Asn Thr Gln Trp Cys Leu Glu Arg His Gly
        35                  40                  45

Val Asp Val Asp Val Ser Val Phe Asp Val Val Ala Asn Pro Gly Gln
    50                  55                  60

Thr Phe Arg Gly Pro Asp Met Thr Ile Phe Tyr Ser Ser Gln Leu Gly
65                  70                  75                  80

Thr Tyr Pro Tyr Tyr Thr Pro Thr Gly Glu Pro Val Phe Gly Gly Leu
                85                  90                  95

Pro Gln Asn Ala Ser Leu Ile Ala His Leu Ala Arg Thr Phe Gln Asp
            100                 105                 110

Ile Leu Ala Ala Ile Pro Ala Pro Asp Phe Ser Gly Leu Ala Val Ile
        115                 120                 125

Asp Trp Glu Ala Trp Arg Pro Arg Trp Ala Phe Asn Trp Asp Thr Lys
    130                 135                 140

Asp Ile Tyr Arg Gln Arg Ser Arg Ala Leu Val Gln Ala Gln His Pro
145                 150                 155                 160

Asp Trp Pro Ala Pro Gln Val Glu Ala Val Ala Gln Asp Gln Phe Gln
                165                 170                 175

Gly Ala Ala Arg Ala Trp Met Ala Gly Thr Leu Gln Leu Gly Arg Ala
            180                 185                 190

Leu Arg Pro Arg Gly Leu Trp Gly Phe Tyr Gly Phe Pro Asp Cys Tyr
        195                 200                 205

Asn Tyr Asp Phe Leu Ser Pro Asn Tyr Thr Gly Gln Cys Pro Ser Gly
    210                 215                 220

Ile Arg Ala Gln Asn Asp Gln Leu Gly Trp Leu Trp Gly Gln Ser Arg
225                 230                 235                 240

Ala Leu Tyr Pro Ser Ile Tyr Met Pro Ala Val Leu Glu Gly Thr Gly
                245                 250                 255

Lys Ser Gln Met Tyr Val Gln His Arg Val Ala Glu Ala Phe Arg Val
            260                 265                 270
```

```
Ala Val Ala Ala Gly Asp Pro Asn Leu Pro Val Leu Pro Tyr Val Gln
        275                 280                 285

Ile Phe Tyr Asp Thr Thr Asn His Phe Leu Pro Leu Asp Glu Leu Glu
    290                 295                 300

His Ser Leu Gly Glu Ser Ala Ala Gln Gly Ala Ala Gly Val Val Leu
305                 310                 315                 320

Trp Val Ser Trp Glu Asn Thr Arg Thr Lys Glu Ser Cys Gln Ala Ile
                325                 330                 335

Lys Glu Tyr Met Asp Thr Thr Leu Gly Pro Phe Ile Leu Asn Val Thr
            340                 345                 350

Ser Gly Ala Leu Leu Cys Ser Gln Ala Leu Cys Ser Gly His Gly Arg
        355                 360                 365

Cys Val Arg Arg Thr Ser His Pro Lys Ala Leu Leu Leu Leu Asn Pro
    370                 375                 380

Ala Ser Phe Ser Ile Gln Leu Thr Pro Gly Gly Gly Pro Leu Ser Leu
385                 390                 395                 400

Arg Gly Ala Leu Ser Leu Glu Asp Gln Ala Gln Met Ala Val Glu Phe
                405                 410                 415

Lys Cys Arg Cys Tyr Pro Gly Trp Gln Ala Pro Trp Cys Glu Arg Lys
            420                 425                 430

Ser Met Trp
        435


<210> SEQ ID NO 76
<211> LENGTH: 2859
<212> TYPE: DNA
<213> ORGANISM: Homo sapiens

<400> SEQUENCE: 76

atgggagtga ggcacccgcc ctgctcccac cggctcctgg ccgtctgcgc cctcgtgtcc      60

ttggcaaccg ctgcactcct ggggcacatc ctactccatg atttcctgct ggttccccga     120

gagctgagtg gctcctcccc agtcctggag gagactcacc cagctcacca gcagggagcc     180

agcagaccag ggccccggga tgcccaggca caccccggcc gtcccagagc agtgcccaca     240

cagtgcgacg tcccccccaa cagccgcttc gattgcgccc ctgacaaggc catcacccag     300

gaacagtgcg aggcccgcgg ctgttgctac atccctgcaa agcaggggct gcagggagcc     360

cagatggggc agccctggtg cttcttccca cccagctacc ccagctacaa gctggagaac     420

ctgagctcct ctgaaatggg ctacacggcc accctgaccc gtaccacccc caccttcttc     480

cccaaggaca tcctgaccct gcggctggac gtgatgatgg agactgagaa ccgcctccac     540

ttcacgatca aagatccagc taacaggcgc tacgaggtgc ccttggagac cccgcatgtc     600

cacagccggg caccgtcccc actctacagc gtggagttct ccgaggagcc cttcggggtg     660

atcgtgcgcc ggcagctgga cggccgcgtg ctgctgaaca cgacggtggc gccccctgttc    720

tttgcggacc agttccttca gctgtccacc tcgctgccct cgcagtatat cacaggcctc     780

gccgagcacc tcagtcccct gatgctcagc accagctgga ccaggatcac cctgtggaac     840

cgggaccttg cgcccacgcc cggtgcgaac ctctacgggt ctcacccttt ctacctggcg     900

ctggaggacg gcgggtcggc acacggggtg ttcctgctaa acagcaatgc catggatgtg     960

gtcctgcagc cgagccctgc ccttagctgg aggtcgacag gtgggatcct ggatgtctac    1020

atcttcctgg gcccagagcc caagagcgtg gtgcagcagt acctggacgt tgtgggatac    1080

ccgttcatgc cgccatactg ggccctgggc ttccacctgt gccgctgggg ctactcctcc    1140
```

```
accgctatca cccgccaggt ggtggagaac atgaccaggg cccacttccc cctggacgtc   1200

cagtggaacg acctggacta catggactcc cggagggact tcacgttcaa caaggatggc   1260

ttccgggact tcccggccat ggtgcaggag ctgcaccagg gcggccggcg ctacatgatg   1320

atcgtggatc ctgccatcag cagctcgggc cctgccggga gctacaggcc ctacgacgag   1380

ggtctgcgga gggggtttt catcaccaac gagaccggcc agccgctgat tgggaaggta   1440

tggcccgggt ccactgcctt ccccgacttc accaacccca cagccctggc ctggtgggag   1500

gacatggtgg ctgagttcca tgaccaggtg cccttcgacg gcatgtggat tgacatgaac   1560

gagccttcca acttcatcag ggctctgag gacggctgcc ccaacaatga gctggagaac   1620

ccaccctacg tgcctggggt ggttgggggg accctccagg cggccaccat ctgtgcctcc   1680

agccaccagt ttctctccac acactacaac ctgcacaacc tctacggcct gaccgaagcc   1740

atcgcctccc acagggcgct ggtgaaggct cgggggacac gcccatttgt gatctcccgc   1800

tcgacctttg ctggccacgg ccgatacgcc ggccactgga cgggggacgt gtggagctcc   1860

tgggagcagc tcgcctcctc cgtgccagaa atcctgcagt ttaacctgct gggggtgcct   1920

ctggtcgggg ccgacgtctg cggcttcctg ggcaacacct cagaggagct gtgtgtgcgc   1980

tggacccagc tgggggcctt ctaccccttc atgcggaacc acaacagcct gctcagtctg   2040

ccccaggagc cgtacagctt cagcgagccg gcccagcagg ccatgaggaa ggccctcacc   2100

ctgcgctacg cactcctccc ccacctctac acactgttcc accaggccca cgtcgcgggg   2160

gagaccgtgg cccggcccct cttcctggag ttccccaagg actctagcac ctggactgtg   2220

gaccaccagc tcctgtgggg ggaggccctg ctcatcaccc cagtgctcca ggccgggaag   2280

gccgaagtga ctggctactt ccccttgggc acatggtacg acctgcagac ggtgccagta   2340

gaggcccttg gcagcctccc acccccacct gcagctcccc gtgagccagc catccacagc   2400

gaggggcagt gggtgacgct gccggccccc ctggacacca tcaacgtcca cctccgggct   2460

gggtacatca tccccctgca gggccctggc ctcacaacca cagagtcccg ccagcagccc   2520

atggccctgg ctgtggccct gaccaagggt ggggaggccc gaggggagct gttctgggac   2580

gatggagaga gcctggaagt gctggagcga ggggcctaca cacaggtcat cttcctggcc   2640

aggaataaca cgatcgtgaa tgagctggta cgtgtgacca gtgagggagc tggcctgcag   2700

ctgcagaagg tgactgtcct gggcgtggcc acggcgcccc agcaggtcct ctccaacggt   2760

gtccctgtct ccaacttcac ctacagcccc gacaccaagg tcctggacat ctgtgtctcg   2820

ctgttgatgg gagagcagtt tctcgtcagc tggtgttag                          2859
```

<210> SEQ ID NO 77
<211> LENGTH: 952
<212> TYPE: PRT
<213> ORGANISM: Homo sapiens

<400> SEQUENCE: 77

```
Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
```

-continued

```
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
        195                 200                 205

Tyr Ser Val Glu Phe Ser Glu Glu Pro Phe Gly Val Ile Val Arg Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
    370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
    450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495
```

```
Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
        515                 520                 525

Ser Glu Asp Gly Cys Pro Asn Asn Glu Leu Glu Asn Pro Pro Tyr Val
    530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
    610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
        675                 680                 685

Glu Pro Ala Gln Gln Ala Met Arg Lys Ala Leu Thr Leu Arg Tyr Ala
    690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Val Glu Ala Leu Gly
    770                 775                 780

Ser Leu Pro Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
    850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910
```

```
Pro Gln Gln Val Leu Ser Asn Gly Val Pro Val Ser Asn Phe Thr Tyr
        915                 920                 925

Ser Pro Asp Thr Lys Val Leu Asp Ile Cys Val Ser Leu Leu Met Gly
    930                 935                 940

Glu Gln Phe Leu Val Ser Trp Cys
945                 950


<210> SEQ ID NO 78
<211> LENGTH: 1893
<212> TYPE: DNA
<213> ORGANISM: Homo sapiens

<400> SEQUENCE: 78

atgccccgct acggagcgtc actccgccag agctgcccca ggtccggccg ggagcaggga     60

caagacggga ccgccggagc cccggactc ctttggatgg gcctggtgct ggcgctggcg    120

ctggcgctgg cgctggcgct ggctctgtct gactctcggg ttctctgggc tccggcagag    180

gctcaccctc tttctcccca aggccatcct gccaggttac atcgcatagt gccccggctc    240

cgagatgtct ttgggtgggg gaacctcacc tgcccaatct gcaaaggtct attcaccgcc    300

atcaacctcg ggctgaagga acccaatgtg gctcgcgtgg gctccgtggc catcaagctg    360

tgcaatctgc tgaagatagc accacctgcc gtgtgccaat ccattgtcca cctctttgag    420

gatgacatgg tggaggtgtg gagacgctca gtgctgagcc catctgaggc ctgtggcctg    480

ctcctgggct ccacctgtgg gcactgggac attttctcat cttggaacat ctctttgcct    540

actgtgccga agccgccccc caaacccccct agccccccag ccccaggtgc ccctgtcagc    600

cgcatcctct tcctcactga cctgcactgg gatcatgact acctggaggg cacggaccct    660

gactgtgcag acccactgtg ctgccgccgg ggttctggcc tgccgcccgc atcccggcca    720

ggtgccggat actggggcga atacagcaag tgtgacctgc ccctgaggac cctggagagc    780

ctgttgagtg ggctgggccc agccggccct tttgatatgg tgtactggac aggagacatc    840

cccgcacatg atgtctggca ccagactcgt caggaccaac tgcgggccct gaccaccgtc    900

acagcacttg tgaggaagtt cctggggcca gtgccagtgt accctgctgt gggtaaccat    960

gaaagcacac ctgtcaatag cttccctccc cccttcattg agggcaacca ctcctcccgc   1020

tggctctatg aagcgatggc caaggcttgg gagccctggc tgcctgccga agccctgcgc   1080

accctcagaa ttggggggtt ctatgctctt tccccatacc ccggtctccg cctcatctct   1140

ctcaatatga atttttgttc ccgtgagaac ttctggctct tgatcaactc cacggatccc   1200

gcaggacagc tccagtggct ggtgggggag cttcaggctg ctgaggatcg aggagacaaa   1260

gtgcatataa ttggccacat tcccccaggg cactgtctga agagctggag ctggaattat   1320

taccgaattg tagccaggta tgagaacacc ctggctgctc agttctttgg ccacactcat   1380

gtggatgaat ttgaggtctt ctatgatgaa gagactctga gccggccgct ggctgtagcc   1440

ttcctggcac ccagtgcaac tacctacatc ggccttaatc ctggttaccg tgtgtaccaa   1500

atagatggaa actactccgg gagctctcac gtggtcctgg accatgagac ctacatcctg   1560

aatctgaccc aggcaaacat accgggagcc ataccgcact ggcagcttct ctacagggct   1620

cgagaaacct atgggctgcc caacacactg cctaccgcct ggcacaacct ggtatatcgc   1680

atgcggggcg acatgcaact tttccagacc ttctggtttc tctaccataa gggccaccca   1740

ccctcggagc cctgtggcac gccctgccgt ctggctactc tttgtgccca gctctctgcc   1800

cgtgctgaca gccctgctct gtgccgccac ctgatgccag atgggagcct cccagaggcc   1860
```

cagagcctgt ggccaaggcc actgttttgc tag 1893

<210> SEQ ID NO 79
<211> LENGTH: 631
<212> TYPE: PRT
<213> ORGANISM: Homo sapiens

<400> SEQUENCE: 79

Met Pro Arg Tyr Gly Ala Ser Leu Arg Gln Ser Cys Pro Arg Ser Gly
1 5 10 15

Arg Glu Gln Gly Gln Asp Gly Thr Ala Gly Ala Pro Gly Leu Leu Trp
20 25 30

Met Gly Leu Val Leu Ala Leu Ala Leu Ala Leu Ala Leu Ala Leu Ala
35 40 45

Leu Ser Asp Ser Arg Val Leu Trp Ala Pro Ala Glu Ala His Pro Leu
50 55 60

Ser Pro Gln Gly His Pro Ala Arg Leu His Arg Ile Val Pro Arg Leu
65 70 75 80

Arg Asp Val Phe Gly Trp Gly Asn Leu Thr Cys Pro Ile Cys Lys Gly
85 90 95

Leu Phe Thr Ala Ile Asn Leu Gly Leu Lys Lys Glu Pro Asn Val Ala
100 105 110

Arg Val Gly Ser Val Ala Ile Lys Leu Cys Asn Leu Leu Lys Ile Ala
115 120 125

Pro Pro Ala Val Cys Gln Ser Ile Val His Leu Phe Glu Asp Asp Met
130 135 140

Val Glu Val Trp Arg Arg Ser Val Leu Ser Pro Ser Glu Ala Cys Gly
145 150 155 160

Leu Leu Leu Gly Ser Thr Cys Gly His Trp Asp Ile Phe Ser Ser Trp
165 170 175

Asn Ile Ser Leu Pro Thr Val Pro Lys Pro Pro Pro Lys Pro Pro Ser
180 185 190

Pro Pro Ala Pro Gly Ala Pro Val Ser Arg Ile Leu Phe Leu Thr Asp
195 200 205

Leu His Trp Asp His Asp Tyr Leu Glu Gly Thr Asp Pro Asp Cys Ala
210 215 220

Asp Pro Leu Cys Cys Arg Arg Gly Ser Gly Leu Pro Pro Ala Ser Arg
225 230 235 240

Pro Gly Ala Gly Tyr Trp Gly Glu Tyr Ser Lys Cys Asp Leu Pro Leu
245 250 255

Arg Thr Leu Glu Ser Leu Leu Ser Gly Leu Gly Pro Ala Gly Pro Phe
260 265 270

Asp Met Val Tyr Trp Thr Gly Asp Ile Pro Ala His Asp Val Trp His
275 280 285

Gln Thr Arg Gln Asp Gln Leu Arg Ala Leu Thr Thr Val Thr Ala Leu
290 295 300

Val Arg Lys Phe Leu Gly Pro Val Pro Val Tyr Pro Ala Val Gly Asn
305 310 315 320

His Glu Ser Thr Pro Val Asn Ser Phe Pro Pro Pro Phe Ile Glu Gly
325 330 335

Asn His Ser Ser Arg Trp Leu Tyr Glu Ala Met Ala Lys Ala Trp Glu
340 345 350

Pro Trp Leu Pro Ala Glu Ala Leu Arg Thr Leu Arg Ile Gly Gly Phe
355 360 365

```
Tyr Ala Leu Ser Pro Tyr Pro Gly Leu Arg Leu Ile Ser Leu Asn Met
    370                 375                 380

Asn Phe Cys Ser Arg Glu Asn Phe Trp Leu Leu Ile Asn Ser Thr Asp
385                 390                 395                 400

Pro Ala Gly Gln Leu Gln Trp Leu Val Gly Glu Leu Gln Ala Ala Glu
                405                 410                 415

Asp Arg Gly Asp Lys Val His Ile Ile Gly His Ile Pro Pro Gly His
            420                 425                 430

Cys Leu Lys Ser Trp Ser Trp Asn Tyr Tyr Arg Ile Val Ala Arg Tyr
        435                 440                 445

Glu Asn Thr Leu Ala Ala Gln Phe Phe Gly His Thr His Val Asp Glu
    450                 455                 460

Phe Glu Val Phe Tyr Asp Glu Glu Thr Leu Ser Arg Pro Leu Ala Val
465                 470                 475                 480

Ala Phe Leu Ala Pro Ser Ala Thr Thr Tyr Ile Gly Leu Asn Pro Gly
                485                 490                 495

Tyr Arg Val Tyr Gln Ile Asp Gly Asn Tyr Ser Gly Ser Ser His Val
            500                 505                 510

Val Leu Asp His Glu Thr Tyr Ile Leu Asn Leu Thr Gln Ala Asn Ile
        515                 520                 525

Pro Gly Ala Ile Pro His Trp Gln Leu Leu Tyr Arg Ala Arg Glu Thr
    530                 535                 540

Tyr Gly Leu Pro Asn Thr Leu Pro Thr Ala Trp His Asn Leu Val Tyr
545                 550                 555                 560

Arg Met Arg Gly Asp Met Gln Leu Phe Gln Thr Phe Trp Phe Leu Tyr
                565                 570                 575

His Lys Gly His Pro Pro Ser Glu Pro Cys Gly Thr Pro Cys Arg Leu
            580                 585                 590

Ala Thr Leu Cys Ala Gln Leu Ser Ala Arg Ala Asp Ser Pro Ala Leu
        595                 600                 605

Cys Arg His Leu Met Pro Asp Gly Ser Leu Pro Glu Ala Gln Ser Leu
    610                 615                 620

Trp Pro Arg Pro Leu Phe Cys
625                 630
```

<210> SEQ ID NO 80
<211> LENGTH: 1170
<212> TYPE: DNA
<213> ORGANISM: Homo sapiens

<400> SEQUENCE: 80

```
atgaactgct gcatcgggct gggagagaaa gctcgcgggt cccaccgggc ctcctaccca      60

agtctcagcg cgcttttcac cgaggcctca attctgggat ttggcagctt tgctgtgaaa     120

gcccaatgga cagaggactg cagaaaatca acctatcctc cttcaggacc aactgtcttc     180

cctgctgtta taaggtacag aggtgcagtt ccatggtaca ccataaatct tgacttacca     240

ccctacaaaa gatggcatga attgatgctt gacaaggcac cagtgcctgg cctacttggc     300

aactttcctg gccctttga agaggaaatg aagggtattg ccgctgttac tgatatacct     360

ttaggagaga ttatttcatt caatattttt tatgaattat ttaccatttg tacttcaata     420

gtagcagaag acaaaaaagg tcatctaata catgggagaa acatggattt tggagtattt     480

cttgggtgga acataaataa tgatacctgg gtcataactg agcaactaaa acctttaaca     540

gtgaatttgg atttccaaag aaacaacaaa actgtcttca aggcttcaag ctttgctggc     600
```

```
tatgtgggca tgttaacagg attcaaacca ggactgttca gtcttacact gaatgaacgt    660

ttcagtataa atggtggtta tctgggtatt ctagaatgga ttctgggaaa gaaagatgtc    720

atgtggatag ggttcctcac tagaacagtt ctggaaaata gcacaagtta tgaagaagcc    780

aagaatttat tgaccaagac caagatattg gccccagcct actttatcct gggaggcaac    840

cagtctgggg aaggttgtgt gattacacga gacagaaagg aatcattgga tgtatatgaa    900

ctcgatgcta agcagggtag atggtatgtg gtacaaacaa attatgaccg ttggaaacat    960

cccttcttcc ttgatgatcg cagaacgcct gcaaagatgt gtctgaaccg caccagccaa   1020

gagaatatct catttgaaac catgtatgat gtcctgtcaa caaaacctgt cctcaacaag   1080

ctgaccgtat acacaacctt gatagatgtt accaaaggtc aattcgaaac ttacctgcgg   1140

gactgccctg acccttgtat aggttggtga                                    1170
```

<210> SEQ ID NO 81
<211> LENGTH: 395
<212> TYPE: PRT
<213> ORGANISM: Homo sapiens

<400> SEQUENCE: 81

```
Met Pro Gly Arg Ser Cys Val Ala Leu Val Leu Leu Ala Ala Ala Val
1               5                   10                  15

Ser Cys Ala Val Ala Gln His Ala Pro Pro Trp Thr Glu Asp Cys Arg
            20                  25                  30

Lys Ser Thr Tyr Pro Pro Ser Gly Pro Thr Tyr Arg Gly Ala Val Pro
        35                  40                  45

Trp Tyr Thr Ile Asn Leu Asp Leu Pro Pro Tyr Lys Arg Trp His Glu
    50                  55                  60

Leu Met Leu Asp Lys Ala Pro Val Leu Lys Val Ile Val Asn Ser Leu
65                  70                  75                  80

Lys Asn Met Ile Asn Thr Phe Val Pro Ser Gly Lys Ile Met Gln Val
                85                  90                  95

Val Asp Glu Lys Leu Pro Gly Leu Leu Gly Asn Phe Pro Gly Pro Phe
            100                 105                 110

Glu Glu Glu Met Lys Gly Ile Ala Ala Val Thr Asp Ile Pro Leu Gly
        115                 120                 125

Glu Ile Ile Ser Phe Asn Ile Phe Tyr Glu Leu Phe Thr Ile Cys Thr
    130                 135                 140

Ser Ile Val Ala Glu Asp Lys Lys Gly His Leu Ile His Gly Arg Asn
145                 150                 155                 160

Met Asp Phe Gly Val Phe Leu Gly Trp Asn Ile Asn Asn Asp Thr Trp
                165                 170                 175

Val Ile Thr Glu Gln Leu Lys Pro Leu Thr Val Asn Leu Asp Phe Gln
            180                 185                 190

Arg Asn Asn Lys Thr Val Phe Lys Ala Ser Ser Phe Ala Gly Tyr Val
        195                 200                 205

Gly Met Leu Thr Gly Phe Lys Pro Gly Leu Phe Ser Leu Thr Leu Asn
    210                 215                 220

Glu Arg Phe Ser Ile Asn Gly Gly Tyr Leu Gly Ile Leu Glu Trp Ile
225                 230                 235                 240

Leu Gly Lys Lys Asp Val Met Trp Ile Gly Phe Leu Thr Arg Thr Val
                245                 250                 255

Leu Glu Asn Ser Thr Ser Tyr Glu Glu Ala Lys Asn Leu Leu Thr Lys
            260                 265                 270
```

```
Thr Lys Ile Leu Ala Pro Ala Tyr Phe Ile Leu Gly Gly Asn Gln Ser
        275                 280                 285

Gly Glu Gly Cys Val Ile Thr Arg Asp Arg Lys Glu Ser Leu Asp Val
    290                 295                 300

Tyr Glu Leu Asp Ala Lys Gln Gly Arg Trp Tyr Val Val Gln Thr Asn
305                 310                 315                 320

Tyr Asp Arg Trp Lys His Pro Phe Phe Leu Asp Asp Arg Arg Thr Pro
                325                 330                 335

Ala Lys Met Cys Leu Asn Arg Thr Ser Gln Glu Asn Ile Ser Phe Glu
            340                 345                 350

Thr Met Tyr Asp Val Leu Ser Thr Lys Pro Val Leu Asn Lys Leu Thr
        355                 360                 365

Val Tyr Thr Thr Leu Ile Asp Val Thr Lys Gly Gln Phe Glu Thr Tyr
    370                 375                 380

Leu Arg Asp Cys Pro Asp Pro Cys Ile Gly Trp
385                 390                 395
```

```
<210> SEQ ID NO 82
<211> LENGTH: 1200
<212> TYPE: DNA
<213> ORGANISM: Homo sapiens

<400> SEQUENCE: 82

atgaaaatgc ggttcttggg gttggtggtc tgtttggttc tctggaccct gcattctgag      60

gggtctggag ggaaactgac agctgtggat cctgaaacaa acatgaatgt gagtgaaatt     120

atctcttact ggggattccc tagtgaggaa tacctagttg agacagaaga tggatatatt     180

ctgtgcctta accgaattcc tcatgggagg aagaaccatt ctgacaaagg tcccaaacca     240

gttgtcttcc tgcaacatgg cttgctggca gattctagta actgggtcac aaaccttgcc     300

aacagcagcc tgggcttcat tcttgctgat gctggttttg acgtgtggat gggcaacagc     360

agaggaaata cctggtctcg gaaacataag acactctcag tttctcagga tgaattctgg     420

gctttcagtt atgatgagat ggcaaaatat gacctaccag cttccattaa cttcattctg     480

aataaaactg gccaagaaca agtgtattat gtgggtcatt ctcaaggcac cactataggt     540

tttatagcat tttcacagat ccctgagctg gctaaaagga ttaaaatgtt ttttgccctg     600

ggtcctgtgg cttccgtcgc cttctgtact agccctatgg ccaaattagg acgattacca     660

gatcatctca ttaaggactt atttggagac aaagaatttc ttccccagag tgcgtttttg     720

aagtggctgg gtacccacgt ttgcactcat gtcatactga aggagctctg tggaaatctc     780

tgttttcttc tgtgtggatt taatgagaga aatttaaata tgtctagagt ggatgtatat     840

acaacacatt ctcctgctgg aacttctgtg caaaacatgt tacactggag ccaggctgtt     900

aaattccaaa agtttcaagc ctttgactgg ggaagcagtg ccaagaatta ttttcattac     960

aaccagagtt atcctcccac atacaatgtg aaggacatgc ttgtgccgac tgcagtctgg    1020

agcgggggtc acgactggct tgcagatgtc tacgacgtca atatcttact gactcagatc    1080

accaacttgg tgttccatga gagcattccg gaatgggagc atcttgactt catttggggc    1140

ctggatgccc cttggaggct ttataataaa attattaatc taatgaggaa atatcagtga    1200
```

```
<210> SEQ ID NO 83
<211> LENGTH: 399
<212> TYPE: PRT
<213> ORGANISM: Homo sapiens

<400> SEQUENCE: 83
```

```
Met Lys Met Arg Phe Leu Gly Leu Val Val Cys Leu Val Leu Trp Thr
1               5                   10                  15

Leu His Ser Glu Gly Ser Gly Gly Lys Leu Thr Ala Val Asp Pro Glu
            20                  25                  30

Thr Asn Met Asn Val Ser Glu Ile Ile Ser Tyr Trp Gly Phe Pro Ser
        35                  40                  45

Glu Glu Tyr Leu Val Glu Thr Glu Asp Gly Tyr Ile Leu Cys Leu Asn
    50                  55                  60

Arg Ile Pro His Gly Arg Lys Asn His Ser Asp Lys Gly Pro Lys Pro
65                  70                  75                  80

Val Val Phe Leu Gln His Gly Leu Leu Ala Asp Ser Ser Asn Trp Val
                85                  90                  95

Thr Asn Leu Ala Asn Ser Ser Leu Gly Phe Ile Leu Ala Asp Ala Gly
            100                 105                 110

Phe Asp Val Trp Met Gly Asn Ser Arg Gly Asn Thr Trp Ser Arg Lys
        115                 120                 125

His Lys Thr Leu Ser Val Ser Gln Asp Glu Phe Trp Ala Phe Ser Tyr
    130                 135                 140

Asp Glu Met Ala Lys Tyr Asp Leu Pro Ala Ser Ile Asn Phe Ile Leu
145                 150                 155                 160

Asn Lys Thr Gly Gln Glu Gln Val Tyr Tyr Val Gly His Ser Gln Gly
                165                 170                 175

Thr Thr Ile Gly Phe Ile Ala Phe Ser Gln Ile Pro Glu Leu Ala Lys
            180                 185                 190

Arg Ile Lys Met Phe Phe Ala Leu Gly Pro Val Ala Ser Val Ala Phe
        195                 200                 205

Cys Thr Ser Pro Met Ala Lys Leu Gly Arg Leu Pro Asp His Leu Ile
    210                 215                 220

Lys Asp Leu Phe Gly Asp Lys Glu Phe Leu Pro Gln Ser Ala Phe Leu
225                 230                 235                 240

Lys Trp Leu Gly Thr His Val Cys Thr His Val Ile Leu Lys Glu Leu
                245                 250                 255

Cys Gly Asn Leu Cys Phe Leu Leu Cys Gly Phe Asn Glu Arg Asn Leu
            260                 265                 270

Asn Met Ser Arg Val Asp Val Tyr Thr Thr His Ser Pro Ala Gly Thr
        275                 280                 285

Ser Val Gln Asn Met Leu His Trp Ser Gln Ala Val Lys Phe Gln Lys
    290                 295                 300

Phe Gln Ala Phe Asp Trp Gly Ser Ser Ala Lys Asn Tyr Phe His Tyr
305                 310                 315                 320

Asn Gln Ser Tyr Pro Pro Thr Tyr Asn Val Lys Asp Met Leu Val Pro
                325                 330                 335

Thr Ala Val Trp Ser Gly Gly His Asp Trp Leu Ala Asp Val Tyr Asp
            340                 345                 350

Val Asn Ile Leu Leu Thr Gln Ile Thr Asn Leu Val Phe His Glu Ser
        355                 360                 365

Ile Pro Glu Trp Glu His Leu Asp Phe Ile Trp Gly Leu Asp Ala Pro
    370                 375                 380

Trp Arg Leu Tyr Asn Lys Ile Ile Asn Leu Met Arg Lys Tyr Gln
385                 390                 395
```

<210> SEQ ID NO 84
<211> LENGTH: 990

<212> TYPE: DNA
<213> ORGANISM: Homo sapiens

<400> SEQUENCE: 84

```
atgtggggc tcaaggttct gctgctacct gtggtgagct ttgctctgta ccctgaggag      60
atactggaca cccactggga gctatggaag aagacccaca ggaagcaata taacaacaag    120
gtggatgaaa tctctcggcg tttaatttgg gaaaaaaacc tgaagtatat ttccatccat    180
aaccttgagg cttctcttgg tgtccataca tatgaactgg ctatgaacca cctgggggac    240
atgaccagtg aagaggtggt tcagaagatg actggactca aagtacccct gtctcattcc    300
cgcagtaatg acacccttta tatcccagaa tgggaaggta gagccccaga ctctgtcgac    360
tatcgaaaga aaggatatgt tactcctgtc aaaaatcagg gtcagtgtgg ttcctgttgg    420
gcttttagct ctgtgggtgc cctggagggc caactcaaga agaaaactgg caaactctta    480
aatctgagtc cccagaacct agtggattgt gtgtctgaga atgatggctg tggagggggc    540
tacatgacca atgccttcca atatgtgcag aagaaccggg gtattgactc tgaagatgcc    600
tacccatatg tgggacagga agagagttgt atgtacaacc caacaggcaa ggcagctaaa    660
tgcagagggt acagagagat ccccgagggg aatgagaaag ccctgaagag ggcagtggcc    720
cgagtgggac ctgtctctgt ggccattgat gcaagcctga cctccttcca gttttacagc    780
aaaggtgtgt attatgatga aagctgcaat agcgataatc tgaaccatgc agttttggca    840
gtgggatatg gaatccagaa gggaaacaag cactggataa ttaaaaacag ctggggagaa    900
aactggggaa acaaaggata tatcctcatg gctcgaaata agaacaacgc ctgtggcatt    960
gccaacctgg ccagcttccc caagatgtga                                     990
```

<210> SEQ ID NO 85
<211> LENGTH: 329
<212> TYPE: PRT
<213> ORGANISM: Homo sapiens

<400> SEQUENCE: 85

```
Met Trp Gly Leu Lys Val Leu Leu Leu Pro Val Val Ser Phe Ala Leu
1               5                   10                  15

Tyr Pro Glu Glu Ile Leu Asp Thr His Trp Glu Leu Trp Lys Lys Thr
            20                  25                  30

His Arg Lys Gln Tyr Asn Asn Lys Val Asp Glu Ile Ser Arg Arg Leu
        35                  40                  45

Ile Trp Glu Lys Asn Leu Lys Tyr Ile Ser Ile His Asn Leu Glu Ala
    50                  55                  60

Ser Leu Gly Val His Thr Tyr Glu Leu Ala Met Asn His Leu Gly Asp
65                  70                  75                  80

Met Thr Ser Glu Glu Val Val Gln Lys Met Thr Gly Leu Lys Val Pro
                85                  90                  95

Leu Ser His Ser Arg Ser Asn Asp Thr Leu Tyr Ile Pro Glu Trp Glu
            100                 105                 110

Gly Arg Ala Pro Asp Ser Val Asp Tyr Arg Lys Lys Gly Tyr Val Thr
        115                 120                 125

Pro Val Lys Asn Gln Gly Gln Cys Gly Ser Cys Trp Ala Phe Ser Ser
    130                 135                 140

Val Gly Ala Leu Glu Gly Gln Leu Lys Lys Lys Thr Gly Lys Leu Leu
145                 150                 155                 160

Asn Leu Ser Pro Gln Asn Leu Val Asp Cys Val Ser Glu Asn Asp Gly
                165                 170                 175
```

```
Cys Gly Gly Gly Tyr Met Thr Asn Ala Phe Gln Tyr Val Gln Lys Asn
            180                 185                 190

Arg Gly Ile Asp Ser Glu Asp Ala Tyr Pro Tyr Val Gly Gln Glu Glu
        195                 200                 205

Ser Cys Met Tyr Asn Pro Thr Gly Lys Ala Ala Lys Cys Arg Gly Tyr
    210                 215                 220

Arg Glu Ile Pro Glu Gly Asn Glu Lys Ala Leu Lys Arg Ala Val Ala
225                 230                 235                 240

Arg Val Gly Pro Val Ser Val Ala Ile Asp Ala Ser Leu Thr Ser Phe
                245                 250                 255

Gln Phe Tyr Ser Lys Gly Val Tyr Tyr Asp Glu Ser Cys Asn Ser Asp
            260                 265                 270

Asn Leu Asn His Ala Val Leu Ala Val Gly Tyr Gly Ile Gln Lys Gly
        275                 280                 285

Asn Lys His Trp Ile Ile Lys Asn Ser Trp Gly Glu Asn Trp Gly Asn
    290                 295                 300

Lys Gly Tyr Ile Leu Met Ala Arg Asn Lys Asn Asn Ala Cys Gly Ile
305                 310                 315                 320

Ala Asn Leu Ala Ser Phe Pro Lys Met
                325
```

<210> SEQ ID NO 86
<211> LENGTH: 1692
<212> TYPE: DNA
<213> ORGANISM: Homo sapiens

<400> SEQUENCE: 86

```
atgggactcc aagcctgcct cctagggctc tttgccctca tcctctctgg caaatgcagt     60

tacagcccgg agcccgacca gcggaggacg ctgcccccag gctgggtgtc cctgggccgt    120

gcggaccctg aggaagagct gagtctcacc tttgccctga gacagcagaa tgtggaaaga    180

ctctcggagc tggtgcaggc tgtgtcggat cccagctctc ctcaatacgg aaaatacctg    240

accctagaga atgtggctga tctggtgagg ccatccccac tgaccctcca cacggtgcaa    300

aaatggctct tggcagccgg agcccagaag tgccattctg tgatcacaca ggactttctg    360

acttgctggc tgagcatccg acaagcagag ctgctgctcc ctggggctga gtttcatcac    420

tatgtgggag gacctacgga aacccatgtt gtaaggtccc cacatcccta ccagcttcca    480

caggccttgg ccccccatgt ggactttgtg gggggactgc accgttttcc cccaacatca    540

tccctgaggc aacgtcctga gccgcaggtg acagggactg taggcctgca tctgggggta    600

accccctctg tgatccgtaa gcgatacaac ttgacctcac aagacgtggg ctctggcacc    660

agcaataaca gccaagcctg tgcccagttc ctggagcagt atttccatga ctcagacctg    720

gctcagttca tgcgcctctt cggtggcaac tttgcacatc aggcatcagt agcccgtgtg    780

gttggacaac agggccgggg ccgggccggg attgaggcca gtctagatgt gcagtacctg    840

atgagtgctg gtgccaacat ctccacctgg gtctacagta gccctggccg gcatgaggga    900

caggagccct tcctgcagtg gctcatgctg ctcagtaatg agtcagccct gccacatgtg    960

catactgtga gctatggaga tgatgaggac tccctcagca gcgcctacat ccagcgggtc   1020

aacactgagc tcatgaaggc tgccgctcgg ggtctcaccc tgctcttcgc ctcaggtgac   1080

agtggggccg ggtgttggtc tgtctctgga agacaccagt tccgccctac cttccctgcc   1140

tccagcccct atgtcaccac agtgggaggc acatccttcc aggaaccttt cctcatcaca   1200
```

```
aatgaaattg ttgactatat cagtggtggt ggcttcagca atgtgttccc acggccttca   1260

taccaggagg aagctgtaac gaagttcctg agctctagcc cccacctgcc accatccagt   1320

tacttcaatg ccagtggccg tgcctaccca gatgtggctg cactttctga tggctactgg   1380

gtggtcagca acagagtgcc cattccatgg gtgtccggaa cctcggcctc tactccagtg   1440

tttgggggga tcctatcctt gatcaatgag cacaggatcc ttagtggccg ccccccctctt   1500

ggctttctca acccaaggct ctaccagcag catggggcag gactctttga tgtaacccgt   1560

ggctgccatg agtcctgtct ggatgaagag gtagagggcc agggtttctg ctctggtcct   1620

ggctgggatc ctgtaacagg ctggggaaca cccaacttcc cagctttgct gaagactcta   1680

ctcaacccct ga                                                       1692


<210> SEQ ID NO 87
<211> LENGTH: 563
<212> TYPE: PRT
<213> ORGANISM: Homo sapiens

<400> SEQUENCE: 87

Met Gly Leu Gln Ala Cys Leu Leu Gly Leu Phe Ala Leu Ile Leu Ser
1               5                   10                  15

Gly Lys Cys Ser Tyr Ser Pro Glu Pro Asp Gln Arg Arg Thr Leu Pro
            20                  25                  30

Pro Gly Trp Val Ser Leu Gly Arg Ala Asp Pro Glu Glu Glu Leu Ser
        35                  40                  45

Leu Thr Phe Ala Leu Arg Gln Gln Asn Val Glu Arg Leu Ser Glu Leu
    50                  55                  60

Val Gln Ala Val Ser Asp Pro Ser Ser Pro Gln Tyr Gly Lys Tyr Leu
65                  70                  75                  80

Thr Leu Glu Asn Val Ala Asp Leu Val Arg Pro Ser Pro Leu Thr Leu
                85                  90                  95

His Thr Val Gln Lys Trp Leu Leu Ala Ala Gly Ala Gln Lys Cys His
            100                 105                 110

Ser Val Ile Thr Gln Asp Phe Leu Thr Cys Trp Leu Ser Ile Arg Gln
        115                 120                 125

Ala Glu Leu Leu Leu Pro Gly Ala Glu Phe His His Tyr Val Gly Gly
    130                 135                 140

Pro Thr Glu Thr His Val Val Arg Ser Pro His Pro Tyr Gln Leu Pro
145                 150                 155                 160

Gln Ala Leu Ala Pro His Val Asp Phe Val Gly Gly Leu His Arg Phe
                165                 170                 175

Pro Pro Thr Ser Ser Leu Arg Gln Arg Pro Glu Pro Gln Val Thr Gly
            180                 185                 190

Thr Val Gly Leu His Leu Gly Val Thr Pro Ser Val Ile Arg Lys Arg
        195                 200                 205

Tyr Asn Leu Thr Ser Gln Asp Val Gly Ser Gly Thr Ser Asn Asn Ser
    210                 215                 220

Gln Ala Cys Ala Gln Phe Leu Glu Gln Tyr Phe His Asp Ser Asp Leu
225                 230                 235                 240

Ala Gln Phe Met Arg Leu Phe Gly Gly Asn Phe Ala His Gln Ala Ser
                245                 250                 255

Val Ala Arg Val Val Gly Gln Gln Gly Arg Gly Arg Ala Gly Ile Glu
            260                 265                 270

Ala Ser Leu Asp Val Gln Tyr Leu Met Ser Ala Gly Ala Asn Ile Ser
        275                 280                 285
```

Thr Trp Val Tyr Ser Ser Pro Gly Arg His Glu Gly Gln Glu Pro Phe
    290                 295                 300

Leu Gln Trp Leu Met Leu Leu Ser Asn Glu Ser Ala Leu Pro His Val
305                 310                 315                 320

His Thr Val Ser Tyr Gly Asp Asp Glu Asp Ser Leu Ser Ser Ala Tyr
                325                 330                 335

Ile Gln Arg Val Asn Thr Glu Leu Met Lys Ala Ala Ala Arg Gly Leu
            340                 345                 350

Thr Leu Leu Phe Ala Ser Gly Asp Ser Gly Ala Gly Cys Trp Ser Val
        355                 360                 365

Ser Gly Arg His Gln Phe Arg Pro Thr Phe Pro Ala Ser Ser Pro Tyr
    370                 375                 380

Val Thr Thr Val Gly Gly Thr Ser Phe Gln Glu Pro Phe Leu Ile Thr
385                 390                 395                 400

Asn Glu Ile Val Asp Tyr Ile Ser Gly Gly Gly Phe Ser Asn Val Phe
                405                 410                 415

Pro Arg Pro Ser Tyr Gln Glu Glu Ala Val Thr Lys Phe Leu Ser Ser
            420                 425                 430

Ser Pro His Leu Pro Pro Ser Ser Tyr Phe Asn Ala Ser Gly Arg Ala
        435                 440                 445

Tyr Pro Asp Val Ala Ala Leu Ser Asp Gly Tyr Trp Val Val Ser Asn
    450                 455                 460

Arg Val Pro Ile Pro Trp Val Ser Gly Thr Ser Ala Ser Thr Pro Val
465                 470                 475                 480

Phe Gly Gly Ile Leu Ser Leu Ile Asn Glu His Arg Ile Leu Ser Gly
                485                 490                 495

Arg Pro Pro Leu Gly Phe Leu Asn Pro Arg Leu Tyr Gln Gln His Gly
            500                 505                 510

Ala Gly Leu Phe Asp Val Thr Arg Gly Cys His Glu Ser Cys Leu Asp
        515                 520                 525

Glu Glu Val Glu Gly Gln Gly Phe Cys Ser Gly Pro Gly Trp Asp Pro
    530                 535                 540

Val Thr Gly Trp Gly Thr Pro Asn Phe Pro Ala Leu Leu Lys Thr Leu
545                 550                 555                 560

Leu Asn Pro

<210> SEQ ID NO 88
<211> LENGTH: 612
<212> TYPE: DNA
<213> ORGANISM: Homo sapiens

<400> SEQUENCE: 88
atggcgtcgc ccggctgcct gtggctcttg gctgtggctc tcctgccatg gacctgcgct 60
tctcgggcgc tgcagcatct ggacccgccg gcgccgctgc cgttggtgat ctggcatggg 120
atgggtgttt ttggactccc tcgatgccca ggagagagct ctcacatctg tgacttcatc 180
cgaaaaacac tgaatgctgg ggcgtactcc aaagttgttc aggaacgcct cgtgcaagcc 240
gaatactggc atgaccccat aaaggaggat gtgtatcgca accacagcat cttcttggca 300
gatataaatc aggagcgggg tatcaatgag tcctacaaga aaaacctgat ggccctgaag 360
aagtttgtga tggtgaaatt cctcaatgat tccattgtgg accctgtaga ttcggagtgg 420
tttggatttt acagaagtgg ccaagccaag gaaaccattc ccttacagga gacctccctg 480
tacacacagg accgcctggg gctaaaggaa atggacaatg caggacagct agtgtttctg 540
gctacagaag gggaccatct tcagttgtct gaagaatggt tttatgccca catcatacca 600
ttccttggat ga 612

<210> SEQ ID NO 89
<211> LENGTH: 306
<212> TYPE: PRT
<213> ORGANISM: Homo sapiens

<400> SEQUENCE: 89

Met Ala Ser Pro Gly Cys Leu Trp Leu Leu Ala Val Ala Leu Leu Pro
1 5 10 15

Trp Thr Cys Ala Ser Arg Ala Leu Gln His Leu Asp Pro Pro Ala Pro
20 25 30

Leu Pro Leu Val Ile Trp His Gly Met Gly Asp Ser Cys Cys Asn Pro
35 40 45

Leu Ser Met Gly Ala Ile Lys Lys Met Val Glu Lys Lys Ile Pro Gly
50 55 60

Ile Tyr Val Leu Ser Leu Glu Ile Gly Lys Thr Leu Met Glu Asp Val
65 70 75 80

Glu Asn Ser Phe Phe Leu Asn Val Asn Ser Gln Val Thr Thr Val Cys
85 90 95

Gln Ala Leu Ala Lys Asp Pro Lys Leu Gln Gln Gly Tyr Asn Ala Met
100 105 110

Gly Phe Ser Gln Gly Gly Gln Phe Leu Arg Ala Val Ala Gln Arg Cys
115 120 125

Pro Ser Pro Pro Met Ile Asn Leu Ile Ser Val Gly Gly Gln His Gln
130 135 140

Gly Val Phe Gly Leu Pro Arg Cys Pro Gly Glu Ser Ser His Ile Cys
145 150 155 160

Asp Phe Ile Arg Lys Thr Leu Asn Ala Gly Ala Tyr Ser Lys Val Val
165 170 175

Gln Glu Arg Leu Val Gln Ala Glu Tyr Trp His Asp Pro Ile Lys Glu
180 185 190

Asp Val Tyr Arg Asn His Ser Ile Phe Leu Ala Asp Ile Asn Gln Glu
195 200 205

Arg Gly Ile Asn Glu Ser Tyr Lys Lys Asn Leu Met Ala Leu Lys Lys
210 215 220

Phe Val Met Val Lys Phe Leu Asn Asp Ser Ile Val Asp Pro Val Asp
225 230 235 240

Ser Glu Trp Phe Gly Phe Tyr Arg Ser Gly Gln Ala Lys Glu Thr Ile
245 250 255

Pro Leu Gln Glu Thr Ser Leu Tyr Thr Gln Asp Arg Leu Gly Leu Lys
260 265 270

Glu Met Asp Asn Ala Gly Gln Leu Val Phe Leu Ala Thr Glu Gly Asp
275 280 285

His Leu Gln Leu Ser Glu Glu Trp Phe Tyr Ala His Ile Ile Pro Phe
290 295 300

Leu Gly
305

<210> SEQ ID NO 90
<211> LENGTH: 1104
<212> TYPE: DNA
<213> ORGANISM: Homo sapiens

<400> SEQUENCE: 90

```
atgataagga attggctgac tatttttatc ctttttcccc tgaagctcgt agagaaatgt      60
gagtcaagcg tcagcctcac tgttcctcct gtcgtaaagc tggagaacgg cagctcgacc     120
aacgtcagcc tcaccctgcg gccaccatta aatgcaaccc tggtgatcac ttttgaaatc     180
acatttcgtt ccaaaaatat tactatcctt gagctccccg atgaagttgt ggtgcctcct     240
ggagtgacaa actcctcttt tcaagtgaca tctcaaaatg ttggacaact tactgtttat     300
ctacatggaa atcactccaa tcagaccggc ccgaggatac gctttcttgt gatccgcagc     360
agcgccatta gcatcataaa ccaggtgatt ggctggatct actttgtggc ctggtccatc     420
tccttctacc ctcaggtgat catgaattgg aggcggaaaa gtgtcattgg tctgagcttc     480
gacttcgtgg ctctgaacct gacgggcttc gtggcctaca gtgtattcaa catcggcctc     540
ctctgggtgc cctacatcaa ggagcagttt ctcctcaaat accccaacgg agtgaacccc     600
gtgaacagca acgacgtctt cttcagcctg cacgcggttg tcctcacgct gatcatcatc     660
gtgcagtgct gcctgtatga gcgcggtggc cagcgcgtgt cctggcctgc catcggcttc     720
ctggtgctcg cgtggctctt cgcatttgtc accatgatcg tggctgcagt gggagtgacc     780
acgtggctgc agtttctctt ctgcttctcc tacatcaagc tcgcagtcac gctggtcaag     840
tattttccac aggcctacat gaacttttac tacaaaagca ctgagggctg gagcattggc     900
aacgtgctcc tggacttcac cgggggcagc ttcagcctcc tgcagatgtt cctccagtcc     960
tacaacaacg accagtggac gctgatcttc ggagacccaa ccaagtttgg actcggggtc    1020
ttctccatcg tcttcgacgt cgtcttcttc atccagcact tctgtttgta cagaaagaga    1080
ccggggtatg accagctgaa ctag                                           1104
```

```
<210> SEQ ID NO 91
<211> LENGTH: 367
<212> TYPE: PRT
<213> ORGANISM: Homo sapiens

<400> SEQUENCE: 91

Met Ile Arg Asn Trp Leu Thr Ile Phe Ile Leu Phe Pro Leu Lys Leu
1               5                   10                  15

Val Glu Lys Cys Glu Ser Ser Val Ser Leu Thr Val Pro Pro Val Val
            20                  25                  30

Lys Leu Glu Asn Gly Ser Ser Thr Asn Val Ser Leu Thr Leu Arg Pro
        35                  40                  45

Pro Leu Asn Ala Thr Leu Val Ile Thr Phe Glu Ile Thr Phe Arg Ser
    50                  55                  60

Lys Asn Ile Thr Ile Leu Glu Leu Pro Asp Glu Val Val Val Pro Pro
65                  70                  75                  80

Gly Val Thr Asn Ser Ser Phe Gln Val Thr Ser Gln Asn Val Gly Gln
                85                  90                  95

Leu Thr Val Tyr Leu His Gly Asn His Ser Asn Gln Thr Gly Pro Arg
            100                 105                 110

Ile Arg Phe Leu Val Ile Arg Ser Ser Ala Ile Ser Ile Ile Asn Gln
        115                 120                 125

Val Ile Gly Trp Ile Tyr Phe Val Ala Trp Ser Ile Ser Phe Tyr Pro
    130                 135                 140

Gln Val Ile Met Asn Trp Arg Arg Lys Ser Val Ile Gly Leu Ser Phe
145                 150                 155                 160

Asp Phe Val Ala Leu Asn Leu Thr Gly Phe Val Ala Tyr Ser Val Phe
```

```
                165                 170                 175

Asn Ile Gly Leu Leu Trp Val Pro Tyr Ile Lys Glu Gln Phe Leu Leu
            180                 185                 190

Lys Tyr Pro Asn Gly Val Asn Pro Val Asn Ser Asn Asp Val Phe Phe
        195                 200                 205

Ser Leu His Ala Val Val Leu Thr Leu Ile Ile Ile Val Gln Cys Cys
    210                 215                 220

Leu Tyr Glu Arg Gly Gly Gln Arg Val Ser Trp Pro Ala Ile Gly Phe
225                 230                 235                 240

Leu Val Leu Ala Trp Leu Phe Ala Phe Val Thr Met Ile Val Ala Ala
                245                 250                 255

Val Gly Val Thr Thr Trp Leu Gln Phe Leu Phe Cys Phe Ser Tyr Ile
            260                 265                 270

Lys Leu Ala Val Thr Leu Val Lys Tyr Phe Pro Gln Ala Tyr Met Asn
        275                 280                 285

Phe Tyr Tyr Lys Ser Thr Glu Gly Trp Ser Ile Gly Asn Val Leu Leu
    290                 295                 300

Asp Phe Thr Gly Gly Ser Phe Ser Leu Leu Gln Met Phe Leu Gln Ser
305                 310                 315                 320

Tyr Asn Asn Asp Gln Trp Thr Leu Ile Phe Gly Asp Pro Thr Lys Phe
                325                 330                 335

Gly Leu Gly Val Phe Ser Ile Val Phe Asp Val Val Phe Phe Ile Gln
            340                 345                 350

His Phe Cys Leu Tyr Arg Lys Arg Pro Gly Tyr Asp Gln Leu Asn
        355                 360                 365


<210> SEQ ID NO 92
<211> LENGTH: 1674
<212> TYPE: DNA
<213> ORGANISM: Homo sapiens

<400> SEQUENCE: 92

atggcggcgg gggcggagtc ggcgcggccg cctctgggcg ggaccgcggg gactagacgt     60

ggccgcgggg cggtgtcatc gcccccgccc cgcccggtcc agccagctcg gcccgggggc    120

ttcgggctgt cgggccggcg ctcccttctc tgccaggtgg cgagtacacc tgctcacgta    180

ggcgtcatga ggtctccggt tcgagacctg gcccggaacg atggcgagga gagcacggac    240

cgcacgcctc ttctaccggg cgccccacgg gccgaagccg ctccagtgtg ctgctctgct    300

cgttacaact tagcaatttt ggcctttttt ggtttcttca ttgtgtatgc attacgtgtg    360

aatctgagtg ttgcgttagt ggatatggta gattcaaata caactttaga agataataga    420

acttccaagg cgtgtccaga gcattctgct cccataaaag ttcatcataa tcaaacgggt    480

aagaagtacc aatgggatgc agaaactcaa ggatggattc tcggttcctt tttttatggc    540

tacatcatca cacagattcc tggaggatat gttgccagca aaataggggg gaaaatgctg    600

ctaggatttg ggatccttgg cactgctgtc ctcaccctgt tcactcccat tgctgcagat    660

ttaggagttg gaccactcat tgtactcaga gcactagaag gactaggaga gggtgttaca    720

tttccagcca tgcatgccat gtggtcttct tgggctcccc ctcttgaaag aagcaaactt    780

cttagcattt catatgcagg agcacagctt gggacagtaa tttctcttcc tctttctgga    840

ataatttgct actatatgaa ttggacttat gtcttctact tttttggtac tattggaata    900

ttttggtttc ttttgtggat ctggttagtt agtgacacac cacaaaaaca caagagaatt    960

tcccattatg aaaaggaata cattctttca tcattaagaa atcagctttc ttcacagaag   1020
```

tcagtgccgt gggtacccat tttaaaatcc ctgccacttt gggctatcgt agttgcacac 1080
ttttcttaca actggacttt ttatacttta ttgacattat tgcctactta tatgaaggag 1140
atcctaaggt tcaatgttca agagaatggg tttttatctt cattgcctta tttaggctct 1200
tggttatgta tgatcctgtc tggtcaagct gctgacaatt taagggcaaa atggaatttt 1260
tcaactttat gtgttcgcag aatttttagc cttataggaa tgattggacc tgcagtattc 1320
ctggtagctg ctggcttcat tggctgtgat tattctttgg ccgttgcttt cctaactata 1380
tcaacaacac tgggaggctt ttgctcttct ggatttagca tcaaccatct ggatattgct 1440
ccttcgtatg ctggtatcct cctgggcatc acaaatacat ttgccactat tccaggaatg 1500
gttgggcccg tcattgctaa aagtctgacc cctgataaca ctgttggaga atggcaaacc 1560
gtgttctata ttgctgctgc tattaatgtt tttggtgcca ttttctttac actattcgcc 1620
aaaggtgaag tacaaaactg ggctctcaat gatcaccatg gacacagaca ctga 1674

<210> SEQ ID NO 93
<211> LENGTH: 557
<212> TYPE: PRT
<213> ORGANISM: Homo sapiens

<400> SEQUENCE: 93

Met Ala Ala Gly Ala Glu Ser Ala Arg Pro Pro Leu Gly Gly Thr Ala
1 5 10 15

Gly Thr Arg Arg Gly Arg Gly Ala Val Ser Ser Pro Pro Pro Arg Pro
20 25 30

Val Gln Pro Ala Arg Pro Gly Gly Phe Gly Leu Ser Gly Arg Arg Ser
35 40 45

Leu Leu Cys Gln Val Ala Ser Thr Pro Ala His Val Gly Val Met Arg
50 55 60

Ser Pro Val Arg Asp Leu Ala Arg Asn Asp Gly Glu Glu Ser Thr Asp
65 70 75 80

Arg Thr Pro Leu Leu Pro Gly Ala Pro Arg Ala Glu Ala Ala Pro Val
85 90 95

Cys Cys Ser Ala Arg Tyr Asn Leu Ala Ile Leu Ala Phe Phe Gly Phe
100 105 110

Phe Ile Val Tyr Ala Leu Arg Val Asn Leu Ser Val Ala Leu Val Asp
115 120 125

Met Val Asp Ser Asn Thr Thr Leu Glu Asp Asn Arg Thr Ser Lys Ala
130 135 140

Cys Pro Glu His Ser Ala Pro Ile Lys Val His His Asn Gln Thr Gly
145 150 155 160

Lys Lys Tyr Gln Trp Asp Ala Glu Thr Gln Gly Trp Ile Leu Gly Ser
165 170 175

Phe Phe Tyr Gly Tyr Ile Ile Thr Gln Ile Pro Gly Gly Tyr Val Ala
180 185 190

Ser Lys Ile Gly Gly Lys Met Leu Leu Gly Phe Gly Ile Leu Gly Thr
195 200 205

Ala Val Leu Thr Leu Phe Thr Pro Ile Ala Ala Asp Leu Gly Val Gly
210 215 220

Pro Leu Ile Val Leu Arg Ala Leu Glu Gly Leu Gly Glu Gly Val Thr
225 230 235 240

Phe Pro Ala Met His Ala Met Trp Ser Ser Trp Ala Pro Pro Leu Glu
245 250 255

```
Arg Ser Lys Leu Leu Ser Ile Ser Tyr Ala Gly Ala Gln Leu Gly Thr
            260                 265                 270

Val Ile Ser Leu Pro Leu Ser Gly Ile Ile Cys Tyr Tyr Met Asn Trp
        275                 280                 285

Thr Tyr Val Phe Tyr Phe Phe Gly Thr Ile Gly Ile Phe Trp Phe Leu
    290                 295                 300

Leu Trp Ile Trp Leu Val Ser Asp Thr Pro Gln Lys His Lys Arg Ile
305                 310                 315                 320

Ser His Tyr Glu Lys Glu Tyr Ile Leu Ser Ser Leu Arg Asn Gln Leu
                325                 330                 335

Ser Ser Gln Lys Ser Val Pro Trp Val Pro Ile Leu Lys Ser Leu Pro
            340                 345                 350

Leu Trp Ala Ile Val Val Ala His Phe Ser Tyr Asn Trp Thr Phe Tyr
        355                 360                 365

Thr Leu Leu Thr Leu Leu Pro Thr Tyr Met Lys Glu Ile Leu Arg Phe
    370                 375                 380

Asn Val Gln Glu Asn Gly Phe Leu Ser Ser Leu Pro Tyr Leu Gly Ser
385                 390                 395                 400

Trp Leu Cys Met Ile Leu Ser Gly Gln Ala Ala Asp Asn Leu Arg Ala
                405                 410                 415

Lys Trp Asn Phe Ser Thr Leu Cys Val Arg Arg Ile Phe Ser Leu Ile
            420                 425                 430

Gly Met Ile Gly Pro Ala Val Phe Leu Val Ala Ala Gly Phe Ile Gly
        435                 440                 445

Cys Asp Tyr Ser Leu Ala Val Ala Phe Leu Thr Ile Ser Thr Thr Leu
    450                 455                 460

Gly Gly Phe Cys Ser Ser Gly Phe Ser Ile Asn His Leu Asp Ile Ala
465                 470                 475                 480

Pro Ser Tyr Ala Gly Ile Leu Leu Gly Ile Thr Asn Thr Phe Ala Thr
                485                 490                 495

Ile Pro Gly Met Val Gly Pro Val Ile Ala Lys Ser Leu Thr Pro Asp
            500                 505                 510

Asn Thr Val Gly Glu Trp Gln Thr Val Phe Tyr Ile Ala Ala Ala Ile
        515                 520                 525

Asn Val Phe Gly Ala Ile Phe Phe Thr Leu Phe Ala Lys Gly Glu Val
    530                 535                 540

Gln Asn Trp Ala Leu Asn Asp His His Gly His Arg His
545                 550                 555


<210> SEQ ID NO 94
<211> LENGTH: 996
<212> TYPE: DNA
<213> ORGANISM: Homo sapiens

<400> SEQUENCE: 94

atgcgcccgg ccttggcggt gggcctggtg ttcgcaggct gctgcagtaa cgtgatcttc      60

ctagagctcc tggcccggaa gcatccagga tgtgggaaca ttgtgacatt tgcacaattt     120

ttatttattg ctgtggaagg cttcctcttt gaagctgatt tgggaaggaa gccaccagct     180

atcccaataa ggtactatgc cataatggtg accatgttct tcaccgtgag cgtggtgaac     240

aactatgccc tgaatctcaa cattgccatg cccctgcata tgatatttag atccggttct     300

ctaattgcca acatgattct aggaattatc attttgaaga aaagatacag tatattcaaa     360

tatacctcca ttgccctggt gtctgtgggg atatttattt gcacttttat gtcagcaaag     420
```

```
caggtgactt cccagtccag cttgagtgag aatgatggat tccaggcatt tgtgtggtgg    480

ttactaggta ttggggcatt gacttttgct cttctgatgt cagcaaggat ggggatattc    540

caagagactc tctacaaacg atttgggaaa cactccaagg aggctttgtt ttataatcac    600

gcccttccac ttccgggttt cgtcttcttg gcttctgata tttatgacca tgcagttcta    660

ttcaataagt ctgagttata tgaaattccc gtcatcggag tgaccctgcc catcatgtgg    720

ttctacctcc tcatgaacat catcactcag tacgtgtgca tccggggtgt gtttatcctc    780

accacagaat gcgcctccct caccgtcacg ctcgtcgtga ccctacgcaa atttgtgagc    840

ctcatctttt ccatcttgta cttccagaac cccttcaccc tgtggcactg gctgggcacc    900

ttgtttgtct tcattgggac cttaatgtac acagaggtgt ggaacaacct agggaccaca    960

aaaagtgagc ctcagaagga cagcaagaag aactga                              996
```

<210> SEQ ID NO 95
<211> LENGTH: 331
<212> TYPE: PRT
<213> ORGANISM: Homo sapiens

<400> SEQUENCE: 95

```
Met Arg Pro Ala Leu Ala Val Gly Leu Val Phe Ala Gly Cys Cys Ser
1               5                   10                  15

Asn Val Ile Phe Leu Glu Leu Leu Ala Arg Lys His Pro Gly Cys Gly
            20                  25                  30

Asn Ile Val Thr Phe Ala Gln Phe Leu Phe Ile Ala Val Glu Gly Phe
        35                  40                  45

Leu Phe Glu Ala Asp Leu Gly Arg Lys Pro Pro Ala Ile Pro Ile Arg
    50                  55                  60

Tyr Tyr Ala Ile Met Val Thr Met Phe Phe Thr Val Ser Val Val Asn
65                  70                  75                  80

Asn Tyr Ala Leu Asn Leu Asn Ile Ala Met Pro Leu His Met Ile Phe
                85                  90                  95

Arg Ser Gly Ser Leu Ile Ala Asn Met Ile Leu Gly Ile Ile Ile Leu
            100                 105                 110

Lys Lys Arg Tyr Ser Ile Phe Lys Tyr Thr Ser Ile Ala Leu Val Ser
        115                 120                 125

Val Gly Ile Phe Ile Cys Thr Phe Met Ser Ala Lys Gln Val Thr Ser
    130                 135                 140

Gln Ser Ser Leu Ser Glu Asn Asp Gly Phe Gln Ala Phe Val Trp Trp
145                 150                 155                 160

Leu Leu Gly Ile Gly Ala Leu Thr Phe Ala Leu Leu Met Ser Ala Arg
                165                 170                 175

Met Gly Ile Phe Gln Glu Thr Leu Tyr Lys Arg Phe Gly Lys His Ser
            180                 185                 190

Lys Glu Ala Leu Phe Tyr Asn His Ala Leu Pro Leu Pro Gly Phe Val
        195                 200                 205

Phe Leu Ala Ser Asp Ile Tyr Asp His Ala Val Leu Phe Asn Lys Ser
    210                 215                 220

Glu Leu Tyr Glu Ile Pro Val Ile Gly Val Thr Leu Pro Ile Met Trp
225                 230                 235                 240

Phe Tyr Leu Leu Met Asn Ile Ile Thr Gln Tyr Val Cys Ile Arg Gly
                245                 250                 255

Val Phe Ile Leu Thr Thr Glu Cys Ala Ser Leu Thr Val Thr Leu Val
            260                 265                 270
```

```
Val Thr Leu Arg Lys Phe Val Ser Leu Ile Phe Ser Ile Leu Tyr Phe
        275                 280                 285

Gln Asn Pro Phe Thr Leu Trp His Trp Leu Gly Thr Leu Phe Val Phe
    290                 295                 300

Ile Gly Thr Leu Met Tyr Thr Glu Val Trp Asn Asn Leu Gly Thr Thr
305                 310                 315                 320

Lys Ser Glu Pro Gln Lys Asp Ser Lys Lys Asn
                325                 330


<210> SEQ ID NO 96
<211> LENGTH: 918
<212> TYPE: DNA
<213> ORGANISM: Homo sapiens

<400> SEQUENCE: 96

atggcggcgg ggctggcgcg gctcctgttg ctcctcgggc tctcggccgg cgggcccgcg     60

ccggcaggtg cagcgaagat gaaggtggtg gaggagccca acgcgtttgg ggtgaacaac    120

ccgttcttgc ctcaggccag tcgcctccag gccaagaggg atccttcacc cgtgtctgga    180

cccgtgcatc tcttccgact ctcgggcaag tgcttcagcc tggtggagtc cacgtacaag    240

tatgagttct gcccgttcca caacgtgacc cagcacgagc agaccttccg ctggaacgcc    300

tacagtggga tcctcggcat ctggcacgag tgggagatcg ccaacaacac cttcacgggc    360

atgtggatga gggacggtga cgcctgccgt tcccggagcc ggcagagcaa ggtggagctg    420

gcgtgtggaa aaagcaaccg gctggcccat gtgtccgagc cgagcacctg cgtctacgcg    480

ctgacgttcg agacccccct cgtctgccac ccccacgcct tgctagtgta cccaaccctg    540

ccagaggccc tgcagcggca gtgggaccag gtagagcagg acctggccga tgagctgatc    600

accccccagg gccatgagaa gttgctgagg acactttttg aggatgctgg ctacttaaag    660

accccagaag aaaatgaacc cacccagctg gagggaggtc ctgacagctt ggggtttgag    720

accctggaaa actgcaggaa ggctcataaa gaactctcaa aggagatcaa aaggctgaaa    780

ggtttgctca cccagcacgg catcccctac acgaggccca cagaaacttc caacttggag    840

cacttgggcc acgagacgcc cagagccaag tctccagagc agctgcgggg tgacccagga    900

ctgcgtggga gtttgtga                                                  918


<210> SEQ ID NO 97
<211> LENGTH: 305
<212> TYPE: PRT
<213> ORGANISM: Homo sapiens

<400> SEQUENCE: 97

Met Ala Ala Gly Leu Ala Arg Leu Leu Leu Leu Leu Gly Leu Ser Ala
1               5                   10                  15

Gly Gly Pro Ala Pro Ala Gly Ala Ala Lys Met Lys Val Val Glu Glu
            20                  25                  30

Pro Asn Ala Phe Gly Val Asn Asn Pro Phe Leu Pro Gln Ala Ser Arg
        35                  40                  45

Leu Gln Ala Lys Arg Asp Pro Ser Pro Val Ser Gly Pro Val His Leu
    50                  55                  60

Phe Arg Leu Ser Gly Lys Cys Phe Ser Leu Val Glu Ser Thr Tyr Lys
65                  70                  75                  80

Tyr Glu Phe Cys Pro Phe His Asn Val Thr Gln His Glu Gln Thr Phe
                85                  90                  95

Arg Trp Asn Ala Tyr Ser Gly Ile Leu Gly Ile Trp His Glu Trp Glu
```

```
            100                 105                 110

Ile Ala Asn Asn Thr Phe Thr Gly Met Trp Met Arg Asp Gly Asp Ala
        115                 120                 125

Cys Arg Ser Arg Ser Arg Gln Ser Lys Val Glu Leu Ala Cys Gly Lys
    130                 135                 140

Ser Asn Arg Leu Ala His Val Ser Glu Pro Ser Thr Cys Val Tyr Ala
145                 150                 155                 160

Leu Thr Phe Glu Thr Pro Leu Val Cys His Pro His Ala Leu Leu Val
                165                 170                 175

Tyr Pro Thr Leu Pro Glu Ala Leu Gln Arg Gln Trp Asp Gln Val Glu
            180                 185                 190

Gln Asp Leu Ala Asp Glu Leu Ile Thr Pro Gln Gly His Glu Lys Leu
        195                 200                 205

Leu Arg Thr Leu Phe Glu Asp Ala Gly Tyr Leu Lys Thr Pro Glu Glu
    210                 215                 220

Asn Glu Pro Thr Gln Leu Glu Gly Gly Pro Asp Ser Leu Gly Phe Glu
225                 230                 235                 240

Thr Leu Glu Asn Cys Arg Lys Ala His Lys Glu Leu Ser Lys Glu Ile
                245                 250                 255

Lys Arg Leu Lys Gly Leu Leu Thr Gln His Gly Ile Pro Tyr Thr Arg
            260                 265                 270

Pro Thr Glu Thr Ser Asn Leu Glu His Leu Gly His Glu Thr Pro Arg
        275                 280                 285

Ala Lys Ser Pro Glu Gln Leu Arg Gly Asp Pro Gly Leu Arg Gly Ser
    290                 295                 300

Leu
305
```

<210> SEQ ID NO 98
<211> LENGTH: 3771
<212> TYPE: DNA
<213> ORGANISM: Homo sapiens

<400> SEQUENCE: 98

```
atgctgttca agctcctgca gagacagacc tatacctgcc tgtcccacag gtatgggctc     60

tacgtgtgct tcttgggcgt cgttgtcacc atcgtctccg ccttccagtt cggagaggtg    120

gttctggaat ggagccgaga tcaataccat gttttgtttg attcctatag agacaatatt    180

gctggaaagt cctttcagaa tcggctttgt ctgcccatgc cgattgacgt tgtttacacc    240

tgggtgaatg gcacagatct tgaactactg aaggaactac agcaggtcag agaacagatg    300

gaggaggagc agaaagcaat gagagaaatc cttgggaaaa acacaacgga acctactaag    360

aagagtgaga agcagttaga gtgtttgcta acacactgca ttaaggtgcc aatgcttgtc    420

ctggacccag ccctgccagc caacatcacc ctgaaggacc tgccatctct ttatccttct    480

tttcattctg ccagtgacat tttcaatgtt gcaaaaccaa aaaacccttc taccaatgtc    540

tcagttgttg tttttgacag tactaaggat gttgaagatg cccactctgg actgcttaaa    600

ggaaatagca gacagacagt atggaggggc tacttgacaa cagataaaga agtccctgga    660

ttagtgctaa tgcaagattt ggctttcctg agtggatttc caccaacatt caaggaaaca    720

aatcaactaa aaacaaaatt gccagaaaat ctttcctcta aagtcaaact gttgcagttg    780

tattcagagg ccagtgtagc gcttctaaaa ctgaataacc ccaaggattt tcaagaattg    840

aataagcaaa ctaagaagaa catgaccatt gatggaaaag aactgaccat aagtcctgca    900
```

```
tatttattat gggatctgag cgccatcagc cagtctaagc aggatgaaga catctctgcc    960
agtcgttttg aagataacga agaactgagg tactcattgc gatctatcga gaggcatgca   1020
ccatgggttc ggaatatttt cattgtcacc aacgggcaga ttccatcctg gctgaacctt   1080
gacaatcctc gagtgacaat agtaacacac caggatgttt ttcgaaattt gagccacttg   1140
cctacccttta gttcacctgc tattgaaagt cacattcatc gcatcgaagg gctgtcccag  1200
aagtttattt acctaaatga tgatgtcatg tttgggaagg atgtctggcc agatgatttt   1260
tacagtcact ccaaaggcca gaaggtttat ttgacatggc ctgtgccaaa ctgtgccgag   1320
ggctgcccag gttcctggat taaggatggc tattgtgaca aggcttgtaa taattcagcc   1380
tgcgattggg atggtgggga ttgctctgga aacagtggag ggagtcgcta tattgcagga   1440
ggtggaggta ctgggagtat tggagttgga cagccctggc agtttggtgg aggaataaac   1500
agtgtctctt actgtaatca gggatgtgcg aattcctggc tcgctgataa gttctgtgac   1560
caagcatgca atgtcttgtc ctgtgggttt gatgctggcg actgtgggca agatcatttt   1620
catgaattgt ataaagtgat ccttctccca aaccagactc actatattat tccaaaaggt   1680
gaatgcctgc cttatttcag ctttgcagaa gtagccaaaa gaggagttga aggtgcctat   1740
agtgacaatc caataattcg acatgcttct attgccaaca agtggaaaac catccacctc   1800
ataatgcaca gtggaatgaa tgccaccaca atacatttta atctcacgtt tcaaaataca   1860
aacgatgaag agttcaaaat gcagataaca gtggaggtgg acacaaggga gggaccaaaa   1920
ctgaattcta cagcccagaa gggttacgaa aatttagtta gtcccataac acttcttcca   1980
gaggcggaaa tcctttttga ggatattccc aaagaaaaac gcttcccgaa gtttaagaga   2040
catgatgtta actcaacaag gagagcccag gaagaggtga aaattcccct ggtaaatatt   2100
tcactccttc caaaagacgc ccagttgagt ctcaatacct tggatttgca actggaacat   2160
ggagacatca ctttgaaagg atacaatttg tccaagtcag ccttgctgag atcatttctg   2220
atgaactcac agcatgctaa aataaaaaat caagctataa taacagatga aacaaatgac   2280
agtttggtgg ctccacagga aaaacaggtt cataaaagca tcttgccaaa cagcttagga   2340
gtgtctgaaa gattgcagag gttgactttt cctgcagtga gtgtaaaagt gaatggtcat   2400
gaccagggtc agaatccacc cctggacttg gagaccacag caagatttag agtggaaact   2460
cacacccaaa aaaccatagg cggaaatgtg acaaaagaaa agccccccatc tctgattgtt  2520
ccactggaaa gccagatgac aaaagaaaag aaaatcacag ggaaagaaaa agagaacagt   2580
agaatggagg aaaatgctga aatcacata ggcgttactg aagtgttact tggaagaaag    2640
ctgcagcatt acacagatag ttacttgggc tttttgccat gggagaaaaa aaagtatttc   2700
caagatcttc tcgacgaaga agagtcattg aagacacaat tggcatactt cactgatagc   2760
aaaaatactg ggaggcaact aaaagataca tttgcagatt ccctcagata tgtaaataaa   2820
attctaaata gcaagtttgg attcacatcg cggaaagtcc ctgctcacat gcctcacatg   2880
attgaccgga ttgttatgca agaactgcaa gatatgttcc ctgaagaatt tgacaagacg   2940
tcatttcaca aagtgcgcca ttctgaggat atgcagtttg ccttctctta tttttattat   3000
ctcatgagtg cagtgcagcc actgaatata tctcaagtct ttgatgaagt tgatacagat   3060
caatctggtg tcttgtctga cagagaaatc cgaacactgg ctaccagaat tcacgaactg   3120
ccgttaagtt tgcaggattt gacaggtctg gaacacatgc taataaattg ctcaaaaatg   3180
cttcctgctg atatcacgca gctaaataat attccaccaa ctcaggaatc ctactatgat   3240
cccaacctgc caccggtcac taaaagtcta gtaacaaact gtaaaccagt aactgacaaa   3300
```

```
atccacaaag catataagga caaaaacaaa tataggtttg aaatcatggg agaagaagaa   3360

atcgctttta aaatgattcg taccaacgtt tctcatgtgg ttggccagtt ggatgacata   3420

agaaaaaacc ctaggaagtt tgtttgcctg aatgacaaca ttgaccacaa tcataaagat   3480

gctcagacag tgaaggctgt tctcagggac ttctatgaat ccatgttccc cataccttcc   3540

caatttgaac tgccaagaga gtatcgaaac cgtttccttc atatgcatga gctgcaggaa   3600

tggagggctt atcgagacaa attgaagttt tggacccatt gtgtactagc aacattgatt   3660

atgtttacta tattctcatt ttttgctgag cagttaattg cacttaagcg gaagatattt   3720

cccagaagga ggatacacaa agaagctagt cccaatcgaa tcagagtata g            3771
```

<210> SEQ ID NO 99
<211> LENGTH: 1256
<212> TYPE: PRT
<213> ORGANISM: Homo sapiens

<400> SEQUENCE: 99

```
Met Leu Phe Lys Leu Leu Gln Arg Gln Thr Tyr Thr Cys Leu Ser His
1               5                   10                  15

Arg Tyr Gly Leu Tyr Val Cys Phe Leu Gly Val Val Val Thr Ile Val
            20                  25                  30

Ser Ala Phe Gln Phe Gly Glu Val Val Leu Glu Trp Ser Arg Asp Gln
        35                  40                  45

Tyr His Val Leu Phe Asp Ser Tyr Arg Asp Asn Ile Ala Gly Lys Ser
    50                  55                  60

Phe Gln Asn Arg Leu Cys Leu Pro Met Pro Ile Asp Val Val Tyr Thr
65                  70                  75                  80

Trp Val Asn Gly Thr Asp Leu Glu Leu Leu Lys Glu Leu Gln Gln Val
                85                  90                  95

Arg Glu Gln Met Glu Glu Glu Gln Lys Ala Met Arg Glu Ile Leu Gly
            100                 105                 110

Lys Asn Thr Thr Glu Pro Thr Lys Lys Ser Glu Lys Gln Leu Glu Cys
        115                 120                 125

Leu Leu Thr His Cys Ile Lys Val Pro Met Leu Val Leu Asp Pro Ala
    130                 135                 140

Leu Pro Ala Asn Ile Thr Leu Lys Asp Leu Pro Ser Leu Tyr Pro Ser
145                 150                 155                 160

Phe His Ser Ala Ser Asp Ile Phe Asn Val Ala Lys Pro Lys Asn Pro
                165                 170                 175

Ser Thr Asn Val Ser Val Val Val Phe Asp Ser Thr Lys Asp Val Glu
            180                 185                 190

Asp Ala His Ser Gly Leu Leu Lys Gly Asn Ser Arg Gln Thr Val Trp
        195                 200                 205

Arg Gly Tyr Leu Thr Thr Asp Lys Glu Val Pro Gly Leu Val Leu Met
    210                 215                 220

Gln Asp Leu Ala Phe Leu Ser Gly Phe Pro Pro Thr Phe Lys Glu Thr
225                 230                 235                 240

Asn Gln Leu Lys Thr Lys Leu Pro Glu Asn Leu Ser Ser Lys Val Lys
                245                 250                 255

Leu Leu Gln Leu Tyr Ser Glu Ala Ser Val Ala Leu Leu Lys Leu Asn
            260                 265                 270

Asn Pro Lys Asp Phe Gln Glu Leu Asn Lys Gln Thr Lys Lys Asn Met
        275                 280                 285
```

```
Thr Ile Asp Gly Lys Glu Leu Thr Ile Ser Pro Ala Tyr Leu Leu Trp
    290                 295                 300

Asp Leu Ser Ala Ile Ser Gln Ser Lys Gln Asp Glu Asp Ile Ser Ala
305                 310                 315                 320

Ser Arg Phe Glu Asp Asn Glu Glu Leu Arg Tyr Ser Leu Arg Ser Ile
                325                 330                 335

Glu Arg His Ala Pro Trp Val Arg Asn Ile Phe Ile Val Thr Asn Gly
            340                 345                 350

Gln Ile Pro Ser Trp Leu Asn Leu Asp Asn Pro Arg Val Thr Ile Val
        355                 360                 365

Thr His Gln Asp Val Phe Arg Asn Leu Ser His Leu Pro Thr Phe Ser
    370                 375                 380

Ser Pro Ala Ile Glu Ser His Ile His Arg Ile Glu Gly Leu Ser Gln
385                 390                 395                 400

Lys Phe Ile Tyr Leu Asn Asp Asp Val Met Phe Gly Lys Asp Val Trp
                405                 410                 415

Pro Asp Asp Phe Tyr Ser His Ser Lys Gly Gln Lys Val Tyr Leu Thr
            420                 425                 430

Trp Pro Val Pro Asn Cys Ala Glu Gly Cys Pro Gly Ser Trp Ile Lys
        435                 440                 445

Asp Gly Tyr Cys Asp Lys Ala Cys Asn Asn Ser Ala Cys Asp Trp Asp
    450                 455                 460

Gly Gly Asp Cys Ser Gly Asn Ser Gly Gly Ser Arg Tyr Ile Ala Gly
465                 470                 475                 480

Gly Gly Gly Thr Gly Ser Ile Gly Val Gly Gln Pro Trp Gln Phe Gly
                485                 490                 495

Gly Gly Ile Asn Ser Val Ser Tyr Cys Asn Gln Gly Cys Ala Asn Ser
            500                 505                 510

Trp Leu Ala Asp Lys Phe Cys Asp Gln Ala Cys Asn Val Leu Ser Cys
        515                 520                 525

Gly Phe Asp Ala Gly Asp Cys Gly Gln Asp His Phe His Glu Leu Tyr
    530                 535                 540

Lys Val Ile Leu Leu Pro Asn Gln Thr His Tyr Ile Ile Pro Lys Gly
545                 550                 555                 560

Glu Cys Leu Pro Tyr Phe Ser Phe Ala Glu Val Ala Lys Arg Gly Val
                565                 570                 575

Glu Gly Ala Tyr Ser Asp Asn Pro Ile Ile Arg His Ala Ser Ile Ala
            580                 585                 590

Asn Lys Trp Lys Thr Ile His Leu Ile Met His Ser Gly Met Asn Ala
        595                 600                 605

Thr Thr Ile His Phe Asn Leu Thr Phe Gln Asn Thr Asn Asp Glu Glu
    610                 615                 620

Phe Lys Met Gln Ile Thr Val Glu Val Asp Thr Arg Glu Gly Pro Lys
625                 630                 635                 640

Leu Asn Ser Thr Ala Gln Lys Gly Tyr Glu Asn Leu Val Ser Pro Ile
                645                 650                 655

Thr Leu Leu Pro Glu Ala Glu Ile Leu Phe Glu Asp Ile Pro Lys Glu
            660                 665                 670

Lys Arg Phe Pro Lys Phe Lys Arg His Asp Val Asn Ser Thr Arg Arg
        675                 680                 685

Ala Gln Glu Glu Val Lys Ile Pro Leu Val Asn Ile Ser Leu Leu Pro
    690                 695                 700

Lys Asp Ala Gln Leu Ser Leu Asn Thr Leu Asp Leu Gln Leu Glu His
```

```
705                 710                 715                 720

Gly Asp Ile Thr Leu Lys Gly Tyr Asn Leu Ser Lys Ser Ala Leu Leu
                725                 730                 735

Arg Ser Phe Leu Met Asn Ser Gln His Ala Lys Ile Lys Asn Gln Ala
            740                 745                 750

Ile Ile Thr Asp Glu Thr Asn Asp Ser Leu Val Ala Pro Gln Glu Lys
        755                 760                 765

Gln Val His Lys Ser Ile Leu Pro Asn Ser Leu Gly Val Ser Glu Arg
    770                 775                 780

Leu Gln Arg Leu Thr Phe Pro Ala Val Ser Val Lys Val Asn Gly His
785                 790                 795                 800

Asp Gln Gly Gln Asn Pro Pro Leu Asp Leu Glu Thr Thr Ala Arg Phe
                805                 810                 815

Arg Val Glu Thr His Thr Gln Lys Thr Ile Gly Gly Asn Val Thr Lys
            820                 825                 830

Glu Lys Pro Pro Ser Leu Ile Val Pro Leu Glu Ser Gln Met Thr Lys
        835                 840                 845

Glu Lys Lys Ile Thr Gly Lys Glu Lys Glu Asn Ser Arg Met Glu Glu
    850                 855                 860

Asn Ala Glu Asn His Ile Gly Val Thr Glu Val Leu Leu Gly Arg Lys
865                 870                 875                 880

Leu Gln His Tyr Thr Asp Ser Tyr Leu Gly Phe Leu Pro Trp Glu Lys
                885                 890                 895

Lys Lys Tyr Phe Gln Asp Leu Leu Asp Glu Glu Glu Ser Leu Lys Thr
            900                 905                 910

Gln Leu Ala Tyr Phe Thr Asp Ser Lys Asn Thr Gly Arg Gln Leu Lys
        915                 920                 925

Asp Thr Phe Ala Asp Ser Leu Arg Tyr Val Asn Lys Ile Leu Asn Ser
    930                 935                 940

Lys Phe Gly Phe Thr Ser Arg Lys Val Pro Ala His Met Pro His Met
945                 950                 955                 960

Ile Asp Arg Ile Val Met Gln Glu Leu Gln Asp Met Phe Pro Glu Glu
                965                 970                 975

Phe Asp Lys Thr Ser Phe His Lys Val Arg His Ser Glu Asp Met Gln
            980                 985                 990

Phe Ala Phe Ser Tyr Phe Tyr Tyr  Leu Met Ser Ala Val  Gln Pro Leu
        995                 1000                 1005

Asn Ile  Ser Gln Val Phe Asp  Glu Val Asp Thr Asp  Gln Ser Gly
    1010                 1015                 1020

Val Leu  Ser Asp Arg Glu Ile  Arg Thr Leu Ala Thr  Arg Ile His
    1025                 1030                 1035

Glu Leu  Pro Leu Ser Leu Gln  Asp Leu Thr Gly Leu  Glu His Met
    1040                 1045                 1050

Leu Ile  Asn Cys Ser Lys Met  Leu Pro Ala Asp Ile  Thr Gln Leu
    1055                 1060                 1065

Asn Asn  Ile Pro Pro Thr Gln  Glu Ser Tyr Tyr Asp  Pro Asn Leu
    1070                 1075                 1080

Pro Pro  Val Thr Lys Ser Leu  Val Thr Asn Cys Lys  Pro Val Thr
    1085                 1090                 1095

Asp Lys  Ile His Lys Ala Tyr  Lys Asp Lys Asn Lys  Tyr Arg Phe
    1100                 1105                 1110

Glu Ile  Met Gly Glu Glu Glu  Ile Ala Phe Lys Met  Ile Arg Thr
    1115                 1120                 1125
```

```
Asn Val  Ser His Val Val Gly  Gln Leu Asp Asp Ile  Arg Lys Asn
    1130                 1135                 1140

Pro Arg  Lys Phe Val Cys Leu  Asn Asp Asn Ile Asp  His Asn His
    1145                 1150                 1155

Lys Asp  Ala Gln Thr Val Lys  Ala Val Leu Arg Asp  Phe Tyr Glu
    1160                 1165                 1170

Ser Met  Phe Pro Ile Pro Ser  Gln Phe Glu Leu Pro  Arg Glu Tyr
    1175                 1180                 1185

Arg Asn  Arg Phe Leu His Met  His Glu Leu Gln Glu  Trp Arg Ala
    1190                 1195                 1200

Tyr Arg  Asp Lys Leu Lys Phe  Trp Thr His Cys Val  Leu Ala Thr
    1205                 1210                 1215

Leu Ile  Met Phe Thr Ile Phe  Ser Phe Phe Ala Glu  Gln Leu Ile
    1220                 1225                 1230

Ala Leu  Lys Arg Lys Ile Phe  Pro Arg Arg Arg Ile  His Lys Glu
    1235                 1240                 1245

Ala Ser  Pro Asn Arg Ile Arg  Val
    1250                 1255
```

<210> SEQ ID NO 100
<211> LENGTH: 1743
<212> TYPE: DNA
<213> ORGANISM: Homo sapiens

<400> SEQUENCE: 100

```
atgacagccc cggcgggtcc gcgcggctca gagaccgagc ggcttctgac ccccaacccc     60

gggtatggga cccaggcggg gccttcaccg gcccctccga cacccccaga agaggaagac    120

cttcgccgtc gtctcaaata ctttttcatg agtccctgcg acaagtttcg agccaagggc    180

cgcaagccct gcaagctgat gctgcaagtg gtcaagatcc tggtggtcac ggtgcagctc    240

atcctgtttg ggctcagtaa tcagctggct gtgacattcc gggaagagaa caccatcgcc    300

ttccgacacc tcttcctgct gggctactcg gacggagcgg atgacacctt cgcagcctac    360

acgcgggagc agctgtacca ggccatcttc catgctgtgg accagtacct ggcgttgcct    420

gacgtgtcac tgggccggta tgcgtatgtc cgtggtgggg gtgacccttg gaccaatggc    480

tcagggcttg ctctctgcca gcggtactac caccgaggcc acgtggaccc ggccaacgac    540

acatttgaca ttgatccgat ggtggttact gactgcatcc aggtggatcc ccccgagcgg    600

ccccctccgc cccccagcga cgatctcacc ctcttggaaa gcagctccag ttacaagaac    660

ctcacgctca aattccacaa gctggtcaat gtcaccatcc acttccggct gaagaccatt    720

aacctccaga gcctcatcaa taatgagatc ccggactgct ataccttcag cgtcctgatc    780

acgtttgaca acaaagcaca cagtgggcgg atccccatca gcctggagac ccaggcccac    840

atccaggagt gtaagcaccc cagtgtcttc cagcacggag acaacagctt ccggctcctg    900

tttgacgtgg tggtcatcct cacctgctcc ctgtccttcc tcctctgcgc ccgctcactc    960

cttcgaggct tcctgctgca gaacgagttt gtggggttca tgtggcggca gcggggacgg   1020

gtcatcagcc tgtgggagcg gctggaattt gtcaatggct ggtacatcct gctcgtcacc   1080

agcgatgtgc tcaccatctc gggcaccatc atgaagatcg gcatcgaggc caagaacttg   1140

gcgagctacg acgtctgcag catcctcctg ggcacctcga cgctgctggt gtgggtgggc   1200

gtgatccgct acctgacctt cttccacaac tacaatatcc tcatcgccac actgcgggtg   1260

gccctgccca gcgtcatgcg cttctgctgc tgcgtggctg tcatctacct gggctactgc   1320
```

```
ttctgtggct ggatcgtgct ggggccctat catgtgaagt tccgctcact ctccatggtg   1380

tctgagtgcc tgttctcgct catcaatggg gacgacatgt ttgtgacgtt cgccgccatg   1440

caggcgcagc agggccgcag cagcctggtg tggctcttct cccagctcta cctttactcc   1500

ttcatcagcc tcttcatcta catggtgctc agcctcttca tcgcgctcat caccggcgcc   1560

tacgacacca tcaagcatcc cggcggcgca ggcgcagagg agagcgagct gcaggcctac   1620

atcgcacagt gccaggacag ccccacctcc ggcaagttcc gccgcgggag cggctcggcc   1680

tgcagccttc tctgctgctg cggaagggac cctcggaggg agcattcgct gctggtgaat   1740

tga                                                                 1743
```

<210> SEQ ID NO 101
<211> LENGTH: 580
<212> TYPE: PRT
<213> ORGANISM: Homo sapiens

<400> SEQUENCE: 101

```
Met Thr Ala Pro Ala Gly Pro Arg Gly Ser Glu Thr Glu Arg Leu Leu
1               5                   10                  15

Thr Pro Asn Pro Gly Tyr Gly Thr Gln Ala Gly Pro Ser Pro Ala Pro
            20                  25                  30

Pro Thr Pro Pro Glu Glu Glu Asp Leu Arg Arg Arg Leu Lys Tyr Phe
        35                  40                  45

Phe Met Ser Pro Cys Asp Lys Phe Arg Ala Lys Gly Arg Lys Pro Cys
    50                  55                  60

Lys Leu Met Leu Gln Val Val Lys Ile Leu Val Val Thr Val Gln Leu
65                  70                  75                  80

Ile Leu Phe Gly Leu Ser Asn Gln Leu Ala Val Thr Phe Arg Glu Glu
                85                  90                  95

Asn Thr Ile Ala Phe Arg His Leu Phe Leu Leu Gly Tyr Ser Asp Gly
            100                 105                 110

Ala Asp Asp Thr Phe Ala Ala Tyr Thr Arg Glu Gln Leu Tyr Gln Ala
        115                 120                 125

Ile Phe His Ala Val Asp Gln Tyr Leu Ala Leu Pro Asp Val Ser Leu
    130                 135                 140

Gly Arg Tyr Ala Tyr Val Arg Gly Gly Gly Asp Pro Trp Thr Asn Gly
145                 150                 155                 160

Ser Gly Leu Ala Leu Cys Gln Arg Tyr Tyr His Arg Gly His Val Asp
                165                 170                 175

Pro Ala Asn Asp Thr Phe Asp Ile Asp Pro Met Val Val Thr Asp Cys
            180                 185                 190

Ile Gln Val Asp Pro Pro Glu Arg Pro Pro Pro Pro Pro Ser Asp Asp
        195                 200                 205

Leu Thr Leu Leu Glu Ser Ser Ser Ser Tyr Lys Asn Leu Thr Leu Lys
    210                 215                 220

Phe His Lys Leu Val Asn Val Thr Ile His Phe Arg Leu Lys Thr Ile
225                 230                 235                 240

Asn Leu Gln Ser Leu Ile Asn Asn Glu Ile Pro Asp Cys Tyr Thr Phe
                245                 250                 255

Ser Val Leu Ile Thr Phe Asp Asn Lys Ala His Ser Gly Arg Ile Pro
            260                 265                 270

Ile Ser Leu Glu Thr Gln Ala His Ile Gln Glu Cys Lys His Pro Ser
        275                 280                 285
```

```
Val Phe Gln His Gly Asp Asn Ser Phe Arg Leu Leu Phe Asp Val Val
    290                 295                 300

Val Ile Leu Thr Cys Ser Leu Ser Phe Leu Leu Cys Ala Arg Ser Leu
305                 310                 315                 320

Leu Arg Gly Phe Leu Leu Gln Asn Glu Phe Val Gly Phe Met Trp Arg
                325                 330                 335

Gln Arg Gly Arg Val Ile Ser Leu Trp Glu Arg Leu Glu Phe Val Asn
            340                 345                 350

Gly Trp Tyr Ile Leu Leu Val Thr Ser Asp Val Leu Thr Ile Ser Gly
        355                 360                 365

Thr Ile Met Lys Ile Gly Ile Glu Ala Lys Asn Leu Ala Ser Tyr Asp
    370                 375                 380

Val Cys Ser Ile Leu Leu Gly Thr Ser Thr Leu Leu Val Trp Val Gly
385                 390                 395                 400

Val Ile Arg Tyr Leu Thr Phe Phe His Asn Tyr Asn Ile Leu Ile Ala
                405                 410                 415

Thr Leu Arg Val Ala Leu Pro Ser Val Met Arg Phe Cys Cys Cys Val
            420                 425                 430

Ala Val Ile Tyr Leu Gly Tyr Cys Phe Cys Gly Trp Ile Val Leu Gly
        435                 440                 445

Pro Tyr His Val Lys Phe Arg Ser Leu Ser Met Val Ser Glu Cys Leu
    450                 455                 460

Phe Ser Leu Ile Asn Gly Asp Asp Met Phe Val Thr Phe Ala Ala Met
465                 470                 475                 480

Gln Ala Gln Gln Gly Arg Ser Ser Leu Val Trp Leu Phe Ser Gln Leu
                485                 490                 495

Tyr Leu Tyr Ser Phe Ile Ser Leu Phe Ile Tyr Met Val Leu Ser Leu
            500                 505                 510

Phe Ile Ala Leu Ile Thr Gly Ala Tyr Asp Thr Ile Lys His Pro Gly
        515                 520                 525

Gly Ala Gly Ala Glu Glu Ser Glu Leu Gln Ala Tyr Ile Ala Gln Cys
    530                 535                 540

Gln Asp Ser Pro Thr Ser Gly Lys Phe Arg Arg Gly Ser Gly Ser Ala
545                 550                 555                 560

Cys Ser Leu Leu Cys Cys Cys Gly Arg Asp Pro Ser Glu Glu His Ser
                565                 570                 575

Leu Leu Val Asn
            580


<210> SEQ ID NO 102
<211> LENGTH: 1233
<212> TYPE: DNA
<213> ORGANISM: Homo sapiens

<400> SEQUENCE: 102

atggtgtgct tccgcctctt cccggttccg ggctcagggc tcgttctggt ctgcctagtc      60

ctgggagctg tgcggtctta tgcattggaa cttaatttga cagattcaga aaatgccact     120

tgcctttatg caaaatggca gatgaatttc acagtacgct atgaaactac aaataaaact     180

tataaaactg taaccatttc agaccatggc actgtgacat ataatggaag catttgtggg     240

gatgatcaga atggtcccaa aatagcagtg cagttcggac ctggcttttc ctggattgcg     300

aattttacca aggcagcatc tacttattca attgacagcg tctcattttc ctacaacact     360

ggtgataaca caacatttcc tgatgctgaa gataaaggaa ttcttactgt tgatgaactt     420
```

```
ttggccatca gaattccatt gaatgacctt tttagatgca atagtttatc aactttggaa    480

aagaatgatg ttgtccaaca ctactgggat gttcttgtac aagcttttgt ccaaaatggc    540

acagtgagca caaatgagtt cctgtgtgat aaagacaaaa cttcaacagt ggcacccacc    600

atacacacca ctgtgccatc tcctactaca acacctactc caaaggaaaa accagaagct    660

ggaacctatt cagttaataa tggcaatgat acttgtctgc tggctaccat ggggctgcag    720

ctgaacatca ctcaggataa ggttgcttca gttattaaca tcaaccccaa tacaactcac    780

tccacaggca gctgccgttc tcacactgct ctacttagac tcaatagcag caccattaag    840

tatctagact ttgtctttgc tgtgaaaaat gaaaaccgat tttatctgaa ggaagtgaac    900

atcagcatgt atttggttaa tggctccgtt ttcagcattg caaataacaa tctcagctac    960

tgggatgccc ccctgggaag ttcttatatg tgcaacaaag agcagactgt ttcagtgtct   1020

ggagcatttc agataaatac ctttgatcta agggttcagc ctttcaatgt gacacaagga   1080

aagtattcta cagctcaaga ctgcagtgca gatgacgaca acttccttgt gcccatagcg   1140

gtgggagctg ccttggcagg agtacttatt ctagtgttgc tggcttattt tattggtctc   1200

aagcaccatc atgctggata tgagcaattt tag                                1233
```

<210> SEQ ID NO 103
<211> LENGTH: 410
<212> TYPE: PRT
<213> ORGANISM: Homo sapiens

<400> SEQUENCE: 103

```
Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
        35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
```

```
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Asp Cys
        355                 360                 365

Ser Ala Asp Asp Asp Asn Phe Leu Val Pro Ile Ala Val Gly Ala Ala
    370                 375                 380

Leu Ala Gly Val Leu Ile Leu Val Leu Leu Ala Tyr Phe Ile Gly Leu
385                 390                 395                 400

Lys His His His Ala Gly Tyr Glu Gln Phe
                405                 410


<210> SEQ ID NO 104
<211> LENGTH: 3837
<212> TYPE: DNA
<213> ORGANISM: Homo sapiens

<400> SEQUENCE: 104

atgaccgctc gcggcctggc ccttggcctc ctcctgctgc tactgtgtcc agcgcaggtg      60

ttttcacagt cctgtgtttg gtatggagag tgtggaattg catatgggga caagaggtac     120

aattgcgaat attctggccc accaaaacca ttgccaaagg atggatatga cttagtgcag     180

gaactctgtc caggattctt ctttggcaat gtcagtctct gttgtgatgt tcggcagctt     240

cagacactaa aagacaacct gcagctgcct ctacagtttc tgtccagatg tccatcctgt     300

ttttataacc tactgaacct gttttgtgag ctgacatgta gccctcgaca gagtcagttt     360

ttgaatgtta cagctactga agattatgtt gatcctgtta caaaccagac gaaaacaaat     420

gtgaaagagt tacaatacta cgtcggacag agttttgcca atgcaatgta caatgcctgc     480

cgggatgtgg aggcccccctc aagtaatgac aaggccctgg gactcctgtg tgggaaggac     540

gctgacgcct gtaatgccac caactggatt gaatacatgt tcaataagga caatggacag     600

gcacctttta ccatcactcc tgtgttttca gattttccag tccatgggat ggagcccatg     660

aacaatgcca ccaaaggctg tgacgagtct gtggatgagg tcacagcacc atgtagctgc     720

caagactgct ctattgtctg tggccccaag ccccagcccc cacctcctcc tgctccctgg     780

acgatccttg gcttggacgc catgtatgtc atcatgtgga tcacctacat ggcgtttttg     840

cttgtgtttt ttggagcatt ttttgcagtg tggtgctaca gaaaacggta ttttgtctcc     900

gagtacactc ccatcgatag caatatagct ttttctgtta atgcaagtga caaaggagag     960

gcgtcctgct gtgaccctgt cagcgcagca tttgagggct gcttgaggcg gctgttcaca    1020

cgctgggggt ctttctgcgt ccgaaaccct ggctgtgtca ttttcttctc gctggtcttc    1080
```

```
attactgcgt gttcgtcagg cctggtgttt gtccgggtca caaccaatcc agttgacctc   1140
tggtcagccc ccagcagcca ggctcgcctg gaaaaagagt actttgacca gcactttggg   1200
cctttcttcc ggacggagca gctcatcatc cgggcccctc tcactgacaa acacatttac   1260
cagccatacc cttcgggagc tgatgtaccc tttggacctc cgcttgacat acagatactg   1320
caccaggttc ttgacttaca aatagccatc gaaaacatta ctgcctctta tgacaatgag   1380
actgtgacac ttcaagacat ctgcttggcc cctctttcac cgtataacac gaactgcacc   1440
attttgagtg tgttaaatta cttccagaac agccattccg tgctggacca caagaaaggg   1500
gacgacttct ttgtgtatgc cgattaccac acgcactttc tgtactgcgt acgggctcct   1560
gcctctctga atgatacaag tttgctccat gacccttgtc tgggtacgtt tggtggacca   1620
gtgttcccgt ggcttgtgtt gggaggctat gatgatcaaa actacaataa cgccactgcc   1680
cttgtgatta ccttccctgt caataattac tataatgata cagagaagct ccagagggcc   1740
caggcctggg aaaaagagtt tattaatttt gtgaaaaact acaagaatcc caatctgacc   1800
atttccttca ctgctgaacg aagtattgaa gatgaactaa atcgtgaaag tgacagtgat   1860
gtcttcaccg ttgtaattag ctatgccatc atgtttctat atatttccct agccttgggg   1920
cacatgaaaa gctgtcgcag gcttctggtg gattcgaagg tctcactagg catcgcgggc   1980
atcttgatcg tgctgagctc ggtggcttgc tccttgggtg tcttcagcta cattgggttg   2040
cccttgaccc tcattgtgat tgaagtcatc ccgttcctgg tgctggctgt tggagtggac   2100
aacatcttca ttctggtgca ggcctaccag agagatgaac gtcttcaagg ggaaaccctg   2160
gatcagcagc tgggcagggt cctaggagaa gtggctccca gtatgttcct gtcatccttt   2220
tctgagactg tagcattttt cttaggagca ttgtccgtga tgccagccgt gcacaccttc   2280
tctctctttg cgggattggc agtcttcatt gactttcttc tgcagattac ctgtttcgtg   2340
agtctcttgg ggttagacat taaacgtcaa gagaaaaatc ggctagacat cttttgctgt   2400
gtcagaggtg ctgaagatgg aacaagcgtc caggcctcag agagctgttt gtttcgcttc   2460
ttcaaaaact cctattctcc acttctgcta aaggactgga tgagaccaat tgtgatagca   2520
atatttgtgg gtgttctgtc attcagcatc gcagtcctga acaaagtaga tattggattg   2580
gatcagtctc tttcgatgcc agatgactcc tacatggtgg attatttcaa atccatcagt   2640
cagtacctgc atgcgggtcc gcctgtgtac tttgtcctgg aggaagggca cgactacact   2700
tcttccaagg ggcagaacat ggtgtgcggc ggcatgggct gcaacaatga ttccctggtg   2760
cagcagatat ttaacgcggc gcagctggac aactataccc gaataggctt cgccccctcg   2820
tcctggatcg acgattattt cgactgggtg aagccacagt cgtcttgctg tcgagtggac   2880
aatatcactg accagttctg caatgcttca gtggttgacc ctgcctgcgt tcgctgcagg   2940
cctctgactc cggaaggcaa acagaggcct caggggggag acttcatgag attcctgccc   3000
atgttccttt cggataaccc taaccccaag tgtggcaaag gggacatgc tgcctatagt    3060
tctgcagtta acatcctcct tggccatggc accagggtcg gagccacgta cttcatgacc   3120
taccacaccg tgctgcagac ctctgctgac tttattgacg ctctgaagaa agcccgactt   3180
atagccagta atgtcaccga aaccatgggc attaacggca gtgcctaccg agtatttcct   3240
tacagtgtgt tttatgtctt ctacgaacag tacctgacca tcattgacga cactatcttc   3300
aacctcggtg tgtccctggg cgcgatattt ctggtgacca tggtcctcct gggctgtgag   3360
ctctggtctg cagtcatcat gtgtgccacc atcgccatgg tcttggtcaa catgtttgga   3420
gttatgtggc tctggggcat cagtctgaac gctgtatcct tggtcaacct ggtgatgagc   3480
```

```
tgtggcatct ccgtggagtt ctgcagccac ataaccagag cgttcacggt gagcatgaaa   3540

ggcagccgcg tggagcgcgc ggaagaggca cttgcccaca tgggcagctc cgtgttcagt   3600

ggaatcacac ttacaaaatt tggagggatt gtggtgttgg cttttgccaa atctcaaatt   3660

ttccagatat tctacttcag gatgtatttg gccatggtct tactgggagc cactcacgga   3720

ttaatatttc tccctgtctt actcagttac atagggccat cagtaaataa agccaaaagt   3780

tgtgccactg aagagcgata caaaggaaca gagcgcgaac ggcttctaaa tttctag      3837
```

<210> SEQ ID NO 105
<211> LENGTH: 1278
<212> TYPE: PRT
<213> ORGANISM: Homo sapiens

<400> SEQUENCE: 105

```
Met Thr Ala Arg Gly Leu Ala Leu Gly Leu Leu Leu Leu Leu Leu Cys
1               5                   10                  15

Pro Ala Gln Val Phe Ser Gln Ser Cys Val Trp Tyr Gly Glu Cys Gly
            20                  25                  30

Ile Ala Tyr Gly Asp Lys Arg Tyr Asn Cys Glu Tyr Ser Gly Pro Pro
        35                  40                  45

Lys Pro Leu Pro Lys Asp Gly Tyr Asp Leu Val Gln Glu Leu Cys Pro
    50                  55                  60

Gly Phe Phe Phe Gly Asn Val Ser Leu Cys Cys Asp Val Arg Gln Leu
65                  70                  75                  80

Gln Thr Leu Lys Asp Asn Leu Gln Leu Pro Leu Gln Phe Leu Ser Arg
                85                  90                  95

Cys Pro Ser Cys Phe Tyr Asn Leu Leu Asn Leu Phe Cys Glu Leu Thr
            100                 105                 110

Cys Ser Pro Arg Gln Ser Gln Phe Leu Asn Val Thr Ala Thr Glu Asp
        115                 120                 125

Tyr Val Asp Pro Val Thr Asn Gln Thr Lys Thr Asn Val Lys Glu Leu
    130                 135                 140

Gln Tyr Tyr Val Gly Gln Ser Phe Ala Asn Ala Met Tyr Asn Ala Cys
145                 150                 155                 160

Arg Asp Val Glu Ala Pro Ser Ser Asn Asp Lys Ala Leu Gly Leu Leu
                165                 170                 175

Cys Gly Lys Asp Ala Asp Ala Cys Asn Ala Thr Asn Trp Ile Glu Tyr
            180                 185                 190

Met Phe Asn Lys Asp Asn Gly Gln Ala Pro Phe Thr Ile Thr Pro Val
        195                 200                 205

Phe Ser Asp Phe Pro Val His Gly Met Glu Pro Met Asn Asn Ala Thr
    210                 215                 220

Lys Gly Cys Asp Glu Ser Val Asp Glu Val Thr Ala Pro Cys Ser Cys
225                 230                 235                 240

Gln Asp Cys Ser Ile Val Cys Gly Pro Lys Pro Gln Pro Pro Pro Pro
                245                 250                 255

Pro Ala Pro Trp Thr Ile Leu Gly Leu Asp Ala Met Tyr Val Ile Met
            260                 265                 270

Trp Ile Thr Tyr Met Ala Phe Leu Leu Val Phe Phe Gly Ala Phe Phe
        275                 280                 285

Ala Val Trp Cys Tyr Arg Lys Arg Tyr Phe Val Ser Glu Tyr Thr Pro
    290                 295                 300

Ile Asp Ser Asn Ile Ala Phe Ser Val Asn Ala Ser Asp Lys Gly Glu
```

```
305                 310                 315                 320

Ala Ser Cys Cys Asp Pro Val Ser Ala Ala Phe Glu Gly Cys Leu Arg
                325                 330                 335

Arg Leu Phe Thr Arg Trp Gly Ser Phe Cys Val Arg Asn Pro Gly Cys
            340                 345                 350

Val Ile Phe Phe Ser Leu Val Phe Ile Thr Ala Cys Ser Ser Gly Leu
        355                 360                 365

Val Phe Val Arg Val Thr Thr Asn Pro Val Asp Leu Trp Ser Ala Pro
    370                 375                 380

Ser Ser Gln Ala Arg Leu Glu Lys Glu Tyr Phe Asp Gln His Phe Gly
385                 390                 395                 400

Pro Phe Phe Arg Thr Glu Gln Leu Ile Ile Arg Ala Pro Leu Thr Asp
                405                 410                 415

Lys His Ile Tyr Gln Pro Tyr Pro Ser Gly Ala Asp Val Pro Phe Gly
            420                 425                 430

Pro Pro Leu Asp Ile Gln Ile Leu His Gln Val Leu Asp Leu Gln Ile
        435                 440                 445

Ala Ile Glu Asn Ile Thr Ala Ser Tyr Asp Asn Glu Thr Val Thr Leu
    450                 455                 460

Gln Asp Ile Cys Leu Ala Pro Leu Ser Pro Tyr Asn Thr Asn Cys Thr
465                 470                 475                 480

Ile Leu Ser Val Leu Asn Tyr Phe Gln Asn Ser His Ser Val Leu Asp
                485                 490                 495

His Lys Lys Gly Asp Asp Phe Phe Val Tyr Ala Asp Tyr His Thr His
            500                 505                 510

Phe Leu Tyr Cys Val Arg Ala Pro Ala Ser Leu Asn Asp Thr Ser Leu
        515                 520                 525

Leu His Asp Pro Cys Leu Gly Thr Phe Gly Gly Pro Val Phe Pro Trp
    530                 535                 540

Leu Val Leu Gly Gly Tyr Asp Asp Gln Asn Tyr Asn Asn Ala Thr Ala
545                 550                 555                 560

Leu Val Ile Thr Phe Pro Val Asn Asn Tyr Tyr Asn Asp Thr Glu Lys
                565                 570                 575

Leu Gln Arg Ala Gln Ala Trp Glu Lys Glu Phe Ile Asn Phe Val Lys
            580                 585                 590

Asn Tyr Lys Asn Pro Asn Leu Thr Ile Ser Phe Thr Ala Glu Arg Ser
        595                 600                 605

Ile Glu Asp Glu Leu Asn Arg Glu Ser Asp Ser Asp Val Phe Thr Val
    610                 615                 620

Val Ile Ser Tyr Ala Ile Met Phe Leu Tyr Ile Ser Leu Ala Leu Gly
625                 630                 635                 640

His Met Lys Ser Cys Arg Arg Leu Leu Val Asp Ser Lys Val Ser Leu
                645                 650                 655

Gly Ile Ala Gly Ile Leu Ile Val Leu Ser Ser Val Ala Cys Ser Leu
            660                 665                 670

Gly Val Phe Ser Tyr Ile Gly Leu Pro Leu Thr Leu Ile Val Ile Glu
        675                 680                 685

Val Ile Pro Phe Leu Val Leu Ala Val Gly Val Asp Asn Ile Phe Ile
    690                 695                 700

Leu Val Gln Ala Tyr Gln Arg Asp Glu Arg Leu Gln Gly Glu Thr Leu
705                 710                 715                 720

Asp Gln Gln Leu Gly Arg Val Leu Gly Glu Val Ala Pro Ser Met Phe
                725                 730                 735
```

```
Leu Ser Ser Phe Ser Glu Thr Val Ala Phe Phe Leu Gly Ala Leu Ser
            740                 745                 750

Val Met Pro Ala Val His Thr Phe Ser Leu Phe Ala Gly Leu Ala Val
        755                 760                 765

Phe Ile Asp Phe Leu Leu Gln Ile Thr Cys Phe Val Ser Leu Leu Gly
    770                 775                 780

Leu Asp Ile Lys Arg Gln Glu Lys Asn Arg Leu Asp Ile Phe Cys Cys
785                 790                 795                 800

Val Arg Gly Ala Glu Asp Gly Thr Ser Val Gln Ala Ser Glu Ser Cys
                805                 810                 815

Leu Phe Arg Phe Phe Lys Asn Ser Tyr Ser Pro Leu Leu Leu Lys Asp
            820                 825                 830

Trp Met Arg Pro Ile Val Ile Ala Ile Phe Val Gly Val Leu Ser Phe
        835                 840                 845

Ser Ile Ala Val Leu Asn Lys Val Asp Ile Gly Leu Asp Gln Ser Leu
    850                 855                 860

Ser Met Pro Asp Asp Ser Tyr Met Val Asp Tyr Phe Lys Ser Ile Ser
865                 870                 875                 880

Gln Tyr Leu His Ala Gly Pro Pro Val Tyr Phe Val Leu Glu Glu Gly
                885                 890                 895

His Asp Tyr Thr Ser Ser Lys Gly Gln Asn Met Val Cys Gly Gly Met
            900                 905                 910

Gly Cys Asn Asn Asp Ser Leu Val Gln Gln Ile Phe Asn Ala Ala Gln
        915                 920                 925

Leu Asp Asn Tyr Thr Arg Ile Gly Phe Ala Pro Ser Ser Trp Ile Asp
    930                 935                 940

Asp Tyr Phe Asp Trp Val Lys Pro Gln Ser Ser Cys Cys Arg Val Asp
945                 950                 955                 960

Asn Ile Thr Asp Gln Phe Cys Asn Ala Ser Val Val Asp Pro Ala Cys
                965                 970                 975

Val Arg Cys Arg Pro Leu Thr Pro Glu Gly Lys Gln Arg Pro Gln Gly
            980                 985                 990

Gly Asp Phe Met Arg Phe Leu Pro  Met Phe Leu Ser Asp  Asn Pro Asn
        995                 1000                 1005

Pro Lys  Cys Gly Lys Gly Gly  His Ala Ala Tyr Ser  Ser Ala Val
    1010                 1015                 1020

Asn Ile  Leu Leu Gly His Gly  Thr Arg Val Gly Ala  Thr Tyr Phe
    1025                 1030                 1035

Met Thr  Tyr His Thr Val Leu  Gln Thr Ser Ala Asp  Phe Ile Asp
    1040                 1045                 1050

Ala Leu  Lys Lys Ala Arg Leu  Ile Ala Ser Asn Val  Thr Glu Thr
    1055                 1060                 1065

Met Gly  Ile Asn Gly Ser Ala  Tyr Arg Val Phe Pro  Tyr Ser Val
    1070                 1075                 1080

Phe Tyr  Val Phe Tyr Glu Gln  Tyr Leu Thr Ile Ile  Asp Asp Thr
    1085                 1090                 1095

Ile Phe  Asn Leu Gly Val Ser  Leu Gly Ala Ile Phe  Leu Val Thr
    1100                 1105                 1110

Met Val  Leu Leu Gly Cys Glu  Leu Trp Ser Ala Val  Ile Met Cys
    1115                 1120                 1125

Ala Thr  Ile Ala Met Val Leu  Val Asn Met Phe Gly  Val Met Trp
    1130                 1135                 1140
```

```
Leu Trp  Gly Ile Ser Leu Asn  Ala Val Ser Leu Val  Asn Leu Val
    1145                 1150                 1155

Met Ser  Cys Gly Ile Ser Val  Glu Phe Cys Ser His  Ile Thr Arg
    1160                 1165                 1170

Ala Phe  Thr Val Ser Met Lys  Gly Ser Arg Val Glu  Arg Ala Glu
    1175                 1180                 1185

Glu Ala  Leu Ala His Met Gly  Ser Ser Val Phe Ser  Gly Ile Thr
    1190                 1195                 1200

Leu Thr  Lys Phe Gly Gly Ile  Val Val Leu Ala Phe  Ala Lys Ser
    1205                 1210                 1215

Gln Ile  Phe Gln Ile Phe Tyr  Phe Arg Met Tyr Leu  Ala Met Val
    1220                 1225                 1230

Leu Leu  Gly Ala Thr His Gly  Leu Ile Phe Leu Pro  Val Leu Leu
    1235                 1240                 1245

Ser Tyr  Ile Gly Pro Ser Val  Asn Lys Ala Lys Ser  Cys Ala Thr
    1250                 1255                 1260

Glu Glu  Arg Tyr Lys Gly Thr  Glu Arg Glu Arg Leu  Leu Asn Phe
    1265                 1270                 1275
```

<210> SEQ ID NO 106
<211> LENGTH: 456
<212> TYPE: DNA
<213> ORGANISM: Homo sapiens

<400> SEQUENCE: 106

```
atgcgtttcc tggcagctac attcctgctc ctggcgctca gcaccgctgc ccaggccgaa     60

ccggtgcagt tcaaggactg cggttctgtg gatggagtta taaaggaagt gaatgtgagc    120

ccatgcccca cccaaccctg ccagctgagc aaaggacagt cttacagcgt caatgtcacc    180

ttcaccagca atattcagtc taaaagcagc aaggccgtgg tgcatggcat cctgatgggc    240

gtcccagttc cctttcccat tcctgagcct gatggttgta agagtggaat taactgccct    300

atccaaaaag acaagaccta tagctacctg aataaactac cagtgaaaag cgaatatccc    360

tctataaaac tggtggtgga gtggcaactt caggatgaca aaaaccaaag tctcttctgc    420

tgggaaatcc cagtacagat cgtttctcat ctctaa                              456
```

<210> SEQ ID NO 107
<211> LENGTH: 151
<212> TYPE: PRT
<213> ORGANISM: Homo sapiens

<400> SEQUENCE: 107

```
Met Arg Phe Leu Ala Ala Thr Phe Leu Leu Leu Ala Leu Ser Thr Ala
1               5                   10                  15

Ala Gln Ala Glu Pro Val Gln Phe Lys Asp Cys Gly Ser Val Asp Gly
            20                  25                  30

Val Ile Lys Glu Val Asn Val Ser Pro Cys Pro Thr Gln Pro Cys Gln
        35                  40                  45

Leu Ser Lys Gly Gln Ser Tyr Ser Val Asn Val Thr Phe Thr Ser Asn
    50                  55                  60

Ile Gln Ser Lys Ser Ser Lys Ala Val Val His Gly Ile Leu Met Gly
65                  70                  75                  80

Val Pro Val Pro Phe Pro Ile Pro Glu Pro Asp Gly Cys Lys Ser Gly
                85                  90                  95

Ile Asn Cys Pro Ile Gln Lys Asp Lys Thr Tyr Ser Tyr Leu Asn Lys
            100                 105                 110
```

```
Leu Pro Val Lys Ser Glu Tyr Pro Ser Ile Lys Leu Val Val Glu Trp
        115                 120                 125

Gln Leu Gln Asp Asp Lys Asn Gln Ser Leu Phe Cys Trp Glu Ile Pro
    130                 135                 140

Val Gln Ile Val Ser His Leu
145                 150


<210> SEQ ID NO 108
<211> LENGTH: 1317
<212> TYPE: DNA
<213> ORGANISM: Homo sapiens

<400> SEQUENCE: 108

atgggaggct gtgcaggctc gcggcggcgc ttttcggatt ccgagggga ggagaccgtc      60

ccggagcccc ggctccctct gttggaccat cagggcgcgc attggaagaa cgcggtgggc    120

ttctggctgc tgggcctttg caacaacttc tcttatgtgg tgatgctgag tgccgcccac    180

gacatcctta gccacaagag gacatcggga aaccagagcc atgtggaccc aggcccaacg    240

ccgatccccc acaacagctc atcacgattt gactgcaact ctgtctctac ggctgctgtg    300

ctcctggcgg acatcctccc cacactcgtc atcaaattgt tggctcctct tggccttcac    360

ctgctgccct acagcccccg ggttctcgtc agtgggattt gtgctgctgg aagcttcgtc    420

ctggttgcct tttctcattc tgtggggacc agcctgtgtg gtgtggtctt cgctagcatc    480

tcatcaggcc ttggggaggt caccttcctc tccctcactg ccttctaccc cagggccgtg    540

atctcctggt ggtcctcagg gactggggga gctgggctgc tgggggccct gtcctacctg    600

ggcctcaccc aggccggcct ctcccctcag cagaccctgc tgtccatgct gggtatccct    660

gccctgctgc tggccagcta tttcttgttg ctcacatctc ctgaggccca ggaccctgga    720

ggggaagaag aagcagagag cgcagcccgg cagcccctca taagaaccga ggccccggag    780

tcgaagccag gctccagctc cagcctctcc cttcgggaaa ggtggacagt gttcaagggt    840

ctgctgtggt acattgttcc cttggtcgta gtttactttg ccgagtattt cattaaccag    900

ggacttttg aactcctctt tttctggaac acttccctga gtcacgctca gcaataccgc    960

tggtaccaga tgctgtacca ggctggcgtc tttgcctccc gctcttctct ccgctgctgt   1020

cgcatccgtt tcacctgggc cctggccctg ctgcagtgcc tcaacctggt gttcctgctg   1080

gcagacgtgt ggttcggctt tctgccaagc atctacctcg tcttcctgat cattctgtat   1140

gaggggctcc tgggaggcgc agcctacgtg aacaccttcc acaacatcgc cctggagacc   1200

agtgatgagc accgggagtt tgcaatggcg gccacctgca tctctgacac actggggatc   1260

tccctgtcgg ggctcctggc tttgcctctg catgacttcc tctgccagct ctcctga      1317


<210> SEQ ID NO 109
<211> LENGTH: 438
<212> TYPE: PRT
<213> ORGANISM: Homo sapiens

<400> SEQUENCE: 109

Met Gly Gly Cys Ala Gly Ser Arg Arg Arg Phe Ser Asp Ser Glu Gly
1               5                   10                  15

Glu Glu Thr Val Pro Glu Pro Arg Leu Pro Leu Leu Asp His Gln Gly
            20                  25                  30

Ala His Trp Lys Asn Ala Val Gly Phe Trp Leu Leu Gly Leu Cys Asn
        35                  40                  45
```

```
Asn Phe Ser Tyr Val Val Met Leu Ser Ala Ala His Asp Ile Leu Ser
    50                  55                  60

His Lys Arg Thr Ser Gly Asn Gln Ser His Val Asp Pro Gly Pro Thr
65                  70                  75                  80

Pro Ile Pro His Asn Ser Ser Ser Arg Phe Asp Cys Asn Ser Val Ser
                85                  90                  95

Thr Ala Ala Val Leu Leu Ala Asp Ile Leu Pro Thr Leu Val Ile Lys
            100                 105                 110

Leu Leu Ala Pro Leu Gly Leu His Leu Leu Pro Tyr Ser Pro Arg Val
        115                 120                 125

Leu Val Ser Gly Ile Cys Ala Ala Gly Ser Phe Val Leu Val Ala Phe
    130                 135                 140

Ser His Ser Val Gly Thr Ser Leu Cys Gly Val Val Phe Ala Ser Ile
145                 150                 155                 160

Ser Ser Gly Leu Gly Glu Val Thr Phe Leu Ser Leu Thr Ala Phe Tyr
                165                 170                 175

Pro Arg Ala Val Ile Ser Trp Trp Ser Ser Gly Thr Gly Gly Ala Gly
            180                 185                 190

Leu Leu Gly Ala Leu Ser Tyr Leu Gly Leu Thr Gln Ala Gly Leu Ser
        195                 200                 205

Pro Gln Gln Thr Leu Leu Ser Met Leu Gly Ile Pro Ala Leu Leu Leu
    210                 215                 220

Ala Ser Tyr Phe Leu Leu Leu Thr Ser Pro Glu Ala Gln Asp Pro Gly
225                 230                 235                 240

Gly Glu Glu Glu Ala Glu Ser Ala Ala Arg Gln Pro Leu Ile Arg Thr
                245                 250                 255

Glu Ala Pro Glu Ser Lys Pro Gly Ser Ser Ser Ser Leu Ser Leu Arg
            260                 265                 270

Glu Arg Trp Thr Val Phe Lys Gly Leu Leu Trp Tyr Ile Val Pro Leu
        275                 280                 285

Val Val Val Tyr Phe Ala Glu Tyr Phe Ile Asn Gln Gly Leu Phe Glu
    290                 295                 300

Leu Leu Phe Phe Trp Asn Thr Ser Leu Ser His Ala Gln Gln Tyr Arg
305                 310                 315                 320

Trp Tyr Gln Met Leu Tyr Gln Ala Gly Val Phe Ala Ser Arg Ser Ser
                325                 330                 335

Leu Arg Cys Cys Arg Ile Arg Phe Thr Trp Ala Leu Ala Leu Leu Gln
            340                 345                 350

Cys Leu Asn Leu Val Phe Leu Leu Ala Asp Val Trp Phe Gly Phe Leu
        355                 360                 365

Pro Ser Ile Tyr Leu Val Phe Leu Ile Ile Leu Tyr Glu Gly Leu Leu
    370                 375                 380

Gly Gly Ala Ala Tyr Val Asn Thr Phe His Asn Ile Ala Leu Glu Thr
385                 390                 395                 400

Ser Asp Glu His Arg Glu Phe Ala Met Ala Ala Thr Cys Ile Ser Asp
                405                 410                 415

Thr Leu Gly Ile Ser Leu Ser Gly Leu Leu Ala Leu Pro Leu His Asp
            420                 425                 430

Phe Leu Cys Gln Leu Ser
        435
```

<210> SEQ ID NO 110
<211> LENGTH: 866
<212> TYPE: DNA

<213> ORGANISM: Homo sapiens

<400> SEQUENCE: 110

```
tcctgcaggc caggcatggc tctgtgagcg ctgatgaggc tgcccgcacg gctcccttcc     60

acctcgacct ctggttctac ttcacactgc agaactgggt tctggacttt gggcgtccca    120

ttgccatgct ggtattccct ctcgagtggt ttccactcaa caagcccagt gttggggact    180

acttccacat ggcctacaac gtcatcacgc cctttctctt gctcaagctc atcgagcggt    240

ccccccgcac cctgccacgc tccatcacgt acgtgagcat catcatcttc atcatgggtg    300

ccagcatcca cctggtgggt gactctgtca accaccgcct gctcttcagt ggctaccagc    360

accacctgtc tgtccgtgag aaccccatca tcaagaatct caagccggag acgctgatcg    420

actcctttga gctgctctac tattatgatg agtacctggg tcactgcatg tggtacatcc    480

ccttcttcct catcctcttc atgtacttca gcggctgctt tactgcctct aaagctgaga    540

gcttgattcc agggcctgcc ctgctcctgg tggcacccag tggcctgtac tactggtacc    600

tggtcaccga gggccagatc ttcatcctct tcatcttcac cttcttcgcc atgctggccc    660

tcgtcctgca ccagaagcgc aagcgcctct tcctggacag caacggcctc ttcctcttct    720

cctccttcgc actgaccctc ttgcttgtgg cgctctgggt cgcctggctg tggaatgacc    780

ctgttctcag gaagaagtac ccgggtgtca tctacgtccc tgagccctgg gctttctaca    840

cccttcacgt cagcagtcgg cactga                                         866
```

<210> SEQ ID NO 111
<211> LENGTH: 311
<212> TYPE: PRT
<213> ORGANISM: Homo sapiens

<400> SEQUENCE: 111

```
Met Glu Ala Thr Arg Arg Arg Gln His Leu Gly Ala Thr Gly Gly Pro
1               5                   10                  15

Gly Ala Gln Leu Gly Ala Ser Phe Leu Gln Ala Arg His Gly Ser Val
            20                  25                  30

Ser Ala Asp Glu Ala Ala Arg Thr Ala Pro Phe His Leu Asp Leu Trp
        35                  40                  45

Phe Tyr Phe Thr Leu Gln Asn Trp Val Leu Asp Phe Gly Arg Pro Ile
    50                  55                  60

Ala Met Leu Val Phe Pro Leu Glu Trp Phe Pro Leu Asn Lys Pro Ser
65                  70                  75                  80

Val Gly Asp Tyr Phe His Met Ala Tyr Asn Val Ile Thr Pro Phe Leu
                85                  90                  95

Leu Leu Lys Leu Ile Glu Arg Ser Pro Arg Thr Leu Pro Arg Ser Ile
            100                 105                 110

Thr Tyr Val Ser Ile Ile Ile Phe Ile Met Gly Ala Ser Ile His Leu
        115                 120                 125

Val Gly Asp Ser Val Asn His Arg Leu Leu Phe Ser Gly Tyr Gln His
    130                 135                 140

His Leu Ser Val Arg Glu Asn Pro Ile Ile Lys Asn Leu Lys Pro Glu
145                 150                 155                 160

Thr Leu Ile Asp Ser Phe Glu Leu Leu Tyr Tyr Tyr Asp Glu Tyr Leu
                165                 170                 175

Gly His Cys Met Trp Tyr Ile Pro Phe Phe Leu Ile Leu Phe Met Tyr
            180                 185                 190

Phe Ser Gly Cys Phe Thr Ala Ser Lys Ala Glu Ser Leu Ile Pro Gly
```

```
        195                 200                 205

Pro Ala Leu Leu Leu Val Ala Pro Ser Gly Leu Tyr Tyr Trp Tyr Leu
    210                 215                 220

Val Thr Glu Gly Gln Ile Phe Ile Leu Phe Ile Phe Thr Phe Phe Ala
225                 230                 235                 240

Met Leu Ala Leu Val Leu His Gln Lys Arg Lys Arg Leu Phe Leu Asp
                245                 250                 255

Ser Asn Gly Leu Phe Leu Phe Ser Ser Phe Ala Leu Thr Leu Leu Leu
            260                 265                 270

Val Ala Leu Trp Val Ala Trp Leu Trp Asn Asp Pro Val Leu Arg Lys
        275                 280                 285

Lys Tyr Pro Gly Val Ile Tyr Val Pro Glu Pro Trp Ala Phe Tyr Thr
    290                 295                 300

Leu His Val Ser Ser Arg His
305                 310


<210> SEQ ID NO 112
<211> LENGTH: 861
<212> TYPE: DNA
<213> ORGANISM: Homo sapiens

<400> SEQUENCE: 112

atgaatcctg cgagcgatgg gggcacatca gagagcattt ttgacctgga ctatgcatcc      60

tgggggatcc gctccacgct gatggtcgct ggctttgtct tctacttggg cgtctttgtg     120

gtctgccacc agctgtcctc ttccctgaat gccacttacc gttctttggt ggccagagag     180

aaggtcttct gggacctggc ggccacgcgt gcagtctttg gtgttcagag cacagccgca     240

ggcctgtggg ctctgctggg ggaccctgtg ctgcatgccg acaaggcgcg tggccagcag     300

aactggtgct ggtttcacat cacgacagca acgggattct tttgctttga aaatgttgca     360

gtccacctgt ccaacttgat cttccggaca tttgacttgt ttctggttat ccaccatctc     420

tttgcctttc ttgggtttct tggctgcttg gtcaatctcc aagctggcca ctatctagct     480

atgaccacgt tgctcctgga gatgagcacg ccctttacct gcgtttcctg gatgctctta     540

aaggcgggct ggtccgagtc tctgttttgg aagctcaacc agtggctgat gattcacatg     600

tttcactgcc gcatggttct aacctaccac atgtggtggg tgtgtttctg gcactgggac     660

ggcctggtca gcagcctgta tctgcctcat ttgacactgt tccttgtcgg actggctctg     720

cttacgctaa tcattaatcc atattggacc cataagaaga ctcagcagct tctcaatccg     780

gtggactgga acttcgcaca gccagaagcc aagagcaggc cagaaggcaa cgggcagctg     840

ctgcggaaga agaggccata g                                               861


<210> SEQ ID NO 113
<211> LENGTH: 286
<212> TYPE: PRT
<213> ORGANISM: Homo sapiens

<400> SEQUENCE: 113

Met Asn Pro Ala Ser Asp Gly Gly Thr Ser Glu Ser Ile Phe Asp Leu
1               5                   10                  15

Asp Tyr Ala Ser Trp Gly Ile Arg Ser Thr Leu Met Val Ala Gly Phe
            20                  25                  30

Val Phe Tyr Leu Gly Val Phe Val Val Cys His Gln Leu Ser Ser Ser
        35                  40                  45

Leu Asn Ala Thr Tyr Arg Ser Leu Val Ala Arg Glu Lys Val Phe Trp
```

```
    50                  55                  60

Asp Leu Ala Ala Thr Arg Ala Val Phe Gly Val Gln Ser Thr Ala Ala
65                  70                  75                  80

Gly Leu Trp Ala Leu Leu Gly Asp Pro Val Leu His Ala Asp Lys Ala
                85                  90                  95

Arg Gly Gln Gln Asn Trp Cys Trp Phe His Ile Thr Thr Ala Thr Gly
            100                 105                 110

Phe Phe Cys Phe Glu Asn Val Ala Val His Leu Ser Asn Leu Ile Phe
        115                 120                 125

Arg Thr Phe Asp Leu Phe Leu Val Ile His His Leu Phe Ala Phe Leu
    130                 135                 140

Gly Phe Leu Gly Cys Leu Val Asn Leu Gln Ala Gly His Tyr Leu Ala
145                 150                 155                 160

Met Thr Thr Leu Leu Leu Glu Met Ser Thr Pro Phe Thr Cys Val Ser
                165                 170                 175

Trp Met Leu Leu Lys Ala Gly Trp Ser Glu Ser Leu Phe Trp Lys Leu
            180                 185                 190

Asn Gln Trp Leu Met Ile His Met Phe His Cys Arg Met Val Leu Thr
        195                 200                 205

Tyr His Met Trp Trp Val Cys Phe Trp His Trp Asp Gly Leu Val Ser
    210                 215                 220

Ser Leu Tyr Leu Pro His Leu Thr Leu Phe Leu Val Gly Leu Ala Leu
225                 230                 235                 240

Leu Thr Leu Ile Ile Asn Pro Tyr Trp Thr His Lys Lys Thr Gln Gln
                245                 250                 255

Leu Leu Asn Pro Val Asp Trp Asn Phe Ala Gln Pro Glu Ala Lys Ser
            260                 265                 270

Arg Pro Glu Gly Asn Gly Gln Leu Leu Arg Lys Lys Arg Pro
        275                 280                 285
```

<210> SEQ ID NO 114
<211> LENGTH: 11406
<212> TYPE: DNA
<213> ORGANISM: Homo sapiens

<400> SEQUENCE: 114

```
atgagcaccg acagtaactc actggcacgt gaatttctga ccgatgtcaa ccggctttgc      60

aatgcagtgg tccagagggt ggaggccagg gaggaagaag aggaggagac gcacatggca     120

acccttggac agtaccttgt ccatggtcga ggatttctat tacttaccaa gctaaattct     180

ataattgatc aggcattgac atgtagagaa gaactcctga ctcttcttct gtctctcctt     240

ccactggtat ggaagatacc tgtccaagaa gaaaaggcaa cagattttaa cctaccgctc     300

tcagcagata taatcctgac caaagaaaag aactcaagtt cacaaagatc cactcaggaa     360

aaattacatt tagaaggaag tgccctgtct agtcaggttt ctgcaaaagt aaatgttttt     420

cgaaaaagca gacgacagcg taaaattacc catcgctatt ctgtaagaga tgcaagaaag     480

acacagctct ccacctcaga ttcagaagcc aattcagatg aaaaaggcat agcaatgaat     540

aagcatagaa ggccccatct gctgcatcat tttttaacat cgtttcctaa acaagaccac     600

cccaaagcta aacttgaccg cttagcaacc aaagaacaga ctcctccaga tgctatggct     660

ttggaaaatt ccagagagat tattccaaga caggggtcaa acactgacat tttaagtgag     720

ccagctgcct tgtctgttat cagtaacatg aacaattctc catttgactt atgtcatgtt     780

ttgttatctt tattagaaaa agtttgtaag tttgacgtta ccttgaatca taattctcct     840
```

```
ttagcagcca gtgtagtgcc cacactaact gaattcctag caggctttgg ggactgctgc    900
agtctgagcg acaacttgga gagtcgagta gtttctgcag gttggaccga agaaccggtg    960
gctttgattc aaaggatgct ctttcgaaca gtgttgcatc ttctgtcagt agatgttagt   1020
actgcagaga tgatgccaga aaatcttagg aaaaatttaa ctgaattgct tagagcagct   1080
ttaaaaatta gaatatgcct agaaaagcag cctgaccctt ttgcaccaag acaaaagaaa   1140
acactgcagg aggttcagga agattttgtg ttttcaaagt atcgtcatag agcccttctt   1200
ttacctgagc ttttggaagg agttcttcag attctgatct gttgtcttca aagtgcagct   1260
tcaaatccct tctacttcag tcaagccatg gatttggttc aagaattcat tcagcatcat   1320
ggatttaatt tatttgaaac agcagttctt caaatggaat ggctggtttt aagagatgga   1380
gttcctcccg aggcctcaga gcatttgaaa gccctaataa atagtgtgat gaaaataatg   1440
agcactgtca aaaaagtgaa atcagagcaa cttcatcatt cgatgtgtac aagaaaaagg   1500
cacagacgat gtgaatattc tcattttatg catcatcacc gagatctctc aggtcttctg   1560
gtttcggctt ttaaaaacca ggtttccaaa aacccatttg aagagactgc agatggagat   1620
gtttattatc ctgagcggtg ctgttgcatt gcagtgtgtg cccatcagtg cttgcgctta   1680
ctacagcagg cttccttgag cagcacttgt gtccagatcc tatcgggtgt tcataacatt   1740
ggaatatgct gttgtatgga tcccaaatct gtaatcattc ctttgctcca tgcttttaaa   1800
ttgccagcac tgaaaaattt tcagcagcat atattgaata tccttaacaa acttattttg   1860
gatcagttag gaggagcaga gatatcacca aaaattaaaa aagcagcttg taatatttgt   1920
actgttgact ctgaccaact agcccaatta gaagagacac tgcagggaaa cttatgtgat   1980
gctgaactct cctcaagttt atccagtcct tcttacagat ttcaagggat cctgcccagc   2040
agtggatctg aagatttgtt gtggaaatgg gatgctttaa aggcttatca gaactttgtt   2100
tttgaagaag acagattaca tagtatacag attgcaaatc acatttgcaa tttaatccag   2160
aaaggcaata tagttgttca gtggaaatta tataattaca tatttaatcc tgtgctccaa   2220
agaggagttg aattagcaca tcattgtcaa cacctaagcg ttacttcagc tcaaagtcat   2280
gtatgtagcc atcataacca gtgcttgcct caggacgtgc ttcagattta tgtaaaaact   2340
ctgcctatcc tgcttaaatc cagggtaata agagatttgt ttttgagttg taatggagta   2400
agtcaaataa tcgaattaaa ttgcttaaat ggtattcgaa gtcattctct aaaagcattt   2460
gaaactctga taatcagcct aggggagcaa cagaaagatg cctcagttcc agatattgat   2520
gggatagaca ttgaacagaa ggagttgtcc tctgtacatg tgggtacttc ttttcatcat   2580
cagcaagctt attcagattc tcctcagagt ctcagcaaat tttatgctgg cctcaaagaa   2640
gcttatccaa agagacggaa gactgttaac caagatgttc atatcaacac aataaaccta   2700
ttcctctgtg tggctttttt atgcgtaagt aaagaagcag agtctgacag ggagtcggcc   2760
aatgactcag aagatacttc tggctatgac agcacagcca gcgagccttt aagtcatatg   2820
ctgccatgta tatctctcga gagccttgtc ttgccttctc ctgaacatat gcaccaagca   2880
gcagacattt ggtctatgtg tcgttggatc tacatgttga gttcagtgtt ccagaaacag   2940
ttttataggc ttggtggttt ccgagtatgc cataagttaa tatttatgat aatacagaaa   3000
ctgttcagaa gtcacaaaga ggagcaagga aaaaaggagg gagatacaag tgtaaatgaa   3060
aaccaggatt taaacagaat ttctcaacct aagagaacta tgaaggaaga tttattatct   3120
ttggctataa aaagtgaccc cataccatca gaactaggta gtctaaaaaa gagtgctgac   3180
```

```
agtttaggta aattagagtt acagcatatt tcttccataa atgtggaaga agtttcagct   3240
actgaagccg ctcccgagga agcaaagcta tttacaagtc aagaaagtga gacctcactt   3300
caaagtatac gacttttgga agcccttctg gccatttgtc ttcatggtgc cagaactagt   3360
caacagaaga tggaattgga gttacctaat cagaacttgt ctgtggaaag tatattattt   3420
gaaatgaggg accatctttc ccagtcaaag gtgattgaaa cacaactagc aaagccttta   3480
tttgatgccc tgcttcgagt tgccctcggg aattattcag cagattttga acataatgat   3540
gctatgactg agaagagtca tcaatctgca gaagaattgt catcccagcc tggtgatttt   3600
tcagaagaag ctgaggattc tcagtgttgt agttttaaac ttttagttga agaagaaggt   3660
tacgaagcag atagtgaaag caatcctgaa gatggcgaaa cccaggatga tggggtagac   3720
ttaaagtctg aaacagaagg tttcagtgca tcaagcagtc caaatgactt actcgaaaac   3780
ctcactcaag ggaaataat ttatcctgag atttgtatgc tggaattaaa tttgctttct   3840
gctagtaaag ccaaacttga tgtgcttgcc catgtatttg agagtttttt gaaaattatt   3900
aggcagaaag aaaagaatgt ttttctgctc atgcaacagg gaactgtgaa aatcttttta   3960
ggagggttct tgagtatttt aacacaggat gattctgatt ttcaagcatg ccagagagta   4020
ttggtggatc ttttggtatc tttgatgagt tcaagaacat gttcagaaga gctaaccctt   4080
cttttgagaa tatttctgga gaaatctcct tgtacaaaaa ttcttcttct gggtattctg   4140
aaaattattg aaagtgatac tactatgagc ccttcacagt atctaacctt ccctttactg   4200
cacgctccaa atttaagcaa cggtgtttca tcacaaaagt atcctgggat tttaaacagt   4260
aaggccatgg gtttattgag aagagcacga gtttcacgga gcaagaaaga ggctgataga   4320
gagagttttc cccatcggct gctttcatct tggcacatag ccccagtcca cctgccgttg   4380
ctggggcaaa actgctggcc acacctatca gaaggtttca gtgtttccct gtggtttaat   4440
gtggagtgta tccatgaagc tgagagtact acagaaaaag gaaagaagat aaagaaaaga   4500
aacaaatcat taattttacc agatagcagt tttgatggta cagagagcga cagaccagaa   4560
ggtgcagagt acataaatcc tggtgaaaga ctcatagaag aaggatgtat tcatataatt   4620
tcactgggat ccaaagcgtt gatgatccaa gtgtgggctg atccccacaa tgccactctt   4680
atctttcgtg tgtgcatgga ttcaaatgat gacatgaaag ctgttttact agcacaggtt   4740
gaatcacagg agaatatttt cctcccaagc aaatggcaac atttagtact cacctactta   4800
cagcagcccc aagggaaaag gaggattcat gggaaaatct ccatatgggt ctctggacag   4860
aggaagcctg atgttacttt ggattttatg cttccaagaa aaacaagttt gtcatctgat   4920
agcaataaaa cattttgcat gattggccat tgtttatcat cccaagaaga gtttttgcag   4980
ttggctggaa aatgggacct gggaaatttg cttctcttca acggagctaa ggttggttca   5040
caagaggcct tttatctgta tgcttgtgga cccaaccata catctgtaat gccatgtaag   5100
tatggcaagc cagtcaatga ctactccaaa tatattaata aagaaatttt gcgatgtgaa   5160
caaatcagag aacttttat gaccaagaaa gatgtggata ttggtctctt aattgaaagt   5220
ctttcagttg tttatacaac ttactgtcct gctcagtata ccatctatga accagtgatt   5280
agacttaaag gtcaaatgaa aacccaactc tctcaaagac ccttcagctc aaaagaagtt   5340
cagagcatct tattagaacc tcatcatcta aagaatctcc aacctactga atataaaact   5400
attcaaggca ttctgcacga aattggtgga actggcatat ttgtttttct ctttgccagg   5460
gttgttgaac tcagtagctg tgaagaaact caagcattag cactgcgagt tatactctca   5520
ttaattaaat acaaccaaca aagagtacat gaattagaaa attgtaatgg actttctatg   5580
```

attcatcagg tgttgatcaa acaaaaatgc attgttgggt tttacatttt gaagaccctt 5640
cttgaaggat gctgtggtga agatattatt tatatgaatg agaatggaga gtttaagttg 5700
gatgtagact ctaatgctat aatccaagat gttaagctgt tagaggaact attgcttgac 5760
tggaagatat ggagtaaagc agagcaaggt gtttgggaaa ctttgctagc agctctagaa 5820
gtcctcatca gagcagatca ccaccagcag atgtttaata ttaagcagtt attgaaagct 5880
caagtggttc atcactttct actgacttgt caggttttgc aggaatacaa agaggggcaa 5940
ctcacaccca tgccccgaga ggtttgtaga tcatttgtga aattatagc agaagtcctt 6000
ggatctcctc cagatttgga attattgaca attatcttca atttcctttt agcagttcac 6060
cctcctacta atacttacgt ttgtcacaat cccacgaact tctacttttc tttgcacata 6120
gatggcaaga tctttcagga gaaagtgcgg tcaatcatgt acctgaggca ttccagcagt 6180
ggaggaaggt cccttatgag ccctggattt atggtaataa gcccatctgg ttttactgct 6240
tcaccatatg aaggagagaa ttcctctaat attattccac aacagatggc cgcccatatg 6300
ctgcgttcta gaagcctacc agcattccct acttcttcac tactaacgca atcacaaaaa 6360
ctgactggaa gtttgggttg tagtatcgac aggttacaaa atattgcaga tacttatgtt 6420
gccacccaat caaagaaaca aaattctttg gggagttccg acacactgaa aaaaggcaaa 6480
gaggacgcat tcatcagtag ctgtgagtct gcaaaaactg tttgtgaaat ggaagctgtc 6540
ctctcagccc aggtctctgt cagtgatgtc ccaaagggag tgctgggatt tccagtggtc 6600
aaagcagatc ataaacagtt gggagcagaa cccaggtcag aagatgacag tcctggggat 6660
gagtcctgcc cacgccgacc tgattaccta aagggattgg cctccttcca gcgaagccac 6720
agcactattg caagccttgg gctagctttt ccttcacaga acggatctgc agctgttggc 6780
cgttggccaa gtcttgttga tagaaacact gatgattggg aaaactttgc ctattctctt 6840
ggttatgagc caaattacaa ccgaactgca agtgctcaca gtgtaactga agactgtttg 6900
gtacctatat gctgtggatt atatgaactc ctaagtgggg ttcttcttat cctgcctgat 6960
gttttgcttg aagatgtgat ggacaagctt attcaagcag atacactttt ggtcctcgtt 7020
aaccacccat caccagctat acaacaaggt gttattaaac tattagatgc atattttgct 7080
agagcatcta aggaacaaaa agataaattt ctgaagaatc gtggattttc cttgctagcc 7140
aaccagttgt atcttcatcg aggaactcaa gaattgttag aatgcttcat cgaaatgttc 7200
tttggtcgac atattggcct tgatgaagaa tttgatctgg aagatgtgag aaacatggga 7260
ttgtttcaga agtggtctgt cattcctatt ctgggactaa tagagacctc tctatatgac 7320
aacatactct tgcataatgc tcttttactt cttctccaaa ttttaaattc ttgttctaag 7380
gtagcagata tgttgctgga taatggtcta ctctatgtgt tatgtaatac agtagcagcc 7440
ctgaatggat tagaaaagaa cattcccatg agtgaatata aattgcttgc ttgtgatata 7500
cagcaacttt tcatagcagt tacaattcat gcttgcagtt cctcaggctc acaatatttt 7560
agggttattg aagaccttat tgtaatgctt ggatatcttc aaaatagcaa aaacaagagg 7620
acacaaaata tggctgttgc actacagctt agagttctcc aggctgctat ggaatttata 7680
aggaccaccg caaatcatga ctctgaaaac ctcacagatt cactccagtc accttctgct 7740
ccccatcatg cagtagttca aaagcggaaa agcattgctg gtcctcgaaa atttcccctt 7800
gctcaaactg aatcgcttct gatgaaaatg cgttcagtgg caaatgatga gcttcatgtg 7860
atgatgcaac ggagaatgag ccaagagaac cctagccaag caactgaaac ggaacttgcg 7920

```
cagagactac agaggctcac tgttttagca gtcaacagga ttatttatca agaatttaat   7980
tcagacatta ttgacatttt gagaactcca gaaaatgtaa ctcaaagcaa gacctcagtt   8040
ttccagaccg aaatttctga ggaaaatatt catcatgaac agtcttctgt tttcaatcca   8100
tttcagaaag aaatttttac atatctggta gaaggattca aagtatctat tggttcaagt   8160
aaagccagtg gttccaagca gcaatggact aaaattctgt ggtcttgtaa ggagaccttc   8220
cgaatgcagc ttgggagact actagtgcat attttgtcgc cagcccacgc tgcacaagag   8280
agaaagcaaa tttttgaaat agttcatgaa ccaaatcatc aggaaatact acgagactgt   8340
ctcagcccat ccctacaaca tggagccaag ttagttttgt atttgtcaga gttgatacat   8400
aatcaccaag gtgaattgac tgaagaagag ctaggcacag cagaactgct tatgaatgct   8460
ttgaagttat gtggtcacaa gtgcatccct cccagtgcat caacaaaagc agaccttatt   8520
aaaatgatca aagaggaaca aaagaaatat gaaactgaag aaggagtgaa taaagctgct   8580
tggcagaaaa cagttaacaa taatcaacaa agtctctttc agcgtctgga ttcaaaatca   8640
aaggatatat ctaaaatagc tgcagatatc acccaggcag tgtctctctc ccaaggaaat   8700
gagagaaaaa aggtgatcca gcatattaga ggaatgtata aagtagattt gagtgccagc   8760
agacattggc aggaacttat tcagcagctg acacatgata gagcagtatg gtatgacccc   8820
atctactatc caacctcatg gcagttggat ccaacagaag ggccaaatcg agagaggaga   8880
cgtttacaga gatgttattt aactattcca aataagtatc tccttaggga tagacagaaa   8940
tcagaagatg ttgtcaaacc accactctct tacctgtttg aagacaaaac tcattcttct   9000
ttctcttcta ctgtcaaaga caaagctgca agtgaatcta taagagtgaa tcgaagatgc   9060
atcagtgttg caccatctag agagacagct ggtgaattgt tactaggtaa atgtggaatg   9120
tattttgtgg aagataatgc ttctgataca gttgaaagtt cgagccttca gggagagttg   9180
gaaccagcat catttttcctg gacatatgaa gaaattaaag aagttcacaa gcgttggtgg   9240
caattgagag ataatgctgt agaaatcttt ctaacaaatg gcagaacact cctgttggca   9300
tttgataaca ccaaggttcg tgatgatgta taccacaata tactcacaaa taacctccct   9360
aatcttctgg aatatggtaa catcaccgct ctgacaaatt tatggtatac tgggcaaatt   9420
actaattttg aatatttgac tcacttaaac aaacatgctg gccgatcctt caatgatctc   9480
atgcagtatc ctgtgttccc atttatactt gctgactacg ttagtgagac acttgacctc   9540
aatgatctgt tgatatacag aaatctctct aaacctatag ctgttcagta taaagaaaaa   9600
gaagatcgtt atgtggacac atacaagtac ttggaggaag agtaccgcaa aggagccaga   9660
gaagatgacc ccatgcctcc cgtgcagccc tatcactatg gctcccacta ttccaatagc   9720
ggcactgtgc ttcacttcct ggtcaggatg cctcctttca ctaaaatgtt tttagcctat   9780
caagatcaaa gttttgacat tccagacaga acttttcatt ctacaaatac aacttggcga   9840
ctctcatctt ttgaatctat gactgatgtg aaagaactta tcccagagtt tttctatctt   9900
ccagagttcc tagttaaccg tgaaggtttt gattttggtg tgcgtcagaa tggtgaacgg   9960
gttaatcacg tcaaccttcc cccttgggcg cgtaatgatc ctcgtctttt tatcctcatc  10020
catcggcagg ctctagagtc tgactacgtg tcgcagaaca tctgtcagtg gattgacttg  10080
gtgtttgggt ataagcaaaa ggggaaggct tctgttcaag cgatcaatgt tttcatcct   10140
gctacatatt ttggaatgga tgtctctgca gttgaagatc cagttcagag acgagcgcta  10200
gaaaccatga taaaaaccta cgggcagact ccccgtcagc tgttccacat ggcccatgtg  10260
agcagacctg gagccaagct caatattgaa ggagagcttc cagctgctgt ggggttgcta  10320
```

```
gtgcagtttg ctttcaggga gacccgagaa caggtcaaag aaatcaccta tccgagtcct  10380

ttgtcatgga taaaaggctt gaaatggggg gaatacgtgg gttcccccag tgctccagta  10440

cctgtggtct gcttcagcca gccccacgga gaaagatttg gctctctcca ggctctgccc  10500

accagagcaa tctgtggttt gtcacggaat ttctgtcttc tgatgacata tagcaaggaa  10560

caaggtgtga gaagcatgaa cagtacggac attcagtggt cagccatcct gagctgggga  10620

tatgctgata atattttaag gttgaagagt aaacaaagtg agcctccagt aaactttatt  10680

caaagttcac aacagtacca ggtgactagt tgtgcttggg tgcctgacag ttgccagctg  10740

tttactggaa gcaaatgcgg tgtcatcaca gcctacacaa acagatttac aagcagcacg  10800

ccatcagaaa tagaaatgga gactcaaata catctctatg gtcacacaga agagataacc  10860

agcttatttg tttgcaaacc atacagtata ctgataagtg tgagcagaga cggaacctgc  10920

atcatatggg atttaaacag gttatgctat gtacaaagtc tggcgggaca caaaagccct  10980

gtcacagctg tctctgccag tgaaacctca ggtgatattg ctactgtgtg tgattcagct  11040

ggcggaggca gtgacctcag actctggacg gtgaacgggg atctcgttgg acatgtccac  11100

tgcagggaga tcatctgttc cgtggctttc tccaaccagc ctgagggagt atctatcaat  11160

gtaatcgctg gggggattaga aaatggaatt gtaaggttat ggagcacatg ggacttaaag  11220

cctgtgagag aaattacatt tcccaaatca aataagccca tcatcagcct tacattttct  11280

tgtgatggcc accatttgta cacagcaaac agtgatggga ccgtgattgc ctggtgtcgg  11340

aaggaccagc agcgcttgaa acagccaatg ttctattcct tccttagcag ctatgcagcc  11400

gggtga                                                             11406
```

<210> SEQ ID NO 115
<211> LENGTH: 3801
<212> TYPE: PRT
<213> ORGANISM: Homo sapiens

<400> SEQUENCE: 115

```
Met Ser Thr Asp Ser Asn Ser Leu Ala Arg Glu Phe Leu Thr Asp Val
1               5                   10                  15

Asn Arg Leu Cys Asn Ala Val Val Gln Arg Val Glu Ala Arg Glu Glu
            20                  25                  30

Glu Glu Glu Glu Thr His Met Ala Thr Leu Gly Gln Tyr Leu Val His
        35                  40                  45

Gly Arg Gly Phe Leu Leu Leu Thr Lys Leu Asn Ser Ile Ile Asp Gln
    50                  55                  60

Ala Leu Thr Cys Arg Glu Glu Leu Leu Thr Leu Leu Leu Ser Leu Leu
65                  70                  75                  80

Pro Leu Val Trp Lys Ile Pro Val Gln Glu Glu Lys Ala Thr Asp Phe
                85                  90                  95

Asn Leu Pro Leu Ser Ala Asp Ile Ile Leu Thr Lys Glu Lys Asn Ser
            100                 105                 110

Ser Ser Gln Arg Ser Thr Gln Glu Lys Leu His Leu Glu Gly Ser Ala
        115                 120                 125

Leu Ser Ser Gln Val Ser Ala Lys Val Asn Val Phe Arg Lys Ser Arg
    130                 135                 140

Arg Gln Arg Lys Ile Thr His Arg Tyr Ser Val Arg Asp Ala Arg Lys
145                 150                 155                 160

Thr Gln Leu Ser Thr Ser Asp Ser Glu Ala Asn Ser Asp Glu Lys Gly
                165                 170                 175
```

```
Ile Ala Met Asn Lys His Arg Arg Pro His Leu Leu His His Phe Leu
            180                 185                 190

Thr Ser Phe Pro Lys Gln Asp His Pro Lys Ala Lys Leu Asp Arg Leu
        195                 200                 205

Ala Thr Lys Glu Gln Thr Pro Pro Asp Ala Met Ala Leu Glu Asn Ser
    210                 215                 220

Arg Glu Ile Ile Pro Arg Gln Gly Ser Asn Thr Asp Ile Leu Ser Glu
225                 230                 235                 240

Pro Ala Ala Leu Ser Val Ile Ser Asn Met Asn Asn Ser Pro Phe Asp
                245                 250                 255

Leu Cys His Val Leu Leu Ser Leu Leu Glu Lys Val Cys Lys Phe Asp
            260                 265                 270

Val Thr Leu Asn His Asn Ser Pro Leu Ala Ala Ser Val Val Pro Thr
        275                 280                 285

Leu Thr Glu Phe Leu Ala Gly Phe Gly Asp Cys Cys Ser Leu Ser Asp
    290                 295                 300

Asn Leu Glu Ser Arg Val Val Ser Ala Gly Trp Thr Glu Glu Pro Val
305                 310                 315                 320

Ala Leu Ile Gln Arg Met Leu Phe Arg Thr Val Leu His Leu Leu Ser
                325                 330                 335

Val Asp Val Ser Thr Ala Glu Met Met Pro Glu Asn Leu Arg Lys Asn
            340                 345                 350

Leu Thr Glu Leu Leu Arg Ala Ala Leu Lys Ile Arg Ile Cys Leu Glu
        355                 360                 365

Lys Gln Pro Asp Pro Phe Ala Pro Arg Gln Lys Lys Thr Leu Gln Glu
    370                 375                 380

Val Gln Glu Asp Phe Val Phe Ser Lys Tyr Arg His Arg Ala Leu Leu
385                 390                 395                 400

Leu Pro Glu Leu Leu Glu Gly Val Leu Gln Ile Leu Ile Cys Cys Leu
                405                 410                 415

Gln Ser Ala Ala Ser Asn Pro Phe Tyr Phe Ser Gln Ala Met Asp Leu
            420                 425                 430

Val Gln Glu Phe Ile Gln His His Gly Phe Asn Leu Phe Glu Thr Ala
        435                 440                 445

Val Leu Gln Met Glu Trp Leu Val Leu Arg Asp Gly Val Pro Pro Glu
    450                 455                 460

Ala Ser Glu His Leu Lys Ala Leu Ile Asn Ser Val Met Lys Ile Met
465                 470                 475                 480

Ser Thr Val Lys Lys Val Lys Ser Glu Gln Leu His His Ser Met Cys
                485                 490                 495

Thr Arg Lys Arg His Arg Arg Cys Glu Tyr Ser His Phe Met His His
            500                 505                 510

His Arg Asp Leu Ser Gly Leu Leu Val Ser Ala Phe Lys Asn Gln Val
        515                 520                 525

Ser Lys Asn Pro Phe Glu Glu Thr Ala Asp Gly Asp Val Tyr Tyr Pro
    530                 535                 540

Glu Arg Cys Cys Cys Ile Ala Val Cys Ala His Gln Cys Leu Arg Leu
545                 550                 555                 560

Leu Gln Gln Ala Ser Leu Ser Ser Thr Cys Val Gln Ile Leu Ser Gly
                565                 570                 575

Val His Asn Ile Gly Ile Cys Cys Cys Met Asp Pro Lys Ser Val Ile
            580                 585                 590
```

```
Ile Pro Leu Leu His Ala Phe Lys Leu Pro Ala Leu Lys Asn Phe Gln
        595                 600                 605

Gln His Ile Leu Asn Ile Leu Asn Lys Leu Ile Leu Asp Gln Leu Gly
    610                 615                 620

Gly Ala Glu Ile Ser Pro Lys Ile Lys Lys Ala Ala Cys Asn Ile Cys
625                 630                 635                 640

Thr Val Asp Ser Asp Gln Leu Ala Gln Leu Glu Glu Thr Leu Gln Gly
                645                 650                 655

Asn Leu Cys Asp Ala Glu Leu Ser Ser Ser Leu Ser Ser Pro Ser Tyr
            660                 665                 670

Arg Phe Gln Gly Ile Leu Pro Ser Ser Gly Ser Glu Asp Leu Leu Trp
        675                 680                 685

Lys Trp Asp Ala Leu Lys Ala Tyr Gln Asn Phe Val Phe Glu Glu Asp
    690                 695                 700

Arg Leu His Ser Ile Gln Ile Ala Asn His Ile Cys Asn Leu Ile Gln
705                 710                 715                 720

Lys Gly Asn Ile Val Val Gln Trp Lys Leu Tyr Asn Tyr Ile Phe Asn
                725                 730                 735

Pro Val Leu Gln Arg Gly Val Glu Leu Ala His His Cys Gln His Leu
            740                 745                 750

Ser Val Thr Ser Ala Gln Ser His Val Cys Ser His His Asn Gln Cys
        755                 760                 765

Leu Pro Gln Asp Val Leu Gln Ile Tyr Val Lys Thr Leu Pro Ile Leu
    770                 775                 780

Leu Lys Ser Arg Val Ile Arg Asp Leu Phe Leu Ser Cys Asn Gly Val
785                 790                 795                 800

Ser Gln Ile Ile Glu Leu Asn Cys Leu Asn Gly Ile Arg Ser His Ser
                805                 810                 815

Leu Lys Ala Phe Glu Thr Leu Ile Ile Ser Leu Gly Glu Gln Gln Lys
            820                 825                 830

Asp Ala Ser Val Pro Asp Ile Asp Gly Ile Asp Ile Glu Gln Lys Glu
        835                 840                 845

Leu Ser Ser Val His Val Gly Thr Ser Phe His His Gln Gln Ala Tyr
    850                 855                 860

Ser Asp Ser Pro Gln Ser Leu Ser Lys Phe Tyr Ala Gly Leu Lys Glu
865                 870                 875                 880

Ala Tyr Pro Lys Arg Arg Lys Thr Val Asn Gln Asp Val His Ile Asn
                885                 890                 895

Thr Ile Asn Leu Phe Leu Cys Val Ala Phe Leu Cys Val Ser Lys Glu
            900                 905                 910

Ala Glu Ser Asp Arg Glu Ser Ala Asn Asp Ser Glu Asp Thr Ser Gly
        915                 920                 925

Tyr Asp Ser Thr Ala Ser Glu Pro Leu Ser His Met Leu Pro Cys Ile
    930                 935                 940

Ser Leu Glu Ser Leu Val Leu Pro Ser Pro Glu His Met His Gln Ala
945                 950                 955                 960

Ala Asp Ile Trp Ser Met Cys Arg Trp Ile Tyr Met Leu Ser Ser Val
                965                 970                 975

Phe Gln Lys Gln Phe Tyr Arg Leu Gly Gly Phe Arg Val Cys His Lys
            980                 985                 990

Leu Ile Phe Met Ile Ile Gln Lys  Leu Phe Arg Ser His  Lys Glu Glu
        995                 1000                 1005

Gln Gly  Lys Lys Glu Gly Asp  Thr Ser Val Asn Glu  Asn Gln Asp
```

```
    1010                1015                1020

Leu Asn  Arg Ile Ser Gln Pro  Lys Arg Thr Met Lys  Glu Asp Leu
    1025                1030                1035

Leu Ser  Leu Ala Ile Lys Ser  Asp Pro Ile Pro Ser  Glu Leu Gly
    1040                1045                1050

Ser Leu  Lys Lys Ser Ala Asp  Ser Leu Gly Lys Leu  Glu Leu Gln
    1055                1060                1065

His Ile  Ser Ser Ile Asn Val  Glu Glu Val Ser Ala  Thr Glu Ala
    1070                1075                1080

Ala Pro  Glu Glu Ala Lys Leu  Phe Thr Ser Gln Glu  Ser Glu Thr
    1085                1090                1095

Ser Leu  Gln Ser Ile Arg Leu  Leu Glu Ala Leu Leu  Ala Ile Cys
    1100                1105                1110

Leu His  Gly Ala Arg Thr Ser  Gln Gln Lys Met Glu  Leu Glu Leu
    1115                1120                1125

Pro Asn  Gln Asn Leu Ser Val  Glu Ser Ile Leu Phe  Glu Met Arg
    1130                1135                1140

Asp His  Leu Ser Gln Ser Lys  Val Ile Glu Thr Gln  Leu Ala Lys
    1145                1150                1155

Pro Leu  Phe Asp Ala Leu Leu  Arg Val Ala Leu Gly  Asn Tyr Ser
    1160                1165                1170

Ala Asp  Phe Glu His Asn Asp  Ala Met Thr Glu Lys  Ser His Gln
    1175                1180                1185

Ser Ala  Glu Glu Leu Ser Ser  Gln Pro Gly Asp Phe  Ser Glu Glu
    1190                1195                1200

Ala Glu  Asp Ser Gln Cys Cys  Ser Phe Lys Leu Leu  Val Glu Glu
    1205                1210                1215

Glu Gly  Tyr Glu Ala Asp Ser  Glu Ser Asn Pro Glu  Asp Gly Glu
    1220                1225                1230

Thr Gln  Asp Asp Gly Val Asp  Leu Lys Ser Glu Thr  Glu Gly Phe
    1235                1240                1245

Ser Ala  Ser Ser Ser Pro Asn  Asp Leu Leu Glu Asn  Leu Thr Gln
    1250                1255                1260

Gly Glu  Ile Ile Tyr Pro Glu  Ile Cys Met Leu Glu  Leu Asn Leu
    1265                1270                1275

Leu Ser  Ala Ser Lys Ala Lys  Leu Asp Val Leu Ala  His Val Phe
    1280                1285                1290

Glu Ser  Phe Leu Lys Ile Ile  Arg Gln Lys Glu Lys  Asn Val Phe
    1295                1300                1305

Leu Leu  Met Gln Gln Gly Thr  Val Lys Asn Leu Leu  Gly Gly Phe
    1310                1315                1320

Leu Ser  Ile Leu Thr Gln Asp  Asp Ser Asp Phe Gln  Ala Cys Gln
    1325                1330                1335

Arg Val  Leu Val Asp Leu Leu  Val Ser Leu Met Ser  Ser Arg Thr
    1340                1345                1350

Cys Ser  Glu Glu Leu Thr Leu  Leu Leu Arg Ile Phe  Leu Glu Lys
    1355                1360                1365

Ser Pro  Cys Thr Lys Ile Leu  Leu Leu Gly Ile Leu  Lys Ile Ile
    1370                1375                1380

Glu Ser  Asp Thr Thr Met Ser  Pro Ser Gln Tyr Leu  Thr Phe Pro
    1385                1390                1395

Leu Leu  His Ala Pro Asn Leu  Ser Asn Gly Val Ser  Ser Gln Lys
    1400                1405                1410
```

```
Tyr Pro  Gly Ile Leu Asn Ser  Lys Ala Met Gly Leu  Leu Arg Arg
    1415                 1420                 1425

Ala Arg  Val Ser Arg Ser Lys  Lys Glu Ala Asp Arg  Glu Ser Phe
    1430                 1435                 1440

Pro His  Arg Leu Leu Ser Ser  Trp His Ile Ala Pro  Val His Leu
    1445                 1450                 1455

Pro Leu  Leu Gly Gln Asn Cys  Trp Pro His Leu Ser  Glu Gly Phe
    1460                 1465                 1470

Ser Val  Ser Leu Trp Phe Asn  Val Glu Cys Ile His  Glu Ala Glu
    1475                 1480                 1485

Ser Thr  Thr Glu Lys Gly Lys  Lys Ile Lys Lys Arg  Asn Lys Ser
    1490                 1495                 1500

Leu Ile  Leu Pro Asp Ser Ser  Phe Asp Gly Thr Glu  Ser Asp Arg
    1505                 1510                 1515

Pro Glu  Gly Ala Glu Tyr Ile  Asn Pro Gly Glu Arg  Leu Ile Glu
    1520                 1525                 1530

Glu Gly  Cys Ile His Ile Ile  Ser Leu Gly Ser Lys  Ala Leu Met
    1535                 1540                 1545

Ile Gln  Val Trp Ala Asp Pro  His Asn Ala Thr Leu  Ile Phe Arg
    1550                 1555                 1560

Val Cys  Met Asp Ser Asn Asp  Asp Met Lys Ala Val  Leu Leu Ala
    1565                 1570                 1575

Gln Val  Glu Ser Gln Glu Asn  Ile Phe Leu Pro Ser  Lys Trp Gln
    1580                 1585                 1590

His Leu  Val Leu Thr Tyr Leu  Gln Gln Pro Gln Gly  Lys Arg Arg
    1595                 1600                 1605

Ile His  Gly Lys Ile Ser Ile  Trp Val Ser Gly Gln  Arg Lys Pro
    1610                 1615                 1620

Asp Val  Thr Leu Asp Phe Met  Leu Pro Arg Lys Thr  Ser Leu Ser
    1625                 1630                 1635

Ser Asp  Ser Asn Lys Thr Phe  Cys Met Ile Gly His  Cys Leu Ser
    1640                 1645                 1650

Ser Gln  Glu Glu Phe Leu Gln  Leu Ala Gly Lys Trp  Asp Leu Gly
    1655                 1660                 1665

Asn Leu  Leu Leu Phe Asn Gly  Ala Lys Val Gly Ser  Gln Glu Ala
    1670                 1675                 1680

Phe Tyr  Leu Tyr Ala Cys Gly  Pro Asn His Thr Ser  Val Met Pro
    1685                 1690                 1695

Cys Lys  Tyr Gly Lys Pro Val  Asn Asp Tyr Ser Lys  Tyr Ile Asn
    1700                 1705                 1710

Lys Glu  Ile Leu Arg Cys Glu  Gln Ile Arg Glu Leu  Phe Met Thr
    1715                 1720                 1725

Lys Lys  Asp Val Asp Ile Gly  Leu Leu Ile Glu Ser  Leu Ser Val
    1730                 1735                 1740

Val Tyr  Thr Thr Tyr Cys Pro  Ala Gln Tyr Thr Ile  Tyr Glu Pro
    1745                 1750                 1755

Val Ile  Arg Leu Lys Gly Gln  Met Lys Thr Gln Leu  Ser Gln Arg
    1760                 1765                 1770

Pro Phe  Ser Ser Lys Glu Val  Gln Ser Ile Leu Leu  Glu Pro His
    1775                 1780                 1785

His Leu  Lys Asn Leu Gln Pro  Thr Glu Tyr Lys Thr  Ile Gln Gly
    1790                 1795                 1800
```

-continued

```
Ile Leu His Glu Ile Gly Gly Thr Gly Ile Phe Val Phe Leu Phe
    1805                1810                1815

Ala Arg Val Val Glu Leu Ser Ser Cys Glu Glu Thr Gln Ala Leu
    1820                1825                1830

Ala Leu Arg Val Ile Leu Ser Leu Ile Lys Tyr Asn Gln Gln Arg
    1835                1840                1845

Val His Glu Leu Glu Asn Cys Asn Gly Leu Ser Met Ile His Gln
    1850                1855                1860

Val Leu Ile Lys Gln Lys Cys Ile Val Gly Phe Tyr Ile Leu Lys
    1865                1870                1875

Thr Leu Leu Glu Gly Cys Cys Gly Glu Asp Ile Ile Tyr Met Asn
    1880                1885                1890

Glu Asn Gly Glu Phe Lys Leu Asp Val Asp Ser Asn Ala Ile Ile
    1895                1900                1905

Gln Asp Val Lys Leu Leu Glu Glu Leu Leu Leu Asp Trp Lys Ile
    1910                1915                1920

Trp Ser Lys Ala Glu Gln Gly Val Trp Glu Thr Leu Leu Ala Ala
    1925                1930                1935

Leu Glu Val Leu Ile Arg Ala Asp His His Gln Gln Met Phe Asn
    1940                1945                1950

Ile Lys Gln Leu Leu Lys Ala Gln Val Val His His Phe Leu Leu
    1955                1960                1965

Thr Cys Gln Val Leu Gln Glu Tyr Lys Glu Gly Gln Leu Thr Pro
    1970                1975                1980

Met Pro Arg Glu Val Cys Arg Ser Phe Val Lys Ile Ile Ala Glu
    1985                1990                1995

Val Leu Gly Ser Pro Pro Asp Leu Glu Leu Leu Thr Ile Ile Phe
    2000                2005                2010

Asn Phe Leu Leu Ala Val His Pro Pro Thr Asn Thr Tyr Val Cys
    2015                2020                2025

His Asn Pro Thr Asn Phe Tyr Phe Ser Leu His Ile Asp Gly Lys
    2030                2035                2040

Ile Phe Gln Glu Lys Val Arg Ser Ile Met Tyr Leu Arg His Ser
    2045                2050                2055

Ser Ser Gly Gly Arg Ser Leu Met Ser Pro Gly Phe Met Val Ile
    2060                2065                2070

Ser Pro Ser Gly Phe Thr Ala Ser Pro Tyr Glu Gly Glu Asn Ser
    2075                2080                2085

Ser Asn Ile Ile Pro Gln Gln Met Ala Ala His Met Leu Arg Ser
    2090                2095                2100

Arg Ser Leu Pro Ala Phe Pro Thr Ser Ser Leu Leu Thr Gln Ser
    2105                2110                2115

Gln Lys Leu Thr Gly Ser Leu Gly Cys Ser Ile Asp Arg Leu Gln
    2120                2125                2130

Asn Ile Ala Asp Thr Tyr Val Ala Thr Gln Ser Lys Lys Gln Asn
    2135                2140                2145

Ser Leu Gly Ser Ser Asp Thr Leu Lys Lys Gly Lys Glu Asp Ala
    2150                2155                2160

Phe Ile Ser Ser Cys Glu Ser Ala Lys Thr Val Cys Glu Met Glu
    2165                2170                2175

Ala Val Leu Ser Ala Gln Val Ser Val Ser Asp Val Pro Lys Gly
    2180                2185                2190

Val Leu Gly Phe Pro Val Val Lys Ala Asp His Lys Gln Leu Gly
```

```
    2195                2200                2205

Ala Glu  Pro Arg Ser Glu Asp  Asp Ser Pro Gly Asp  Glu Ser Cys
    2210                2215                2220

Pro Arg  Arg Pro Asp Tyr Leu  Lys Gly Leu Ala Ser  Phe Gln Arg
    2225                2230                2235

Ser His  Ser Thr Ile Ala Ser  Leu Gly Leu Ala Phe  Pro Ser Gln
    2240                2245                2250

Asn Gly  Ser Ala Ala Val Gly  Arg Trp Pro Ser Leu  Val Asp Arg
    2255                2260                2265

Asn Thr  Asp Asp Trp Glu Asn  Phe Ala Tyr Ser Leu  Gly Tyr Glu
    2270                2275                2280

Pro Asn  Tyr Asn Arg Thr Ala  Ser Ala His Ser Val  Thr Glu Asp
    2285                2290                2295

Cys Leu  Val Pro Ile Cys Cys  Gly Leu Tyr Glu Leu  Leu Ser Gly
    2300                2305                2310

Val Leu  Leu Ile Leu Pro Asp  Val Leu Leu Glu Asp  Val Met Asp
    2315                2320                2325

Lys Leu  Ile Gln Ala Asp Thr  Leu Leu Val Leu Val  Asn His Pro
    2330                2335                2340

Ser Pro  Ala Ile Gln Gln Gly  Val Ile Lys Leu Leu  Asp Ala Tyr
    2345                2350                2355

Phe Ala  Arg Ala Ser Lys Glu  Gln Lys Asp Lys Phe  Leu Lys Asn
    2360                2365                2370

Arg Gly  Phe Ser Leu Leu Ala  Asn Gln Leu Tyr Leu  His Arg Gly
    2375                2380                2385

Thr Gln  Glu Leu Leu Glu Cys  Phe Ile Glu Met Phe  Phe Gly Arg
    2390                2395                2400

His Ile  Gly Leu Asp Glu Glu  Phe Asp Leu Glu Asp  Val Arg Asn
    2405                2410                2415

Met Gly  Leu Phe Gln Lys Trp  Ser Val Ile Pro Ile  Leu Gly Leu
    2420                2425                2430

Ile Glu  Thr Ser Leu Tyr Asp  Asn Ile Leu Leu His  Asn Ala Leu
    2435                2440                2445

Leu Leu  Leu Leu Gln Ile Leu  Asn Ser Cys Ser Lys  Val Ala Asp
    2450                2455                2460

Met Leu  Leu Asp Asn Gly Leu  Leu Tyr Val Leu Cys  Asn Thr Val
    2465                2470                2475

Ala Ala  Leu Asn Gly Leu Glu  Lys Asn Ile Pro Met  Ser Glu Tyr
    2480                2485                2490

Lys Leu  Leu Ala Cys Asp Ile  Gln Gln Leu Phe Ile  Ala Val Thr
    2495                2500                2505

Ile His  Ala Cys Ser Ser Ser  Gly Ser Gln Tyr Phe  Arg Val Ile
    2510                2515                2520

Glu Asp  Leu Ile Val Met Leu  Gly Tyr Leu Gln Asn  Ser Lys Asn
    2525                2530                2535

Lys Arg  Thr Gln Asn Met Ala  Val Ala Leu Gln Leu  Arg Val Leu
    2540                2545                2550

Gln Ala  Ala Met Glu Phe Ile  Arg Thr Thr Ala Asn  His Asp Ser
    2555                2560                2565

Glu Asn  Leu Thr Asp Ser Leu  Gln Ser Pro Ser Ala  Pro His His
    2570                2575                2580

Ala Val  Val Gln Lys Arg Lys  Ser Ile Ala Gly Pro  Arg Lys Phe
    2585                2590                2595
```

-continued

```
Pro Leu Ala Gln Thr Glu Ser Leu Leu Met Lys Met Arg Ser Val
    2600                2605                2610

Ala Asn Asp Glu Leu His Val Met Met Gln Arg Arg Met Ser Gln
    2615                2620                2625

Glu Asn Pro Ser Gln Ala Thr Glu Thr Glu Leu Ala Gln Arg Leu
    2630                2635                2640

Gln Arg Leu Thr Val Leu Ala Val Asn Arg Ile Ile Tyr Gln Glu
    2645                2650                2655

Phe Asn Ser Asp Ile Ile Asp Ile Leu Arg Thr Pro Glu Asn Val
    2660                2665                2670

Thr Gln Ser Lys Thr Ser Val Phe Gln Thr Glu Ile Ser Glu Glu
    2675                2680                2685

Asn Ile His His Glu Gln Ser Ser Val Phe Asn Pro Phe Gln Lys
    2690                2695                2700

Glu Ile Phe Thr Tyr Leu Val Glu Gly Phe Lys Val Ser Ile Gly
    2705                2710                2715

Ser Ser Lys Ala Ser Gly Ser Lys Gln Gln Trp Thr Lys Ile Leu
    2720                2725                2730

Trp Ser Cys Lys Glu Thr Phe Arg Met Gln Leu Gly Arg Leu Leu
    2735                2740                2745

Val His Ile Leu Ser Pro Ala His Ala Ala Gln Glu Arg Lys Gln
    2750                2755                2760

Ile Phe Glu Ile Val His Glu Pro Asn His Gln Glu Ile Leu Arg
    2765                2770                2775

Asp Cys Leu Ser Pro Ser Leu Gln His Gly Ala Lys Leu Val Leu
    2780                2785                2790

Tyr Leu Ser Glu Leu Ile His Asn His Gln Gly Glu Leu Thr Glu
    2795                2800                2805

Glu Glu Leu Gly Thr Ala Glu Leu Leu Met Asn Ala Leu Lys Leu
    2810                2815                2820

Cys Gly His Lys Cys Ile Pro Pro Ser Ala Ser Thr Lys Ala Asp
    2825                2830                2835

Leu Ile Lys Met Ile Lys Glu Glu Gln Lys Lys Tyr Glu Thr Glu
    2840                2845                2850

Glu Gly Val Asn Lys Ala Ala Trp Gln Lys Thr Val Asn Asn Asn
    2855                2860                2865

Gln Gln Ser Leu Phe Gln Arg Leu Asp Ser Lys Ser Lys Asp Ile
    2870                2875                2880

Ser Lys Ile Ala Ala Asp Ile Thr Gln Ala Val Ser Leu Ser Gln
    2885                2890                2895

Gly Asn Glu Arg Lys Lys Val Ile Gln His Ile Arg Gly Met Tyr
    2900                2905                2910

Lys Val Asp Leu Ser Ala Ser Arg His Trp Gln Glu Leu Ile Gln
    2915                2920                2925

Gln Leu Thr His Asp Arg Ala Val Trp Tyr Asp Pro Ile Tyr Tyr
    2930                2935                2940

Pro Thr Ser Trp Gln Leu Asp Pro Thr Glu Gly Pro Asn Arg Glu
    2945                2950                2955

Arg Arg Arg Leu Gln Arg Cys Tyr Leu Thr Ile Pro Asn Lys Tyr
    2960                2965                2970

Leu Leu Arg Asp Arg Gln Lys Ser Glu Asp Val Val Lys Pro Pro
    2975                2980                2985
```

```
Leu Ser  Tyr Leu Phe Glu Asp  Lys Thr His Ser Ser  Phe Ser Ser
    2990                 2995                 3000

Thr Val  Lys Asp Lys Ala Ala  Ser Glu Ser Ile Arg  Val Asn Arg
    3005                 3010                 3015

Arg Cys  Ile Ser Val Ala Pro  Ser Arg Glu Thr Ala  Gly Glu Leu
    3020                 3025                 3030

Leu Leu  Gly Lys Cys Gly Met  Tyr Phe Val Glu Asp  Asn Ala Ser
    3035                 3040                 3045

Asp Thr  Val Glu Ser Ser Ser  Leu Gln Gly Glu Leu  Glu Pro Ala
    3050                 3055                 3060

Ser Phe  Ser Trp Thr Tyr Glu  Glu Ile Lys Glu Val  His Lys Arg
    3065                 3070                 3075

Trp Trp  Gln Leu Arg Asp Asn  Ala Val Glu Ile Phe  Leu Thr Asn
    3080                 3085                 3090

Gly Arg  Thr Leu Leu Leu Ala  Phe Asp Asn Thr Lys  Val Arg Asp
    3095                 3100                 3105

Asp Val  Tyr His Asn Ile Leu  Thr Asn Asn Leu Pro  Asn Leu Leu
    3110                 3115                 3120

Glu Tyr  Gly Asn Ile Thr Ala  Leu Thr Asn Leu Trp  Tyr Thr Gly
    3125                 3130                 3135

Gln Ile  Thr Asn Phe Glu Tyr  Leu Thr His Leu Asn  Lys His Ala
    3140                 3145                 3150

Gly Arg  Ser Phe Asn Asp Leu  Met Gln Tyr Pro Val  Phe Pro Phe
    3155                 3160                 3165

Ile Leu  Ala Asp Tyr Val Ser  Glu Thr Leu Asp Leu  Asn Asp Leu
    3170                 3175                 3180

Leu Ile  Tyr Arg Asn Leu Ser  Lys Pro Ile Ala Val  Gln Tyr Lys
    3185                 3190                 3195

Glu Lys  Glu Asp Arg Tyr Val  Asp Thr Tyr Lys Tyr  Leu Glu Glu
    3200                 3205                 3210

Glu Tyr  Arg Lys Gly Ala Arg  Glu Asp Asp Pro Met  Pro Pro Val
    3215                 3220                 3225

Gln Pro  Tyr His Tyr Gly Ser  His Tyr Ser Asn Ser  Gly Thr Val
    3230                 3235                 3240

Leu His  Phe Leu Val Arg Met  Pro Pro Phe Thr Lys  Met Phe Leu
    3245                 3250                 3255

Ala Tyr  Gln Asp Gln Ser Phe  Asp Ile Pro Asp Arg  Thr Phe His
    3260                 3265                 3270

Ser Thr  Asn Thr Thr Trp Arg  Leu Ser Ser Phe Glu  Ser Met Thr
    3275                 3280                 3285

Asp Val  Lys Glu Leu Ile Pro  Glu Phe Phe Tyr Leu  Pro Glu Phe
    3290                 3295                 3300

Leu Val  Asn Arg Glu Gly Phe  Asp Phe Gly Val Arg  Gln Asn Gly
    3305                 3310                 3315

Glu Arg  Val Asn His Val Asn  Leu Pro Pro Trp Ala  Arg Asn Asp
    3320                 3325                 3330

Pro Arg  Leu Phe Ile Leu Ile  His Arg Gln Ala Leu  Glu Ser Asp
    3335                 3340                 3345

Tyr Val  Ser Gln Asn Ile Cys  Gln Trp Ile Asp Leu  Val Phe Gly
    3350                 3355                 3360

Tyr Lys  Gln Lys Gly Lys Ala  Ser Val Gln Ala Ile  Asn Val Phe
    3365                 3370                 3375

His Pro  Ala Thr Tyr Phe Gly  Met Asp Val Ser Ala  Val Glu Asp
```

3380 3385 3390

Pro Val Gln Arg Arg Ala Leu Glu Thr Met Ile Lys Thr Tyr Gly
3395 3400 3405

Gln Thr Pro Arg Gln Leu Phe His Met Ala His Val Ser Arg Pro
3410 3415 3420

Gly Ala Lys Leu Asn Ile Glu Gly Glu Leu Pro Ala Ala Val Gly
3425 3430 3435

Leu Leu Val Gln Phe Ala Phe Arg Glu Thr Arg Glu Gln Val Lys
3440 3445 3450

Glu Ile Thr Tyr Pro Ser Pro Leu Ser Trp Ile Lys Gly Leu Lys
3455 3460 3465

Trp Gly Glu Tyr Val Gly Ser Pro Ser Ala Pro Val Pro Val Val
3470 3475 3480

Cys Phe Ser Gln Pro His Gly Glu Arg Phe Gly Ser Leu Gln Ala
3485 3490 3495

Leu Pro Thr Arg Ala Ile Cys Gly Leu Ser Arg Asn Phe Cys Leu
3500 3505 3510

Leu Met Thr Tyr Ser Lys Glu Gln Gly Val Arg Ser Met Asn Ser
3515 3520 3525

Thr Asp Ile Gln Trp Ser Ala Ile Leu Ser Trp Gly Tyr Ala Asp
3530 3535 3540

Asn Ile Leu Arg Leu Lys Ser Lys Gln Ser Glu Pro Pro Val Asn
3545 3550 3555

Phe Ile Gln Ser Ser Gln Gln Tyr Gln Val Thr Ser Cys Ala Trp
3560 3565 3570

Val Pro Asp Ser Cys Gln Leu Phe Thr Gly Ser Lys Cys Gly Val
3575 3580 3585

Ile Thr Ala Tyr Thr Asn Arg Phe Thr Ser Ser Thr Pro Ser Glu
3590 3595 3600

Ile Glu Met Glu Thr Gln Ile His Leu Tyr Gly His Thr Glu Glu
3605 3610 3615

Ile Thr Ser Leu Phe Val Cys Lys Pro Tyr Ser Ile Leu Ile Ser
3620 3625 3630

Val Ser Arg Asp Gly Thr Cys Ile Ile Trp Asp Leu Asn Arg Leu
3635 3640 3645

Cys Tyr Val Gln Ser Leu Ala Gly His Lys Ser Pro Val Thr Ala
3650 3655 3660

Val Ser Ala Ser Glu Thr Ser Gly Asp Ile Ala Thr Val Cys Asp
3665 3670 3675

Ser Ala Gly Gly Gly Ser Asp Leu Arg Leu Trp Thr Val Asn Gly
3680 3685 3690

Asp Leu Val Gly His Val His Cys Arg Glu Ile Ile Cys Ser Val
3695 3700 3705

Ala Phe Ser Asn Gln Pro Glu Gly Val Ser Ile Asn Val Ile Ala
3710 3715 3720

Gly Gly Leu Glu Asn Gly Ile Val Arg Leu Trp Ser Thr Trp Asp
3725 3730 3735

Leu Lys Pro Val Arg Glu Ile Thr Phe Pro Lys Ser Asn Lys Pro
3740 3745 3750

Ile Ile Ser Leu Thr Phe Ser Cys Asp Gly His His Leu Tyr Thr
3755 3760 3765

Ala Asn Ser Asp Gly Thr Val Ile Ala Trp Cys Arg Lys Asp Gln
3770 3775 3780

Gln Arg Leu Lys Gln Pro Met Phe Tyr Ser Phe Leu Ser Ser Tyr
3785 3790 3795

Ala Ala Gly
3800

<210> SEQ ID NO 116
<211> LENGTH: 5568
<212> TYPE: DNA
<213> ORGANISM: Homo sapiens

<400> SEQUENCE: 116
atggctgcgt cggagctcta cacaaagttt gccagggttt ggatacctga tccagaggaa 60
gtctggaagt cagcagagct gctcaaagat tataagccag gagataaagt cctcctgctt 120
cacctcgagg aaggaaagga tttggaatac catctagatc caaagaccaa ggagctgcct 180
cacttacgaa atcctgacat acttgttggt gaaaatgacc tcacagccct cagctatctt 240
catgagcctg ctgtgctcca taatctcaga gtccgcttta ttgattccaa acttatttat 300
acgtattgtg gtatagtcct agtagctata aatccctatg aacagctgcc tatttatgga 360
gaagatatta ttaatgcata cagtggtcag aacatgggtg atatggatcc acatatcttt 420
gcagtagctg aagaagctta caagcaaatg gccagagatg aacgaaatca gtccatcatc 480
gtaagtggag agtctggggc aggaaaaaca gtctcagcta agtatgccat gcgatacttt 540
gcaactgtga gtggttctgc cagtgaggcc aatgtggagg aaaaggtctt ggcctccaac 600
cccatcatgg agtccattgg aaatgctaaa acaaccagga atgataatag cagccgtttt 660
gggaagtata ttgagattgg ttttgataag agatatcgaa tcattggtgc caatatgaga 720
acttatcttt tagagaaatc cagagtggta ttccaggcag aagaggagag aaactatcat 780
atcttctatc agctttgtgc ctcagcaaag ttacctgaat ttaaaatgct acgattagga 840
aatgcagata actttaatta cacaaaacaa ggaggcagtc ctgtgattga aggagtggat 900
gatgcaaagg agatggcaca tactaggcag gcctgcactt tgctaggaat tagtgaatct 960
catcaaatgg gaattttccg aatacttgct ggcatccttc acttaggcaa tgttggattt 1020
acatcccgag atgcagacag ctgcacaata cctcccaagc atgaacctct ctgcatcttc 1080
tgtgaactca tgggtgtgga ctatgaggag atgtgtcact ggctctgcca tcggaaactg 1140
gctactgcca cagagacata catcaagccc atctccaagc tgcaggccac gaatgcccgc 1200
gatgctttgg ccaagcacat ctatgccaag ctctttaact ggattgtaga taatgtcaat 1260
caggctctcc attctgctgt caaacagcac tcttttattg gtgtgctaga catttacgga 1320
tttgaaacat ttgagataaa tagttttgaa cagttttgca taaattatgc aaatgaaaaa 1380
ctacagcaac aattcaatat gcatgtcttc aaattggagc aagaagaata tatgaaggaa 1440
caaattccat ggacactcat agatttttat gataatcagc cttgtattaa tcttatagaa 1500
tcaaaactag gcattctaga tttactggat gaggaatgca agatgcctaa aggcacagat 1560
gacacctggg cccaaaaatt gtacaacaca catttgaaca aatgtgcact ctttgaaaag 1620
cctcgtctat caaacaaagc tttcatcatc caacattttg ctgacaaagt ggaataccag 1680
tgtgaaggat ttctcgaaaa gaataaagac accgtttttg aagaacaaat taaagttctt 1740
aaatcaagca agtttaagat gctaccagaa ctatttcaag atgatgagaa ggccatcagt 1800
ccaacttcag ccacctcctc agggcgcaca cccctcacac gaactcctgc aaagcccacc 1860
aaaggcagac caggccaaat ggccaaagag cacaagaaaa cagtggggca tcagttcaga 1920

```
aactccctgc acctgcttat ggagacactc aatgccacta cccctcacta tgtgcgctgt   1980
atcaagccta atgacttcaa gttcccattc acgtttgatg agaagagggc agtgcagcag   2040
ctgagagcat gtggtgtcct ggaaaccatc cgaatcagtg cggccggttt cccctcacgg   2100
tggacttacc aagaattttt cagccgctac cgtgtcctaa tgaagcagaa agatgtgctg   2160
agtgacagaa agcaaacatg caagaatgtg ttagagaaac tgatactgga caaggacaaa   2220
taccagtttg gtaagacaaa gatctttttc cgtgccggtc aagtggccta tctagaaaaa   2280
ttgagagctg acaaactgag agctgcctgc atccggatcc agaagaccat ccgagggtgg   2340
ctgctgagaa agaagtacct acgcatgcgg aaggcagcca tcaccatgca gagatacgtg   2400
cggggctacc aggcccgatg ctatgctaag tttctgcgca gaaccaaggc agcaaccatc   2460
attcaaaagt actggcgcat gtatgtggtc cgcaggaggt acaagattag acgagctgcc   2520
actatcgttc ttcagtctta cttgcgaggc ttcttggcca gaaataggta tcgcaagata   2580
ctccgtgagc acaaagcagt catcattcag aagcgagtcc ggggctggct ggcccgcaca   2640
cactacaaga ggagcatgca tgccatcatc taccttcagt gctgcttcag gcggatgatg   2700
gccaagcgtg agctaaagaa gctcaaaatc gaggctcgct cagtggagcg ctataagaag   2760
ctgcacatcg gcatggagaa caagatcatg cagctgcagc gcaaagttga tgagcagaac   2820
aaagactaca aatgccttgt ggagaaacta accaatctgg aaggaatata caactctgag   2880
actgagaaac tacgaagtga cttagaacgt cttcaactaa gtgaagagga agcgaaagtt   2940
gccactgggc gggtccttag tctgcaggaa gaaattgcca agctccggaa agacctggag   3000
caaactcgtt cagagaaaaa atgcattgag gaacatgcag atcgatacaa acaagaaaca   3060
gagcagctgg tatcaaatct gaaggaagaa aatactttgc tgaagcaaga aaaagaagcc   3120
ctcaatcacc gcatcgtgca gcaggctaag gagatgacag aaactatgga gaagaagtta   3180
gtagaagaaa cgaaacaact ggaactcgac cttaatgatg aaaggctgag atatcagaac   3240
cttctgaatg agttcagtcg cctggaagaa agatatgatg acctcaagga agagatgacc   3300
cttatggtgc atgtgcctaa gcctggacac aagagaacag actccaccca cagcagcaac   3360
gagtctgaat atatctttag ctctgaaatt gcagaaatgg aagacattcc atcaaggaca   3420
gaggaaccaa gtgagaagaa ggtacctctg gacatgtcat tgttccttaa gctccagaag   3480
cgggtcacag agctggagca ggagaagcag gtgatgcagg atgagctgga ccgcaaggag   3540
gagcaggtgc tccgcagcaa ggccaaggaa gaagaaagac cacaaattag aggtgcagaa   3600
ctggaatatg agtcactcaa gcgtcaagaa ctagaatcag aaaacaaaaa actgaagaat   3660
gagctaaatg agttgcgcaa ggccctcagt gagaaaagtg ccccagaggt gaccgcccca   3720
ggtgcacctg cctaccgtgt cctcatggag cagctgacct ctgtgagcga ggagcttgat   3780
gtccgcaagg aggaagtcct catcttaagg tctcaactgg tgagccagaa agaggccatc   3840
caacccaagg atgacaagaa tacaatgaca gattccacaa tacttttgga agatgtacaa   3900
aaaatgaaag ataaaggtga aatagcacaa gcatacattg gtttgaaaga aacaaataga   3960
tcatctgctc tggattacca tgagttgaat gaggatggag agctgtggct ggtttatgaa   4020
gggttaaaac aagccaacag gctcctggaa tcccagctgc agtcacagaa gaggagccat   4080
gagaatgagg ccgaggccct ccgtggggag atccagagcc tgaaggagga gaacaaccga   4140
cagcagcagc tgctggccca gaacctgcag ctgcccccag aggcccgcat tgaggccagc   4200
ctgcagcacg agatcacccg gctgaccaac gaaaacttgg atttgatgga acaacttgaa   4260
aaacaggata agacggtccg taaactgaaa aaacaactga aagtatttgc caaaaaaatt   4320
```

ggcgaactag aagtgggcca gatggagaac atatccccag gacagatcat tgatgaaccc 4380
atccgaccag tcaacattcc caggaaagaa aaggatttcc aagggatgct ggaatacaag 4440
aaggaggatg agcaaaaact tgttaagaac ctgattctgg aactgaagcc acgtggtgta 4500
gcagtcaatt tgattccagg attaccggca tatatcctgt tcatgtgtgt tcgacatgct 4560
gactacctga atgatgatca gaaagtaagg tcgttgctaa catcaacaat taacagcatc 4620
aaaaaagtat tgaagaaaag aggtgatgat tttgaaaccg tctccttctg gctctctaac 4680
acatgccgat tttgcactg cttgaaacag tacagtggag aagagggctt tatgaagcac 4740
aacacatctc gccagaatga acactgcctc accaatttg acctggctga gtatcggcag 4800
gtgctgagtg acttggccat tcagatctac cagcagctcg tgcgggtgtt agagaacatc 4860
cttcagccaa tgattgtctc aggcatgctg gaacatgaaa cgattcaggg cgtgtctggg 4920
gtgaagccca cagggttgag aaagcgaacc tccagtatcg ccgatgaggg cacctacaca 4980
ctggactcca tcctccggca gctcaactcc ttccactcgg tcatgtgtca gcatggcatg 5040
gaccctgaac tgatcaagca ggtggtcaag cagatgttct acatcatagg ggccatcacc 5100
ctgaacaacc ttctcctgcg gaaggacatg tgctcctgga gtaaaggcat gcagatcagg 5160
tacaatgtca gtcaactgga agaatggctg cgtgacaaga atctgatgaa tagtggggct 5220
aaagaaaccc tggaacctct cattcaggct gctcaacttt tgcaagtgaa aaagaaaaca 5280
gatgatgatg cagaagccat ttgttctatg tgcaatgctt taactactgc ccagattgtg 5340
aaagtgttga atttgtatac tccagttaat gagtttgaag aaagagtctc tgtgtcgttc 5400
attcgtacta tacagatgcg tttacgagac aggaaagact ctccccagct gctcatggat 5460
gctaaacaca tctttcctgt cacctttcct ttcaacccat cttccctcgc actagaaacc 5520
atccagattc cagccagcct cggcctgggc ttcatttcac gggtctga 5568

<210> SEQ ID NO 117
<211> LENGTH: 1855
<212> TYPE: PRT
<213> ORGANISM: Homo sapiens

<400> SEQUENCE: 117

Met Ala Ala Ser Glu Leu Tyr Thr Lys Phe Ala Arg Val Trp Ile Pro
1 5 10 15

Asp Pro Glu Glu Val Trp Lys Ser Ala Glu Leu Leu Lys Asp Tyr Lys
20 25 30

Pro Gly Asp Lys Val Leu Leu Leu His Leu Glu Glu Gly Lys Asp Leu
35 40 45

Glu Tyr His Leu Asp Pro Lys Thr Lys Glu Leu Pro His Leu Arg Asn
50 55 60

Pro Asp Ile Leu Val Gly Glu Asn Asp Leu Thr Ala Leu Ser Tyr Leu
65 70 75 80

His Glu Pro Ala Val Leu His Asn Leu Arg Val Arg Phe Ile Asp Ser
85 90 95

Lys Leu Ile Tyr Thr Tyr Cys Gly Ile Val Leu Val Ala Ile Asn Pro
100 105 110

Tyr Glu Gln Leu Pro Ile Tyr Gly Glu Asp Ile Ile Asn Ala Tyr Ser
115 120 125

Gly Gln Asn Met Gly Asp Met Asp Pro His Ile Phe Ala Val Ala Glu
130 135 140

Glu Ala Tyr Lys Gln Met Ala Arg Asp Glu Arg Asn Gln Ser Ile Ile

```
145                 150                 155                 160

Val Ser Gly Glu Ser Gly Ala Gly Lys Thr Val Ser Ala Lys Tyr Ala
                165                 170                 175

Met Arg Tyr Phe Ala Thr Val Ser Gly Ser Ala Ser Glu Ala Asn Val
            180                 185                 190

Glu Glu Lys Val Leu Ala Ser Asn Pro Ile Met Glu Ser Ile Gly Asn
        195                 200                 205

Ala Lys Thr Thr Arg Asn Asp Asn Ser Ser Arg Phe Gly Lys Tyr Ile
    210                 215                 220

Glu Ile Gly Phe Asp Lys Arg Tyr Arg Ile Ile Gly Ala Asn Met Arg
225                 230                 235                 240

Thr Tyr Leu Leu Glu Lys Ser Arg Val Val Phe Gln Ala Glu Glu Glu
                245                 250                 255

Arg Asn Tyr His Ile Phe Tyr Gln Leu Cys Ala Ser Ala Lys Leu Pro
            260                 265                 270

Glu Phe Lys Met Leu Arg Leu Gly Asn Ala Asp Asn Phe Asn Tyr Thr
        275                 280                 285

Lys Gln Gly Gly Ser Pro Val Ile Glu Gly Val Asp Asp Ala Lys Glu
    290                 295                 300

Met Ala His Thr Arg Gln Ala Cys Thr Leu Leu Gly Ile Ser Glu Ser
305                 310                 315                 320

His Gln Met Gly Ile Phe Arg Ile Leu Ala Gly Ile Leu His Leu Gly
                325                 330                 335

Asn Val Gly Phe Thr Ser Arg Asp Ala Asp Ser Cys Thr Ile Pro Pro
            340                 345                 350

Lys His Glu Pro Leu Cys Ile Phe Cys Glu Leu Met Gly Val Asp Tyr
        355                 360                 365

Glu Glu Met Cys His Trp Leu Cys His Arg Lys Leu Ala Thr Ala Thr
    370                 375                 380

Glu Thr Tyr Ile Lys Pro Ile Ser Lys Leu Gln Ala Thr Asn Ala Arg
385                 390                 395                 400

Asp Ala Leu Ala Lys His Ile Tyr Ala Lys Leu Phe Asn Trp Ile Val
                405                 410                 415

Asp Asn Val Asn Gln Ala Leu His Ser Ala Val Lys Gln His Ser Phe
            420                 425                 430

Ile Gly Val Leu Asp Ile Tyr Gly Phe Glu Thr Phe Glu Ile Asn Ser
        435                 440                 445

Phe Glu Gln Phe Cys Ile Asn Tyr Ala Asn Glu Lys Leu Gln Gln Gln
    450                 455                 460

Phe Asn Met His Val Phe Lys Leu Glu Gln Glu Glu Tyr Met Lys Glu
465                 470                 475                 480

Gln Ile Pro Trp Thr Leu Ile Asp Phe Tyr Asp Asn Gln Pro Cys Ile
                485                 490                 495

Asn Leu Ile Glu Ser Lys Leu Gly Ile Leu Asp Leu Leu Asp Glu Glu
            500                 505                 510

Cys Lys Met Pro Lys Gly Thr Asp Asp Thr Trp Ala Gln Lys Leu Tyr
        515                 520                 525

Asn Thr His Leu Asn Lys Cys Ala Leu Phe Glu Lys Pro Arg Leu Ser
    530                 535                 540

Asn Lys Ala Phe Ile Ile Gln His Phe Ala Asp Lys Val Glu Tyr Gln
545                 550                 555                 560

Cys Glu Gly Phe Leu Glu Lys Asn Lys Asp Thr Val Phe Glu Glu Gln
                565                 570                 575
```

```
Ile Lys Val Leu Lys Ser Ser Lys Phe Lys Met Leu Pro Glu Leu Phe
            580                 585                 590

Gln Asp Asp Glu Lys Ala Ile Ser Pro Thr Ser Ala Thr Ser Ser Gly
        595                 600                 605

Arg Thr Pro Leu Thr Arg Thr Pro Ala Lys Pro Thr Lys Gly Arg Pro
    610                 615                 620

Gly Gln Met Ala Lys Glu His Lys Lys Thr Val Gly His Gln Phe Arg
625                 630                 635                 640

Asn Ser Leu His Leu Leu Met Glu Thr Leu Asn Ala Thr Thr Pro His
                645                 650                 655

Tyr Val Arg Cys Ile Lys Pro Asn Asp Phe Lys Phe Pro Phe Thr Phe
            660                 665                 670

Asp Glu Lys Arg Ala Val Gln Gln Leu Arg Ala Cys Gly Val Leu Glu
        675                 680                 685

Thr Ile Arg Ile Ser Ala Ala Gly Phe Pro Ser Arg Trp Thr Tyr Gln
    690                 695                 700

Glu Phe Phe Ser Arg Tyr Arg Val Leu Met Lys Gln Lys Asp Val Leu
705                 710                 715                 720

Ser Asp Arg Lys Gln Thr Cys Lys Asn Val Leu Glu Lys Leu Ile Leu
                725                 730                 735

Asp Lys Asp Lys Tyr Gln Phe Gly Lys Thr Lys Ile Phe Phe Arg Ala
            740                 745                 750

Gly Gln Val Ala Tyr Leu Glu Lys Leu Arg Ala Asp Lys Leu Arg Ala
        755                 760                 765

Ala Cys Ile Arg Ile Gln Lys Thr Ile Arg Gly Trp Leu Leu Arg Lys
    770                 775                 780

Lys Tyr Leu Arg Met Arg Lys Ala Ala Ile Thr Met Gln Arg Tyr Val
785                 790                 795                 800

Arg Gly Tyr Gln Ala Arg Cys Tyr Ala Lys Phe Leu Arg Arg Thr Lys
                805                 810                 815

Ala Ala Thr Ile Ile Gln Lys Tyr Trp Arg Met Tyr Val Val Arg Arg
            820                 825                 830

Arg Tyr Lys Ile Arg Arg Ala Ala Thr Ile Val Leu Gln Ser Tyr Leu
        835                 840                 845

Arg Gly Phe Leu Ala Arg Asn Arg Tyr Arg Lys Ile Leu Arg Glu His
    850                 855                 860

Lys Ala Val Ile Ile Gln Lys Arg Val Arg Gly Trp Leu Ala Arg Thr
865                 870                 875                 880

His Tyr Lys Arg Ser Met His Ala Ile Ile Tyr Leu Gln Cys Cys Phe
                885                 890                 895

Arg Arg Met Met Ala Lys Arg Glu Leu Lys Lys Leu Lys Ile Glu Ala
            900                 905                 910

Arg Ser Val Glu Arg Tyr Lys Lys Leu His Ile Gly Met Glu Asn Lys
        915                 920                 925

Ile Met Gln Leu Gln Arg Lys Val Asp Glu Gln Asn Lys Asp Tyr Lys
    930                 935                 940

Cys Leu Val Glu Lys Leu Thr Asn Leu Glu Gly Ile Tyr Asn Ser Glu
945                 950                 955                 960

Thr Glu Lys Leu Arg Ser Asp Leu Glu Arg Leu Gln Leu Ser Glu Glu
                965                 970                 975

Glu Ala Lys Val Ala Thr Gly Arg Val Leu Ser Leu Gln Glu Glu Ile
            980                 985                 990
```

```
Ala Lys Leu Arg Lys Asp Leu Glu  Gln Thr Arg Ser Glu  Lys Lys Cys
        995                 1000                 1005

Ile Glu  Glu His Ala Asp Arg  Tyr Lys Gln Glu Thr  Glu Gln Leu
    1010                 1015                 1020

Val Ser  Asn Leu Lys Glu Glu  Asn Thr Leu Leu Lys  Gln Glu Lys
    1025                 1030                 1035

Glu Ala  Leu Asn His Arg Ile  Val Gln Gln Ala Lys  Glu Met Thr
    1040                 1045                 1050

Glu Thr  Met Glu Lys Lys Leu  Val Glu Glu Thr Lys  Gln Leu Glu
    1055                 1060                 1065

Leu Asp  Leu Asn Asp Glu Arg  Leu Arg Tyr Gln Asn  Leu Leu Asn
    1070                 1075                 1080

Glu Phe  Ser Arg Leu Glu Glu  Arg Tyr Asp Asp Leu  Lys Glu Glu
    1085                 1090                 1095

Met Thr  Leu Met Val His Val  Pro Lys Pro Gly His  Lys Arg Thr
    1100                 1105                 1110

Asp Ser  Thr His Ser Ser Asn  Glu Ser Glu Tyr Ile  Phe Ser Ser
    1115                 1120                 1125

Glu Ile  Ala Glu Met Glu Asp  Ile Pro Ser Arg Thr  Glu Glu Pro
    1130                 1135                 1140

Ser Glu  Lys Lys Val Pro Leu  Asp Met Ser Leu Phe  Leu Lys Leu
    1145                 1150                 1155

Gln Lys  Arg Val Thr Glu Leu  Glu Gln Glu Lys Gln  Val Met Gln
    1160                 1165                 1170

Asp Glu  Leu Asp Arg Lys Glu  Glu Gln Val Leu Arg  Ser Lys Ala
    1175                 1180                 1185

Lys Glu  Glu Glu Arg Pro Gln  Ile Arg Gly Ala Glu  Leu Glu Tyr
    1190                 1195                 1200

Glu Ser  Leu Lys Arg Gln Glu  Leu Glu Ser Glu Asn  Lys Lys Leu
    1205                 1210                 1215

Lys Asn  Glu Leu Asn Glu Leu  Arg Lys Ala Leu Ser  Glu Lys Ser
    1220                 1225                 1230

Ala Pro  Glu Val Thr Ala Pro  Gly Ala Pro Ala Tyr  Arg Val Leu
    1235                 1240                 1245

Met Glu  Gln Leu Thr Ser Val  Ser Glu Glu Leu Asp  Val Arg Lys
    1250                 1255                 1260

Glu Glu  Val Leu Ile Leu Arg  Ser Gln Leu Val Ser  Gln Lys Glu
    1265                 1270                 1275

Ala Ile  Gln Pro Lys Asp Asp  Lys Asn Thr Met Thr  Asp Ser Thr
    1280                 1285                 1290

Ile Leu  Leu Glu Asp Val Gln  Lys Met Lys Asp Lys  Gly Glu Ile
    1295                 1300                 1305

Ala Gln  Ala Tyr Ile Gly Leu  Lys Glu Thr Asn Arg  Ser Ser Ala
    1310                 1315                 1320

Leu Asp  Tyr His Glu Leu Asn  Glu Asp Gly Glu Leu  Trp Leu Val
    1325                 1330                 1335

Tyr Glu  Gly Leu Lys Gln Ala  Asn Arg Leu Leu Glu  Ser Gln Leu
    1340                 1345                 1350

Gln Ser  Gln Lys Arg Ser His  Glu Asn Glu Ala Glu  Ala Leu Arg
    1355                 1360                 1365

Gly Glu  Ile Gln Ser Leu Lys  Glu Glu Asn Asn Arg  Gln Gln Gln
    1370                 1375                 1380

Leu Leu  Ala Gln Asn Leu Gln  Leu Pro Pro Glu Ala  Arg Ile Glu
```

```
    1385                1390                1395

Ala Ser  Leu Gln His Glu Ile  Thr Arg Leu Thr Asn  Glu Asn Leu
    1400                1405                1410

Asp Leu  Met Glu Gln Leu Glu  Lys Gln Asp Lys Thr  Val Arg Lys
    1415                1420                1425

Leu Lys  Lys Gln Leu Lys Val  Phe Ala Lys Lys Ile  Gly Glu Leu
    1430                1435                1440

Glu Val  Gly Gln Met Glu Asn  Ile Ser Pro Gly Gln  Ile Ile Asp
    1445                1450                1455

Glu Pro  Ile Arg Pro Val Asn  Ile Pro Arg Lys Glu  Lys Asp Phe
    1460                1465                1470

Gln Gly  Met Leu Glu Tyr Lys  Lys Glu Asp Glu Gln  Lys Leu Val
    1475                1480                1485

Lys Asn  Leu Ile Leu Glu Leu  Lys Pro Arg Gly Val  Ala Val Asn
    1490                1495                1500

Leu Ile  Pro Gly Leu Pro Ala  Tyr Ile Leu Phe Met  Cys Val Arg
    1505                1510                1515

His Ala  Asp Tyr Leu Asn Asp  Asp Gln Lys Val Arg  Ser Leu Leu
    1520                1525                1530

Thr Ser  Thr Ile Asn Ser Ile  Lys Lys Val Leu Lys  Lys Arg Gly
    1535                1540                1545

Asp Asp  Phe Glu Thr Val Ser  Phe Trp Leu Ser Asn  Thr Cys Arg
    1550                1555                1560

Phe Leu  His Cys Leu Lys Gln  Tyr Ser Gly Glu Glu  Gly Phe Met
    1565                1570                1575

Lys His  Asn Thr Ser Arg Gln  Asn Glu His Cys Leu  Thr Asn Phe
    1580                1585                1590

Asp Leu  Ala Glu Tyr Arg Gln  Val Leu Ser Asp Leu  Ala Ile Gln
    1595                1600                1605

Ile Tyr  Gln Gln Leu Val Arg  Val Leu Glu Asn Ile  Leu Gln Pro
    1610                1615                1620

Met Ile  Val Ser Gly Met Leu  Glu His Glu Thr Ile  Gln Gly Val
    1625                1630                1635

Ser Gly  Val Lys Pro Thr Gly  Leu Arg Lys Arg Thr  Ser Ser Ile
    1640                1645                1650

Ala Asp  Glu Gly Thr Tyr Thr  Leu Asp Ser Ile Leu  Arg Gln Leu
    1655                1660                1665

Asn Ser  Phe His Ser Val Met  Cys Gln His Gly Met  Asp Pro Glu
    1670                1675                1680

Leu Ile  Lys Gln Val Val Lys  Gln Met Phe Tyr Ile  Ile Gly Ala
    1685                1690                1695

Ile Thr  Leu Asn Asn Leu Leu  Leu Arg Lys Asp Met  Cys Ser Trp
    1700                1705                1710

Ser Lys  Gly Met Gln Ile Arg  Tyr Asn Val Ser Gln  Leu Glu Glu
    1715                1720                1725

Trp Leu  Arg Asp Lys Asn Leu  Met Asn Ser Gly Ala  Lys Glu Thr
    1730                1735                1740

Leu Glu  Pro Leu Ile Gln Ala  Ala Gln Leu Leu Gln  Val Lys Lys
    1745                1750                1755

Lys Thr  Asp Asp Asp Ala Glu  Ala Ile Cys Ser Met  Cys Asn Ala
    1760                1765                1770

Leu Thr  Thr Ala Gln Ile Val  Lys Val Leu Asn Leu  Tyr Thr Pro
    1775                1780                1785
```

```
Val Asn  Glu Phe Glu Glu Arg  Val Ser Val Ser Phe  Ile Arg Thr
    1790                 1795                 1800

Ile Gln  Met Arg Leu Arg Asp  Arg Lys Asp Ser Pro  Gln Leu Leu
    1805                 1810                 1815

Met Asp  Ala Lys His Ile Phe  Pro Val Thr Phe Pro  Phe Asn Pro
    1820                 1825                 1830

Ser Ser  Leu Ala Leu Glu Thr  Ile Gln Ile Pro Ala  Ser Leu Gly
    1835                 1840                 1845

Leu Gly  Phe Ile Ser Arg Val
    1850                 1855
```

<210> SEQ ID NO 118
<211> LENGTH: 666
<212> TYPE: DNA
<213> ORGANISM: Homo sapiens

<400> SEQUENCE: 118

```
atgtctgatg gagattatga ttacctcatc aagtttttag ctttgggaga ctctggtgta     60

gggaagacca gtgtacttta ccaatataca gatggtaaat ttaactccaa atttatcaca    120

acagtgggca ttgatttcag ggaaaaaaga gtggtgtaca gagccagtgg gccggatgga    180

gccactggca gaggccagag aatccacctg cagttatggg acacagcagg gcaggagagg    240

tttcgtagct taacgacagc gttcttcaga gatgctatgg gttttcttct actttttgat    300

ctgacaaatg agcaaagttt cctcaatgtc agaaactgga taagccagct acagatgcat    360

gcatattgtg aaaacccaga tatagtgctg tgtggaaaca agagtgatct ggaggaccag    420

agagtagtga aagaggagga agccatagca ctcgcagaga aatatggaat cccctacttt    480

gaaactagtg ctgccaatgg gacaaacata agccaagcaa ttgagatgct tctggacctg    540

ataatgaagc gaatggaacg gtgtgtggac aagtcctgga ttcctgaagg agtggtgcga    600

tcaaatggtc atgcctctac ggatcagtta agtgaagaaa aggagaaagg ggcatgtggc    660

tgttga                                                                666
```

<210> SEQ ID NO 119
<211> LENGTH: 221
<212> TYPE: PRT
<213> ORGANISM: Homo sapiens

<400> SEQUENCE: 119

```
Met Ser Asp Gly Asp Tyr Asp Tyr Leu Ile Lys Phe Leu Ala Leu Gly
1               5                   10                  15

Asp Ser Gly Val Gly Lys Thr Ser Val Leu Tyr Gln Tyr Thr Asp Gly
            20                  25                  30

Lys Phe Asn Ser Lys Phe Ile Thr Thr Val Gly Ile Asp Phe Arg Glu
        35                  40                  45

Lys Arg Val Val Tyr Arg Ala Ser Gly Pro Asp Gly Ala Thr Gly Arg
    50                  55                  60

Gly Gln Arg Ile His Leu Gln Leu Trp Asp Thr Ala Gly Gln Glu Arg
65                  70                  75                  80

Phe Arg Ser Leu Thr Thr Ala Phe Phe Arg Asp Ala Met Gly Phe Leu
                85                  90                  95

Leu Leu Phe Asp Leu Thr Asn Glu Gln Ser Phe Leu Asn Val Arg Asn
            100                 105                 110

Trp Ile Ser Gln Leu Gln Met His Ala Tyr Cys Glu Asn Pro Asp Ile
        115                 120                 125
```

```
Val Leu Cys Gly Asn Lys Ser Asp Leu Glu Asp Gln Arg Val Val Lys
    130                 135                 140

Glu Glu Glu Ala Ile Ala Leu Ala Glu Lys Tyr Gly Ile Pro Tyr Phe
145                 150                 155                 160

Glu Thr Ser Ala Ala Asn Gly Thr Asn Ile Ser Gln Ala Ile Glu Met
                165                 170                 175

Leu Leu Asp Leu Ile Met Lys Arg Met Glu Arg Cys Val Asp Lys Ser
            180                 185                 190

Trp Ile Pro Glu Gly Val Val Arg Ser Asn Gly His Ala Ser Thr Asp
        195                 200                 205

Gln Leu Ser Glu Glu Lys Glu Lys Gly Ala Cys Gly Cys
    210                 215                 220


<210> SEQ ID NO 120
<211> LENGTH: 1803
<212> TYPE: DNA
<213> ORGANISM: Homo sapiens

<400> SEQUENCE: 120

atggggaaga aactggatct ttccaagctc actgatgaag aggcccagca tgtcttggaa      60

gttgttcaac gagattttga cctccgaagg aaagaagagg aacggctaga ggcgttgaag     120

ggcaagatta agaaggaaag ctccaagagg gagctgcttt ccgacactgc ccatctgaac     180

gagacccact gcgcccgctg cctgcagccc taccagctgc ttgtgaatag caaaaggcag     240

tgcctggaat gtggcctctt cacctgcaaa agctgtggcc gcgtccaccc ggaggagcag     300

ggctggatct gtgacccctg ccatctggcc agagtcgtga agatcggctc actggagtgg     360

tactatgagc atgtgaaagc ccgcttcaag aggttcggaa gtgccaaggt catccggtcc     420

ctccacgggc ggctgcaggg tggagctggg cctgaactga tatctgaaga gagaagtgga     480

gacagcgacc agacagatga ggatggagaa cctggctcag aggcccaggc ccaggcccag     540

ccctttggca gcaaaaaaaa gcgcctcctc tccgtccacg acttcgactt cgagggagac     600

tcagatgact ccactcagcc tcaaggtcac tccctgcacc tgtcctcagt ccctgaggcc     660

agggacagcc cacagtccct cacagatgag tcctgctcag agaaggcagc ccctcacaag     720

gctgagggcc tggaggaggc tgatactggg gcctctgggt gccactccca tccggaagag     780

cagccgacca gcatctcacc ttccagacac ggcgccctgg ctgagctctg cccgcctgga     840

ggctcccaca ggatggccct ggggactgct gctgcactcg ggtcgaatgt catcaggaat     900

gagcagctgc cctgcagta cttggccgat gtggacacct ctgatgagga aagcatccgg     960

gctcacgtga tggcctccca ccattccaag cggagaggcc gggcgtcttc tgagagtcag    1020

atctttgagc tgaataagca tatttcagct gtggaatgcc tgctgaccta cctggagaac    1080

acagttgtgc ctcccttggc caagggtcta ggtgctggag tgcgcacgga ggccgatgta    1140

gaggaggagg ccctgaggag gaagctggag gagctgacca gcaacgtcag tgaccaggag    1200

acctcgtccg aggaggagga agccaaggac gaaaaggcag agcccaacag ggacaaatca    1260

gttgggcctc tcccccaggc ggacccggag gtgggcacgg ctgcccatca aaccaacaga    1320

caggaaaaaa gcccccagga ccctggggac cccgtccagt acaacaggac cacagatgag    1380

gagctgtcag agctggagga cagagtggca gtgacggcct cagaagtcca gcaggcagag    1440

agcgaggttt cagacattga atccaggatt gcagccctga gggccgcagg gctcacggtg    1500

aagccctcgg gaaagccccg gaggaagtca aacctcccga tatttctccc tcgagtggct    1560
```

gggaaacttg gcaagagacc agaggaccca aatgcagacc cttcaagtga ggccaaggca 1620
atggctgtgc cctatcttct gagaagaaag ttcagtaatt ccctgaaaag tcaaggtaaa 1680
gatgatgatt cttttgatcg gaaatcagtg taccgaggct cgctgacaca gagaaacccc 1740
aacgcgagga aaggaatggc cagccacacc ttcgcgaaac ctgtggtggc ccaccagtcc 1800
taa 1803

<210> SEQ ID NO 121
<211> LENGTH: 600
<212> TYPE: PRT
<213> ORGANISM: Homo sapiens

<400> SEQUENCE: 121

Met Gly Lys Lys Leu Asp Leu Ser Lys Leu Thr Asp Glu Glu Ala Gln
1 5 10 15

His Val Leu Glu Val Val Gln Arg Asp Phe Asp Leu Arg Arg Lys Glu
20 25 30

Glu Glu Arg Leu Glu Ala Leu Lys Gly Lys Ile Lys Lys Glu Ser Ser
35 40 45

Lys Arg Glu Leu Leu Ser Asp Thr Ala His Leu Asn Glu Thr His Cys
50 55 60

Ala Arg Cys Leu Gln Pro Tyr Gln Leu Leu Val Asn Ser Lys Arg Gln
65 70 75 80

Cys Leu Glu Cys Gly Leu Phe Thr Cys Lys Ser Cys Gly Arg Val His
85 90 95

Pro Glu Glu Gln Gly Trp Ile Cys Asp Pro Cys His Leu Ala Arg Val
100 105 110

Val Lys Ile Gly Ser Leu Glu Trp Tyr Tyr Glu His Val Lys Ala Arg
115 120 125

Phe Lys Arg Phe Gly Ser Ala Lys Val Ile Arg Ser Leu His Gly Arg
130 135 140

Leu Gln Gly Gly Ala Gly Pro Glu Leu Ile Ser Glu Glu Arg Ser Gly
145 150 155 160

Asp Ser Asp Gln Thr Asp Glu Asp Gly Glu Pro Gly Ser Glu Ala Gln
165 170 175

Ala Gln Ala Gln Pro Phe Gly Ser Lys Lys Lys Arg Leu Leu Ser Val
180 185 190

His Asp Phe Asp Phe Glu Gly Asp Ser Asp Asp Ser Thr Gln Pro Gln
195 200 205

Gly His Ser Leu His Leu Ser Ser Val Pro Glu Ala Arg Asp Ser Pro
210 215 220

Gln Ser Leu Thr Asp Glu Ser Cys Ser Glu Lys Ala Ala Pro His Lys
225 230 235 240

Ala Glu Gly Leu Glu Glu Ala Asp Thr Gly Ala Ser Gly Cys His Ser
245 250 255

His Pro Glu Glu Gln Pro Thr Ser Ile Ser Pro Ser Arg His Gly Ala
260 265 270

Leu Ala Glu Leu Cys Pro Pro Gly Gly Ser His Arg Met Ala Leu Gly
275 280 285

Thr Ala Ala Ala Leu Gly Ser Asn Val Ile Arg Asn Glu Gln Leu Pro
290 295 300

Leu Gln Tyr Leu Ala Asp Val Asp Thr Ser Asp Glu Glu Ser Ile Arg
305 310 315 320

Ala His Val Met Ala Ser His His Ser Lys Arg Arg Gly Arg Ala Ser

```
                325                 330                 335

Ser Glu Ser Gln Ile Phe Glu Leu Asn Lys His Ile Ser Ala Val Glu
            340                 345                 350

Cys Leu Leu Thr Tyr Leu Glu Asn Thr Val Val Pro Pro Leu Ala Lys
        355                 360                 365

Gly Leu Gly Ala Gly Val Arg Thr Glu Ala Asp Val Glu Glu Glu Ala
    370                 375                 380

Leu Arg Arg Lys Leu Glu Glu Leu Thr Ser Asn Val Ser Asp Gln Glu
385                 390                 395                 400

Thr Ser Ser Glu Glu Glu Glu Ala Lys Asp Glu Lys Ala Glu Pro Asn
            405                 410                 415

Arg Asp Lys Ser Val Gly Pro Leu Pro Gln Ala Asp Pro Glu Val Gly
            420                 425                 430

Thr Ala Ala His Gln Thr Asn Arg Gln Glu Lys Ser Pro Gln Asp Pro
        435                 440                 445

Gly Asp Pro Val Gln Tyr Asn Arg Thr Thr Asp Glu Glu Leu Ser Glu
    450                 455                 460

Leu Glu Asp Arg Val Ala Val Thr Ala Ser Glu Val Gln Gln Ala Glu
465                 470                 475                 480

Ser Glu Val Ser Asp Ile Glu Ser Arg Ile Ala Ala Leu Arg Ala Ala
            485                 490                 495

Gly Leu Thr Val Lys Pro Ser Gly Lys Pro Arg Arg Lys Ser Asn Leu
            500                 505                 510

Pro Ile Phe Leu Pro Arg Val Ala Gly Lys Leu Gly Lys Arg Pro Glu
        515                 520                 525

Asp Pro Asn Ala Asp Pro Ser Ser Glu Ala Lys Ala Met Ala Val Pro
    530                 535                 540

Tyr Leu Leu Arg Arg Lys Phe Ser Asn Ser Leu Lys Ser Gln Gly Lys
545                 550                 555                 560

Asp Asp Asp Ser Phe Asp Arg Lys Ser Val Tyr Arg Gly Ser Leu Thr
            565                 570                 575

Gln Arg Asn Pro Asn Ala Arg Lys Gly Met Ala Ser His Thr Phe Ala
            580                 585                 590

Lys Pro Val Val Ala His Gln Ser
        595                 600
```

<210> SEQ ID NO 122
<211> LENGTH: 3285
<212> TYPE: DNA
<213> ORGANISM: Homo sapiens

<400> SEQUENCE: 122

```
atgtccagca atagttttcc ttacaatgag cagtccggag gaggggaggc gacggagctg      60

ggtcaggagg cgacctcaac catttccccc tcgggggcct tcggcctctt tagcagcgat     120

ttgaagaaga atgaagatct aaagcaaatg ttagagagca acaaagattc tgctaaactg     180

gatgctatga agcggattgt tgggatgatt gcaaaaggga aaaatgcatc tgaactgttt     240

cctgctgttg tgaagaatgt ggccagtaaa aatattgaga tcaagaagtt ggtatatgtt     300

tacctggttc gatatgctga agaacagcag gatcttgcac tcctgtccat aagcactttt     360

cagcgagctc tgaaggaccc aaaccaacta attcgtgcaa gcgctttgag agttctgtca     420

agtattagag tgccaattat tgtacctatc atgatgcttg ctattaagga agcttctgct     480

gacttatcac catatgttag gaagaatgca gcccatgcaa tacaaaaatt atacagcctt     540
```

-continued

```
gatccagagc agaaggaaat gttaattgaa gtaattgaaa aacttctgaa agataaaagc    600
acattggtag ctggcagtgt tgtgatggct tttgaagaag tatgcccgga cagaatagat    660
ctgattcata aaaattaccg caagctatgt aacttactag tggatgttga agagtggggg    720
caggttgtca taatccacat gctaactcga tatgctcgga cacagtttgt cagcccttgg    780
aaagagggtg atgaattaga agacaatgga aagaatttct acgaatctga tgatgatcag    840
aaggaaaaga ctgacaaaaa gaagaagccg tatactatgg atccagatca tagactctta    900
attagaaata caaagccttt gcttcagagc aggaatgctg cggtggttat ggcagttgct    960
cagctgtatt ggcacatatc accaaaatct gaagctggca taatttctaa atcactagtg   1020
cgtttacttc gtagcaatag ggaggtgcag tatattgtcc tacaaaatat agcaactatg   1080
tcaattcaaa gaaaggggat gtttgaacct tatctgaaga gtttctatgt taggtcaact   1140
gatccaacta tgatcaagac actgaagctt gaaattttga caaacttggc aaatgaagcc   1200
aacatatcaa ctcttcttcg agaatttcag acctatgtga aaagccagga taaacaattt   1260
gcagcagcca ctattcagac tataggcaga tgtgcaacca acatcttgga agtcactgac   1320
acgtgcctca atggcttggt ctgtctgctg tccaacaggg atgaaatagt tgttgctgaa   1380
agtgtggttg ttataaagaa attactgcaa atgcaacctg cacaacatgg tgaaattatt   1440
aaacatatgg ccaaactcct ggacagtatc actgttcctg ttgctagagc aagtattctt   1500
tggctaattg gagaaaactg tgaacgagtt cctaaaattg cccctgatgt tttgaggaag   1560
atggctaaaa gcttcactag tgaagatgat ctggtaaaac tgcagatatt aaatctggga   1620
gcaaaattgt atttaaccaa ctccaaacag acaaaattgc ttacccagta catattaaat   1680
ctcggcaagt atgatcaaaa ctacgacatc agagaccgta caagatttat taggcagctt   1740
attgttccga atgtaaagag tggagcttta agtaaatatg ccaaaaaaat attcctagca   1800
caaaagcctg caccactgct tgagtctcct tttaaagata gagatcattt ccagcttggc   1860
accttatctc atactctcaa cattaaagct actgggtacc tggaattatc taattggcca   1920
gaggtggcgc ccgacccatc agttcgaaat gtagaagtaa tagagttggc aaaagaatgg   1980
accccagcag gaaaagcaaa gcaagagaat tctgctaaga agttttattc tgaatctgag   2040
gaagaggagg actcttctga tagtagcagt gacagtgaga gtgaatctgg aagtgaaagt   2100
ggagaacaag gcgaaagtgg ggaggaagga gacagcaatg aggacagcag tgaggactcc   2160
tccagtgagc aggacagtga gagtggacgg gagtcaggcc tagaaaacaa aagaacagcc   2220
aagaggaact caaaagccaa aggaaaaagt gattctgaag atggggagaa ggaaaatgaa   2280
aaatctaaaa cttcagattc ttcaaatgac gaatctagtt caatagaaga cagttcttcc   2340
gattctgaat cagagtcaga acctgaaagt gaatctgaat ccagaagagt cactaaggag   2400
aaagaaaaga aaacaaagca agatagaact cctcttacca aagatgtttc acttctagat   2460
ctggatgatt ttaacccagt atccactcca gttgcacttc ccacaccagc tctttctcca   2520
agtttgatgg ctgatcttga aggtttacac ttgtcaactt cctcttcagt catcagtgtc   2580
agtactcctg catttgtacc aacgaaaact cacgtgctgc ttcatcgaat gagtggaaaa   2640
ggactagctg cccattattt ctttccaaga cagccttgca tttttggtga taagatggtc   2700
tctatacaaa taacactgaa taacactact gatcgaaaga tagaaaatat ccacataggg   2760
gaaaaaaaac ttcctatagg catgaaaatg catgttttta atccaataga ctctcttgag   2820
cctgagggat ccattacagt ttcaatgggt attgactttt gtgattctac tcagactgcc   2880
agtttccagt tgtgtaccaa ggatgattgc ttcaatgtta atattcagcc acctgttgga   2940
```

```
gaactgcttt tacctgtggc catgtcagag aaagatttta agaaagagca aggagtgcta   3000

acaggaatga atgaaacttc tgctgtaatc attgctgcac cacagaattt cactccctct   3060

gtgatctttc agaaggttgt aaatgtagcc aatgtaggtg cagtcccttc tggccaggat   3120

aatatacaca ggtttgcagc taaaactgtg cacagtgggt cattgatgct agtcacagtg   3180

gaactgaagg aaggctctac agcccagctt atcataaaca ctgagaaaac tgtgattggc   3240

tctgttctgc tgcgggaact gaagcctgtc ctgtctcagg ggtaa                     3285
```

<210> SEQ ID NO 123
<211> LENGTH: 1094
<212> TYPE: PRT
<213> ORGANISM: Homo sapiens

<400> SEQUENCE: 123

```
Met Ser Ser Asn Ser Phe Pro Tyr Asn Glu Gln Ser Gly Gly Gly Glu
1               5                   10                  15

Ala Thr Glu Leu Gly Gln Glu Ala Thr Ser Thr Ile Ser Pro Ser Gly
            20                  25                  30

Ala Phe Gly Leu Phe Ser Ser Asp Leu Lys Lys Asn Glu Asp Leu Lys
        35                  40                  45

Gln Met Leu Glu Ser Asn Lys Asp Ser Ala Lys Leu Asp Ala Met Lys
    50                  55                  60

Arg Ile Val Gly Met Ile Ala Lys Gly Lys Asn Ala Ser Glu Leu Phe
65                  70                  75                  80

Pro Ala Val Val Lys Asn Val Ala Ser Lys Asn Ile Glu Ile Lys Lys
                85                  90                  95

Leu Val Tyr Val Tyr Leu Val Arg Tyr Ala Glu Glu Gln Gln Asp Leu
            100                 105                 110

Ala Leu Leu Ser Ile Ser Thr Phe Gln Arg Ala Leu Lys Asp Pro Asn
        115                 120                 125

Gln Leu Ile Arg Ala Ser Ala Leu Arg Val Leu Ser Ser Ile Arg Val
    130                 135                 140

Pro Ile Ile Val Pro Ile Met Met Leu Ala Ile Lys Glu Ala Ser Ala
145                 150                 155                 160

Asp Leu Ser Pro Tyr Val Arg Lys Asn Ala Ala His Ala Ile Gln Lys
                165                 170                 175

Leu Tyr Ser Leu Asp Pro Glu Gln Lys Glu Met Leu Ile Glu Val Ile
            180                 185                 190

Glu Lys Leu Leu Lys Asp Lys Ser Thr Leu Val Ala Gly Ser Val Val
        195                 200                 205

Met Ala Phe Glu Glu Val Cys Pro Asp Arg Ile Asp Leu Ile His Lys
    210                 215                 220

Asn Tyr Arg Lys Leu Cys Asn Leu Leu Val Asp Val Glu Glu Trp Gly
225                 230                 235                 240

Gln Val Val Ile Ile His Met Leu Thr Arg Tyr Ala Arg Thr Gln Phe
                245                 250                 255

Val Ser Pro Trp Lys Glu Gly Asp Glu Leu Glu Asp Asn Gly Lys Asn
            260                 265                 270

Phe Tyr Glu Ser Asp Asp Asp Gln Lys Glu Lys Thr Asp Lys Lys Lys
        275                 280                 285

Lys Pro Tyr Thr Met Asp Pro Asp His Arg Leu Leu Ile Arg Asn Thr
    290                 295                 300

Lys Pro Leu Leu Gln Ser Arg Asn Ala Ala Val Val Met Ala Val Ala
```

```
305                 310                 315                 320

Gln Leu Tyr Trp His Ile Ser Pro Lys Ser Glu Ala Gly Ile Ile Ser
                325                 330                 335

Lys Ser Leu Val Arg Leu Leu Arg Ser Asn Arg Glu Val Gln Tyr Ile
            340                 345                 350

Val Leu Gln Asn Ile Ala Thr Met Ser Ile Gln Arg Lys Gly Met Phe
        355                 360                 365

Glu Pro Tyr Leu Lys Ser Phe Tyr Val Arg Ser Thr Asp Pro Thr Met
    370                 375                 380

Ile Lys Thr Leu Lys Leu Glu Ile Leu Thr Asn Leu Ala Asn Glu Ala
385                 390                 395                 400

Asn Ile Ser Thr Leu Leu Arg Glu Phe Gln Thr Tyr Val Lys Ser Gln
                405                 410                 415

Asp Lys Gln Phe Ala Ala Ala Thr Ile Gln Thr Ile Gly Arg Cys Ala
            420                 425                 430

Thr Asn Ile Leu Glu Val Thr Asp Thr Cys Leu Asn Gly Leu Val Cys
        435                 440                 445

Leu Leu Ser Asn Arg Asp Glu Ile Val Val Ala Glu Ser Val Val Val
    450                 455                 460

Ile Lys Lys Leu Leu Gln Met Gln Pro Ala Gln His Gly Glu Ile Ile
465                 470                 475                 480

Lys His Met Ala Lys Leu Leu Asp Ser Ile Thr Val Pro Val Ala Arg
                485                 490                 495

Ala Ser Ile Leu Trp Leu Ile Gly Glu Asn Cys Glu Arg Val Pro Lys
            500                 505                 510

Ile Ala Pro Asp Val Leu Arg Lys Met Ala Lys Ser Phe Thr Ser Glu
        515                 520                 525

Asp Asp Leu Val Lys Leu Gln Ile Leu Asn Leu Gly Ala Lys Leu Tyr
    530                 535                 540

Leu Thr Asn Ser Lys Gln Thr Lys Leu Leu Thr Gln Tyr Ile Leu Asn
545                 550                 555                 560

Leu Gly Lys Tyr Asp Gln Asn Tyr Asp Ile Arg Asp Arg Thr Arg Phe
                565                 570                 575

Ile Arg Gln Leu Ile Val Pro Asn Val Lys Ser Gly Ala Leu Ser Lys
            580                 585                 590

Tyr Ala Lys Lys Ile Phe Leu Ala Gln Lys Pro Ala Pro Leu Leu Glu
        595                 600                 605

Ser Pro Phe Lys Asp Arg Asp His Phe Gln Leu Gly Thr Leu Ser His
    610                 615                 620

Thr Leu Asn Ile Lys Ala Thr Gly Tyr Leu Glu Leu Ser Asn Trp Pro
625                 630                 635                 640

Glu Val Ala Pro Asp Pro Ser Val Arg Asn Val Glu Val Ile Glu Leu
                645                 650                 655

Ala Lys Glu Trp Thr Pro Ala Gly Lys Ala Lys Gln Glu Asn Ser Ala
            660                 665                 670

Lys Lys Phe Tyr Ser Glu Ser Glu Glu Glu Asp Ser Ser Asp Ser
        675                 680                 685

Ser Ser Asp Ser Glu Ser Glu Ser Gly Ser Glu Ser Gly Glu Gln Gly
    690                 695                 700

Glu Ser Gly Glu Glu Gly Asp Ser Asn Glu Asp Ser Ser Glu Asp Ser
705                 710                 715                 720

Ser Ser Glu Gln Asp Ser Glu Ser Gly Arg Glu Ser Gly Leu Glu Asn
                725                 730                 735
```

```
Lys Arg Thr Ala Lys Arg Asn Ser Lys Ala Lys Gly Lys Ser Asp Ser
            740                 745                 750

Glu Asp Gly Glu Lys Glu Asn Glu Lys Ser Lys Thr Ser Asp Ser Ser
        755                 760                 765

Asn Asp Glu Ser Ser Ser Ile Glu Asp Ser Ser Ser Asp Ser Glu Ser
    770                 775                 780

Glu Ser Glu Pro Glu Ser Glu Ser Glu Ser Arg Arg Val Thr Lys Glu
785                 790                 795                 800

Lys Glu Lys Lys Thr Lys Gln Asp Arg Thr Pro Leu Thr Lys Asp Val
                805                 810                 815

Ser Leu Leu Asp Leu Asp Asp Phe Asn Pro Val Ser Thr Pro Val Ala
            820                 825                 830

Leu Pro Thr Pro Ala Leu Ser Pro Ser Leu Met Ala Asp Leu Glu Gly
        835                 840                 845

Leu His Leu Ser Thr Ser Ser Ser Val Ile Ser Val Ser Thr Pro Ala
    850                 855                 860

Phe Val Pro Thr Lys Thr His Val Leu Leu His Arg Met Ser Gly Lys
865                 870                 875                 880

Gly Leu Ala Ala His Tyr Phe Phe Pro Arg Gln Pro Cys Ile Phe Gly
                885                 890                 895

Asp Lys Met Val Ser Ile Gln Ile Thr Leu Asn Asn Thr Thr Asp Arg
            900                 905                 910

Lys Ile Glu Asn Ile His Ile Gly Glu Lys Lys Leu Pro Ile Gly Met
        915                 920                 925

Lys Met His Val Phe Asn Pro Ile Asp Ser Leu Glu Pro Glu Gly Ser
    930                 935                 940

Ile Thr Val Ser Met Gly Ile Asp Phe Cys Asp Ser Thr Gln Thr Ala
945                 950                 955                 960

Ser Phe Gln Leu Cys Thr Lys Asp Asp Cys Phe Asn Val Asn Ile Gln
                965                 970                 975

Pro Pro Val Gly Glu Leu Leu Leu Pro Val Ala Met Ser Glu Lys Asp
            980                 985                 990

Phe Lys Lys Glu Gln Gly Val Leu  Thr Gly Met Asn Glu  Thr Ser Ala
        995                 1000                1005

Val Ile  Ile Ala Ala Pro Gln  Asn Phe Thr Pro Ser  Val Ile Phe
    1010                 1015                 1020

Gln Lys  Val Val Asn Val Ala  Asn Val Gly Ala Val  Pro Ser Gly
    1025                 1030                 1035

Gln Asp  Asn Ile His Arg Phe  Ala Ala Lys Thr Val  His Ser Gly
    1040                 1045                 1050

Ser Leu  Met Leu Val Thr Val  Glu Leu Lys Glu Gly  Ser Thr Ala
    1055                 1060                 1065

Gln Leu  Ile Ile Asn Thr Glu  Lys Thr Val Ile Gly  Ser Val Leu
    1070                 1075                 1080

Leu Arg  Glu Leu Lys Pro Val  Leu Ser Gln Gly
    1085                 1090


<210> SEQ ID NO 124
<211> LENGTH: 1515
<212> TYPE: DNA
<213> ORGANISM: Homo sapiens

<400> SEQUENCE: 124

atgtttcccc gcgagaagac gtggaacatc tcgttcgcgg gctgcggctt cctcggcgtc      60
```

```
tactacgtcg gcgtggcctc ctgcctccgc gagcacgcgc ccttcctggt ggccaacgcc    120

acgcacatct acggcgcctc ggccggggcg ctcacggcca cggcgctggt caccggggtc    180

tgcctgggtg aggctggtgc caagttcatt gaggtatcta aagaggcccg gaagcggttc    240

ctgggccccc tgcacccctc cttcaacctg gtaaagatca tccgcagttt cctgctgaag    300

gtcctgcctg ctgatagcca tgagcatgcc agtgggcgcc tgggcatctc cctgacccgc    360

gtgtcagacg gcgagaatgt cattatatcc cacttcaact ccaaggacga gctcatccag    420

gccaatgtct gcagcggttt catccccgtg tactgtgggc tcatccctcc ctccctccag    480

ggggtgcgct acgtggatgg tggcatttca gacaacctgc cactctatga gcttaagaac    540

accatcacag tgtccccctt ctcgggcgag agtgacatct gtccgcagga cagctccacc    600

aacatccacg agctgcgggt caccaacacc agcatccagt tcaacctgcg caacctctac    660

cgcctctcca aggccctctt cccgccggag cccctggtgc tgcgagagat gtgcaagcag    720

ggataccggg atggcctgcg ctttctgcag cggaacggcc tcctgaaccg gcccaacccc    780

ttgctggcgt tgccccccgc ccgcccccac ggcccagagg acaaggacca ggcagtggag    840

agcgcccaag cggaggatta ctcgcagctg cccggagaag atcacatcct ggagcacctg    900

cccgcccggc tcaatgaggc cctgctggag gcctgcgtgg agcccacgga cctgctgacc    960

accctctcca acatgctgcc tgtgcgtctg gccacggcca tgatggtgcc ctacacgctg   1020

ccgctggaga gcgctctgtc cttcaccatc cgcttgctgg agtggctgcc cgacgttccc   1080

gaggacatcc ggtggatgaa ggagcagacg ggcagcatct gccagtacct ggtgatgcgc   1140

gccaagagga agctgggcag gcacctgccc tccaggctgc cggagcaggt ggagctgcgc   1200

cgcgtccagt cgctgccgtc cgtgccgctg tcctgcgccg cctacagaga ggcactgccc   1260

ggctggatgc gcaacaacct ctcgctgggg gacgcgctgg ccaagtggga ggagtgccag   1320

cgccagctgc tgctcggcct cttctgcacc aacgtggcct tcccgcccga agctctgcgc   1380

atgcgcgcac ccgccgaccc ggctcccgcc cccgcggacc cagcatcccc gcagcaccag   1440

ctggccgggc ctgccccctt gctgagcacc cctgctcccg aggcccggcc cgtgatcggg   1500

gccctggggc tgtga                                                    1515
```

```
<210> SEQ ID NO 125
<211> LENGTH: 504
<212> TYPE: PRT
<213> ORGANISM: Homo sapiens

<400> SEQUENCE: 125

Met Phe Pro Arg Glu Lys Thr Trp Asn Ile Ser Phe Ala Gly Cys Gly
1               5                   10                  15

Phe Leu Gly Val Tyr Tyr Val Gly Val Ala Ser Cys Leu Arg Glu His
            20                  25                  30

Ala Pro Phe Leu Val Ala Asn Ala Thr His Ile Tyr Gly Ala Ser Ala
        35                  40                  45

Gly Ala Leu Thr Ala Thr Ala Leu Val Thr Gly Val Cys Leu Gly Glu
    50                  55                  60

Ala Gly Ala Lys Phe Ile Glu Val Ser Lys Glu Ala Arg Lys Arg Phe
65                  70                  75                  80

Leu Gly Pro Leu His Pro Ser Phe Asn Leu Val Lys Ile Ile Arg Ser
                85                  90                  95

Phe Leu Leu Lys Val Leu Pro Ala Asp Ser His Glu His Ala Ser Gly
            100                 105                 110
```

```
Arg Leu Gly Ile Ser Leu Thr Arg Val Ser Asp Gly Glu Asn Val Ile
        115                 120                 125

Ile Ser His Phe Asn Ser Lys Asp Glu Leu Ile Gln Ala Asn Val Cys
    130                 135                 140

Ser Gly Phe Ile Pro Val Tyr Cys Gly Leu Ile Pro Pro Ser Leu Gln
145                 150                 155                 160

Gly Val Arg Tyr Val Asp Gly Gly Ile Ser Asp Asn Leu Pro Leu Tyr
                165                 170                 175

Glu Leu Lys Asn Thr Ile Thr Val Ser Pro Phe Ser Gly Glu Ser Asp
            180                 185                 190

Ile Cys Pro Gln Asp Ser Ser Thr Asn Ile His Glu Leu Arg Val Thr
        195                 200                 205

Asn Thr Ser Ile Gln Phe Asn Leu Arg Asn Leu Tyr Arg Leu Ser Lys
    210                 215                 220

Ala Leu Phe Pro Pro Glu Pro Leu Val Leu Arg Glu Met Cys Lys Gln
225                 230                 235                 240

Gly Tyr Arg Asp Gly Leu Arg Phe Leu Gln Arg Asn Gly Leu Leu Asn
                245                 250                 255

Arg Pro Asn Pro Leu Leu Ala Leu Pro Pro Ala Arg Pro His Gly Pro
            260                 265                 270

Glu Asp Lys Asp Gln Ala Val Glu Ser Ala Gln Ala Glu Asp Tyr Ser
        275                 280                 285

Gln Leu Pro Gly Glu Asp His Ile Leu Glu His Leu Pro Ala Arg Leu
    290                 295                 300

Asn Glu Ala Leu Leu Glu Ala Cys Val Glu Pro Thr Asp Leu Leu Thr
305                 310                 315                 320

Thr Leu Ser Asn Met Leu Pro Val Arg Leu Ala Thr Ala Met Met Val
                325                 330                 335

Pro Tyr Thr Leu Pro Leu Glu Ser Ala Leu Ser Phe Thr Ile Arg Leu
            340                 345                 350

Leu Glu Trp Leu Pro Asp Val Pro Glu Asp Ile Arg Trp Met Lys Glu
        355                 360                 365

Gln Thr Gly Ser Ile Cys Gln Tyr Leu Val Met Arg Ala Lys Arg Lys
    370                 375                 380

Leu Gly Arg His Leu Pro Ser Arg Leu Pro Glu Gln Val Glu Leu Arg
385                 390                 395                 400

Arg Val Gln Ser Leu Pro Ser Val Pro Leu Ser Cys Ala Ala Tyr Arg
                405                 410                 415

Glu Ala Leu Pro Gly Trp Met Arg Asn Asn Leu Ser Leu Gly Asp Ala
            420                 425                 430

Leu Ala Lys Trp Glu Glu Cys Gln Arg Gln Leu Leu Leu Gly Leu Phe
        435                 440                 445

Cys Thr Asn Val Ala Phe Pro Pro Glu Ala Leu Arg Met Arg Ala Pro
    450                 455                 460

Ala Asp Pro Ala Pro Ala Pro Ala Asp Pro Ala Ser Pro Gln His Gln
465                 470                 475                 480

Leu Ala Gly Pro Ala Pro Leu Leu Ser Thr Pro Ala Pro Glu Ala Arg
                485                 490                 495

Pro Val Ile Gly Ala Leu Gly Leu
            500
```

<210> SEQ ID NO 126
<211> LENGTH: 83

<212> TYPE: PRT
<213> ORGANISM: Homo sapiens

<400> SEQUENCE: 126

Ser Leu Pro Cys Asp Ile Cys Lys Asp Val Val Thr Ala Ala Gly Asp
1               5                   10                  15

Met Leu Lys Asp Asn Ala Thr Glu Glu Glu Ile Leu Val Tyr Leu Glu
            20                  25                  30

Lys Thr Cys Asp Trp Leu Pro Lys Pro Asn Met Ser Ala Ser Cys Lys
        35                  40                  45

Glu Ile Val Asp Ser Tyr Leu Pro Val Ile Leu Asp Ile Ile Lys Gly
    50                  55                  60

Glu Met Ser Arg Pro Gly Glu Val Cys Ser Ala Leu Asn Leu Cys Glu
65                  70                  75                  80

Ser Leu Gln

<210> SEQ ID NO 127
<211> LENGTH: 1509
<212> TYPE: DNA
<213> ORGANISM: Homo sapiens

<400> SEQUENCE: 127
atgagctgcc ccgtgcccgc ctgctgcgcg ctgctgctag tcctggggct ctgccgggcg 60
cgtccccgga acgcactgct gctcctcgcg gatgacggag gctttgagag tggcgcgtac 120
aacaacagcg ccatcgccac cccgcacctg gacgccttgg cccgccgcag cctcctcttt 180
cgcaatgcct tcacctcggt cagcagctgc tctcccagcc gcgccagcct cctcactggc 240
ctgccccagc atcagaatgg gatgtacggg ctgcaccagg acgtgcacca cttcaactcc 300
ttcgacaagg tgcggagcct gccgctgctg ctcagccaag ctggtgtgcg cacaggcatc 360
atcgggaaga agcacgtggg gccggagacc gtgtacccgt ttgactttgc gtacacggag 420
gagaatggct ccgtcctcca ggtggggcgg aacatcacta gaattaagct gctcgtccgg 480
aaattcctgc agactcagga tgaccggcct ttcttcctct acgtcgcctt ccacgacccc 540
caccgctgtg ggcactccca gccccagtac ggaaccttct gtgagaagtt tggcaacgga 600
gagagcggca tgggtcgtat cccagactgg accccccagg cctacgaccc actggacgtg 660
ctggtgcctt acttcgtccc caacaccccg gcagcccgag ccgacctggc cgctcagtac 720
accaccgtcg gccgcatgga ccaaggagtt ggactggtgc tccaggagct gcgtgacgcc 780
ggtgtcctga acgacacact ggtgatcttc acgtccgaca acgggatccc cttccccagc 840
ggcaggacca acctgtactg gccgggcact gctgaaccct tactggtgtc atccccggag 900
cacccaaaac gctggggcca agtcagcgag gcctacgtga gcctcctaga cctcacgccc 960
accatcttgg attggttctc gatcccgtac cccagctacg ccatctttgg ctcgaagacc 1020
atccacctca ctggccggtc cctcctgccg gcgctggagg ccgagcccct ctgggccacc 1080
gtctttggca gccagagcca ccacgaggtc accatgtcct accccatgcg ctccgtgcag 1140
caccggcact tccgcctcgt gcacaacctc aacttcaaga tgccctttcc catcgaccag 1200
gacttctacg tctcacccac cttccaggac ctcctgaacc gcaccacagc tggtcagccc 1260
acgggctggt acaaggacct ccgtcattac tactaccggg cgcgctggga gctctacgac 1320
cggagccggg acccccacga gacccagaac ctggccaccg acccgcgctt tgctcagctt 1380
ctggagatgc ttcgggacca gctggccaag tggcagtggg agacccacga ccccctgggtg 1440 tgcgcccccg acggcgtcct ggaggagaag ctctctcccc agtgccagcc cctccacaat 1500
gagctgtga 1509

<210> SEQ ID NO 128
<211> LENGTH: 502
<212> TYPE: PRT
<213> ORGANISM: Homo sapiens

<400> SEQUENCE: 128

Met Ser Cys Pro Val Pro Ala Cys Cys Ala Leu Leu Leu Val Leu Gly
1 5 10 15

Leu Cys Arg Ala Arg Pro Arg Asn Ala Leu Leu Leu Leu Ala Asp Asp
20 25 30

Gly Gly Phe Glu Ser Gly Ala Tyr Asn Asn Ser Ala Ile Ala Thr Pro
35 40 45

His Leu Asp Ala Leu Ala Arg Arg Ser Leu Leu Phe Arg Asn Ala Phe
50 55 60

Thr Ser Val Ser Ser Cys Ser Pro Ser Arg Ala Ser Leu Leu Thr Gly
65 70 75 80

Leu Pro Gln His Gln Asn Gly Met Tyr Gly Leu His Gln Asp Val His
85 90 95

His Phe Asn Ser Phe Asp Lys Val Arg Ser Leu Pro Leu Leu Leu Ser
100 105 110

Gln Ala Gly Val Arg Thr Gly Ile Ile Gly Lys Lys His Val Gly Pro
115 120 125

Glu Thr Val Tyr Pro Phe Asp Phe Ala Tyr Thr Glu Glu Asn Gly Ser
130 135 140

Val Leu Gln Val Gly Arg Asn Ile Thr Arg Ile Lys Leu Leu Val Arg
145 150 155 160

Lys Phe Leu Gln Thr Gln Asp Asp Arg Pro Phe Phe Leu Tyr Val Ala
165 170 175

Phe His Asp Pro His Arg Cys Gly His Ser Gln Pro Gln Tyr Gly Thr
180 185 190

Phe Cys Glu Lys Phe Gly Asn Gly Glu Ser Gly Met Gly Arg Ile Pro
195 200 205

Asp Trp Thr Pro Gln Ala Tyr Asp Pro Leu Asp Val Leu Val Pro Tyr
210 215 220

Phe Val Pro Asn Thr Pro Ala Ala Arg Ala Asp Leu Ala Ala Gln Tyr
225 230 235 240

Thr Thr Val Gly Arg Met Asp Gln Gly Val Gly Leu Val Leu Gln Glu
245 250 255

Leu Arg Asp Ala Gly Val Leu Asn Asp Thr Leu Val Ile Phe Thr Ser
260 265 270

Asp Asn Gly Ile Pro Phe Pro Ser Gly Arg Thr Asn Leu Tyr Trp Pro
275 280 285

Gly Thr Ala Glu Pro Leu Leu Val Ser Ser Pro Glu His Pro Lys Arg
290 295 300

Trp Gly Gln Val Ser Glu Ala Tyr Val Ser Leu Leu Asp Leu Thr Pro
305 310 315 320

Thr Ile Leu Asp Trp Phe Ser Ile Pro Tyr Pro Ser Tyr Ala Ile Phe
325 330 335

Gly Ser Lys Thr Ile His Leu Thr Gly Arg Ser Leu Leu Pro Ala Leu
340 345 350

Glu Ala Glu Pro Leu Trp Ala Thr Val Phe Gly Ser Gln Ser His His
355 360 365

```
Glu Val Thr Met Ser Tyr Pro Met Arg Ser Val Gln His Arg His Phe
    370                 375                 380

Arg Leu Val His Asn Leu Asn Phe Lys Met Pro Phe Pro Ile Asp Gln
385                 390                 395                 400

Asp Phe Tyr Val Ser Pro Thr Phe Gln Asp Leu Leu Asn Arg Thr Thr
                405                 410                 415

Ala Gly Gln Pro Thr Gly Trp Tyr Lys Asp Leu Arg His Tyr Tyr Tyr
            420                 425                 430

Arg Ala Arg Trp Glu Leu Tyr Asp Arg Ser Arg Asp Pro His Glu Thr
        435                 440                 445

Gln Asn Leu Ala Thr Asp Pro Arg Phe Ala Gln Leu Leu Glu Met Leu
    450                 455                 460

Arg Asp Gln Leu Ala Lys Trp Gln Trp Glu Thr His Asp Pro Trp Val
465                 470                 475                 480

Cys Ala Pro Asp Gly Val Leu Glu Glu Lys Leu Ser Pro Gln Cys Gln
                485                 490                 495

Pro Leu His Asn Glu Leu
            500
```

<210> SEQ ID NO 129
<211> LENGTH: 1569
<212> TYPE: DNA
<213> ORGANISM: Homo sapiens

<400> SEQUENCE: 129

```
atggcggcgg ttgtcgcggc gacgaggtgg tggcagctgt tgctggtgct cagcgccgcg     60

gggatggggg cctcgggcgc cccgcagccc cccaacatcc tgctcctgct catggacgac    120

atgggatggg gtgacctcgg ggtgtatgga gagccctcca gagagacccc gaatttggac    180

cggatggctg cagaagggct gcttttccca aacttctatt ctgccaaccc tctgtgctcg    240

ccatcgaggg cggcactgct cacaggacgg ctacccatcc gcaatggctt ctacaccacc    300

aacgcccatg ccagaaacgc ctacacaccg caggagattg tgggcggcat cccagactcg    360

gagcagctcc tgccggagct tctgaagaag gccggctacg tcagcaagat tgtcggcaag    420

tggcatctgg gtcacaggcc ccagttccac cccctgaagc acggatttga tgagtggttt    480

ggatccccca actgccactt tggaccttat gacaacaagg ccaggcccaa catccctgtg    540

tacagggact gggagatggt tggcagatat tatgaagaat ttcctattaa tctgaagacg    600

ggggaagcca acctcaccca gatctacctg caggaagccc tggacttcat taagagacag    660

gcacggcacc accccttttt cctctactgg gctgtcgacg ccacgcacgc acccgtctat    720

gcctccaaac ccttcttggg caccagtcag cgagggcggt atggagacgc cgtccgggag    780

attgatgaca gcattgggaa gatactggag ctcctccaag acctgcacgt cgcggacaac    840

accttcgtct tcttcacgtc ggacaacggc gctgccctca tttccgcccc cgaacaaggt    900

ggcagcaacg gcccctttct gtgtgggaag cagaccacgt ttgaaggagg gatgagggag    960

cctgccctcg catggtggcc agggcacgtc actgcaggcc aggtgagcca ccagctgggc   1020

agcatcatgg acctcttcac caccagcctg gcccttgcgg gcctgacgcc gcccagcgac   1080

agggccattg atggcctcaa cctcctcccc accctcctgc agggccggct gatggacagg   1140

cctatcttct attaccgtgg cgacacgctg atggcggcca ccctcgggca gcacaaggct   1200

cacttctgga cctggaccaa ctcctgggag aacttcagac agggcattga tttctgccct   1260

gggcagaacg tttcaggggt cacaactcac aatctggaag accacacgaa gctgcccctg   1320
```

```
atcttccacc tgggacggga cccaggggag aggttccccc tcagctttgc cagcgccgag   1380

taccaggagg ccctcagcag gatcacctcg gtcgtccagc agcaccagga ggccttggtc   1440

cccgcgcagc cccagctcaa cgtgtgcaac tgggcggtca tgaactgggc acctccgggc   1500

tgtgaaaagt tagggaagtg tctgacacct ccagaatcca ttcccaagaa gtgcctctgg   1560

tcccactag                                                           1569
```

```
<210> SEQ ID NO 130
<211> LENGTH: 522
<212> TYPE: PRT
<213> ORGANISM: Homo sapiens

<400> SEQUENCE: 130

Met Ala Ala Val Val Ala Ala Thr Arg Trp Trp Gln Leu Leu Leu Val
1               5                   10                  15

Leu Ser Ala Ala Gly Met Gly Ala Ser Gly Ala Pro Gln Pro Pro Asn
            20                  25                  30

Ile Leu Leu Leu Leu Met Asp Asp Met Gly Trp Gly Asp Leu Gly Val
        35                  40                  45

Tyr Gly Glu Pro Ser Arg Glu Thr Pro Asn Leu Asp Arg Met Ala Ala
    50                  55                  60

Glu Gly Leu Leu Phe Pro Asn Phe Tyr Ser Ala Asn Pro Leu Cys Ser
65                  70                  75                  80

Pro Ser Arg Ala Ala Leu Leu Thr Gly Arg Leu Pro Ile Arg Asn Gly
                85                  90                  95

Phe Tyr Thr Thr Asn Ala His Ala Arg Asn Ala Tyr Thr Pro Gln Glu
            100                 105                 110

Ile Val Gly Gly Ile Pro Asp Ser Glu Gln Leu Leu Pro Glu Leu Leu
        115                 120                 125

Lys Lys Ala Gly Tyr Val Ser Lys Ile Val Gly Lys Trp His Leu Gly
    130                 135                 140

His Arg Pro Gln Phe His Pro Leu Lys His Gly Phe Asp Glu Trp Phe
145                 150                 155                 160

Gly Ser Pro Asn Cys His Phe Gly Pro Tyr Asp Asn Lys Ala Arg Pro
                165                 170                 175

Asn Ile Pro Val Tyr Arg Asp Trp Glu Met Val Gly Arg Tyr Tyr Glu
            180                 185                 190

Glu Phe Pro Ile Asn Leu Lys Thr Gly Glu Ala Asn Leu Thr Gln Ile
        195                 200                 205

Tyr Leu Gln Glu Ala Leu Asp Phe Ile Lys Arg Gln Ala Arg His His
    210                 215                 220

Pro Phe Phe Leu Tyr Trp Ala Val Asp Ala Thr His Ala Pro Val Tyr
225                 230                 235                 240

Ala Ser Lys Pro Phe Leu Gly Thr Ser Gln Arg Gly Arg Tyr Gly Asp
                245                 250                 255

Ala Val Arg Glu Ile Asp Asp Ser Ile Gly Lys Ile Leu Glu Leu Leu
            260                 265                 270

Gln Asp Leu His Val Ala Asp Asn Thr Phe Val Phe Phe Thr Ser Asp
        275                 280                 285

Asn Gly Ala Ala Leu Ile Ser Ala Pro Glu Gln Gly Gly Ser Asn Gly
    290                 295                 300

Pro Phe Leu Cys Gly Lys Gln Thr Thr Phe Glu Gly Gly Met Arg Glu
305                 310                 315                 320
```

Pro Ala Leu Ala Trp Trp Pro Gly His Val Thr Ala Gly Gln Val Ser
325 330 335

His Gln Leu Gly Ser Ile Met Asp Leu Phe Thr Thr Ser Leu Ala Leu
340 345 350

Ala Gly Leu Thr Pro Pro Ser Asp Arg Ala Ile Asp Gly Leu Asn Leu
355 360 365

Leu Pro Thr Leu Leu Gln Gly Arg Leu Met Asp Arg Pro Ile Phe Tyr
370 375 380

Tyr Arg Gly Asp Thr Leu Met Ala Ala Thr Leu Gly Gln His Lys Ala
385 390 395 400

His Phe Trp Thr Trp Thr Asn Ser Trp Glu Asn Phe Arg Gln Gly Ile
405 410 415

Asp Phe Cys Pro Gly Gln Asn Val Ser Gly Val Thr Thr His Asn Leu
420 425 430

Glu Asp His Thr Lys Leu Pro Leu Ile Phe His Leu Gly Arg Asp Pro
435 440 445

Gly Glu Arg Phe Pro Leu Ser Phe Ala Ser Ala Glu Tyr Gln Glu Ala
450 455 460

Leu Ser Arg Ile Thr Ser Val Val Gln Gln His Gln Glu Ala Leu Val
465 470 475 480

Pro Ala Gln Pro Gln Leu Asn Val Cys Asn Trp Ala Val Met Asn Trp
485 490 495

Ala Pro Pro Gly Cys Glu Lys Leu Gly Lys Cys Leu Thr Pro Pro Glu
500 505 510

Ser Ile Pro Lys Lys Cys Leu Trp Ser His
515 520

<210> SEQ ID NO 131
<211> LENGTH: 1602
<212> TYPE: DNA
<213> ORGANISM: Homo sapiens

<400> SEQUENCE: 131
atgggtccgc gcggcgcggc gagcttgccc cgaggccccg gacctcggcg gctgctcctc 60
cccgtcgtcc tcccgctgct gctgctgctg ttgttggcgc cgccgggctc gggcgccggg 120
gccagccggc cgccccacct ggtcttcttg ctggcagacg acctaggctg gaacgacgtc 180
ggcttccacg gctcccgcat ccgcacgccg cacctggacg cgctggcggc cggcggggtg 240
ctcctggaca actactacac gcagccgctg tgcacgccgt cgcggagcca gctgctcact 300
ggccgctacc agatccgtac aggtttacag caccaaataa tctggccctg tcagcccagc 360
tgtgttcctc tggatgaaaa actcctgccc cagctcctaa aagaagcagg ttatactacc 420
catatggtcg gaaaatggca cctgggaatg taccggaaag aatgccttcc aacccgccga 480
ggatttgata cctactttgg atatctcctg ggtagtgaag attattattc ccatgaacgc 540
tgtacattaa ttgacgctct gaatgtcaca cgatgtgctc ttgattttcg agatggcgaa 600
gaagttgcaa caggatataa aaatatgtat tcaacaaaca tattcaccaa aagggctata 660
gccctcataa ctaaccatcc accagagaag cctctgtttc tctaccttgc tctccagtct 720
gtgcatgagc cccttcaggt ccctgaggaa tacttgaagc catatgactt tatccaagac 780
aagaacaggc atcactatgc aggaatggtg tcccttatgg atgaagcagt aggaaatgtc 840
actgcagctt taaaaagcag tgggctctgg aacaacacgg tgttcatctt ttctacagat 900
aacggagggc agactttggc agggggtaat aactggcccc ttcgaggaag aaaatggagc 960

```
ctgtgggaag gaggcgtccg aggggtgggc tttgtggcaa gccccttgct gaagcagaag   1020

ggcgtgaaga accgggagct catccacatc tctgactggc tgccaacact cgtgaagctg   1080

gccaggggac acaccaatgg cacaaagcct ctggatggct tcgacgtgtg gaaaaccatc   1140

agtgaaggaa gcccatcccc cagaattgag ctgctgcata atattgaccc gaacttcgtg   1200

gactcttcac cgtgtcccag gaacagcatg gctccagcaa aggatgactc ttctcttcca   1260

gaatattcag cctttaacac atctgtccat gctgcaatta gacatggaaa ttggaaactc   1320

ctcacgggct acccaggctg tggttactgg ttccctccac cgtctcaata caatgtttct   1380

gagataccct catcagaccc accaaccaag accctctggc tctttgatat tgatcgggac   1440

cctgaagaaa gacatgacct gtccagagaa tatcctcaca tcgtcacaaa gctcctgtcc   1500

cgcctacagt tctaccataa acactcagtc cccgtgtact tccctgcaca ggaccccccgc  1560

tgtgatccca aggccactgg ggtgtggggc ccttggatgt ag                      1602
```

<210> SEQ ID NO 132
<211> LENGTH: 533
<212> TYPE: PRT
<213> ORGANISM: Homo sapiens

<400> SEQUENCE: 132

```
Met Gly Pro Arg Gly Ala Ala Ser Leu Pro Arg Gly Pro Gly Pro Arg
1               5                   10                  15

Arg Leu Leu Leu Pro Val Val Leu Pro Leu Leu Leu Leu Leu Leu Leu
            20                  25                  30

Ala Pro Pro Gly Ser Gly Ala Gly Ala Ser Arg Pro Pro His Leu Val
        35                  40                  45

Phe Leu Leu Ala Asp Asp Leu Gly Trp Asn Asp Val Gly Phe His Gly
    50                  55                  60

Ser Arg Ile Arg Thr Pro His Leu Asp Ala Leu Ala Ala Gly Gly Val
65                  70                  75                  80

Leu Leu Asp Asn Tyr Tyr Thr Gln Pro Leu Cys Thr Pro Ser Arg Ser
                85                  90                  95

Gln Leu Leu Thr Gly Arg Tyr Gln Ile Arg Thr Gly Leu Gln His Gln
            100                 105                 110

Ile Ile Trp Pro Cys Gln Pro Ser Cys Val Pro Leu Asp Glu Lys Leu
        115                 120                 125

Leu Pro Gln Leu Leu Lys Glu Ala Gly Tyr Thr Thr His Met Val Gly
    130                 135                 140

Lys Trp His Leu Gly Met Tyr Arg Lys Glu Cys Leu Pro Thr Arg Arg
145                 150                 155                 160

Gly Phe Asp Thr Tyr Phe Gly Tyr Leu Leu Gly Ser Glu Asp Tyr Tyr
                165                 170                 175

Ser His Glu Arg Cys Thr Leu Ile Asp Ala Leu Asn Val Thr Arg Cys
            180                 185                 190

Ala Leu Asp Phe Arg Asp Gly Glu Glu Val Ala Thr Gly Tyr Lys Asn
        195                 200                 205

Met Tyr Ser Thr Asn Ile Phe Thr Lys Arg Ala Ile Ala Leu Ile Thr
    210                 215                 220

Asn His Pro Pro Glu Lys Pro Leu Phe Leu Tyr Leu Ala Leu Gln Ser
225                 230                 235                 240

Val His Glu Pro Leu Gln Val Pro Glu Glu Tyr Leu Lys Pro Tyr Asp
                245                 250                 255

Phe Ile Gln Asp Lys Asn Arg His His Tyr Ala Gly Met Val Ser Leu
```

```
            260                 265                 270

Met Asp Glu Ala Val Gly Asn Val Thr Ala Ala Leu Lys Ser Ser Gly
        275                 280                 285

Leu Trp Asn Asn Thr Val Phe Ile Phe Ser Thr Asp Asn Gly Gly Gln
    290                 295                 300

Thr Leu Ala Gly Gly Asn Asn Trp Pro Leu Arg Gly Arg Lys Trp Ser
305                 310                 315                 320

Leu Trp Glu Gly Gly Val Arg Gly Val Gly Phe Val Ala Ser Pro Leu
                325                 330                 335

Leu Lys Gln Lys Gly Val Lys Asn Arg Glu Leu Ile His Ile Ser Asp
            340                 345                 350

Trp Leu Pro Thr Leu Val Lys Leu Ala Arg Gly His Thr Asn Gly Thr
        355                 360                 365

Lys Pro Leu Asp Gly Phe Asp Val Trp Lys Thr Ile Ser Glu Gly Ser
    370                 375                 380

Pro Ser Pro Arg Ile Glu Leu Leu His Asn Ile Asp Pro Asn Phe Val
385                 390                 395                 400

Asp Ser Ser Pro Cys Pro Arg Asn Ser Met Ala Pro Ala Lys Asp Asp
                405                 410                 415

Ser Ser Leu Pro Glu Tyr Ser Ala Phe Asn Thr Ser Val His Ala Ala
            420                 425                 430

Ile Arg His Gly Asn Trp Lys Leu Leu Thr Gly Tyr Pro Gly Cys Gly
        435                 440                 445

Tyr Trp Phe Pro Pro Pro Ser Gln Tyr Asn Val Ser Glu Ile Pro Ser
    450                 455                 460

Ser Asp Pro Pro Thr Lys Thr Leu Trp Leu Phe Asp Ile Asp Arg Asp
465                 470                 475                 480

Pro Glu Glu Arg His Asp Leu Ser Arg Glu Tyr Pro His Ile Val Thr
                485                 490                 495

Lys Leu Leu Ser Arg Leu Gln Phe Tyr His Lys His Ser Val Pro Val
            500                 505                 510

Tyr Phe Pro Ala Gln Asp Pro Arg Cys Asp Pro Lys Ala Thr Gly Val
        515                 520                 525

Trp Gly Pro Trp Met
    530
```

<210> SEQ ID NO 133
<211> LENGTH: 3837
<212> TYPE: DNA
<213> ORGANISM: Homo sapiens

<400> SEQUENCE: 133

```
atgaccgctc gcggcctggc ccttggcctc ctcctgctgc tactgtgtcc agcgcaggtg     60

ttttcacagt cctgtgtttg gtatggagag tgtggaattg catatgggga caagaggtac    120

aattgcgaat attctggccc accaaaacca ttgccaaagg atggatatga cttagtgcag    180

gaactctgtc caggattctt ctttggcaat gtcagtctct gttgtgatgt tcggcagctt    240

cagacactaa aagacaacct gcagctgcct ctacagtttc tgtccagatg tccatcctgt    300

ttttataacc tactgaacct gttttgtgag ctgacatgta gccctcgaca gagtcagttt    360

ttgaatgtta cagctactga agattatgtt gatcctgtta caaaccagac gaaaacaaat    420

gtgaaagagt tacaatacta cgtcggacag agttttgcca atgcaatgta caatgcctgc    480

cgggatgtgg aggccccctc aagtaatgac aaggccctgg gactcctgtg tgggaaggac    540
```

```
gctgacgcct gtaatgccac caactggatt gaatacatgt tcaataagga caatggacag    600
gcacctttta ccatcactcc tgtgttttca gattttccag tccatgggat ggagcccatg    660
aacaatgcca ccaaaggctg tgacgagtct gtggatgagg tcacagcacc atgtagctgc    720
caagactgct ctattgtctg tggccccaag ccccagcccc cacctcctcc tgctccctgg    780
acgatccttg gcttggacgc catgtatgtc atcatgtgga tcacctacat ggcgtttttg    840
cttgtgtttt ttggagcatt ttttgcagtg tggtgctaca gaaaacggta ttttgtctcc    900
gagtacactc ccatcgatag caatatagct ttttctgtta atgcaagtga caaaggagag    960
gcgtcctgct gtgaccctgt cagcgcagca tttgagggct gcttgaggcg gctgttcaca   1020
cgctgggggt ctttctgcgt ccgaaaccct ggctgtgtca ttttcttctc gctggtcttc   1080
attactgcgt gttcgtcagg cctggtgttt gtccgggtca caaccaatcc agttgacctc   1140
tggtcagccc ccagcagcca ggctcgcctg gaaaaagagt actttgacca gcactttggg   1200
cctttcttcc ggacggagca gctcatcatc cgggcccctc tcactgacaa acacatttac   1260
cagccatacc cttcgggagc tgatgtaccc tttggacctc cgcttgacat acagatactg   1320
caccaggttc ttgacttaca aatagccatc gaaaacatta ctgcctctta tgacaatgag   1380
actgtgacac ttcaagacat ctgcttggcc cctctttcac cgtataacac gaactgcacc   1440
attttgagtg tgttaaatta cttccagaac agccattccg tgctggacca caagaaaggg   1500
gacgacttct ttgtgtatgc cgattaccac acgcactttc tgtactgcgt acgggctcct   1560
gcctctctga atgatacaag tttgctccat gacccttgtc tgggtacgtt tggtggacca   1620
gtgttcccgt ggcttgtgtt gggaggctat gatgatcaaa actacaataa cgccactgcc   1680
cttgtgatta ccttccctgt caataattac tataatgata cagagaagct ccagagggcc   1740
caggcctggg aaaaagagtt tattaatttt gtgaaaaact acaagaatcc caatctgacc   1800
atttccttca ctgctgaacg aagtattgaa gatgaactaa atcgtgaaag tgacagtgat   1860
gtcttcaccg ttgtaattag ctatgccatc atgtttctat atatttccct agccttgggg   1920
cacatgaaaa gctgtcgcag gcttctggtg gattcgaagg tctcactagg catcgcgggc   1980
atcttgatcg tgctgagctc ggtggcttgc tccttgggtg tcttcagcta cattgggttg   2040
cccttgaccc tcattgtgat tgaagtcatc ccgttcctgg tgctggctgt tggagtggac   2100
aacatcttca ttctggtgca ggcctaccag agagatgaac gtcttcaagg ggaaaccctg   2160
gatcagcagc tgggcagggt cctaggagaa gtggctccca gtatgttcct gtcatccttt   2220
tctgagactg tagcattttt cttaggagca ttgtccgtga tgccagccgt gcacaccttc   2280
tctctctttg cgggattggc agtcttcatt gactttcttc tgcagattac ctgtttcgtg   2340
agtctcttgg ggttagacat taaacgtcaa gagaaaaatc ggctagacat cttttgctgt   2400
gtcagaggtg ctgaagatgg aacaagcgtc caggcctcag agagctgttt gtttcgcttc   2460
ttcaaaaact cctattctcc acttctgcta aaggactgga tgagaccaat tgtgatagca   2520
atatttgtgg gtgttctgtc attcagcatc gcagtcctga acaaagtaga tattggattg   2580
gatcagtctc tttcgatgcc agatgactcc tacatggtgg attatttcaa atccatcagt   2640
cagtacctgc atgcgggtcc gcctgtgtac tttgtcctgg aggaagggca cgactacact   2700
tcttccaagg ggcagaacat ggtgtgcggc ggcatgggct gcaacaatga ttccctggtg   2760
cagcagatat ttaacgcggc gcagctggac aactataccc gaataggctt cgcccccctcg   2820
tcctggatcg acgattattt cgactgggtg aagccacagt cgtcttgctg tcgagtggac   2880
aatatcactg accagttctg caatgcttca gtggttgacc ctgcctgcgt tcgctgcagg   2940
```

cctctgactc cggaaggcaa acagaggcct caggggggag acttcatgag attcctgccc 3000
atgttccttt cggataaccc taaccccaag tgtggcaaag gggacatgc tgcctatagt 3060 tctgcagtta acatcctcct tggccatggc accagggtcg gagccacgta cttcatgacc 3120
taccacaccg tgctgcagac ctctgctgac tttattgacg ctctgaagaa agcccgactt 3180
atagccagta atgtcaccga aaccatgggc attaacggca gtgcctaccg agtatttcct 3240
tacagtgtgt tttatgtctt ctacgaacag tacctgacca tcattgacga cactatcttc 3300
aacctcggtg tgtccctggg cgcgatattt ctggtgacca tggtcctcct gggctgtgag 3360
ctctggtctg cagtcatcat gtgtgccacc atcgccatgg tcttggtcaa catgtttgga 3420
gttatgtggc tctggggcat cagtctgaac gctgtatcct tggtcaacct ggtgatgagc 3480
tgtggcatct ccgtggagtt ctgcagccac ataaccagag cgttcacggt gagcatgaaa 3540
ggcagccgcg tggagcgcgc ggaagaggca cttgcccaca tgggcagctc cgtgttcagt 3600
ggaatcacac ttacaaaatt tggagggatt gtggtgttgg cttttgccaa atctcaaatt 3660
ttccagatat tctacttcag gatgtatttg gccatggtct tactgggagc cactcacgga 3720
ttaatatttc tccctgtctt actcagttac atagggccat cagtaaataa agccaaaagt 3780
tgtgccactg aagagcgata caaaggaaca gagcgcgaac ggcttctaaa tttctag 3837

<210> SEQ ID NO 134
<211> LENGTH: 1278
<212> TYPE: PRT
<213> ORGANISM: Homo sapiens

<400> SEQUENCE: 134

Met Thr Ala Arg Gly Leu Ala Leu Gly Leu Leu Leu Leu Leu Leu Cys
1 5 10 15

Pro Ala Gln Val Phe Ser Gln Ser Cys Val Trp Tyr Gly Glu Cys Gly
20 25 30

Ile Ala Tyr Gly Asp Lys Arg Tyr Asn Cys Glu Tyr Ser Gly Pro Pro
35 40 45

Lys Pro Leu Pro Lys Asp Gly Tyr Asp Leu Val Gln Glu Leu Cys Pro
50 55 60

Gly Phe Phe Phe Gly Asn Val Ser Leu Cys Cys Asp Val Arg Gln Leu
65 70 75 80

Gln Thr Leu Lys Asp Asn Leu Gln Leu Pro Leu Gln Phe Leu Ser Arg
85 90 95

Cys Pro Ser Cys Phe Tyr Asn Leu Leu Asn Leu Phe Cys Glu Leu Thr
100 105 110

Cys Ser Pro Arg Gln Ser Gln Phe Leu Asn Val Thr Ala Thr Glu Asp
115 120 125

Tyr Val Asp Pro Val Thr Asn Gln Thr Lys Thr Asn Val Lys Glu Leu
130 135 140

Gln Tyr Tyr Val Gly Gln Ser Phe Ala Asn Ala Met Tyr Asn Ala Cys
145 150 155 160

Arg Asp Val Glu Ala Pro Ser Ser Asn Asp Lys Ala Leu Gly Leu Leu
165 170 175

Cys Gly Lys Asp Ala Asp Ala Cys Asn Ala Thr Asn Trp Ile Glu Tyr
180 185 190

Met Phe Asn Lys Asp Asn Gly Gln Ala Pro Phe Thr Ile Thr Pro Val
195 200 205

Phe Ser Asp Phe Pro Val His Gly Met Glu Pro Met Asn Asn Ala Thr

-continued

```
    210                 215                 220

Lys Gly Cys Asp Glu Ser Val Asp Glu Val Thr Ala Pro Cys Ser Cys
225                 230                 235                 240

Gln Asp Cys Ser Ile Val Cys Gly Pro Lys Pro Gln Pro Pro Pro Pro
                245                 250                 255

Pro Ala Pro Trp Thr Ile Leu Gly Leu Asp Ala Met Tyr Val Ile Met
            260                 265                 270

Trp Ile Thr Tyr Met Ala Phe Leu Leu Val Phe Phe Gly Ala Phe Phe
        275                 280                 285

Ala Val Trp Cys Tyr Arg Lys Arg Tyr Phe Val Ser Glu Tyr Thr Pro
    290                 295                 300

Ile Asp Ser Asn Ile Ala Phe Ser Val Asn Ala Ser Asp Lys Gly Glu
305                 310                 315                 320

Ala Ser Cys Cys Asp Pro Val Ser Ala Ala Phe Glu Gly Cys Leu Arg
                325                 330                 335

Arg Leu Phe Thr Arg Trp Gly Ser Phe Cys Val Arg Asn Pro Gly Cys
            340                 345                 350

Val Ile Phe Phe Ser Leu Val Phe Ile Thr Ala Cys Ser Ser Gly Leu
        355                 360                 365

Val Phe Val Arg Val Thr Thr Asn Pro Val Asp Leu Trp Ser Ala Pro
    370                 375                 380

Ser Ser Gln Ala Arg Leu Glu Lys Glu Tyr Phe Asp Gln His Phe Gly
385                 390                 395                 400

Pro Phe Phe Arg Thr Glu Gln Leu Ile Ile Arg Ala Pro Leu Thr Asp
                405                 410                 415

Lys His Ile Tyr Gln Pro Tyr Pro Ser Gly Ala Asp Val Pro Phe Gly
            420                 425                 430

Pro Pro Leu Asp Ile Gln Ile Leu His Gln Val Leu Asp Leu Gln Ile
        435                 440                 445

Ala Ile Glu Asn Ile Thr Ala Ser Tyr Asp Asn Glu Thr Val Thr Leu
    450                 455                 460

Gln Asp Ile Cys Leu Ala Pro Leu Ser Pro Tyr Asn Thr Asn Cys Thr
465                 470                 475                 480

Ile Leu Ser Val Leu Asn Tyr Phe Gln Asn Ser His Ser Val Leu Asp
                485                 490                 495

His Lys Lys Gly Asp Asp Phe Phe Val Tyr Ala Asp Tyr His Thr His
            500                 505                 510

Phe Leu Tyr Cys Val Arg Ala Pro Ala Ser Leu Asn Asp Thr Ser Leu
        515                 520                 525

Leu His Asp Pro Cys Leu Gly Thr Phe Gly Gly Pro Val Phe Pro Trp
    530                 535                 540

Leu Val Leu Gly Gly Tyr Asp Asp Gln Asn Tyr Asn Asn Ala Thr Ala
545                 550                 555                 560

Leu Val Ile Thr Phe Pro Val Asn Asn Tyr Tyr Asn Asp Thr Glu Lys
                565                 570                 575

Leu Gln Arg Ala Gln Ala Trp Glu Lys Glu Phe Ile Asn Phe Val Lys
            580                 585                 590

Asn Tyr Lys Asn Pro Asn Leu Thr Ile Ser Phe Thr Ala Glu Arg Ser
        595                 600                 605

Ile Glu Asp Glu Leu Asn Arg Glu Ser Asp Ser Asp Val Phe Thr Val
    610                 615                 620

Val Ile Ser Tyr Ala Ile Met Phe Leu Tyr Ile Ser Leu Ala Leu Gly
625                 630                 635                 640
```

```
His Met Lys Ser Cys Arg Arg Leu Leu Val Asp Ser Lys Val Ser Leu
                645                 650                 655

Gly Ile Ala Gly Ile Leu Ile Val Leu Ser Ser Val Ala Cys Ser Leu
            660                 665                 670

Gly Val Phe Ser Tyr Ile Gly Leu Pro Leu Thr Leu Ile Val Ile Glu
        675                 680                 685

Val Ile Pro Phe Leu Val Leu Ala Val Gly Val Asp Asn Ile Phe Ile
    690                 695                 700

Leu Val Gln Ala Tyr Gln Arg Asp Glu Arg Leu Gln Gly Glu Thr Leu
705                 710                 715                 720

Asp Gln Gln Leu Gly Arg Val Leu Gly Glu Val Ala Pro Ser Met Phe
                725                 730                 735

Leu Ser Ser Phe Ser Glu Thr Val Ala Phe Phe Leu Gly Ala Leu Ser
            740                 745                 750

Val Met Pro Ala Val His Thr Phe Ser Leu Phe Ala Gly Leu Ala Val
        755                 760                 765

Phe Ile Asp Phe Leu Leu Gln Ile Thr Cys Phe Val Ser Leu Leu Gly
    770                 775                 780

Leu Asp Ile Lys Arg Gln Glu Lys Asn Arg Leu Asp Ile Phe Cys Cys
785                 790                 795                 800

Val Arg Gly Ala Glu Asp Gly Thr Ser Val Gln Ala Ser Glu Ser Cys
                805                 810                 815

Leu Phe Arg Phe Phe Lys Asn Ser Tyr Ser Pro Leu Leu Leu Lys Asp
            820                 825                 830

Trp Met Arg Pro Ile Val Ile Ala Ile Phe Val Gly Val Leu Ser Phe
        835                 840                 845

Ser Ile Ala Val Leu Asn Lys Val Asp Ile Gly Leu Asp Gln Ser Leu
    850                 855                 860

Ser Met Pro Asp Asp Ser Tyr Met Val Asp Tyr Phe Lys Ser Ile Ser
865                 870                 875                 880

Gln Tyr Leu His Ala Gly Pro Pro Val Tyr Phe Val Leu Glu Glu Gly
                885                 890                 895

His Asp Tyr Thr Ser Ser Lys Gly Gln Asn Met Val Cys Gly Gly Met
            900                 905                 910

Gly Cys Asn Asn Asp Ser Leu Val Gln Gln Ile Phe Asn Ala Ala Gln
        915                 920                 925

Leu Asp Asn Tyr Thr Arg Ile Gly Phe Ala Pro Ser Ser Trp Ile Asp
    930                 935                 940

Asp Tyr Phe Asp Trp Val Lys Pro Gln Ser Ser Cys Cys Arg Val Asp
945                 950                 955                 960

Asn Ile Thr Asp Gln Phe Cys Asn Ala Ser Val Val Asp Pro Ala Cys
                965                 970                 975

Val Arg Cys Arg Pro Leu Thr Pro Glu Gly Lys Gln Arg Pro Gln Gly
            980                 985                 990

Gly Asp Phe Met Arg Phe Leu Pro  Met Phe Leu Ser Asp  Asn Pro Asn
        995                 1000                1005

Pro Lys  Cys Gly Lys Gly Gly  His Ala Ala Tyr Ser  Ser Ala Val
    1010                1015                1020

Asn Ile  Leu Leu Gly His Gly  Thr Arg Val Gly Ala  Thr Tyr Phe
    1025                1030                1035

Met Thr  Tyr His Thr Val Leu  Gln Thr Ser Ala Asp  Phe Ile Asp
    1040                1045                1050
```

Ala Leu Lys Lys Ala Arg Leu Ile Ala Ser Asn Val Thr Glu Thr
1055 1060 1065

Met Gly Ile Asn Gly Ser Ala Tyr Arg Val Phe Pro Tyr Ser Val
1070 1075 1080

Phe Tyr Val Phe Tyr Glu Gln Tyr Leu Thr Ile Ile Asp Asp Thr
1085 1090 1095

Ile Phe Asn Leu Gly Val Ser Leu Gly Ala Ile Phe Leu Val Thr
1100 1105 1110

Met Val Leu Leu Gly Cys Glu Leu Trp Ser Ala Val Ile Met Cys
1115 1120 1125

Ala Thr Ile Ala Met Val Leu Val Asn Met Phe Gly Val Met Trp
1130 1135 1140

Leu Trp Gly Ile Ser Leu Asn Ala Val Ser Leu Val Asn Leu Val
1145 1150 1155

Met Ser Cys Gly Ile Ser Val Glu Phe Cys Ser His Ile Thr Arg
1160 1165 1170

Ala Phe Thr Val Ser Met Lys Gly Ser Arg Val Glu Arg Ala Glu
1175 1180 1185

Glu Ala Leu Ala His Met Gly Ser Ser Val Phe Ser Gly Ile Thr
1190 1195 1200

Leu Thr Lys Phe Gly Gly Ile Val Val Leu Ala Phe Ala Lys Ser
1205 1210 1215

Gln Ile Phe Gln Ile Phe Tyr Phe Arg Met Tyr Leu Ala Met Val
1220 1225 1230

Leu Leu Gly Ala Thr His Gly Leu Ile Phe Leu Pro Val Leu Leu
1235 1240 1245

Ser Tyr Ile Gly Pro Ser Val Asn Lys Ala Lys Ser Cys Ala Thr
1250 1255 1260

Glu Glu Arg Tyr Lys Gly Thr Glu Arg Glu Arg Leu Leu Asn Phe
1265 1270 1275

<210> SEQ ID NO 135
<211> LENGTH: 1224
<212> TYPE: DNA
<213> ORGANISM: Homo sapiens

<400> SEQUENCE: 135
atgcgccgga acctgcgctt ggggccaagc tctggagctg acgcgcaggg gcaaggcgcc 60
ccgcgtcccg gactggcggc tccgcgcatg ctcctcccac cggcgtcgca ggcctcgaga 120
ggctccggaa gtactgggtg cagcctgatg gcgcaggagg tagacacggc acagggcgcc 180
gagatgcggc ggggcgcggg cgcggctcgg ggacgcgctt cctggtgctg ggccctggcg 240
ctgctttggc tcgcggtggt tccgggctgg tcccgggtct cgggcatccc ctcccggcgc 300
cactggccgg tgccctacaa gcgctttgac ttccgtccaa aacctgatcc ttattgtcaa 360
gctaagtata ctttctgtcc aactggctca cctatcccag ttatggaggg tgatgatgac 420
attgaagttt ttcgattaca agccccagta tgggaattta aatatggaga cctcctggga 480
cacttgaaaa ttatgcatga tgccattgga ttcagaagta cattaactgg caagaactac 540
acaatggaat ggtatgaact tttccaactt ggcaactgta catttcccca tctccgacct 600
gaaatggatg cccctttctg gtgtaatcaa ggcgctgcct gctttttttga gggaattgat 660 gatgttcact ggaaggaaaa tgggacatta gttcaagtag caactatatc aggaaacatg 720
ttcaaccaaa tggcaaagtg ggtgaaacag gacaatgaaa caggaattta ttatgagaca 780

```
tggaatgtaa aagccagccc agaaaagggg gcagagacat ggtttgattc ctacgactgt    840

tccaaatttg tgttaaggac ctttaacaag ttggctgaat ttggagcaga gttcaagaac    900

atagaaacca actatacaag aatatttctt tacagtggag aacctactta tctgggaaat    960

gaaacatctg tttttgggcc aacaggaaac aagactcttg gtttagccat aaaaagattt   1020

tattacccct tcaaaccaca tttgccaact aaagaatttc tgttgagtct cttgcaaatt   1080

tttgatgcag tgattgtgca caaacagttc tatttgtttt ataattttga atattggttt   1140

ttacctatga aattcccttt tattaaaata acatatgaag aaatcccttt acctatcaga   1200

aacaaaacac tctctggttt ataa                                          1224
```

<210> SEQ ID NO 136
<211> LENGTH: 358
<212> TYPE: PRT
<213> ORGANISM: Homo sapiens

<400> SEQUENCE: 136

```
Met Ala Gln Glu Val Asp Thr Ala Gln Gly Ala Glu Met Arg Arg Gly
1               5                   10                  15

Ala Gly Ala Ala Arg Gly Arg Ala Ser Trp Cys Trp Ala Leu Ala Leu
            20                  25                  30

Leu Trp Leu Ala Val Val Pro Gly Trp Ser Arg Val Ser Gly Ile Pro
        35                  40                  45

Ser Arg Arg His Trp Pro Val Pro Tyr Lys Arg Phe Asp Phe Arg Pro
    50                  55                  60

Lys Pro Asp Pro Tyr Cys Gln Ala Lys Tyr Thr Phe Cys Pro Thr Gly
65                  70                  75                  80

Ser Pro Ile Pro Val Met Glu Gly Asp Asp Ile Glu Val Phe Arg
                85                  90                  95

Leu Gln Ala Pro Val Trp Glu Phe Lys Tyr Gly Asp Leu Leu Gly His
            100                 105                 110

Leu Lys Ile Met His Asp Ala Ile Gly Phe Arg Ser Thr Leu Thr Gly
        115                 120                 125

Lys Asn Tyr Thr Met Glu Trp Tyr Glu Leu Phe Gln Leu Gly Asn Cys
    130                 135                 140

Thr Phe Pro His Leu Arg Pro Glu Met Asp Ala Pro Phe Trp Cys Asn
145                 150                 155                 160

Gln Gly Ala Ala Cys Phe Phe Glu Gly Ile Asp Asp Val His Trp Lys
                165                 170                 175

Glu Asn Gly Thr Leu Val Gln Val Ala Thr Ile Ser Gly Asn Met Phe
            180                 185                 190

Asn Gln Met Ala Lys Trp Val Lys Gln Asp Asn Glu Thr Gly Ile Tyr
        195                 200                 205

Tyr Glu Thr Trp Asn Val Lys Ala Ser Pro Glu Lys Gly Ala Glu Thr
    210                 215                 220

Trp Phe Asp Ser Tyr Asp Cys Ser Lys Phe Val Leu Arg Thr Phe Asn
225                 230                 235                 240

Lys Leu Ala Glu Phe Gly Ala Glu Phe Lys Asn Ile Glu Thr Asn Tyr
                245                 250                 255

Thr Arg Ile Phe Leu Tyr Ser Gly Glu Pro Thr Tyr Leu Gly Asn Glu
            260                 265                 270

Thr Ser Val Phe Gly Pro Thr Gly Asn Lys Thr Leu Gly Leu Ala Ile
        275                 280                 285

Lys Arg Phe Tyr Tyr Pro Phe Lys Pro His Leu Pro Thr Lys Glu Phe
```

```
    290                 295                 300

Leu Leu Ser Leu Leu Gln Ile Phe Asp Ala Val Ile Val His Lys Gln
305                 310                 315                 320

Phe Tyr Leu Phe Tyr Asn Phe Glu Tyr Trp Phe Leu Pro Met Lys Phe
                325                 330                 335

Pro Phe Ile Lys Ile Thr Tyr Glu Glu Ile Pro Leu Pro Ile Arg Asn
            340                 345                 350

Lys Thr Leu Ser Gly Leu
        355


<210> SEQ ID NO 137
<211> LENGTH: 1692
<212> TYPE: DNA
<213> ORGANISM: Homo sapiens

<400> SEQUENCE: 137

atgggactcc aagcctgcct cctagggctc tttgccctca tcctctctgg caaatgcagt     60

tacagcccgg agcccgacca gcggaggacg ctgcccccag gctgggtgtc cctgggccgt    120

gcggaccctg aggaagagct gagtctcacc tttgccctga gacagcagaa tgtggaaaga    180

ctctcggagc tggtgcaggc tgtgtcggat cccagctctc ctcaatacgg aaaatacctg    240

accctagaga atgtggctga tctggtgagg ccatccccac tgaccctcca cacggtgcaa    300

aaatggctct tggcagccgg agcccagaag tgccattctg tgatcacaca ggactttctg    360

acttgctggc tgagcatccg acaagcagag ctgctgctcc ctggggctga gtttcatcac    420

tatgtgggag gacctacgga aacccatgtt gtaaggtccc cacatcccta ccagcttcca    480

caggccttgg ccccccatgt ggactttgtg gggggactgc accgttttcc cccaacatca    540

tccctgaggc aacgtcctga gccgcaggtg acagggactg taggcctgca tctgggggta    600

accccctctg tgatccgtaa gcgatacaac ttgacctcac aagacgtggg ctctggcacc    660

agcaataaca gccaagcctg tgcccagttc ctggagcagt atttccatga ctcagacctg    720

gctcagttca tgcgcctctt cggtggcaac tttgcacatc aggcatcagt agcccgtgtg    780

gttggacaac agggccgggg ccgggccggg attgaggcca gtctagatgt gcagtacctg    840

atgagtgctg gtgccaacat ctccacctgg gtctacagta gccctggccg gcatgaggga    900

caggagccct tcctgcagtg gctcatgctg ctcagtaatg agtcagccct gccacatgtg    960

catactgtga gctatggaga tgatgaggac tccctcagca gcgcctacat ccagcgggtc   1020

aacactgagc tcatgaaggc tgccgctcgg ggtctcaccc tgctcttcgc ctcaggtgac   1080

agtggggccg ggtgttggtc tgtctctgga agacaccagt tccgccctac cttccctgcc   1140

tccagcccct atgtcaccac agtgggaggc acatccttcc aggaaccttt cctcatcaca   1200

aatgaaattg ttgactatat cagtggtggt ggcttcagca atgtgttccc acggccttca   1260

taccaggagg aagctgtaac gaagttcctg agctctagcc cccacctgcc accatccagt   1320

tacttcaatg ccagtggccg tgcctaccca gatgtggctg cactttctga tggctactgg   1380

gtggtcagca acagagtgcc cattccatgg gtgtccggaa cctcggcctc tactccagtg   1440

tttgggggga tcctatcctt gatcaatgag cacaggatcc ttagtggccg cccccctctt   1500

ggctttctca acccaaggct ctaccagcag catggggcag gactctttga tgtaacccgt   1560

ggctgccatg agtcctgtct ggatgaagag gtagagggcc agggtttctg ctctggtcct   1620

ggctgggatc ctgtaacagg ctggggaaca cccaacttcc cagctttgct gaagactcta   1680

ctcaacccct ga                                                       1692
```

<210> SEQ ID NO 138
<211> LENGTH: 563
<212> TYPE: PRT
<213> ORGANISM: Homo sapiens

<400> SEQUENCE: 138

Met Gly Leu Gln Ala Cys Leu Leu Gly Leu Phe Ala Leu Ile Leu Ser
1 5 10 15

Gly Lys Cys Ser Tyr Ser Pro Glu Pro Asp Gln Arg Arg Thr Leu Pro
20 25 30

Pro Gly Trp Val Ser Leu Gly Arg Ala Asp Pro Glu Glu Glu Leu Ser
35 40 45

Leu Thr Phe Ala Leu Arg Gln Gln Asn Val Glu Arg Leu Ser Glu Leu
50 55 60

Val Gln Ala Val Ser Asp Pro Ser Ser Pro Gln Tyr Gly Lys Tyr Leu
65 70 75 80

Thr Leu Glu Asn Val Ala Asp Leu Val Arg Pro Ser Pro Leu Thr Leu
85 90 95

His Thr Val Gln Lys Trp Leu Leu Ala Ala Gly Ala Gln Lys Cys His
100 105 110

Ser Val Ile Thr Gln Asp Phe Leu Thr Cys Trp Leu Ser Ile Arg Gln
115 120 125

Ala Glu Leu Leu Leu Pro Gly Ala Glu Phe His His Tyr Val Gly Gly
130 135 140

Pro Thr Glu Thr His Val Val Arg Ser Pro His Pro Tyr Gln Leu Pro
145 150 155 160

Gln Ala Leu Ala Pro His Val Asp Phe Val Gly Gly Leu His Arg Phe
165 170 175

Pro Pro Thr Ser Ser Leu Arg Gln Arg Pro Glu Pro Gln Val Thr Gly
180 185 190

Thr Val Gly Leu His Leu Gly Val Thr Pro Ser Val Ile Arg Lys Arg
195 200 205

Tyr Asn Leu Thr Ser Gln Asp Val Gly Ser Gly Thr Ser Asn Asn Ser
210 215 220

Gln Ala Cys Ala Gln Phe Leu Glu Gln Tyr Phe His Asp Ser Asp Leu
225 230 235 240

Ala Gln Phe Met Arg Leu Phe Gly Gly Asn Phe Ala His Gln Ala Ser
245 250 255

Val Ala Arg Val Val Gly Gln Gln Gly Arg Gly Arg Ala Gly Ile Glu
260 265 270

Ala Ser Leu Asp Val Gln Tyr Leu Met Ser Ala Gly Ala Asn Ile Ser
275 280 285

Thr Trp Val Tyr Ser Ser Pro Gly Arg His Glu Gly Gln Glu Pro Phe
290 295 300

Leu Gln Trp Leu Met Leu Leu Ser Asn Glu Ser Ala Leu Pro His Val
305 310 315 320

His Thr Val Ser Tyr Gly Asp Asp Glu Asp Ser Leu Ser Ser Ala Tyr
325 330 335

Ile Gln Arg Val Asn Thr Glu Leu Met Lys Ala Ala Ala Arg Gly Leu
340 345 350

Thr Leu Leu Phe Ala Ser Gly Asp Ser Gly Ala Gly Cys Trp Ser Val
355 360 365

Ser Gly Arg His Gln Phe Arg Pro Thr Phe Pro Ala Ser Ser Pro Tyr

```
    370                 375                 380

Val Thr Thr Val Gly Gly Thr Ser Phe Gln Glu Pro Phe Leu Ile Thr
385                 390                 395                 400

Asn Glu Ile Val Asp Tyr Ile Ser Gly Gly Gly Phe Ser Asn Val Phe
                405                 410                 415

Pro Arg Pro Ser Tyr Gln Glu Glu Ala Val Thr Lys Phe Leu Ser Ser
            420                 425                 430

Ser Pro His Leu Pro Pro Ser Ser Tyr Phe Asn Ala Ser Gly Arg Ala
        435                 440                 445

Tyr Pro Asp Val Ala Ala Leu Ser Asp Gly Tyr Trp Val Val Ser Asn
    450                 455                 460

Arg Val Pro Ile Pro Trp Val Ser Gly Thr Ser Ala Ser Thr Pro Val
465                 470                 475                 480

Phe Gly Gly Ile Leu Ser Leu Ile Asn Glu His Arg Ile Leu Ser Gly
                485                 490                 495

Arg Pro Pro Leu Gly Phe Leu Asn Pro Arg Leu Tyr Gln Gln His Gly
            500                 505                 510

Ala Gly Leu Phe Asp Val Thr Arg Gly Cys His Glu Ser Cys Leu Asp
        515                 520                 525

Glu Glu Val Glu Gly Gln Gly Phe Cys Ser Gly Pro Gly Trp Asp Pro
    530                 535                 540

Val Thr Gly Trp Gly Thr Pro Asn Phe Pro Ala Leu Leu Lys Thr Leu
545                 550                 555                 560

Leu Asn Pro


<210> SEQ ID NO 139
<211> LENGTH: 1236
<212> TYPE: DNA
<213> ORGANISM: Homo sapiens

<400> SEQUENCE: 139

atgctgctga agacagtgct cttgctggga catgtggccc aggtgctgat gctggacaat     60

gggctcctgc agacaccacc catgggctgg ctggcctggg aacgcttccg ctgcaacatt    120

aactgtgatg aggacccaaa gaactgcata agtgaacagc tcttcatgga gatggctgac    180

cggatggcac aggatggatg gcgggacatg ggctacacat acctcaacat tgatgactgc    240

tggatcggtg gtcgcgatgc cagtggccgc ctgatgccgg atcccaagcg cttccctcat    300

ggcattcctt tcctggctga ctacgttcac tccctgggcc tgaagttggg tatctacgcg    360

gacatgggca acttcacctg catgggttac ccaggcacca cactggacaa ggtggtccag    420

gatgctcaga ccttcgccga gtggaaggta gacatgctca agctggatgg ctgcttctcc    480

acccccgagg agcgggccca ggggtacccc aagatggctg ctgccctgaa tgccacaggc    540

cgccccatcg ccttctcctg cagctggcca gcctatgaag gcggcctccc cccaagggtg    600

aactacagtc tgctggcgga catctgcaac ctctggcgta actatgatga catccaggac    660

tcctggtgga gcgtgctctc catcctgaat tggttcgtgg agcaccagga catactgcag    720

ccagtggccg gccctgggca ctggaatgac cctgacatgc tgctcattgg gaactttggt    780

ctcagcttag agcaatcccg ggcccagatg gccctgtgga cggtgctggc agcccccctc    840

ttgatgtcca cagacctgcg taccatctcc gcccagaaca tggacattct gcagaatcca    900

ctcatgatca aaatcaacca ggatccctta ggcatccagg gacgcaggat tcacaaggaa    960

aaatctctca tcgaagtgta catgcggcct ctgtccaaca aggctagcgc cttagtcttc   1020
```

```
ttcagctgca ggaccgatat gccttatcgc taccactcct cccttggcca gctgaacttc   1080

accgggtctg tgatatatga ggcccaggac gtctactcag gtgacatcat cagtggcctc   1140

cgagatgaaa ccaacttcac agtgatcatc aacccttcag ggtagtgat gtggtacctg   1200

tatcccatca agaacctgga gatgtcccag cagtga                             1236


<210> SEQ ID NO 140
<211> LENGTH: 411
<212> TYPE: PRT
<213> ORGANISM: Homo sapiens

<400> SEQUENCE: 140

Met Leu Leu Lys Thr Val Leu Leu Leu Gly His Val Ala Gln Val Leu
1               5                   10                  15

Met Leu Asp Asn Gly Leu Leu Gln Thr Pro Pro Met Gly Trp Leu Ala
            20                  25                  30

Trp Glu Arg Phe Arg Cys Asn Ile Asn Cys Asp Glu Asp Pro Lys Asn
        35                  40                  45

Cys Ile Ser Glu Gln Leu Phe Met Glu Met Ala Asp Arg Met Ala Gln
    50                  55                  60

Asp Gly Trp Arg Asp Met Gly Tyr Thr Tyr Leu Asn Ile Asp Asp Cys
65                  70                  75                  80

Trp Ile Gly Gly Arg Asp Ala Ser Gly Arg Leu Met Pro Asp Pro Lys
                85                  90                  95

Arg Phe Pro His Gly Ile Pro Phe Leu Ala Asp Tyr Val His Ser Leu
            100                 105                 110

Gly Leu Lys Leu Gly Ile Tyr Ala Asp Met Gly Asn Phe Thr Cys Met
        115                 120                 125

Gly Tyr Pro Gly Thr Thr Leu Asp Lys Val Val Gln Asp Ala Gln Thr
    130                 135                 140

Phe Ala Glu Trp Lys Val Asp Met Leu Lys Leu Asp Gly Cys Phe Ser
145                 150                 155                 160

Thr Pro Glu Glu Arg Ala Gln Gly Tyr Pro Lys Met Ala Ala Ala Leu
                165                 170                 175

Asn Ala Thr Gly Arg Pro Ile Ala Phe Ser Cys Ser Trp Pro Ala Tyr
            180                 185                 190

Glu Gly Gly Leu Pro Pro Arg Val Asn Tyr Ser Leu Leu Ala Asp Ile
        195                 200                 205

Cys Asn Leu Trp Arg Asn Tyr Asp Asp Ile Gln Asp Ser Trp Trp Ser
    210                 215                 220

Val Leu Ser Ile Leu Asn Trp Phe Val Glu His Gln Asp Ile Leu Gln
225                 230                 235                 240

Pro Val Ala Gly Pro Gly His Trp Asn Asp Pro Asp Met Leu Leu Ile
                245                 250                 255

Gly Asn Phe Gly Leu Ser Leu Glu Gln Ser Arg Ala Gln Met Ala Leu
            260                 265                 270

Trp Thr Val Leu Ala Ala Pro Leu Leu Met Ser Thr Asp Leu Arg Thr
        275                 280                 285

Ile Ser Ala Gln Asn Met Asp Ile Leu Gln Asn Pro Leu Met Ile Lys
    290                 295                 300

Ile Asn Gln Asp Pro Leu Gly Ile Gln Gly Arg Arg Ile His Lys Glu
305                 310                 315                 320

Lys Ser Leu Ile Glu Val Tyr Met Arg Pro Leu Ser Asn Lys Ala Ser
                325                 330                 335
```

Ala Leu Val Phe Phe Ser Cys Arg Thr Asp Met Pro Tyr Arg Tyr His
            340                 345                 350

Ser Ser Leu Gly Gln Leu Asn Phe Thr Gly Ser Val Ile Tyr Glu Ala
        355                 360                 365

Gln Asp Val Tyr Ser Gly Asp Ile Ile Ser Gly Leu Arg Asp Glu Thr
    370                 375                 380

Asn Phe Thr Val Ile Ile Asn Pro Ser Gly Val Val Met Trp Tyr Leu
385                 390                 395                 400

Tyr Pro Ile Lys Asn Leu Glu Met Ser Gln Gln
                405                 410

<210> SEQ ID NO 141
<211> LENGTH: 1488
<212> TYPE: DNA
<213> ORGANISM: Homo sapiens

<400> SEQUENCE: 141
atgaggtctc cggttcgaga cctggcccgg aacgatggcg aggagagcac ggaccgcacg 60
cctcttctac cgggcgcccc acgggccgaa gccgctccag tgtgctgctc tgctcgttac 120
aacttagcaa ttttggcctt ttttggtttc ttcattgtgt atgcattacg tgtgaatctg 180
agtgttgcgt tagtggatat ggtagattca aatacaactt tagaagataa tagaacttcc 240
aaggcgtgtc cagagcattc tgctcccata aaagttcatc ataatcaaac gggtaagaag 300
taccaatggg atgcagaaac tcaaggatgg attctcggtt ccttttttta tggctacatc 360
atcacacaga ttcctggagg atatgttgcc agcaaaatag gggggaaaat gctgctagga 420
tttgggatcc ttggcactgc tgtcctcacc ctgttcactc ccattgctgc agatttagga 480
gttggaccac tcattgtact cagagcacta gaaggactag gagagggtgt tacatttcca 540
gccatgcatg ccatgtggtc ttcttgggct ccccctcttg aaagaagcaa acttcttagc 600
atttcatatg caggagcaca gcttgggaca gtaatttctc ttcctctttc tggaataatt 660
tgctactata tgaattggac ttatgtcttc tactttttg gtactattgg aatattttgg 720
tttcttttgt ggatctggtt agttagtgac acaccacaaa aacacaagag aatttcccat 780
tatgaaaagg aatacattct ttcatcatta agaaatcagc tttcttcaca gaagtcagtg 840
ccgtgggtac ccattttaaa atccctgcca ctttgggcta tcgtagttgc acacttttct 900
tacaactgga ctttttatac tttattgaca ttattgccta cttatatgaa ggagatccta 960
aggttcaatg ttcaagagaa tgggttttta tcttcattgc cttatttagg ctcttggtta 1020
tgtatgatcc tgtctggtca agctgctgac aatttaaggg caaaatggaa tttttcaact 1080
ttatgtgttc gcagaatttt tagccttata ggaatgattg gacctgcagt attcctggta 1140
gctgctggct tcattggctg tgattattct ttggccgttg ctttcctaac tatatcaaca 1200
acactgggag gcttttgctc ttctggattt agcatcaacc atctggatat tgctccttcg 1260
tatgctggta tcctcctggg catcacaaat acatttgcca ctattccagg aatggttggg 1320
cccgtcattg ctaaaagtct gacccctgat aacactgttg gagaatggca aaccgtgttc 1380
tatattgctg ctgctattaa tgtttttggt gccattttct ttacactatt cgccaaaggt 1440
gaagtacaaa actgggctct caatgatcac catggacaca gacactga 1488

<210> SEQ ID NO 142
<211> LENGTH: 495
<212> TYPE: PRT
<213> ORGANISM: Homo sapiens

<400> SEQUENCE: 142

Met Arg Ser Pro Val Arg Asp Leu Ala Arg Asn Asp Gly Glu Glu Ser
1               5                   10                  15

Thr Asp Arg Thr Pro Leu Leu Pro Gly Ala Pro Arg Ala Glu Ala Ala
            20                  25                  30

Pro Val Cys Cys Ser Ala Arg Tyr Asn Leu Ala Ile Leu Ala Phe Phe
        35                  40                  45

Gly Phe Phe Ile Val Tyr Ala Leu Arg Val Asn Leu Ser Val Ala Leu
    50                  55                  60

Val Asp Met Val Asp Ser Asn Thr Thr Leu Glu Asp Asn Arg Thr Ser
65                  70                  75                  80

Lys Ala Cys Pro Glu His Ser Ala Pro Ile Lys Val His His Asn Gln
                85                  90                  95

Thr Gly Lys Lys Tyr Gln Trp Asp Ala Glu Thr Gln Gly Trp Ile Leu
            100                 105                 110

Gly Ser Phe Phe Tyr Gly Tyr Ile Ile Thr Gln Ile Pro Gly Gly Tyr
        115                 120                 125

Val Ala Ser Lys Ile Gly Gly Lys Met Leu Leu Gly Phe Gly Ile Leu
    130                 135                 140

Gly Thr Ala Val Leu Thr Leu Phe Thr Pro Ile Ala Ala Asp Leu Gly
145                 150                 155                 160

Val Gly Pro Leu Ile Val Leu Arg Ala Leu Glu Gly Leu Gly Glu Gly
                165                 170                 175

Val Thr Phe Pro Ala Met His Ala Met Trp Ser Ser Trp Ala Pro Pro
            180                 185                 190

Leu Glu Arg Ser Lys Leu Leu Ser Ile Ser Tyr Ala Gly Ala Gln Leu
        195                 200                 205

Gly Thr Val Ile Ser Leu Pro Leu Ser Gly Ile Ile Cys Tyr Tyr Met
    210                 215                 220

Asn Trp Thr Tyr Val Phe Tyr Phe Phe Gly Thr Ile Gly Ile Phe Trp
225                 230                 235                 240

Phe Leu Leu Trp Ile Trp Leu Val Ser Asp Thr Pro Gln Lys His Lys
                245                 250                 255

Arg Ile Ser His Tyr Glu Lys Glu Tyr Ile Leu Ser Ser Leu Arg Asn
            260                 265                 270

Gln Leu Ser Ser Gln Lys Ser Val Pro Trp Val Pro Ile Leu Lys Ser
        275                 280                 285

Leu Pro Leu Trp Ala Ile Val Val Ala His Phe Ser Tyr Asn Trp Thr
    290                 295                 300

Phe Tyr Thr Leu Leu Thr Leu Leu Pro Thr Tyr Met Lys Glu Ile Leu
305                 310                 315                 320

Arg Phe Asn Val Gln Glu Asn Gly Phe Leu Ser Ser Leu Pro Tyr Leu
                325                 330                 335

Gly Ser Trp Leu Cys Met Ile Leu Ser Gly Gln Ala Ala Asp Asn Leu
            340                 345                 350

Arg Ala Lys Trp Asn Phe Ser Thr Leu Cys Val Arg Arg Ile Phe Ser
        355                 360                 365

Leu Ile Gly Met Ile Gly Pro Ala Val Phe Leu Val Ala Ala Gly Phe
    370                 375                 380

Ile Gly Cys Asp Tyr Ser Leu Ala Val Ala Phe Leu Thr Ile Ser Thr
385                 390                 395                 400

Thr Leu Gly Gly Phe Cys Ser Ser Gly Phe Ser Ile Asn His Leu Asp
                405                 410                 415

```
Ile Ala Pro Ser Tyr Ala Gly Ile Leu Leu Gly Ile Thr Asn Thr Phe
            420                 425                 430

Ala Thr Ile Pro Gly Met Val Gly Pro Val Ile Ala Lys Ser Leu Thr
        435                 440                 445

Pro Asp Asn Thr Val Gly Glu Trp Gln Thr Val Phe Tyr Ile Ala Ala
    450                 455                 460

Ala Ile Asn Val Phe Gly Ala Ile Phe Phe Thr Leu Phe Ala Lys Gly
465                 470                 475                 480

Glu Val Gln Asn Trp Ala Leu Asn Asp His His Gly His Arg His
                485                 490                 495


<210> SEQ ID NO 143
<211> LENGTH: 2010
<212> TYPE: DNA
<213> ORGANISM: Homo sapiens

<400> SEQUENCE: 143

atggctcggc gcggctggcg gcgggcaccc ctccgccgtg gcgtcggcag cagtccccga     60

gcccgcaggc tcatgcggcc cctttggttg ctcctcgcag tgggcgtctt tgactgggca    120

ggggcttcgg acggcggcgg cggagaggct agagccatgg acgaggagat cgtgtccgag    180

aagcaagccg aggagagcca ccggcaggac agcgccaacc tgctcatctt catcctgctg    240

ctcaccctca ccattctcac aatctggctc ttcaagcacc gccgggcccg cttcctgcac    300

gaaaccggcc tggctatgat ttatggtctt ttggtgggcc ttgtgcttcg gtatggcatt    360

catgttccga gtgatgtaaa taatgtgacc ctgagctgtg aagtgcagtc aagtccaact    420

accttactgg ttacttttga tccagaagta tttttcaaca tattacttcc tcctatcata    480

ttttatgcag gttatagcct gaaaaggaga catttttttc gaaatcttgg gtctatccta    540

gcatacgctt ttcttggaac agcaatttct tgtttcgtta ttgggtcaat aatgtatggc    600

tgtgtaacgc tgatgaaggt aacgggacaa cttgcaggag atttttactt tacagattgc    660

ctactgtttg gtgccattgt atcagcaact gatccagtga ctgttcttgc tatattccac    720

gagcttcaag ttgatgttga actctatgca cttctttttg gtgaaagtgt cctcaatgat    780

gctgttgcca tagtgctgtc ctcctcaata gtggcatacc agccagctgg agacaacagt    840

cacacctttg atgtcacagc gatgttcaag tctattggga tcttccttgg aatcttcagt    900

ggatcttttg caatgggtgc tgctactgga gtggtgacag ctttagtgac aaagttcacc    960

aaattacggg agttccagtt gttggagaca ggcctgttct tcttgatgtc ctggagtacc   1020

ttcctcttgg ctgaagcatg gggcttcaca ggtgtagttg cagtattgtt ttgtggcatc   1080

acacaagcac attatacgta taataatttg tccacggagt ctcagcatag aactaaacag   1140

ttgtttgagc ttctcaattt cttggcagag aatttcatct tctcctacat ggggctgaca   1200

ctgttcacct tccagaacca tgtctttaac ccaacatttg tagtaggagc atttgttgct   1260

attttcttgg gaagagctgc caatatttac cccttgtccc tcttacttaa tttgggtaga   1320

agaagtaaga ttggatcaaa ttttcaacac atgatgatgt ttgctggcct tcgtggtgca   1380

atggcatttg ccttggccat tcgagatact gccacttatg cacggcaaat gatgttcagc   1440

accacgcttc tgattgtgtt ttttaccgtg tgggtatttg gtggtggcac cactgcaatg   1500

ctgtcatgct tgcatatcag ggttggtgtt gattcagacc aagaacactt gggtgttcct   1560

gaaaatgaaa ggagaactac caaagcagag agtgcttggc ttttccggat gtggtacaac   1620

tttgatcata actatctgaa gcctctgctg acccacagcg ggcctccgct gacaacaaca   1680
```

ctccctgcct gctgtggacc catcgccagg tgcctcacca gcccccaggc ttacgaaaac 1740
caggaacagt tgaaagatga tgattctgat cttattctca atgatggtga catcagtttg 1800
acatatggag attctactgt gaacactgaa ccggccacat ccagcgcccc aaggagattt 1860
atgggaaaca gttctgaaga tgccttggat cgggagcttg catttgggga ccatgaactg 1920
gtcattcgag gaacacgcct ggttcttcca atggatgatt ctgaaccccc gctaaatttg 1980
ttagataata cgagacatgg tccagcctaa 2010

<210> SEQ ID NO 144
<211> LENGTH: 669
<212> TYPE: PRT
<213> ORGANISM: Homo sapiens

<400> SEQUENCE: 144

Met Ala Arg Arg Gly Trp Arg Arg Ala Pro Leu Arg Arg Gly Val Gly
1 5 10 15

Ser Ser Pro Arg Ala Arg Arg Leu Met Arg Pro Leu Trp Leu Leu Leu
20 25 30

Ala Val Gly Val Phe Asp Trp Ala Gly Ala Ser Asp Gly Gly Gly Gly
35 40 45

Glu Ala Arg Ala Met Asp Glu Glu Ile Val Ser Glu Lys Gln Ala Glu
50 55 60

Glu Ser His Arg Gln Asp Ser Ala Asn Leu Leu Ile Phe Ile Leu Leu
65 70 75 80

Leu Thr Leu Thr Ile Leu Thr Ile Trp Leu Phe Lys His Arg Arg Ala
85 90 95

Arg Phe Leu His Glu Thr Gly Leu Ala Met Ile Tyr Gly Leu Leu Val
100 105 110

Gly Leu Val Leu Arg Tyr Gly Ile His Val Pro Ser Asp Val Asn Asn
115 120 125

Val Thr Leu Ser Cys Glu Val Gln Ser Ser Pro Thr Thr Leu Leu Val
130 135 140

Thr Phe Asp Pro Glu Val Phe Phe Asn Ile Leu Leu Pro Pro Ile Ile
145 150 155 160

Phe Tyr Ala Gly Tyr Ser Leu Lys Arg Arg His Phe Phe Arg Asn Leu
165 170 175

Gly Ser Ile Leu Ala Tyr Ala Phe Leu Gly Thr Ala Ile Ser Cys Phe
180 185 190

Val Ile Gly Ser Ile Met Tyr Gly Cys Val Thr Leu Met Lys Val Thr
195 200 205

Gly Gln Leu Ala Gly Asp Phe Tyr Phe Thr Asp Cys Leu Leu Phe Gly
210 215 220

Ala Ile Val Ser Ala Thr Asp Pro Val Thr Val Leu Ala Ile Phe His
225 230 235 240

Glu Leu Gln Val Asp Val Glu Leu Tyr Ala Leu Leu Phe Gly Glu Ser
245 250 255

Val Leu Asn Asp Ala Val Ala Ile Val Leu Ser Ser Ser Ile Val Ala
260 265 270

Tyr Gln Pro Ala Gly Asp Asn Ser His Thr Phe Asp Val Thr Ala Met
275 280 285

Phe Lys Ser Ile Gly Ile Phe Leu Gly Ile Phe Ser Gly Ser Phe Ala
290 295 300

Met Gly Ala Ala Thr Gly Val Val Thr Ala Leu Val Thr Lys Phe Thr

```
305                 310                 315                 320

Lys Leu Arg Glu Phe Gln Leu Leu Glu Thr Gly Leu Phe Phe Leu Met
                325                 330                 335

Ser Trp Ser Thr Phe Leu Leu Ala Glu Ala Trp Gly Phe Thr Gly Val
            340                 345                 350

Val Ala Val Leu Phe Cys Gly Ile Thr Gln Ala His Tyr Thr Tyr Asn
        355                 360                 365

Asn Leu Ser Thr Glu Ser Gln His Arg Thr Lys Gln Leu Phe Glu Leu
    370                 375                 380

Leu Asn Phe Leu Ala Glu Asn Phe Ile Phe Ser Tyr Met Gly Leu Thr
385                 390                 395                 400

Leu Phe Thr Phe Gln Asn His Val Phe Asn Pro Thr Phe Val Val Gly
                405                 410                 415

Ala Phe Val Ala Ile Phe Leu Gly Arg Ala Ala Asn Ile Tyr Pro Leu
            420                 425                 430

Ser Leu Leu Leu Asn Leu Gly Arg Arg Ser Lys Ile Gly Ser Asn Phe
        435                 440                 445

Gln His Met Met Met Phe Ala Gly Leu Arg Gly Ala Met Ala Phe Ala
    450                 455                 460

Leu Ala Ile Arg Asp Thr Ala Thr Tyr Ala Arg Gln Met Met Phe Ser
465                 470                 475                 480

Thr Thr Leu Leu Ile Val Phe Phe Thr Val Trp Val Phe Gly Gly Gly
                485                 490                 495

Thr Thr Ala Met Leu Ser Cys Leu His Ile Arg Val Gly Val Asp Ser
            500                 505                 510

Asp Gln Glu His Leu Gly Val Pro Glu Asn Glu Arg Arg Thr Thr Lys
        515                 520                 525

Ala Glu Ser Ala Trp Leu Phe Arg Met Trp Tyr Asn Phe Asp His Asn
    530                 535                 540

Tyr Leu Lys Pro Leu Leu Thr His Ser Gly Pro Pro Leu Thr Thr Thr
545                 550                 555                 560

Leu Pro Ala Cys Cys Gly Pro Ile Ala Arg Cys Leu Thr Ser Pro Gln
                565                 570                 575

Ala Tyr Glu Asn Gln Glu Gln Leu Lys Asp Asp Asp Ser Asp Leu Ile
            580                 585                 590

Leu Asn Asp Gly Asp Ile Ser Leu Thr Tyr Gly Asp Ser Thr Val Asn
        595                 600                 605

Thr Glu Pro Ala Thr Ser Ser Ala Pro Arg Arg Phe Met Gly Asn Ser
    610                 615                 620

Ser Glu Asp Ala Leu Asp Arg Glu Leu Ala Phe Gly Asp His Glu Leu
625                 630                 635                 640

Val Ile Arg Gly Thr Arg Leu Val Leu Pro Met Asp Asp Ser Glu Pro
                645                 650                 655

Pro Leu Asn Leu Leu Asp Asn Thr Arg His Gly Pro Ala
            660                 665
```

<210> SEQ ID NO 145
<211> LENGTH: 2706
<212> TYPE: DNA
<213> ORGANISM: Homo sapiens

<400> SEQUENCE: 145

```
atggagccgc cgctcccggt cggagcccag ccgcttgcca ctgtcgaggg tatggagatg      60

aagggtcctc tccgggagcc ctgcgccctg accctagccc agaggaacgg gcaatatgag     120
```

```
ttaataatcc agttgcatga gaaggaacag catgttcaag atatcattcc tataaatagc    180
cacttcagat gtgttcaaga agcagaagaa actcttttga ttgacatagc ttctaacagt    240
ggctgcaaaa ttcgggttca gggggactgg atcagagagc gccgctttga aatccctgat    300
gaggaacact gtttgaagtt cctctcagct gtccttgctg ctcagaaagc tcagtcacag    360
cttcttgttc cagagcaaaa ggactcatct agctggtacc agaaattaga cactaaggac    420
aaaccttctg tttttcagg gcttcttgga tttgaagaca atttttcttc tatgaatttg    480
gacaagaaaa taaattcaca aaatcagcct actgggattc atcgggaacc cccacctcca    540
cccttttcag tgaataaaat gcttccacgt gaaaaagaag cttctaacaa ggagcagccc    600
aaagtgacca acaccatgcg gaagctcttt gtaccaaata cccaatctgg gcagcgggag    660
ggtctcatca aacatatcct ggcaaagcga gagaaagaat atgtcaacat tcagactttc    720
agattttttg ttggaacttg gaatgtgaat ggccagtctc cagatagcgg gttagaacct    780
tggctgaact gtgatcccaa tcctcctgat atctactgca ttggattcca agaactggac    840
ttgagcacag aagccttctt ctactttgaa tctgtgaagg aacaagaatg gtccatggct    900
gtagagagag gtttgcattc caaagccaag tataagaaag ttcaactggt gcgccttgtt    960
gggatgatgc ttcttatatt tgccagaaag gatcagtgtc gatacattcg tgatattgct   1020
acagaaacag ttggaactgg aatcatgggg aaaatgggaa acaaaggtgg ggtagctgtg   1080
agatttgtat ttcacaacac caccttttgc attgtcaatt cccatctggc tgcacacgtg   1140
gaggactttg agagaaggaa tcaagattat aaggacattt gtgcgagaat gagttttgtg   1200
gtcccaaatc agaccctccc gcagttgaac atcatgaaac atgaggttgt catttggttg   1260
ggagatttga attatagact ttgcatgcct gatgccaatg aggtgaaaag tcttattaat   1320
aagaaagacc ttcagagact cttgaaattc gaccagctaa atattcagcg cacacagaaa   1380
aaagcttttg ttgacttcaa tgaaggggaa atcaagttca tccccactta taagtatgac   1440
tctaaaacag accggtggga ttccagtggg aaatgccggg ttccagcctg gtgtgaccga   1500
attctttgga gaggaacaaa tgttaatcag cttaattatc ggagtcacat ggaactgaaa   1560
accagcgacc acaagcctgt tagcgccctc ttccatattg gggtgaaggt tgtggatgaa   1620
cgaaggtacc ggaaagtctt tgaagatagt gtacgcatca tggacagaat ggaaaatgac   1680
ttccttcctt ccttagaact cagcaggagg gagtttgtgt ttgaaaatgt gaagtttcgg   1740
caactacaaa aggagaagtt ccagatcagc aacaatggac aggttccctg ccatttttct   1800
ttcatcccta aacttaatga cagccagtac tgcaagccat ggcttcgggc tgaacctttt   1860
gagggctact tggagccaaa tgagacagtg gacatttctc ttgatgtgta tgtcagcaaa   1920
gactctgtaa ccatcctgaa ctcgggagaa gataagattg aagatattct cgtccttcac   1980
ctggatcgag gcaaagatta cttcttgact atcagtggaa attacctccc aagttgtttt   2040
ggcacatcct tagaggctct gtgccgtatg aaaagaccaa tccgagaagt tcctgttacc   2100
aaactcatag acttggaaga agacagcttc ctagaaaagg agaaatccct tctgcaaatg   2160
gttcctttgg atgaaggtgc cagtgagaga ccccttcagg ttcccaagga gatctggctt   2220
ctagtagatc acctattcaa atacgcctgt caccaggagg acctgttcca gacccctgga   2280
atgcaggaag agctccagca gatcattgat tgtctggata ccagcattcc tgagacaatc   2340
cctggcagca accactctgt ggctgaagca ctgctcattt tcttggaagc cctgccagag   2400
ccagtcatct gttacgagct gtatcagcga tgtcttgact ctgcttatga tccccggatc   2460
```

tgccgacagg tgatctccca gcttccgaga tgccatagaa atgttttccg ttacttgatg 2520
gcattccttc gagaactctt aaaattctct gaatacaata gcgtcaatgc caacatgatc 2580
gctactctct tcactagtct tctcctgagg cctccaccca accttatggc aagacagact 2640
ccaagtgacc gccagcgtgc tattcagttc cttctgggct ttctgcttgg gagcgaagaa 2700
gactaa 2706

<210> SEQ ID NO 146
<211> LENGTH: 901
<212> TYPE: PRT
<213> ORGANISM: Homo sapiens

<400> SEQUENCE: 146

Met Glu Pro Pro Leu Pro Val Gly Ala Gln Pro Leu Ala Thr Val Glu
1 5 10 15

Gly Met Glu Met Lys Gly Pro Leu Arg Glu Pro Cys Ala Leu Thr Leu
20 25 30

Ala Gln Arg Asn Gly Gln Tyr Glu Leu Ile Ile Gln Leu His Glu Lys
35 40 45

Glu Gln His Val Gln Asp Ile Ile Pro Ile Asn Ser His Phe Arg Cys
50 55 60

Val Gln Glu Ala Glu Glu Thr Leu Leu Ile Asp Ile Ala Ser Asn Ser
65 70 75 80

Gly Cys Lys Ile Arg Val Gln Gly Asp Trp Ile Arg Glu Arg Arg Phe
85 90 95

Glu Ile Pro Asp Glu Glu His Cys Leu Lys Phe Leu Ser Ala Val Leu
100 105 110

Ala Ala Gln Lys Ala Gln Ser Gln Leu Leu Val Pro Glu Gln Lys Asp
115 120 125

Ser Ser Ser Trp Tyr Gln Lys Leu Asp Thr Lys Asp Lys Pro Ser Val
130 135 140

Phe Ser Gly Leu Leu Gly Phe Glu Asp Asn Phe Ser Ser Met Asn Leu
145 150 155 160

Asp Lys Lys Ile Asn Ser Gln Asn Gln Pro Thr Gly Ile His Arg Glu
165 170 175

Pro Pro Pro Pro Pro Phe Ser Val Asn Lys Met Leu Pro Arg Glu Lys
180 185 190

Glu Ala Ser Asn Lys Glu Gln Pro Lys Val Thr Asn Thr Met Arg Lys
195 200 205

Leu Phe Val Pro Asn Thr Gln Ser Gly Gln Arg Glu Gly Leu Ile Lys
210 215 220

His Ile Leu Ala Lys Arg Glu Lys Glu Tyr Val Asn Ile Gln Thr Phe
225 230 235 240

Arg Phe Phe Val Gly Thr Trp Asn Val Asn Gly Gln Ser Pro Asp Ser
245 250 255

Gly Leu Glu Pro Trp Leu Asn Cys Asp Pro Asn Pro Pro Asp Ile Tyr
260 265 270

Cys Ile Gly Phe Gln Glu Leu Asp Leu Ser Thr Glu Ala Phe Phe Tyr
275 280 285

Phe Glu Ser Val Lys Glu Gln Glu Trp Ser Met Ala Val Glu Arg Gly
290 295 300

Leu His Ser Lys Ala Lys Tyr Lys Lys Val Gln Leu Val Arg Leu Val
305 310 315 320

Gly Met Met Leu Leu Ile Phe Ala Arg Lys Asp Gln Cys Arg Tyr Ile

```
                325                 330                 335

Arg Asp Ile Ala Thr Glu Thr Val Gly Thr Gly Ile Met Gly Lys Met
            340                 345                 350

Gly Asn Lys Gly Gly Val Ala Val Arg Phe Val Phe His Asn Thr Thr
        355                 360                 365

Phe Cys Ile Val Asn Ser His Leu Ala Ala His Val Glu Asp Phe Glu
    370                 375                 380

Arg Arg Asn Gln Asp Tyr Lys Asp Ile Cys Ala Arg Met Ser Phe Val
385                 390                 395                 400

Val Pro Asn Gln Thr Leu Pro Gln Leu Asn Ile Met Lys His Glu Val
                405                 410                 415

Val Ile Trp Leu Gly Asp Leu Asn Tyr Arg Leu Cys Met Pro Asp Ala
            420                 425                 430

Asn Glu Val Lys Ser Leu Ile Asn Lys Lys Asp Leu Gln Arg Leu Leu
        435                 440                 445

Lys Phe Asp Gln Leu Asn Ile Gln Arg Thr Gln Lys Lys Ala Phe Val
    450                 455                 460

Asp Phe Asn Glu Gly Glu Ile Lys Phe Ile Pro Thr Tyr Lys Tyr Asp
465                 470                 475                 480

Ser Lys Thr Asp Arg Trp Asp Ser Ser Gly Lys Cys Arg Val Pro Ala
                485                 490                 495

Trp Cys Asp Arg Ile Leu Trp Arg Gly Thr Asn Val Asn Gln Leu Asn
            500                 505                 510

Tyr Arg Ser His Met Glu Leu Lys Thr Ser Asp His Lys Pro Val Ser
        515                 520                 525

Ala Leu Phe His Ile Gly Val Lys Val Val Asp Glu Arg Arg Tyr Arg
    530                 535                 540

Lys Val Phe Glu Asp Ser Val Arg Ile Met Asp Arg Met Glu Asn Asp
545                 550                 555                 560

Phe Leu Pro Ser Leu Glu Leu Ser Arg Arg Glu Phe Val Phe Glu Asn
                565                 570                 575

Val Lys Phe Arg Gln Leu Gln Lys Glu Lys Phe Gln Ile Ser Asn Asn
            580                 585                 590

Gly Gln Val Pro Cys His Phe Ser Phe Ile Pro Lys Leu Asn Asp Ser
        595                 600                 605

Gln Tyr Cys Lys Pro Trp Leu Arg Ala Glu Pro Phe Glu Gly Tyr Leu
    610                 615                 620

Glu Pro Asn Glu Thr Val Asp Ile Ser Leu Asp Val Tyr Val Ser Lys
625                 630                 635                 640

Asp Ser Val Thr Ile Leu Asn Ser Gly Glu Asp Lys Ile Glu Asp Ile
                645                 650                 655

Leu Val Leu His Leu Asp Arg Gly Lys Asp Tyr Phe Leu Thr Ile Ser
            660                 665                 670

Gly Asn Tyr Leu Pro Ser Cys Phe Gly Thr Ser Leu Glu Ala Leu Cys
        675                 680                 685

Arg Met Lys Arg Pro Ile Arg Glu Val Pro Val Thr Lys Leu Ile Asp
    690                 695                 700

Leu Glu Glu Asp Ser Phe Leu Glu Lys Glu Lys Ser Leu Leu Gln Met
705                 710                 715                 720

Val Pro Leu Asp Glu Gly Ala Ser Glu Arg Pro Leu Gln Val Pro Lys
                725                 730                 735

Glu Ile Trp Leu Leu Val Asp His Leu Phe Lys Tyr Ala Cys His Gln
            740                 745                 750
```

```
Glu Asp Leu Phe Gln Thr Pro Gly Met Gln Glu Glu Leu Gln Gln Ile
        755                 760                 765

Ile Asp Cys Leu Asp Thr Ser Ile Pro Glu Thr Ile Pro Gly Ser Asn
    770                 775                 780

His Ser Val Ala Glu Ala Leu Leu Ile Phe Leu Glu Ala Leu Pro Glu
785                 790                 795                 800

Pro Val Ile Cys Tyr Glu Leu Tyr Gln Arg Cys Leu Asp Ser Ala Tyr
                805                 810                 815

Asp Pro Arg Ile Cys Arg Gln Val Ile Ser Gln Leu Pro Arg Cys His
            820                 825                 830

Arg Asn Val Phe Arg Tyr Leu Met Ala Phe Leu Arg Glu Leu Leu Lys
        835                 840                 845

Phe Ser Glu Tyr Asn Ser Val Asn Ala Asn Met Ile Ala Thr Leu Phe
    850                 855                 860

Thr Ser Leu Leu Leu Arg Pro Pro Pro Asn Leu Met Ala Arg Gln Thr
865                 870                 875                 880

Pro Ser Asp Arg Gln Arg Ala Ile Gln Phe Leu Leu Gly Phe Leu Leu
                885                 890                 895

Gly Ser Glu Glu Asp
            900


<210> SEQ ID NO 147
<211> LENGTH: 2724
<212> TYPE: DNA
<213> ORGANISM: Homo sapiens

<400> SEQUENCE: 147

atgcccacgg ccgccgcccc catcatcagc tcggtccaga agctggttct gtatgagact     60

agagctagat actttctagt tgggagcaat aatgcagaaa cgaaatatcg tgtcttgaag    120

attgatagaa cagaaccaaa agatttggtc ataattgatg acaggcatgt ctatactcaa    180

caagaagtaa gggaacttct tggccgcttg gatcttggaa atagaacaaa gatgggacag    240

aaaggatcct cgggcttatt tcgagcggtt tcagcttttg gtgttgtggg ttttgtcagg    300

ttcttagaag gctattatat tgtgttaata actaaaagga ggaagatggc ggatattgga    360

ggtcatgcaa tctataaggt cgaagataca aatatgatct atatacccaa tgattctgta    420

cgggttactc atcctgatga agctaggtat ctacgaatat ttcaaaatgt ggacctatct    480

agcaattttt actttagtta cagctatgat ttgtcccact cacttcaata taatctcact    540

gtcttgcgaa tgcccctgga gatgttaaag tcagaaatga cccagaatcg ccaagagagc    600

tttgacatct ttgaagatga aggattaatt acacaaggtg gaagcggggt atttgggatc    660

tgtagtgagc cttatatgaa atatgtatgg aatggtgaac ttctggatat aattaaaagt    720

actgtgcatc gtgactggct tttgtatatt attcatgggt tctgtgggca gtcaaagctg    780

ttgatctatg gacgaccagt gtatgtcact ctaatagcta gaagatccag taaatttgct    840

ggcacccgtt ttcttaaaag aggtgcaaac tgtgagggtg atgttgcaaa tgaagtggag    900

actgaacaaa tactctgcga tgcttctgtg atgtctttca ctgcaggaag ttattcttca    960

tatgtacaag ttagaggatc tgtgccctta tactggtctc aggacatttc aactatgatg   1020

cctaaaccac ctattacatt ggatcaggca gatccatttg cacatgtggc tgcccttcac   1080

tttgaccaga tgttccagag gtttggctct cccatcatca tcttgaattt agtgaaggaa   1140

cgagagaaaa gaaagcatga aagaattctg agtgaagaac ttgttgctgc tgtgacctat   1200
```

```
ctcaaccaat ttttgcctcc tgagcacact attgtttata ttccctggga catggccaag   1260

tataccaaaa gcaagctgtg taatgttctt gatcgactaa atgtgattgc agaaagtgtg   1320

gtgaagaaaa caggtttctt tgtaaaccgc cctgattctt actgtagcat tttgcggcca   1380

gatgaaaagt ggaatgaact aggaggatgt gtgattccca ctggtcgcct gcagactggc   1440

atccttcgaa ccaactgtgt ggactgttta gatcgcacca acacagcaca gtttatggtg   1500

ggaaaatgtg ctctggccta tcagctgtat tcactgggac tgattgacaa acctaatcta   1560

cagtttgata cagatgcagt taggttattt gaggaactct atgaagatca tggtgatacc   1620

ctatcccttc agtatggtgg ttctcaactt gttcatcgtg tgaaaaccta cagaaagata   1680

gcaccatgga cccagcactc caaagacatc atgcaaaccc tgtctagata ttacagcaat   1740

gctttttcag atgccgatag acaagattcc attaatctct tcctgggagt tttccatccc   1800

actgaaggga aacctcatct ctgggagctc ccaacagatt tttatttgca tcacaaaaat   1860

accatgagac ttttgccaac aagaagaagt tatacttact ggtggacacc agaggtgata   1920

aagcatttac cattgcccta tgatgaagtt atctgtgctg tgaacttaaa gaagttgata   1980

gtgaagaaat tccacaaata tgaagaagag attgatatcc acaatgagtt ctttcggcca   2040

tatgagttga gcagctttga tgataccttt tgcttggcta tgacaagctc agcacgtgac   2100

tttatgccta agaccgttgg aattgatcca agtccattta ctgtgcgtaa accagatgaa   2160

actggaaaat cagtattggg aaacaaaagc aatagagaag aagctgtatt acagcggaaa   2220

acggcagcca gcgccccgcc gccccccagc gaggaggctg tgtccagcag ctctgaggat   2280

gactctggga ctgatcggga agaagagggc tctgtgtctc agcgctccac tcccgtgaag   2340

atgactgatg caggagacag tgccaaagtg accgagaatg tggtccaacc catgaaggag   2400

ctatatggaa ttaacctctc agatggcctc tcagaagaag atttctccat ttattcaaga   2460

tttgttcagc tggggcagag tcaacataaa caagacaaga atagccagca gccctgttct   2520

aggtgctcag atggagttat aaaactaaca cccatctcgg ctttctcgca agataacatc   2580

tatgaagttc agcccccaag agtagacaga aaatctacag agatcttcca agcccacatc   2640

caggccagcc aaggtatcat gcagccccta ggaaaagagg actcctccat gtaccgagag   2700

tacatcagga accgctacct gtga                                          2724
```

<210> SEQ ID NO 148
<211> LENGTH: 907
<212> TYPE: PRT
<213> ORGANISM: Homo sapiens

<400> SEQUENCE: 148

```
Met Pro Thr Ala Ala Ala Pro Ile Ile Ser Ser Val Gln Lys Leu Val
1               5                   10                  15

Leu Tyr Glu Thr Arg Ala Arg Tyr Phe Leu Val Gly Ser Asn Asn Ala
            20                  25                  30

Glu Thr Lys Tyr Arg Val Leu Lys Ile Asp Arg Thr Glu Pro Lys Asp
        35                  40                  45

Leu Val Ile Ile Asp Asp Arg His Val Tyr Thr Gln Gln Glu Val Arg
    50                  55                  60

Glu Leu Leu Gly Arg Leu Asp Leu Gly Asn Arg Thr Lys Met Gly Gln
65                  70                  75                  80

Lys Gly Ser Ser Gly Leu Phe Arg Ala Val Ser Ala Phe Gly Val Val
                85                  90                  95

Gly Phe Val Arg Phe Leu Glu Gly Tyr Tyr Ile Val Leu Ile Thr Lys
```

```
            100                 105                 110

Arg Arg Lys Met Ala Asp Ile Gly Gly His Ala Ile Tyr Lys Val Glu
        115                 120                 125

Asp Thr Asn Met Ile Tyr Ile Pro Asn Asp Ser Val Arg Val Thr His
    130                 135                 140

Pro Asp Glu Ala Arg Tyr Leu Arg Ile Phe Gln Asn Val Asp Leu Ser
145                 150                 155                 160

Ser Asn Phe Tyr Phe Ser Tyr Ser Tyr Asp Leu Ser His Ser Leu Gln
                165                 170                 175

Tyr Asn Leu Thr Val Leu Arg Met Pro Leu Glu Met Leu Lys Ser Glu
            180                 185                 190

Met Thr Gln Asn Arg Gln Glu Ser Phe Asp Ile Phe Glu Asp Glu Gly
        195                 200                 205

Leu Ile Thr Gln Gly Gly Ser Gly Val Phe Gly Ile Cys Ser Glu Pro
    210                 215                 220

Tyr Met Lys Tyr Val Trp Asn Gly Glu Leu Leu Asp Ile Ile Lys Ser
225                 230                 235                 240

Thr Val His Arg Asp Trp Leu Leu Tyr Ile Ile His Gly Phe Cys Gly
                245                 250                 255

Gln Ser Lys Leu Leu Ile Tyr Gly Arg Pro Val Tyr Val Thr Leu Ile
            260                 265                 270

Ala Arg Arg Ser Ser Lys Phe Ala Gly Thr Arg Phe Leu Lys Arg Gly
        275                 280                 285

Ala Asn Cys Glu Gly Asp Val Ala Asn Glu Val Glu Thr Glu Gln Ile
    290                 295                 300

Leu Cys Asp Ala Ser Val Met Ser Phe Thr Ala Gly Ser Tyr Ser Ser
305                 310                 315                 320

Tyr Val Gln Val Arg Gly Ser Val Pro Leu Tyr Trp Ser Gln Asp Ile
                325                 330                 335

Ser Thr Met Met Pro Lys Pro Pro Ile Thr Leu Asp Gln Ala Asp Pro
            340                 345                 350

Phe Ala His Val Ala Ala Leu His Phe Asp Gln Met Phe Gln Arg Phe
        355                 360                 365

Gly Ser Pro Ile Ile Ile Leu Asn Leu Val Lys Glu Arg Glu Lys Arg
    370                 375                 380

Lys His Glu Arg Ile Leu Ser Glu Glu Leu Val Ala Ala Val Thr Tyr
385                 390                 395                 400

Leu Asn Gln Phe Leu Pro Pro Glu His Thr Ile Val Tyr Ile Pro Trp
                405                 410                 415

Asp Met Ala Lys Tyr Thr Lys Ser Lys Leu Cys Asn Val Leu Asp Arg
            420                 425                 430

Leu Asn Val Ile Ala Glu Ser Val Val Lys Lys Thr Gly Phe Phe Val
        435                 440                 445

Asn Arg Pro Asp Ser Tyr Cys Ser Ile Leu Arg Pro Asp Glu Lys Trp
    450                 455                 460

Asn Glu Leu Gly Gly Cys Val Ile Pro Thr Gly Arg Leu Gln Thr Gly
465                 470                 475                 480

Ile Leu Arg Thr Asn Cys Val Asp Cys Leu Asp Arg Thr Asn Thr Ala
                485                 490                 495

Gln Phe Met Val Gly Lys Cys Ala Leu Ala Tyr Gln Leu Tyr Ser Leu
            500                 505                 510

Gly Leu Ile Asp Lys Pro Asn Leu Gln Phe Asp Thr Asp Ala Val Arg
        515                 520                 525
```

```
Leu Phe Glu Glu Leu Tyr Glu Asp His Gly Asp Thr Leu Ser Leu Gln
    530                 535                 540

Tyr Gly Gly Ser Gln Leu Val His Arg Val Lys Thr Tyr Arg Lys Ile
545                 550                 555                 560

Ala Pro Trp Thr Gln His Ser Lys Asp Ile Met Gln Thr Leu Ser Arg
                565                 570                 575

Tyr Tyr Ser Asn Ala Phe Ser Asp Ala Asp Arg Gln Asp Ser Ile Asn
            580                 585                 590

Leu Phe Leu Gly Val Phe His Pro Thr Glu Gly Lys Pro His Leu Trp
        595                 600                 605

Glu Leu Pro Thr Asp Phe Tyr Leu His His Lys Asn Thr Met Arg Leu
    610                 615                 620

Leu Pro Thr Arg Arg Ser Tyr Thr Tyr Trp Trp Thr Pro Glu Val Ile
625                 630                 635                 640

Lys His Leu Pro Leu Pro Tyr Asp Glu Val Ile Cys Ala Val Asn Leu
                645                 650                 655

Lys Lys Leu Ile Val Lys Lys Phe His Lys Tyr Glu Glu Glu Ile Asp
            660                 665                 670

Ile His Asn Glu Phe Phe Arg Pro Tyr Glu Leu Ser Ser Phe Asp Asp
        675                 680                 685

Thr Phe Cys Leu Ala Met Thr Ser Ser Ala Arg Asp Phe Met Pro Lys
    690                 695                 700

Thr Val Gly Ile Asp Pro Ser Pro Phe Thr Val Arg Lys Pro Asp Glu
705                 710                 715                 720

Thr Gly Lys Ser Val Leu Gly Asn Lys Ser Asn Arg Glu Glu Ala Val
                725                 730                 735

Leu Gln Arg Lys Thr Ala Ala Ser Ala Pro Pro Pro Pro Ser Glu Glu
            740                 745                 750

Ala Val Ser Ser Ser Ser Glu Asp Asp Ser Gly Thr Asp Arg Glu Glu
        755                 760                 765

Glu Gly Ser Val Ser Gln Arg Ser Thr Pro Val Lys Met Thr Asp Ala
    770                 775                 780

Gly Asp Ser Ala Lys Val Thr Glu Asn Val Val Gln Pro Met Lys Glu
785                 790                 795                 800

Leu Tyr Gly Ile Asn Leu Ser Asp Gly Leu Ser Glu Glu Asp Phe Ser
                805                 810                 815

Ile Tyr Ser Arg Phe Val Gln Leu Gly Gln Ser Gln His Lys Gln Asp
            820                 825                 830

Lys Asn Ser Gln Gln Pro Cys Ser Arg Cys Ser Asp Gly Val Ile Lys
        835                 840                 845

Leu Thr Pro Ile Ser Ala Phe Ser Gln Asp Asn Ile Tyr Glu Val Gln
    850                 855                 860

Pro Pro Arg Val Asp Arg Lys Ser Thr Glu Ile Phe Gln Ala His Ile
865                 870                 875                 880

Gln Ala Ser Gln Gly Ile Met Gln Pro Leu Gly Lys Glu Asp Ser Ser
                885                 890                 895

Met Tyr Arg Glu Tyr Ile Arg Asn Arg Tyr Leu
            900                 905
```

<210> SEQ ID NO 149
<211> LENGTH: 2241
<212> TYPE: DNA
<213> ORGANISM: Homo sapiens

<400> SEQUENCE: 149

```
atggacttct tggaggagcc aatccctggt gtagggacct atgatgattt caatacaatt      60
gattgggtga gagagaagtc tcgagaccgg gataggcacc gagagattac caataaaagc     120
aaagagtcaa catgggcctt aattcacagt gtgagtgatg ctttttccgg ctggttgttg     180
atgctcctta ttgggctttt atcaggttcg ttagctggtt tgatagacat ctctgctcat     240
tggatgacag acttaaaaga aggtatatgc acagggggat tctggtttaa ccatgaacat     300
tgttgctgga actctgagca tgtcaccttt gaagagagag acaaatgtcc agagtggaat     360
agttggtccc agcttatcat cagcacagat gagggagcct ttgcctacat agtcaattat     420
ttcatgtacg tcctctgggc tctcctattt gccttccttg ccgtatctct tgtcaaggtg     480
tttgcgcctt atgcctgtgg ctctggaatc cctgagataa aaactatctt gagtggtttc     540
attattaggg gctatttggg taagtggact ctggttatca aaaccatcac cttggtgctg     600
gcagtgtcat ctggcttgag cctgggcaaa gagggccctc tagtgcacgt ggcttgctgc     660
tgtgggaaca tcctgtgcca ctgcttcaac aaatacagga agaatgaagc caagcgcaga     720
gaggtcttgt cggctgcagc agcagctggt gtatctgtag cctttggagc acctataggt     780
ggagtattat tcagccttga agaggtcagc tactattttc ccctcaaaac attgtggcgt     840
tcattctttg ctgccttggt ggcagcattc actctacgct ccatcaatcc atttgggaac     900
agccgcctgg tactatttta tgtggagttt cacaccccat ggcatctctt tgagctcgtg     960
ccattcattc tgctgggcat atttggtggt ctgtggggag cactgtttat ccgcacaaac    1020
attgcctggt gtcggaagcg aaagaccacc cagttgggca agtatcctgt tatagaggta    1080
ctcgtcgtga cagccatcac tgccatcctg gctttcccca atgaatacac tcggatgagc    1140
acaagtgagc tcatttctga gctgtttaat gactgtggcc ttctggactc ctccaagctc    1200
tgtgattatg agaaccgttt caacacaagc aaagggggtg aactgcctga cagaccggct    1260
ggcgtgggag tctacagtgc aatgtggcag ctggctttaa cactcatact gaaaattgtc    1320
attactatat tcacctttgg catgaagatc ccttctggcc tctttatccc tagcatggct    1380
gttggtgcta tagcaggtcg acttctagga gtaggaatgg aacagctggc ttattaccac    1440
caggaatgga ccgtcttcaa tagctggtgt agtcagggag ctgattgcat cacccccggc    1500
ctttatgcaa tggttggggc tgcagcctgc ttaggtgggg tgactcggat gactgtttct    1560
cttgttgtca taatgtttga actgactggt ggcttagaat acatcgtgcc tctgatggct    1620
gcagccatga caagcaagtg ggtggcagat gctcttgggc gggagggcat ctatgatgcc    1680
cacatccgtc tcaatggata ccccttttctt gaagccaaag aagagtttgc tcataagacc    1740
ctggcaatgg atgtgatgaa accccggaga aatgatcctt tgttgactgt ccttactcag    1800
gacagtatga ctgtggaaga tgtagagacc ataatcagtg aaaccactta cagtggcttc    1860
ccagtggtgg tatcccggga gtcccaaaga cttgtgggct ttgtcctccg aagagatctc    1920
attatttcaa ttgaaaatgc tcgaaagaaa caggatgggg ttgttagcac ttccatcatt    1980
tatttcacgg agcattctcc tccattgcca ccatacactc cacccactct aaagcttcgg    2040
aacatcctcg atctcagccc cttcactgtg actgacctta cacccatgga gatcgtagtg    2100
gatattttcc gaaagctggg actgcggcag tgcctggtta cacacaacgg gcgattgctt    2160
ggaatcatta ccaaaaagga tgtgttaaag catatagcac agatggcgaa ccaagatcct    2220
gattccattc tcttcaacta g                                              2241
```

<210> SEQ ID NO 150
<211> LENGTH: 746
<212> TYPE: PRT
<213> ORGANISM: Homo sapiens

<400> SEQUENCE: 150

```
Met Asp Phe Leu Glu Glu Pro Ile Pro Gly Val Gly Thr Tyr Asp Asp
1               5                   10                  15

Phe Asn Thr Ile Asp Trp Val Arg Glu Lys Ser Arg Asp Arg Asp Arg
            20                  25                  30

His Arg Glu Ile Thr Asn Lys Ser Lys Glu Ser Thr Trp Ala Leu Ile
        35                  40                  45

His Ser Val Ser Asp Ala Phe Ser Gly Trp Leu Leu Met Leu Leu Ile
    50                  55                  60

Gly Leu Leu Ser Gly Ser Leu Ala Gly Leu Ile Asp Ile Ser Ala His
65                  70                  75                  80

Trp Met Thr Asp Leu Lys Glu Gly Ile Cys Thr Gly Gly Phe Trp Phe
                85                  90                  95

Asn His Glu His Cys Cys Trp Asn Ser Glu His Val Thr Phe Glu Glu
            100                 105                 110

Arg Asp Lys Cys Pro Glu Trp Asn Ser Trp Ser Gln Leu Ile Ile Ser
        115                 120                 125

Thr Asp Glu Gly Ala Phe Ala Tyr Ile Val Asn Tyr Phe Met Tyr Val
    130                 135                 140

Leu Trp Ala Leu Leu Phe Ala Phe Leu Ala Val Ser Leu Val Lys Val
145                 150                 155                 160

Phe Ala Pro Tyr Ala Cys Gly Ser Gly Ile Pro Glu Ile Lys Thr Ile
                165                 170                 175

Leu Ser Gly Phe Ile Ile Arg Gly Tyr Leu Gly Lys Trp Thr Leu Val
            180                 185                 190

Ile Lys Thr Ile Thr Leu Val Leu Ala Val Ser Ser Gly Leu Ser Leu
        195                 200                 205

Gly Lys Glu Gly Pro Leu Val His Val Ala Cys Cys Cys Gly Asn Ile
    210                 215                 220

Leu Cys His Cys Phe Asn Lys Tyr Arg Lys Asn Glu Ala Lys Arg Arg
225                 230                 235                 240

Glu Val Leu Ser Ala Ala Ala Ala Ala Gly Val Ser Val Ala Phe Gly
                245                 250                 255

Ala Pro Ile Gly Gly Val Leu Phe Ser Leu Glu Glu Val Ser Tyr Tyr
            260                 265                 270

Phe Pro Leu Lys Thr Leu Trp Arg Ser Phe Phe Ala Ala Leu Val Ala
        275                 280                 285

Ala Phe Thr Leu Arg Ser Ile Asn Pro Phe Gly Asn Ser Arg Leu Val
    290                 295                 300

Leu Phe Tyr Val Glu Phe His Thr Pro Trp His Leu Phe Glu Leu Val
305                 310                 315                 320

Pro Phe Ile Leu Leu Gly Ile Phe Gly Gly Leu Trp Gly Ala Leu Phe
                325                 330                 335

Ile Arg Thr Asn Ile Ala Trp Cys Arg Lys Arg Lys Thr Thr Gln Leu
            340                 345                 350

Gly Lys Tyr Pro Val Ile Glu Val Leu Val Val Thr Ala Ile Thr Ala
        355                 360                 365

Ile Leu Ala Phe Pro Asn Glu Tyr Thr Arg Met Ser Thr Ser Glu Leu
    370                 375                 380
```

```
Ile Ser Glu Leu Phe Asn Asp Cys Gly Leu Leu Asp Ser Ser Lys Leu
385                 390                 395                 400

Cys Asp Tyr Glu Asn Arg Phe Asn Thr Ser Lys Gly Gly Glu Leu Pro
                405                 410                 415

Asp Arg Pro Ala Gly Val Gly Val Tyr Ser Ala Met Trp Gln Leu Ala
            420                 425                 430

Leu Thr Leu Ile Leu Lys Ile Val Ile Thr Ile Phe Thr Phe Gly Met
        435                 440                 445

Lys Ile Pro Ser Gly Leu Phe Ile Pro Ser Met Ala Val Gly Ala Ile
    450                 455                 460

Ala Gly Arg Leu Leu Gly Val Gly Met Glu Gln Leu Ala Tyr Tyr His
465                 470                 475                 480

Gln Glu Trp Thr Val Phe Asn Ser Trp Cys Ser Gln Gly Ala Asp Cys
                485                 490                 495

Ile Thr Pro Gly Leu Tyr Ala Met Val Gly Ala Ala Ala Cys Leu Gly
            500                 505                 510

Gly Val Thr Arg Met Thr Val Ser Leu Val Val Ile Met Phe Glu Leu
        515                 520                 525

Thr Gly Gly Leu Glu Tyr Ile Val Pro Leu Met Ala Ala Ala Met Thr
    530                 535                 540

Ser Lys Trp Val Ala Asp Ala Leu Gly Arg Glu Gly Ile Tyr Asp Ala
545                 550                 555                 560

His Ile Arg Leu Asn Gly Tyr Pro Phe Leu Glu Ala Lys Glu Glu Phe
                565                 570                 575

Ala His Lys Thr Leu Ala Met Asp Val Met Lys Pro Arg Arg Asn Asp
            580                 585                 590

Pro Leu Leu Thr Val Leu Thr Gln Asp Ser Met Thr Val Glu Asp Val
        595                 600                 605

Glu Thr Ile Ile Ser Glu Thr Thr Tyr Ser Gly Phe Pro Val Val Val
    610                 615                 620

Ser Arg Glu Ser Gln Arg Leu Val Gly Phe Val Leu Arg Arg Asp Leu
625                 630                 635                 640

Ile Ile Ser Ile Glu Asn Ala Arg Lys Lys Gln Asp Gly Val Val Ser
                645                 650                 655

Thr Ser Ile Ile Tyr Phe Thr Glu His Ser Pro Pro Leu Pro Pro Tyr
            660                 665                 670

Thr Pro Pro Thr Leu Lys Leu Arg Asn Ile Leu Asp Leu Ser Pro Phe
        675                 680                 685

Thr Val Thr Asp Leu Thr Pro Met Glu Ile Val Val Asp Ile Phe Arg
    690                 695                 700

Lys Leu Gly Leu Arg Gln Cys Leu Val Thr His Asn Gly Arg Leu Leu
705                 710                 715                 720

Gly Ile Ile Thr Lys Lys Asp Val Leu Lys His Ile Ala Gln Met Ala
                725                 730                 735

Asn Gln Asp Pro Asp Ser Ile Leu Phe Asn
            740                 745
```

<210> SEQ ID NO 151
<211> LENGTH: 828
<212> TYPE: DNA
<213> ORGANISM: Homo sapians

<400> SEQUENCE: 151
atgacagatg acaaagatgt gcttcgagat gtgtggtttg gacgaattcc aacttgtttc     60

```
acgctatatc aggatgagat aactgaaagg gaagcagaac catactattt gcttttgcca    120

agagtaagtt atttgacgtt ggtaactgac aaagtgaaaa agcactttca gaaggttatg    180

agacaagaag acattagtga gatatggttt gaatatgaag gcacaccact gaaatggcat    240

tatccaattg gtttgctatt tgatcttctt gcatcaagtt cagctcttcc ttggaacatc    300

acagtacatt ttaagagttt tccagaaaaa gaccttctgc actgtccatc taaggatgca    360

attgaagctc attttatgtc atgtatgaaa gaagctgatg ctttaaaaca taaaagtcaa    420

gtaatcaatg aaatgcagaa aaaagatcac aagcaactct ggatgggatt gcaaaatgac    480

agatttgacc agttttgggc catcaatcgg aaactcatgg aatatcctgc agaagaaaat    540

ggatttcgtt atatcccctt tagaatatat cagacaacga ctgaaagacc tttcattcag    600

aagctgtttc gtcctgtggc tgcagatgga cagttgcaca cactaggaga tctcctcaaa    660

gaagtttgtc cttctgctat tgatcctgaa gatggggaaa aaaagaatca agtgatgatt    720

catggaattg agccaatgtt ggaaacacct ctgcagtggc tgagtgaaca tctgagctac    780

ccggataatt ttcttcatat tagtatcatc ccacagccaa cagattga                 828
```

```
<210> SEQ ID NO 152
<211> LENGTH: 275
<212> TYPE: PRT
<213> ORGANISM: Homo sapiens

<400> SEQUENCE: 152

Met Thr Asp Asp Lys Asp Val Leu Arg Asp Val Trp Phe Gly Arg Ile
1               5                   10                  15

Pro Thr Cys Phe Thr Leu Tyr Gln Asp Glu Ile Thr Glu Arg Glu Ala
            20                  25                  30

Glu Pro Tyr Tyr Leu Leu Leu Pro Arg Val Ser Tyr Leu Thr Leu Val
        35                  40                  45

Thr Asp Lys Val Lys Lys His Phe Gln Lys Val Met Arg Gln Glu Asp
    50                  55                  60

Ile Ser Glu Ile Trp Phe Glu Tyr Glu Gly Thr Pro Leu Lys Trp His
65                  70                  75                  80

Tyr Pro Ile Gly Leu Leu Phe Asp Leu Leu Ala Ser Ser Ser Ala Leu
                85                  90                  95

Pro Trp Asn Ile Thr Val His Phe Lys Ser Phe Pro Glu Lys Asp Leu
            100                 105                 110

Leu His Cys Pro Ser Lys Asp Ala Ile Glu Ala His Phe Met Ser Cys
        115                 120                 125

Met Lys Glu Ala Asp Ala Leu Lys His Lys Ser Gln Val Ile Asn Glu
    130                 135                 140

Met Gln Lys Lys Asp His Lys Gln Leu Trp Met Gly Leu Gln Asn Asp
145                 150                 155                 160

Arg Phe Asp Gln Phe Trp Ala Ile Asn Arg Lys Leu Met Glu Tyr Pro
                165                 170                 175

Ala Glu Glu Asn Gly Phe Arg Tyr Ile Pro Phe Arg Ile Tyr Gln Thr
            180                 185                 190

Thr Thr Glu Arg Pro Phe Ile Gln Lys Leu Phe Arg Pro Val Ala Ala
        195                 200                 205

Asp Gly Gln Leu His Thr Leu Gly Asp Leu Leu Lys Glu Val Cys Pro
    210                 215                 220

Ser Ala Ile Asp Pro Glu Asp Gly Glu Lys Lys Asn Gln Val Met Ile
225                 230                 235                 240
```

His Gly Ile Glu Pro Met Leu Glu Thr Pro Leu Gln Trp Leu Ser Glu
245 250 255

His Leu Ser Tyr Pro Asp Asn Phe Leu His Ile Ser Ile Ile Pro Gln
260 265 270

Pro Thr Asp
275

<210> SEQ ID NO 153
<211> LENGTH: 2112
<212> TYPE: DNA
<213> ORGANISM: Homo sapiens

<400> SEQUENCE: 153
atggcggcag ctacgggggga tcctggactc tctaaactgc agtttgcccc ttttagtagt 60
gccttggatg ttgggttttg gcatgagttg acccagaaga agctgaacga gtatcggctg 120
gatgaagctc ccaaggacat taagggttat tactacaatg gtgactctgc tgggctgcca 180
gctcgcttaa cattggagtt cagtgctttt gacatgagtg ctcccacccc agcccgttgc 240
tgcccagcta ttggaacact gtataacacc aacacactcg agtctttcaa gactgcagat 300
aagaagctcc ttttggaaca agcagcaaat gagatatggg aatccataaa atcaggcact 360
gctcttgaaa accctgtact cctcaacaag ttcctcctct tgacatttgc agatctaaag 420
aagtaccact tctactattg gttttgctat cctgccctct gtcttccaga gagtttacct 480
ctcattcagg ggccagtggg tttggatcaa aggttttcac taaaacagat tgaagcacta 540
gagtgtgcat atgataatct ttgtcaaaca gaaggagtca cagctcttcc ttacttctta 600
atcaagtatg atgagaacat ggtgctggtt tccttgctta aacactacag tgatttcttc 660
caaggtcaaa ggacgaagat aacaattggt gtatatgatc cctgtaactt agcccagtac 720
cctggatggc ctttgaggaa tttttggtc ctagcagccc acagatggag tagcagtttc 780
cagtctgttg aagttgtttg cttccgtgac cgtaccatgc agggggcgag agacgttgcc 840
cacagcatca tcttcgaagt gaagcttcca gaaatggcat ttagcccaga ttgtcctaaa 900
gcagttggat gggaaaagaa ccagaaagga ggcatgggac caaggatggt gaacctcagt 960
gaatgtatgg accctaaaag gttagctgag tcatcagtgg atctaaatct caaactgatg 1020
tgttggagat tggttcctac tttagacttg gacaaggttg tgtctgtcaa atgtctgctg 1080
cttggagccg gcaccttggg ttgcaatgta gctaggacgt tgatgggttg ggcgtgaga 1140 cacatcacat ttgtggacaa tgccaagatc tcctactcca atcctgtgag gcagcctctc 1200
tatgagtttg aagattgcct agggggtggt aagcccaagg ctctggcagc agcggaccgg 1260
ctccagaaaa tattccccgg tgtgaatgcc agaggattca acatgagcat acctatgcct 1320
gggcatccag tgaacttctc cagtgtcact ctggagcaag cccgcagaga tgtggagcaa 1380
ctggagcagc tcatcgaaag ccatgatgtc gtcttcctat tgatggacac cagggagagc 1440
cggtggcttc ctgccgtcat tgctgcaagc aagagaaagc tggtcatcaa tgctgctttg 1500
ggatttgaca catttgttgt catgagacat ggtctgaaga aaccaaagca gcaaggagct 1560
ggggacttgt gtccaaacca ccctgtggca tctgctgacc tcctgggctc atcgcttttt 1620
gccaacatcc ctggttacaa gcttggctgc tacttctgca atgatgtggt ggccccagga 1680
gattcaacca gagaccggac cttggaccag cagtgcactg tgagtcgtcc aggactggcc 1740
gtgattgcag gagccctggc cgtggaattg atggtatctg ttttgcagca tccagaaggg 1800
ggctatgcca ttgccagcag cagtgacgat cggatgaatg agcctccaac ctctcttggg 1860
cttgtgcctc accagatccg gggatttctt tcacggtttg ataatgtcct tcccgtcagc 1920
ctggcatttg acaaatgtac agcttgttct tccaaagttc ttgatcaata tgaacgagaa 1980
ggatttaact tcctagccaa ggtgtttaat tcttcacatt ccttcttaga agacttgact 2040
ggtcttacat tgctgcatca agaaacccaa gctgctgaga tctgggacat gagcgatgat 2100
gagaccatct ga 2112

<210> SEQ ID NO 154
<211> LENGTH: 703
<212> TYPE: PRT
<213> ORGANISM: Homo sapiens

<400> SEQUENCE: 154

Met Ala Ala Ala Thr Gly Asp Pro Gly Leu Ser Lys Leu Gln Phe Ala
1 5 10 15

Pro Phe Ser Ser Ala Leu Asp Val Gly Phe Trp His Glu Leu Thr Gln
20 25 30

Lys Lys Leu Asn Glu Tyr Arg Leu Asp Glu Ala Pro Lys Asp Ile Lys
35 40 45

Gly Tyr Tyr Tyr Asn Gly Asp Ser Ala Gly Leu Pro Ala Arg Leu Thr
50 55 60

Leu Glu Phe Ser Ala Phe Asp Met Ser Ala Pro Thr Pro Ala Arg Cys
65 70 75 80

Cys Pro Ala Ile Gly Thr Leu Tyr Asn Thr Asn Thr Leu Glu Ser Phe
85 90 95

Lys Thr Ala Asp Lys Lys Leu Leu Leu Glu Gln Ala Ala Asn Glu Ile
100 105 110

Trp Glu Ser Ile Lys Ser Gly Thr Ala Leu Glu Asn Pro Val Leu Leu
115 120 125

Asn Lys Phe Leu Leu Leu Thr Phe Ala Asp Leu Lys Lys Tyr His Phe
130 135 140

Tyr Tyr Trp Phe Cys Tyr Pro Ala Leu Cys Leu Pro Glu Ser Leu Pro
145 150 155 160

Leu Ile Gln Gly Pro Val Gly Leu Asp Gln Arg Phe Ser Leu Lys Gln
165 170 175

Ile Glu Ala Leu Glu Cys Ala Tyr Asp Asn Leu Cys Gln Thr Glu Gly
180 185 190

Val Thr Ala Leu Pro Tyr Phe Leu Ile Lys Tyr Asp Glu Asn Met Val
195 200 205

Leu Val Ser Leu Leu Lys His Tyr Ser Asp Phe Phe Gln Gly Gln Arg
210 215 220

Thr Lys Ile Thr Ile Gly Val Tyr Asp Pro Cys Asn Leu Ala Gln Tyr
225 230 235 240

Pro Gly Trp Pro Leu Arg Asn Phe Leu Val Leu Ala Ala His Arg Trp
245 250 255

Ser Ser Ser Phe Gln Ser Val Glu Val Val Cys Phe Arg Asp Arg Thr
260 265 270

Met Gln Gly Ala Arg Asp Val Ala His Ser Ile Ile Phe Glu Val Lys
275 280 285

Leu Pro Glu Met Ala Phe Ser Pro Asp Cys Pro Lys Ala Val Gly Trp
290 295 300

Glu Lys Asn Gln Lys Gly Gly Met Gly Pro Arg Met Val Asn Leu Ser
305 310 315 320

Glu Cys Met Asp Pro Lys Arg Leu Ala Glu Ser Ser Val Asp Leu Asn

```
                325                 330                 335

Leu Lys Leu Met Cys Trp Arg Leu Val Pro Thr Leu Asp Leu Asp Lys
            340                 345                 350

Val Val Ser Val Lys Cys Leu Leu Leu Gly Ala Gly Thr Leu Gly Cys
        355                 360                 365

Asn Val Ala Arg Thr Leu Met Gly Trp Gly Val Arg His Ile Thr Phe
    370                 375                 380

Val Asp Asn Ala Lys Ile Ser Tyr Ser Asn Pro Val Arg Gln Pro Leu
385                 390                 395                 400

Tyr Glu Phe Glu Asp Cys Leu Gly Gly Gly Lys Pro Lys Ala Leu Ala
                405                 410                 415

Ala Ala Asp Arg Leu Gln Lys Ile Phe Pro Gly Val Asn Ala Arg Gly
            420                 425                 430

Phe Asn Met Ser Ile Pro Met Pro Gly His Pro Val Asn Phe Ser Ser
        435                 440                 445

Val Thr Leu Glu Gln Ala Arg Arg Asp Val Glu Gln Leu Glu Gln Leu
    450                 455                 460

Ile Glu Ser His Asp Val Val Phe Leu Leu Met Asp Thr Arg Glu Ser
465                 470                 475                 480

Arg Trp Leu Pro Ala Val Ile Ala Ala Ser Lys Arg Lys Leu Val Ile
                485                 490                 495

Asn Ala Ala Leu Gly Phe Asp Thr Phe Val Val Met Arg His Gly Leu
            500                 505                 510

Lys Lys Pro Lys Gln Gln Gly Ala Gly Asp Leu Cys Pro Asn His Pro
        515                 520                 525

Val Ala Ser Ala Asp Leu Leu Gly Ser Ser Leu Phe Ala Asn Ile Pro
    530                 535                 540

Gly Tyr Lys Leu Gly Cys Tyr Phe Cys Asn Asp Val Val Ala Pro Gly
545                 550                 555                 560

Asp Ser Thr Arg Asp Arg Thr Leu Asp Gln Gln Cys Thr Val Ser Arg
                565                 570                 575

Pro Gly Leu Ala Val Ile Ala Gly Ala Leu Ala Val Glu Leu Met Val
            580                 585                 590

Ser Val Leu Gln His Pro Glu Gly Gly Tyr Ala Ile Ala Ser Ser Ser
        595                 600                 605

Asp Asp Arg Met Asn Glu Pro Pro Thr Ser Leu Gly Leu Val Pro His
    610                 615                 620

Gln Ile Arg Gly Phe Leu Ser Arg Phe Asp Asn Val Leu Pro Val Ser
625                 630                 635                 640

Leu Ala Phe Asp Lys Cys Thr Ala Cys Ser Ser Lys Val Leu Asp Gln
                645                 650                 655

Tyr Glu Arg Glu Gly Phe Asn Phe Leu Ala Lys Val Phe Asn Ser Ser
            660                 665                 670

His Ser Phe Leu Glu Asp Leu Thr Gly Leu Thr Leu Leu His Gln Glu
        675                 680                 685

Thr Gln Ala Ala Glu Ile Trp Asp Met Ser Asp Asp Glu Thr Ile
    690                 695                 700
```

<210> SEQ ID NO 155
<211> LENGTH: 7650
<212> TYPE: DNA
<213> ORGANISM: Homo sapiens

<400> SEQUENCE: 155

-continued

```
atgcttggaa ccggacctgc cgccgccacc accgctgcca ccacatctag caatgtgagc     60
gtcctgcagc agtttgccag tggcctaaag agccggaatg aggaaaccag ggccaaagcc    120
gccaaggagc tccagcacta tgtcaccatg gaactccgag agatgagtca agaggagtct    180
actcgcttct atgaccaact gaaccatcac atttttgaat tggtttccag ctcagatgcc    240
aatgagagga aaggtggcat cttggccata gctagcctca taggagtgga aggtgggaat    300
gccacccgaa ttggcagatt tgccaactat cttcggaacc tcctcccctc caatgaccca    360
gttgtcatgg aaatggcatc caaggccatt ggccgtcttg ccatggcagg ggacactttt    420
accgctgagt acgtggaatt tgaggtgaag cgagccctgg aatggctggg tgctgaccgc    480
aatgagggcc ggagacatgc agctgtcctg gttctccgtg agctggccat cagcgtccct    540
accttcttct tccagcaagt gcaacccttc tttgacaaca tttttgtggc cgtgtgggac    600
cccaaacagg ccatccgtga gggagctgta gccgcccttc gtgcctgtct gattctcaca    660
acccagcgtg agccgaagga gatgcagaag cctcagtggt acaggcacac atttgaagaa    720
gcagagaagg gatttgatga gaccttggcc aaagagaagg gcatgaatcg ggatgatcgg    780
atccatggag ccttgttgat ccttaacgag ctggtccgaa tcagcagcat ggagggagag    840
cgtctgagag aagaaatgga agaaatcaca cagcagcagc tggtacacga caagtactgc    900
aaagatctca tgggcttcgg aacaaaacct cgtcacatta ccccccttcac cagtttccag    960
gctgtacagc cccagcagtc aaatgccttg gtggggctgc tggggtacag ctctcaccaa   1020
ggcctcatgg gatttgggac ctcccccagt ccagctaagt ccaccctggt ggagagccgg   1080
tgttgcagag acttgatgga ggagaaattt gatcaggtgt gccagtgggt gctgaaatgc   1140
aggaatagca agaactcgct gatccaaatg acaatcctta atttgttgcc ccgcttggct   1200
gcattccgac cttctgcctt cacagatacc cagtatctcc aagataccat gaaccatgtc   1260
ctaagctgtg tcaagaagga gaaggaacgt acagcggcct tccaagccct ggggctactt   1320
tctgtggctg tgaggtctga gtttaaggtc tatttgcctc gcgtgctgga catcatccga   1380
gcggccctgc ccccaaagga cttcgcccat aagaggcaga aggcaatgca ggtggatgcc   1440
acagtcttca cttgcatcag catgctggct cgagcaatgg ggccaggcat ccagcaggat   1500
atcaaggagc tgctggagcc catgctggca gtgggactaa gccctgccct cactgcagtg   1560
ctctacgacc tgagccgtca gattccacag ctaaagaagg acattcaaga tgggctactg   1620
aaaatgctgt ccctggtcct tatgcacaaa ccccttcgcc acccaggcat gcccaagggc   1680
ctggcccatc agctggcctc tcctggcctc acgaccctcc ctgaggccag cgatgtgggc   1740
agcatcactc ttgccctccg aacgcttggc agctttgaat ttgaaggcca ctctctgacc   1800
caatttgttc gccactgtgc ggatcatttc ctgaacagtg agcacaagga gatccgcatg   1860
gaggctgccc gcacctgctc ccgcctgctc acaccctcca tccacctcat cagtggccat   1920
gctcatgtgg ttagccagac cgcagtgcaa gtggtggcag atgtgcttag caaactgctc   1980
gtagttggga taacagatcc tgaccctgac attcgctact gtgtcttggc gtccctggac   2040
gagcgctttg atgcacacct ggcccaggcg gagaacttgc aggccttgtt tgtggctctg   2100
aatgaccagg tgtttgagat ccgggagctg gccatctgca ctgtgggccg actcagtagc   2160
atgaaccctg cctttgtcat gcctttcctg cgcaagatgc tcatccagat tttgacagag   2220
ttggagcaca gtgggattgg aagaatcaaa gagcagagtg cccgcatgct ggggcacctg   2280
gtctccaatg ccccccgact catccgcccc tacatggagc ctattctgaa ggcattaatt   2340
ttgaaactga aagatccaga ccctgatcca aacccaggtg tgatcaataa tgtcctggca   2400
```

```
acaataggag aattggcaca ggttagtggc ctggaaatga ggaaatgggt tgatgaactt   2460
tttattatca tcatggacat gctccaggat tcctctttgt tggccaaaag gcaggtggct   2520
ctgtggaccc tgggacagtt ggtggccagc actggctatg tagtagagcc ctacaggaag   2580
taccctactt tgcttgaggt gctactgaat tttctgaaga ctgagcagaa ccagggtaca   2640
cgcagagagg ccatccgtgt gttagggctt ttaggggctt tggatcctta caagcacaaa   2700
gtgaacattg gcatgataga ccagtcccgg gatgcctctg ctgtcagcct gtcagaatcc   2760
aagtcaagtc aggattcctc tgactatagc actagtgaaa tgctggtcaa catgggaaac   2820
ttgcctctgg atgagttcta cccagctgtg tccatggtgg ccctgatgcg gatcttccga   2880
gaccagtcac tctctcatca tcacaccatg gttgtccagg ccatcacctt catcttcaag   2940
tccctgggac tcaaatgtgt gcagttcctg ccccaggtca tgcccacgtt ccttaacgtc   3000
attcgagtct gtgatggggc catccgggaa tttttgttcc agcagctggg aatgttggtg   3060
tcctttgtga agagccacat cagaccttat atggatgaaa tagtcaccct catgagagaa   3120
ttctgggtca tgaacacctc aattcagagc acgatcattc ttctcattga gcaaattgtg   3180
gtagctcttg gggtgaatt taagctctac ctgccccagc tgatcccaca catgctgcgt   3240
gtcttcatgc atgacaacag cccaggccgc attgtctcta tcaagttact ggctgcaatc   3300
cagctgtttg gcgccaacct ggatgactac ctgcatttac tgctgcctcc tattgttaag   3360
ttgtttgatg cccctgaagc tccactgcca tctcgaaagg cagcgctaga gactgtggac   3420
cgcctgacgg agtccctgga tttcactgac tatgcctccc ggatcattca ccctattgtt   3480
cgaacactgg accagagccc agaactgcgc tccacagcca tggacacgct gtcttcactt   3540
gtttttcagc tggggaagaa gtaccaaatt ttcattccaa tggtgaataa agttctggtg   3600
cgacaccgaa tcaatcatca gcgctatgat gtgctcatct gcagaattgt caagggatac   3660
acacttgctg atgaagagga ggatcctttg atttaccagc atcggatgct taggagtggc   3720
caaggggatg cattggctag tggaccagtg gaaacaggac ccatgaagaa actgcacgtc   3780
agcaccatca acctccaaaa ggcctggggc gctgccagga gggtctccaa agatgactgg   3840
ctggaatggc tgagacggct gagcctggag ctgctgaagg actcatcatc gccctccctg   3900
cgctcctgct gggccctggc acaggcctac aacccgatgg ccagggatct cttcaatgct   3960
gcatttgtgt cctgctggtc tgaactgaat gaagatcaac aggatgagct catcagaagc   4020
atcgagttgg ccctcacctc acaagacatc gctgaagtca cacagaccct cttaaacttg   4080
gctgaattca tggaacacag tgacaagggc cccctgccac tgagagatga caatggcatt   4140
gttctgctgg gtgagagagc tgccaagtgc cgagcatatg ccaaagcact acactacaaa   4200
gaactggagt tccagaaagg ccccaccct gccattctag aatctctcat cagcattaat   4260
aataagctac agcagccgga ggcagcggcc ggagtgttag aatatgccat gaaacacttt   4320
ggagagctgg agatccaggc tacctggtat gagaaactgc acgagtggga ggatgccctt   4380
gtggcctatg acaagaaaat ggacaccaac aaggacgacc cagagctgat gctgggccgc   4440
atgcgctgcc tcgaggcctt gggggaatgg ggtcaactcc accagcagtg ctgtgaaaag   4500
tggaccctgg ttaatgatga gacccaagcc aagatggccc ggatggctgc tgcagctgca   4560
tggggtttag gtcagtggga cagcatggaa gaatacacct gtatgatccc tcgggacacc   4620
catgatgggg cattttatag agctgtgctg gcactgcatc aggacctctt ctccttggca   4680
caacagtgca ttgacaaggc cagggacctg ctggatgctg aattaactgc gatggcagga   4740
```

-continued

```
gagagttaca gtcgggcata tggggccatg gtttcttgcc acatgctgtc cgagctggag   4800
gaggttatcc agtacaaact tgtccccgag cgacgagaga tcatccgcca gatctggtgg   4860
gagagactgc agggctgcca gcgtatcgta gaggactggc agaaaatcct tatggtgcgg   4920
tcccttgtgg tcagccctca tgaagacatg agaacctggc tcaagtatgc aagcctgtgc   4980
ggcaagagtg gcaggctggc tcttgctcat aaaactttag tgttgctcct gggagttgat   5040
ccgtctcggc aacttgacca tcctctgcca acagttcacc ctcaggtgac ctatgcctac   5100
atgaaaaaca tgtggaagag tgcccgcaag atcgatgcct tccagcacat gcagcatttt   5160
gtccagacca tgcagcaaca ggcccagcat gccatcgcta ctgaggacca gcagcataag   5220
caggaactgc acaagctcat ggcccgatgc ttcctgaaac ttggagagtg gcagctgaat   5280
ctacagggca tcaatgagag cacaatcccc aaagtgctgc agtactacag cgccgccaca   5340
gagcacgacc gcagctggta caaggcctgg catgcgtggg cagtgatgaa cttcgaagct   5400
gtgctacact acaaacatca gaaccaagcc cgcgatgaga agaagaaact gcgtcatgcc   5460
agcggggcca acatcaccaa cgccaccact gccgccacca cggccgccac tgccaccacc   5520
actgccagca ccgagggcag caacagtgag agcgaggccg agagcaccga gaacagcccc   5580
accccatcgc cgctgcagaa gaaggtcact gaggatctgt ccaaaaccct cctgatgtac   5640
acggtgcctg ccgtccaggg cttcttccgt tccatctcct tgtcacgagg caacaacctc   5700
caggatacac tcagagttct caccttatgg tttgattatg gtcactggcc agatgtcaat   5760
gaggccttag tggagggggt gaaagccatc cagattgata cctggctaca ggttatacct   5820
cagctcattg caagaattga tacgcccaga cccttggtgg gacgtctcat tcaccagctt   5880
ctcacagaca ttggtcggta ccacccccag gccctcatct acccactgac agtggcttct   5940
aagtctacca cgacagcccg gcacaatgca gccaacaaga ttctgaagaa catgtgtgag   6000
cacagcaaca ccctggtcca gcaggccatg atggtgagcg aggagctgat ccgagtggcc   6060
atcctctggc atgagatgtg gcatgaaggc ctggaagagg catctcgttt gtactttggg   6120
gaaaggaacg tgaaaggcat gtttgaggtg ctggagccct tgcatgctat gatggaacgg   6180
ggcccccaga ctctgaagga aacatccttt aatcaggcct atggtcgaga tttaatggag   6240
gcccaagagt ggtgcaggaa gtacatgaaa tcagggaatg tcaaggacct cacccaagcc   6300
tgggacctct attatcatgt gttccgacga atctcaaagc agctgcctca gctcacatcc   6360
ttagagctgc aatatgtttc cccaaaactt ctgatgtgcc gggaccttga attggctgtg   6420
ccaggaacat atgaccccaa ccagccaatc attcgcattc agtccatagc accgtctttg   6480
caagtcatca catccaagca gaggccccgg aaattgacac ttatgggcag caacggacat   6540
gagtttgttt tccttctaaa aggccatgaa gatctgcgcc aggatgagcg tgtgatgcag   6600
ctcttcggcc tggttaacac ccttctggcc aatgacccaa catctcttcg gaaaaacctc   6660
agcatccaga gatacgctgt catcccttta tcgaccaact cgggcctcat tggctgggtt   6720
ccccactgtg acacactgca cgccctcatc cgggactaca gggagaagaa gaagatcctt   6780
ctcaacatcg agcatcgcat catgttgcgg atggctccgg actatgacca cttgactctg   6840
atgcagaagg tggaggtgtt tgagcatgcc gtcaataata cagctgggga cgacctggcc   6900
aagctgctgt ggctgaaaag ccccagctcc gaggtgtggt ttgaccgaag aaccaattat   6960
acccgttctt tagcggtcat gtcaatggtt gggtatattt taggcctggg agatagacac   7020
ccatccaacc tgatgctgga ccgtctgagt gggaagatcc tgcacattga ctttggggac   7080
tgctttgagg ttgctatgac ccgagagaag tttccagaga agattccatt tagactaaca   7140
```

agaatgttga ccaatgctat ggaggttaca ggcctggatg gcaactacag aatcacatgc 7200
cacacagtga tggaggtgct gcgagagcac aaggacagtg tcatggccgt gctggaagcc 7260
tttgtctatg accccttgct gaactggagg ctgatggaca caaataccaa aggcaacaag 7320
cgatcccgaa cgaggacgga ttcctactct gctggccagt cagtcgaaat tttggacggt 7380
gtggaacttg gagagccagc ccataagaaa acggggacca cagtgccaga atctattcat 7440
tctttcattg gagacggttt ggtgaaacca gaggccctaa ataagaaagc tatccagatt 7500
attaacaggg ttcgagataa gctcactggt cgggacttct ctcatgatga cactttggat 7560
gttccaacgc aagttgagct gctcatcaaa caagcgacat cccatgaaaa cctctgccag 7620
tgctatattg gctggtgccc tttctggtaa 7650

<210> SEQ ID NO 156
<211> LENGTH: 2549
<212> TYPE: PRT
<213> ORGANISM: Homo sapiens

<400> SEQUENCE: 156

Met Leu Gly Thr Gly Pro Ala Ala Ala Thr Thr Ala Ala Thr Thr Ser
1 5 10 15

Ser Asn Val Ser Val Leu Gln Gln Phe Ala Ser Gly Leu Lys Ser Arg
20 25 30

Asn Glu Glu Thr Arg Ala Lys Ala Ala Lys Glu Leu Gln His Tyr Val
35 40 45

Thr Met Glu Leu Arg Glu Met Ser Gln Glu Glu Ser Thr Arg Phe Tyr
50 55 60

Asp Gln Leu Asn His His Ile Phe Glu Leu Val Ser Ser Ser Asp Ala
65 70 75 80

Asn Glu Arg Lys Gly Gly Ile Leu Ala Ile Ala Ser Leu Ile Gly Val
85 90 95

Glu Gly Gly Asn Ala Thr Arg Ile Gly Arg Phe Ala Asn Tyr Leu Arg
100 105 110

Asn Leu Leu Pro Ser Asn Asp Pro Val Val Met Glu Met Ala Ser Lys
115 120 125

Ala Ile Gly Arg Leu Ala Met Ala Gly Asp Thr Phe Thr Ala Glu Tyr
130 135 140

Val Glu Phe Glu Val Lys Arg Ala Leu Glu Trp Leu Gly Ala Asp Arg
145 150 155 160

Asn Glu Gly Arg Arg His Ala Ala Val Leu Val Leu Arg Glu Leu Ala
165 170 175

Ile Ser Val Pro Thr Phe Phe Phe Gln Gln Val Gln Pro Phe Phe Asp
180 185 190

Asn Ile Phe Val Ala Val Trp Asp Pro Lys Gln Ala Ile Arg Glu Gly
195 200 205

Ala Val Ala Ala Leu Arg Ala Cys Leu Ile Leu Thr Thr Gln Arg Glu
210 215 220

Pro Lys Glu Met Gln Lys Pro Gln Trp Tyr Arg His Thr Phe Glu Glu
225 230 235 240

Ala Glu Lys Gly Phe Asp Glu Thr Leu Ala Lys Glu Lys Gly Met Asn
245 250 255

Arg Asp Asp Arg Ile His Gly Ala Leu Leu Ile Leu Asn Glu Leu Val
260 265 270

Arg Ile Ser Ser Met Glu Gly Glu Arg Leu Arg Glu Glu Met Glu Glu

```
        275                 280                 285

Ile Thr Gln Gln Gln Leu Val His Asp Lys Tyr Cys Lys Asp Leu Met
    290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                325                 330                 335

Ser Ser His Gln Gly Leu Met Gly Phe Gly Thr Ser Pro Ser Pro Ala
            340                 345                 350

Lys Ser Thr Leu Val Glu Ser Arg Cys Cys Arg Asp Leu Met Glu Glu
        355                 360                 365

Lys Phe Asp Gln Val Cys Gln Trp Val Leu Lys Cys Arg Asn Ser Lys
    370                 375                 380

Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
                405                 410                 415

Met Asn His Val Leu Ser Cys Val Lys Lys Glu Lys Glu Arg Thr Ala
            420                 425                 430

Ala Phe Gln Ala Leu Gly Leu Leu Ser Val Ala Val Arg Ser Glu Phe
        435                 440                 445

Lys Val Tyr Leu Pro Arg Val Leu Asp Ile Ile Arg Ala Ala Leu Pro
    450                 455                 460

Pro Lys Asp Phe Ala His Lys Arg Gln Lys Ala Met Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
            500                 505                 510

Leu Ser Pro Ala Leu Thr Ala Val Leu Tyr Asp Leu Ser Arg Gln Ile
        515                 520                 525

Pro Gln Leu Lys Lys Asp Ile Gln Asp Gly Leu Leu Lys Met Leu Ser
    530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
                565                 570                 575

Ser Asp Val Gly Ser Ile Thr Leu Ala Leu Arg Thr Leu Gly Ser Phe
            580                 585                 590

Glu Phe Glu Gly His Ser Leu Thr Gln Phe Val Arg His Cys Ala Asp
        595                 600                 605

His Phe Leu Asn Ser Glu His Lys Glu Ile Arg Met Glu Ala Ala Arg
    610                 615                 620

Thr Cys Ser Arg Leu Leu Thr Pro Ser Ile His Leu Ile Ser Gly His
625                 630                 635                 640

Ala His Val Val Ser Gln Thr Ala Val Gln Val Val Ala Asp Val Leu
                645                 650                 655

Ser Lys Leu Leu Val Val Gly Ile Thr Asp Pro Asp Pro Asp Ile Arg
            660                 665                 670

Tyr Cys Val Leu Ala Ser Leu Asp Glu Arg Phe Asp Ala His Leu Ala
        675                 680                 685

Gln Ala Glu Asn Leu Gln Ala Leu Phe Val Ala Leu Asn Asp Gln Val
    690                 695                 700
```

```
Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
                725                 730                 735

Ile Leu Thr Glu Leu Glu His Ser Gly Ile Gly Arg Ile Lys Glu Gln
            740                 745                 750

Ser Ala Arg Met Leu Gly His Leu Val Ser Asn Ala Pro Arg Leu Ile
        755                 760                 765

Arg Pro Tyr Met Glu Pro Ile Leu Lys Ala Leu Ile Leu Lys Leu Lys
    770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
                805                 810                 815

Val Asp Glu Leu Phe Ile Ile Ile Met Asp Met Leu Gln Asp Ser Ser
            820                 825                 830

Leu Leu Ala Lys Arg Gln Val Ala Leu Trp Thr Leu Gly Gln Leu Val
        835                 840                 845

Ala Ser Thr Gly Tyr Val Val Glu Pro Tyr Arg Lys Tyr Pro Thr Leu
    850                 855                 860

Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
                885                 890                 895

Tyr Lys His Lys Val Asn Ile Gly Met Ile Asp Gln Ser Arg Asp Ala
            900                 905                 910

Ser Ala Val Ser Leu Ser Glu Ser Lys Ser Ser Gln Asp Ser Ser Asp
        915                 920                 925

Tyr Ser Thr Ser Glu Met Leu Val Asn Met Gly Asn Leu Pro Leu Asp
    930                 935                 940

Glu Phe Tyr Pro Ala Val Ser Met Val Ala Leu Met Arg Ile Phe Arg
945                 950                 955                 960

Asp Gln Ser Leu Ser His His His Thr Met Val Val Gln Ala Ile Thr
                965                 970                 975

Phe Ile Phe Lys Ser Leu Gly Leu Lys Cys Val Gln Phe Leu Pro Gln
            980                 985                 990

Val Met Pro Thr Phe Leu Asn Val  Ile Arg Val Cys Asp  Gly Ala Ile
        995                 1000                 1005

Arg Glu  Phe Leu Phe Gln Gln  Leu Gly Met Leu Val  Ser Phe Val
    1010                 1015                 1020

Lys Ser  His Ile Arg Pro Tyr  Met Asp Glu Ile Val  Thr Leu Met
    1025                 1030                 1035

Arg Glu  Phe Trp Val Met Asn  Thr Ser Ile Gln Ser  Thr Ile Ile
    1040                 1045                 1050

Leu Leu  Ile Glu Gln Ile Val  Val Ala Leu Gly Gly  Glu Phe Lys
    1055                 1060                 1065

Leu Tyr  Leu Pro Gln Leu Ile  Pro His Met Leu Arg  Val Phe Met
    1070                 1075                 1080

His Asp  Asn Ser Pro Gly Arg  Ile Val Ser Ile Lys  Leu Leu Ala
    1085                 1090                 1095

Ala Ile  Gln Leu Phe Gly Ala  Asn Leu Asp Asp Tyr  Leu His Leu
    1100                 1105                 1110
```

```
Leu Leu  Pro Pro Ile Val Lys  Leu Phe Asp Ala Pro  Glu Ala Pro
    1115                 1120                 1125

Leu Pro  Ser Arg Lys Ala Ala  Leu Glu Thr Val Asp  Arg Leu Thr
    1130                 1135                 1140

Glu Ser  Leu Asp Phe Thr Asp  Tyr Ala Ser Arg Ile  Ile His Pro
    1145                 1150                 1155

Ile Val  Arg Thr Leu Asp Gln  Ser Pro Glu Leu Arg  Ser Thr Ala
    1160                 1165                 1170

Met Asp  Thr Leu Ser Ser Leu  Val Phe Gln Leu Gly  Lys Lys Tyr
    1175                 1180                 1185

Gln Ile  Phe Ile Pro Met Val  Asn Lys Val Leu Val  Arg His Arg
    1190                 1195                 1200

Ile Asn  His Gln Arg Tyr Asp  Val Leu Ile Cys Arg  Ile Val Lys
    1205                 1210                 1215

Gly Tyr  Thr Leu Ala Asp Glu  Glu Glu Asp Pro Leu  Ile Tyr Gln
    1220                 1225                 1230

His Arg  Met Leu Arg Ser Gly  Gln Gly Asp Ala Leu  Ala Ser Gly
    1235                 1240                 1245

Pro Val  Glu Thr Gly Pro Met  Lys Lys Leu His Val  Ser Thr Ile
    1250                 1255                 1260

Asn Leu  Gln Lys Ala Trp Gly  Ala Ala Arg Arg Val  Ser Lys Asp
    1265                 1270                 1275

Asp Trp  Leu Glu Trp Leu Arg  Arg Leu Ser Leu Glu  Leu Leu Lys
    1280                 1285                 1290

Asp Ser  Ser Ser Pro Ser Leu  Arg Ser Cys Trp Ala  Leu Ala Gln
    1295                 1300                 1305

Ala Tyr  Asn Pro Met Ala Arg  Asp Leu Phe Asn Ala  Ala Phe Val
    1310                 1315                 1320

Ser Cys  Trp Ser Glu Leu Asn  Glu Asp Gln Gln Asp  Glu Leu Ile
    1325                 1330                 1335

Arg Ser  Ile Glu Leu Ala Leu  Thr Ser Gln Asp Ile  Ala Glu Val
    1340                 1345                 1350

Thr Gln  Thr Leu Leu Asn Leu  Ala Glu Phe Met Glu  His Ser Asp
    1355                 1360                 1365

Lys Gly  Pro Leu Pro Leu Arg  Asp Asp Asn Gly Ile  Val Leu Leu
    1370                 1375                 1380

Gly Glu  Arg Ala Ala Lys Cys  Arg Ala Tyr Ala Lys  Ala Leu His
    1385                 1390                 1395

Tyr Lys  Glu Leu Glu Phe Gln  Lys Gly Pro Thr Pro  Ala Ile Leu
    1400                 1405                 1410

Glu Ser  Leu Ile Ser Ile Asn  Asn Lys Leu Gln Gln  Pro Glu Ala
    1415                 1420                 1425

Ala Ala  Gly Val Leu Glu Tyr  Ala Met Lys His Phe  Gly Glu Leu
    1430                 1435                 1440

Glu Ile  Gln Ala Thr Trp Tyr  Glu Lys Leu His Glu  Trp Glu Asp
    1445                 1450                 1455

Ala Leu  Val Ala Tyr Asp Lys  Lys Met Asp Thr Asn  Lys Asp Asp
    1460                 1465                 1470

Pro Glu  Leu Met Leu Gly Arg  Met Arg Cys Leu Glu  Ala Leu Gly
    1475                 1480                 1485

Glu Trp  Gly Gln Leu His Gln  Gln Cys Cys Glu Lys  Trp Thr Leu
    1490                 1495                 1500

Val Asn  Asp Glu Thr Gln Ala  Lys Met Ala Arg Met  Ala Ala Ala
```

```
    1505                1510                1515

Ala Ala  Trp Gly Leu Gly Gln  Trp Asp Ser Met Glu  Glu Tyr Thr
    1520                1525                1530

Cys Met  Ile Pro Arg Asp Thr  His Asp Gly Ala Phe  Tyr Arg Ala
    1535                1540                1545

Val Leu  Ala Leu His Gln Asp  Leu Phe Ser Leu Ala  Gln Gln Cys
    1550                1555                1560

Ile Asp  Lys Ala Arg Asp Leu  Leu Asp Ala Glu Leu  Thr Ala Met
    1565                1570                1575

Ala Gly  Glu Ser Tyr Ser Arg  Ala Tyr Gly Ala Met  Val Ser Cys
    1580                1585                1590

His Met  Leu Ser Glu Leu Glu  Glu Val Ile Gln Tyr  Lys Leu Val
    1595                1600                1605

Pro Glu  Arg Arg Glu Ile Ile  Arg Gln Ile Trp Trp  Glu Arg Leu
    1610                1615                1620

Gln Gly  Cys Gln Arg Ile Val  Glu Asp Trp Gln Lys  Ile Leu Met
    1625                1630                1635

Val Arg  Ser Leu Val Val Ser  Pro His Glu Asp Met  Arg Thr Trp
    1640                1645                1650

Leu Lys  Tyr Ala Ser Leu Cys  Gly Lys Ser Gly Arg  Leu Ala Leu
    1655                1660                1665

Ala His  Lys Thr Leu Val Leu  Leu Leu Gly Val Asp  Pro Ser Arg
    1670                1675                1680

Gln Leu  Asp His Pro Leu Pro  Thr Val His Pro Gln  Val Thr Tyr
    1685                1690                1695

Ala Tyr  Met Lys Asn Met Trp  Lys Ser Ala Arg Lys  Ile Asp Ala
    1700                1705                1710

Phe Gln  His Met Gln His Phe  Val Gln Thr Met Gln  Gln Gln Ala
    1715                1720                1725

Gln His  Ala Ile Ala Thr Glu  Asp Gln Gln His Lys  Gln Glu Leu
    1730                1735                1740

His Lys  Leu Met Ala Arg Cys  Phe Leu Lys Leu Gly  Glu Trp Gln
    1745                1750                1755

Leu Asn  Leu Gln Gly Ile Asn  Glu Ser Thr Ile Pro  Lys Val Leu
    1760                1765                1770

Gln Tyr  Tyr Ser Ala Ala Thr  Glu His Asp Arg Ser  Trp Tyr Lys
    1775                1780                1785

Ala Trp  His Ala Trp Ala Val  Met Asn Phe Glu Ala  Val Leu His
    1790                1795                1800

Tyr Lys  His Gln Asn Gln Ala  Arg Asp Glu Lys Lys  Lys Leu Arg
    1805                1810                1815

His Ala  Ser Gly Ala Asn Ile  Thr Asn Ala Thr Thr  Ala Ala Thr
    1820                1825                1830

Thr Ala  Ala Thr Ala Thr Thr  Thr Ala Ser Thr Glu  Gly Ser Asn
    1835                1840                1845

Ser Glu  Ser Glu Ala Glu Ser  Thr Glu Asn Ser Pro  Thr Pro Ser
    1850                1855                1860

Pro Leu  Gln Lys Lys Val Thr  Glu Asp Leu Ser Lys  Thr Leu Leu
    1865                1870                1875

Met Tyr  Thr Val Pro Ala Val  Gln Gly Phe Phe Arg  Ser Ile Ser
    1880                1885                1890

Leu Ser  Arg Gly Asn Asn Leu  Gln Asp Thr Leu Arg  Val Leu Thr
    1895                1900                1905
```

```
Leu Trp  Phe Asp Tyr Gly His  Trp Pro Asp Val Asn  Glu Ala Leu
    1910                 1915                 1920

Val Glu  Gly Val Lys Ala Ile  Gln Ile Asp Thr Trp  Leu Gln Val
    1925                 1930                 1935

Ile Pro  Gln Leu Ile Ala Arg  Ile Asp Thr Pro Arg  Pro Leu Val
    1940                 1945                 1950

Gly Arg  Leu Ile His Gln Leu  Leu Thr Asp Ile Gly  Arg Tyr His
    1955                 1960                 1965

Pro Gln  Ala Leu Ile Tyr Pro  Leu Thr Val Ala Ser  Lys Ser Thr
    1970                 1975                 1980

Thr Thr  Ala Arg His Asn Ala  Ala Asn Lys Ile Leu  Lys Asn Met
    1985                 1990                 1995

Cys Glu  His Ser Asn Thr Leu  Val Gln Gln Ala Met  Met Val Ser
    2000                 2005                 2010

Glu Glu  Leu Ile Arg Val Ala  Ile Leu Trp His Glu  Met Trp His
    2015                 2020                 2025

Glu Gly  Leu Glu Glu Ala Ser  Arg Leu Tyr Phe Gly  Glu Arg Asn
    2030                 2035                 2040

Val Lys  Gly Met Phe Glu Val  Leu Glu Pro Leu His  Ala Met Met
    2045                 2050                 2055

Glu Arg  Gly Pro Gln Thr Leu  Lys Glu Thr Ser Phe  Asn Gln Ala
    2060                 2065                 2070

Tyr Gly  Arg Asp Leu Met Glu  Ala Gln Glu Trp Cys  Arg Lys Tyr
    2075                 2080                 2085

Met Lys  Ser Gly Asn Val Lys  Asp Leu Thr Gln Ala  Trp Asp Leu
    2090                 2095                 2100

Tyr Tyr  His Val Phe Arg Arg  Ile Ser Lys Gln Leu  Pro Gln Leu
    2105                 2110                 2115

Thr Ser  Leu Glu Leu Gln Tyr  Val Ser Pro Lys Leu  Leu Met Cys
    2120                 2125                 2130

Arg Asp  Leu Glu Leu Ala Val  Pro Gly Thr Tyr Asp  Pro Asn Gln
    2135                 2140                 2145

Pro Ile  Ile Arg Ile Gln Ser  Ile Ala Pro Ser Leu  Gln Val Ile
    2150                 2155                 2160

Thr Ser  Lys Gln Arg Pro Arg  Lys Leu Thr Leu Met  Gly Ser Asn
    2165                 2170                 2175

Gly His  Glu Phe Val Phe Leu  Leu Lys Gly His Glu  Asp Leu Arg
    2180                 2185                 2190

Gln Asp  Glu Arg Val Met Gln  Leu Phe Gly Leu Val  Asn Thr Leu
    2195                 2200                 2205

Leu Ala  Asn Asp Pro Thr Ser  Leu Arg Lys Asn Leu  Ser Ile Gln
    2210                 2215                 2220

Arg Tyr  Ala Val Ile Pro Leu  Ser Thr Asn Ser Gly  Leu Ile Gly
    2225                 2230                 2235

Trp Val  Pro His Cys Asp Thr  Leu His Ala Leu Ile  Arg Asp Tyr
    2240                 2245                 2250

Arg Glu  Lys Lys Lys Ile Leu  Leu Asn Ile Glu His  Arg Ile Met
    2255                 2260                 2265

Leu Arg  Met Ala Pro Asp Tyr  Asp His Leu Thr Leu  Met Gln Lys
    2270                 2275                 2280

Val Glu  Val Phe Glu His Ala  Val Asn Asn Thr Ala  Gly Asp Asp
    2285                 2290                 2295
```

Leu Ala Lys Leu Leu Trp Leu Lys Ser Pro Ser Ser Glu Val Trp
2300 2305 2310

Phe Asp Arg Arg Thr Asn Tyr Thr Arg Ser Leu Ala Val Met Ser
2315 2320 2325

Met Val Gly Tyr Ile Leu Gly Leu Gly Asp Arg His Pro Ser Asn
2330 2335 2340

Leu Met Leu Asp Arg Leu Ser Gly Lys Ile Leu His Ile Asp Phe
2345 2350 2355

Gly Asp Cys Phe Glu Val Ala Met Thr Arg Glu Lys Phe Pro Glu
2360 2365 2370

Lys Ile Pro Phe Arg Leu Thr Arg Met Leu Thr Asn Ala Met Glu
2375 2380 2385

Val Thr Gly Leu Asp Gly Asn Tyr Arg Ile Thr Cys His Thr Val
2390 2395 2400

Met Glu Val Leu Arg Glu His Lys Asp Ser Val Met Ala Val Leu
2405 2410 2415

Glu Ala Phe Val Tyr Asp Pro Leu Leu Asn Trp Arg Leu Met Asp
2420 2425 2430

Thr Asn Thr Lys Gly Asn Lys Arg Ser Arg Thr Arg Thr Asp Ser
2435 2440 2445

Tyr Ser Ala Gly Gln Ser Val Glu Ile Leu Asp Gly Val Glu Leu
2450 2455 2460

Gly Glu Pro Ala His Lys Lys Thr Gly Thr Thr Val Pro Glu Ser
2465 2470 2475

Ile His Ser Phe Ile Gly Asp Gly Leu Val Lys Pro Glu Ala Leu
2480 2485 2490

Asn Lys Lys Ala Ile Gln Ile Ile Asn Arg Val Arg Asp Lys Leu
2495 2500 2505

Thr Gly Arg Asp Phe Ser His Asp Asp Thr Leu Asp Val Pro Thr
2510 2515 2520

Gln Val Glu Leu Leu Ile Lys Gln Ala Thr Ser His Glu Asn Leu
2525 2530 2535

Cys Gln Cys Tyr Ile Gly Trp Cys Pro Phe Trp
2540 2545

<210> SEQ ID NO 157
<211> LENGTH: 1686
<212> TYPE: DNA
<213> ORGANISM: Homo sapiens

<400> SEQUENCE: 157
atggcaaata tgaatagtga ttctaggcat cttggcacct ctgaggtaga tcatgaaaga 60
gatcctggac ctatgaatat ccagtttgag ccatcggatc taagatccaa aaggcctttc 120
tgtatagagc ccacaaacat cgtgaatgtg aatcatgtca ttcagagggt tagtgaccat 180
gcctctgcca tgaacaagag aattcattac tacagccggc tcaccactcc tgcagacaag 240
gcactgattg ccccagacca tgtagttcca gctccagaag agtgctatgt gtatagtcca 300
ttgggctctg cttataaact tcaaagttac actgaaggat acggtaaaaa caccagttta 360
gtaaccattt ttatgatttg gaataccatg atgggaacat ctatactaag cattccttgg 420
ggcataaaac aggctggatt tactactgga atgtgtgtca tcatactgat gggcctttta 480
acactttatt gctgctacag agtagtgaaa tcacggacta tgatgttttc gttggatacc 540
actagctggg aatatccaga tgtctgcaga cattatttcg gctcctttgg gcagtggtcg 600

```
agtctccttt tctccttggt gtctctcatt ggagcaatga tagtttattg ggtgcttatg     660

tcaaattttc tttttaatac tggaaagttt atttttaatt ttattcatca cattaatgac     720

acagacacta tactgagtac caataatagc aaccctgtga tttgtccaag tgccgggagt     780

ggaggccatc ctgacaacag ctctatgatt ttctatgcca atgacacagg agcccaacag     840

tttgaaaagt ggtgggataa gtccaggaca gtcccctttt atcttgtagg gctcctcctc     900

ccactgctca atttcaagtc tccttcattt ttttcaaaat ttaatatcct aggcacagtg     960

tctgtccttt atttgatttt ccttgtcacc tttaaggctg ttcgcttggg atttcatttg    1020

gaatttcatt ggtttatacc aacagaattt tttgtaccag agataagatt tcagtttcca    1080

cagctgactg gagtgcttac ccttgctttt tttattcata attgtatcat cacactcttg    1140

aagaacaaca agaaacaaga aaacaatgtg agggacttgt gcattgctta tatgctggtg    1200

acattaactt atctctatat tggagtcctg gtttttgctt catttccttc accaccatta    1260

tccaaagatt gtattgagca gaatttttta gacaacttcc ctagcagtga caccctgtcc    1320

ttcattgcaa ggatattcct gctgttccag atgatgactg tatacccact cttaggctac    1380

ctggctcgtg tccagctttt gggccatatc ttcggtgaca tttatcctag cattttccat    1440

gtgctgattc ttaatctaat tattgtggga gctggagtga tcatggcctg tttctaccca    1500

aacataggag ggatcataag atattcagga gcagcatgtg gactggcctt tgtattcata    1560

tacccatctc tcatctatat aatttccctc caccaagaag agcgtctgac atggcctaaa    1620

ttaatcttcc acgttttcat catcattttg ggcgtggcta acctgattgt tcagtttttt    1680

atgtga                                                               1686
```

<210> SEQ ID NO 158
<211> LENGTH: 561
<212> TYPE: PRT
<213> ORGANISM: Homo sapiens

<400> SEQUENCE: 158

```
Met Ala Asn Met Asn Ser Asp Ser Arg His Leu Gly Thr Ser Glu Val
1               5                   10                  15

Asp His Glu Arg Asp Pro Gly Pro Met Asn Ile Gln Phe Glu Pro Ser
            20                  25                  30

Asp Leu Arg Ser Lys Arg Pro Phe Cys Ile Glu Pro Thr Asn Ile Val
        35                  40                  45

Asn Val Asn His Val Ile Gln Arg Val Ser Asp His Ala Ser Ala Met
    50                  55                  60

Asn Lys Arg Ile His Tyr Tyr Ser Arg Leu Thr Thr Pro Ala Asp Lys
65                  70                  75                  80

Ala Leu Ile Ala Pro Asp His Val Val Pro Ala Pro Glu Glu Cys Tyr
                85                  90                  95

Val Tyr Ser Pro Leu Gly Ser Ala Tyr Lys Leu Gln Ser Tyr Thr Glu
            100                 105                 110

Gly Tyr Gly Lys Asn Thr Ser Leu Val Thr Ile Phe Met Ile Trp Asn
        115                 120                 125

Thr Met Met Gly Thr Ser Ile Leu Ser Ile Pro Trp Gly Ile Lys Gln
    130                 135                 140

Ala Gly Phe Thr Thr Gly Met Cys Val Ile Ile Leu Met Gly Leu Leu
145                 150                 155                 160

Thr Leu Tyr Cys Cys Tyr Arg Val Val Lys Ser Arg Thr Met Met Phe
                165                 170                 175
```

```
Ser Leu Asp Thr Thr Ser Trp Glu Tyr Pro Asp Val Cys Arg His Tyr
            180                 185                 190

Phe Gly Ser Phe Gly Gln Trp Ser Ser Leu Leu Phe Ser Leu Val Ser
        195                 200                 205

Leu Ile Gly Ala Met Ile Val Tyr Trp Val Leu Met Ser Asn Phe Leu
    210                 215                 220

Phe Asn Thr Gly Lys Phe Ile Phe Asn Phe Ile His His Ile Asn Asp
225                 230                 235                 240

Thr Asp Thr Ile Leu Ser Thr Asn Asn Ser Asn Pro Val Ile Cys Pro
                245                 250                 255

Ser Ala Gly Ser Gly Gly His Pro Asp Asn Ser Ser Met Ile Phe Tyr
            260                 265                 270

Ala Asn Asp Thr Gly Ala Gln Gln Phe Glu Lys Trp Trp Asp Lys Ser
        275                 280                 285

Arg Thr Val Pro Phe Tyr Leu Val Gly Leu Leu Leu Pro Leu Leu Asn
    290                 295                 300

Phe Lys Ser Pro Ser Phe Phe Ser Lys Phe Asn Ile Leu Gly Thr Val
305                 310                 315                 320

Ser Val Leu Tyr Leu Ile Phe Leu Val Thr Phe Lys Ala Val Arg Leu
                325                 330                 335

Gly Phe His Leu Glu Phe His Trp Phe Ile Pro Thr Glu Phe Phe Val
            340                 345                 350

Pro Glu Ile Arg Phe Gln Phe Pro Gln Leu Thr Gly Val Leu Thr Leu
        355                 360                 365

Ala Phe Phe Ile His Asn Cys Ile Ile Thr Leu Leu Lys Asn Asn Lys
    370                 375                 380

Lys Gln Glu Asn Asn Val Arg Asp Leu Cys Ile Ala Tyr Met Leu Val
385                 390                 395                 400

Thr Leu Thr Tyr Leu Tyr Ile Gly Val Leu Val Phe Ala Ser Phe Pro
                405                 410                 415

Ser Pro Pro Leu Ser Lys Asp Cys Ile Glu Gln Asn Phe Leu Asp Asn
            420                 425                 430

Phe Pro Ser Ser Asp Thr Leu Ser Phe Ile Ala Arg Ile Phe Leu Leu
        435                 440                 445

Phe Gln Met Met Thr Val Tyr Pro Leu Leu Gly Tyr Leu Ala Arg Val
    450                 455                 460

Gln Leu Leu Gly His Ile Phe Gly Asp Ile Tyr Pro Ser Ile Phe His
465                 470                 475                 480

Val Leu Ile Leu Asn Leu Ile Ile Val Gly Ala Gly Val Ile Met Ala
                485                 490                 495

Cys Phe Tyr Pro Asn Ile Gly Gly Ile Ile Arg Tyr Ser Gly Ala Ala
            500                 505                 510

Cys Gly Leu Ala Phe Val Phe Ile Tyr Pro Ser Leu Ile Tyr Ile Ile
        515                 520                 525

Ser Leu His Gln Glu Glu Arg Leu Thr Trp Pro Lys Leu Ile Phe His
    530                 535                 540

Val Phe Ile Ile Ile Leu Gly Val Ala Asn Leu Ile Val Gln Phe Phe
545                 550                 555                 560

Met
```

<210> SEQ ID NO 159
<211> LENGTH: 1050
<212> TYPE: DNA
<213> ORGANISM: Homo sapiens

<400> SEQUENCE: 159
atggcggcgg aggaggagga ggtggactct gccgacaccg gagagaggtc aggatggcta 60
actggttggc tccccacatg gtgccctacg tctatatcac accttaaaga agctgaagag 120
aagatgttaa aatgtgtgcc ttgcacatac aaaaaagaac ctgttcgtat atctaatgga 180
aataaaatat ggacactgaa gttctctcat aatatttcaa ataagactcc acttgtcctt 240
ctccatggtt ttggaggagg tcttgggctc tgggcactga attttggaga tctttgcacc 300
aacagacctg tctatgcttt tgacctattg ggttttggac gaagtagtag acccaggttt 360
gacagtgatg cagaagaagt ggagaatcag tttgtggaat ccattgaaga gtggagatgt 420
gccctaggat tggacaaaat gatcttgctt gggcacaacc taggtggatt cttggctgct 480
gcttactcgc tgaagtaccc atcaagggtt aatcatctca ttttagtgga gccttggggt 540
ttccctgaac gaccagacct tgctgatcaa gacagaccaa ttccagtttg gatcagagcc 600
ttgggagcag cattgactcc ctttaaccct ttagctggcc taaggattgc aggacccttt 660
ggtttaagtc tagtgcagcg tttaaggcct gatttcaaac gaaagtattc ttcaatgttc 720
gaagacgata ctgtgacaga atacatctac cactgtaatg tgcagactcc aagtggtgag 780
acagctttca agaatatgac tattccttat ggatgggcaa aaaggccaat gctccagcga 840
attggtaaaa tgcaccctga cattccagtt tcagtgatct ttggcgcccg atcctgcata 900
gatggcaatt ctggcaccag catccagtcc ttacgaccac attcatatgt gaagacaata 960
gctattcttg ggcaggaca ttatgtatat gcagatcaac cagaagaatt caaccagaaa 1020
gtaaaggaga tctgcgacac tgtggactga 1050

<210> SEQ ID NO 160
<211> LENGTH: 349
<212> TYPE: PRT
<213> ORGANISM: Homo sapiens

<400> SEQUENCE: 160

Met Ala Ala Glu Glu Glu Glu Val Asp Ser Ala Asp Thr Gly Glu Arg
1 5 10 15

Ser Gly Trp Leu Thr Gly Trp Leu Pro Thr Trp Cys Pro Thr Ser Ile
20 25 30

Ser His Leu Lys Glu Ala Glu Glu Lys Met Leu Lys Cys Val Pro Cys
35 40 45

Thr Tyr Lys Lys Glu Pro Val Arg Ile Ser Asn Gly Asn Lys Ile Trp
50 55 60

Thr Leu Lys Phe Ser His Asn Ile Ser Asn Lys Thr Pro Leu Val Leu
65 70 75 80

Leu His Gly Phe Gly Gly Gly Leu Gly Leu Trp Ala Leu Asn Phe Gly
85 90 95

Asp Leu Cys Thr Asn Arg Pro Val Tyr Ala Phe Asp Leu Leu Gly Phe
100 105 110

Gly Arg Ser Ser Arg Pro Arg Phe Asp Ser Asp Ala Glu Glu Val Glu
115 120 125

Asn Gln Phe Val Glu Ser Ile Glu Glu Trp Arg Cys Ala Leu Gly Leu
130 135 140

Asp Lys Met Ile Leu Leu Gly His Asn Leu Gly Gly Phe Leu Ala Ala
145 150 155 160

Ala Tyr Ser Leu Lys Tyr Pro Ser Arg Val Asn His Leu Ile Leu Val
165 170 175

```
Glu Pro Trp Gly Phe Pro Glu Arg Pro Asp Leu Ala Asp Gln Asp Arg
            180                 185                 190

Pro Ile Pro Val Trp Ile Arg Ala Leu Gly Ala Ala Leu Thr Pro Phe
        195                 200                 205

Asn Pro Leu Ala Gly Leu Arg Ile Ala Gly Pro Phe Gly Leu Ser Leu
    210                 215                 220

Val Gln Arg Leu Arg Pro Asp Phe Lys Arg Lys Tyr Ser Ser Met Phe
225                 230                 235                 240

Glu Asp Asp Thr Val Thr Glu Tyr Ile Tyr His Cys Asn Val Gln Thr
                245                 250                 255

Pro Ser Gly Glu Thr Ala Phe Lys Asn Met Thr Ile Pro Tyr Gly Trp
            260                 265                 270

Ala Lys Arg Pro Met Leu Gln Arg Ile Gly Lys Met His Pro Asp Ile
        275                 280                 285

Pro Val Ser Val Ile Phe Gly Ala Arg Ser Cys Ile Asp Gly Asn Ser
    290                 295                 300

Gly Thr Ser Ile Gln Ser Leu Arg Pro His Ser Tyr Val Lys Thr Ile
305                 310                 315                 320

Ala Ile Leu Gly Ala Gly His Tyr Val Tyr Ala Asp Gln Pro Glu Glu
                325                 330                 335

Phe Asn Gln Lys Val Lys Glu Ile Cys Asp Thr Val Asp
            340                 345


<210> SEQ ID NO 161
<211> LENGTH: 532
<212> TYPE: DNA
<213> ORGANISM: artificial sequence
<220> FEATURE:
<223> OTHER INFORMATION: modified promoter sequence

<400> SEQUENCE: 161

gttacataac ttatggtaaa tggcctgcct ggctgactgc ccaatgaccc ctgcccaatg     60

atgtcaataa tgatgtatgt tcccatgtaa tgccaatagg gactttccat tgatgtcaat    120

gggtggagta tttatggtaa ctgcccactt ggcagtacat caagtgtatc atatgccaag    180

tatgccccct attgatgtca atgatggtaa atggcctgcc tggcattatg cccagtacat    240

gaccttatgg gactttccta cttggcagta catctatgta ttagtcattg ctattaccat    300

gggaattcac tagtggagaa gagcatgctt gagggctgag tgcccctcag tgggcagaga    360

gcacatggcc cacagtccct gagaagttgg ggggaggggt gggcaattga actggtgcct    420

agagaaggtg gggcttgggt aaactgggaa agtgatgtgg tgtactggct ccaccttttt    480

ccccagggtg gggagaacc atatataagt gcagtagtct ctgtgaacat tc            532


<210> SEQ ID NO 162
<211> LENGTH: 1611
<212> TYPE: DNA
<213> ORGANISM: Homo sapiens

<400> SEQUENCE: 162

atggagtttt caagtccttc cagagaggaa tgtcccaagc ctttgagtag ggtaagcatc     60

atggctggca gcctcacagg tttgcttcta cttcaggcag tgtcgtgggc atcaggtgcc    120

cgcccctgca tccctaaaag cttcggctac agctcggtgg tgtgtgtctg caatgccaca    180

tactgtgact cctttgaccc cccgaccttt cctgcccttg gtaccttcag ccgctatgag    240

agtacacgca gtgggcgacg gatggagctg agtatggggc ccatccaggc taatcacacg    300
```

```
ggcacaggcc tgctactgac cctgcagcca gaacagaagt tccagaaagt gaagggattt    360

ggaggggcca tgacagatgc tgctgctctc aacatccttg ccctgtcacc ccctgcccaa    420

aatttgctac ttaaatcgta cttctctgaa gaaggaatcg gatataacat catccgggta    480

cccatggcca gctgtgactt ctccatccgc acctacacct atgcagacac ccctgatgat    540

ttccagttgc acaacttcag cctcccagag gaagatacca agctcaagat acccctgatt    600

caccgagccc tgcagttggc ccagcgtccc gtttcactcc ttgccagccc ctggacatca    660

cccacttggc tcaagaccaa tggagcggtg aatgggaagg ggtcactcaa gggacagccc    720

ggagacatct accaccagac ctgggccaga tactttgtga agttcctgga tgcctatgct    780

gagcacaagt tacagttctg ggcagtgaca gctgaaaatg agccttctgc tgggctgttg    840

agtggatacc ccttccagtg cctgggcttc acccctgaac atcagcgaga cttcattgcc    900

cgtgacctag gtcctaccct cgccaacagt actcaccaca atgtccgcct actcatgctg    960

gatgaccaac gcttgctgct gccccactgg gcaaaggtgg tactgacaga cccagaagca   1020

gctaaatatg ttcatggcat tgctgtacat tggtacctgg actttctggc tccagccaac   1080

gccaccctag gggagacaca ccgcctgttc cccaacacca tgctctttgc ctcagaggcc   1140

tgtgtgggct ccaagttctg ggagcagagt gtgcggctag gctcctggga tcgagggatg   1200

cagtacagcc acagcatcat cacgaacctc ctgtaccatg tggtcggctg gaccgactgg   1260

aaccttgccc tgaaccccga aggaggaccc aattgggtgc gtaactttgt cgacagtccc   1320

atcattgtag acatcaccaa ggacacgttt tacaaacagc ccatgttcta ccaccttggc   1380

cacttcagca agttcattcc tgagggctcc cagagagtgg ggctggttgc cagtcagaag   1440

aacgacctgg acgcagtggc actgatgcat cccgatggct ctgctgttgt ggtcgtgcta   1500

aaccgctcct ctaaggatgt gcctcttacc atcaaggatc ctgctgtggg cttcctggag   1560

acaatctcac ctggctactc cattcacacc tacctgtggc gtcgccagtg a             1611
```

<210> SEQ ID NO 163
<211> LENGTH: 1611
<212> TYPE: DNA
<213> ORGANISM: Homo sapiens

<400> SEQUENCE: 163

```
atggagtttt caagtccttc cagagaggaa tgtcccaagc ctttgagtag ggtaagcatc     60

atggctggca gcctcacagg tttgcttcta cttcaggcag tgtcgtgggc atcaggtgcc    120

cgcccctgca tccctaaaag cttcggctac agctcggtgg tgtgtgtctg caatgccaca    180

tactgtgact cctttgaccc cccgaccttt cctgcccttg gtaccttcag ccgctatgag    240

agtacacgca gtgggcgacg gatggagctg agtatggggc ccatccaggc taatcacacg    300

ggcacaggcc tgctactgac cctgcagcca gaacagaagt tccagaaagt gaagggattt    360

ggaggggcca tgacagatgc tgctgctctc aacatccttg ccctgtcacc ccctgcccaa    420

aatttgctac ttaaatcgta cttctctgaa gaaggaatcg gatataacat catccgggta    480

cccatggcca gctccgactt ctccatccgc acctacacct atgcagacac ccctgatgat    540

ttccagttgc acaacttcag cctcccagag gaagatacca agctcaagat acccctgatt    600

caccgagccc tgcagttggc ccagcgtccc gtttcactcc ttgccagccc ctggacatca    660

cccacttggc tcaagaccaa tggagcggtg aatgggaagg ggtcactcaa gggacagccc    720

ggagacatct accaccagac ctgggccaga tactttgtga agttcctgga tgcctatgct    780
```

```
gagcacaagt tacagttctg ggcagtgaca gctgaaaatg agccttctgc tgggctgttg    840

agtggatacc ccttccagtg cctgggcttc acccctgaac atcagcgaga cttcattgcc    900

cgtgacctag gtcctaccct cgccaacagt actcaccaca atgtccgcct actcatgctg    960

gatgaccaac gcttgctgct gccccactgg gcaaaggtgg tactgacaga cccagaagca   1020

gctaaatatg ttcatggcat tgctgtacat tggtacctgg actttctggc tccagccaaa   1080

gccaccctag ggagacacac ccgcctgttc cccaacacca tgctctttgc ctcagaggcc   1140

tgtgtgggct ccaagttctg ggagcagagt gtgcggctag gctcctggga tcgagggatg   1200

cagtacagcc acagcatcat cacgaacctc ctgtaccatg tggtcggctg gaccgactgg   1260

aaccttgccc tgaaccccga aggaggaccc aattgggtgc gtaactttgt cgacagtccc   1320

atcattgtag acatcaccaa ggacacgttt tacaaacagc ccatgttcta ccaccttggc   1380

cacttcagca agttcattcc tgagggctcc cagagagtgg ggctggttgc cagtcagaag   1440

aacgacctgg acgcagtggc actgatgcat cccgatggct ctgctgttgt ggtcgtgcta   1500

aaccgctcct ctaaggatgt gcctcttacc atcaaggatc ctgctgtggg cttcctggag   1560

acaatctcac ctggctactc cattcacacc tacctgtggc gtcgccagtg a            1611
```

```
<210> SEQ ID NO 164
<211> LENGTH: 952
<212> TYPE: PRT
<213> ORGANISM: Homo sapiens

<400> SEQUENCE: 164

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
        195                 200                 205

Tyr Ser Val Glu Phe Ser Glu Glu Pro Phe Gly Val Ile Val Arg Arg
    210                 215                 220

Gln Leu Asp Gly Arg Val Leu Leu Asn Thr Thr Val Ala Pro Leu Phe
```

```
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
    370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
    450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
        515                 520                 525

Ser Glu Asp Gly Cys Pro Asn Asn Glu Leu Glu Asn Pro Pro Tyr Val
    530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
    610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655
```

-continued

```
Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
        675                 680                 685

Glu Pro Ala Gln Gln Ala Met Arg Lys Ala Leu Thr Leu Arg Tyr Ala
    690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Val Glu Ala Leu Gly
    770                 775                 780

Ser Leu Pro Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
    850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
        915                 920                 925

Ser Pro Asp Thr Lys Val Leu Asp Ile Cys Val Ser Leu Leu Met Gly
    930                 935                 940

Glu Gln Phe Leu Val Ser Trp Cys
945                 950
```

VECTOR COMPOSITIONS AND METHODS OF USING SAME FOR TREATMENT OF LYSOSOMAL STORAGE DISORDERS

RELATED APPLICATIONS

This application is a National Stage application under 35 U.S.C. § 371 of International Application No. PCT/US2020/040770, filed Jul. 2, 2020, which claims the benefit of provisional application U.S. Ser. No. 62/869,781, filed Jul. 2, 2019 and U.S. Ser. No. 62/869,808, filed Jul. 2, 2019, the contents of which are herein incorporated by reference in their entirety.

INCORPORATION OF SEQUENCE LISTING

The contents of the text file named "M6PT-002/01WO_SeqList.txt," which was created on Jul. 1, 2020 and is 611 KB in size, are hereby incorporated by reference in their entirety.

TECHNICAL FIELD

The disclosed disclosures relate to compositions and methods for treating lysosomal storage disorders. More particularly, the disclosed disclosures relate to the field of treating lysosomal disorders using improved gene therapy and improved enzyme replacement therapy (ERT).

BACKGROUND

Lysosomal storage disorders (LSDs) relate to inherited metabolic disorders that result from defects in lysosomal function. Currently, about 50 distinct LSDs have been identified but a small number of these (fewer than 10) are reported to have treatments. Therefore, there is an unmet need in the art for safe and effective treatments for LSDs. The disclosure provides two solutions for this unmet need, through either enzyme replacement therapy (ERT) or gene therapy.

SUMMARY

The disclosure provides a composition comprising a vector comprising a sequence encoding a promoter, a first polynucleotide sequence encoding a lysosomal enzyme and a second polynucleotide sequence encoding a modified N-acetylglucosamine-1-phosphotransferase (GlcNAc-1 PTase, PTase), wherein the promoter is capable of driving expression in a mammalian cell and wherein the promoter is operably linked to the first polynucleotide and to the second polynucleotide.

In some embodiments of the compositions of the disclosure, the vector further comprises a sequence encoding an Internal Ribosome Entry Site (IRES). In some embodiments, the sequence encoding the IRES is positioned between the sequence encoding the lysosomal enzyme and the sequence encoding the modified GlcNAc-1 PTase. In some embodiments, the from 5' to 3', the vector comprises the sequence encoding the modified GlcNAc-1 PTase, the sequence encoding the IRES and the sequence encoding the lysosomal enzyme. In some embodiments, the from 5' to 3', the vector comprises the sequence encoding the lysosomal enzyme, the sequence encoding the IRES and the sequence encoding the modified GlcNAc-1 PTase.

In some embodiments of the compositions of the disclosure, the vector further comprises a sequence encoding a cleavage site. In some embodiments, the cleavage site comprise a sequence encoding a 2A self-cleaving peptide.

In some embodiments of the compositions of the disclosure, the vector is an expression vector. In some embodiments, the expression vector comprises a plasmid.

In some embodiments of the compositions of the disclosure, the vector is a delivery vector. In some embodiments, the delivery vector comprises a viral vector. In some embodiments, the viral vector comprises an AAV vector or a lentiviral vector. In some embodiments, the AAV vector comprises a sequence isolated or derived from an AAV of serotype AAV1, AAV2, AAV3, AAV4, AAV5, AAV6, AAV7, AAV8 or AAV9. In some embodiments, the delivery vector comprises a non-viral vector. In some embodiments the non-viral vector comprises a liposome, a lipid nanoparticle (LNP), a micelle, a polymersome, a nanoparticle, a polymer nanoparticle, or an exosome.

In some embodiments of the compositions of the disclosure, the vector is a viral vector. In some embodiments, the viral vector comprises an AAV vector or a lentiviral vector. In some embodiments, the AAV vector comprises a sequence isolated or derived from an AAV of serotype AAV1, AAV2, AAV3, AAV4, AAV5, AAV6, AAV7, AAV8 or AAV9. In some embodiments of the compositions of the disclosure, the vector is a non-viral vector. In some embodiments the non-viral vector comprises a liposome, a lipid nanoparticle (LNP), a micelle, a polymersome, a nanoparticle, a polymer nanoparticle, or an exosome.

In some embodiments of the compositions of the disclosure, the vector is a viral vector. In some embodiments, the vector is a lentiviral vector. In some embodiments, the vector is an adenoviral vector or an adeno-associated viral (AAV) vector. In some embodiments, the AAV vector comprises a serotype selected from the group consisting of AAV1, AAV2, AAV3, AAV4, AAV5, AAV6, AAV7, AAV8, and AAV9. In some embodiments, the AAV vector comprises a sequence encoding a capsid isolated or derived from one or more of a serotype selected from the group consisting of AAV1, AAV2, AAV3, AAV4, AAV5, AAV6, AAV7, AAV8, and AAV9. In some embodiments, the AAV vector comprises a sequence encoding at least one inverted terminal repeat (ITR) isolated or derived from one or more of a serotype selected from the group consisting of AAV1, AAV2, AAV3, AAV4, AAV5, AAV6, AAV7, AAV8, and AAV9.

In some embodiments of the compositions of the disclosure, the vector is a bicistronic vector.

In some embodiments of the compositions of the disclosure, the vector is a multicistronic vector.

In some embodiments of the compositions of the disclosure, the promoter comprises a ubiquitous promoter. In some embodiments, the promoter is capable of driving expression in a mammalian cell. In some embodiments, the promoter is capable of driving expression in a human cell.

In some embodiments of the compositions of the disclosure, the promoter comprises a cell type specific promoter. In some embodiments, the promoter is capable of driving expression in a mammalian cell. In some embodiments, the promoter is capable of driving expression in a human cell. In some embodiments, the promoter is capable of driving expression in a neural cell, including but not limited to a neuron or a glial cell. In some embodiments, the promoter is capable of driving expression in a muscle cell, including but not limited to a smooth muscle cell, striated muscle cell or cardiac muscle cell. In some embodiments, the promoter is capable of driving expression in a lung cell. In some embodiments, the promoter is capable of driving expression in a bone cell. In some embodiments, the promoter is capable of driving expression in a blood cell, including but not limited to a red blood cell, white blood cell, progenitor thereof or a hematopoietic stem cell. In some embodiments, the promoter is capable of driving expression in an immune cell, including but not limited to a T-cell, a B-cell or a macrophage. In some embodiments, the promoter is capable of driving expression in a cell of the spleen or pancreas. In some embodiments, the promoter is capable of driving expression in a cell of the kidney.

In some embodiments of the compositions of the disclosure, the promoter is a human T-lymphotropic virus type I (HTLV-I) promoter.

In some embodiments of the compositions of the disclosure, the promoter is a CBh promoter. In some embodiments, the CBh promoter comprises a CMV early enhancer fused to modified chicken β-actin promoter.

In some embodiments of the compositions of the disclosure, the promoter is a CEF or hCEFI promoter. In some embodiments, the hCEFI promoter comprises a human CMV enhancer operably linked to a human EF1a promoter. In some embodiments, the hCEFI promoter comprises the sequence of SEQ ID NO: 161.

In some embodiments of the compositions of the disclosure, the promoter comprises a constitutive promoter. In some embodiments, the constitutive promoter comprises a Cytomegalovirus (CMV) promoter.

In some embodiments of the compositions of the disclosure, the vector comprises a nucleic acid sequence of SEQ ID NO: 1.

In some embodiments of the compositions of the disclosure, the polynucleotide encoding a modified GlcNAc-1 PTase comprises a nucleic acid sequence of SEQ ID NO: 4.

In some embodiments of the compositions of the disclosure, the lysosomal enzyme is involved in at least one lysosomal storage disorder (LSD) as listed in Table 1A, Table 1B or Table 1C.

In some embodiments of the compositions of the disclosure, the lysosomal enzyme comprises at least one lysosomal enzyme listed in Table 1A, Table 1B or Table 1C.

In some embodiments of the compositions of the disclosure, the lysosomal enzyme is selected from the group consisting of β-glucocebrosidase (GCase/GBA, encoded by the GBA gene), Galactosylceremidase (GALC), α-Galactosidase (encoded by the GLA gene), α-N-acetylglucosaminidase (NAGLU), acid α-glucosidase (GAA) and lysosomal acid α-mannosidase (LAMAN).

In some embodiments of the compositions of the disclosure, the lysosomal enzyme comprises β-glucocebrosidase (GCase/GBA). In some embodiments, the polynucleotide encoding the lysosomal enzyme comprises a nucleic acid sequence of SEQ ID NO: 5.

In some embodiments of the compositions of the disclosure, the lysosomal enzyme comprises Galactosylceremidase (GALC). In some embodiments, the polynucleotide encoding the lysosomal enzyme comprises a nucleic acid sequence of SEQ ID NO: 6. In some embodiments, the polynucleotide encoding the lysosomal enzyme comprises a nucleic acid sequence of SEQ ID NO: 23.

In some embodiments of the compositions of the disclosure, the lysosomal enzyme comprises α-Galactosidase (GLA). In some embodiments, the polynucleotide encoding the lysosomal enzyme comprises a nucleic acid sequence of SEQ ID NO: 7.

In some embodiments of the compositions of the disclosure, the lysosomal enzyme comprises α-N-acetylglucosaminidase (NAGLU). In some embodiments, the polynucleotide encoding the lysosomal enzyme comprises a nucleic acid sequence of SEQ ID NO: 8.

In some embodiments of the compositions of the disclosure, the lysosomal enzyme comprises acid α-glucosidase (GAA). In some embodiments, the polynucleotide encoding the lysosomal enzyme comprises a nucleic acid sequence of SEQ ID NO: 9.

In some embodiments of the compositions of the disclosure, the lysosomal enzyme comprises lysosomal acid α-mannosidase (LAMAN). In some embodiments, the polynucleotide encoding the lysosomal enzyme comprises a nucleic acid sequence of SEQ ID NO: 10.

The disclosure provides a method of treating a lysosomal storage disorder (LSD), the method comprising administering to a subject an effective amount of a composition of the disclosure, wherein the composition increases the phosphorylation of a lysosomal enzyme responsible of the LSD, thereby treating the LSD. The disclosure provides a method of treating a lysosomal storage disorder (LSD), the method comprising administering to a subject an effective amount of a composition of the disclosure, wherein the composition increases the N-linked oligosaccharide phosphorylation of a lysosomal enzyme responsible of the LSD, thereby treating the LSD. In some embodiments, the subject presents a sign or a symptom of the LSD. In some embodiments, the subject has been diagnosed with the LSD.

The disclosure provides a method of preventing an occurrence or an onset of a lysosomal storage disorder (LSD), the method comprising administering to a subject an effective amount of a composition of the disclosure, wherein the composition increases the phosphorylation of a lysosomal enzyme responsible of the LSD, thereby preventing the occurrence of the LSD in the subject. In some embodiments, the subject is at risk of the occurrence or the onset of the LSD. In some embodiments, the subject presents a sign or a symptom of the LSD.

The disclosure provides a method of ameliorating the phosphorylation of a lysosomal enzyme responsible for a lysosomal storage disorder (LSD), the method comprising administering to a subject an effective amount of a composition of the disclosure, wherein the composition increases the phosphorylation of the lysosomal enzyme. In some embodiments, the subject presents a sign or a symptom of the LSD. In some embodiments, the subject is at risk of the occurrence or the onset of the LSD. In some embodiments, the subject has been diagnosed with the LSD.

The disclosure provides a method of ameliorating the phosphorylation of a lysosomal enzyme responsible for a lysosomal storage disorder (LSD), the method comprising contacting to a cell, an effective amount of a composition of the disclosure, wherein the composition increases the phosphorylation of the lysosomal enzyme. In some embodiments, the cell is in vitro or ex vivo. In some embodiments, the cell is in vivo. In some embodiments, a subject comprises the cell. In some embodiments, the subject presents a sign or a symptom of the LSD. In some embodiments, the subject is at risk of the occurrence or the onset of the LSD. In some embodiments, the subject has been diagnosed with the LSD.

In some embodiments of the methods of the disclosure, the lysosomal enzyme is involved in at least one lysosomal storage disorder (LSD) as listed in Table 1A, Table 1B or Table 1C.

In some embodiments of the methods of the disclosure, the lysosomal enzyme is at least one as listed in Table 1A, Table 1B or Table 1C.

In some embodiments of the methods of the disclosure, the lysosomal enzyme comprises one or more of β-glucocebrosidase (GCase/GBA), Galactosylceremidase (GALC), α-Galactosidase (GLA), α-N-acetylglucosaminidase (NAGLU), acid α-glucosidase (GAA) and lysosomal acid α-mannosidase (LAMAN).

In some embodiments of the methods of the disclosure, the administering comprises a systemic route of administration. In some embodiments, the systemic route of administration is enteral, parenteral, oral, intramuscular (IM), subcutaneous (SC), intravenous (IV), intra-arterial (IA), intraspinal, intraventricular, intrathecal, intracerebroventricular.

In some embodiments of the methods of the disclosure, the administering comprises a local route of administration.

In some embodiments of the methods of the disclosure, the subject is a human. In some embodiments, the subject is a male. In some embodiments, the subject is a female.

BRIEF DESCRIPTION OF THE DRAWINGS

For the purpose of illustrating the disclosure, there are depicted in the drawings certain embodiments of the disclosure. However, the disclosure is not limited to the precise arrangements and instrumentalities of the embodiments depicted in the drawings.

FIG. 1A: CMV-S1S3 vector. FIG. 1B: pLL01: pCMV-MCS-IRES-S1S3 vector. FIG. 1C: Graph illustrating the level of expression of CMV-S1S3 and pLL01 (CPM: Counts per minute).

FIG. 2A: pLL11: pCMV-hGBA-IRES-S1S3 vector. FIG. 2B: GBA activity in conditional medium. FIG. 1C: Histogram illustrating the percent of PTase activity.

DETAILED DESCRIPTION

Figures 1A, 1B, 1C:
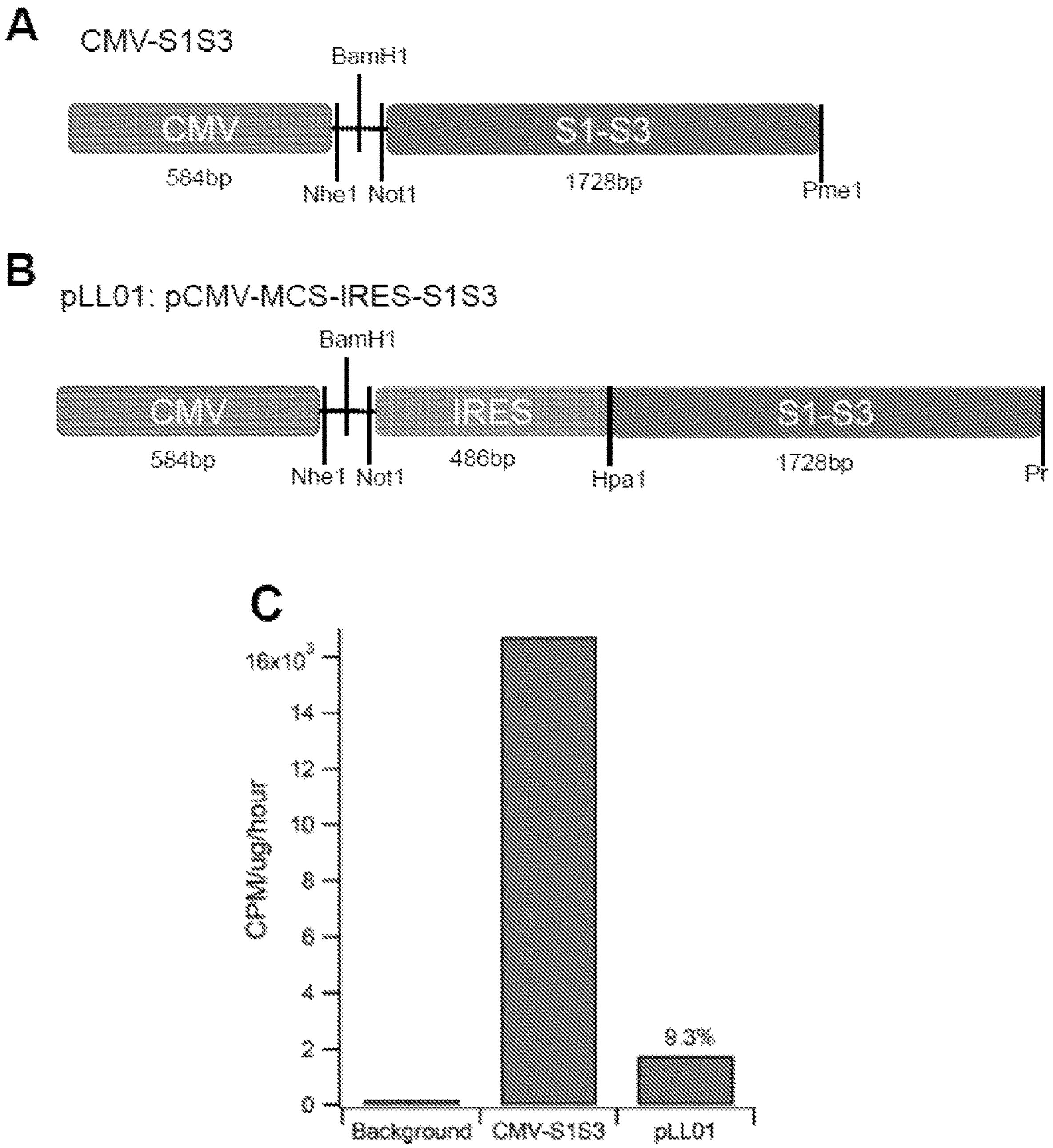
FIGS. 1A-1C are series of diagrams and a graph depicting the S1-S3 biscistronic vector.

Lysosomal storage disorders (LSDs) relate to inherited metabolic disorders that result from defects in lysosomal function. Currently, about 50 distinct LSDs have been identified but a small number of these (fewer than 10) are reported to have treatments. Patients are currently treated by intravenous infusion of enzyme replacement therapies (ERTs), which supplement the missing enzyme in patients to address their symptoms of disease. The goal of ERT is to introduce sufficient amounts of normal enzyme into the lysosomes of the defective cells to clear the storage material and restore lysosome function. In order to insure efficient uptake of the ERTs into the affected lysosomes, it is imperative that ERTs contain high levels of Mannose 6-phosphate (M6P). Ideally patients with LSDs should be treated by administering the missing enzyme with highly saturated level of M6P to enable effective delivery to lysosomes. However, this process is very challenging as the phosphorylation process that enables the addition of M6P to the lysosomal is inherently inefficient. The recent discovery of S1-S3 variant of GlcNAc-1PTase significantly improves the phosphorylation process of lysosomal enzymes. Additionally, there is a need for a gene therapy approach that would provide the patient with a long-term cure of LSD.

The disclosure provides expression vectors, compositions and methods for generating lysosomal enzymes operably linked to a S1-S3 variant of GlcNAc-1-Phosphotransferase. The S1-S3 variant of GlcNAc-1-Phosphotransferase significantly increases transport of operably linked lysosomal enzymes into cells and out of the blood serum or the kidneys for increased update, distribution, and lysosomal enzymatic activity.

The disclosure provides gene therapy vectors, compositions and methods for generating lysosomal enzymes operably linked to a S1-S3 variant of GlcNAc-1-Phosphotransferase. The disclosure demonstrates that expression of the S1-S3 variant increases the uptake, distribution and activity of endogenous lysosomal enzymes.

The disclosure provides ERT, vectors, compositions and methods for generating lysosomal enzymes with appropriate phosphorylated N-linked oligosaccharides by co-expression with S1-S3 PTase via a novel bicistronic vector. The bicistronic expression of S1-S3 PTase and lysosomal enzyme significantly increases the M6P content of the lysosomal enzyme being expressed. Having well phosphorylated enzymes allows for the efficient uptake and lysosomal delivery of the enzyme. This enables for better tissue distribution, cellular uptake, lysosomal targeting and substrate reduction. The disclosure provides gene therapy vectors, compositions and methods for generating high levels of expression or high levels of activity of M6P lysosomal enzymes by co-expression the S1-S3 PTase. The bicistronic expression of the S1-S3 variant of PTase significantly increases the M6P content level in lysosomal enzymes. Through the high M6P on the surface of lysosomal enzymes, the enzymes could be delivered to tissue cells with increased uptake, distribution and efficacy in vitro and in vivo.

Vectors, compositions and methods of the disclosure may be used for enzyme replacement therapy (ERT).

Alternatively or in addition, vectors, compositions and methods of the disclosure may be used for gene therapy.

A number of lysosomal enzymes are described and their uses in both ERT and gene therapy are demonstrated. Importantly, the vectors, compositions and methods of the disclosure may be used with any lysosomal enzyme to increase cellular uptake of the lysosomal enzyme and, consequently, increase activity of the lysosomal enzyme in one or more bodily tissues.

In some embodiments, the compositions and methods of the disclosure comprising the S1-S3 PTase operably linked to a lysosomal protein, increase uptake and activity of the lysosomal protein in one or more of the spleen, the brain, one or more lungs, or one or more muscles of a subject.

In some embodiments, the vectors, compositions and methods of the disclosure comprising the S1-S3 GlcNAc-1-Phosphotransferase, including those embodiments in which a bicistronic vector comprises a sequence encoding the S1-S3GlcNAc-1-Phosphotransferase and a sequence encoding a lysosomal protein, increase uptake and activity of the encoded lysosomal protein in one or more of the spleen, the brain, one or more lungs, or one or more muscles of a subject.

Exemplary Embodiments

The disclosure provides a composition comprising a vector comprising a polynucleotide encoding a lysosomal enzyme and a polynucleotide encoding a modified GlcNAc-1 phosphotransferase (GlcNAc-1 PTase).

The disclosure provides a composition comprising a bicistronic vector comprising a polynucleotide encoding a lysosomal enzyme and a polynucleotide encoding a modified GlcNAc-1 phosphotransferase (GlcNAc-1 PTase).

In some embodiments of the compositions of the disclosure, the bicistronic vector comprises an Internal Ribosome Entry Site (IRES) located before the polynucleotide encoding a modified GlcNAc-1 PTase and after the polynucleotide encoding a lysosomal enzyme. In some embodiments, the bicistronic vector comprises an IRES located after the polynucleotide encoding a modified GlcNAc-1 PTase and before the polynucleotide encoding a lysosomal enzyme.

In some embodiments of the compositions of the disclosure, the bicistronic vector comprises a promoter. In some embodiments, the bicistronic vector comprises a constitutive promoter. In some embodiments, the constitutive promoter comprises a Cytomegalovirus (CMV) promoter. In some embodiments, the promoter is operably linked to the polynucleotide encoding a lysosomal enzyme or the polynucleotide encoding a modified GlcNAc-1 PTase. In some embodiments, the promoter is operably linked to the polynucleotide encoding a lysosomal enzyme and the polynucleotide encoding a modified GlcNAc-1 PTase.

In some embodiments of the compositions of the disclosure, the bicistronic vector comprises a nucleic acid sequence of SEQ ID NO: 1.

In some embodiments of the compositions of the disclosure, the polynucleotide encoding a modified GlcNAc-1 phosphotransferase comprises a nucleic acid sequence of SEQ ID NO: 4.

In some embodiments of the compositions of the disclosure, the encoded lysosomal enzyme is involved in at least one lysosomal storage disorder (LSD) as listed in Table 1. In some embodiments, the encoded lysosomal enzyme or a variant thereof causes at least one lysosomal storage disorder (LSD) as listed in Table 1A, Table 1B or Table 1C. In some embodiments, an activity or a function of the encoded lysosomal enzyme or a variant thereof is decreased, inhibited or deregulated in at least one lysosomal storage disorder (LSD) as listed in Table 1A, Table 1B or Table 1C.

In some embodiments of the compositions of the disclosure, the lysosomal enzyme comprises a lysosomal enzyme listed in Table 1A, Table 1B or Table 1C. In some embodiments, the lysosomal enzyme comprises at least one lysosomal enzyme listed in Table 1A, Table 1B or Table 1C. In some embodiments, the lysosomal enzyme comprises one or more lysosomal enzyme(s) listed in Table 1A, Table 1B or Table 1C. In some embodiments, the lysosomal enzyme is selected from the group consisting of β-glucocebrosidase (GCase, GBA), Galactosylceremidase (GALC), α-Galactosidase (GLA), α-N-acetylglucosaminidase (NAGLU), acid α-glucosidase (GAA) and lysosomal acid α-mannosidase (LAMAN). In some embodiments, the lysosomal enzyme comprises β-glucocebrosidase (GCase, GBA). In some embodiments, the lysosomal enzyme comprises Galactosylceremidase (GALC). In some embodiments, the lysosomal enzyme comprises α-Galactosidase (GLA). In some embodiments, the lysosomal enzyme comprises α-N-acetylglucosaminidase (NAGLU). In some embodiments, the lysosomal enzyme comprises acid α-glucosidase (GAA). In some embodiments, the lysosomal enzyme comprises lysosomal acid α-mannosidase (LAMAN). In some embodiments, the polynucleotide encoding the lysosomal enzyme comprises a nucleic acid sequence of SEQ ID NOs: 5-10.

The disclosure provides a composition comprising a bicistronic vector comprising a constitutive promoter, an Internal Ribosome Entry Site (IRES) and a polynucleotide encoding a modified GlcNAc-1 phosphotransferase (GlcNAc-1 PTase).

In some embodiments of the compositions of the disclosure, the composition further comprises a pharmaceutically-acceptable carrier.

In some embodiments of the vectors of the disclosure, the vector is a viral vector. In some embodiments, the viral vector is an adenovirus, an adeno-associated viruses (AAV), a retrovirus or a lentivirus. In some embodiments, the viral vector comprises an adenovirus. In some embodiments, the viral vector comprises an AAV vector. In some embodiments, the AAV vector comprises a sequence isolated or derived from one or more AAV of serotype AAV1, AAV2, AAV3, AAV4, AAV5, AAV6, AAV7, AAV8 and AAV9. In some embodiments, the AAV vector comprises a sequence isolated or derived from an AAV of serotype 1 (AAV1). In some embodiments, the AAV vector comprises a sequence isolated or derived from an AAV of serotype 2 (AAV2). In some embodiments, the AAV vector comprises a sequence isolated or derived from an AAV of serotype 3 (AAV3). In some embodiments, the AAV vector comprises a sequence isolated or derived from an AAV of serotype 4 (AAV4). In some embodiments, the AAV vector comprises a sequence isolated or derived from an AAV of serotype 5 (AAV5). In some embodiments, the AAV vector comprises a sequence isolated or derived from an AAV of serotype 6 (AAV6). In some embodiments, the AAV vector comprises a sequence isolated or derived from an AAV of serotype 7 (AAV7). In some embodiments, the AAV vector comprises a sequence isolated or derived from an AAV of serotype 8 (AAV8). In some embodiments, the AAV vector comprises a sequence isolated or derived from an AAV of serotype 9 (AAV9).

In some embodiments of the vectors of the disclosure, the vector is an expression vector. In some embodiments, the expression vector comprises the polynucleotide sequence of SEQ ID NO: 1.

The disclosure provides a cell comprising a vector of the disclosure. In some embodiments, the cell is a mammalian cell. In some embodiments, the cell is a primate cell. In some embodiments, the cell is a human cell. In some embodiments, the cell is a cultured cell. In some embodiments, the cell is an immortalized or stabilized cell line. In some embodiments, the cell is a Chinese hamster ovary (CHO) cell. In some embodiments, the cell is a Human embryonic kidney 293 (HEK293) cell.

The disclosure provides a cell comprising a bicistronic vector of the disclosure. In some embodiments, the cell is a mammalian cell. In some embodiments, the cell is a primate cell. In some embodiments, the cell is a human cell. In some embodiments, the cell is a cultured cell. In some embodiments, the cell is an immortalized or stabilized cell line. In some embodiments, the cell is a Chinese hamster ovary (CHO) cell. In some embodiments, the cell is a Human embryonic kidney 293 (HEK293) cell.

The disclosure provides a cell comprising composition of the disclosure. In some embodiments, the cell is a mammalian cell. In some embodiments, the cell is a primate cell. In some embodiments, the cell is a human cell. In some embodiments, the cell is a cultured cell. In some embodiments, the cell is an immortalized or stabilized cell line. In some embodiments, the cell is a Chinese hamster ovary (CHO) cell. In some embodiments, the cell is a Human embryonic kidney 293 (HEK293) cell.

The disclosure provides a pharmaceutical composition comprising a lysosomal enzyme expressed by a vector of the disclosure and a pharmaceutically acceptable carrier.

The disclosure provides a method of treating a lysosomal storage disorder (LSD), the method comprising administering to a subject a composition of the disclosure, thereby treating the LSD.

The disclosure provides a method of treating a lysosomal storage disorder (LSD), the method comprising administering to a subject a therapeutically-effective amount of a composition of the disclosure, wherein the composition increases phosphorylation of a lysosomal enzyme, thereby treating the LSD.

The disclosure provides a method of treating a subject suffering from a lysosomal storage disorder (LSD), the method comprising administering to the subject a pharmaceutical composition of the disclosure, thereby increasing the phosphorylation of a lysosomal enzyme and treating the subject.

The disclosure provides a method of preventing the occurrence of a lysosomal storage disorder (LSD) in a subject in need thereof, the method comprising administering to the subject a pharmaceutical composition of the disclosure, thereby increasing the phosphorylation of a lysosomal enzyme and preventing the occurrence of a LSD in the subject.

The disclosure provides a method of ameliorating the phosphorylation of a lysosomal enzyme responsible for a lysosomal storage disorder (LSD) in a subject in need thereof, the method comprising administering to the subject a composition of the disclosure, wherein the composition increases the phosphorylation of the lysosomal enzyme.

In some embodiments of the methods of the disclosure, the lysosomal enzyme is involved in at least one lysosomal storage disorder (LSD) as listed in Table 1A, Table 1B or Table 1C.

In some embodiments of the methods of the disclosure, the lysosomal enzyme comprises a lysosomal storage disorder (LSD) listed in Table 1A, Table 1B or Table 1C. In some embodiments, the lysosomal enzyme comprises at least one lysosomal storage disorder (LSD) listed in Table 1A, Table 1B or Table 1C. In some embodiments, the lysosomal enzyme comprises one or more lysosomal storage disorder(s) (LSD(s)) listed in Table 1A, Table 1B or Table 1C.

Enzyme Replacement Therapy (ERT)

Provided herein are compositions comprising a bicistronic expression vector comprising a polynucleotide encoding a lysosomal enzyme and a polynucleotide encoding a modified GlcNAc-1 phosphotransferase (GlcNAc-1 PTase). In some embodiments, the disclosed bicistronic expression vector comprises an Internal Ribosome Entry Site (IRES) located before the polynucleotide encoding a modified GlcNAc-1 PTase and after the polynucleotide encoding a lysosomal enzyme. In other embodiments, the disclosed bicistronic expression vector comprises an IRES located after the polynucleotide encoding a modified GlcNAc-1 PTase and before the polynucleotide encoding a lysosomal enzyme.

Provided herein are mammalian cells comprising the disclosed bicistronic expression vector.

Provided herein are pharmaceutical composition comprising a lysosomal enzyme expressed by the biscistronic vector as disclosed herein and a pharmaceutically acceptable carrier.

Provided herein are methods for treating a subject suffering from a lysosomal storage disorder (LSD) and methods preventing the occurrence of a lysosomal storage disorder (LSD) in a subject in need thereof.

Gene Therapy

Provided herein are compositions comprising a bicistronic viral vector comprising a polynucleotide encoding a lysosomal enzyme and a polynucleotide encoding a modified GlcNAc-1 phosphotransferase (GlcNAc-1 PTase). In some embodiments, the disclosed bicistronic viral vector comprises an Internal Ribosome Entry Site (IRES) located before the polynucleotide encoding a modified GlcNAc-1 PTase and after the polynucleotide encoding a lysosomal enzyme. In other embodiments, the disclosed bicistronic viral vector comprises an IRES located after the polynucleotide encoding a modified GlcNAc-1 PTase and before the polynucleotide encoding a lysosomal enzyme. In some embodiments, the viral vector is an adenovirus, an adeno-associated viruses (AAV), a retrovirus or a lentivirus.

Provided herein are methods for treating a subject suffering from a lysosomal storage disorder (LSD) and methods preventing the occurrence of a lysosomal storage disorder (LSD) in a subject in need thereof by administering to the subject the disclosed bicistronic viral vector.

Further provided herein are methods for ameliorating the phosphorylation of a lysosomal enzyme responsible for an LSD in a subject in need thereof.

Provided herein are compositions and methods of using a bicistronic vector for treating or preventing a lysosomal storage disorder (LSD) in a subject.

The disclosure provides compositions comprising a bicistronic vector comprising a promoter, an Internal Ribosome Entry Site (IRES), a polynucleotide encoding a lysosomal enzyme and a polynucleotide encoding a modified GlcNAc-1 phosphotransferase (GlcNAc-1 PTase). Methods of the disclosure comprise administering to a subject a pharmaceutical composition comprising the bicistronic vector as disclosed herein.

Definitions

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing some embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

The terms "2A" or "2A peptide" or "2A-like peptide" is a self-processing viral peptide. The 2A peptide can separate different protein coding sequences in a single ORF transcription unit (Ryan et al., 1991, J Gen Virol 72:2727-2732). Although termed a "self-cleaving" peptide or protease site, the mechanism by which the 2A sequence generates two proteins from one transcript occurs by ribosome skipping where a normal peptide bond is impaired at 2A, resulting in two discontinuous protein fragments from one translation event. Linking with 2A peptide sequences results in cellular expression of multiple, discrete proteins (in essentially equimolar quantities) derived from a single ORF (de Felipe et al., 2006, Trends Biotechnol 24:68-75).

The term "biological" or "biological sample" refers to a sample obtained from an organism or from components (e.g., cells) of an organism. The sample may be of any biological tissue or fluid. Frequently the sample will be a "clinical sample" which is a sample derived from a patient. Such samples include, but are not limited to, bone marrow, cardiac tissue, sputum, blood, lymphatic fluid, blood cells (e.g., white cells), tissue or fine needle biopsy samples, urine, peritoneal fluid, and pleural fluid, or cells therefrom. Biological samples may also include sections of tissues such as frozen sections taken for histological purposes.

As used herein, the terms "derivative" specifies that a derivative of a virus can have a nucleic acid or amino acid sequence difference in respect to a template viral nucleic acid or amino acid sequence.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide. In some embodiments, the disclosed vector is referred herein as a viral vector. In some embodiments, the disclosed vector is referred herein as an expression vector.

As used herein, "higher" refers to expression levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments therebetween, than a control reference. A disclosed herein an expression level higher than a reference value refers to an expression level (mRNA or protein) that is higher than a normal or control level from an expression (mRNA or protein) measured in a healthy subject or defined or used in the art.

As used herein, "lower" refers to expression levels which are at least 10% lower or more, for example, 20%, 30%, 40%, or 50%, 60%, 70%, 80%, 90% lower or more, and/or 1.1 fold, 1.2 fold, 1.4 fold, 1.6 fold, 1.8 fold, 2.0 fold lower or more, and any and all whole or partial increments in between, than a control reference. A disclosed herein an expression level lower than a reference value refers to an expression level (mRNA or protein) that is lower than a normal or control level from an expression (mRNA or protein) measured in a healthy subject or defined or used in the art.

As used herein, the terms "control," or "reference" can be used interchangeably and refer to a value that is used as a standard of comparison.

As used herein, by "combination therapy" is meant that a first agent is administered in conjunction with another agent. "In combination with" or "In conjunction with" refers to administration of one treatment modality in addition to another treatment modality. As such, "in combination with" refers to administration of one treatment modality before, during, or after delivery of the other treatment modality to the individual. Such combinations are considered to be part of a single treatment regimen or regime. For example, a vector or a composition comprising a vector of the disclosure may be provided or administered to a subject in combination with a second therapeutic agent. In some embodiments the vectors and compositions of the disclosure are provided or administered to a subject simultaneously or sequentially with the second therapeutic agent. In some embodiments the vectors and compositions of the disclosure are provided or administered to a subject simultaneously with the second therapeutic agent. In some embodiments the vectors and compositions of the disclosure are provided or administered to a subject sequentially with the second therapeutic agent. In some embodiments the vectors and compositions of the disclosure are provided or administered to a subject prior to administration of the second therapeutic agent. In some embodiments the vectors and compositions of the disclosure are provided or administered to a subject following administration of the second therapeutic agent. In some embodiments, the second therapeutic agent comprises a second vector of composition of the disclosure. In some embodiments, the second therapeutic agent comprises a variant form of a lysosomal enzyme of the disclosure, including a vector or a composition of the disclosure encoding same. In some embodiments, the second therapeutic agent comprises one or more agents to alleviate a sign or symptom of a lysosomal storage disorder. In some embodiments, the second therapeutic agent comprises one or more anti-inflammatory or immunosuppressive agents.

The term "operably linked," as used herein, means that expression of a nucleic acid sequence is under the control of a promoter with which it is spatially connected. A promoter may be positioned 5' (upstream) of the nucleic acid sequence under its control.

As used herein, "primary cells" refer to cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that may comprise a protein or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein, may mean a synthetic or naturally-derived molecule that is capable of conferring, activating or enhancing expression of a nucleic acid. As used herein, the promoter is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

The term "RNA" as used herein is defined as ribonucleic acid.

The term "treatment" as used within the context of the present invention is meant to include therapeutic treatment as well as prophylactic, or suppressive measures for the disease or disorder. As used herein, the term "treatment" and associated terms such as "treat" and "treating" means the reduction of the progression, severity and/or duration of a disease condition or at least one symptom thereof. The term 'treatment' therefore refers to any regimen that can benefit a subject. The treatment may be in respect of an existing condition or may be prophylactic (preventative treatment). Treatment may include curative, alleviative or prophylactic effects. References herein to "therapeutic" and "prophylactic" treatments are to be considered in their broadest context. The term "therapeutic" does not necessarily imply that a subject is treated until total recovery. Similarly, "prophylactic" does not necessarily mean that the subject will not eventually contract a disease condition. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids.

As used herein, the term "pharmaceutical composition" refers to a mixture of at least one compound useful within the invention with other chemical components, such as carriers, stabilizers, diluents, adjuvants, dispersing agents, suspending agents, thickening agents, and/or excipients. The pharmaceutical composition facilitates administration of the compound to an organism. Multiple techniques of administering a compound exist in the art including, but not limited to: intra-tumoral, intravenous, intrapleural, oral, aerosol, parenteral, ophthalmic, pulmonary and topical administration.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline;

Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

As used herein, the term "effective amount" or "therapeutically effective amount" means the amount of the virus particle or infectious units generated from vector of the invention which is required to prevent the particular disease condition, or which reduces the severity of and/or ameliorates the disease condition or at least one symptom thereof or condition associated therewith.

A "subject" or "patient," as used therein, may be a human or non-human mammal. Non-human mammals include, for example, livestock and pets, such as ovine, bovine, porcine, canine, feline and murine mammals. Preferably, the subject is a human.

Ranges: throughout this disclosure, some embodiments can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compositions

Provided herein are compositions and methods for treating or preventing a lysosomal storage disorder (LSD) in a subject by administering to the subject a pharmaceutical comprising a bicistronic expression vector.

In some embodiments, the disclosure provides a composition comprising a bicistronic vector comprising a polynucleotide encoding a lysosomal enzyme and a polynucleotide encoding a modified GlcNAc-1 phosphotransferase (GlcNAc-1 PTase). In one embodiment, the polynucleotide encoding a lysosomal enzyme and the polynucleotide encoding a modified GlcNAc-1 phosphotransferase (GlcNAc-1 PTase) are operably linked.

In some embodiments, the disclosure provides a composition comprising a bicistronic vector comprising a constitutive promoter, an Internal Ribosome Entry Site (IRES) and a polynucleotide encoding a modified GlcNAc-1 phosphotransferase (GlcNAc-1 PTase).

In some embodiments, the bicistronic vector comprises an IRES located before the polynucleotide encoding a modified GlcNAc-1 PTase and after the polynucleotide encoding a lysosomal enzyme. In other embodiments, the bicistronic vector comprises an IRES located after the polynucleotide encoding a modified GlcNAc-1 PTase and before the polynucleotide encoding a lysosomal enzyme.

The sequence of the IRES can be a sequence known in the art or a variant thereof. The IRES variant be a can be modified or mutated. In one embodiment, the sequence IRES comprises SEQ ID NO: 3. In other embodiment, the sequence of the IRES is at least 70%, at least 75%, at least 80%, at least 85%, at least 90%, at least 95%, at least 99% similar to SEQ ID NO: 3.

In one embodiment, the polynucleotide of a lysosomal enzyme is operably linked to a 2A DNA encoding a 2A peptide, which is in turn operably the polynucleotide of a modified GlcNAc-1 phosphotransferase (GlcNAc-1 PTase). Various 2A peptides known in the art can be used in the disclosed bicistronic vector including but not limited to T2A, P2A, E2A and F2A. In some embodiments, the addition of GSG residues can be added to the 5'end of the peptide to improve cleavage efficiency.

In some embodiments, the bicistronic viral vector comprises a promoter operably linked to the polynucleotide encoding a lysosomal enzyme and the polynucleotide encoding a modified GlcNAc-1 PTase.

In some embodiments, the bicistronic expression vector comprises a promoter.

A promoter may be constitutive, inducible/repressible or cell type specific. In certain embodiments, the promoter may be constitutive. Non-limiting examples of constitutive promoters for mammalian cells include CMV, UBC, EF1 a, SV40, PGK, CAG, CBA/CAGGS/ACTB, CBh, MeCP2, U6 and H1. In some embodiments, the presently disclosed bicistronic vector comprises a constitutive promoter. In some embodiments, the constitutive promoter is a Cytomegalovirus (CMV) promoter. In some embodiments, the polynucleotide of CMV promoter comprises a nucleic acid sequence of SEQ ID NO: 2.

In other embodiments, the promoter may be an inducible promoter. The inducible promoter may be selected from the group consisting of: tetracycline, heat shock, steroid hormone, heavy metal, phorbol ester, adenovirus E1A element, interferon, and serum inducible promoters.

In different embodiments, the promoter may be cell type specific. For example, cell type specific promoters for neurons (e.g. syapsin), astrocytes (e.g. GFAP), oligodendrocytes (e.g. myelin basic protein), microglia (e.g. CX3CR1), neuroendocrine cells (e.g. chromogranin A), muscle cells (e.g. desmin, Mb), or cardiomyocytes (e.g. alpha myosin heavy-chain promoter) could be used. In an exemplary embodiment, a promoter may be the Nrl (rod photoreceptor-specific) promoter or the HBB (haemoglobin beta) promoter. A promoter may further comprise one or more specific transcriptional regulatory sequences to further enhance expression and/or to alter the spatial expression and/or temporal expression of a nucleic acid.

Enhancer sequences found on a vector also regulates expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the present bicistronic vector comprises one or more enhancers to boost transcription of the gene present within the vector. Non-limiting examples of enhancer include the CMV enhancer and the SP1 enhancer.

In some embodiments more than one promoter can be operably linked to each polynucleotide encoding a polypeptide, the promoters may be the same or different. The distance between the promoter and a nucleic acid sequence to be expressed may be approximately the same as the distance between that promoter and the native nucleic acid sequence it controls. As is known in the art, variation in this distance may be accommodated without loss of promoter function.

In order to assess the expression of the polypeptides within the bicistronic vector, the vector can also comprise either a selectable marker gene or a reporter gene or both to facilitate identification and selection of expressing cells from the population of cells sought to be transfected or infected through viral vectors. In some embodiments, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In some embodiments in which a non-viral delivery system is utilized, an exemplary delivery vehicle is a liposome. The use of lipid formulations is contemplated for the introduction of the nucleic acids into a host cell (in vitro, ex vivo or in vivo). In some embodiments, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the disclosure.

Vectors for Gene Therapy

The vectors to be used for treating or preventing LSDs in a subject as disclosed herein, are suitable for replication and, optionally, integration in eukaryotic cells. Typical vectors contain transcription and translation terminators, initiation sequences, and promoters useful for regulation of the expression of the desired nucleic acid sequence.

The vectors of the present disclosure may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the disclosure provides a gene therapy vector.

The isolated nucleic acid of the disclosure can be cloned into a number of types of vectors. For example, the nucleic acid can be cloned into a vector including, but not limited to a plasmid, a phagemid, a phage derivative, an animal virus, and a cosmid. Vectors of interest include expression vectors, replication vectors, probe generation vectors, and sequencing vectors.

Further, the vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In a preferred embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method In some embodiments, the disclosed bicistronic viral vector comprises an adenovirus (e.g. Ad-SYE, AdSur-SYE, Ad5/3-MDA7/IL-24, Ad-SB, Ad-CRISPR, oncolytic Ad); an adeno-associated virus, AAV (e.g. AAV-MeCP2, AAV1, AAV5, Dual AAV9 AAV8, AAV9, AAVrh10, AAVhu37); a herpes simplex virus, HSV (e.g. HSV1, HSV2, HSV-1, HF10 Oncolytic HSV-2); a Rretrovirus (e.g. RRV/Toca 511, GRV); a lentivirus (e.g. HIV-1, HIV-2); an alphavirus (SFV, M1); a flavivirus (Kunjin virus); a rhabdovirus (VSV); a measles virus (e.g. MV-Edm); a Newcastle disease virus (e.g. NDV90); an anhinga Picornaviruses Coxsackievirus (e.g. CVB3, CAV21, EV1); or a poxvirus (e.g. PANVAC, VV, VV-GLV-1h153, CPXV).

In one embodiment the disclosed bicistronic viral vector is an adenovirus, an adeno-associated viruses (AAV), an alphavirus, a flavivirus, a herpes simplex virus (HSV), a measles virus, a rhabdovirus, a retrovirus, a lentivirus, a Newcastle disease virus (NDV), a poxvirus, or a picornavirus. In one embodiment the disclosed bicistronic viral vector is an adenovirus, an adeno-associated viruses (AAV), a retrovirus or a lentivirus.

In one embodiment, the polynucleotide encoding a lysosomal enzyme and a polynucleotide encoding a modified GlcNAc-1 PTase are contained within an AAV vector. More than 30 naturally occurring serotypes of AAV are available. Many natural variants in the AAV capsid exist, allowing identification and use of an AAV with properties specifically suited for skeletal muscle. AAV viruses may be engineered using conventional molecular biology techniques, making it possible to optimize these particles for cell specific delivery of nucleic acid sequences, for minimizing immunogenicity, for tuning stability and particle lifetime, for efficient degradation, for accurate delivery to the nucleus, to name a few.

The use of AAVs is a common mode of exogenous delivery of DNA as it is relatively non-toxic, provides efficient gene transfer, and can be easily optimized for specific purposes. Among the serotypes of AAVs isolated from human or non-human primates (NHP) and well characterized, human serotype 2 is the first AAV that was developed as a gene transfer vector; it has been widely used for efficient gene transfer experiments in different target tissues and animal models. Clinical trials of the experimental application of AAV2 based vectors to some human disease models are in progress, and include therapies for diseases such as for example, cystic fibrosis and hemophilia B. Other useful AAV serotypes include AAV1, AAV3, AAV4, AAV5, AAV6, AAV7, AAV8 and AAV9.

Desirable AAV fragments for assembly into vectors include the cap proteins, including the vp1, vp2, vp3 and hypervariable regions, the rep proteins, including rep 78, rep 68, rep 52, and rep 40, and the sequences encoding these proteins. These fragments may be readily utilized in a variety of vector systems and host cells. Such fragments may be used alone, in combination with other AAV serotype sequences or fragments, or in combination with elements from other AAV or non-AAV viral sequences. As used herein, artificial AAV serotypes include, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid. Thus exemplary AAVs, or artificial AAVs, suitable for expression of a lysosomal enzyme of interest and a modified GlcNAc-1 PTase, include AAV2/8 (see U.S. Pat. No. 7,282,199), AAV2/5 (available from the National Institutes of Health), AAV2/9 (International Patent Publication No. WO2005/033321), AAV2/6 (U.S. Pat. No. 6,156,303), and AAVrh8 (International Patent Publication No. WO2003/042397), among others.

In one embodiment, the vectors useful in the compositions and methods described herein contain, at a minimum, sequences encoding a selected AAV serotype capsid, e.g., an AAV8 capsid, or a fragment thereof. In another embodiment, useful vectors contain, at a minimum, sequences encoding a selected AAV serotype rep protein, e.g., AAV8 rep protein, or a fragment thereof. Optionally, such vectors may contain both AAV cap and rep proteins. In vectors in which both AAV rep and cap are provided, the AAV rep and AAV cap sequences can both be of one serotype origin, e.g., all AAV8 origin. Alternatively, vectors may be used in which the rep sequences are from an AAV serotype which differs from that which is providing the cap sequences. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector, such as AAV2/8 described in U.S. Pat. No. 7,282,199.

A suitable recombinant adeno-associated virus (AAV) is generated by culturing a host cell which contains a nucleic acid sequence encoding an adeno-associated virus (AAV) serotype capsid protein, or fragment thereof, as defined herein; a functional rep gene; a minigene composed of, at a minimum, AAV inverted terminal repeats (ITRs) and a polynucleotide encoding a lysosomal enzyme and a polynucleotide encoding a modified GlcNAc-1 PTase; and sufficient helper functions to permit packaging of the minigene into the AAV capsid protein. The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art.

Most suitably, such a stable host cell will contain the required component(s) under the control of a constitutive promoter. However, the required component(s) may be under the control of an inducible promoter. Examples of suitable inducible and constitutive promoters are provided elsewhere herein, and are well known in the art. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing the rAAV of the disclosure may be delivered to the packaging host cell in the form of any genetic element which transfers the sequences carried thereon. The selected genetic element may be delivered using any suitable method, including those described herein and any others available in the art. The methods used to construct any embodiment of this disclosure are known to those with skill in nucleic acid manipulation and include genetic engineering, recombinant engineering, and synthetic techniques (see, e.g., Sambrook et al, Molecular Cloning: A Laboratory Manual, Cold Spring Harbor Press, Cold Spring Harbor, N.Y). Similarly, methods of generating rAAV virions are well known and the selection of a suitable method is not a limitation on the present disclosure (see, e.g., K. Fisher et al, 1993 J. Virol., 70:520-532 and U.S. Pat. No. 5,478,745, among others).

Unless otherwise specified, the AAV ITRs, and other selected AAV components described herein, may be readily selected from among any AAV serotype, including, without limitation, AAV1, AAV2, AAV3, AAV4, AAV5, AAV6, AAV7, AAV8, AAV9 or other known or as yet unknown AAV serotypes. These ITRs or other AAV components may be readily isolated from an AAV serotype using techniques available to those of skill in the art. Such an AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank, PubMed, or the like.

In some embodiments, the bicistronic vector comprises a nucleic acid sequence of SEQ ID NO: 1. In other embodiments, the bicistronic vector comprises a nucleic acid sequence having at least 20%, at least 30%, at least 40%, at least 50%, at least 60%, at least 70%, at least 75%, at least 80%, at least 85%, at least 90%, at least 95%, at least 99% similarity with SEQ ID NO: 1.

In some embodiments, the encoded lysosomal enzyme is involved in at least one lysosomal storage disorder (LSD) as listed in Table 1A, Table 1B or Table 1C below. In other embodiments, the lysosomal enzyme is at least one as listed in Table 1A, Table 1B or Table 1C below.

TABLE 1A

ERT Embodiment (enzymes with (Uniprot Accession Nos.))

| ENZYMES INVOLVED IN LYSOSOMAL STORAGE DISORDERS | SEQ ID NOs: | DISEASE (LSD) |
|---|---|---|
| 1. DEFECTS IN GLYCAN DEGRADATION | | |
| 1.1. Defects in glycoprotein degradation | | |
| Neuraminidase Q99519 | 24 and 25 | Sialidosis, Type I&II |
| Cathepsin A P10619 | 26 and 27 | Galactosialidosis |
| α-Mannosidase 000754 | 28 and 29 | α-Mannosidosis, types I and II |
| β-Mannosidase 000462 | 30 and 31 | Aspartylglucosaminuria |
| Glycosylasparaginase P20933 | 32 and 33 | β-Mannosidosis |
| α-L-Fucosidase P04066 | 34 and 35 | Fucosidosis |

TABLE 1A-continued

| ERT Embodiment (enzymes with (Uniprot Accession Nos.)) | | |
|---|---|---|
| ENZYMES INVOLVED IN LYSOSOMAL STORAGE DISORDERS | SEQ ID NOs: | DISEASE (LSD) |
| α-N-Acetylglucosaminidase P54802 | 36 and 37 | Kanzaki disease, Schindler disease, TypeI&III |
| 1.2. Defects in glycolipid degradation | | |
| 1.2a. GM1 Ganglioside | | |
| β-Galactosidase-1 P16278 | 38 and 39 | GMI gangliosidosis Type 1, II & III |
| | | GM2-gangliosidosis, Tay-Sachs disease |
| Hexosaminidase α-subunit P06865 | 40 and 41 | GM2-gangliosidosis, |
| Hexosaminidase β-subunit P07686 | 42 and 43 | Sandhoff disease |
| | | GM2 gangliosidosis, AB |
| GM2 activator protein Pl7900 | 44 and 45 | viriant |
| Acid beta-glucosidase P04062 | 46 and 47 | Gaucher disease |
| Saposin C P07602 | 48, 49 and 50 | Gaucher disease, atypical |
| 1.2b. Defects in the degradation of sulfatide | | |
| Arylsulfatase A P15289 | 52 and 53 | Metachromatic leukodystrophy |
| Saposin B P07602 | 48, 49 and 51 | Metachromatic leukodystrophy |
| sulfatase-modifying factor-1 Q8NBK3 | 54 and 55 | Multiple sulfatase deficiency |
| Galactosylceramidase P54803 | 56 and 57 | Krabbe disease |
| 1.2c. Defects in degradation of globotriaosylceramide | | |
| alpha-galactosidase A P06280 | 58 and 59 | Fabry |
| 1.3. Defects in degradation of Glycosaminoglycan (Mucopolysaccharidoses) | | |
| 1.3a. Degradation of heparan sulphate | | |
| Iduronate 2-sulfatase P22304 | 60 and 61 | MPS II (Hunter) |
| alpha-L-iduronidase P35475 | 62 and 63 | MPS I (Hurler, Scheie) |
| N-sulfoglucosamine sulfohydrolase P51688 | 64 and 65 | MPS IIIa (Sanfilippo A) |
| heparan acetyl-CoA:alpha-glucosaminide N-acetyltransferase Q68CP4 | 66 and 67 | MPS IIIc (Sanfilippo C) |
| N-alpha-acetylglucosaminidase P54802 | 36 and 37 | MPS IIIb (Sanfilippo B) |
| β-glucuronidase P08236 | 68 and 69 | MPS VII (Sly) |
| N-acetyl glucosamine 6-sulfatase P15586 | 70 and 71 | MPS IIId (Sanfilippo D) |
| 1.3b Degradation of other mucopolysaccharides | | |
| N-Acetylgalactosamine 4-sulfatase P15848 | 72 and 73 | MPS VI |
| galactosamine-6-sulfate sulfatase P34059 | 129 and 130 | MPS IVA (Morquio A) |
| Hyaluronidase 1 Q12794 | 74 and 75 | MPS IX |
| 1.4. Defects in degradation of glycogen | | |
| acid alpha-1,4-glucosidase P10253 | 76 and 77 | Pompe |
| 2. DEFECTS IN LIPID DEGRADATION | | |
| 2.1 Defects in degradation of sphingomyelin | | |
| acid sphingomyelinase P17405 | 78 and 79 | Niemann Pick type A and B |
| Acid ceramidase Q13510 | 80 and 81 | Farber lipogranulomatosis |
| 2.2 Defects in degradation of triglycerides and cholesteryls ester | | |
| Acid lipase P38571 | 82 and 83 | Wolman and cholesteryl ester storage disease |
| 3. DEFECTS IN PROTEIN DEGRADATION | | |
| Cathepsin K P43235 | 84 and 85 | Pycnodysostosis |
| Tripeptidyl peptidase O14773 | 86 and 87 | Ceroide lipofuscinosis 2 |
| Palmitoyl-protein thioesterase 1 P50897 | 88 and 89 | Ceroide lipofuscinosis 1 |
| 4. DEFECTS IN LYSOSOMAL TRANSPORTERS | | |
| Cystinosin (cystin transport) O60931 | 90 and 91 | Cystinosis |
| SOLUTE CARRIER FAMILY 17 (ACIDIC SUGAR TRANSPORTER), MEMBER 5 H0UI05 | 92 and 93 | Salla disease |

TABLE 1A-continued

| ERT Embodiment (enzymes with (Uniprot Accession Nos.)) | | |
|---|---|---|
| ENZYMES INVOLVED IN LYSOSOMAL STORAGE DISORDERS | SEQ ID NOs: | DISEASE (LSD) |
| 5. DEFECTS IN LYSOSOMAL TRAFFICKING PROTEINS | | |
| UDP-N-acetylglucosamine Q96950 | 94 and 95 | Mucolipidosis III gamma (1-cell) |
| N-acetylglucosamine-1-phosphotransferase γ-subunit Q9UJJ9 | 96 and 97 | |
| N-acetylglucosamine-1 -phosphotransferase alpha/beta-subunits Q3T906 | 98 and 99 | Mucolipidosis III alpha/beta |
| Mucolipin-l (cation channel) Q9GZU1 | 100 and 101 | Mucolipidosis IV |
| Lysosome-associated membrane protein 2 (LAMP-2) P13473 | 102 and 103 | Danon |
| Niemann-Pick Cl 015118 | 104 and 105 | Niemann Pick type C1 & D |
| Epididymal secretory protein HE1 P61916 | 106 and 107 | Niemann-pick disease, type C2 |
| ceroid lipofuscinosis-3 Q13286 | 108 and 109 | Ceroid lipofuscinosis, neuronal, 3 |
| ceroid lipofuscinosis-6 Q9NWW5 | 110 and 111 | Ceroid lipofuscinosis 6 |
| ceroid lipofuscinosis-8 Q9UBY8 | 112 and 113 | Ceroid lipofuscinosis 8 |
| Lysosomal trafficking regulator Q99698 | 114 and 115 | Chediak-Higashi |
| myosin 5A Q9Y4I1 | 116 and 117 | Griscelli Type 1 |
| Ras-associated protein RAB27A P51159 | 118 and 119 | Griscelli Type 2 |
| Melanophilin Q9BV36 | 120 and 121 | Griscelli Type 3 |
| AP3 P-subunit 000203 | 122 and 123 | Hermansky Pudliak 2 |

TABLE 1B

| Gene Therapy Embodiment (enzymes with (Uniprot Accession Nos.)) | | |
|---|---|---|
| ENZYMES INVOLVED IN LYSOSOMAL STORAGE DISORDERS | SEQ ID NO: | DISEASE (LSD) |
| 1. DEFECTS IN GLYCAN DEGRADATION 1.1. Defects in glycoprotein degradation | | |
| Neuraminidase Q99519 | 24 and 25 | Sialidosis, Type I&II |
| Cathepsin A P10619 | 26 and 27 | Galactosialidosis |
| α-Mannosidase 000754 | 28 and 29 | α-Mannosidosis, types I and II |
| β-Mannosidase 000462 | 30 and 31 | P-Mannosidosis |
| Glycosylasparaginase P20933 | 32 and 33 | Aspartylglucosaminuria |
| α-L-Fucosidase P04066 | 34 and 35 | Fucosidosis |
| α-N-Acetylglucosaminidase P54802 | 36 and 37 | Kanzaki disease, Schindler disease, TypeI&III |
| Neuraminidase Q99519 | 24 and 25 | |
| 1.2. Defects in glycolipid degradation 1.2a. GMI Ganglioside | | |
| β-Galactosidase-1 P16278 | 38 and 39 | GMI gangliosidosis Type 1, II & III |
| | | GM2-gangliosidosis, Tay-Sachs disease |
| Hexosaminidase α-subunit P06865 | 40 and 41 | GM2-gangliosidosis, Sandhoff disease |
| Hexosaminidase β-subunit P07686 | 42 and 43 | GM2 gangliosidosis, AB viriant |
| GM2 activator protein Pl7900 | 44 and 45 | |
| Acid beta-glucosidase P04062 | 46 and 47 | Gaucher disease |
| Saposin C P07602 | 48, 49 and 50 | Gaucher disease, atypical |
| 1.2b. Defects in the degradation of sulfatide | | |
| Arylsulfatase A P15289 | 52 and 53 | Metachromatic leukodystrophy |
| Saposin B P07602 | 48, 49 and 51 | Metachromatic leukodystrophy |
| sulfatase-modifying factor-1 Q8NBK3 | 54 and 55 | Multiple sulfatase deficiency |
| Galactosylceramidase P54803 | 56 and 57 | Krabbe disease |
| 1.2c. Defects in degradation of globotriaosylceramide | | |
| alpha-galactosidase A P06280 | 58 and 59 | Fabry |
| Arylsulfatase A P15289 | 52 and 53 | |
| 1.3. Defects in degradation of Glycosaminoglycan (Mucopolysaccharidoses) | | |

TABLE 1B-continued

| Gene Therapy Embodiment (enzymes with (Uniprot Accession Nos.)) | | |
|---|---|---|
| ENZYMES INVOLVED IN LYSOSOMAL STORAGE DISORDERS | SEQ ID NO: | DISEASE (LSD) |
| 1.3a. Degradation of heparan sulphate | | |
| Iduronate 2-sulfatase P22304 | 60 and 61 | MPS II (Hunter) |
| alpha-L-iduronidase P35475 | 62 and 63 | MPS I (Hurler, Scheie) |
| N-sulfoglucosamine sulfohydrolase P51688 | 64 and 65 | MPS IIIa (Sanfilippo A) |
| heparan acetyl-CoA:alpha-glucosaminide N-acetyltransferase Q68CP4 | 66 and 67 | MPS IIIc (Sanfilippo C) |
| N-alpha-acetylglucosaminidase P54802 | 36 and 37 | MPS IIIb (Sanfdippo B) |
| P-glucuronidase P08236 | 68 and 69 | MPS VII (Sly) |
| N-acetyl glucosamine 6-sulfatase P15586 | 70 and 71 | MPS IIId (Sanfdippo D) |
| 1.3bDegradation of other mucopolysaccharides | | |
| N-Acetylgalactosamine 4-sulfatase P15848 | 72 and 73 | MPS VI |
| galactosamine-6-sulfate sulfatase P34059 | 129 and 130 | MPS IVA (Morquio A) |
| Hyaluronidase 1 Q12794 | 74 and 75 | MPS IX |
| 1.4. Defects in degradation of glycogen | | |
| acid alpha-1,4-glucosidase P1025 3 | | |
| 2. DEFECTS IN LIPID DEGRADATION | | |
| 2.1 Defects in degradation of sphingomyelin | | |
| acid sphingomyelinase P17405 | 76 and 77 | Pompe |
| Acid ceramidase Q13510 | 78 and 79 | Niemann Pick type A and B |
| 2.2 Defects in degradation of triglycerides and | | |
| cholesteryls ester | 80 and 81 | Farber lipogranulomatosis |
| Acid lipase P38571 | 82 and 83 | Wolman and cholesteryl ester storage disease |
| 3. DEFECTS IN PROTEIN DEGRADATION | | |
| Cathepsin K P43235 | 84 and 85 | Pycnodysostosis |
| Tripeptidyl peptidase 014773 | 86 and 87 | Ceroide lipofuscinosis 2 |
| Palmitoyl-protein thioesterase 1 P50897 | 88 and 89 | Ceroide lipofuscinosis 1 |
| 4. DEFECTS IN LYSOSOMAL TRANSPORTERS | | |
| Cystinosin (cystin transport) 060931 | 90 and 91 | Cystinosis |
| SOLUTE CARRIER FAMILY 17 (ACIDIC SUGAR TRANSPORTER), MEMBER 5 H0UI05 | 92 and 93 | Salla disease |
| 5. DEFECTS IN LYSOSOMAL TRAFFICKING PROTEINS | | |
| UDP-N-acetylglucosamine Q96950 | 94 and 95 | Mucolipidosis III gamma (1-cell) |
| N-acetylglucosamine-1-phosphotransferase γ-subunit Q9UJJ9 | 96 and 97 | |
| N-acetylglucosamine-1-phosphotransferase alpha/beta-subunits Q3T906 | 98 and 99 | Mucolipidosis III alpha/beta |
| Mucolipin-l (cation channel) Q9GZU1 | 100 and 101 | Mucolipidosis IV |
| Lysosome-associated membrane protein 2 | | Danon |
| (LAMP-2) P13473 | 102 and 103 | Niemann Pick type C1 & D |
| Niemann-Pick C1 015118 | 104 and 105 | Niemann-pick disease, type |
| Epididymal secretory protein HEI P61916 | 106 and 107 | C2 |
| | | Ceroid lipofuscinosis, |
| ceroid lipofuscinosis-3 Q13286 | 108 and 109 | neuronal, 3 |
| ceroid lipofuscinosis-6 Q9NWW5 | 110 and 111 | Ceroid lipofuscinosis 6 |
| ceroid lipofuscinosis-8 Q9UBY8 | 112 and 113 | Ceroid lipofuscinosis 8 |
| Lysosomal trafficking regulator Q99698 | 114 and 115 | Chediak-Higashi |
| myosin 5A Q9Y4I1 | 116 and 117 | Griscelli Type 1 |
| Ras-associated protein RAB27A P51159 | 118 and 119 | Griscelli Type 2 |
| Melanophilin Q9BV36 | 120 and 121 | Griscelli Type 3 |
| AP3 P-subunit 000203 | 122 and 123 | Hermansky Pudliak 2 |

TABLE 1C

Lysosomal Disorders (Protein (UniProt Accession No.)

| Clinical Name | Subtype | Protein | SEQ ID NO: | Gene | SEQ ID NO: | Exemplary Second Therapeutic Agent |
|---|---|---|---|---|---|---|
| activator deficiency, GM2-gangliosidosis; GM2-gangliosidosis, AB variant | AB variant GM2-gangliosidosis | GM2-activator protein (P17900) | 45 | GM2A | 44 | |
| alpha-mannosidosis | type 1, mild form | α-mannosidase (O00754) | 29 | MAN2B1 | 28 | |
| | type 2, moderate form | α-mannosidase (O00754) | 29 | MAN2B1 | 28 | |
| | type 3, neonatal, severe | α-mannosidase (O00754) | 29 | MAN2B1 | 28 | |
| beta-mannosidosis | beta-mannosidosis | lysosomal β-mannosidase (O00462) | 31 | MANBA | 30 | |
| aspartylglucosaminuria | aspartylglucosaminuria | Glycosylasparaginase (P20933) | 33 | AGA | 32 | |
| lysosomal acid lipase deficiency | cholesteryl ester storage disease (later-onset) | lysosomal acid lipase (P38571) | 83 | LIPA | 82 | sebelipase alfa (Kanuma ™) |
| lysosomal acid lipase deficiency | Wolman disease (infantile) | lysosomal acid lipase (P38571) | 83 | LIPA | 82 | sebelipase alfa (Kanuma ™) |
| cystinosis | adult nonnephropathic | Cystinosin (O60931) | 91 | CTNS | 90 | cysteamine (Cystagon, Procysbi) |
| | late-onset juvenile or adolescent nephropathic type | Cystinosin (O60931) | 91 | CTNS | 90 | cysteamine (Cystagon, Procysbi) |
| | infantile nephropathic | Cystinosin (O60931) | 91 | CTNS | 90 | |
| Chanarin-Dorfman syndrome | neutral lipid storage disease with ichthyosis; NLSDI | 1-acylglycerol-3-phosphate O-acyltransferase (Q8WTS1) | 160 | CGI58, ABHD5 | 159 | |
| | neutral lipid storage disease with myopathy; NLSDM | adipose triglyceride lipase (Q96AD5) | 125 | PNPLA2 | 124 | |
| Danon disease | Danon disease | lysosome-associated membrane protein-2 (P13473) | 103 | LAMP2 | 102 | |
| Fabry disease | Fabry disease type I, classic | α-galactosidase A (P06280) | 59 | GLA | 58 | agalsidase beta (Fabrazyme ®); migalastat (Galafold ®) |
| | Fabry disease type II, late-onset | α-galactosidase A (P06280) | 59 | GLA | 58 | agalsidase beta (Fabrazyme ®); migalastat (Galafold ®) |
| Farber disease; Farber lipogranulomatosis | acid ceramidase deficiency | acid ceramidase (Q13510) | 81 | ASAH1 | 80 | |
| fucosidosis | fucosidosis | α-L-fucosidase (P04066) | 35 | FUCA1 | 34 | |
| galactosialidosis (combined neuraminidase & beta-galactosidase deficiency) | cathepsin A deficiency | protective protein/cathepsin A (P10619) | 27 | CTSA | 26 | |
| Gaucher disease | type I Gaucher disease | acid β-glucosidase (P04062) | 47 | GBA | 46 | pharmacologic recombinant human glucocerebrosidase glycoproteins |
| | type II Gaucher disease | acid β-glucosidase (P04062) | 47 | GBA | 46 | pharmacologic recombinant human glucocerebrosidase glycoproteins |
| | type III Gaucher disease | acid β-glucosidase (P04062) | 47 | GBA | 46 | pharmacologic recombinant human glucocerebrosidase glycoproteins |
| | type IIIC Gaucher disease | acid β-glucosidase (P04062) | 47 | GBA | 46 | pharmacologic recombinant human glucocerebrosidase glycoproteins |
| | Gaucher disease, atypical, due to saposin C deficiency | saposin C (P07602) | 50 and 49 | PSAP | 48 | |
| GM1-gangliosidosis | infantile GM1-gangliosidosis | β-galactosidase-1 (P16278) | 39 | GLB1 | 38 | |
| | late-infantile/juvenile GM1-gangliosidosis | β-galactosidase-1 (P16278) | 39 | GLB1 | 38 | |
| | adult/chronic GM1-gangliosidosis | β-galactosidase-1 (P16278) | 39 | GLB1 | 38 | |
| Globoid cell leukodystrophy, Krabbe disease | Early Infantile Onset | galactosylceramide β-galactosidase (P54803) | 57 | GALC | 56 | hematopoietic stem cell transplantation using umbilical cord blood from healthy donors |
| | Late infantile onset | galactosylceramide β-galactosidase (P54803) | 57 | GALC | 56 | |
| | Juvenile Onset | galactosylceramide β-galactosidase (P54803) | 57 | GALC | 56 | |
| | Adult Onset | galactosylceramide β-galactosidase (P54803) | 57 | GALC | 56 | |
| | Krabbe disease, atypical, due to saposin A deficiency | Saposin A (P07602) | 126 | PSAP | 48 | |

TABLE 1C-continued

| Lysosomal Disorders (Protein (UniProt Accession No.) | | | | | | |
|---|---|---|---|---|---|---|
| Clinical Name | Subtype | Protein | SEQ ID NO: | Gene | SEQ ID NO: | Exemplary Second Therapeutic Agent |
| Metachromatic Leukodystrophy | late infantile | arylsulfatase A (P15289) | 53 | ARSA | 52 | |
| | juvenile | arylsulfatase A (P15289) | 53 | ARSA | 52 | |
| | adult | arylsulfatase A (P15289) | 53 | ARSA | 52 | |
| | partial cerebroside sulfate deficiency | arylsulfatase A (P15289) | 53 | ARSA | 52 | |
| | pseudoarylsulfatase A deficiency | arylsulfatase A (P15289) | 53 | ARSA | 52 | |
| | metachromatic leukodystrophy due to saposin B deficiency | saposin B | 51 | PSAP | 48 | |
| Mucopolysaccharidoses disorders: | | | | | | |
| MPS I, Hurler syndrome | | α-L-iduronidase (P35475) | 63 | IDUA | 62 | hematopoietic stem cell transplantation from healthy donors; & laronidase (Aldurazyme ®) |
| MPS I, Hurler-Scheie syndrome | | α-L-iduronidase (P35475) | 63 | IDUA | 62 | laronidase (Aldurazyme ®) |
| MPS I, Scheie syndrome | | α-L-iduronidase (P35475) | 63 | IDUA | 62 | laronidase (Aldurazyme ®) |
| MPS II, Hunter syndrome | Classic severe/MPS IIA | iduronate 2-sulfatase (P22304) | 61 | IDS | 60 | |
| MPS II, Hunter syndrome | Attenuated/MPS IIB | iduronate 2-sulfatase (P22304) | 61 | IDS | 60 | |
| Sanfilippo syndrome Type A/MPS IIIA | | heparan N-sulfatase (P51688) | 128 | SGSH | 127 | rhHNS |
| Sanfdippo syndrome Type B/MPS IIIB | | N-α-acetylglucosaminidase (P54802) | 37 | NAGLU | 36 | |
| Sanfilippo syndrome Type C/MPS IIIC | | heparan acetyl CoA: α-glucosaminide acetyltransferase (Q68CP4) | 67 | HGSNAT | 66 | |
| Sanfilippo syndrome Type D/MPS IIID | | N-acetylglucosamine 6-sulfatase (P34059) | 130 | GNS | 129 | |
| Morquio syndrome, type A/ MPS IVA | | N-acetylglucosamine 6-sulfatase (P34059) | 130 | GNS | 129 | elosulfase alfa (VIMIZIM ®) |
| Morquio syndrome, type B/ MPS IVB | | β-galactosidase (P16278) | 39 | GLB1 | 38 | |
| MPS IX hyaluronidase deficiency | | Hyaluronidase (Q12794) | 75 | HYAL1 | 74 | |
| MPS VI Maroteaux-Lamy syndrome | | arylsulfatase B (P15848) | 132 | ARSB | 131 | |
| MPS VII Sly syndrome | | β-glucuronidase (P08236) | 69 | GUSB | 68 | vestronidase alfa (Mepsevii ®) |
| mucolipidosis I, sialidosis | type I | Neuraminidase (Q99519) | 25 | NEU1 | 24 | |
| | type II | Neuraminidase (Q99519) | 25 | NEU1 | 24 | |
| I-cell disease, Leroy disease, mucolipidosis II | | N-acetylglucosamine-1-phosphotransferase subunits alpha/ beta (Q3T906) | 99 | GNPTAB | 98 | |
| Pseudo-Hurler polydystrophy/ mucolipidosis type III | | N-acetylglucosamine-1-phosphotransferase subunits alpha/ beta (Q3T906) | 99 | GNPTAB | 98 | |
| mucolipidosis IIIC/ML III GAMMA | | gamma subunit of N-acetylglucosamine-1-phosphotransferase (Q9UJJ9) | 97 | GNPTG | 96 | |
| mucolipidosis type IV | | mucolipin-1 (Q9GZU1) | 101 | MCOLN1 | 100 | |
| multiple sulfatase deficiency | juvenile sulfatidosis | sulfatase-modifying factor-1 (Q8NBK3) | 55 | SUMF1 | 54 | |
| Niemann-Pick disease | type A | acid sphingomyelinase (P17405) | 79 | SMPD1 | 78 | |
| | type B | acid sphingomyelinase (P17405) | 79 | SMPD1 | 78 | |
| | type C1/chronic neuronopathic form | epididymal secretory protein HE1 (O15118) | 134 | NPC1 | 133 | 2-hydroxy-propyl-beta-cyclodextrin; Vorinostat arimoclomol |
| | type C2 | NPC intracellular cholesterol transporter 2 (P61916) | 107 | NPC2 | 106 | |
| | type D/Nova Scotian type | epididymal secretory protein HE1 (also known as NPC intracellular cholesterol transporter 1; (O15118)) | 134 | NPC1 | 133 | |
| Neuronal Ceroid Lipofuscinoses: | | | | | | |
| CLN6 disease-Atypical Late Infantile, Late-Onset variant, Early Juvenile | | Ceroid-lipofuscinosis neuronal protein 6 (Q9NWW5) | 111 | CLN6 | 110 | |
| Batten-Spielmeyer-Vogt/ Juvenile NCL/CLN3 disease | | Ceroid-lipofuscinosis neuronal protein 3 (Q13286) | 109 | CLN3 | 108 | |

TABLE 1C-continued

| Lysosomal Disorders (Protein (UniProt Accession No.) | | | | | | |
|---|---|---|---|---|---|---|
| Clinical Name | Subtype | Protein | SEQ ID NO: | Gene | SEQ ID NO: | Exemplary Second Therapeutic Agent |
| Finnish Variant Late Infantile CLN5 | | Ceroid-lipofuscinosis neuronal protein 5 (also known as Ceroid lipofuscinosis-5) (O75503) | 136 | CLN5 | 135 | |
| Jansky-Bielschowsky disease/Late infantile CLN2/TPP1 Disease | | Tripeptidyl-peptidase 1 (O14773) | 139 | TPP1 | 138 | |
| Kufs/Adult-onset NCL/ CLN4 disease | type A | Ceroid-lipofuscinosis neuronal protein 6 (Q9NWW5) | 111 | CLN6 | 110 | |
| | type B | Ceroid-lipofuscinosis neuronal protein 6 (Q9NWW5) | 111 | CLN6 | 110 | |
| Northern Epilepsy/variant late infantile CLN8 | | Ceroid-lipofuscinosis neuronal protein 8 (Q9UBY8) | 113 | CLN8 | 112 | |
| Santavuori-Haltia/Infantile CLN1/PPT disease | | palmitoyl-protein thioesterase-1 (P50897) | 89 | PPT1 | 88 | |
| Pompe disease (glycogen storage disease type II) | infantile Pompe disease | acid maltase (acid α-1,4-glucosidase) (P10253) | 77 | GAA | 76 | alglucosidase alfa (Lumizyme ®) |
| | late-onset Pompe disease | acid maltase (acid α-1,4-glucosidase) (P10253) | 77 | GAA | 76 | alglucosidase alfa (Lumizyme ®) |
| Pycnodysostosis | | cathepsin K (P43235) | 85 | CTSK | 84 | |
| Sandhoff disease/GM2 gangliosidosis | infantile | hexosaminidase (P07686) | 43 | HEXB | 42 | |
| Sandhoff disease/GM2 gangliosidosis | juvenile | hexosaminidase (P07686) | 43 | HEXB | 42 | |
| Sandhoff disease/GM2 Gangliosidosis | adult-onset | hexosaminidase B (P07686) | 43 | HEXB | 42 | |
| Schindler disease | type I/infantile | α-N-acetylgalactosaminidase (P17050) | 140 | NAGA | 139 | |
| | type III/intermediate, variable | α-N-acetylgalactosaminidase (P17050) | 140 | NAGA | 139 | |
| Kanzaki disease | Schindler disease type II | α-N-acetylgalactosaminidase (P17050) | 140 | NAGA | 139 | |
| Salla disease | adult form of sialic acid storage disease | Sialin (Q9NRA2) | 142 | SLC17A5 | 141 | |
| infantile free sialic acid storage disease (ISSD) | infantile form of sialic acid storage disease | Sialin (Q9NRA2) | 142 | SLC17A5 | 141 | |
| spinal muscular atrophy with progressive myoclonic epilepsy (SMAPME) | myoclonus, hereditary, with progressive distal muscular atrophy | acid ceramidase (Q13510) | 81 | ASAH1 | 80 | |
| Tay-Sachs disease/GM2 gangliosidosis | infantile Tay-Sachs disease | hexosaminidase A (P06865) | 41 | HEXA | 40 | |
| | juvenile-onset Tay-Sachs disease | hexosaminidase A (P06865) | 41 | HEXA | 40 | |
| | late-onset Tay-Sachs disease | hexosaminidase A (P06865) | 41 | HEXA | 40 | |
| Christianson syndrome | MRXSCH | monovalent sodium-selective sodium/hydrogen exchanger (NHE) (Q92581) | 144 | SLC9A6 | 143 | |
| Lowe oculocerebrorenal syndrome | | Inositol polyphosphate 5-phosphatase (also known as PIP(2) 5-phosphatase) (Q01968) | 146 | OCRL | 145 | |
| Charcot-Marie-Tooth type 4J, CMT4J | | Polyphosphoinositide phosphatase (Q92562) | 148 | FIG4 | 147 | |
| Yunis-Varon syndrome | | Polyphosphoinositide phosphatase (Q92562) | 148 | FIG4 | 147 | |
| bilateral temporooccipital polymicrogyria (BTOP) | | Polyphosphoinositide phosphatase (Q92562) | 148 | FIG4 | 147 | |
| X-linked hypercalciuric nephrolithiasis, Dent-1 | | H(+)/Cl(−) exchange transporter 5 (P51795) | 150 | CLCN5 | 149 | |
| Dent disease 2 | | Inositol polyphosphate 5-phosphatase (also known as PIP(2) 5-phosphatase) (Q01968) | 146 | OCRL | 145 | |
| | | Autophagy protein 5 (Q9H1Y0) | 152 | ATG5 | 151 | |
| | | Ubiquitin-like modifier-activating enzyme ATG7 (O95352) | 154 | ATG7 | 153 | |
| | | Serine/threonine-protein kinase mTOR (P42345) | 156 | mTORC1 | 155 | |
| | | Sodium-coupled neutral amino acid transporter 9 (Q8NBW4) | 158 | SLC38A9 | 157 | |

In some embodiments, the lysosomal enzyme is selected from the group consisting of β-glucocebrosidase (GBA), Galactosylceremidase (GALC), α-Galactosidase (GLA), α-N-acetylglucosaminidase (NAGLU), acid α-glucosidase (GAA) and lysosomal acid α-mannosidase (LAMAN). In yet other embodiments, the polynucleotide encoding the lysosomal enzyme comprises a nucleic acid sequence of SEQ ID NOs: 5-10. In other embodiments, the lysosomal enzyme is encoded by a polynucleotide having at least 50%, at least 60%, at least 70%, at least 75%, at least 80%, at least 85%, at least 90%, at least 95%, at least 99% similarity with of SEQ ID NOs: 5-10.

In some embodiments, the S1-S3 PTase is encoded by a polynucleotide comprising a nucleic acid sequence of SEQ ID NO: 4. In other embodiments, the GlcNAc-1 PTase is encoded by a polynucleotide having at least 50%, at least 60%, at least 70%, at least 75%, at least 80%, at least 85%, at least 90%, at least 95%, at least 99% similarity with of SEQ ID NO: 4.

The present disclosure should also be construed to include any form of a polypeptide or polynucleotide having substantial homology to the ones disclosed herein.

Preferably, a polypeptide which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of the peptides disclosed herein.

The polypeptide may alternatively be made by recombinant means or by cleavage from a longer polypeptide. The composition of a peptide may be confirmed by amino acid analysis or sequencing. The variants of the polypeptides according to the present disclosure may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present disclosure, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two polypeptides is determined by comparing the amino acid sequence and its conserved amino acid substitutes of one polypeptide to a sequence of a second polypeptide. Variants are defined to include polypeptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to bind to ubiquitin or to a ubiquitylated protein. The present disclosure includes amino acid sequences that are at least 60%, 65%, 70%, 72%, 74%, 76%, 78%, 80%, 90%, or 95% similar or identical to the original amino acid sequence. The degree of identity between two polypeptides is determined using computer algorithms and methods that are widely known for the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

The polypeptides disclosed herein can be post-translationally modified. For example, post-translational modifications that fall within the scope of the present disclosure include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts to a standard translation reaction.

The polypeptides of the disclosure may include unnatural amino acids formed by post-translational modification or by introducing unnatural amino acids during translation. A variety of approaches are available for introducing unnatural amino acids during protein translation.

The term "functionally equivalent" as used herein refers to a polypeptide that preferably retains at least one biological function or activity of the specific amino acid sequence of a lysosomal enzyme of the disclosure.

A polypeptide may be conjugated with other molecules, such as proteins, to prepare fusion proteins. This may be accomplished, for example, by the synthesis of N-terminal or C-terminal fusion proteins provided that the resulting fusion protein retains the functionality of a lysosomal enzyme of the disclosure.

A polypeptide may be phosphorylated using conventional methods. In one embodiment, the presently disclosed lysosomal enzyme can be phosphorylated thanks to the presently disclosed modified GlcNAc-1 phosphotransferase (GlcNAc-1 PTase).

Cyclic derivatives of the peptides or chimeric proteins are also contemplated herein. Cyclization may allow the peptide or chimeric protein to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component.

Cyclization may also be achieved using an azobenzene-containing amino acids. The components that form the bonds may be side chains of amino acids, non-amino acid components or a combination of the two. In one embodiment, cyclic peptides may comprise a beta-turn in the right position. Beta-turns may be introduced into the peptides of the disclosure by adding the amino acids Pro-Gly at the right position. It may be desirable to produce a cyclic peptide which is more flexible than the cyclic peptides containing peptide bond linkages as described above. A more flexible peptide may be prepared by introducing cysteines at the right and left position of the peptide and forming a disulfide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

Tags

In one embodiment, the polypeptides as disclosed herein further comprise the amino acid sequence of a tag. The tag includes but is not limited to: polyhistidine tags (His-tags)

(for example H6 and H10, etc.) or other tags for use in IMAC systems, for example, Ni2+ affinity columns, etc., GST fusions, MBP fusions, streptavidine-tags, the BSP biotinylation target sequence of the bacterial enzyme BIRA and tag epitopes that are directed by antibodies (for example c-myc tags, FLAG-tags, HPC4-tag among others). As will be observed by a person skilled in the art, the tag peptide can be used for purification, inspection, selection and/or visualization of the fusion protein of the disclosure. In one embodiment, the tag is a detection tag and/or a purification tag. It will be appreciated that the tag sequence will not interfere in the function of the protein of the disclosure.

Leader and Secretory Sequence

Accordingly, the polypeptides of the disclosure can be fused to another polypeptide or tag, such as a leader or secretory sequence or a sequence which is employed for purification or for detection. In some embodiments, the polypeptide of the disclosure comprises the glutathione-S-transferase protein tag which provides the basis for rapid high-affinity purification of the polypeptide of the disclosure. Indeed, this GST-fusion protein can then be purified from cells via its high affinity for glutathione. Agarose beads can be coupled to glutathione, and such glutathione-agarose beads bind GST-proteins. Thus, in a particular embodiment, the polypeptide can be bound to a solid support. In some embodiments, if the polypeptide comprises a GST moiety, the polypeptide is coupled to a glutathione-modified support. In some embodiments, the glutathione modified support is a glutathione-agarose bead. Additionally, a sequence encoding a protease cleavage site can be included between the affinity tag and the polypeptide sequence, thus permitting the removal of the binding tag after incubation with this specific enzyme and thus facilitating the purification of the corresponding protein of interest.

The polypeptides disclosed herein can also be fused to, or integrated into, a target protein, and/or a targeting domain capable of directing the chimeric protein to a desired cellular component or cell type or tissue. The chimeric proteins may also contain additional amino acid sequences or domains. The chimeric proteins are recombinant in the sense that the various components are from different sources, and as such are not found together in nature (i.e. are heterologous).

In some embodiments of the compositions of the disclosure, polypeptides comprise peptidomimetics of the lysosomal proteins of the disclosure or a vector encodes a peptidomimetic of the lysosomal proteins of the disclosure. Peptidomimetics are compounds based on, or derived from, peptides and proteins.

N-terminal or C-terminal fusion proteins comprising a peptide or chimeric protein of the disclosure conjugated with other molecules may be prepared by fusing, through recombinant techniques, the N-terminal or C-terminal of the peptide or chimeric protein, and the sequence of a selected protein or selectable marker with a desired biological function. The resultant fusion proteins contain a lysosomal enzyme comprising peptide or chimeric protein fused to the selected protein or marker protein as described herein. Examples of proteins which may be used to prepare fusion proteins include immunoglobulins, glutathione-S-transferase (GST), hemagglutinin (HA), and truncated myc.

The polypeptides and chimeric proteins presently disclosed may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

Modified Cell

In some embodiments, the disclosure provides a cell comprising a vector of the disclosure. In some embodiments, the vector is a viral vector (e.g., an AAV or a lentiviral vector). In some embodiments, the vector is a non-viral vector (e.g., a liposome, a nanoparticle, a lipid nanoparticle, a micelle, a polymersome, an exosome). In some embodiments, the vector is an expression vector. In some embodiments, the vector contains at least one element allowing for bicistronic, polycistronic or multicistronic expression of at least two sequences. In some embodiments, the vector comprises a sequence encoding a lysosomal enzyme of the disclosure. Alternatively or in addition, in some embodiments, the vector comprises a sequence encoding a S1S3 construct of the disclosure. In some embodiments, the lysosomal enzyme is one or more of the enzymes listed in Table 1A, Table 1B or Table 1C. In some embodiments, the vector comprises a nucleic acid or amino acid sequence encoding the lysosomal enzyme is one or more of the enzymes listed in Table 1A, Table 1B or Table 1C.

In some embodiments the cell comprising a vector of the disclosure is a modified cell of the disclosure. In some embodiments, the cell comprising a vector of the disclosure is non-naturally occurring.

In some embodiments, the cell is a mammalian cell capable of expressing a human sequence and/or producing a human protein. In some embodiments, the mammalian cell is isolated or derived from a mouse, rat, guinea pig, rabbit, cat, dog, or non-human primate.

In some embodiments, the cell is a human cell capable of expressing a human sequence and/or producing a human protein.

In some embodiments, the cell is a primary cell, modified to express a vector of the disclosure and cultured ex vivo. In some embodiments, the cultured cell is immortalized or otherwise modified to facilitate propagation of the cell in vitro indefinitely, generating a cultured cell line.

Host Cell

In some embodiments, the disclosure provides a cell comprising a bicistronic vector of the disclosure. The cell may be a prokaryotic cell or a eukaryotic cell. Appropriate cells include, but are not limited to, bacterial, yeast, fungal, insect, and mammalian cells.

In some embodiments, the disclosure provides a mammalian cell comprising a bicistronic vector of the disclosure.

A host cell comprising the disclosed bicistronic vector may be used for protein expression and, optionally, purification. Methods for expressing and, optionally, purifying an expressed protein from a host are standard in the art.

In some embodiments, the host cell comprising a vector of the disclosure may be used to produce a polypeptide encoded by an enzyme construct of the disclosure. Generally, production of a polypeptide of the disclosure involves transfecting host cells with a vector comprising an enzyme construct and then culturing the cells so that they transcribe and translate the desired polypeptide. The isolated host cells may then be lysed to extract the expressed polypeptide for subsequent purification.

In some embodiments, the host cell is a prokaryotic cell. Non-limiting examples of suitable prokaryotic cells include *E. coli* and other Enterobacteriaceae, *Escherichia* sp., *Campylobacter* sp., *Wolinella* sp., *Desulfovibrio* sp. *Vibrio* sp., *Pseudomonas* sp. *Bacillus* sp., *Listeria* sp., *Staphylococcus* sp., *Streptococcus* sp., *Peptostreptococcus* sp.,

*Megasphaera* sp., *Pectinatus* sp., *Selenomonas* sp., *Zymophilus* sp., *Actinomyces* sp., *Arthrobacter* sp., *Frankia* sp., *Micromonospora* sp., *Nocardia* sp., *Propionibacterium* sp., *Streptomyces* sp., *Lactobacillus* sp., *Lactococcus* sp., *Leuconostoc* sp., *Pediococcus* sp., *Acetobacterium* sp., *Eubacterium* sp., *Heliobacterium* sp., *Heliospirillum* sp., *Sporomusa* sp., *Spiroplasma* sp., *Ureaplasma* sp., *Erysipelothrix* sp., *Corynebacterium* sp. *Enterococcus* sp., *Clostridium* sp., *Mycoplasma* sp., *Mycobacterium* sp., *Actinobacteria* sp., *Salmonella* sp., *Shigella* sp., *Moraxella* sp., *Helicobacter* sp, *Stenotrophomonas* sp., *Micrococcus* sp., *Neisseria* sp., *Bdellovibrio* sp., *Hemophilus* sp., *Klebsiella* sp., *Proteus mirabilis, Enterobacter cloacae, Serratia* sp., *Citrobacter* sp., *Proteus* sp., *Serratia* sp., *Yersinia* sp., *Acinetobacter* sp., *Actinobacillus* sp. *Bordetella* sp., *Brucella* sp., *Capnocytophaga* sp., *Cardiobacterium* sp., *Eikenella* sp., *Francisella* sp., *Haemophilus* sp., *Kingella* sp., *Pasteurella* sp., *Flavobacterium* sp. *Xanthomonas* sp., *Burkholderia* sp., *Aeromonas* sp., *Plesiomonas* sp., *Legionella* sp. and alpha-proteobaeteria such as *Wolbachia* sp., cyanobacteria, spirochaetes, green sulfur and green non-sulfur bacteria, Gram-negative cocci, Gram negative bacilli which are fastidious, Enterobacteriaceae-glucose-fermenting gram-negative bacilli, Gram negative bacilli-non-glucose fermenters, Gram negative bacilli-glucose fermenting, oxidase positive. Particularly useful bacterial host cells for protein expression include Gram negative bacteria, such as *Escherichia coli, Pseudomonas fiuorescens, Pseudomonas haloplanctis, Pseudomonas putida* AC 10, *Pseudomonas* pseudof lava, *Bartonella henselae, Pseudomonas syringae, Caulobacter crescentus, Zymomonas mobilis, Rhizobium meliloti, Myxococcus xanthus* and Gram positive bacteria such as *Bacillus subtilis, Corynebacterium, Streptococcus cremoris, Streptococcus lividans*, and *Streptomyces lividans. E. coli* is one of the most widely used expression hosts. Accordingly, the techniques for overexpression in *E. coli* are well developed and readily available to one of skill in the art.

Further, *Pseudomonas fluorescens*, is commonly used for high level production of recombinant proteins (i.e. for the development bio-therapeutics and vaccines).

In some embodiments, a host cell is a yeast or fungal cell. Particularly useful fungal host cells for protein expression include *Aspergillus oryzae, Aspergillus niger, Trichoderma reesei, Aspergillus nidulans, Fusarium graminearum*. Particularly useful yeast host cells for protein expression include *Candida albicans, Candida maltose, Hansenula polymorpha, Kluyveromyces fragilis, Kluyveromyces lactis, Pichia guillerimondii, Pichia pastoris, Saccharomyces cerevisiae, Schizosaccharomyces pombe*, and *Yarrowia lipolytica.*

In some embodiments, a host cell is an insect cell. Non-limiting examples include *Spodoptera frugiperda* cell lines (such as the Sf9 or Sf21), *Drosophila* cell lines, or mosquito cell lines (such as *Aedes albopictus* derived cell lines).

In some embodiments, a host cell is a mammalian cell. Useful mammalian host cells for protein expression include Chinese hamster ovary (CHO) cells, HeLa cells, Human embryonic kidney 293 (HEK293) cells, baby hamster kidney (BHK) cells, monkey kidney cells (COS), human hepatocellular carcinoma cells (eg. Hep G2), human embryonic kidney cells, *Bos primigenius*, and *Mus musculus*. In a specific embodiment, the host cells are CHO cells. Additionally, the mammalian host cell may be an established, commercially-available cell line (e.g., American Type Culture Collection (ATCC), Manassas, VA). The host cell may be an immortalized cell. Alternatively, the host cell may be a primary cell.

In some embodiments, the host cell has been engineered to produce high levels of a protein of interest.

Methods of the Disclosure

In some embodiments, the disclosure provides a method of treating a subject suffering from a lysosomal storage disorder (LSD) is disclosed herein. The method comprises administering to the subject a pharmaceutical composition comprising the lysosomal enzyme expressed by the biscistronic vector as disclosed elsewhere herein, thereby increasing the phosphorylation of a lysosomal enzyme and treating the subject.

In some embodiments, the disclosure provides a method of preventing the occurrence of a lysosomal storage disorder (LSD) in a subject in need thereof. The method comprises administering to the subject a pharmaceutical composition comprising the lysosomal enzyme expressed by the biscistronic vector as disclosed elsewhere herein, thereby increasing the phosphorylation of a lysosomal enzyme and preventing the occurrence of a LSD in the subject.

In some embodiments, the lysosomal enzyme is involved in at least one lysosomal storage disorder (LSD) as listed in Table 1. In other embodiments, the lysosomal enzyme is at least one as listed in Table 1.

In further embodiments, the administering comprises an administration route selected from the group consisting of enteral, parenteral, oral, intramuscular (IM), subcutaneous (SC), intravenous (IV), and intra-arterial (IA). Additional administration routes that can be used for the disclosed methods are described in detail elsewhere herein.

Combination Therapies

The compositions and methods for treating or preventing LSDs as described herein may be useful when combined with at least one additional compound useful for treating LSDs. The additional compound may comprise a commercially available compound, known to treat, prevent, or reduce the symptoms of LSDs. The compound could be but is not limited to an ERT known in the art.

Pharmaceutical Compositions and Formulations

Also provided herein is a pharmaceutical composition comprising a lysosomal enzyme expressed by the biscistronic vector of the disclosure.

Such a pharmaceutical composition is in a form suitable for administration to a subject, or the pharmaceutical composition may further comprise one or more pharmaceutically acceptable carriers, one or more additional ingredients, or some combination of these. The various components of the pharmaceutical composition may be present in the form of a physiologically acceptable salt, such as in combination with a physiologically acceptable cation or anion, as is well known in the art.

In some embodiments of the disclosure, the pharmaceutical composition useful for practicing the method of the disclosure may be administered to deliver a dose of between 1 ng/kg/day and 100 mg/kg/day. In some embodiments of the disclosure, the pharmaceutical composition useful for practicing the disclosure may be administered to deliver a dose of between 1 ng/kg/day and 500 mg/kg/day. The relative amounts of the active ingredient, the pharmaceutically acceptable carrier, and any additional ingredients in a pharmaceutical composition of the disclosure will vary, depending upon the identity, size, and condition of the subject treated and further depending upon the route by which the composition is to be administered. By way of example, the composition may comprise between 0.1% and 100% (w/w) active ingredient.

In some embodiments of the disclosure, the pharmaceutical composition useful for practicing the method of the disclosure may be administered to deliver a dose of between 1 ng/kg and 100 mg/kg. In some embodiments of the disclosure, the pharmaceutical composition useful for practicing the disclosure may be administered to deliver a dose of between 1 ng/kg and 500 mg/kg. In some embodiments of the disclosure, the pharmaceutical composition is provided daily, weekly, bi-weekly, monthly, or annually. The relative amounts of the active ingredient, the pharmaceutically acceptable carrier, and any additional ingredients in a pharmaceutical composition of the disclosure will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the disclosure may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration is readily apparent to the skilled artisan and depends upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit. In some embodiments, the presently disclosed compositions can be formulated in a natural capsid, a modified capsid, as a naked RNA, or encapsulated in a protective coat.

The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it is understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the disclosure is contemplated include, but are not limited to, humans and other primates, mammals including commercially relevant mammals such as cattle, pigs, horses, sheep, cats, and dogs. In one embodiment, the subject is a human or a non-human mammal such as but not limited to an equine, an ovine, a bovine, a porcine, a canine, a feline and a murine. In one embodiment, the subject is a human.

In one embodiment, the compositions are formulated using one or more pharmaceutically acceptable excipients or carriers. In some embodiments, the disclosure provides a pharmaceutical composition for treating a subject suffering from LSDs. In some embodiments, the disclosure provides a pharmaceutical composition comprising a lysosomal enzyme expressed by a biscistronic vector of the disclosure and a pharmaceutically acceptable carrier.

Pharmaceutically acceptable carriers, which are useful, include, but are not limited to, glycerol, water, saline, ethanol and other pharmaceutically acceptable salt solutions such as phosphates and salts of organic acids. The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In some embodiments, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

The disclosed composition may comprise a preservative from about 0.005% to 2.0% by total weight of the composition. The preservative is used to prevent spoilage in the case of exposure to contaminants in the environment. Examples of preservatives useful in accordance with the disclosure included but are not limited to those selected from the group consisting of benzyl alcohol, sorbic acid, parabens, imidurea and combinations thereof. In some embodiments, the preservative is a combination of about 0.5% to 2.0% benzyl alcohol and 0.05% to 0.5% sorbic acid.

The composition may include an antioxidant and a chelating agent which inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. In some embodiments, BHT and disodium edetate are the antioxidant and the chelating agent respectively for some compounds, however, other suitable and equivalent antioxidants and chelating agents may be substituted therefore as would be known to those skilled in the art.

Administration/Dosing

The regimen of administration may affect what constitutes an effective amount. For example, the therapeutic formulations may be administered to the patient subject either prior to or after a surgical intervention related to a lysosomal storage disorder (LSD), or shortly after the patient was diagnosed with a lysosomal storage disorder (LSD). Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present disclosure to a patient subject, preferably a mammal, more preferably a human, may be carried out using known procedures, at dosages and for periods of time effective to treat a lysosomal storage disorder (LSD) in the subject. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the disclosure is from about 0.01 and 50 mg/kg of body weight/per day.

The compound can be administered to a subject as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon any number of factors, such as, but not limited to, the type and severity of the disease being treated, and the type and age of the animal. Actual dosage levels of the active ingredients in the pharmaceutical compositions of this disclosure may be varied so as to obtain an amount of the active ingredient that is effective to achieve the desired therapeutic response for a particular patient, composition, and mode of administration, without being toxic to the patient. A medical doctor, e.g., physician or veterinarian, having ordinary skill in the art may readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In some embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the disclosure are dictated by and directly dependent on (a) the unique characteristics of the therapeutic compound and the particular therapeutic effect to be achieved, and (b) the limitations inherent in the art of compounding/formulating such a therapeutic compound for the treatment of LSDs.

Routes of Administration

One skilled in the art will recognize that although more than one route can be used for administration, a particular route can provide a more immediate and more effective reaction than another route.

Routes of administration of the disclosed compositions include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, intra-cisterna magna (ICM), intraspinal, intraventricular, intracerebroventricular, subcutaneous, intramuscular, intradermal, intra-arterial, intravenous, intrabronchial, inhalation, and topical administration. Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present disclosure are not limited to the particular formulations and compositions that are described herein. In one embodiment, the treatment of LSD comprises an administration route selected from the group consisting of inhalation, oral, rectal, vaginal, parenteral, topical, transdermal, pulmonary, intranasal, buccal, ophthalmic, intra-hepatic arterial, intrapleural, intrathecal, intra-tumoral, intravenal and any combination thereof.

Gene Therapy Administration

One skilled in the art recognizes that different methods of delivery may be utilized to administer a vector into a cell. Examples include: (1) methods utilizing physical means, such as electroporation (electricity), a gene gun (physical force) or applying large volumes of a liquid (pressure); and (2) methods wherein the vector is complexed to another entity, such as a liposome, aggregated protein or transporter molecule.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present disclosure (for instance, the cost associated with synthesis). One skilled in the art can easily make any necessary adjustments in accordance with the exigencies of the particular situation.

Cells containing the therapeutic agent may also contain a suicide gene i.e., a gene which encodes a product that can be used to destroy the cell. In many gene therapy situations, it is desirable to be able to express a gene for therapeutic purposes in a host, cell but also to have the capacity to destroy the host cell at will. The therapeutic agent can be linked to a suicide gene, whose expression is not activated in the absence of an activator compound. When death of the cell in which both the agent and the suicide gene have been introduced is desired, the activator compound is administered to the cell thereby activating expression of the suicide gene and killing the cell. Examples of suicide gene/prodrug combinations which may be used are herpes simplex virus-thymidine kinase (HSV-tk) and ganciclovir, acyclovir; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

Therapeutic

The present disclosure encompasses a method to treat a deficient lysosomal enzyme in a subject diagnosed with LSD or in a subject at risk for developing an LDS. The method improves phosphorylation of lysosomal enzymes thereby treating the subject or preventing the occurrence of the LSD in the subject. Further, the method improves quality of life in a patient. In one embodiment, the method of the present disclosure comprises administering to a subject, a composition comprising a polynucleotide encoding a lysosomal enzyme and a polynucleotide encoding a GlcNAc-1 PTase.

| Nucleic Acid Sequences: |
|---|
| pLL01 bicistronic vector sequence (SEQ ID NO: 1) (CMV promoter: italic and underline. IRES: bold and italic. S1-S3: bold and underline.) |
| 1 GACGGATCGG GAGATCTCCC GATCCCCTAT GGTGCACTCT CAGTACAATC TGCTCTGATG |
| 61 CCGCATAGTT AAGCCAGTAT CTGCTCCCTG CTTGTGTGTT GGAGGTCGCT GAGTAGTGCG |
| 121 CGAGCAAAAT TTAAGCTACA ACAAGGCAAG GCTTGACCGA CAATTGCATG AAGAATCTGC |
| 181 TTAGGGTTAG GCGTTTTGCG CTGCTTCGCG ATGTACGGGC CAGATATACG CGTTGACATT |
| 241 GATTATTGAG TAGTTATTAA TAGTAATCAA TTACGGGGTC ATTAGTTCAT AGCCCATATA |
| 301 TGGAGTTCCG CGTTACATAA CTTACGGTAA ATGGCCCGCC TGGCTGACCG CCCAACGACC |
| 361 CCCGCCCATT GACGTCAATA ATGACGTATG TTCCCATAGT AACGCCAATA GGGACTTTCC |
| 421 ATTGACGTCA ATGGGTGGAG TATTTACGGT AAACTGCCCA CTTGGCAGTA CATCAAGTGT |
| 481 ATCATATGCC AAGTACGCCC CCTATTGACG TCAATGACGG TAAATGGCCC GCCTGGCATT |
| 541 ATGCCCAGTA CATGACCTTA TGGGACTTTC CTACTTGGCA GTACATCTAC GTATTAGTCA |
| 601 TCGCTATTAC CATGGTGATG CGGTTTTGGC AGTACATCAA TGGGCGTGGA TAGCGGTTTG |
| 661 ACTCACGGGG ATTTCCAAGT CTCCACCCCA TTGACGTCAA TGGGAGTTTG TTTTGGCACC |
| 721 AAAATCAACG GGACTTTCCA AAATGTCGTA ACAACTCCGC CCCATTGACG CAAATGGGCG |
| 781 GTAGGCGTGT ACGGTGGGAG GTCTATATAA GCAGAGCTCT CTGGCTAACT AGAGAACCCA |
| 841 CTGCTTACTG GCTTATCGAA ATTAATACGA CTCACTATAG GGAGACCCAA GCTGGCTAGC |
| 901 GTTTAAACTT AAGCTTGGTA CCGAGCTCGG ATCCACTAGT CCAGTGTGGT GGAATTCTGC |
| 961 AGATATCCAG CACAGTGGCG GCCGCtgatt aacctcagga ctagtGGTTA TTTTCCACCA |
| 1021 TATTGCCGTC TTTTGGCAAT GTGAGGGCCC GGAAACCTGG CCCTGTCTTC TTGACGAGCA |
| 1081 TTCCTAGGGG TCTTTCCCCT CTCGCCAAAG GAATGCAAGG TGTGTTGAAT GTCGTGAAGG |
| 1141 AAGCAGTTCC TCTGGAAGCT TCTTGAAGAC AAACAACGTC TGTAGCGACC CTTTGCAGGC |
| 1201 AGCGGAACCC CCCACCTGGC GACAGGTGCC TCTGCGGCCA AAAGCCACGT GTATAAGATA |
| 1261 CACCTGCAAA GGCGGCACAA CCCCAGTGCC ACGTTGTGAG TTGGATAGTT GTGGAAAGAG |
| 1321 TCAAATGGCT CACCTCAAGC GTATTCAACA AGGGGCTGAA GGATGCCCAG AAGGTACCCC |
| 1381 ATTGTATGGG ATCTGATCTG GGGCCTCGGT GCACATGCTT TACATGTGTT TAGTCGAGGT |
| 1441 TAAAAAACGT CTAGGCCCCC CGAACCACGG GGACGTGGTT TTCCTTTFAA AGTTTGTTAA |
| 1501 Catgctgttc aagctcctgc agagacagac ctatacctgc ctgtcccaca ggtatgggct |
| 1561 ctacgtgtgc ttcttgggcg tcgttgtcac catcgtctcc gccttccagt tcggagaggt |
| 1621 ggttctggaa tggagccgag atcaatacca tgttttgttt gattcctata gagacaatat |
| 1681 tgctggaaag tcctttcaga atcggctttg tctgcccatg ccgattgacg ttgtttacac |
| 1741 ctgggtgaat ggcacagatc ttgaactact gaaggaacta ACAGAATTAA AAAGATCAAA |
| 1801 ACGTGATCCA TTAATACCAG AATGTCAAGG TAAACAAACA CCAGAAAAAG ATAAATGTTA |
| 1861 TAGAGATgac atctctgcca gtcgttttga agataacgaa gaactgaggt actcattgcg |
| 1921 atctatcgag aggcatgcac catgggttcg gaatattttc attgtcacca acgggcagat |
| 1981 tccatcctgg ctgaaccttg acaatcctcg agtgacaata gtaacacacc aggatgtttt |
| 2041 tcgaaatttg agccacttgc ctacctttag ttcacctgct attgaaagtc acattcatcg |
| 2101 catcgaaggg ctgtcccaga agtttattta cctaaatgat gatgtcatgt ttgggaagga |
| 2161 tgtctggcca gatgattttt acagtcactc caaaggccag aaggtttatt tgacatggcc |
| 2221 tgtgccaaac GGAGGTAGCG GAGGTgatac atttgcagat tccctcagat atgtaaataa |
| 2281 aattctaaat agcaagtttg gattcacatc gcggaaagtc cctgctcaca tgcctcacat |
| 2341 gattgaccgg attgttatgc aagaactgca agatatgttc cctgaagaat ttgacaagac |
| 2401 gtcatttcac aaagtgcgcc attctgagga tatgcagttt gccttctctt atttttatta |
| 2461 tctcatgagt gcagtgcagc cactgaatat atctcaagtc tttgatgaag ttgatacaga |
| 2521 tcaatctggt gtcttgtctg acagagaaat ccgaacactg gctaccagaa ttcacgaact |
| 2581 gccgttaagt ttgcaggatt tgacaggtct ggaacacatg ctaataaatt gctcaaaaat |
| 2641 gcttcctgct gatatcacgc agctaaataa tattccacca actcaggaat cctactatga |
| 2701 tcccaacctg ccaccggtca ctaaaagtct agtaacaaac tgtaaaccag taactgacaa |
| 2761 aatccacaaa gcatataagg acaaaaacaa atataggttt gaaatcatgg gagaagaaga |
| 2821 aatcgctttt aaaatgattc gtaccaacgt ttctcatgtg gttggccagt tggatgacat |
| 2881 aagaaaaaac cctaggaagt ttgtttgcct gaatgacaac attgaccaca atcataaaga |
| 2941 tgctcagaca gtgaaggctg ttctcaggga cttctatgaa tccatgttcc ccataccttc |

-continued

Nucleic Acid Sequences:

3001 ccaatttgaa ctgccaagag agtatcgaaa ccgtttcctt catatgcatg agctgcagga
3061 atggagggct tatcgagaca aattgaagtt ttggacccat tgtgtactag caacattgat
3121 tatgtttact atattctcat tttttgctga gcagttaatt gcacttaagc ggaagatatt
3181 tcccagaagg aggatacaca aagaagctag tcccaatcga atcagagtaT CTAGAGGAgg
3241 taagcctatc cctaaccctc tcctcggtct cgattctacg tgaGTTTAAA CCCGCTGATC
3301 AGCCTCGACT GTGCCTTCTA GTTGCCAGCC ATCTGTTGTT TGCCCCTCCC CCGTGCCTTC
3361 CTTGACCCTG GAAGGTGCCA CTCCCACTGT CCTTTCCTAA TAAAATGAGG AAATTGCATC
3421 GCATTGTCTG AGTAGGTGTC ATTCTATTCT GGGGGGTGGG GTGGGGCAGG ACAGCAAGGG
3481 GGAGGATTGG GAAGACAATA GCAGGCATGC TGGGGATGCG GTGGGCTCTA TGGCTTCTGA
3541 GGCGGAAAGA ACCAGCTGGG GCTCTAGGGG GTATCCCCAC GCGCCCTGTA GCGGCGCATT
3601 AAGCGCGGCG GGTGTGGTGG TTACGCGCAG CGTGACCGCT ACACTTGCCA GCGCCCTAGC
3661 GCCCGCTCCT TTCGCTTTCT TCCCTTCCTT TCTCGCCACG TTCGCCGGCT TTCCCCGTCA
3721 AGCTCTAAAT CGGGGGCTCC CTTTAGGGTT CCGATTTAGT GCTTTACGGC ACCTCGACCC
3781 CAAAAAACTT GATTAGGGTG ATGGTTCACG TAGTGGGCCA TCGCCCTGAT AGACGGTTTT
3841 TCGCCCTTTG ACGTTGGAGT CCACGTTCTT TAATAGTGGA CTCTTGTTCC AAACTGGAAC
3901 AACACTCAAC CCTATCTCGG TCTATTCTTT TGATTTATAA GGGATTTTGC CGATTTCGGC
3961 CTATTGGTTA AAAAATGAGC TGATTTAACA AAAATTTAAC GCGAATTAAT TCTGTGGAAT
4021 GTGTGTCAGT TAGGGTGTGG AAAGTCCCCA GGCTCCCCAG CAGGCAGAAG TATGCAAAGC
4081 ATGCATCTCA ATTAGTCAGC AACCAGGTGT GGAAAGTCCC CAGGCTCCCC AGCAGGCAGA
4141 AGTATGCAAA GCATGCATCT CAATTAGTCA GCAACCATAG TCCCGCCCCT AACTCCGCCC
4201 ATCCCGCCCC TAACTCCGCC CAGTTCCGCC CATTCTCCGC CCCATGGCTG ACTAATTTTT
4261 TTTATTTATG CAGAGGCCGA GGCCGCCTCT GCCTCTGAGC TATTCCAGAA GTAGTGAGGA
4321 GGCTTTTTTG GAGGCCTAGG CTTTTGCAAA AAGCTCCCGG GAGCTTGTAT ATCCATTTTC
4381 GGATCTGATC AAGAGACAGG ATGAGGATCG TTTCGCATGA TTGAACAAGA TGGATTGCAC
4441 GCAGGTTCTC CGGCCGCTTG GGTGGAGAGG CTATTCGGCT ATGACTGGGC ACAACAGACA
4501 ATCGGCTGCT CTGATGCCGC CGTGTTCCGG CTGTCAGCGC AGGGGCGCCC GGTTCTTTTT
4561 GTCAAGACCG ACCTGTCCGG TGCCCTGAAT GAACTGCAGG ACGAGGCAGC GCGGCTATCG
4621 TGGCTGGCCA CGACGGGCGT TCCTTGCGCA GCTGTGCTCG ACGTTGTCAC TGAAGCGGGA
4681 AGGGACTGGC TGCTATTGGG CGAAGTGCCG GGGCAGGATC TCCTGTCATC TCACCTTGCT
4741 CCTGCCGAGA AAGTATCCAT CATGGCTGAT GCAATGCGGC GGCTGCATAC GCTTGATCCG
4801 GCTACCTGCC CATTCGACCA CCAAGCGAAA CATCGCATCG AGCGAGCACG TACTCGGATG
4861 GAAGCCGGTC TTGTCGATCA GGATGATCTG GACGAAGAGC ATCAGGGGCT CGCGCCAGCC
4921 GAACTGTTCG CCAGGCTCAA GGCGCGCATG CCCGACGGCG AGGATCTCGT CGTGACCCAT
4981 GGCGATGCCT GCTTGCCGAA TATCATGGTG GAAAATGGCC GCTTTTCTGG ATTCATCGAC
5041 TGTGGCCGGC TGGGTGTGGC GGACCGCTAT CAGGACATAG CGTTGGCTAC CCGTGATATT
5101 GCTGAAGAGC TTGGCGGCGA ATGGGCTGAC CGCTTCCTCG TGCTTTACGG TATCGCCGCT
5161 CCCGATTCGC AGCGCATCGC CTTCTATCGC CTTCTTGACG AGTTCTTCTG AGCGGGACTC
5221 TGGGGTTCGA AATGACCGAC CAAGCGACGC CCAACCTGCC ATCACGAGAT TTCGATTCCA
5281 CCGCCGCCTT CTATGAAAGG TTGGGCTTCG GAATCGTTTT CCGGGACGCC GGCTGGATGA
5341 TCCTCCAGCG CGGGGATCTC ATGCTGGAGT TCTTCGCCCA CCCCAACTTG TTTATTGCAG
5401 CTTATAATGG TTACAAATAA AGCAATAGCA TCACAAATTT CACAAATAAA GCATTTTTTT
5461 CACTGCATTC TAGTTGTGGT TTGTCCAAAC TCATCAATGT ATCTTATCAT GTCTGTATAC
5521 CGTCGACCTC TAGCTAGAGC TTGGCGTAAT CATGGTCATA GCTGTTTCCT GTGTGAAATT
5581 GTTATCCGCT CACAATTCCA CACAACATAC GAGCCGGAAG CATAAAGTGT AAAGCCTGGG
5641 GTGCCTAATG AGTGAGCTAA CTCACATTAA TTGCGTTGCG CTCACTGCCC GCTTTCCAGT
5701 CGGGAAACCT GTCGTGCCAG CTGCATTAAT GAATCGGCCA ACGCGCGGGG AGAGGCGGTT
5761 TGCGTATTGG GCGCTCTTCC GCTTCCTCGC TCACTGACTC GCTGCGCTCG GTCGTTCGGC
5821 TGCGGCGAGC GGTATCAGCT CACTCAAAGG CGGTAATACG GTTATCCACA GAATCAGGGG
5881 ATAACGCAGG AAAGAACATG TGAGCAAAAG GCCAGCAAAA GGCCAGGAAC CGTAAAAAGG
5941 CCGCGTTGCT GGCGTTTTTC CATAGGCTCC GCCCCCCTGA CGAGCATCAC AAAAATCGAC
6001 GCTCAAGTCA GAGGTGGCGA AACCCGACAG GACTATAAAG ATACCAGGCG TTTCCCCCTG
6061 GAAGCTCCCT CGTGCGCTCT CCTGTTCCGA CCCTGCCGCT TACCGGATAC CTGTCCGCCT
6121 TTCTCCCTTC GGGAAGCGTG GCGCTTTCTC ATAGCTCACG CTGTAGGTAT CTCAGTTCGG
6181 TGTAGGTCGT TCGCTCCAAG CTGGGCTGTG TGCACGAACC CCCCGTTCAG CCCGACCGCT
6241 GCGCCTTATC CGGTAACTAT CGTCTTGAGT CCAACCCGGT AAGACACGAC TTATCGCCAC
6301 TGGCAGCAGC CACTGGTAAC AGGATTAGCA GAGCGAGGTA TGTAGGCGGT GCTACAGAGT
6361 TCTTGAAGTG GTGGCCTAAC TACGGCTACA CTAGAAGAAC AGTATTTGGT ATCTGCGCTC
6421 TGCTGAAGCC AGTTACCTTC GGAAAAAGAG TTGGTAGCTC TTGATCCGGC AAACAAACCA
6481 CCGCTGGTAG CGGTTTTTTT GTTTGCAAGC AGGAGATTAC GCGCAGAAAA AAAGGATCTC
6541 AAGAAGATCC TTTGATCTTT TCTACGGGGT CTGACGCTCA GTGGAACGAA AACTCAGGTT
6601 AAGGGATTTT GGTCATGAGA TTATCAAAAA GGATCTTCAC CTAGATCCTT TTAAATTAAA
6661 AATGAAGTTT TAAATCAATC TAAAGTATAT ATGAGTAAAC TTGGTCTGAC AGTTACCAAT
6721 GCTTAATCAG TGAGGCACCT ATCTCAGCGA TCTGTCTATT TCGTTCATCC ATAGTTGCCT
6781 GACTCCCCGT CGTGTAGATA ACTACGATAC GGGAGGGCTT ACCATCTGGC CCCAGTGCTG
6841 CAATGATACC GCGAGACCCA CGCTCACCGG CTCCAGATTT ATCAGCAATA AACCAGCCAG
6901 CCGGAAGGGC CGAGCGCAGA AGTGGTCCTG CAACTTTATC CGCCTCCATC CAGTCTATTA
6961 ATTGTTGCCG GGAAGCTAGA GTAAGTAGTT CGCCAGTTAA TAGTTTGCGC AACGTTGTTG
7021 CCATTGCTAC AGGCATCGTG GTGTCACGCT CGTCGTTTGG TATGGCTTCA TTCAGCTCCG
7081 GTTCCCAACG ATCAAGGCGA GTTACATGAT CCCCCATGTT GTGCAAAAAA GCGGTTAGCT
7141 CCTTCGGTCC TCCGATCGTT GTCAGAAGTA AGTTGGCCGC AGTGTTATCA CTCATGGTTA
7201 TGGCAGCACT GCATAATTCT CTTACTGTCA TGCCATCCGT AAGATGCTTT TCTGTGACTG
7261 GTGAGTACTC AACCAAGTCA TTCTGAGAAT AGTGTATGCG GCGACCGAGT TGCTCTTGCC
7321 CGGCGTCAAT ACGGGATAAT ACCGCGCCAC ATAGCAGAAC TTTAAAAGTG CTCATCATTG
7381 GAAAACGTTC TTCGGGGCGA AAACTCTCAA GGATCTTACC GCTGTTGAGA TCCAGTTCGA
7441 TGTAACCCAC TCGTGCACCC AACTGATCTT CAGCATCTTT TACTTTCACC AGCGTTTCTG
7501 GGTGAGCAAA AACAGGAAGG CAAAATGCCG CAAAAAAGGG AATAAGGGCG ACACGGAAAT
7561 GTTGAATACT CATACTCTTC CTTTTTCAAT ATTATTGAAG CATTTATCAG GGTTATTGTC -continued

| Nucleic Acid Sequences: |
|---|

```
7621 TCATGAGCGG ATACATATTT GAATGTATTT AGAAAAATAA ACAAATAGGG GTTCCGCGCA
7681 CATTTCCCCG AAAAGTGCCA CCTGACGTC.
```

CMV sequence (SEQ ID NO: 2)

```
   1 CGTTACATAA CTTACGGTAA ATGGCCCGCC TGGCTGACCG CCCAACGACC CCCGCCCATT
  61 GACGTCAATA ATGACGTATG TTCCCATAGT AACGCCAATA GGGACTTTCC ATTGACGTCA
 121 ATGGGTGGAG TATTTACGGT AAACTGCCCA CTTGGCAGTA CATCAAGTGT ATCATATGCC
 181 AAGTACGCCC CCTATTGACG TCAATGACGG TAAATGGCCC GCCTGGCATT ATGCCCAGTA
 241 CATGACCTTA TGGGACTTTC CTACTTGGCA GTACATCTAC GTATTAGTCA TCGCTATTAC
 301 CATGGTGATG CGGTTTTGGC AGTACATCAA TGGGCGTGGA TAGCGGTTTG ACTCACGGGG
 361 ATTTCCAAGT CTCCACCCCA TTGACGTCAA TGGGAGTTTG TTTTGGCACC AAAATCAACG
 421 GGACTTTCCA AAATGTCGTA ACAACTCCGC CCCATTGACG CAAATGGGCG GTAGGCGTGT
 481 ACGGTGGGAG GTCTATATAA GCAGAGCT.
```

IRES sequence (SEQ ID NO: 3)

```
   1 GGTTATTTTC CACCATATTG CCGTCTTTTG GCAATGTGAG GGCCCGGAAA CCTGGCCCTG
  61 TCTTCTTGAC GAGCATTCCT AGGGGTCTTT CCCCTCTCGC CAAAGGAATG CAAGGTCTGT
 121 TGAATGTCGT GAAGGAAGCA GTTCCTCTGG AAGCTTCTTG AAGACAAACA ACGTCTGTAG
 181 CGACCCTTTG CAGGCAGCGG AACCCCCCAC CTGGCGACAG GTGCCTCTGC GGCCAAAAGC
 241 CACGTGTATA AGATACACCT GCAAAGGCGG CACAACCCCA GTGCCACGTT GTGAGTTGGA
 301 TAGTTGTGGA AAGAGTCAAA TGGCTCACCT CAAGCGTATT CAACAAGGGG CTGAAGGATG
 361 CCCAGAAGGT ACCCCATTGT ATGGGATCTG ATCTGGGGCC TCGGTGCACA TGCTTTACAT
 421 GTGTTTAGTC GAGGTTAAAA AACGTCTAGG CCCCCCGAAC CACGGGGACG TGGTTTTCCT
 481 TTGAAA.
```

Modified GlcNAc-1 phosphotransferase (GlcNAc-1 PTase), S1-S3 sequence (SEQ ID No: 4)

```
   1 atgctgttca agctcctgca gagacagacc tatacctgcc tgtcccacag gtatgggctc
  61 tacgtgtgct tcttgggcgt cgttgtcacc atcgtctccg ccttccagtt cggagaggtg
 121 gttctggaat ggagccgaga tcaataccat gttttgtttg attcctatag agacaatatt
 181 gctggaaagt cctttcagaa tcggctttgt ctgcccatgc cgattgacgt tgtttacacc
 241 tgggtgaatg gcacagatct tgaactactg aaggaactaA CAGAATTAAA AAGATCAAAA
 301 CGTGATCCAT TAATACCAGA ATGTCAAGGT AAACAAACAC CAGAAAAAGA TAAATGTTAT
 361 AGAGATGaca tctctgccag tcgttttgaa gataacgaag aactgaggta ctcattgcga
 421 tctatcgaga ggcatgcacc atgggttcgg aatattttca ttgtcaccaa cgggcagatt
 481 ccatcctggc tgaaccttga caatcctcga gtgacaatag taacacacca ggatgttttt
 541 cgaaatttga gccacttgcc tacctttagt tcacctgcta ttgaaagtca cattcatcgc
 601 atcgaagggc tgtcccagaa gtttatttac ctaaatgatg atgtcatgtt tgggaaggat
 661 gtctggccag atgattttta cagtcactcc aaaggccaga aggtttattt gacatggcct
 721 gtgccaaacG GAGGTAGCGG AGGTgataca tttgcagatt ccctcagata tgtaaataaa
 781 attctaaata gcaagtttgg attcacatcg cggaaagtcc ctgctcacat gcctcacatg
 841 attgaccgga ttgttatgca agaactgcaa gatatgttcc ctgaagaatt tgacaagacg
 901 tcatttcaca aagtgcgcca ttctgaggat atgcagtttg ccttctctta tttttattat
 961 ctcatgagtg cagtgcagcc actgaatata tctcaagtct ttgatgaagt tgatacagat
1021 caatctggtg tcttgtctga cagagaaatc cgaacactgg ctaccagaat tcacgaactg
1081 ccgttaagtt tgcaggattt gacaggtctg gaacacatgc taataaattg ctcaaaaatg
1141 cttcctgctg atatcacgca gctaaataat attccaccaa ctcaggaatc ctactatgat
1201 cccaacctgc caccggtcac taaaagtcta gtaacaaact gtaaaccagt aactgacaaa
1261 atccacaaag catataagga caaaaacaaa tataggtttg aaatcatggg agaagaagaa
1321 atcgctttta aaatgattcg taccaacgtt tctcatgtgg ttggccagtt ggatgacata
1381 agaaaaaacc ctaggaagtt tgtttgcctg aatgacaaca ttgaccacaa tcataaagat
1441 gctcagacag tgaaggctgt tctcagggac ttctatgaat ccatgttccc catacettcc
1501 caatttgaac tgccaagaga gtatcgaaac cgtttccttc atatgcatga gctgcaggaa
1561 tggagggctt atcgagacaa attgaagttt tggacccatt gtgtactagc aacattgatt
1621 atgtttacta tattctcatt ttttgctgag cagttaattg cacttaagcg gaagatattt
1681 cccagaagga ggatacacaa agaagctagt cccaatcgaa tcagagta.
```

hGBA wild type sequence (SEQ ID NO: 5):

```
   1 ATGGAGTTTT CAAGTCCTTC CAGAGAGGAA TGTCCCAAGC CTTTGAGTAG GGTAAGCATC
  61 ATGGCTGGCA GCCTCACAGG ATTGCTTCTA CTTCAGGCAG TGTCGTGGGC ATCAGGTGCC
 121 CGCCCCTGCA TCCCTAAAAG CTTCGGCTAC AGCTCGGTGG TGTGTGTCTG CAATGCCACA
 181 TACTGTGACT CCTTTGACCC CCCGACCTTT CCTGCCCTTG GTACCTTCAG CCGCTATGAG
 241 AGTACAGGCA GTGGGCGACG GATGGAGCTG AGTATGGGGC CCATCCAGGC TAATCACACG
 301 GGCACAGGCC TGCTACTGAC CCTGCAGCCA GAACAGAAGT TCCAGAAAGT GAAGGGATTT
 361 GGAGGGGCCA TGACAGATGC TGCTGCTCTC AACATCCTTG CCCTGTCACC CCCTGCCCAA
 421 AATTTGCTAC TTAAATCGTA CTTCTCTGAA GAAGGAATCG GATATAACAT CATCCGGGTA
 481 CCCATGGCCA GCTGTGACTT CTCCATCCGC ACCTACACCT ATGCAGACAC CCCTGATGAT
 541 TTCCAGTTGC ACAACTTCAG CCTCCCAGAG GAAGATACCA AGCTCAAGAT ACCCCTGATT
 601 CACCGAGCCC TGCAGTTGGC CCAGCGTCCC GTTTCACTCC TTGCCAGCCC CTGGACATCA
 661 CCCACTTGGC TCAAGACCAA TGGAGCGGTG AATGGGAAGG GGTCACTCAA GGGACAGCCC
 721 GGAGACATCT ACCACCAGAC CTGGGCCAGA TACTTTGTGA AGTTCCTGGA TGCCTATGCT
 781 GAGCACAAGT TACAGTTCTG GGCAGTGACA GCTGAAAATG AGCCTTCTGC TGGGCTGTTG
 841 AGTGGATACC CCTTCCAGTG CCTGGGCTTC ACCCCTGAAC ATCAGCGAGA CTTCATTGCC
 901 CGTGACCTAG GTCCTACCCT CGCCAACAGT ACTCACCACA ATGTCCGCCT ACTCATGCTG
 961 GATGACCAAC GCTTGCTGCT GCCCCACTGG GCAAAGGTGG TACTGACAGA CCCAGAAGGA
1021 GCTAAATATG TTCATGGCAT TGCTGTACAT TGGTACCTGG ACTTTCTGGC TCCAGCCAAA
1081 GCCACCCTAG GGGAGACACA CCGCCTGTTC CCCAACACCA TGCTCTTTGC CTCAGAGGCC
```

-continued

Nucleic Acid Sequences:

1141 TGTGTGGGCT CCAAGTTCTG GGAGCAGAGT GTGCGGCTAG GCTCCTGGGA TCGAGGGATG
1201 CAGTACAGCC ACAGCATCAT CACGAACCTC CTGTACCATG TGGTCGGCTG GACCGACTGG
1261 AACCTTGCCC TGAACCCCGA AGGAGGACCC AATTGGGTGC GTAACTTTGT CGACAGTCCC
1321 ATCATTGTAG ACATCACCAA GGACACGTTT TACAAACAGC CCATGTTCTA CCACCTTGGC
1381 CACTTCAGCA AGTTCATTCC TGAGGGCTCC CAGAGAGTGG GGCTGGTTGC CAGTCAGAAG
1441 AACGACCTGG ACGCAGTGGC ACTGATGCAT CCCGATGGCT CTGCTGTTGT GGTCGTGCTA
1501 AACCGCTCCT CTAAGGATGT GCCTCTTACC ATCAAGGATC CTGCTGTGGG CTTCCTGGAG
1561 ACAATCTCAC CTGGCTACTC CATTCACACC TACCTGTGGC GTCGCCAGTG A.

hGBA natural variant sequence (SEQ ID NO: 162): hGBA (K360N) sequence
Bolded and underlined nucleotide at the mutation site
1 ATGGAGTTTT CAAGTCCTTC CAGAGAGGAA TGTCCCAAGC CTTTGAGTAG GGTAAGCATC
61 ATGGCTGGCA GCCTCACAGG TTTGCTTCTA CTTCAGGCAG TGTCGTGGGC ATCAGGTGCC
121 CGCCCCTGCA TCCCTAAAAG CTTCGGCTAC AGCTCGGTGG TGTGTGTCTG CAATGCCACA
181 TACTGTGACT CCTTTGACCC CCCGACCTTT CCTGCCCTTG GTACCTTCAG CCGCTATGAG
241 AGTACAGGCA GTGGGCGACG GATGGAGCTG AGTATGGGGC CCATCCAGGC TAATCACACG
301 GGCACAGGCC TGCTACTGAC CCTGCAGCCA GAACAGAAGT TCCAGAAAGT GAAGGGATTT
361 GGAGGGGCCA TGACAGATGC TGCTGCTCTC AACATCCTTG CCCTGTCACC CCCTGCCCAA
421 AATTTGCTAC TTAAATCGTA CTTCTCTGAA GAAGGAATCG GATATAACAT CATCCGGGTA
481 CCCATGGCCA GCTGTGACTT CTCCATCCGC ACCTACACCT ATGCAGACAC CCCTGATGAT
541 TTCCAGTTGC ACAACTTCAG CCTCCCAGAG GAAGATACCA AGCTCAAGAT ACCCCTGATT
601 CACCGAGCCC TGCAGTTGGC CCAGCGTCCC GTTTCACTCC TTGCCAGCCC CTGGACATCA
661 CCCACTTGGC TCAAGACCAA TGGAGCGGTG AATGGGAAGG GGTCACTCAA GGGACAGCCC
721 GGAGACATCT ACCACCAGAC CTGGGCCAGA TACTTTGTGA AGTTCCTGGA TGCCTATGCT
781 GAGCACAAGT TACAGTTCTG GGCAGTGACA GCTGAAAATG AGCCTTCTGC TGGGCTGTTG
841 AGTGGATACC CCTTCCAGTG CCTGGGCTTC ACCCCTGAAC ATCAGCGAGA CTTCATTGCC
901 CGTGACCTAG GTCCTACCCT CGCCAACAGT ACTCACCACA ATGTCCGCCT ACTCATGCTG
961 GATGACCAAC GCTTGCTGCT GCCCCACTGG GCAAAGGTGG TACTGACAGA CCCAGAAGCA
1021 GCTAAATATG TTCATGGCAT TGCTGTACAT TGGTACCTGG ACTTTCTGGC TCCAGCCAA<u>C</u>
1081 GCCACCCTAG GGGAGACACA CCGCCTGTTC CCCAACACCA TGCTCTTTGC CTCAGAGGCC
1141 TGTGTGGGCT CCAAGTTCTG GGAGCAGAGT GTGCGGCTAG GCTCCTGGGA TCGAGGGATG
1201 CAGTACAGCC ACAGCATCAT CACGAACCTC CTGTACCATG TGGTCGGCTG GACCGACTGG
1261 AACCTTGCCC TGAACCCCGA AGGAGGACCC AATTGGGTGC GTAACTTTGT CGACAGTCCC
1321 ATCATTGTAG ACATCACCAA GGACACGTTT TACAAACAGC CCATGTTCTA CCACCTTGGC
1381 CACTTCAGCA AGTTCATTCC TGAGGGCTCC CAGAGAGTGG GGCTGGTTGC CAGTCAGAAG
1441 AACGACCTGG ACGCAGTGGC ACTGATGCAT CCCGATGGCT CTGCTGTTGT GGTCGTGCTA
1501 AACCGCTCCT CTAAGGATGT GCCTCTTACC ATCAAGGATC CTGCTGTGGG CTTCCTGGAG
1561 ACAATCTCAC CTGGCTACTC CATTCACACC TACCTGTGGC GTCGCCAGTG A.

hGBA engineered variant sequence (SEQ ID NO: 163): hGBA (C165S) sequence
Bolded and underlined nucleotide at the mutation site
1 ATGGAGTTTT CAAGTCCTTC CAGAGAGGAA TGTCCCAAGC CTTTGAGTAG GGTAAGCATC
61 ATGGCTGGCA GCCTCACAGG TTTGCTTCTA CTTCAGGCAG TGTCGTGGGC ATCAGGTGCC
121 CGCCCCTGCA TCCCTAAAAG CTTCGGCTAC AGCTCGGTGG TGTGTGTCTG CAATGCCACA
181 TACTGTGACT CCTTTGACCC CCCGACCTTT CCTGCCCTTG GTACCTTCAG CCGCTATGAG
241 AGTACACGCA GTGGGCGACG GATGGAGCTG AGTATGGGGC CCATCCAGGC TAATCACACG
301 GGCACAGGCC TGCTACTGAC CCTGCAGCCA GAACAGAAGT TCCAGAAAGT GAAGGGATTT
361 GGAGGGGCCA TGACAGATGC TGCTGCTCTC AACATCCTTG CCCTGTCACC CCCTGCCCAA
421 AATTTGCTAC TTAAATCGTA CTTCTCTGAA GAAGGAATCG GATATAACAT CATCCGGGTA
481 CCCATGGCCA GCT<u>CC</u>GACTT CTCCATCCGC ACCTACACCT ATGCAGACAC CCCTGATGAT
541 TTCCAGTTGC ACAACTTCAG CCTCCCAGAG GAAGATACCA AGCTCAAGAT ACCCCTGATT
601 CACCGAGCCC TGCAGTTGGC CCAGCGTCCC GTTTCACTCC TTGCCAGCCC CTGGACATCA
661 CCCACTTGGC TCAAGACCAA TGGAGCGGTG AATGGGAAGG GGTCACTCAA GGGACAGCCC
721 GGAGACATCT ACCACCAGAC CTGGGCCAGA TACTTTGTGA AGTTCCTGGA TGCCTATGCT
781 GAGCACAAGT TACAGTTCTG GGCAGTGACA GCTGAAAATG AGCCTTCTGC TGGGCTGTTG
841 AGTGGATACC CCTTCCAGTG CCTGGGCTTC ACCCCTGAAC ATCAGCGAGA CTTCATTGCC
901 CGTGACCTAG GTCCTACCCT CGCCAACAGT ACTCACCACA ATGTCCGCCT ACTCATGCTG
961 GATGACCAAC GCTTGCTGCT GCCCCACTGG GCAAAGGTGG TACTGACAGA CCCAGAAGCA
1021 GCTAAATATG TTCATGGCAT TGCTGTACAT TGGTACCTGG ACTTTCTGGC TCCAGCCAAA
1081 GCCACCCTAG GGGAGACACA CCGCCTGTTC CCCAACACCA TGCTCTTTGC CTCAGAGGCC
1141 TGTGTGGGCT CCAAGTTCTG GGAGCAGAGT GTGCGGCTAG GCTCCTGGGA TCGAGGGATG
1201 CAGTACAGCC ACAGCATCAT CACGAACCTC CTGTACCATG TGGTCGGCTG GACCGACTGG
1261 AACCTTGCCC TGAACCCCGA AGGAGGACCC AATTGGGTGC GTAACTTTGT CGACAGTCCC
1321 ATCATTGTAG ACATCACCAA GGACACGTTT TACAAACAGC CCATGTTCTA CCACCTTGGC
1381 CACTTCAGCA AGTTCATTCC TGAGGGCTCC CAGAGAGTGG GGCTGGTTGC CAGTCAGAAG
1441 AACGACCTGG ACGCAGTGGC ACTGATGCAT CCCGATGGCT CTGCTGTTGT GGTCGTGCTA
1501 AACCGCTCCT CTAAGGATGT GCCTCTTACC ATCAAGGATC CTGCTGTGGG CTTCCTGGAG
1561 ACAATCTCAC CTGGCTACTC CATTCACACC TACCTGTGGC GTCGCCAGTG A.

mGALC sequence (SEQ ID NO: 6):
1 ATGGCTAACA GCCAACCTAZ GGCTTCCCAC CAACGCCAAC CAAAAGTCAT GACCGCCGCC
61 GCGGGCTCGG CGAGCCGTGI TGCGGTGCCC TTATTGTTGT GTGCGCTGCT AGTGCCCGGT
121 GGCGCCTACG TGCTGGACGZ CTCTGACGGC CTGGGCAGAC AGTTCGACGG CATCGGCGCT
181 GTGTCTGGCG GCGGAGCCAC AAGCAGACTC CTGGTCAACT ACCCCGAGCC CTACAGAAGC
241 GAGATCCTGG ACTACCTGTT CAAGCCCAAC TTCGGCGCCA GCCTGCACAT CCTGAAGGTG
301 GAAATCGGCG GCGACGGCCA GACCACCGAC GGCACAGAGC CCAGCCACAT GCACTACGAG
361 CTGGATGAGA ACTACTTCAG AGGCTACGAG TGGTGGCTGA TGAAGGAAGC CAAGAAGAGA -continued

| Nucleic Acid Sequences: |
|---|

```
 421 AACCCCGACA TCATCCTGAT GGGCCTGCCT TGGAGCTTCC CCGGCTGGCT GGGCAAGGGC
 481 TTCAGCTGGC CCTACGTGAA CCTGCAGCTG ACCGCCTACT ACGTCGTGCG GTGGATTCTG
 541 GGCGCCAAGC ACTACCACGA CCTGGACATC GACTACATCG GCATCTGGAA CGAGAGGCCC
 601 TTCGACGCCA ACTACATCAA AGAACTGAGG AAGATGCTGG ATTACCAGGG CCTGCAGAGA
 661 GTGCGGATCA TTGCCAGCGA CAACCTGTGG GAGCCCATCA GCAGCTCCCT GCTGCTGGAC
 721 CAGGACCTGT GGAAGGTCGT CGACGTGATC GGCGCCCACT ACCCTGGCAC CTACACCGTG
 781 TGGAACGCCA AGATGAGCGG CAAGAAGCTG TGGTCCAGCG AGGACTTCAG CACCATCAAC
 841 AGCAACGTGG GAGCCGGCTG CTGGTCCAGA ATCCTGAACC AGAATTACAT CAACGGCAAC
 901 ATGACCAGCA CAATCGCCTG GNAACCTGGN GGCCAGCTAC TACGAGGACT GCCCTACGGC
 961 AGATCCGGCC TGATGACCGC CCAGGAACCT TGGAGCGGCC ACTACGTGGT GGCTTCCCCA
1021 ATCTGGGTGT CCGCCCACAC CACCCAGTTC ACCCAGCCTG GCTGGTACTA CCTGAAAACC
1081 GTGGGCCACC TGGAAAAGGG CGGCAGCTAC GTGGCCCTGA CCGATGGCCT GGGCAACCTG
1141 ACCATCATCA TCGAGACAAT GAGCCACCAG CACAGCATGT GCATCAGACC CTACCTGCCC
1201 TACTACAACG TGTCCCACCA GCTGGCCACA TTCACCCTGA AGGGCAGCCT GAGAGAGATC
1261 CAGGAACTGC AGGTCTGGTA CACCAAGCTG GGCACCCCCC AGCAGAGACT GCACTTCAAG
1321 CAGCTGGACA CCCTGTGGCT GCTGGACGGC AGCGGCAGCT TCACCCTGGA ACTGGAAGAG
1381 GACGAAATCT TCACCCTGAC CACACTGACC ACCGGCAGAA AGGGCAGCTA CCCCCCACCT
1441 CCTAGCAGCA AGCCATTCCC CACCAACTAC AAGGACGACT TCAACGTGGA ATACCCCCTG
1501 TTCAGCGAGG CCCCCAACTT CGCCGACCAG ACCGGCGTGT TCGAGTACTA CATGAACAAC
1561 GAGGACAGAG AGCACAGGTT CACCCTGAGA CAGGTGCTGA ACCAGAGGCC CATCACCTGG
1621 GCTGCCGACG CCAGCAGCAC CATCTCCGTG ATCGGGGACC ACCACTGGAC CAACATGACC
1681 GTGCAGTGCG AGGTGTACAT CGAGACACCT AGAAGCGGCG GAGTGTTTAT CGCCGGCAGA
1741 GTGAACAAGG GCGGCATCCT GATCAGATCC GCTACAGGCG TGTTCTTCTG GATCTTCGCC
1801 AACGGCAGCT ACAGAGTGAC CGCCGACCTG GGCGGCTGGA TCACATACGC CTCTGGCCAC
1861 GCCGACGTGA CCGCCAAGAG ATGGTACACC CTGACCCTGG GCATCAAGGG CTACTTCGCC
1921 TTCGGCATGC TGAACGGCAC CATCCTGTGG AAGAACGTGC GCGTGAAGTA CCCCGGCCAC
1981 GGCTGGGCTG CCATCGGCAC CCACACATTC GAGTTCGCCC AGTTCGACAA CTTTCGCGTG
2041 GAAGCTGCTC GC.
```

hGLA sequence (SEQ ID NO: 7):

```
   1 ATGCAGCTGA SGAACCCAGA ACTACATCTG GGCTGCGCGC TTGCGCTTCG CTTCCTGGCC
  61 CTCGTTTCCT SGGACATCCC TGGGGCTAGA GCACTGGACA ATGGATTGGC AAGGACGCCT
 121 ACCATGGGCT SGCTGCACTG GGAGCGCTTC ATGTGCAACC TTGACTGCCA GGAAGAGCCA
 181 GATTCCTGCA TCAGTGAGAA GCTCTTCATG GAGATGGCAG AGCTCATGGT CTCAGAAGGC
 241 TGGAAGGATG CAGGTTATGA GTACCTCTGC ATTGATGACT GTTGGATGGC TCCCCAAAGA
 301 GATTCAGAAG SCAGACTTCA GGCAGACCCT CAGCGCTTTC CTCATGGGAT TCGCCAGCTA
 361 GCTAATTATG TTCACAGCAA AGGACTGAAG CTAGGGATTT ATGCAGATGT TGGAAATAAA
 421 ACCTGCGCAG SCTTCCCTGG GAGTTTTGGA TACTACGACA TTGATGCCCA CACCTTTGCT
 481 GACTGGGGAG TAGATCTGCT AAAATTTGAT GGTTGTTACT GTGACAGTTT GGAAAATTTG
 541 GCAGATGGTT ATAAGCACAT GTCCTTGGCC CTGAATAGGA CTGGCAGAAG CATTGTGTAC
 601 TCCTGTGAGT GGCCTCTTTA TATGTGGCCC TTTCAAAAGC CCAATTATAC AGAAATCCGA
 661 CAGTACTGCA ATCACTGGCG AAATTTTGCT GACATTGATG ATTCCTGGAA AAGTATAAAG
 721 AGTATCTTGG ACTGGACATC TTTTAACCAG GAGAGAATTG TTGATGTTGC TGGACCAGGG
 781 GGTTGGAATG ACCCAGATAT GTTAGTGATT GGCAACTTTG GCCTCAGCTG CAATCAGCAA
 841 GTAACTCAGA TGGCCCTCTG GGCTATCATG GCTGCTCCTT TATTCATGTC GAATGACCTC
 901 CGACACATCA SCCCTCAAGC CAAAGCTCTC CTTCAGGATA AGGACGTAAT TGCCATCAAT
 961 CAGGACCCCT TGGGCAAGCA AGGGTACCAG CTTAGACAGG GAGACAACTT TGAAGTGTGG
1021 GAACGACCTC PCTCAGGCTT AGCCTGGGCT GTAGCTATGA TAAACCGGCA CGAGATTGGT
1081 GGACCTCGCT CTTATACCAT CGCAGTTGCT TCCCTGGGTA AAGGAGTGGC CTGTAATCCT
1141 GCCTGCTTCA TCACACAGCT CCTCCCTGTG AAAAGGAAGC TAGGGTTCTA TGAATGGACT
1201 TCAAGGTTAA GAAGTCACAT AAATCCCACA GGCACTGTTT TGCTTCAGCT AGAAAATACA
1261 ATGCAGATGT CATTAAAAGA CTTACTTTAA.
```

hNAGLU sequence (SEQ ID NO: 8):

```
   1 ATGGAGGCGG TGGCGGTGGC CGCGGCGGTG GGGGTCCTTC TCCTGGCCGG CGCCGGGGGC
  61 GCGGCAGGCG ACGAGGCCCG GGAGGCGGCG GCCGTGCGGG CGCTCGTGGC CCGGCTGCTG
 121 GGGCCAGGCC CCGCGGCCGA CTTCTCCGTG TCGGTGGAGC GCGCTCTGGC TGCCAAGCCG
 181 GGCTTGGACA CCTACAGCCT GGGCGGCGGC GGCGCGGCGC GCGTGCGGGT GCGCGGCTCC
 241 ACGGGCGTGG CGGCCGCCGC GGGGCTGCAC CGCTACCTGC GCGACTTCTG TGGCTGCCAC
 301 GTGGCCTGGT CCGGCTCTCA GCTGCGCCTG CCGCGGCCAC TGCCAGCCGT GCCGGGGGAG
 361 CTGACCGAGG CCACGCCCAA CAGGTACCGC TATTACCAGA ATGTGTGCAC GCAAAGCTAC
 421 TCTTTCGTGT GGTGGGACTG GGCCCGCTGG GAGCGAGAGA TAGACTGGAT GGCGCTGAAT
 481 GGCATCAACC TGGCACTGGC CTGGAGCGGC CAGGAGGCCA TCTGGCAGCG GGTGTACCTG
 541 GCCTTGGGCC TGACCCAGGC AGAGATCAAT GAGTTCTTTA CTGGTCCTGC CTTCCTGGCC
 601 TGGGGGCGAA TGGGCAACCT GCACACCTGG GATGGCCCCC TGCCCCCCTC CTGGCACATC
 661 AAGCAGCTTT ACCTGCAGCA CCGGGTCCTG GACCAGATGC GCTCCTTCGG CATGACCCCA
 721 GTGCTGCCTG CATTCGCGGG GCATGTTCCC GAGGCTGTGA CCAGGGTGTT CCCTCAGGTC
 781 AATGTCACGA AGATGGGCAG TTGGGGCCAC TTTAACTGTT CCTACTCCTG CTCCTTCCTT
 841 CTGGCTCCGG AAGACCCCAT ATTCCCCATC ATCGGGAGCC TCTTCCTGCG AGAGCTGATC
 901 AAAGAGTTTG GCACAGACCA CATCTATGGG GCCGACACTT TCAATGAGAT GCAGCCACCT
 961 TCCTCAGAGC CCTCCTACCT TGCCGCAGCC ACCACTGCCG TCTATGAGGC CATGACTGCA
1021 GTGGATACTG AGGCTGTGTG GCTGCTCCAA GGCTGGCTCT TCCAGCACCA GCCGCAGTTC
1081 TGGGGGCCCG CCCAGATCAG GGCTGTGCTG GGAGCTGTGC CCCGTGGCCG CCTCCTGGTT
1141 CTGGACCTGT TTGCTGAGAG CCAGCCTGTG TATACCCGCA CTGCCTCCTT CCAGGGCCAG
1201 CCCTTCATCT GGTGCATGCT GCACAACTTT GGGGGAAACC ATGGTCTTTT TGGAGCCCTA
1261 GAGGCTGTGA ACGGAGGCCC AGAAGCTGCC CGCCTCTTCC CCAACTCCAC CATGGTAGGC
1321 ACGGGCATGG CCCCCGAGGG CATCAGCCAG AACGAAGTGG TCTATTCCCT CATGGCTGAG
```

-continued

| Nucleic Acid Sequences: |
|---|

```
1381 CTGGGCTGGC GAAAGGACCC AGTGCCAGAT TTGGCAGCCT GGGTGACCAG CTTTGCCGCC
1441 CGGCGGTATG GGGTCTCCCA CCCGGACGCA GGGGCAGCGT GGAGGCTACT GCTCCGGAGT
1501 GTGTACAACT GCTCCGGGGA GGCCTGCAGG GGCCACAATC GTAGCCCGCT GGTCAGGCGG
1561 CCGTCCCTAC AGATGAATAC CAGCATCTGG TACAACCGAT CTGATGTGTT TGAGGCCTGG
1621 CGGCTGCTGC TCACATCTGC TCCCTCCCTG GCCACCAGCC CCGCCTTCCG CTACGACCTG
1681 CTGGACCTCA CTCGGCAGGC AGTGCAGGAG CTGGTCAGCT TGTACTATGA GGAGGCAAGA
1741 AGCGCCTACC TGAGCAAGGA GCTGGCCTCC CTGTTGAGGG CTGGAGGCGT CCTGGCCTAT
1801 GAGCTGCTGC CGGCACTGGA CGAGGTGCTG GCTAGTGACA GCCGCTTCTT GCTGGGCAGC
1861 TGGCTAGAGC AGGCCCGAGC AGCGGCAGTC AGTGAGGCCG AGGCCGATTT CTACGAGCAG
1921 AACAGCCGCT ACCAGCTGAC CTTGTGGGGG CCAGAAGGCA ACATCCTGGA CTATGCCAAC
1981 AAGCAGCTGG CGGGGTTGGT GGCCAACTAC TACACCCCTC GCTGGCGGCT TTTCCTGGAG
2041 GCGCTGGTTG ACAGTGTGGC CCAGGGCATC CCTTTCCAAC AGCACCAGTT TGACAAAAAT
2101 GTCTTCCAAC TGGAGCAGGC CTTCGTTCTC AGCAAGCAGA GGTACCCCAG CCAGCCGCGA
2161 GGAGACACTG TGGACCTGGC CAAGAAGATC TTCCTCAAAT ATTACCCCCG CTGGGTGGCC
2221 GGCTCTTGGT GA.
```

hGAA sequence (SEQ ID NO: 9):

```
   1 ATGGGAGTGA GGCACCCGCC CTGCTCCCAC CGGCTCCTGG CCGTCTGCGC CCTCGTGTCC
  61 TTGGCAACCG CTGCACTCCT GGGGCACATC CTACTCCATG ATTTCCTGCT GGTTCCCCGA
 121 GAGCTGAGTG GCTCCTCCCC AGTCCTGGAG GAGACTCACC CAGCTCACCA GCAGGGAGCC
 181 AGCAGACCAG GGCCCCGGGA TGCCCAGGCA CACCCCGGCC GTCCCAGAGC AGTGCCCACA
 241 CAGTGCGACG TCCCCCCCAA CAGCCGCTTC GATTGCGCCC CTGACAAGGC CATCAGCCAG
 301 GAACAGTGCG AGGCCCGCGG CTGTTGCTAC ATCCCTGCAA AGCAGGGGCT GCAGGGAGCC
 361 CAGATGGGGC AGCCCTGGTG CTTCTTCCCA CCCAGCTACC CCAGCTACAA GGTGGAGAAC
 421 CTGAGCTCCT CTGAAATGGG CTACACGGCC ACCCTGACCC GTACCACCCC CACCTTCTTC
 481 CCCAAGGACA TCCTGACCCT GCGGCTGGAC GTGATGATGG AGACTGAGAA CCGCCTCCAC
 541 TTCACGATCA AAGATCCAGC TAACAGGCGC TACGAGGTGC CCTTGGAGAC CCCGCATGTC
 601 CACAGCCGGG CACCGTCCCC ACTCTACAGC GTGGAGTTCT CCGAGGAGCC CTTCGGGGTG
 661 ATCGTGCGCC GGCAGCTGGA CGGCCGCGTG CTGCTGAACA CGACGGTGGC GCCCCTGTTC
 721 TTTGCGGACC AGTTCCTTCA GCTGTCCACC TCGCTGCCCT CGCAGTATAT CACAGGCCTC
 781 GCCGAGCACC TCAGTCCCCT GATGCTCAGC ACCAGCTGGA CCAGGATCAC CCTGTGGAAC
 841 CGGGACCTTG CGCCCACGCC CGGTGCGAAC CTCTACGGGT CTCACCCTTT CTACCTGGCG
 901 CTGGAGGACG GCGGGTCGGC ACACGGGGTG TTCCTGCTAA ACAGCAATGC CATGGATGTG
 961 GTCCTGCAGC CGAGCCCTGC CCTTAGCTGG AGGTCGACAG GTGGGATCCT GGATGTCTAC
1021 ATCTTCCTGG GCCCAGAGCC CAAGAGCGTG GTGCAGCAGT ACCTGGACGT TGTGGGATAC
1081 CCGTTCATGC CGCCATACTG GGGCCTGGGC TTCCACCTGT GCCGCTGGGG CTACTCCTCC
1141 ACCGCTATCA CCCGCCAGGT GGTGGAGAAC ATGACCAGGG CCCACTTCCC CCTGGACGTC
1201 CAGTGGAACG ACCTGGACTA CATGGACTCC CGGAGGGACT TCACGTTCAA CAAGGATGGC
1261 TTCCGGGACT TCCCGGCCAT GGTGCAGGAG CTGCACCAGG GCGGCCGGCG CTACATGATG
1321 ATCGTGGATC CTGCCATCAG CAGCTCGGGC CCTGCCGGGA GCTACAGGCC CTACGACGAG
1381 GGTCTGCGGA GGGGGGTTTT CATCACCAAC GAGACCGGCC AGCCGCTGAT TGGGAAGGTA
1441 TGGCCCGGGT CCACTGCCTT CCCCGACTTC ACCAACCCCA CAGCCCTGGC CTGGTGGGAG
1501 GACATGGTGG CTGAGTTCCA TGACCAGGTG CCCTTCGACG GCATGTGGAT TGACATGAAC
1561 GAGCCTTCCA ACTTCATCAG GGGCTCTGAG GACGGCTGCC CCAACAATGA GCTGGAGAAC
1621 CCACCCTACG TGCCTGGGGT GGTTGGGGGG ACCCTCCAGG CGGCCACCAT CTGTGCCTCC
1681 AGCCACCAGT TTCTCTCCAC ACACTACAAC CTGCAGAAGG TCTACGGCCT GACCGAAGCC
1741 ATCGCCTCCC ACAGGGCGCT GGTGAAGGCT CGGGGGACAC GCCCATTTGT GATCTCCCGC
1801 TCGACCTTTG CTGGCCACGG CCGATACGCC GGCCACTGGA CGGGGGACGT GTGGAGCTCC
1861 TGGGAGCAGC TCGCCTCCTC CGTGCCAGAA ATCCTGCAGT TTAACCTGCT GGGGGTGCCT
1921 CTGGTCGGGG CCGACGTCTG CGGCTTCCTG GGCAACACCT CAGAGGAGCT GTGTGTGCGC
1981 TGGACCCAGC TGGGGGCCTT CTACCCCTTC ATGCGGAACC ACAACAGCCT GCTCAGTCTG
2041 CCCCAGGAGC CGTACAGCTT CAGCGAGCCG GCCCAGCAGG CCATGAGGAA GGCCCTCACC
2101 CTGCGCTACG CACTCCTCCC CCACCTCTAC ACACTGTTCC ACCAGGCCCA CGTCGCGGGG
2161 GAGACCGTGG CCCGGCCCCT CTTCCTGGAG TTCCCCAAGG ACTCTAGCAC CTGGACTGTG
2221 GACCACCAGC TCCTGTGGGG GGAGGCCCTG CTCATCACCC CAGTGCTCCA GGCCGGGAAG
2281 GCCGAAGTGA CTGGCTACTT CCCCTTGGGC ACATGGTACG ACCTGCAGAC GGTGCCAGTA
2341 GAGGCCCTTG GCAGCCTCCC ACCCCCACCT GCAGCTCCCC GTGAGCCAGC CATCCACAGC
2401 GAGGGGCAGT GGGTGACGCT GCCGGCCCCC CTGGACACCA TCAACGTCCA CCTCCGGGCT
2461 GGGTACATCA TCCCCCTGCA GGGCCCTGGC CTCACAACCA CAGAGTCCCG CCAGCAGCCC
2521 ATGGCCCTGG CTGTGGCCCT GACCAAGGGT GGGGAGGCCC GAGGGGAGCT GTTCTGGGAC
2581 GATGGAGAGA GCCTGGAAGT GCTGGAGCGA GGGGCCTACA CACAGGTCAT CTTCCTGGCC
2641 AGGAATAACA CGATCGTGAA TGAGCTGGTA CGTGTGACCA GTGAGGGAGC TGGCCTGCAG
2701 CTGCAGAAGG TGACTGTCCT GGGCGTGGCC ACGGCGCCCC AGCAGGTCCT CTCCAACGGT
2761 GTCCCTGTCT CCAACTTCAC CTACAGCCCC GACACCAAGG TCCTGGACAT CTGTGTCTCG
2821 CTGTTGATGG GAGAGCAGTT TCTCGTCAGC TGGTGTTAG.
```

hGAA (SEQ ID NO: 164; UniProt Accession No. P10253-1)

```
   1 MGVRHPPCSH RLLAVCALVS LATAALLGHI OLHDFLLVPR ELSGSSPVLE ETHPAHQQGA
  61 SRPGPRDAQA IPGRPRAVPT QCDVPPNSRF DCAPDKAITQ ZQCEARGCCY IPAKQGLQGA
 121 QMGQPWCFFP PSYPSYKLEN LSSSEMGYTA TLTRTTPTFF PKDILTLRLD VMMETENRLH
 181 FTIKDPANRR YEVPLETPHV ISRAPSPLYS VEFSEEPFGV IVRRQLDGRV LLNTTVAPLF
 241 FADQFLQLST SLPSQYITGL AEHLSPIMLS FSWTRITLWN RDLAPTPGAN LYGSHPFYLA
 301 LEDGGSAHGV FLLNSNAMDV VLQPSPALSW RSTGGILDVY IFLGPEPKSV VQQYLDVVGY
 361 PFMPPYWGLG FHLCRWGYSS TAITRQVVEN MTRAHFPLDV QWNDLDYMDS RRDFTFNKDG
 421 FRDFPAMVQE OHQGGRRYMM IVDPAISSSG PAGSYRPYDE GLRRGVFITN ETGQPLIGKV
 481 WPGSTAFPDF INPTALAWWE DMVAEFHDOV PFDGMWIDMN EPSNFIRGSE DGCPNNELEN
 541 PPYVPGVVGG TLQAATICAS SHQFLSTHYN LHNLYGLTEA IASHRALVKA RGTRPFVISR
```

-continued

| Nucleic Acid Sequences: |
|---|

```
 601 STFAGHGRYA SHWTGDVWSS WEQLASSVPE ILQFNLLGVP LVGADVCGFL GNTSEELCVR
 661 WTQLGAFYPF MRNHNSLLSL PQEPYSFSEP AQQAMRKALT LRYALLPHLY TLFHQAHVAG
 721 ETVARPLFLE TPKDSSTWTV DHQLLWGEAL LITPVLQAGK AEVTGYFPLG TWYDLQTVPV
 781 EALGSLPPPP AAPREPAIHS ZGQWVTLPAP LDTINVHLRA GYIIPLQGPG LTTTESRQQP
 841 MALAVALTKG SEARGELEWD DGESLEVLER GAYTQVIFLA RNNTIVNELV RVTSEGAGLQ
 901 LQKVTVLGVA TAPQQVLSNG VPVSNFTYSP DTKVLDICVS LLMGEQFLVS WC.
```

hLAMAN sequence (SEQ ID NO: 10):

```
   1 ATGGGCGCCT ACGCGCGGGC TTCGGGGGTC TGCGCTCGCG GCTGCCTGGA CTCAGCAGGC
  61 CCCTGGACCA TGTCCCGCGC CCTGCGGCCA CCGCTCCCGC CTCTCTGCTT TTTCCTTTTG
 121 TTGCTGGCGG CTGCCGGTGC TCGGGCCGGG GGATACGAGA CATGCCCCAC AGTGCAGCCG
 181 AACATGCTGA ACGTGCACCT GCTGCCTCAC ACACATGATG ACGTGGGCTG GCTCAAAACC
 241 GTGGACCAGT ACTTTTATGG AATCAAGAAT GACATCCAGC ACGCCGGTGT GCAGTACATC
 301 CTGGACTCGG TCATCTCTGC CTTGCTGGCA GATCCCACCC GTCGCTTCAT TTACGTGGAG
 361 ATTGCCTTCT TCTCCCGTTG GTGGCACCAG CAGACAAATG CCACACAGGA AGTCGTGCGA
 421 GACCTTGTGC GCCAGGGGCG CCTGGAGTTC GCCAATGGTG GCTGGGTGAT GAACGATGAG
 481 GCAGCCACCC ACTACGGTGC CATCGTGGAC CAGATGACAC TTGGGCTGCG CTTTCTGGAG
 541 GACACATTTG GCAATGATGG GCGACCCCGT GTGGCCTGGC ACATTGACCC CTTCGGCCAC
 601 TCTCGGGAGC AGGCCTCGCT GTTTGCGCAG ATGGGCTTCG ACGGCTTCTT CTTTGGGCGC
 661 CTTGATTATC AAGATAAGTG GGTACGGATG CAGAAGCTGG AGATGGAGCA GGTGTGGCGG
 721 GCCAGGACCA GCCTGAAGCC CCCGACCGCG GACCTCTTCA CTGGTGTGCT TCCCAATGGT
 781 TACAACCCGC CAAGGAATCT GTGCTGGGAT GTGCTGTGTG TCGATCAGCC GCTGGTGGAG
 841 GACCCTCGCA GCCCCGAGTA CAACGCCAAG GAGCTGGTCG ATTACTTCCT AAATGTGGCC
 901 ACTGCCCAGG GCCGGTATTA CCGCACCAAC CACACTGTGA TGACCATGGG CTCGGACTTC
 961 CAATATGAGA ATGCCAACAT GTGGTTCAAG AACCTTGACA AGCTCATCCG GCTGGTAAAT
1021 GCGCAGCAGG CAAAAGGAAG CAGTGTCCAT GTTCTCTACT CCACCCCCGC TTGTTACCTC
1081 TGGGAGCTGA ACAAGGCCAA CCTCACCTGG TCAGTGAAAC ATGACGACTT CTTCCCTTAC
1141 GCGGATGGCC CCCACCAGTT CTGGACCGGT TACTTTTCCA GTCGGCCGGC CCTCAAACGC
1201 TACGAGCGCC TCAGCTACAA CTTCCTGCAG GTGTGCAACC AGCTGGAGGC GCTGGTGGGC
1261 CTGGCGGCCA ACGTGGGACC CTATGGCTCC GGAGACAGTG CACCCCTCAA TGAGGCGATG
1321 GCTGTGCTCC AGCATCACGA CGCCGTCAGC GGCACCTCCC GCCAGCACGT GGCCAACGAC
1381 TACGCGCGCC AGCTTGCGGC AGGCTGGGGG CCTTGCGAGG TTCTTCTGAG CAACGCGCTG
1441 GCGCGGCTCA GAGGCTTCAA AGATCACTTC ACCTTTTGCC AACAGCTAAA CATCAGCATC
1501 TGCCCGCTCA GCCAGACGGC GGCGCGCTTC CAGGTCATCG TTTATAATCC CCTGGGGCGG
1561 AAGGTGAATT GGATGGTACG GCTGCCGGTC AGCGAAGGCG TTTTCGTTGT GAAGGACCCC
1621 AATGGCAGGA CAGTGCCCAG CGATGTGGTA ATATTTCCCA GCTCAGACAG CCAGGCGCAC
1681 CCTCCGGAGC TGCTGTTCTC AGCCTCACTG CCCGCCCTGG GCTTCAGCAC CTATTCAGTA
1741 GCCCAGGTGC CTCGCTGGAA GCCCCAGGCC CGCGCACCAC AGCCCATCCC CAGAAGATCC
1801 TGGTCCCCTG CTTTAACCAT CGAAAATGAG CACATCCGGG CAACGTTTGA TCCTGACACA
1861 GGGCTGTTGA TGGAGATTAT GAACATGAAT CAGCAACTCC TGCTGCCTGT TCGCCAGACC
1921 TTCTTCTGGT ACAACGCCAG TATAGGTGAC AACGAAAGTG ACCAGGCCTC AGGTGCCTAC
1981 ATCTTCAGAC CCAACCAACA GAAACCGCTG CCTGTGAGCC GCTGGGCTCA GATCCACCTG
2041 GTGAAGACAC CCTTGGTGCA GGAGGTGCAC CAGAACTTCT CAGCTTGGTG TTCCCAGGTG
2101 GTTCGCCTGT ACCCAGGACA GCGGCACCTG GAGCTAGAGT GGTCGGTGGG GCCGATACCT
2161 GTGGGCGACA CCTGGGGGAA GGAGGTCATC AGCCGTTTTG ACACACCGCT GGAGACAAAG
2221 GGACGCTTCT ACACAGACAG CAATGGCCGG GAGATCCTGG AGAGGAGGCG GGATTATCGA
2281 CCCACCTGGA AACTGAACCA GACGGAGCCC GTGGCAGGAA ACTACTATCC AGTCAACACC
2341 CGGATTTACA TCACGGATGG AAACATGCAG CTGACTGTGC TGACTGACCG CTCCCAGGGG
2401 GGCAGCAGCC TGAGAGATGG CTCGCTGGAG CTCATGGTGC ACCGAAGGCT GGTGAAGGAC
2461 GATGGACGCG GAGTATCGGA GCCACTAATG GAGAACGGGT CGGGGGCGTG GGTGCGAGGG
2521 CGCCACCTGG TGCTGCTGGA CACAGCCCAG GCTGCAGCCG CCGGACACCG GCTCCTGGCG
2581 GAGCAGGAGG TCCTGGCCCC TCAGGTGGTG CTGGCCCCGG GTGGCGGCGC CGCCTACAAT
2641 CTCGGGGCTC CTCCGCGCAC GCAGTTCTCA GGGCTGCGCA GGGACCTGCC GCCCTCGGTG
2701 CACCTGCTCA CGCTGGCCAG CTGGGGCCCC GAAATGGTGC TGCTGCGCTT GGAGCACCAG
2761 TTTGCCGTAG GAGAGGATTC CGGACGTAAC CTGAGCGCCC CCGTTACCTT GAACTTGAGG
2821 GACCTGTTCT CCACCTTCAC CATCACCCGC CTGCAGGAGA CCACGCTGGT GGCCAACCAG
2881 CTCCGCGAGG CAGCCTCCAG GCTCAAGTGG ACAACAAACA CAGGCCCCAC ACCCCACCAA
2941 ACTCCGTACC AGCTGGACCC GGCCAACATC ACGCTGGAAC CCATGGAAAT CCGCACTTTC
3001 CTGGCCTCAG TTCAATGGAA GGAGGTGGAT GGT.
```

hGALC sequence (SEQ ID NO: 23; GenBank Accession No: BC036518.2):

```
   1 aaaagctatg actgcggccg cgggttcggc gggccgcgcc gcggtgccct tgctgctgtg
  61 tgcgctgctg gcgcccggcg gcgcgtacgt gctcgacgac tccgacgggc tgggccggga
 121 gttcgacggc atcggcgcgg tcagcggcgg cggggcaacc tcccgacttc tagtaaatta
 181 cccagagccc tatcgttctc agatattgga ttatctcttt aagccgaatt ttggtgcctc
 241 tttgcatatt ttaaaagtgg aaataggtgg tgatgggcag acaacagatg gcactgagcc
 301 ctcccacatg cattatgcac tagatgagaa ttatttccga ggatacgagt ggtggttgat
 361 gaaagaagct aagaagagga atcccaatat tacactcatt gggttgccat ggtcattccc
 421 tggatggctg ggaaaaggtt tcgactggcc ttatgtcaat cttcagctga ctgcctatta
 481 tgtcgtgacc tggattgtgg gcgccaagcg ttaccatgat ttggacattg attatattgg
 541 aatttggaat gagaggtcat ataatgccaa ttatattaag atattaagaa aaatgctgaa
 601 ttatcaaggt ctccagcgag tgaaaatcat agcaagtgat aatctctggg agtccatctc
 661 tgcatccatg ctccttgatg ccgaactctt caaggtggtt gatgttatag ggctcatta
 721 tcctggaacc cattcagcaa aagatgcaaa gttgactggg aagaagcttt ggtcttctga
 781 agactttagc actttaaata gtgacatggg tgcaggctgc tggggtcgca ttttaaatca
 841 gaattatatc aatggctata tgacttccac aatcgcatgg aatttagtgg ctagttacta
 901 tgaacagttg ccttatggga gatgcgggtt gatgacggcc caggagccat ggagtgggca
```

-continued

Nucleic Acid Sequences:

```
 961 ctacgtggta gaatctcctg tctgggtatc agctcatacc actcagttta ctcaacctgg
1021 ctggtattac ctgaagacag ttggccattt agagaaagga ggaagctacg tagctctgac
1081 tgatggctta gggaacctca ccatcatcat tgaaaccatg agtcataaac attctaagtg
1141 catacggcca tttcttcctt atttcaatgt gtcacaacaa tttgccacct ttgttcttaa
1201 gggatctttt agtgaaatac cagagctaca ggtatggtat accaaacttg gaaaaacatc
1261 cgaaagattt ctttttaagc agctggattc tctatggctc cttgacagcg atggcagttt
1321 cacactgagc ctgcatgaag atgagctgtt cacactcacc actctcaeca ctggtcgcaa
1381 aggcagctac ccgcttcctc caaaatccca gcccttccca agtacctata aggatgattt
1441 caatgttgat tacccatttt ttagtgaagc tccaaacttt gctgatcaaa ctggtgtatt
1501 tgaatatttt acaaatattg aagaccctgg cgagcatcac ttcacgctac gccaagttct
1561 caaccagaga cccattacgt gggctgccga tgcatccaac acaatcagta ttataggaga
1621 ctacaactgg accaatctga ctacaaagtg tgatgtttac atagagaccc ctgacacagg
1681 aggtgtgttc attgcaggaa gagtaaataa aggtggtatt ttgattagaa gtgccagagg
1741 aattttcttc tggattttg caaatggatc ttacagggtt acaggtgatt tagctggatg
1801 gattatatat gctttaggac gtgttgaagt tacagcaaaa aaatggtata cactcacgtt
1861 aactattaag ggtcatttcg cctctggcat gctgaatgac aagtetetgt ggacagacat
1921 ccctgtgaat tttccaaaga atggctgggc tgcaattgga actcactcct ttgaatttgc
1981 acagtttgac aactttcttg tggaagccac acgctaatac ttaacagggc atcatagaat
2041 actctggatt ttcttccctt ctttttggtt ttggttcaga gccaattctt gtttcattgg
2101 aacagtatat gaggcttttg agactaaaaa taatgaagag taaaagggga gagaaattta
2161 tttttaattt accctgtgga agattttatt agaattaatt ccaaggggaa aactggtgaa
2221 tctttaacat tacctggtgt gttccctaac attcaaactg tgcattggcc ataccettag
2281 gagtggtttg agtagtacag acctcgaagc cttgctgcta acactgaggt agctctcttc
2341 atcttatttg caagcggtcc tgtagatggc agtaacttga tcatcactga gatgtattta
2401 tgcatgctga ccgtgtgtcc aagtgagcca gtgtcttcat cacaagatga tgctgccata
2461 atagaaagct gaagaacact agaagtagct ttttgaaaac cacttcaacc tgttatgctt
2521 tatgctctaa aaagtatttt ttttatttc ctttttaaga tgatactttt gaaatgeagg
2581 atatgatgag tgggatgatt ttaaaaatgc ctctttaata aactacctct aacactattt
2641 ctgtggtaat agatattagc agattaattg ggttatttgc attatttaat tttttgatt
2701 ccaagttttg gtcttgtaac cactataact ctctgtgaac atttttccag gtggctggaa
2761 gaaggaagaa aacctgatat agccaatgct gttgtagtcg tttcctcagc ctcatctcac
2821 tgtgctgtgg tctgtcctca catgtgcact ggtaacagac tcacacagct gatgaatget
2881 tttctctcct tatgtgtgga aggaggggag cacttagaca tttgctaact cccagaattg
2941 gatcatctcc taagatgtac ttacttttta aagtccaaat atgtttatat ttaaatatac
3001 gtgagcatgt tcatcatgtt gtatgattta tactaagcat taatgtggct ctatgtagca
3061 aatcagttat tcatgtaggt aaagtaaatc tagaattatt tataagaatt actcattgaa
3121 ctaattctac tatttaggaa tttgtaagag tctaacatag gcttagctac agtgaagttt
3181 tgcattgctt ttgaagacaa gaagataagt gctagaataa ataagattac agagaaaatt
3241 ttttgttaaa accaagtgat ttccagctga tgtatctaat attttttaaa acgaacatta
3301 tagaggtgta atttatttac aataaaatgt tcctacttta aatatacaat tcagtgagtt
3361 ttgataaatt gatataccca tgtaaccaac actccagtca agcttcagaa tatttccatc
3421 accccagaag gttctcttgt atacctgctc agtcagttcc tttcactccc gattgttggc
3481 agccattgat aggaattcta tcactatagg ttagttttct ttgttccaga acatcatgaa
3541 agcggcgtca tgtactgtgt attcttatga atggtttctt tccatcagca taatgatttg
3601 agatttgtcc atgttgtgtg attcagtggt ttgttccttc ttatttctga agagttttcc
3661 attgtatgaa tataccacaa tttgtttcct ccccaccagt ttctgatact acaattaaaa
3721 ctgtctacat ttacaaaaaa aaaaaaaaa.

CEF promoter sequence (SEQ ID NO: 161):
   1 gttacataac ttatggtaaa tggcctgcct ggctgactgc ccaatgaccc ctgcccaatg
  61 atgtcaataa tgatgtatgt tcccatgtaa tgccaatagg gactttccat tgatgtcaat
 121 gggtggagta tttatggtaa ctgcccactt ggcagtacat caagtgtatc atatgccaag
 181 tatgccccct attgatgtca atgatggtaa atggcctgcc tggcattatg cccagtacat
 241 gaccttatgg gactttccta cttggcagta catctatgta ttagtcattg ctattaccat
 301 gggaattcac tagtggagaa gagcatgctt gagggctgag tgcccctcag tgggcagaga
 361 gcacatggcc cacagtccct gagaagttgg ggggaggggt gggcaattga actggtgcct
 421 agagaaggtg gggcttgggt aaactgggaa agtgatgtgg tgtactggct ccaccttttt
 481 ccccagggtg ggggagaacc atatataagt gcagtagtct ctgtgaacat tc.
```

TABLE 2

Primers used in the study.

| Primer | Sequence | SEQ ID NO: | Restriction Enzyme |
|---|---|---|---|
| GBA-F | ctgctagccaccATGGAGTTTTCAAGTCCTTC | 11 | NheI |
| GBA-R | atagcggccgcTCACTGGCGACGCCACAGGT | 12 | NotI |
| GAA-F | ctgctagccaccATGGGAGTGAGGCACCCGCCCTG | 13 | NheI |
| GAA-R | atagcggccgctcaACACCAGCTGACGAGAAACTGCTC | 14 | NotI |
| GALC-F | ctgctagccaccATGGCTAACAGCCAACCTAAGGC | 15 | NheI |

TABLE 2-continued

| Primers used in the study. | | | |
|---|---|---|---|
| Primer | Sequence | SEQ ID NO: | Restriction Enzyme |
| GALC-R | atagcggccgctcaGCGAGCAGCTTCCACGCGAAAGTTG | 16 | NotI |
| NAGLU-F | ctgctagccaccATGGAAGCCGTGGCTGTCGCAG | 17 | NheI |
| NAGLU-R | atagcggccgctcaCCAACTACCAGCCACCCATCTAG | 18 | NotI |
| GLA-F | ctggatccaccATGCAGCTGAGGAACCCAGAAC | 19 | BamHI |
| GLA-R | atagcggccgctcaAAGTAAGTCTTTTAATGACATCTG | 20 | NotI |
| LAMAN-F | ctgctagccaccATGGGCGCCTACGCGCGGGCTTC | 21 | NheI |
| LAMAN-R | atagcggccgctcaACCATCCACCTCCTTCCATTGAAC | 22 | NotI |

Examples

The disclosure is now described with reference to the following Examples. These Examples are provided for the purpose of illustration only and the disclosure should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present disclosure and practice the claimed methods. The following working examples therefore, specifically point out the preferred embodiments of the present disclosure, and are not to be construed as limiting in any way the remainder of the disclosure.

The materials and methods employed in these experiments are now described.

Cell lines: The HEK293T cells were maintained in DMEM (Corning) containing 0.11 g/L sodium pyruvate and 4.5 g/L glucose, supplemented with 10% (vol/vol) FBS (Gibco), 100,000 U/L penicillin, 100 mg/L streptomycin (Invitrogen) and 2 mM L-glutamine (Invitrogen). Expi293 cells (Invitrogen) were grown in suspension in Expi293 expression medium (Invitrogen).

DNA constructs: The CMV-S1S3 plasmid was provided by Prof. Stuart Kornfeld at Washington University School of Medicine in St. Louis. Bicistronic vector pLL01 was created in two steps as follows: in the first step, a 486 bp IRES sequence was amplified from the Ptase α/β and γ bicistronic construct (provided by Prof. Stuart Kornfeld) and the S1-S3 gene fragment was obtained from plasmid CMV-S1S3 by PCR. These two fragments were linked together subsequently in the second step by overlap extension PCR to form IRES-S1S3 fragment. The IRES-S1S3 fragment was digested with HpaI and PmeI restriction enzymes (NEB) and ligated into pcDNA3.1(+) vector. To generate pLL11, pLL21, pLL31, pLL41, pLL51 and pLL61 bicistronic plasmids, hGBA, hGAA, mGALC, hNAGLU, hGLA and hLAMAN gene were amplified by their specific primers (Table 1) and inserted into the bicistronic vector (pLL01).

Phosphotransferase Assay: HEK293T or Expi293 cells were harvested and lysed in lysis buffer (25 mM Tris-Cl, pH 7.2, 150 mM NaCl, 1% Triton X-100, and protease inhibitor cocktail). 5 μl of cell extract was incubated in phosphotransferase assay buffer (50 mM Tris-Cl, pH 7.4, 10 mM MgCl2, 10 mM MnCl2, 2 mg/mL BSA, 2 mM ATP) in the presence of 75 mM UDP-GlcNAc, 1 mCi UDP-[3H]GlcNAc, and 100 mM aMM in a final volume of 50 μL for 0.5 hour at 37° C. The reactions were stopped by the addition of 1 mL of 2 mM EDTA, pH 8.0, and the samples were subjected to QAE-Sephadex chromatography.

Enzyme Production: Expi293 cells were transfected with empty vector, bicistronic plasmids or its single expression plasmid. The media was harvested after 2-3 days. For the production of GBA, the conditional medium containing 30 μM of isofagomine during cell culture to stabilize the secreted enzyme was dialyzed in PBS buffer at 4° C. overnight to remove isofagomine for enzyme activity assay.

Enzyme activity assay: The following substrates are used for enzymes activity assay: 4-methylumbelliferyl [3-D-glucopyranoside (GCase/GBA enzyme substrate, M3633, Sigma), 4-methylumbelliferyl α-D-glucopyranoside (GAA enzyme substrate, M9766, Sigma), 6-Hexadecanoylamino-4-methylumbelliferyl [3-D-galactopyranoside (GALC enzyme substrate, EH05989, Carbosynth), 4-methylumbelliferyl-N-acetyl-α-D-glucosaminide (NAGLU enzyme substrate, 474500, Millipore), 4-methylumbelliferyl α-D-galactopyranoside (GLA enzyme substrate, M7633, Sigma), and 4-methylumbelliferyl α-D-mannopyranoside (LAMAN enzyme substrate, M3657, Sigma). GBA enzyme activity was assayed in citrate-phosphate buffer, pH5.0, 0.25% TX-100, 0.25% Na Taurocholate with 1 mM GBA substrate. GAA enzyme activity was carried in citrate buffer, pH4.0, 0.25% TX-100 with 1 mM GAA substrate. GALC enzyme activity was performed in citrate-phosphate buffer, pH4.0, 0.25% TX-100, 0.6% Na Taurocholate, 0.2% Oleic acid with 0.1 mM GALC substrate. NAGLU enzyme activity was assayed in citrate buffer, pH4.0, 0.25% TX-100 with 1 mM NAGLU substrate. GLA enzyme activity was assayed in citrate buffer, pH4.5, 0.25% TX-100 with 1 mM GLA substrate. LAMAN enzyme activity was assayed in citrate buffer, pH4.0, 0.25% TX-100 with 1 mM LAMAN substrate.

CI-MPR binding assay: CI-MPR binding was performed in high binding 96 well plate (Costar 3601). The plate was immobilized with 50 μl purified bovine CI-MPR at 10 μg/ml at room temperature (RT) for 1 hour and blocked by 2% BSA at RT for another 1 hour. Aliquots of conditional media from transfected Expi293 cells were diluted with Hepes buffer (40 mM Hepes, pH6.8, 150 mM NaCl, 0.05% Tween-20) and incubated with the immobilized CI-MPR at RT for 1 hour to bind the phosphorylated lysosomal enzymes. After three times wash, the lysosomal enzyme activity was assayed by 4-Methylumbelliferone method.

Example 1: Generation of an Empty Bicistronic Vector Containing Phosphotransferase (S1-S3) for Lysosomal Enzyme Expression The GlcNAc-1-phosphotransferase (GlcNAc-1-PTase, also referred to as Ptase), which is an α2β2γ2 hexamer encoded by two genes (GNPTAB and GNPTG), is involved in the generation of phosphorylated oligosaccharide that is required for lysosomal targeting via the cation-independent mannose 6-phosphate receptor (CI-MPR). The phosphorylation of expressed lysosomal enzymes significantly increases by co-transfection with an engineered truncated Ptase (S1-S3). This study utilizes a S1-S3 construct for the production of phosphorylated lysosomal enzymes for the treatment of lysosomal storage diseases (LSD, such as but not limited to Gaucher disease, Pompe disease, and α-Mannosidosis).

To produce highly phosphorylated therapeutic lysosomal enzymes for enzyme replacement therapy (ERT), a therapeutic lysosomal enzyme and S1-S3 is co-expressed simultaneously in the same cells. Since the S1-S3 and lysosomal enzyme are expressed in different vectors, in order to produce highly phosphorylated therapeutic lysosomal enzyme, a stable cell line with expression of lysosomal enzyme and S1-S3 are generated by two steps: (a) create a stable cell line expressing Ptase S1-S3; (b) based on the S1-S3 stable cell line, generate a second cell line which add the expression of therapeutic lysosomal enzyme into it. To avoid this two-step and time-consuming procedure, disclosed herein is a bicistronic vector by introducing an Internal Ribosome Entry Site (IRES), which is able to express two separate genes under a single promoter.

Bicistronic expression may also be applied gene therapy for lysosomal storage diseases (LSD). An empty bicistronic vector—pLL01 containing a 486 bp IRES sequence and S1-S3 gene under cytomegalovirus (CMV) promoter in pcDNA3.1(+) plasmid vector (FIG. 1B). The bicistronic vector pLL01 has three unique restriction enzyme cleavage sites in the multi-cloning sites which are located in front of IRES sequence and allowed to insert therapeutic lysosomal enzyme gene. To examine the expression of S1-S3 using the bicistronic vector pLL01, HEK293 cells were transfected with equivalent amount plasmid of pcDNA3.1(+), CMV-S1S3 (FIG. 1A) or pLL01. 48 hour later, cells were harvested and lysed in lysis buffer (25 mM Tris buffer, pH7.4, 150 mM NaCl, 1% TX-100 with protease inhibitor cocktail). Phosphotransferase activity analysis of whole cell extracts expressing pcDNA3.1(+), CMV-S1S3 or pLL01 was performed to determine the expression of S1-S3. As shown in FIG. 1C, comparing to sample CMV-S1S3, the phosphotransferase activity in pcDNA3.1(+) sample is negligible, but the bicistronic vector pLL01 maintains 9.3% activity.

Example 2: Bicistronic Expression Enhances Phosphorylation of Therapeutic Lysosomal Enzymes Since the expression of S1-S3 in the bicistronic vector was low (9.3%) (see Example 1), this study was designed to determine whether the low S1-S3 activity would be enough to phosphorylate lysosomal enzymes. Six different lysosomal enzymes were tested in the present bicistronic vector. The enzymes were as follow: acid β-Glucosidase (GBA), acid α-Glucosidase (GAA), Galactosylceramidase (GALC), α-N-acetylglucosaminidase (NAGLU), α-Galactosidase (GLA) and acid α-mannosidase (LAMAN).

Figures 2A, 2B, 2C:
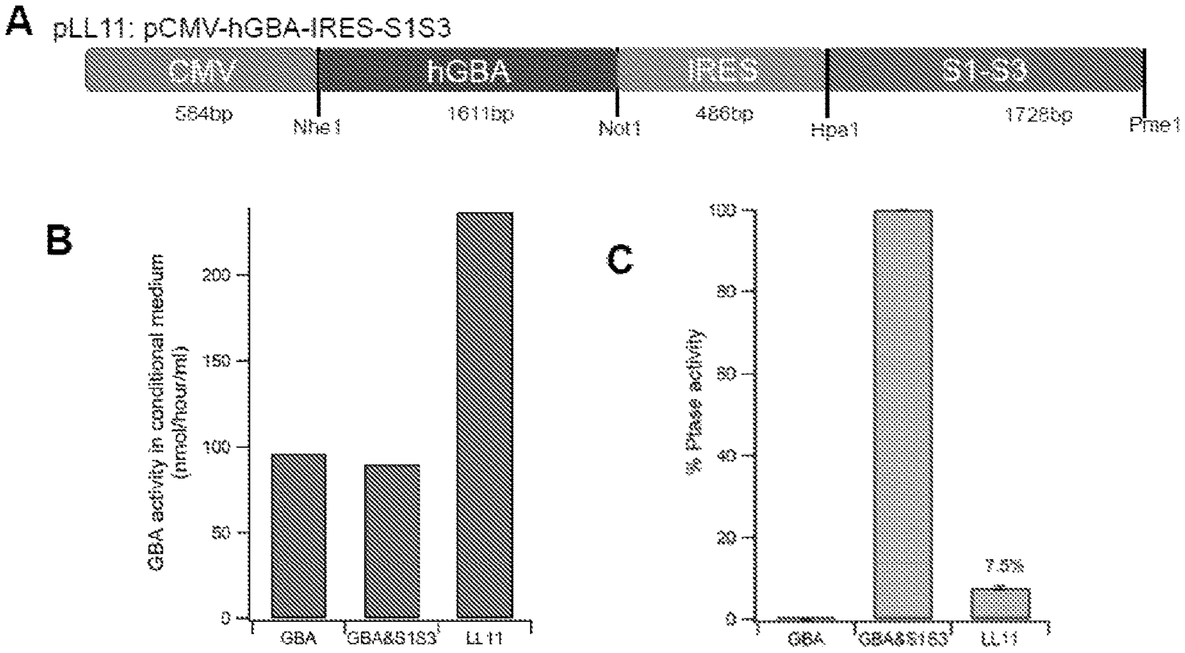
FIGS. 2A-2C are series of a diagram and histogram depicting the generation of GBA biscistronic expression plasmid in S1-S3 biscistronic vector.

Acid β-Glucosidase (GBA): GBA is a lysosomal enzyme which degrades its substrate glycocerebroside in lysosome. The deficiency of GBA in lysosome causes Gaucher disease which is the most common lysosomal storage disease (LSD). To test the phosphorylation of GBA in the presently disclosed bicistronic vector, GBA bicistronic plasmid—pLL11 was generated by inserting a 1611 bp human GBA cDNA sequence with a stop codon into the bicistronic empty vector—pLL01 through NheI and NotI restriction sites (FIG. 2A). The same amount of pLL11 and GBA plasmid with or without CMV-S1S3 plasmid were transfected into Expi293 cells. 48 hours later, the cells and conditional medium were harvested separately. Surprisingly, the GBA activity in the pLL11 conditional medium is 240 nmol/hour/ml which is more than 2 times higher than the medium prepared by GBA alone (96 nmol/hour/ml) or GBA and S1-S3 co-transfection (90 nmol/hour/ml, FIG. 2B). In addition to the GBA expression, the S1-S3 expression was quantified by phosphotransferase assay using cell extract. Similar to the bicistronic vector pLL01 lacking GBA, pLL11 sample has 7.5% phosphotransferase expression, comparing to the co-transfection sample of GBA&S1-53 (FIG. 2C).

Figures 3A, 3B, 3C:
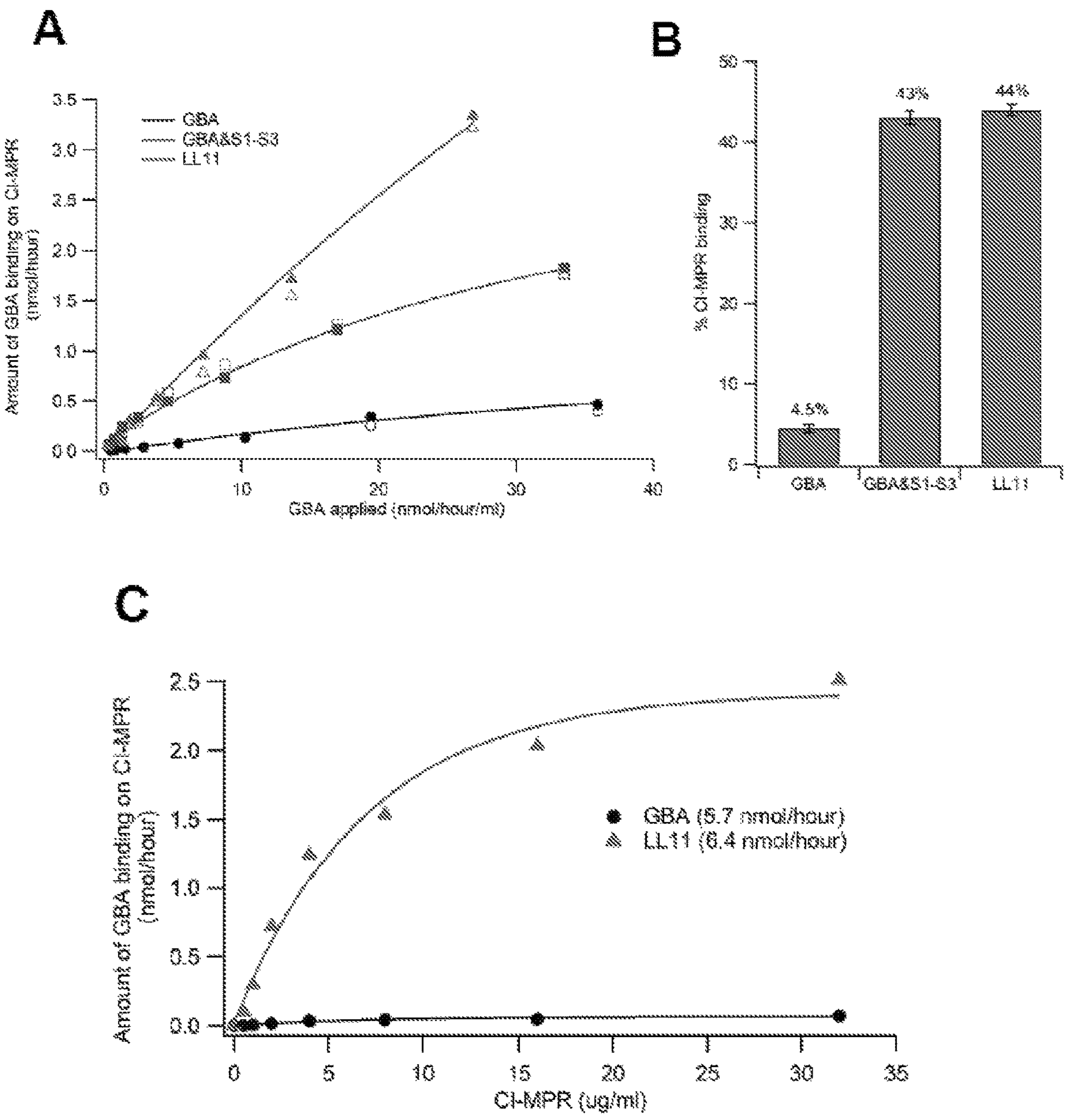
FIGS. 3A-3C are series of graphs and a histogram showing that bicistronic expression increases the phosphorylation of GBA enzyme.

Since the S1-S3 expression was decreased in the bicistronic vector, the consequence of the low phosphotransferase expression on the phosphorylation of GBA was determined. For this purpose, the conditional medium of pLL11, GBA alone and GBA co-transfected with S1-S3 were harvested and the degree of phosphorylation was quantitated by performing cation-independent mannose 6-phospohate receptor (CI-MPR) binding experiment. The GBA produced in the presently disclosed bicistronic vector has even higher binding to CI-MPR in the plateau phase (FIG. 3A). Nevertheless, when the percentage of receptor binding was calculated by using the linear range points, 44% of GBA generated in the disclosed bicistronic vector were bound to the CI-MPR which is the same as the GBA produced by co-transfection with S1-S3 (43%) and is ten times higher than the GBA produced by endogenous phosphotransferase (4.5%, FIG. 3B).

Titration have been widely used in the art to determine the concentration of an identified analyte. The concentration of CI-MPR in the binding experiment was titrated. Serial diluted CI-MPR was immobilized in 96 well plate, and similar amount of GBA enzyme which was produced by the presently disclosed bicistronic vector or endogenous phosphatase (Ptase) was added into the plate for receptor binding assay. As shown in FIG. 3C, the binding of GBA from the pLL11 sample was dependent on the concentration of CI-MPR, and it saturated when the receptor concentration reached 15 μg/ml, while the binding of GBA produced by endogenous Ptase stays in the low level. The present data indicated that the disclosed bicistronic vector greatly elevates the phosphorylation level of GBA enzyme.

Figures 4A, 4B, 4C, 4D:
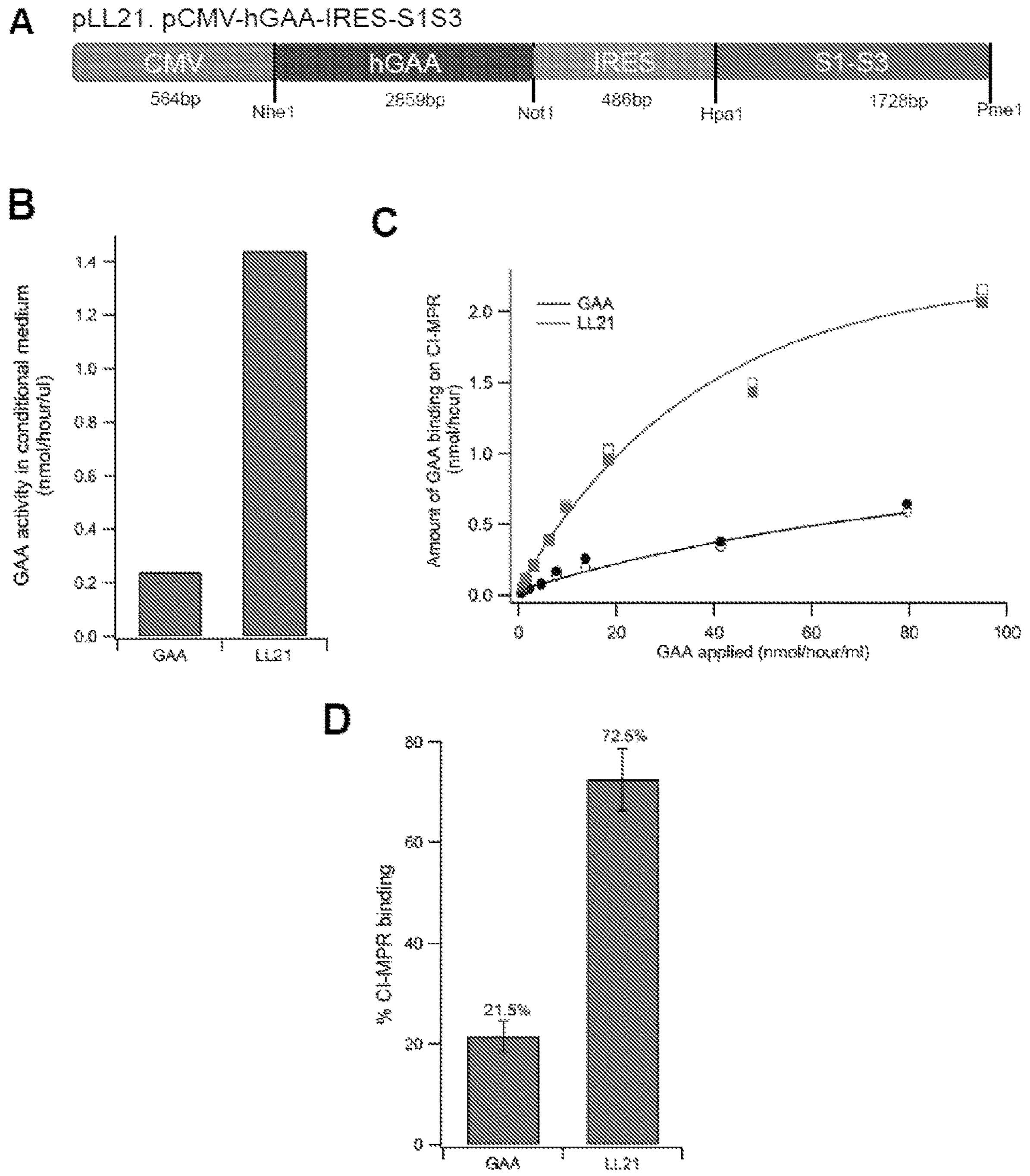
FIGS. 4A-4D are series of a diagram, a graph and histograms showing that bicistronic expression increases the phosphorylation of GAA enzyme.

Acid α-Glucosidase (GAA): Lysosomal enzyme GAA is essential for the degradation of glycogen to glucose in lysosome. Mutation in GAA gene is associated with a lysosomal storage disorder—Pompe disease. In order to create GAA bicistronic plasmid—pLL21, a 2859 base pair (bp) human GAA gene fragment containing stop codon was amplified and inserted into bicistronic vector pLL01 after digestion by restriction enzymes NheI and NotI (FIG. 4A). Sequence verified pLL21 and GAA plasmids were transfected in Expi293 cells. 48 hours later, conditional medium was collected for GAA activity and CI-MPR binding experiments. Similar to GBA, the GAA activity in pLL21 conditional medium was higher than GAA single expression (FIG. 4B). The binding of pLL21 conditional medium was faster and higher than GAA single conditional medium (FIG. 4C). During 1 hour incubation time, 72.5% of GAA from pLL21 conditional medium binds to CI-MPR, but the CI-MPR binding of GAA from GAA single expression is only 21.5% (FIG. 4D). These data suggested that the presently disclosed bicistronic expression platform can greatly increase the phosphorylation of GAA enzyme.

Figures 5A, 5B, 5C, 5D:
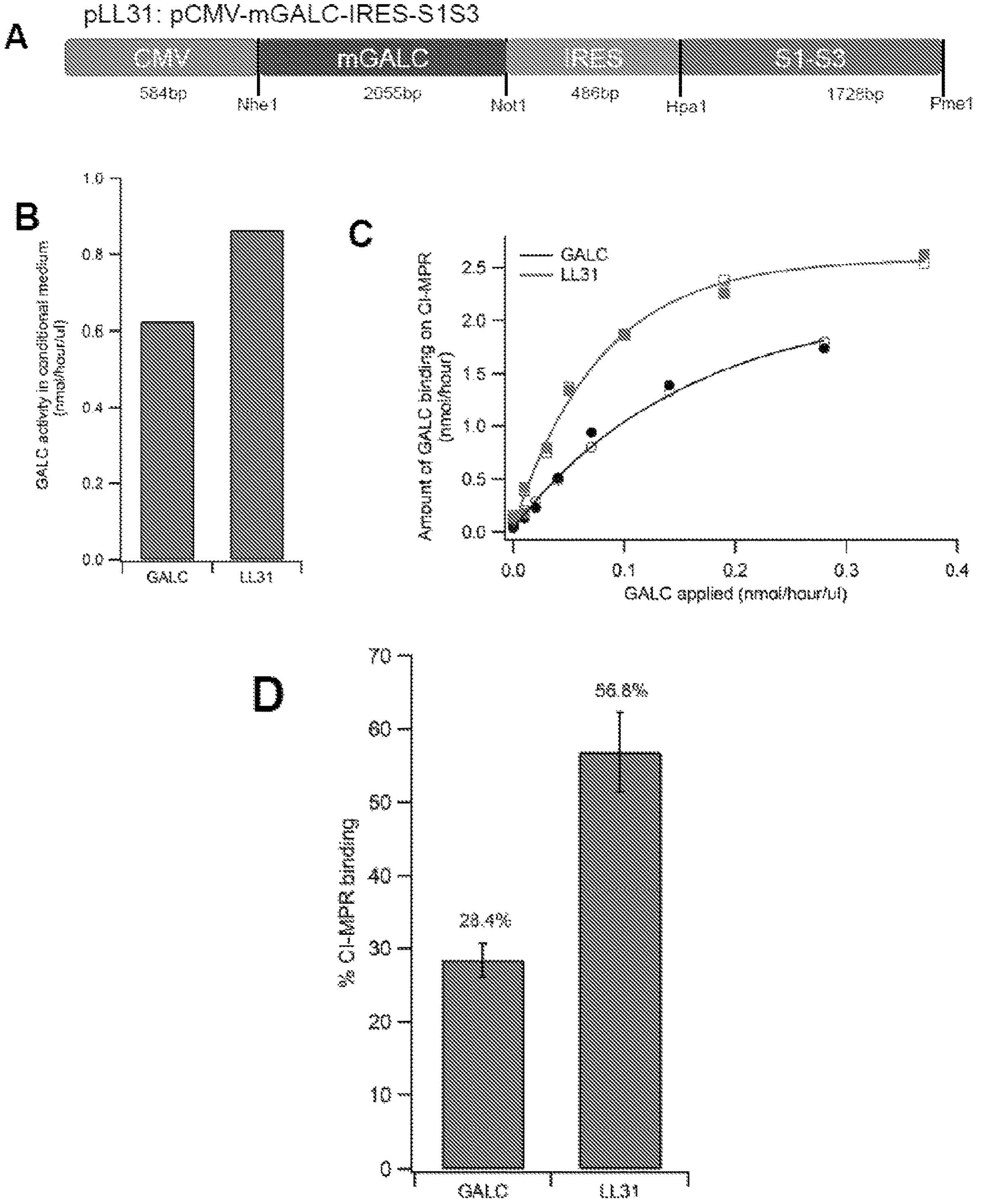
FIGS. 5A-5D are series of a diagram, a graph and histograms showing that bicistronic expression increases the phosphorylation of GALC enzyme.
Figures 6A, 6B, 6C, 6D:
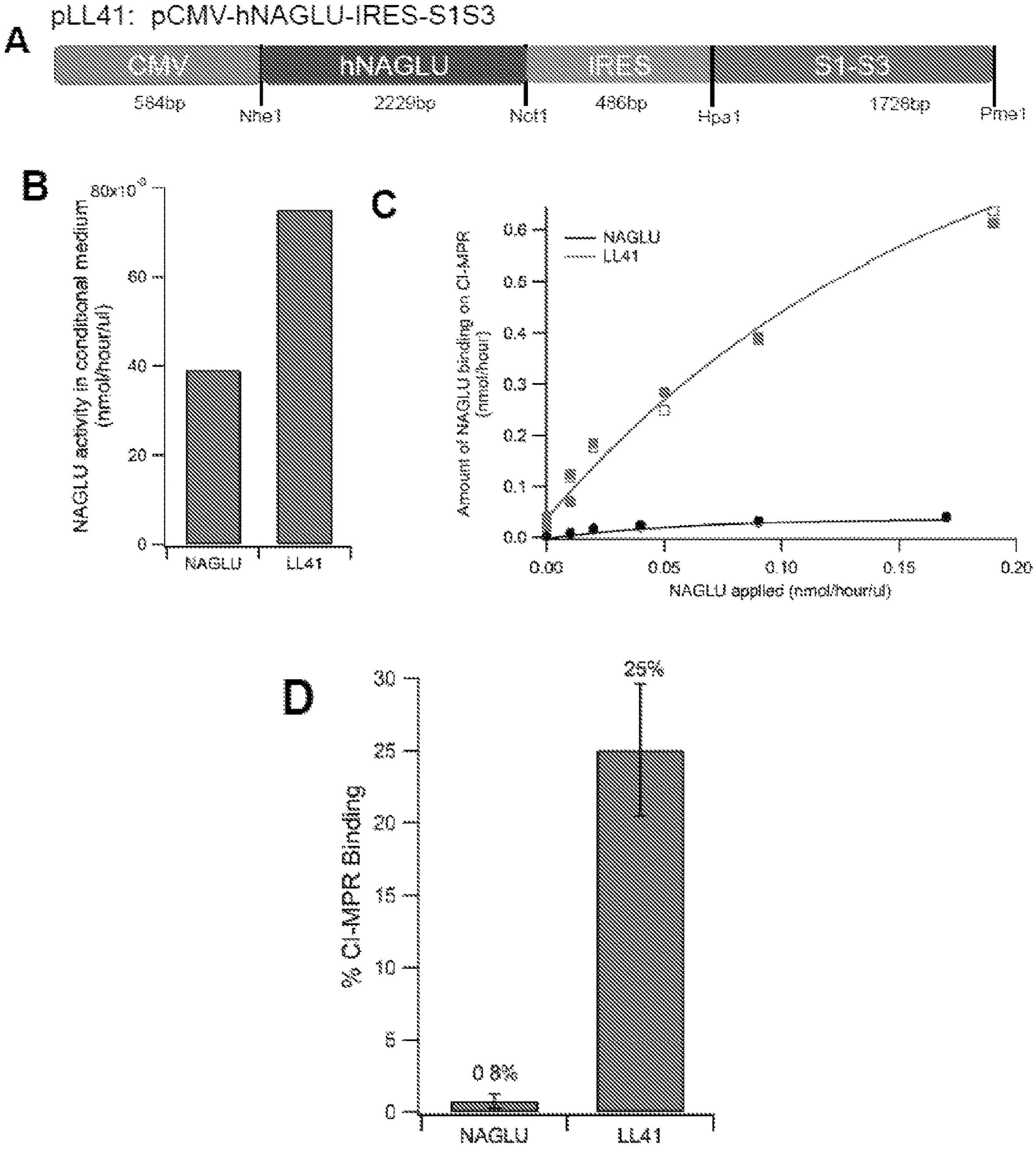
FIGS. 6A-6D are series of a diagram, a graph and histograms showing that bicistronic expression increases the phosphorylation of NAGLU enzyme.
Figures 7A, 7B, 7C, 7D:
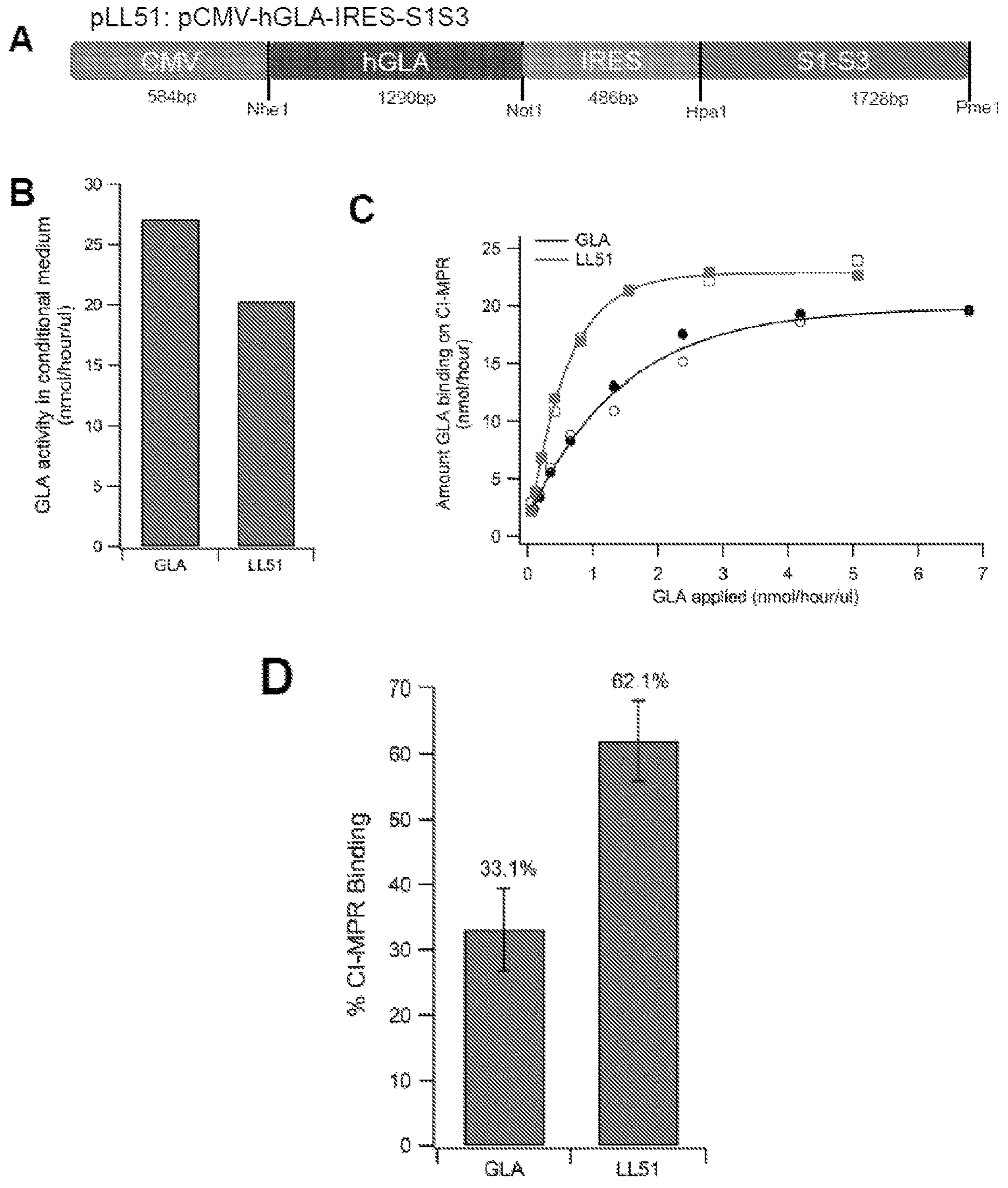
FIGS. 7A-7D are series of a diagram, a graph and histograms showing that bicistronic expression increases the phosphorylation of GLA enzyme.
Figures 8A, 8B, 8C, 8D:
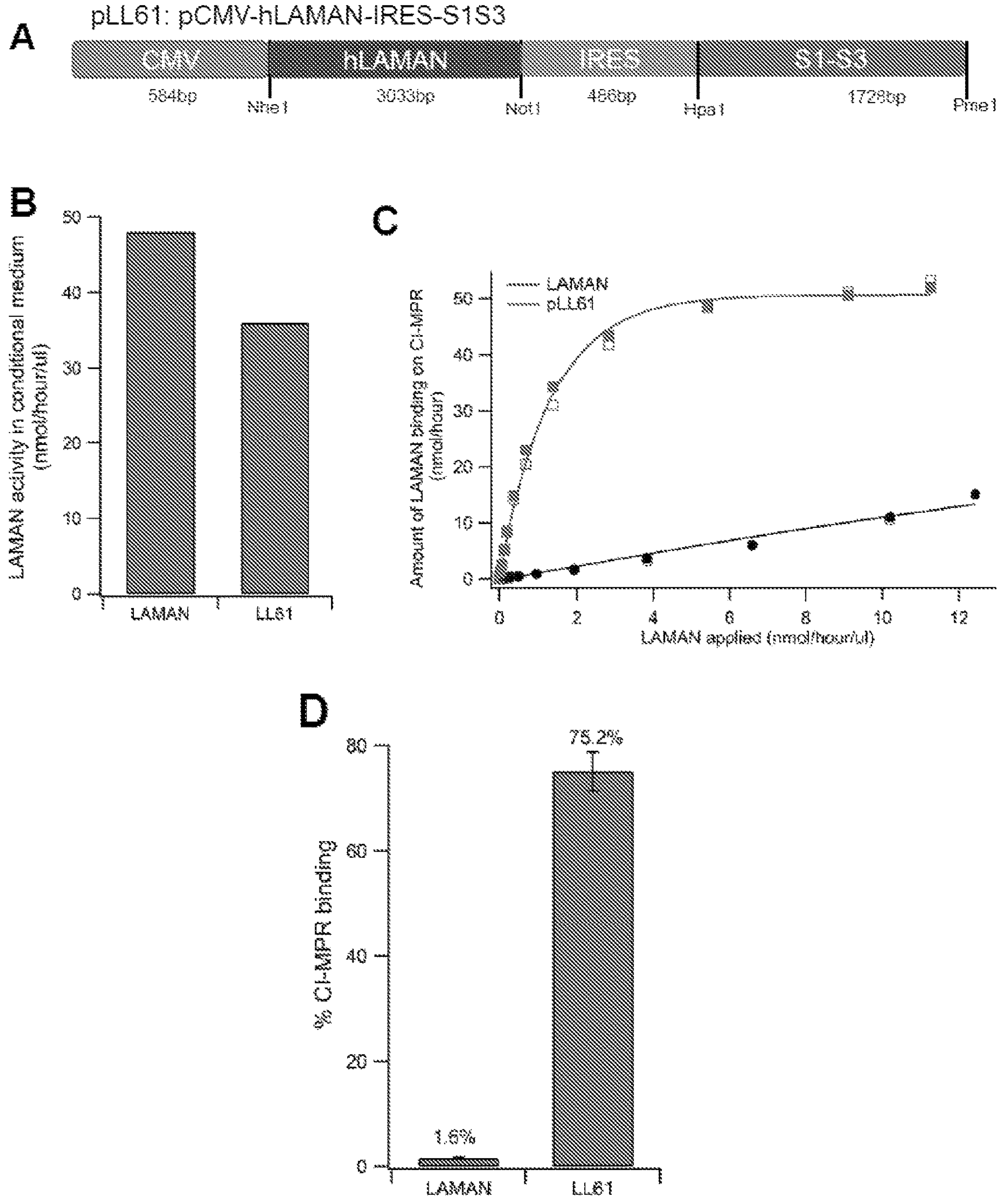
FIGS. 8A-8D are series of a diagram, a graph and histograms showing that bicistronic expression increases the phosphorylation of LAMAN enzyme.
Figures 9A, 9B, 9C, 9D, 9E:
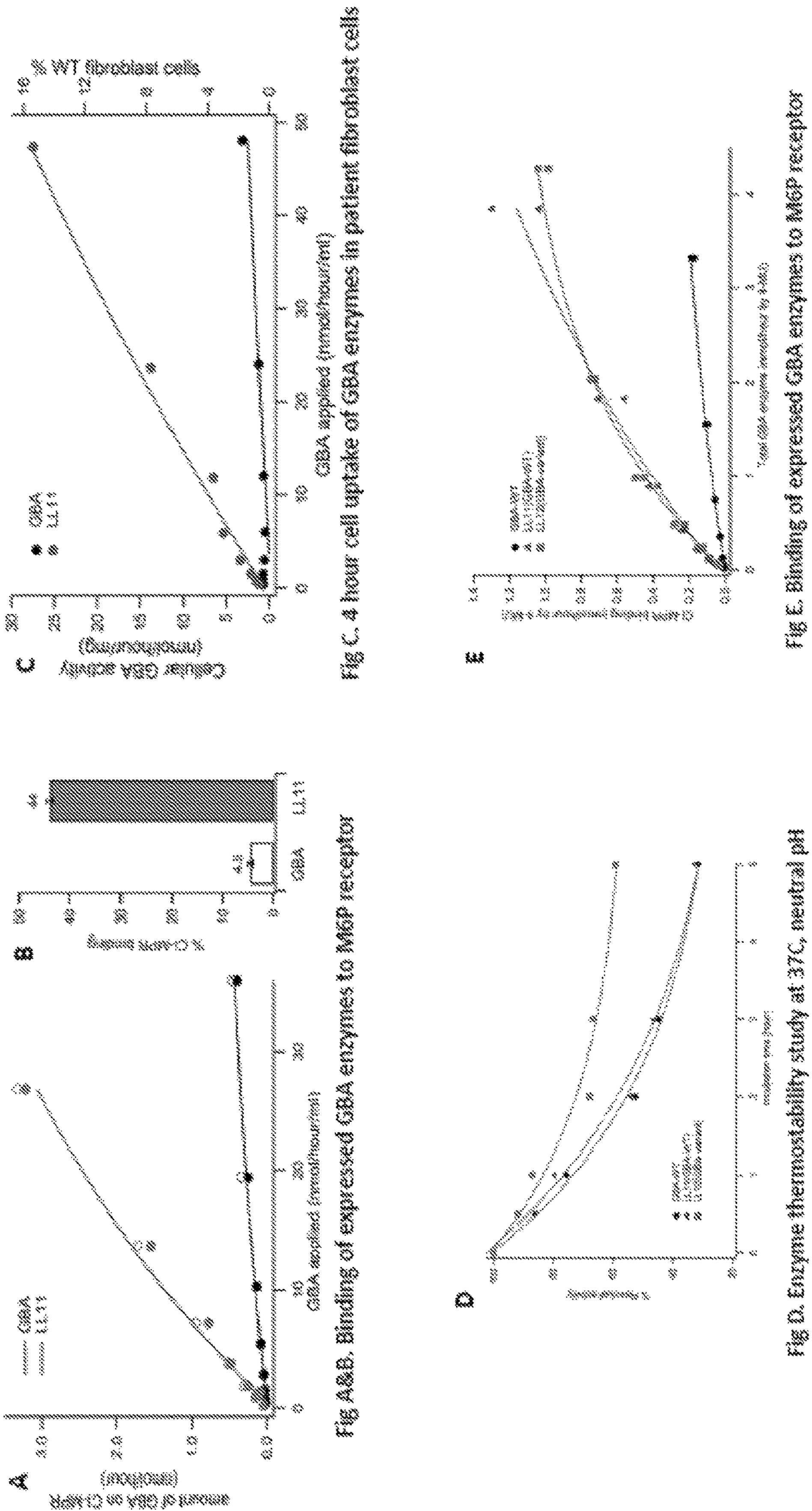
FIGS. 9A-9E are series of graphs demonstrating that an S1-S3 PTase bicistronic vector of the disclosure significantly increases the CI-MPR binding of GBA enzyme and its cell uptake in the treatment of Gaucher disease (A-C). Panels D and E demonstrate that a single point mutation in the GBA enzyme increases its stability but does not affect its binding toward CI-MPR.
Figures 10A, 10B, 10C:
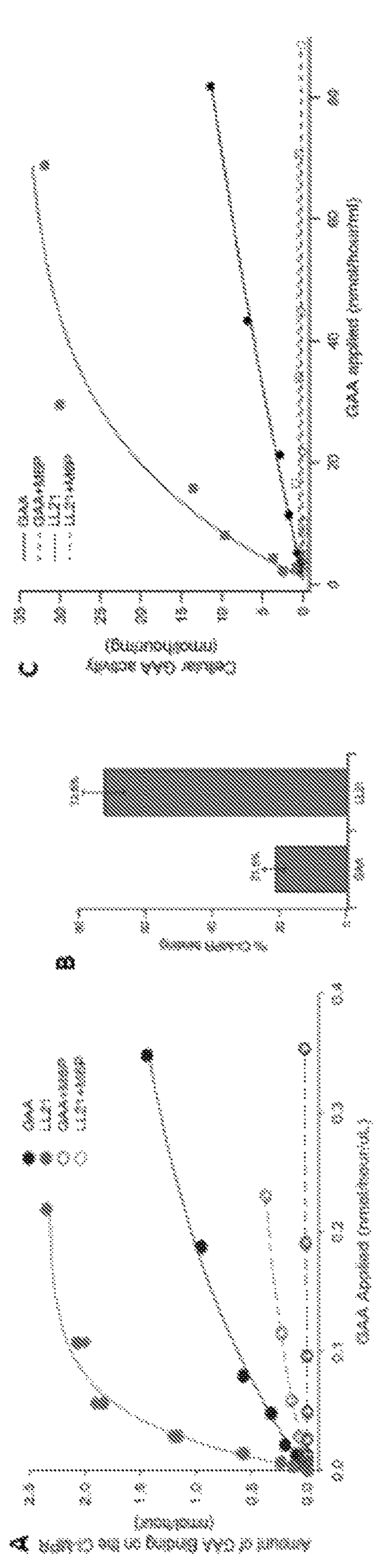
FIGS. 10A-10C are series of graphs demonstrating that an S1-S3 PTase bicistronic vector of the disclosure significantly increases the CI-MPR binding of GAA enzyme and its cell uptake in the treatment of Pompe Disease.
Figures 11A, 11B, 11C:
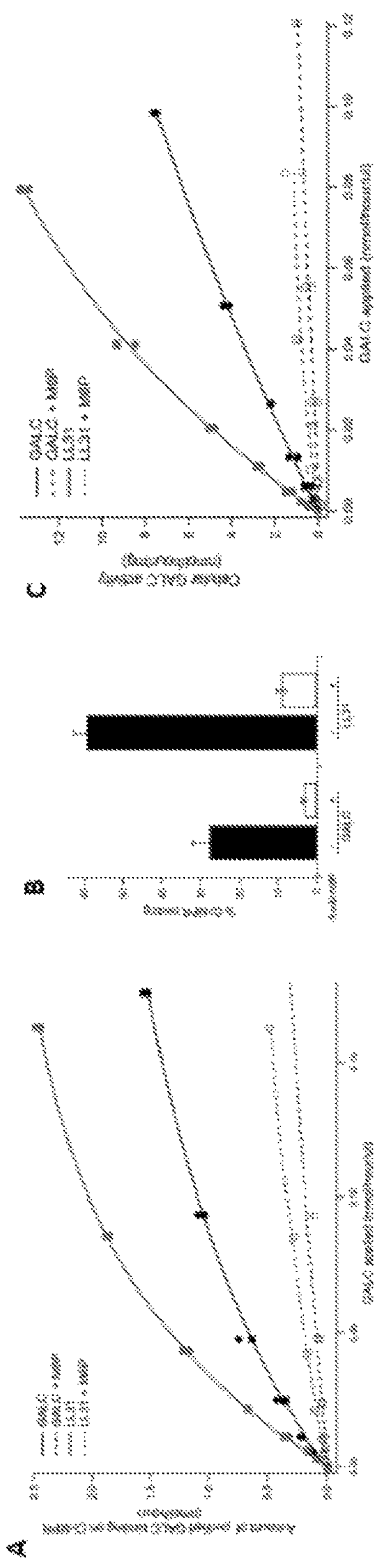
FIGS. 11A-11C are series of graphs demonstrating that an S1-S3 PTase bicistronic vector of the disclosure significantly increases the CI-MPR binding of GALC enzyme and its cell uptake in the treatment of Krabbe Disease.
Figures 12A, 12B, 12C:
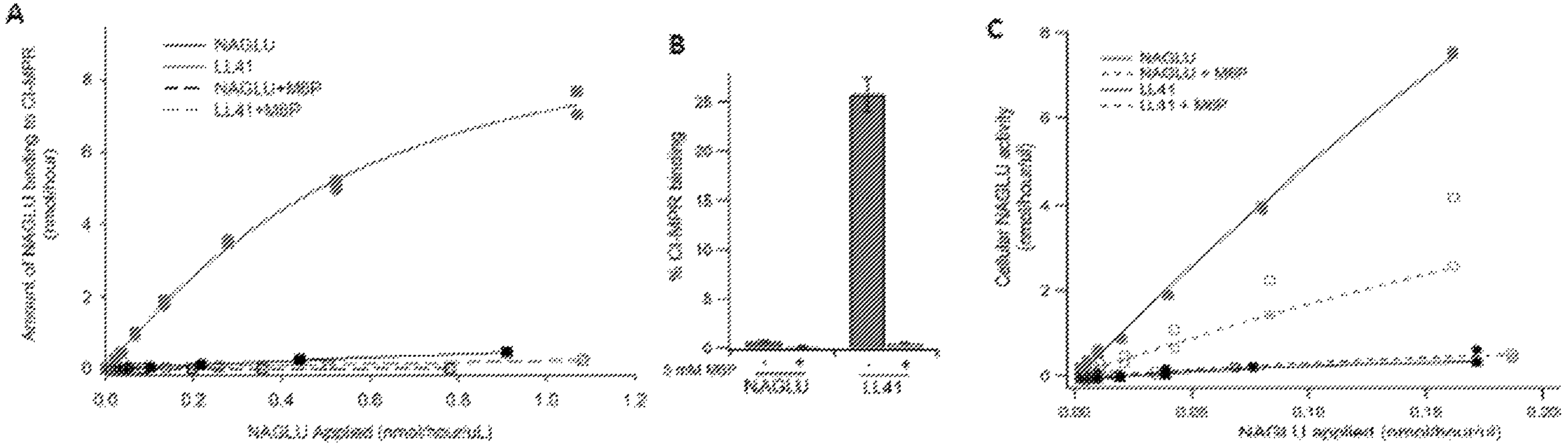
FIGS. 12A-12C are series of graphs demonstrating that an S1-S3 PTase bicistronic vector of the disclosure significantly increases the CI-MPR binding of NAGLU enzyme and its cell uptake in the treatment of MPS IIIB Disease.
Figures 13A, 13B, 13C:
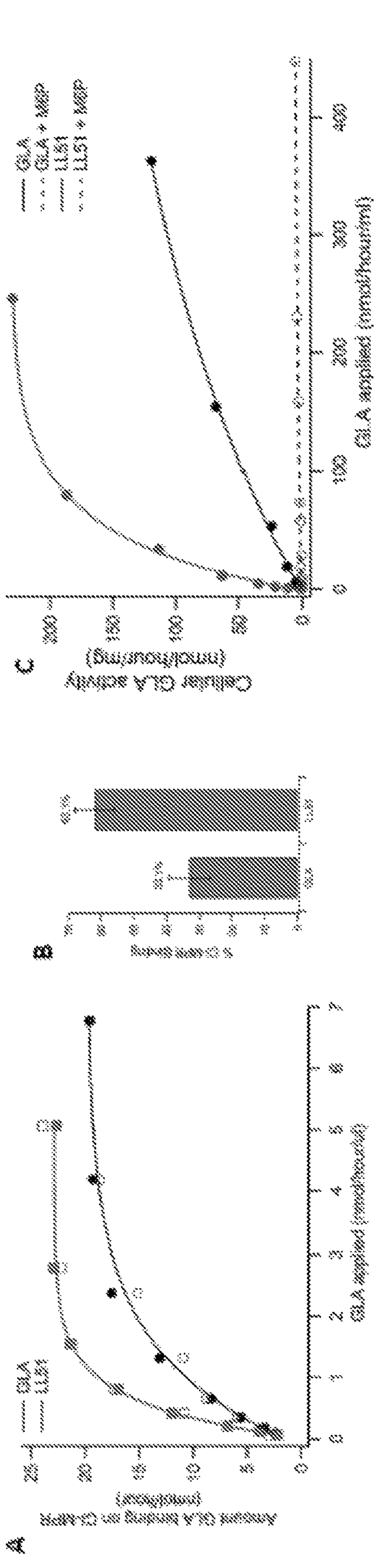
FIGS. 13A-13C are series of graphs demonstrating that an S1-S3 PTase bicistronic vector of the disclosure significantly increases the CI-MPR binding of GLA enzyme and its cell uptake in the treatment of Fabry Disease.
Figures 14A, 14B, 14C:
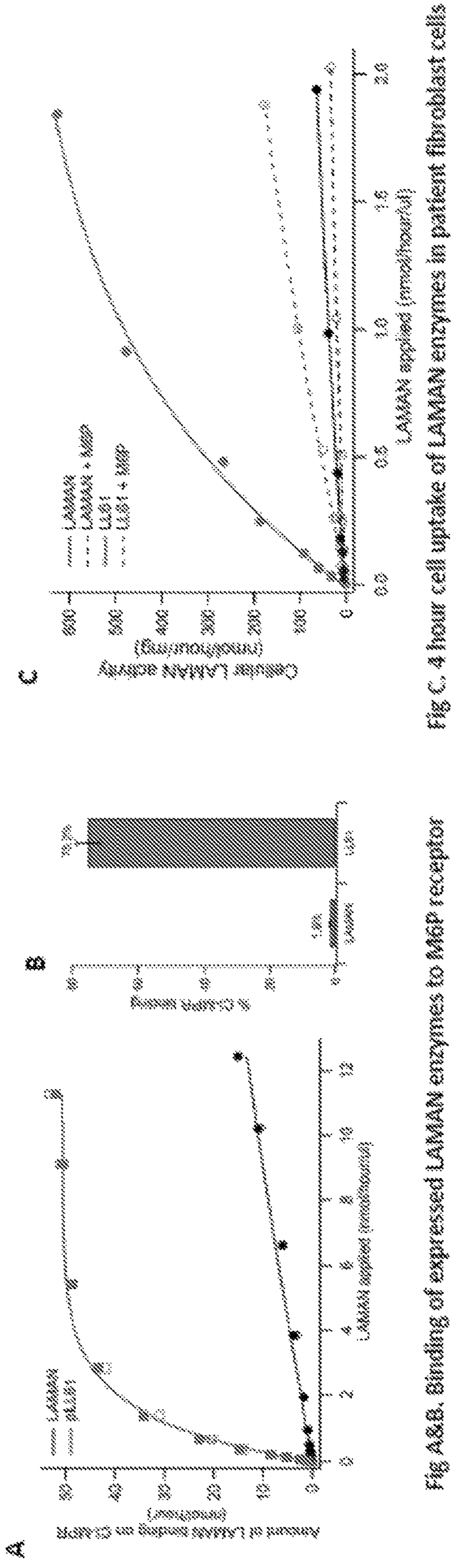
FIGS. 14A-14C are series of graphs demonstrating that an S1-S3 PTase bicistronic vector of the disclosure significantly increases the CI-MPR binding of LAMAN enzyme and its cell uptake in the treatment of α-Mannosidosis.
Figures 15A, 15B:
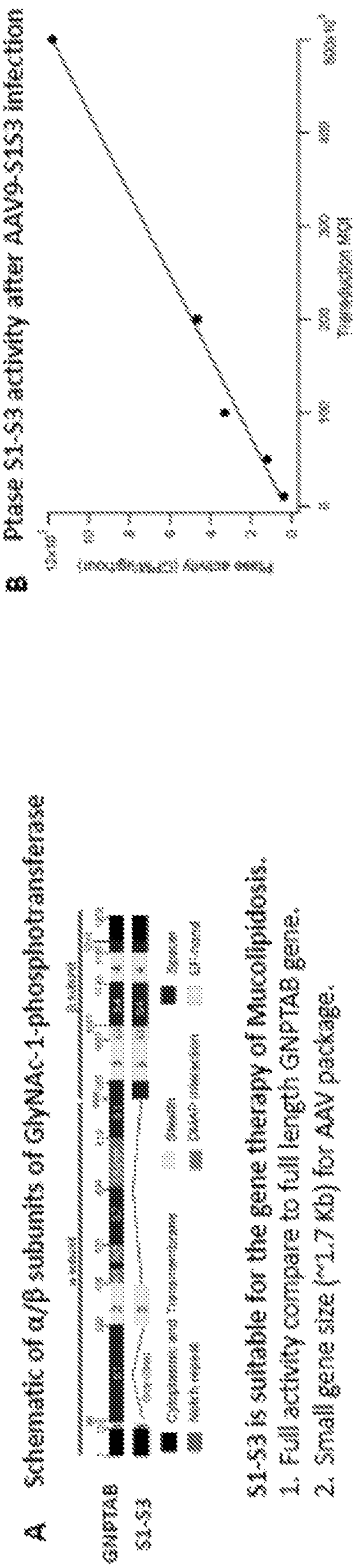
FIGS. 15A-15B are a schematic diagram and a graph demonstrating that an S1-S3 PTase bicistronic vector of the disclosure delivered by AAV9 vector may be used as a gene therapy in the treatment of Mucolipidosis Disease.

Galactosylceramidase (GALC): In lysosome, GALC enzyme is responsible for the catabolism of galactosylceramide by removing galactose from ceramide derivatives. Genetic deficiency of GALC enzyme is responsible for Krabbe disease. To test GALC enzyme in the presently disclosed bicistronic expression, bicistronic plasmid pLL31 was generated by inserting a mouse GALC gene into vector pLL01 (FIG. 5A). The GALC enzyme activity in pLL31 conditional medium which was harvested in pLL31 transfected Expi293 cells is similar to GALC alone medium (0.86 nmol/μl/h vs 0.62 nmol/μl/h, FIG. 5B). CI-MPR receptor binding results showed that the bicistronic expression of GALC with S1-S3 increases its CI-MPR binding from 28.4% to 56.8% (FIGS. 5C&D).

α-N-acetylglucosaminidase (NAGLU): NAGLU gene encodes an enzyme that degrades heparin sulfate in lysosome. Defect in the NAGLU enzyme results in Sanfilippo syndrome type B, also known as Mucopolysaccharidosis (MPS) IIIB. When the NAGLU enzyme produced in cell line for ERT does not have any phosphate in the mannose residues. And the clinical trials for its ERT failed early this year. To express NAGLU in the presently disclosed bicistronic vector, the same procedure as described above was used. A 2229 bp human NAGLU gene was inserted into pLL01 bicistronic vector (FIG. 6A), and the NAGLU bicistronic plasmid-pLL41 and NAGLU single expression plasmid were transfected into Expi293 cells. By using the conditional medium, the NAGLU activity in sample pLL41 was shown to be higher than NAGLU single expression sample (FIG. 6B). In term of CI-MPR binding, hardly any NAGLU binding was detected from NAGLU single expression sample, even though we put a high amount enzyme (up to 9 nmol/hour, FIGS. 6C-6D). However, the NAGLU produced by the bicistronic vector binds to CI-MPR up to 25% (FIGS. 6C-6D).

α-Galactosidase (GLA): Lysosomal enzyme GLA hydrolyzes melibiose into galactose and glucose and is able to metabolize globotriaosylceramide (GL-3). A deficiency of GLA enzyme activity causes an X-linker disorder—Fabry disease. To make GLA bicistronic plasmid—pLL51, human GLA gene fragment and bicistronic vector pLL01 were digested with BamHI and NotI, and ligated by T4 ligase (FIG. 7A). Correct pLL51 clone and GLA single plasmid are transfected and expressed in Expi293 cells. GLA activity assay and CI-MPR binding experiments are carried by using their conditional mediums. As shown in FIG. 7B, the GLA activity in either GLA alone or pLL51 conditional medium are similar. The titration curves using these two mediums suggest pLL51 sample binds to CI-MPR more and faster than GLA sample (FIG. 7C). The overall binding percentage for pLL51 sample is 62.1%, which is almost double of GLA sample (33.1%, FIG. 7D).

acid α-mannosidase (LAMAN): The genetic disease α-Mannosidosis is caused by defect in the Lysosomal enzyme LAMAN which is encoded by the MAN2B1 gene. Since the human LAMAN enzyme is barely phosphorylated, hLAMAN is a good candidate for the disclosed bicistronic expression. 3033 bp human LAMAN gene was inserted into pLL01 bicistronic vector (FIG. 8A) and expressed in Expi293 cells for later study. The LAMAN activity in LAMAN bicistronic plasmid pLL61 conditional medium is slightly lower than LAMAN single expression (FIG. 8B). When their binding to CI-MPR was titrated, LAMAN enzyme binding to CI-MPR was hardly detected by using LAMAN single expression sample, but a large amount of LAMAN enzyme from pLL61 sample was found to interact with CI-MPR (FIG. 8C). The binding of LAMAN to CI-MPR increase from 1.6% to 75.2% with S1-S3 bicistronic expression (FIG. 8D).

The above six enzymes can be categorized into two groups based on their basal phosphorylation levels. Group one is low phosphorylation lysosomal enzymes (GBA, NAGLU and LAMAN) which are poor substrates for wild-type Ptase during enzyme production. The second group is high phosphorylation enzymes (GAA, GALC and GLA). The enzymes are considered as good substrates for wild-type Ptase and received a fair amount of phosphate. The presently disclosed bicistronic expression of S1-S3 was shown to significantly increase the phosphorylation of six lysosomal enzymes, independent of their basal phosphorylation level. In view of these findings, the bicistronic vector pLL01 disclosed herein can be used to product highly phosphorylated lysosomal enzymes to treat all lysosomal storage diseases. Clearly, the presently disclosed bicistronic vector greatly benefits ERT and gene therapy for the treatment of lysosomal storage disorders.

Example 3: Treatment of Gaucher Disease

Enzyme Replacement Therapy (ERT)

An expression vector comprising a sequence encoding GBA and a sequence encoding a S1-S3 Ptase may be used to treat or prevent a sign or symptom of Gaucher Disease. The following studies demonstrate that expression of (GCase/GBA)-S1-S3 in the art-recognized standard mouse model of Gaucher Disease leads to expression of the (GCase/GBA)-S1-S3, transportation of the v-S1-S3 into cells from the circulating blood stream and an increased activity of v in cells taking up the v-S1-S3 complex. A small increase in (GCase/GBA) activity resulting from the expression and uptake of the GBA-S1-S3 complex leads to a significant functional recovery of function in the mouse model.

The expression of GBA utilizing the bicistronic expression vector with S1-S3 PTase, generates a recombinant protein with higher levels of phosphorylated oligosaccharides that can be used to treat or prevent a sign or symptom of Gaucher Disease. The following studies demonstrate that ERT using recombinant protein expressed using the bicistronic vector with S1-S3 PTase in the art-recognized standard mouse model of Gaucher Disease leads to a longer half-life, greater uptake by tissue, greater substrate reduction and better correction of tissue pathology compared to the current standard of care.

Figure 16A:
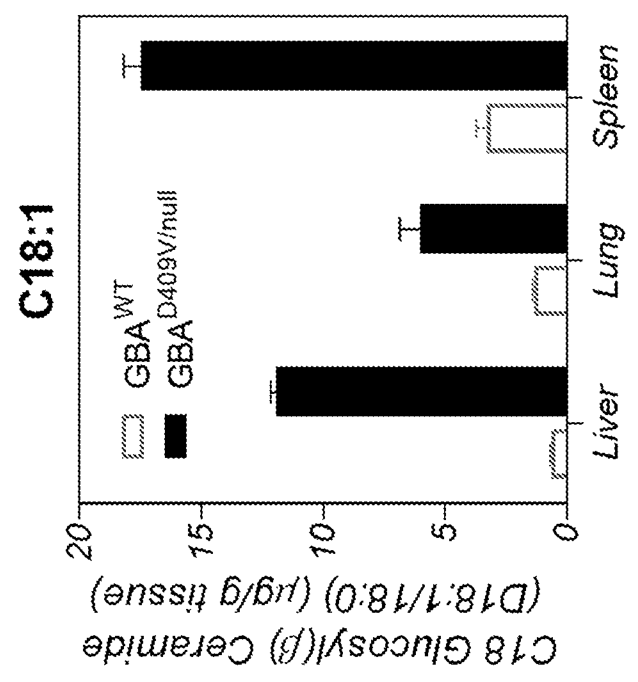
FIGS. 16A-16B are a pair of graphs depicting elevated glucosylceramide levels observed in the liver, lung and spleen of 20 week old Gaucher$^{D409V/null}$ mice. The accumulation of GBA's natural substrate, glucocerebroside was determined in tissue homogenates. The accumulation of GC in the lung is a statistically and therapeutically valuable result, which is a known unmet need of the current standard of care. 20 aliquots of tissue homogenates and appropriate controls were glucocylceramides were extracted by adding 200 μL of Methanol/ACN/H2O (v:v:v=85:10:5), a mixing for 5 min at 800 rpm followed by centrifuging for 15 min at 3220 g 4° C.; 3). 50 μL of supernatant was recovered, dried with nitrogen and resuspended with Methanol/ACN/H2O (v:v:v=85:10:5) and directly injected for LC-MS/MS analysis.
Figure 16B:
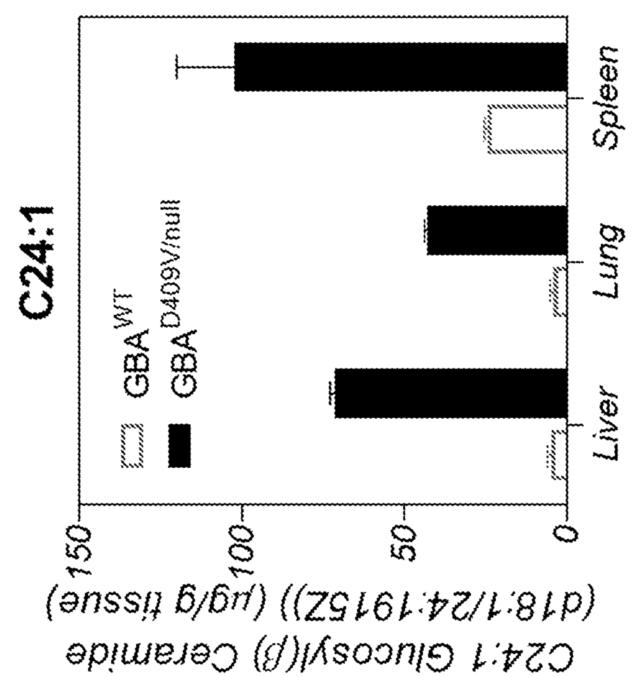

FIGS. 16A-16B are a pair of graphs depicting elevated glucosylceramide levels observed in the liver, lung and spleen of 20 week old Gaucher$^{D409V/null}$ mice. The accumulation of GBA's natural substrate, glucocerebroside was determined in tissue homogenates. The accumulation of GC in the lung is a statistically and therapeutically valuable result, which is a known unmet need of the current standard of care. 20 μL aliquots of tissue homogenates and appropriate controls were glucocylceramides were extracted by adding 200 μL of Methanol/ACN/H2O (v:v:v=85:10:5), a mixing for 5 min at 800 rpm followed by centrifuging for 15 min at 3220 g 4° C.; 3). 50 μL of supernatant was recovered, dried with nitrogen and resuspended with Methanol/ACN/H2O (v:v:v=85:10:5) and directly injected for LC-MS/MS analysis.

Figures 17A, 17B, 17C:
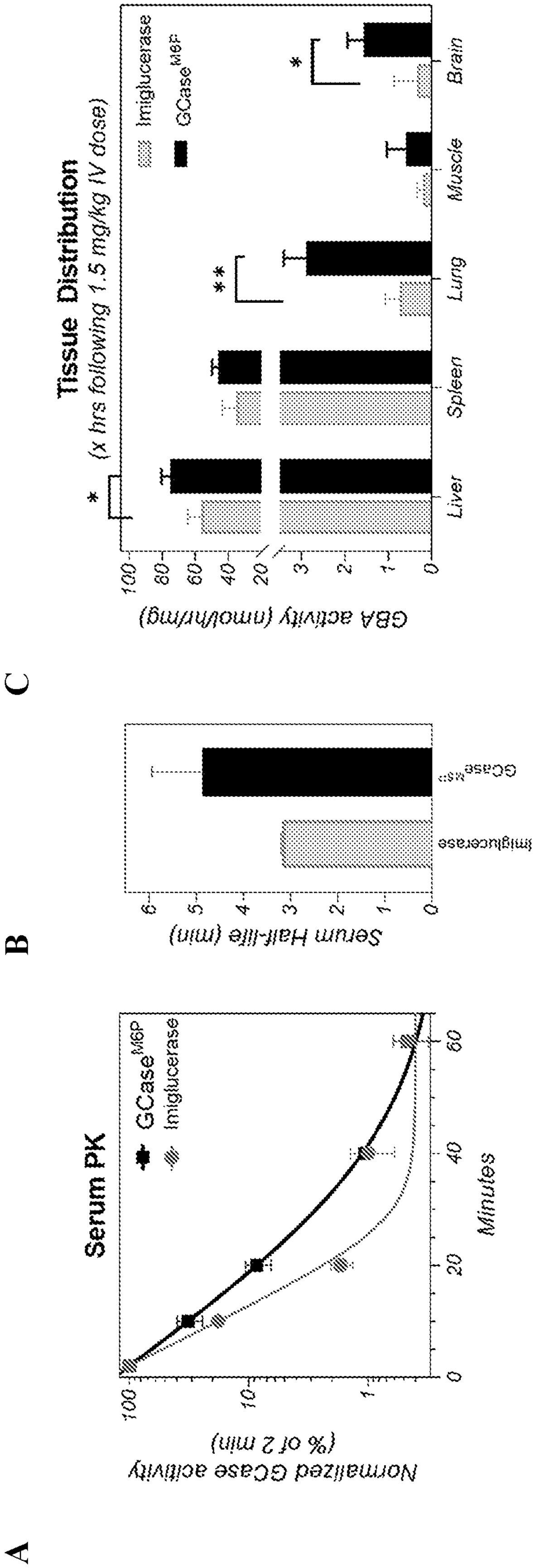
FIGS. 17A-17C are a series of graphs demonstrating that GCase$^{M6P}$ has a longer half-life and greater tissue uptake in the GBA$^{D409V/null}$ mouse model compared to imiglucerase. A PK/PD study in the Gaucher D409V/Null mouse model was performed using the standard of care, imiglucerase, and purified GBA produced by transiently co-expressed utilizing the bicistronic vector that encoded for the S1-S3 PTase and a natural variant of GBA in Expi293 cells. This variant of GCase has greater stability at neutral and slightly alkali conditions. Briefly, 3 animals received a tail vein injection of ~1.5 mg/kg of recombinant GCase. For the serum pharmacokinetic data, plasma samples were collected at 2, 10, 20, 40 and 60 mins. Activity measured using a synthetic substrate, 4-methylumbelliferyl-beta-D-glucopyranoside (4MU-Glc). The activity was normalized in the individual animals by setting the 2 min time point as 100% activity and subsequent time points are a percent of the t=2 min time point. The stabilized GCase expressed in the presence of S1-S3 PTase appears to have a longer half-life. This longer half-life is a combination of the enzyme having greater stability and the different clearance pathways. To determine how much GCase was taken up by the tissue, 2 hrs after enzyme injection, tissue was recovered, homogenized and activity measured using the 4MU-Glc substrate. The activity was normalized to total protein in the homogenate as determined by the BCA method for protein determination. The true advantage of a stabile GCases with appropriate phosphorylation is observed in the tissue uptake data shown. For all tissues evaluated there is more activity found in the stabilized GCase expressed utilizing the bicistronic S1-S3 PTase vector platform S1'S3 PTase. This is most dramatic in the lung, muscle and brain where imiglucerase has little activity. When the tissue and sera data is taken together, the advantage of a more stable GCase with greater N-linked oligosaccharide phosphorylation is apparent for delivering more enzyme to affected tissue. This is the first time that a significant amount of GCase has been delivered to the lung, muscle and heart at these doses.
Figures 18A, 18B, 18C:
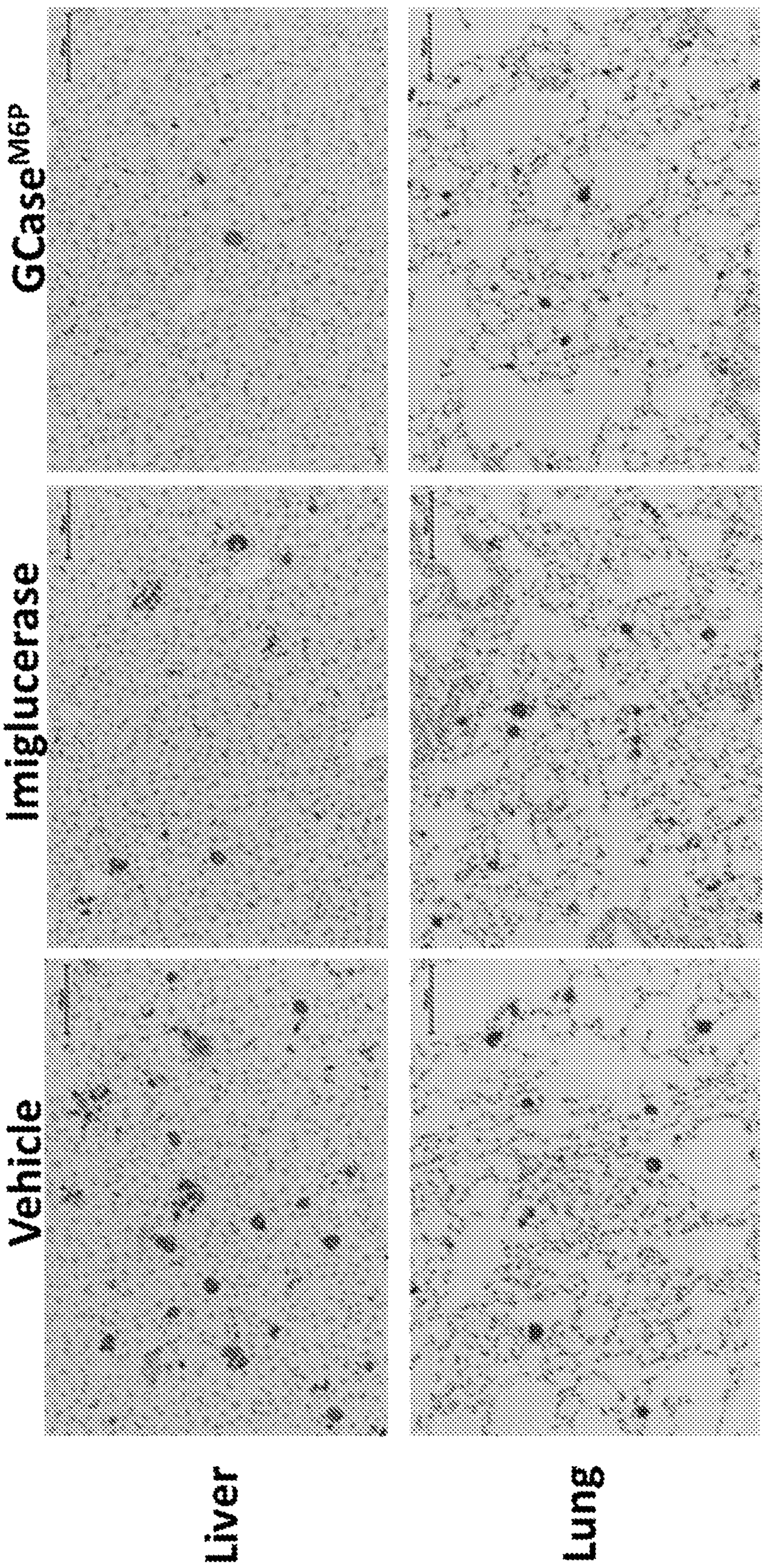
FIGS. 18A-18E are a series of photographs and bar graphs demonstrating that GCase$^{M6P}$ ERT reduced tissue macrophages (anti-CD68 staining) better than imiglucerase in the GBA$^{D409V/null}$ mouse model. An efficacy study in the D409V Gaucher mouse model was performed using the standard of care, Cerezyme, and purified GBA (M0111) transiently co-expressed in Expi293 cells utilizing the bicistronic vector that encodes for the S1S3 PTase and a natural variant of GBA with reported greater stability at neutral and slightly alkali conditions. ~20 weeks old Gaucher mice were treated with ~1.5 mg/kg) enzymes weekly for four weeks. Four weeks later, the tissue of Liver and Lung was harvested and fixed in 4% paraformaldehyde-PBS, pH 7.4 for immunohistochemistry with CD68 antibody. M0111 has greater efficacy compared to the current standard of care as evidenced by the reduction of macrophage in affected tissue as visualized by CD68 Ab.
Figures 18D, 18E:
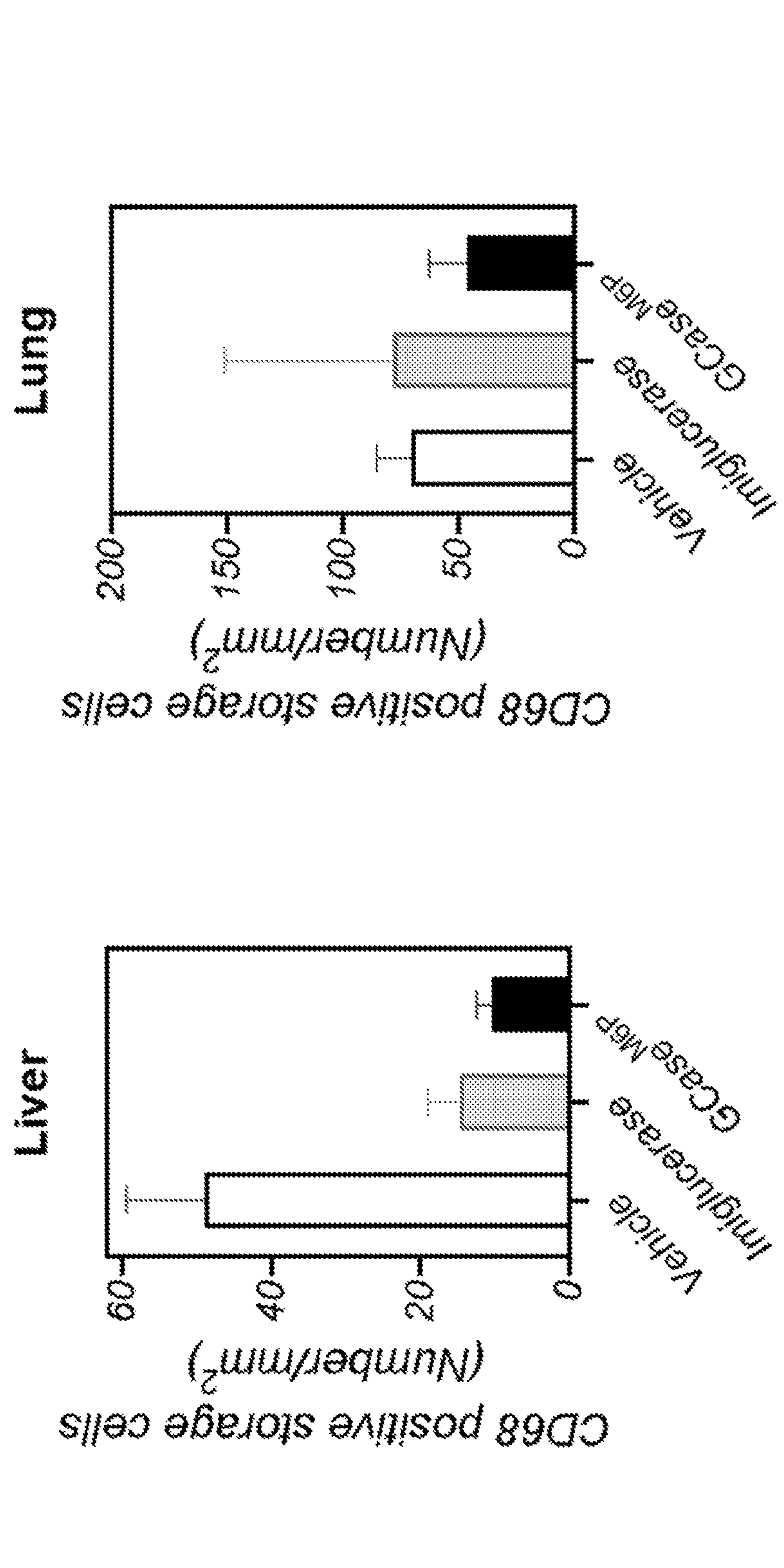

FIGS. 17A-17C are a series of graphs demonstrating that GCase$^{M6P}$ has a longer half-life and greater tissue uptake in the GBA$^{D409V/null}$ mouse model compared to imiglucerase. A PK/PD study in the Gaucher D409V/Null mouse model was performed using the standard of care, imiglucerase, and purified GBA produced by transiently co-expressed utilizing the bicistronic vector that encoded for the S1-S3 PTase and a natural variant of GBA in Expi293 cells. This variant of GCase has greater stability at neutral and slightly alkali conditions. Briefly, 3 animals received a tail vein injection of ~1.5 mg/kg of recombinant GCase. For the serum pharmacokinetic data, plasma samples were collected at 2, 10, 20, 40 and 60 mins. Activity measured using a synthetic substrate, 4-methylumbelliferyl-beta-D-glucopyranoside (4MU-Glc). The activity was normalized in the individual animals by setting the 2 min time point as 100% activity and subsequent time points are a percent of the t=2 min time point. The stabilized GCase expressed in the presence of S1-S3 PTase appears to have a longer half-life. This longer half-life is a combination of the enzyme having greater stability and the different clearance pathways. To determine how much GCase was taken up by the tissue, 2 hrs after enzyme injection, tissue was recovered, homogenized and activity measured using the 4MU-Glc substrate. The activity was normalized to total protein in the homogenate as determined by the BCA method for protein determination. The true advantage of a stabile GCases with appropriate phosphorylation is observed in the tissue uptake data shown. For all tissues evaluated there is more activity found in the stabilized GCase expressed utilizing the bicistronic S1-S3 PTase vector platform S1'S3 PTase. This is most dramatic in the lung, muscle and brain where imiglucerase has little activity. When the tissue and sera data is taken together, the advantage of a more stable GCase with greater N-linked oligosaccharide phosphorylation is apparent for delivering more enzyme to affected tissue. This is the first time that a significant amount of GCase has been delivered to the lung, muscle and heart at these doses.

FIGS. 18A-18E are a series of photographs and bar graphs demonstrating that GCase$^{M6P}$ ERT reduced tissue macrophages (anti-CD68 staining) better than imiglucerase in the GBA$^{D409V/null}$ mouse model. An efficacy study in the D409V Gaucher mouse model was performed using the standard of care, Cerezyme, and purified GBA (M0111) transiently co-expressed in Expi293 cells utilizing the bicistronic vector that encodes for the S1S3 PTase and a natural variant of GBA with reported greater stability at neutral and slightly alkali conditions. —20 weeks old Gaucher mice were treated with ~1.5 mg/kg) enzymes weekly for four weeks. Four weeks later, the tissue of Liver and Lung was harvested and fixed in 4% paraformaldehyde-PBS, pH 7.4 for immunohistochemistry with CD68 antibody. M0111 has greater efficacy compared to the current standard of care as evidenced by the reduction of macrophage in affected tissue as visualized by CD68 Ab.

Figures 19A, 19B, 19C:
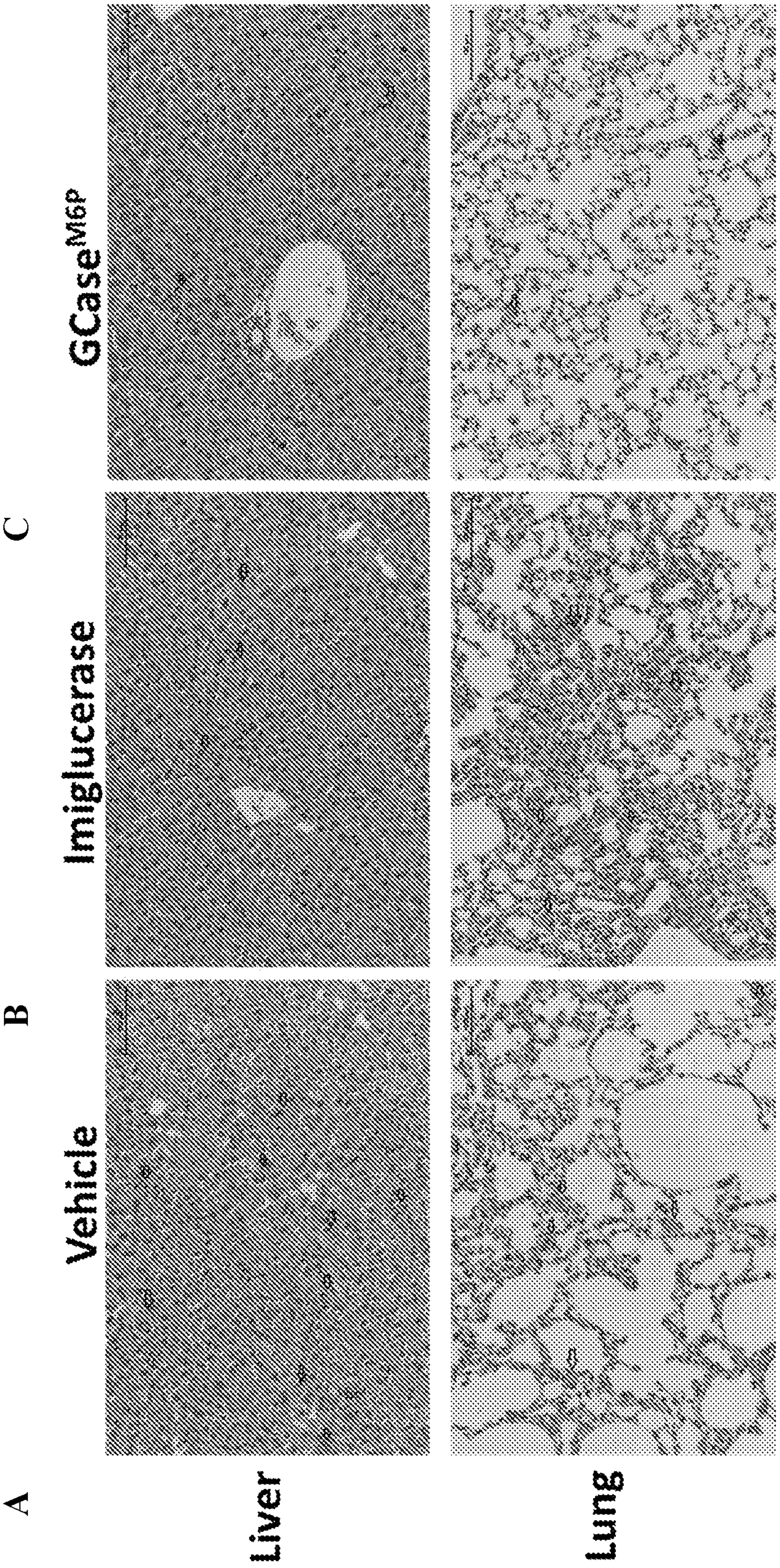
FIGS. 19A-19C are a series of photographs demonstrating that GCase$^{M6P}$ ERT reduced the number and size of Gaucher storage cells (Hematoxylin and Eosin (H&E) staining) better than imiglucerase in the GBA$^{D409V/null}$ mouse model. An efficacy study in the D409A Gaucher mouse model was performed using the standard of care, Cerezyme, and purified GBA transiently co-expressed in Expi293 cells utilizing the bicistronic vector that encoded for the S1-S3 PTase and a natural variant of GBA with reported greater stability at neutral and slightly alkali conditions. ~20 weeks old Gaucher mice were treated with ~1.5 mg/kg enzymes weekly for four weeks. Four weeks later, the tissue of Liver and Lung was harvested and fixed in 4% paraformaldehyde-PBS, pH 7.4 for formalin for hematoxylin and eosin (H&E) staining. GCase$^{M6P}$ has greater efficacy compared to the current standard of care as evidenced by the reduction of storage cells in affected tissue as visualized by H&E staining.

FIGS. 19A-19C are a series of photographs demonstrating that GCase$^{M6P}$ ERT reduced the number and size of Gaucher storage cells (Hematoxylin and Eosin (H&E) staining) better than imiglucerase in the GBA$^{D409V/null}$ mouse model. An efficacy study in the D409A Gaucher mouse model was performed using the standard of care, Cerezyme, and purified GBA transiently co-expressed in Expi293 cells utilizing the bicistronic vector that encoded for the S1-S3 PTase and a natural variant of GBA with reported greater stability at neutral and slightly alkali conditions. —20 weeks old Gaucher mice were treated with ~1.5 mg/kg enzymes weekly for four weeks. Four weeks later, the tissue of Liver and Lung was harvested and fixed in 4% paraformaldehyde-PBS, pH 7.4 for formalin for hematoxylin and eosin (H&E) staining. GCase$^{M6P}$ has greater efficacy compared to the current standard of care as evidenced by the reduction of storage cells in affected tissue as visualized by H&E staining.

Figures 20A, 20B:
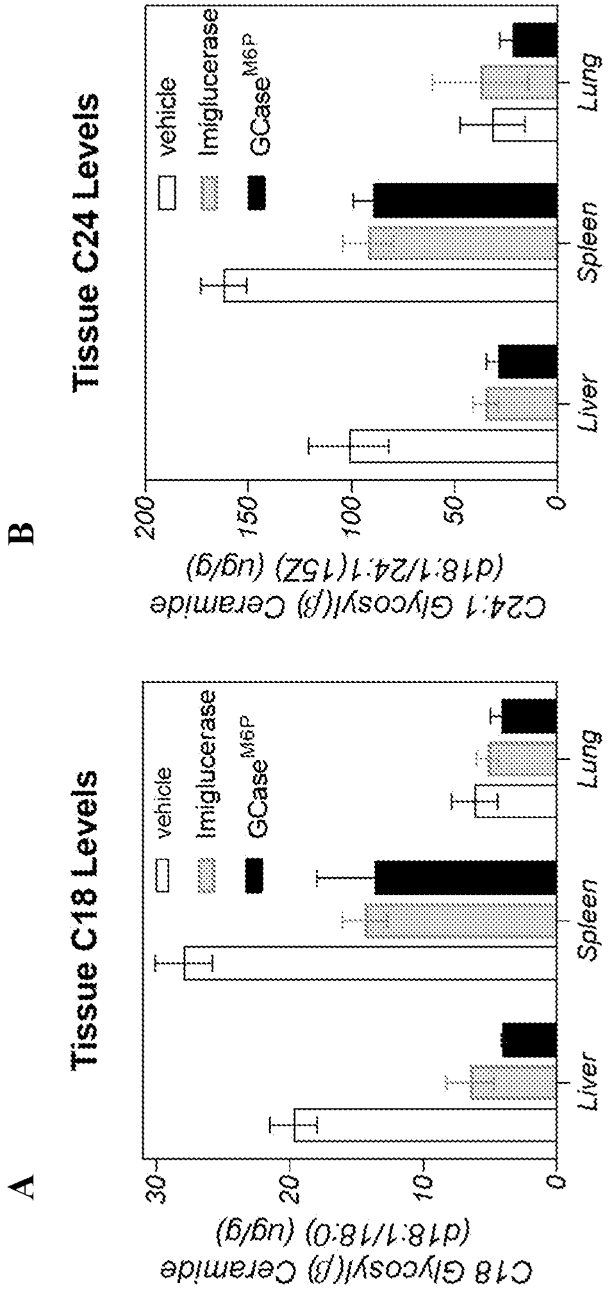
FIGS. 20A-20B are a pair of graphs demonstrating that GCase$^{M6P}$ ERT reduced accumulated substrate better than imiglucerase in the GBA$^{D409V/null}$ mouse model. ~20 weeks old Gaucher mice were treated weekly with ~1.5 mg/kg enzymes for four weeks. Tissue samples were collected and homogenized for glycosylceramide analysis. The accumulation of GCase's natural substrate, glucocerebroside was determined in tissue homogenates. Of significant value is the accumulation of GC in the lung which is a known unmet need for the current standard of care. 20 μL aliquots of tissue homogenates and appropriate controls were glucocylceramides were extracted by adding 200 μL of Methanol/ACN/H2O (v:v:v=85:10:5), mixing for 5 min at 800 rpm followed by centrifuging for 15 min at 3220 g 4° C.; 3). 50 μL of supernatant was recovered, dried with nitrogen and resuspended with Methanol/ACN/H2O (v:v:v=85:10:5) and directly injected for LC-MS/MS analysis. For the two ceramides measured, GCase$^{M6P}$ treated animals had lower levels following ERT therapy over the imiglucerase.
Figures 21A, 21B, 21C, 21D:
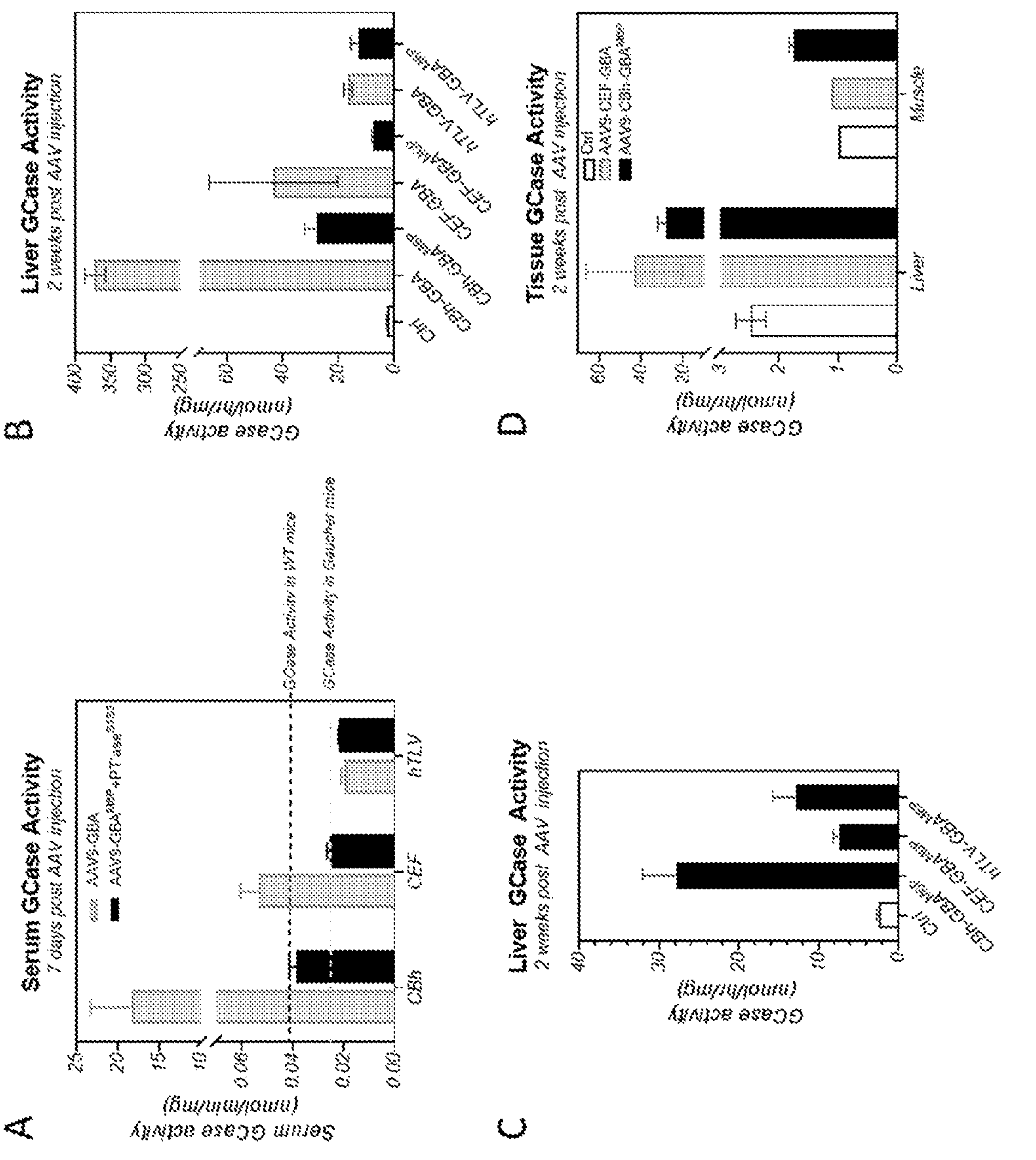
FIGS. 21A-21D are a series of graphs showing the results of in vivo AAV mediate gene therapy studies for the treatment of Gaucher Disease. To determine the effect of AAV9 gene therapy with the bicistronic expression transgene of stable GBA+S1-S3 PTase with three different promotors. 15 wk old GBA$^{D409V/null}$ mice were dosed with a moderate dose of AAV9-stable GBA+S1-S3 PTase, 5E11 vg. To determine how much GBA was generated by the tissue, 2 weeks later after AAV9 injection, tissue was recovered, homogenized and activity measured using the 4MU-Glc substrate. The activity was normalized to total protein in the homogenate as determined by the BCA method for protein determination.

FIGS. 20A-20B are a pair of graphs demonstrating that GCase$^{M6P}$ ERT reduced accumulated substrate better than imiglucerase in the GBA$^{D409V/null}$ mouse model. ~20 weeks old Gaucher mice were treated weekly with ~1.5 mg/kg enzymes for four weeks. Tissue samples were collected and homogenized for glycosylceramide analysis. The accumulation of GCase's natural substrate, glucocerebroside was determined in tissue homogenates. Of significant value is the accumulation of GC in the lung which is a known unmet need for the current standard of care. 20 μL aliquots of tissue homogenates and appropriate controls were glucocylceramides were extracted by adding 200 μL of Methanol/ACN/H2O (v:v:v=85:10:5), mixing for 5 min at 800 rpm followed by centrifuging for 15 min at 3220 g 4° C.; 3). 50 μL of supernatant was recovered, dried with nitrogen and resuspended with Methanol/ACN/H2O (v:v:v=85:10:5) and directly injected for LC-MS/MS analysis. For the two ceramides measured, GCase$^{M6P}$ treated animals had lower levels following ERT therapy over the imiglucerase.

Gene Therapy

An delivery vector with a bicistronic vector comprising a sequence encoding GBA and a sequence encoding the S1-S3 PTase may be used to treat or prevent a sign or symptom of Gaucher Disease. In some embodiments, the delivery vector is a viral vector. In some embodiments, the viral vector is an AAV vector. In some embodiments, the AAV vector is an AAV1, AAV2, AAV3, AAV4, AAV5, AAV6, AAV7, AAV8 or AAV9 vector. In some embodiments the viral vector is a lentiviral vector. In some embodiments, the vector is a non-viral vector. In some embodiments, the non-viral vector is a liposome, an LNP, a polymer nanoparticle, a nanoparticle, a micelle, an polymersome or an exosome. The following studies demonstrate that expression of GBA and S1-S3 PTase utilizing the bicistronic vector in the art-recognized standard mouse model of Gaucher Disease leads to expression of GBA$^{M6P}$, increased activity in tissue and serum, and reduced substrate. This demonstrates that having a phosphorylated transgene product with high affinity for the CI-MPR can lead to effective therapies even at low activities levels due to efficient cellular uptake and lysosomal targeting.

FIGS. 21A-21D are a series of graphs showing the results of in vivo AAV mediate gene therapy studies for the treatment of Gaucher Disease. To determine the effect of AAV9 gene therapy with the bicistronic expression transgene of stable GBA+S1-S3 PTase with three different promotors. 15 wk old GBA$^{D409V/null}$ mice were dosed with a moderate dose of AAV9-stable GBA+ S1-S3 PTase, 5E11 vg. To determine how much GBA was generated by the tissue, 2 weeks later after AAV9 injection, tissue was recovered, homogenized and activity measured using the 4MU-Glc substrate. The activity was normalized to total protein in the homogenate as determined by the BCA method for protein determination.

Figures 29A, 29B, 29C:
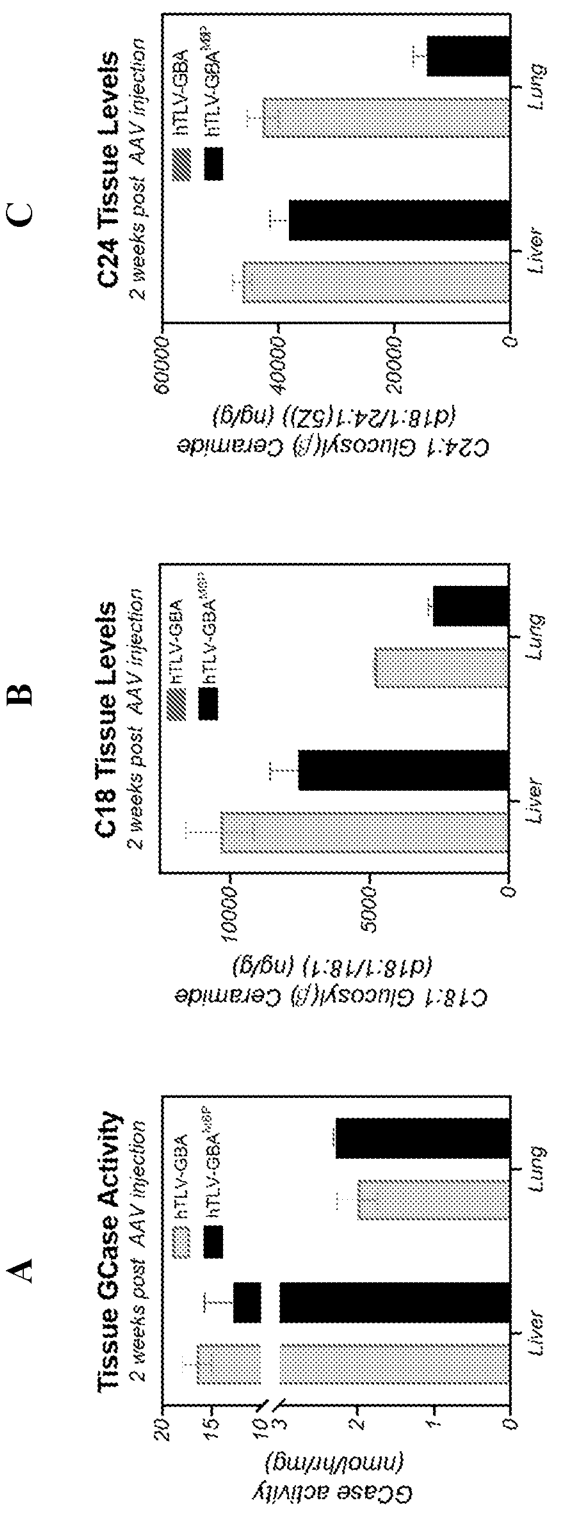
FIGS. 29A-29C are a series of graphs depicting enzyme activity and select GCase substrates in the lung and liver 2 weeks post injection of AAV9-hTLV-$GBA^{M6P}$ gene therapy in Gaucher mice. AAV9-hTLV-GBA-S1S3 is otherwise known as AAV9-hTLV-$GBA^{M6P}$ wherein the M6P denotes the S1S3 construct. Two weeks following AAV9 hTLV-GBA or AAV9 hTLV-$GBA^{M6P}$ (transgene with bicistronic vector with GBA and S1-S3 PTase) There was elevated expression in the liver for both constructs (FIG. 29A) When liver glucosyl-β-ceramide levels were measured (FIG. 29B,C), the greatest reduction in accumulated substrate was observed for the AAV9 hTLV-$GBA^{M6P}$ treated animals even though there was lower GCase activity in the liver compared to the AAV9 hTLV-GBA treated animals. This greater substrate reduction with less activity indicates the importance of N-linked oligosaccharide phosphorylation for gene therapy in terms cell uptake and lysosomal targeting. In the lung, the GCase activity for the AAV9 treated animals is low. However, the AAV9-hTLV-$GBA^{M6P}$ treated animals showed significant reduction in the lung for accumulated glucosyl-β-ceramide levels (FIG. 29B, C). Little reduction was observed for the AAV9-hTLV-GBA treated animals. This demonstrates that having a phosphorylated transgene product with high affinity for the CI-MPR can lead to effective therapies even at low activities levels due to efficient cellular uptake and lysosomal targeting.

FIGS. 29A-29C are a series of graphs depicting enzyme activity and select GCase substrates in the lung and liver 2 weeks post injection of AAV9-hTLV-GBA$^{M6P}$ gene therapy in Gaucher mice. AAV9-hTLV-GBA-S1S3 is otherwise known as AAV9-hTLV-GBA$^{M6P}$ wherein the M6P denotes the S1S3 construct. Two weeks following AAV9 hTLV-GBA or AAV9 hTLV-GBA$^{M6P}$ (transgene with bicistronic vector with GBA and S1-S3 PTase) There was elevated expression in the liver for both constructs (FIG. 29A) When liver glucosyl-β-ceramide levels were measured (FIGS. 29B and C), the greatest reduction in accumulated substrate was observed for the AAV9 hTLV-GBA$^{M6P}$ treated animals even though there was lower GCase activity in the liver compared to the AAV9 hTLV-GBA treated animals. This greater substrate reduction with less activity indicates the importance of N-linked oligosaccharide phosphorylation for gene therapy in terms cell uptake and lysosomal targeting. In the lung, the GCase activity for the AAV9 treated animals is low. However, the AAV9-hTLV-GBA$^{M6P}$ treated animals showed significant reduction in the lung for accumulated glucosyl-β-ceramide levels (FIG. 29B, C). Little reduction was observed for the AAV9-hTLV-GBA treated animals. This demonstrates that having a phosphorylated transgene product with high affinity for the CI-MPR can lead to effective therapies even at low activities levels due to efficient cellular uptake and lysosomal targeting.

Example 4: Treatment of α-Mannosidosis

Enzyme Replacement Therapy (ERT)

An expression vector comprising a sequence encoding LAMAN and a sequence encoding a S1-S3 Ptase may be used to treat or prevent a sign or symptom of α-Mannosidosis. The following studies demonstrate that expression of LAMAN-S1-S3 in a mouse model leads to expression of the LAMAN-S1-S3, transportation of the LAMAN-S1-S3 into cells from the circulating blood stream and an increased activity of LAMAN in cells taking up the LAMAN-S1-S3 complex. A small increase in LAMAN resulting from the expression and uptake of the LAMAN-S1-S3 complex leads to a significant functional recovery of function in the mouse model.

The expression of LAMAN utilizing the bicistronic expression vector with S1-S3 PTase, generates a recombinant protein with higher levels of phosphorylated oligosaccharides that can be used to treat or prevent a sign or symptom of α-Mannosidosis. The following studies demonstrate that ERT using recombinant LAMAN protein expressed using the bicistronic vector with S1-S3 PTase in the wild type mice leads to a greater uptake and boarder distribution in tissues.

Figures 22A, 22B, 22C:
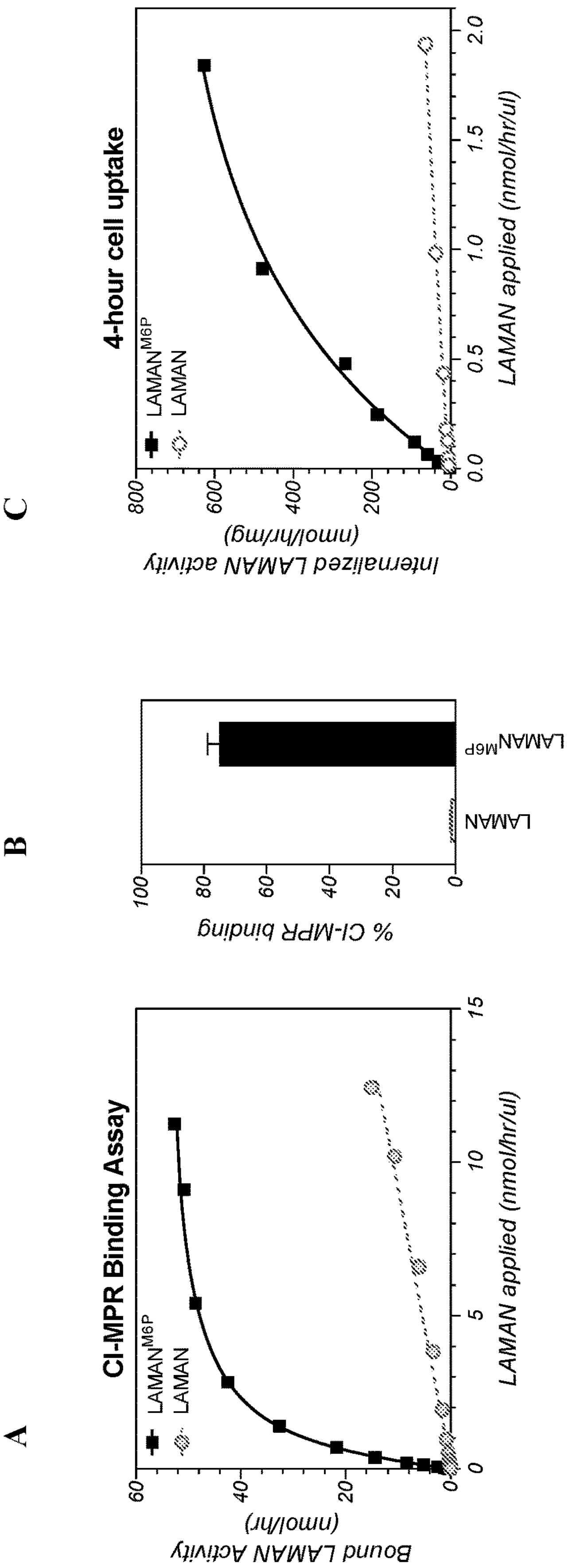
FIGS. 22A-22C are a series of graphs depicting the results of in vitro studies for the use of lysosomal alpha-mannosidase (LAMAN) as ERT.

FIGS. 22A-22C are a series of graphs depicting the results of in vitro studies for the use of lysosomal alpha-mannosidase (LAMAN) as ERT.

Figures 23A, 23B:
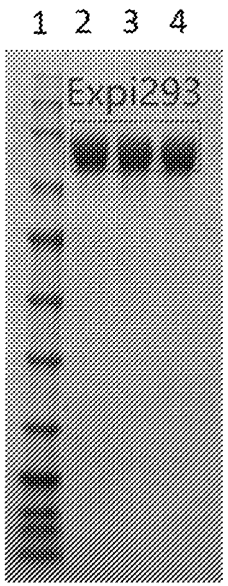
FIGS. 23A-23B is a photograph and corresponding data table depicting LAMAN enzyme expression, purification, and characterization. Two preparations of LAMAN were transiently co-expressed in Expi293 cells with (M0611) or without the bicistronic vector that encoded for the S1-S3 PTases. Both were purified by utilization of the HPC4 affinity tag. The significant increase in phosphorylation was demonstrated by measuring the amount of LAMAN that kind bind to immobilized cation-independent mannose 6-phosphate receptor in a dose dependent manner. The amount of LAMAN bound was based on its activity using it synthetic substrate 4-Methylumbelliferyl-α-D-Mannopyranoside (4MU-Man). The specificity of binding via phosphorylated oligosaccharides was confirmed by the ability of added mannose 6-phosphate to block binding. Of note is the ability of LAMAN$^{M6P}$ (M0611) to bind the receptor even in the presence of M6P. LAMAN$^{M6P}$ (M0611, P-0030) and LAMAN (P-0031) were chosen for in vivo animal study.

FIGS. 23A-23B is a photograph and corresponding data table depicting LAMAN enzyme expression, purification, and characterization. Two preparations of LAMAN were transiently co-expressed in Expi293 cells with (M0611) or without the bicistronic vector that encoded for the S1-S3 PTases. Both were purified by utilization of the HPC4 affinity tag. The significant increase in phosphorylation was demonstrated by measuring the amount of LAMAN that kind bind to immobilized cation-independent mannose 6-phosphate receptor in a dose dependent manner. The amount of LAMAN bound was based on its activity using it synthetic substrate 4-Methylumbelliferyl-α-D-Mannopyranoside (4MU-Man). The specificity of binding via phosphorylated oligosaccharides was confirmed by the ability of added mannose 6-phosphate to block binding. Of note is the ability of LAMAN$^{M6P}$ (M0611) to bind the receptor even in the presence of M6P. LAMAN$^{M6P}$ (M0611, P-0030) and LAMAN (P-0031) were chosen for in vivo animal study.

Figure 23C:
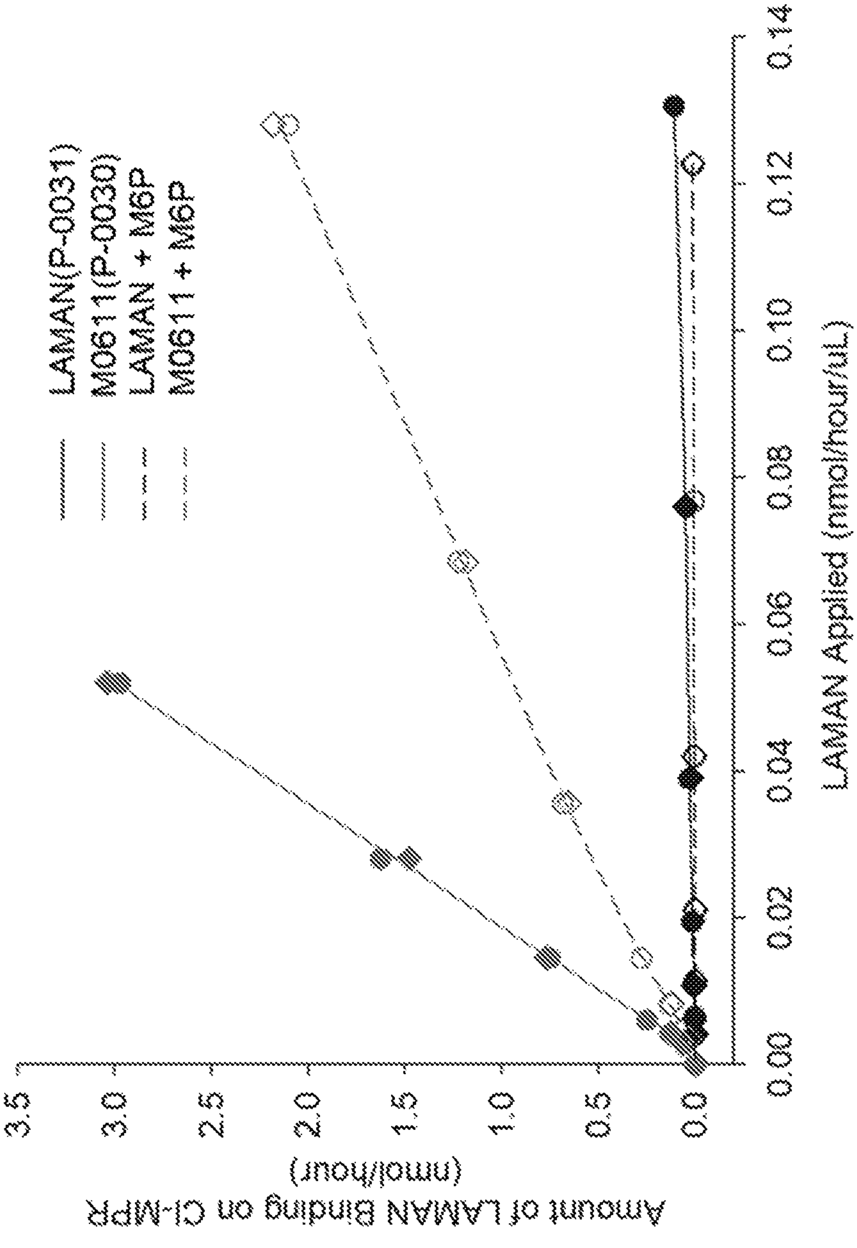
FIG. 23C a graph depicting LAMAN$^{M6P}$ (M0611) enzyme expression, purification, and characterization. Two preparations of LAMAN were transiently co-expressed in Expi293 cells with or without the bicistronic vector that encoded for the S1-S3 variant of PTase. Both were purified by utilization of the HPC4 tag. The significant increase in phosphorylation was demonstrated by measuring the amount of LAMAN that kind bind to immobilized cation-independent mannose 6-phosphate receptor in a dose dependent manner. The amount of bound LAMAN was determined by activity using a synthetic substrate 4-Methylumbelliferyl-α-D-Mannopyranoside (4MU-Man). The specificity of binding via phosphorylated oligosaccharides was confirmed by the ability of added mannose 6-phosphate to block binding. Of note is the ability of M0611 to bind the receptor even in the presence of M6P. LAMAN M6P (M0611, P-0030) and LAMAN (P-0031) were chosen for in vivo animal study.

FIG. 23C a graph depicting LAMAN$^{M6P}$ (M0611) enzyme expression, purification, and characterization. Two preparations of LAMAN were transiently co-expressed in Expi293 cells with or without the bicistronic vector that encoded for the S1-S3 variant of PTase. Both were purified by utilization of the HPC4 tag. The significant increase in phosphorylation was demonstrated by measuring the amount of LAMAN that kind bind to immobilized cation-independent mannose 6-phosphate receptor in a dose dependent manner. The amount of bound LAMAN was determined by activity using a synthetic substrate 4-Methylumbelliferyl-α-D-Mannopyranoside (4MU-Man). The specificity of binding via phosphorylated oligosaccharides was confirmed by the ability of added mannose 6-phosphate to block binding. Of note is the ability of M0611 to bind the receptor even in the presence of M6P. LAMAN$^{M6P}$ (M0611, P-0030) and LAMAN (P-0031) were chosen for in vivo animal study.

Figures 24A, 24B:
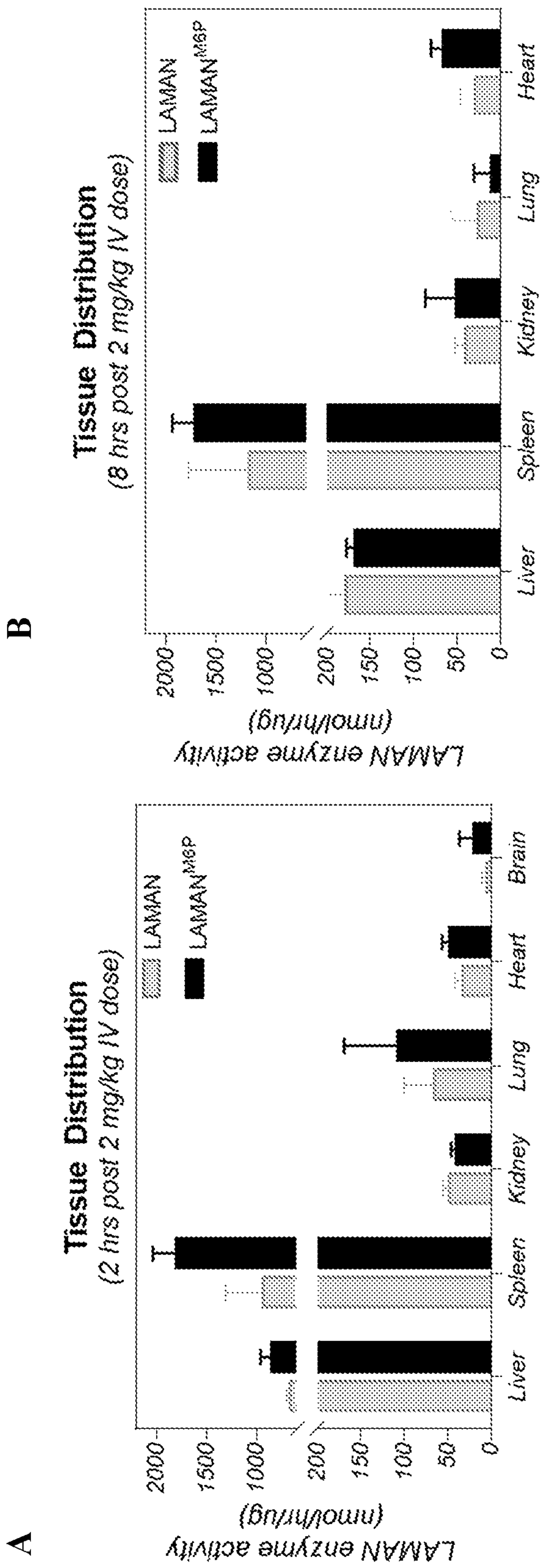
FIGS. 24A-24B are a pair of graphs demonstrating the biodistribution of LAMAN and LAMAN$^{M6P}$ enzymes in wild type mice for enzyme replacement therapy. To evaluate the difference in tissue uptake between LAMAN and LAMAN$^{M6P}$ (LAMAN co-expressed with S1-S3 PTase), 2 mg/kg of each prep was injected via tail vein into wild type mice (n=4). 2 and 8 hrs after dosing, tissue was recovered, homogenized and activity measured using the 4MU-Man substrate. The activity was normalized to total protein in the homogenate as determined by the BCA method for protein determination. An advantage of LAMAN$^{M6P}$ (LAMAN co-expressed with S1S3 PTase) is observed in the tissue uptake data. For liver, spleen, heart, lung, and brain there was greater activity in the tissue at 2 hours. This trend was also true at 8 hours with the exception of the lung. This might be a result of the high variation observed in the analysis of this tissue. The only exception to this observation was the kidney. Endogenous LAMAN activity is subtracted from all samples. Higher LAMAN enzyme activity was detected in most tissues of the mice which were injected with our LAMAN$^{M6P}$ enzyme.

FIGS. 24A-24B are a pair of graphs demonstrating the biodistribution of LAMAN and LAMAN$^{M6P}$ enzymes in wild type mice for enzyme replacement therapy. To evaluate the difference in tissue uptake between LAMAN and LAMAN$^{M6P}$ (LAMAN co-expressed with S1-S3 PTase), 2 mg/kg of each prep was injected via tail vein into wild type mice (n=4). 2 and 8 hrs after dosing, tissue was recovered, homogenized and activity measured using the 4MU-Man substrate. The activity was normalized to total protein in the homogenate as determined by the BCA method for protein determination. An advantage of LAMAN$^{M6P}$ (LAMAN co-expressed with S1S3 PTase) is observed in the tissue uptake data. For liver, spleen, heart, lung, and brain there was greater activity in the tissue at 2 hours. This trend was also true at 8 hours with the exception of the lung. This might be a result of the high variation observed in the analysis of this tissue. The only exception to this observation was the kidney. Endogenous LAMAN activity is subtracted from all samples. Higher LAMAN enzyme activity was detected in most tissues of the mice which were injected with our LAMAN$^{M6P}$ enzyme.

Figures 25A, 25B:
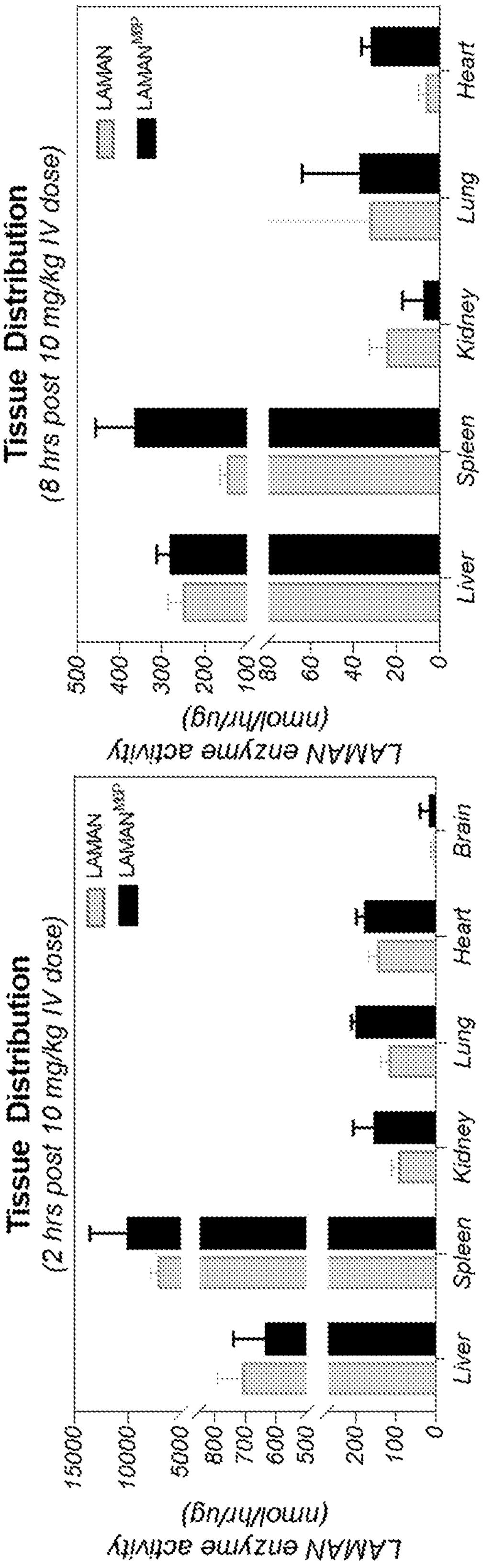
FIGS. 25A-25B are a pair of graphs demonstrating the biodistribution of αLAMAN and LAMAN$^{M6P}$ enzymes in wild type mice for enzyme replacement therapy. To evaluate the difference in tissue uptake between LAMAN and $LAMAN^{M6P}$ (LAMAN co-expressed with S1-S3 PTase), 10 mg/kg of each prep was injected via tail vein into wild type mice (n=4). 2 and 8 hrs after dosing, tissue was recovered, homogenized and activity measured using the 4MU-Man substrate. The activity was normalized to total protein in the homogenate as determined by the BCA method for protein determination. An advantage of $LAMAN^{M6P}$ (LAMAN co-expressed with S1-S3 PTase) is observed in the tissue uptake data. For liver, spleen, heart, lung, and brain there was greater activity in the tissue at 2 hours. This trend was also true at 8 hours with the exception of the Kidney. This might be a result of the high variation observed in the analysis of this tissue.

FIGS. 25A-25B are a pair of graphs demonstrating the biodistribution of αLAMAN and LAMAN$^{M6P}$ enzymes in wild type mice for enzyme replacement therapy. To evaluate the difference in tissue uptake between LAMAN and LAMAN$^{M6P}$ (LAMAN co-expressed with S1-S3 PTase), 10 mg/kg of each prep was injected via tail vein into wild type mice (n=4). 2 and 8 hrs after dosing, tissue was recovered, homogenized and activity measured using the 4MU-Man substrate. The activity was normalized to total protein in the homogenate as determined by the BCA method for protein determination. An advantage of LAMAN' (LAMAN co-expressed with S1-S3 PTase) is observed in the tissue uptake data. For liver, spleen, heart, lung, and brain there was greater activity in the tissue at 2 hours. This trend was also true at 8 hours with the exception of the Kidney. This might be a result of the high variation observed in the analysis of this tissue.

Gene Therapy

A delivery vector comprising a sequence encoding LAMAN and a sequence encoding the S1-S3 modified GlcNAc-1 phosphotransferase (GlcNAc-1 PTase) may be used to treat or prevent a sign or symptom of α-Mannosidosis. In some embodiments, the delivery vector is a viral vector. In some embodiments, the viral vector is an AAV vector. In some embodiments, the AAV vector is an AAV1, AAV2, AAV3, AAV4, AAV5, AAV6, AAV7, AAV8 or AAV9 vector. In some embodiments the viral vector is a lentiviral vector. In some embodiments, the vector is a non-viral vector. In some embodiments, the non-viral vector is a liposome, an LNP, a polymer nanoparticle, a nanoparticle, a micelle, an polymersome or an exosome. The following studies demonstrate that expression of LAMAN-S1-S3 in a mouse model of α-Mannosidosis leads to expression of the LAMAN-S1-S3, transportation of the LAMAN-S1-S3 into cells from the circulating blood stream and an increased activity of LAMAN in cells taking up the LAMAN-S1-S3 complex. A small increase in v resulting from the expression and uptake of the LAMAN-S1-S3 complex leads to a significant functional recovery of function in the mouse model.

Alternatively or in addition, a delivery vector comprising a sequence encoding the S1-S3 modified GlcNAc-1 phosphotransferase (GlcNAc-1 PTase) may be used to treat or prevent a sign or symptom of α-Mannosidosis. The expression of S1-S3 may increase the uptake of endogenous LAMAN by body tissues, thereby inducing a significant functional recovery of function in the mouse model.

Example 5: Treatment of Mucolipidosis

Enzyme Replacement Therapy (ERT)

An expression vector comprising a sequence encoding the S1-S3 modified GlcNAc-1 phosphotransferase (GlcNAc-1 PTase) may be used to treat or prevent a sign or symptom of Mucolipidosis. The following studies demonstrate that expression of S1-S3 leads to expression of the S1-S3, transportation of the S1-S3 as well as one or more lysosomal enzymes into cells from the circulating blood stream and an increased activity of one or more lysosomal enzymes in cells taking up the S1-S3 complex. A small increase in the S1-S3 complex resulting from the expression and uptake of the S1-S3 complex and one or more lysosomal enzymes leads to a significant functional recovery of function.

Gene Therapy

A delivery vector comprising a sequence encoding a S1-S3 modified GlcNAc-1 phosphotransferase (GlcNAc-1 PTase) may be used to treat or prevent a sign or symptom of Mucolipidosis. In some embodiments, the delivery vector is a viral vector. In some embodiments, the viral vector is an AAV vector. In some embodiments, the AAV vector is an AAV1, AAV2, AAV3, AAV4, AAV5, AAV6, AAV7, AAV8 or AAV9 vector. In some embodiments the viral vector is a lentiviral vector. In some embodiments, the vector is a non-viral vector. In some embodiments, the non-viral vector is a liposome, an LNP, a polymer nanoparticle, a nanoparticle, a micelle, an polymersome or an exosome. A delivery vector comprising a sequence encoding a soluble S1-S3 modified GlcNAc-1 phosphotransferase (GlcNAc-1 PTase) may be used to treat or prevent a sign or symptom of Mucolipidosis. A delivery vector comprising a sequence encoding a S1-S3 modified GlcNAc-1 phosphotransferase (GlcNAc-1 PTase) may be used to treat or prevent a sign or symptom of Mucolipidosis. The following studies demonstrate that expression of S1-S3 PTase leads to expression of the S1-S3 PTase, S1-S3 cellular activity results in the correction of serum level of mis-trafficked lysosomal enzymes by increasing their N-linked oligosaccharide phosphorylation allowing for efficient targeting to the lysosome.

Alternatively or in addition, a delivery vector comprising a sequence encoding the S1-S3 modified GlcNAc-1 phosphotransferase (GlcNAc-1 PTase) may be used to treat or prevent a sign or symptom of Mucolipidosis. The expression of S1-S3 PTase may increase the uptake of one or more endogenous lysosomal enzymes by body tissues, thereby inducing a significant functional recovery of function in the mouse model.

Figure 26A:
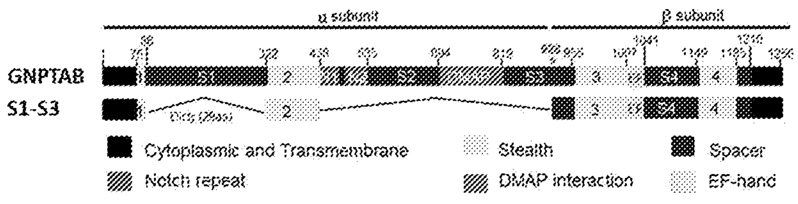
FIGS. 26A-26B is a schematic diagram and a graph depicting the AAV9 design and in vitro testing for a Mucolipidosis gene therapy (GTx). 293T cells was transduced with various M0021 (AAV9-CAGp-S1-S3) virus and cultured for 2 days before PTase activity assay.
Figure 26B:
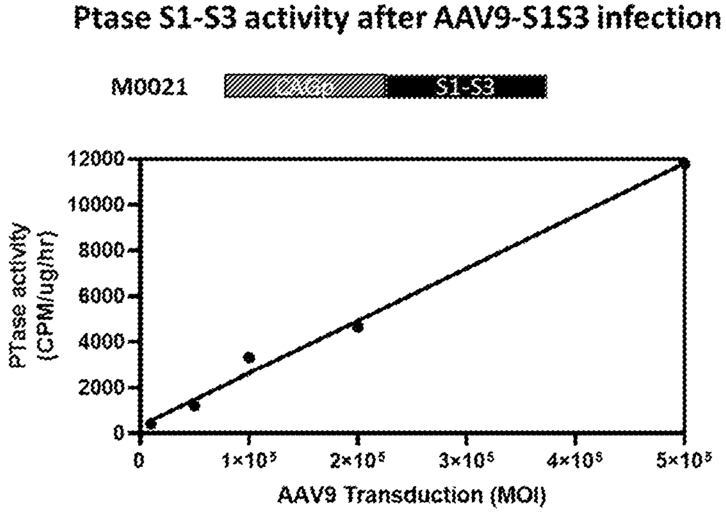

FIGS. 26A-26B is a schematic diagram and a graph depicting the AAV9 design and in vitro testing for a Mucolipidosis gene therapy (GTx). 293T cells was transduced with various M0021 (AAV9-CAGp-S1-S3) virus and cultured for 2 days before PTase activity assay.

Figures 27A, 27B:
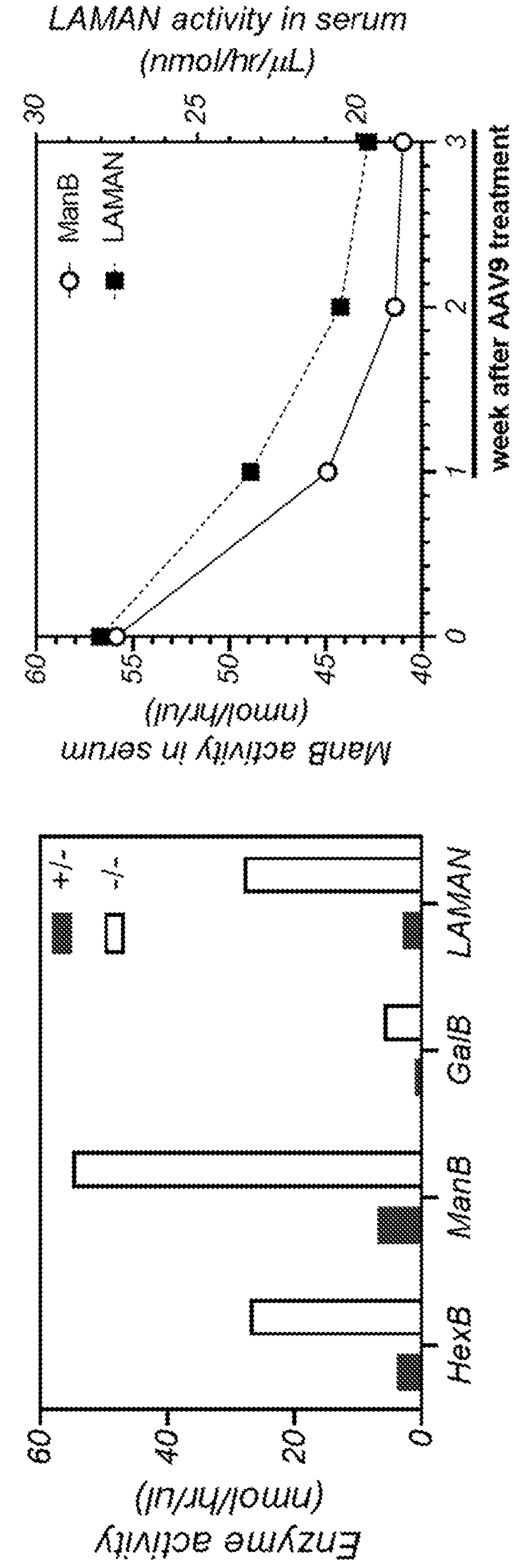
FIGS. 27A-27B are a pair of graphs demonstrating that M0021 treatment decreases the serum lysosomal enzymes level in ML II mouse. To determine the effect of S1-S3 PTase Gene Therapy, a 34 week old female mouse was dose with a moderate dose of M0021 (AAV9-CAGp-S1-S3), 4e12 vg (2e13 vg/kg). One of the phenotypes of ML II is elevated serum level of lysosomal enzyme due to their inability to be targeted to the lysosome within the cell. An encouraging results was observed when there was a decrease in LAMAN and ManB activity in the serum after just 1 week of receiving the therapy. This result is important since it demonstrates the ability to effect a described phenotype of the MLII mouse model.

FIGS. 27A-27B are a pair of graphs demonstrating that M0021 treatment decreases the serum lysosomal enzymes level in ML II mouse. To determine the effect of S1-S3 PTase Gene Therapy, a 34 week old female mouse was dose with a moderate dose of M0021 (AAV9-CAGp-S1-S3), 4e12 vg (2e13 vg/kg). One of the phenotypes of ML II is elevated serum level of lysosomal enzyme due to their inability to be targeted to the lysosome within the cell. An encouraging results was observed when there was a decrease in LAMAN and ManB activity in the serum after just 1 week of receiving the therapy. This result is important since it demonstrates the ability to effect a described phenotype of the MLII mouse model.

Figures 28A, 28B, 28C:
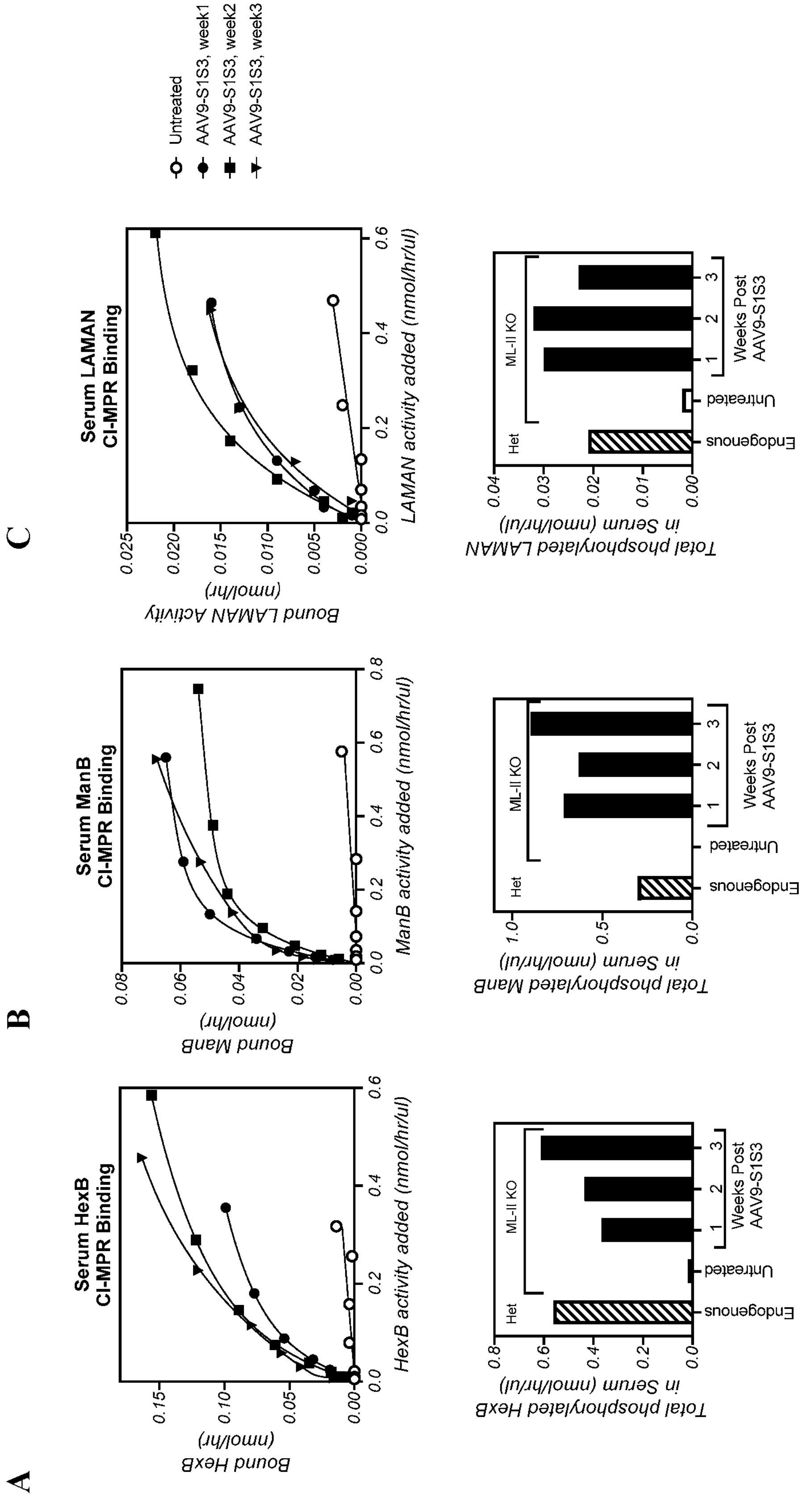
FIGS. 28A-28C are a series of graphs demonstrating that M0021 treatment increases the phosphorylation of lysosomal enzymes in ML II. To further understand the impact on S1-S3 PTase gene therapy in decreasing the serum activity of LAMAN and ManB, CI-MPR binding of the enzyme found in the serum was evaluated using the immobilized receptor binding assay described earlier. Briefly, a known about of activity in added in increasing amounts to immobilized CI-MPR. The unbound enzyme is washed away and the remaining bound enzyme is measured using the appropriate synthetic substrate; Man-b-4MU (ManB, LAMAN 4MU-Man (LAMAN). AAV9-S1S3 Gene therapy in ML II mouse increases the glycan phosphorylation of lysosomal enzymes. The total phosphorylated lysosomal enzymes in serum normalized to normal levels or slightly higher after 3 weeks.

FIGS. 28A-28C are a series of graphs demonstrating that M0021 treatment increases the phosphorylation of lysosomal enzymes in ML II. To further understand the impact on S1-S3 PTase gene therapy in decreasing the serum activity of LAMAN and ManB, CI-MPR binding of the enzyme found in the serum was evaluated using the immobilized receptor binding assay described earlier. Briefly, a known about of activity in added in increasing amounts to immobilized CI-MPR. The unbound enzyme is washed away and the remaining bound enzyme is measured using the appropriate synthetic substrate; Man-b-4MU (ManB, LAMAN 4MU-Man (LAMAN). AAV9-S1S3 Gene therapy in ML II mouse increases the glycan phosphorylation of lysosomal enzymes. The total phosphorylated lysosomal enzymes in serum normalized to normal levels or slightly higher after 3 weeks.

The disclosures of each and every patent, patent application, and publication cited herein are hereby incorporated herein by reference in their entirety. While this disclosure has been disclosed with reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

What is claimed:

1. A composition comprising a vector comprising a sequence encoding a promoter, a first polynucleotide encoding a lysosomal enzyme and a second polynucleotide encoding a modified GlcNAc-1 phosphotransferase (GlcNAc-1 PTase), wherein the promoter is capable of driving expression in a mammalian cell and wherein the promoter is operably linked to the first polynucleotide and to the second polynucleotide, wherein the vector further comprises a sequence encoding an Internal Ribosome Entry Site (IRES), wherein the polynucleotide encoding a modified GlcNAc-1 phosphotransferase comprises a nucleic acid sequence of SEQ ID NO: 4.

2. The composition of claim 1, wherein the sequence encoding the IRES is positioned between the sequence encoding the lysosomal enzyme and the sequence encoding the modified GlcNAc-1 PTase.

3. The composition of claim 2, wherein from 5' to 3', the vector comprises the sequence encoding the modified GlcNAc-1 PTase, the sequence encoding the IRES and the sequence encoding the lysosomal enzyme, or wherein from 5' to 3', the vector comprises the sequence encoding the lysosomal enzyme, the sequence encoding the IRES and the sequence encoding the modified GlcNAc-1 PTase.

4. The composition of claim 1, wherein the vector further comprises a sequence encoding a cleavage site.

5. The composition of any one of claim 1, wherein the vector is an expression vector, or a delivery vectorr.

6. The composition of claim 1, wherein the vector is a lentiviral vector, an adenoviral vector or an adeno-associated viral (AAV) vector:

a) comprises a serotype selected from the group consisting of AAV1, AAV2, AAV3, AAV4, AAV5, AAV6, AAV7, AAV8, and AAV9;

b) comprises a sequence encoding a capsid isolated or derived from one or more of a serotype selected from the group consisting of AAV1, AAV2, AAV3, AAV4, AAV5, AAV6, AAV7, AAV8, and AAV9; and/or c) comprises a sequence encoding at least one inverted terminal repeat (ITR) isolated or derived from one or more of a serotype selected from the group consisting of AAV1, AAV2, AAV3, AAV4, AAV5, AAV6, AAV7, AAV8, and AAV9.

7. The composition of claim 1, wherein the vector is a bicistronic or multicistronic vector.

8. The composition of claim 1, wherein the promoter comprises a constitutive promoter.

9. The composition of claim 1, wherein the vector comprises a nucleic acid sequence of SEQ ID NO: 1.

10. The composition of claim 1, wherein the lysosomal enzyme:

a) is selected from the group consisting of β-glucocebrosidase (GBA), Galactosylceramidase (GALC), α-Galactosidase (GLA), α-N-acetylglucosaminidase (NAGLU), acid α-glucosidase (GAA) and lysosomal acid α-mannosidase (LAMAN);

b) comprises β-glucocerebrosidase (GBA);

c) comprises Galactosylceramidase (GALC);

d) comprises α-Galactosidase (GLA);

e) comprises α-N-acetylglucosaminidase (NAGLU);

f) comprises acid α-glucosidase (GAA); or g) comprises lysosomal acid α-mannosidase (LAMAN).

11. A composition according to claim 1, for a method of:

a) treating a lysosomal storage disorder (LSD), the method comprising administering to a subject an effective amount of the composition of claim 1, wherein the composition increases the phosphorylation of a lysosomal enzyme responsible of the LSD, thereby treating the LSD;

b) A method of preventing an occurrence or an onset of a lysosomal storage disorder (LSD), the method comprising administering to a subject an effective amount of the composition of claim 1, wherein the composition increases the phosphorylation of a lysosomal enzyme responsible of the LSD, thereby preventing the occurrence of the LSD in the subject;

c) ameliorating the phosphorylation of a lysosomal enzyme responsible for a lysosomal storage disorder (LSD), the method comprising administering to a subject an effective amount of the composition of claim 1, wherein the composition increases the phosphorylation of the lysosomal enzyme; or d) ameliorating the phosphorylation of a lysosomal enzyme responsible for a lysosomal storage disorder (LSD), the method comprising contacting to a cell, an effective amount of the composition of claim 1, wherein the composition increases the phosphorylation of the lysosomal enzyme.

12. The method of claim 11, wherein the administering comprises:

a) a systemic route of administration; or b) a local route of administration.

13. The method of claim 11, wherein the subject is a human.

14. The method of claim 11, wherein the subject is a male.

15. The method of claim 11, wherein the subject is a female.

* * * * *